US010993420B2

(12) United States Patent
Grosveld et al.

(10) Patent No.: US 10,993,420 B2
(45) Date of Patent: May 4, 2021

(54) PRODUCTION OF HEAVY CHAIN ONLY ANTIBODIES IN TRANSGENIC MAMMALS

(71) Applicant: ERASMUS UNIVERSITY MEDICAL CENTER, Rotterdam (NL)

(72) Inventors: Franklin Gerardus Grosveld, Rotterdam (NL); Richard Wilhelm Janssens, Rotterdam (NL)

(73) Assignee: ERASMUS UNIVERSITY MEDICAL CENTER, Rotterdam (NL)

( * ) Notice: Subject to any disclaimer, the term of this patent is extended or adjusted under 35 U.S.C. 154(b) by 313 days.

(21) Appl. No.: 14/211,243

(22) Filed: Mar. 14, 2014

(65) Prior Publication Data

US 2014/0356908 A1 Dec. 4, 2014

Related U.S. Application Data

(60) Provisional application No. 61/852,343, filed on Mar. 15, 2013.

(51) Int. Cl.

| | |
|---|---|
| ***A01K 67/027*** | (2006.01) |
| ***C12N 15/85*** | (2006.01) |
| ***C07K 16/06*** | (2006.01) |
| ***C07K 16/18*** | (2006.01) |
| ***C07K 16/00*** | (2006.01) |
| *C12P 21/00* | (2006.01) |

(52) U.S. Cl.

CPC .......... *A01K 67/0278* (2013.01); *C07K 16/00* (2013.01); *C07K 16/06* (2013.01); *C07K 16/18* (2013.01); *C12N 15/8509* (2013.01); *A01K 2207/15* (2013.01); *A01K 2217/052* (2013.01); *A01K 2217/072* (2013.01); *A01K 2217/075* (2013.01); *A01K 2217/15* (2013.01); *A01K 2227/105* (2013.01); *A01K 2267/01* (2013.01); *C07K 2317/569* (2013.01); *C07K 2317/60* (2013.01); *C07K 2317/92* (2013.01); *C12N 2015/8518* (2013.01); *C12N 2830/46* (2013.01); *C12P 21/005* (2013.01)

(58) Field of Classification Search

CPC . A01K 67/0278; A01K 2217/15; C07K 16/00
See application file for complete search history.

(56) References Cited

U.S. PATENT DOCUMENTS

| | | | | |
|---|---|---|---|---|
| 5,487,890 | A | 1/1996 | Taylor | |
| 5,591,669 | A | 1/1997 | Krimpenfort | |
| 5,843,440 | A | 12/1998 | Pouletty | |
| 5,877,397 | A | 3/1999 | Lonberg | |
| 6,150,584 | A | 11/2000 | Kucherlapati | |
| 6,162,963 | A | 12/2000 | Kucherlapati | |
| 7,534,604 | B2 | 5/2009 | Fandl | |
| 7,731,969 | B1 | 6/2010 | Tucker | |
| 7,785,903 | B2 | 8/2010 | Bond | |
| 8,754,287 | B2 * | 6/2014 | MacDonald | A01K 67/0275 800/18 |
| 8,883,150 | B2 | 11/2014 | Craig | |
| 8,921,522 | B2 | 12/2014 | Grosveld | |
| 8,921,524 | B2 | 12/2014 | Grosveld | |
| 9,346,877 | B2 | 5/2016 | Grosveld | |
| 9,353,179 | B2 | 5/2016 | Grosveld | |
| 2003/0022240 | A1 | 1/2003 | Luo | |
| 2003/0058074 | A1 | 3/2003 | Valle | |
| 2003/0070185 | A1 | 4/2003 | Jakobovits | |
| 2003/0091561 | A1 | 5/2003 | vandeWinkel | |
| 2003/0166877 | A1 | 9/2003 | Gillies | |
| 2006/0026703 | A1 | 2/2006 | Lonberg | |
| 2006/0246477 | A1 | 11/2006 | Hermans | |
| 2007/0292936 | A1 | 12/2007 | Barthelemy | |
| 2009/0271880 | A1 | 10/2009 | Grosveld | |
| 2009/0307787 | A1 | 12/2009 | Grosveld | |
| 2010/0197897 | A1 | 8/2010 | Grosveld | |
| 2010/0216974 | A1 | 8/2010 | Grosveld | |
| 2011/0145937 | A1 † | 6/2011 | MacDonald | |
| 2012/0151610 | A1 | 6/2012 | Craig | |
| 2013/0046079 | A1 * | 2/2013 | Bruggemann | A01K 67/0276 530/387.3 |
| 2013/0323235 | A1 | 12/2013 | Craig | |
| 2013/0344057 | A1 | 12/2013 | Grosveld | |
| 2013/0345405 | A1 | 12/2013 | Grosveld | |
| 2015/0113668 | A1 * | 4/2015 | Bruggemann | A01K 67/0278 800/4 |

FOREIGN PATENT DOCUMENTS

| | | | |
|---|---|---|---|
| EP | 0143151 | A2 | 6/1985 |
| EP | 0368684 | B1 | 5/1990 |
| EP | 0368684 | B2 | 3/1994 |
| EP | 0463151 | B1 | 6/1996 |
| EP | 0436597 | B1 | 4/1997 |

(Continued)

OTHER PUBLICATIONS

Raina et al. Gene 554:96-100, 2015.*
Naito et al. J of Reproduction and Fertility 113:137-134, 1998.*
Liable et al. Biotechnology Journal 10:109-120, 2015.*
Carlson et al. PNAS 109(43):17382-17387, Oct. 2012.*
Lilico et al. Scientific Reports 3:Article No. 2847. Dio:10.1038/srep02847. pp. 1-4, Oct. 10, 2013.*
Gaj et al. Trends in Technology 31(7):397-405, Jul. 2013.*
Tong et al. Journal of Genetics and Genomics 39:275-280, 2012.*
Ji et al. Transgenic Research 24:227-235, 2015.*
Crescentod Claims Triple Knockout Mice Have No IgH, Kappa Light Chain or Lamda Light Cains, genengnews.com/topics/drug-discovery, dated Sep. 2010. printed Feb. 4, 2010, pp. 1-2. (Year: 2010).*

(Continued)

*Primary Examiner* — Marcia S Noble
(74) *Attorney, Agent, or Firm* — Saul Ewing Arnstein & Lehr LLP; Doreen Y. Trujillo

(57) ABSTRACT

A transgenic non-human mammal containing a heterologous heavy chain gene locus that is capable of producing soluble heavy chain only antibodies and antigen-binding fragments thereof following immunization.

18 Claims, 87 Drawing Sheets
(53 of 87 Drawing Sheet(s) Filed in Color)
Specification includes a Sequence Listing.

(56) References Cited

FOREIGN PATENT DOCUMENTS

| | | | |
|---|---|---|---|
| EP | 0623679 B1 | 6/2003 | |
| EP | 1399559 B1 | 3/2004 | |
| GB | 1 956 092 A1 * | 9/2008 | ............ C12N 15/13 |
| RU | 2335507 C2 | 10/2008 | |
| WO | 9404678 | 3/1994 | |
| WO | 9946300 | 9/1999 | |
| WO | 0212437 A2 | 2/2002 | |
| WO | 02/066630 A1 † | 8/2002 | |
| WO | 0285944 A2 | 10/2002 | |
| WO | 02085945 A2 | 10/2002 | |
| WO | 02100348 A2 | 12/2002 | |
| WO | 03000737 A2 | 1/2003 | |
| WO | 03002609 A2 | 1/2003 | |
| WO | 03035694 A2 | 5/2003 | |
| WO | 2004003019 A2 | 1/2004 | |
| WO | 2004049794 A2 | 6/2004 | |
| WO | 2004058820 A2 | 7/2004 | |
| WO | 2004076677 A2 | 9/2004 | |
| WO | 2006008548 A2 | 1/2006 | |
| WO | 2006047367 | 5/2006 | |
| WO | 2006122825 A2 | 11/2006 | |
| WO | 2007/096779 A2 † | 8/2007 | |
| WO | 2008035216 A2 | 3/2008 | |
| WO | 2008151081 A1 | 12/2008 | |
| WO | 2009/013620 A2 † | 1/2009 | |
| WO | 2010/109165 A2 † | 9/2010 | |
| WO | 2011072204 A1 | 6/2011 | |
| WO | 2012122512 A1 | 9/2012 | |
| WO | 2012141798 A1 | 10/2012 | |
| WO | 2013171505 | 11/2013 | |

OTHER PUBLICATIONS

Matheson et al. International Immunology 21 (8):957-966, 2009 (Year: 2009).*

Lonberg. Current Opinions in Immunology 20:450-459, 2009 (Year: 2009).*

'Shin-Seikagaku Jikken Kouza 12, Bunshi-Men'ekigaku III-Kougen, Koutai, Hotai-' (New Biochemical Experimental Seminar 12, Molecular Immnology III-antigen, antibody, and complement-) 1992, K.K. Tokyo Kagaku Dojin, pp. 1-11, English Translation Excerpts.

Anderson, S.M. et al., 'New markers for murine memory B cells that define mutated and unmutated subsets,' J. Exp. Med., vol. 204, No. 9, pp. 2103-2114, 2007.

Babcock, John S. et al., A novel strategy for generating monoclonal antibodies from single, isolated lymphocytes producing antibodies of defined specificities (PCR/antibody-forming cells/VH and VL genes/immunoglobulin/plaque assays), Proceedings of the National Academy of Science, Jul. 1996, pp. 7843-7848, vol. 93, Immunology, USA.

Barthelemy, Pierre A. et al., Comprehensive Analysis of the Factors Contributing to the Stability and Solubility of Autonomous Human VH Domains, The Journal of Biological Chemistry, Feb. 8, 2008, pp. 3639-3654, vol. 283, No. 6, Printed in the U.S.A.

Bernasconi, N.L., et al., 'Maintenance of Serological Memory by Polyclonal Activation of Human Memory B Cells', Science, vol. 298, No. 5601, pp. 2199-2202, 2002.

Biburger, M., et al., 'A Novel Bispecific Tetravalent Antibody Fusion Protein to Target Costimulatory Activity for T-cell Activation to Tumor Cells Overexpressing ErbB2/HER2', J. Mol. Biol., vol. 346, pp. 1299-1311, 2005.

Boder, E.T., et al., 'Yeast surface display for screening combinatorial polypeptide libraries', Nat. Biotechnol., vol. 15, No. 6, pp. 553-557, 1997.

Boersma, W.J.A., et al., 'Summary of workshop findings for porcine B-cell markers', Veterinary Immunology and Immunopathology, vol. 80, Nos. 1-2, pp. 63-78, 2001.

Boland, MJ et al., "Adult mice generated from induced pluripotent stem cells," Nature, Sep. 3, 2009, 461(7260), pp. 91-94.

Bond, C.J., et al., 'Contributions of CDR3 to VHH domain stability and the design of monobody scaffolds for naive antibody libraries', J. Mol. Biol., vol. 332, No. 3, pp. 643-655, 2003.

Bond, Christopher J. et al., A Structure-Based Database of Antibody Variable Domain Diversity, Journal of Molecular Biology, 2005, pp. 699-709, vol. 348, Elsevier, Ltd.

Brandt, C.R., et al., Loss of a Consensus Splice Signal in a Mutant Immunoglobulin Gene Eliminates the CH.sub.1 Domain Exon from the mRNA, Molecular and Cellular Biology, vol. 4, No. 7, pp. 1270-1277, 1984.

Brophy, B., et al., 'Cloned transgenic cattle produce milk with higher levels of .beta.-casein and .kappa.-casein', Nature Biotechnology, vol. 21, pp. 157-162, 2003.

Brorson, K. et al., 'Mutational Analysis of Avidity and Fine Specificity of Anti-Levan Antibodies,' J. Immunol., vol. 163, pp. 6694-6701 (1999).

Bruggemann, M., et al., 'A repertoire of monoclonal antibodies with human heavy chains from transgenic mice', Proc. Natl. Acad. Sci. USA, vol. 86, pp. 6709-6713, 1989.

Bruggemann, M., et al., 'Heavy-chain-only antibody expression and B-cell development in the mouse', Critical Reviews in Immunology, vol. 26, No. 5, pp. 377-390, 2006.

Bruggemann, M., et al., 'Strategies for expressing human antibody repertoires in transgenic mice', Immunology Today, vol. 17, No. 8, pp. 391-397, 1996.

Bruggemann, Marianne, Human Antibody Expression in Transgenic Mice, Archivum Immunologiac et Therapiac Expermentalis, 2001, pp. 203-208, PL ISSN 0004-069X.

Brummell, D.A. et al., "Probing the Combining site of an anti-carbohydrate antibody by saturation-mutagenesis: role of the heavy-chain CDR3 residues," Biochemistry, vol. 32, pp. 1180-1187 (1993).

Burks, E. et al., 'In vitro scanning saturation mutagenesis of an antibody binding pocket,' PNAS, vol. 94, pp. 412-417 (1997).

Cai, Xiaohong et al., A melanoma-specific VH antibdy cloned from a fusion phage library of a vaccinated melanoma patient, Proceedings of the National Academy of Science, Jun. 1996, pp. 6280-6285, vol. 93, Medical Sciences.

Cai, Xiaohong et al., Comparison of fusion phage libraries displaying VH or single-chain Fv antibody fragments derived from the antibody repertoire of a vaccinated melanoma patient as a source of melanoma-specific targeting molecules, Proceedings of the National Academy of Sciences, Aug. 1997, Immunology, pp. 9261-9266, vol. 94, The National Academy of Sciences 0027-8424/97/949261-6.

Carter, B., et al., 'Bispecific human IgG by design,' Journal of Immunological Methods, vol. 248, Nos. 1-2, pp. 7-15, 2001.

Clark, Dr. Michael Ronald FSB, Curriculum Vitae, Nov. 18, 2014, pp. 1-21.

Clark, Mike, Statement, May 18, 2015, pp. 1-9, Document ID No. 5556275-1-BFLECK.

Colbere-Garapin, F., et al., 'A new dominant hybrid selective marker for higher eukaryotic cells', J. Mol. Biol., vol. 150, pp. 1-14, 1981.

Colman, P.M. et al., "Effects of amino acid sequence changes on antibody-antigen interactions," Research in Immunol., vol. 145, pp. 33-36 (1994).

Corcoran, Anne, Curriculum Vitae, pp. 1-3.

Corcoran, Anne, Statement, May 15, 2015, pp. 1-10.

Corcos, Daniel, Curriculum Vitae, pp. 1-5.

Corcos, Daniel, In the Matter of European Patent No. EP 1776383 and the opposition thereto by Crescendo Biologies Limited, May 20, 2015, pp. 1-13.

Coronella, J. A. et al., Amplification of IgG VH and VL (Fab) from single human plasma cells and B cells, Nucleic Acids Research, 2000, pp. 1-7, vol. 28, No. 20 e85, Oxford University Press.

Crescendo Biologics, "Crescendo Biologies Announces the Crescendo Mouse," 2013, retrieved from the Internet, URL: http://www.crescendobiologics.com/dev/uploads/Downloads/160113 Crescendo Mouse Press Release, pdf, retrieved on Jul. 30, 2014.

Crotty, S., et al., 'Cutting Edge: Long-Term B Cell Memory in Humans after Smallpox Vaccination', J. Immunology, vol. 171, pp. 4969-4973, 2003.

(56) References Cited

OTHER PUBLICATIONS

Damak, S., et al., 'Improved Wool Production in Transgenic Sheep Expressing Insulin-like Growth Factor 1', Bio/technology, vol. 14, pp. 185-188, 1996.
Davies, J., 'Single antibody domains as small recognition units: design and in vitro antigen selection of camelized, human VH domains with improved protein stability', Protein Engineering, vol. 9, No. 6, pp. 531-537, 1996.
Davies, Julian et al., 'Camelising' human antibody fragments: NMR studies on VH domains, FEBS Letters, 1994, pp. 285-290, vol. 339, FEBS 13683, Elsevier, Federation of European Biochemical Societies.
Davies Julian et al., Antibody VH Domains as Small Recognition Units, BioTechnology, May 13, 1995, vol. 13, pp. 475-479, Nature Publishing Group.
De Bruijn, Marella, et al., "Distinct mouse bone marrow macrophage precursors identified by differential expression of ER-MP12 and ER-MP20 antigens," Eur. J. Immunol., 1994, vol. 24, pp. 2279-2284.
De Genst, et al., 'Strong in Vivo Maturation Compensates for Structurally Restricted H3 Loops in Antibody Repertoires', J. Biol. Chem., vol. 280, No. 14, pp. 14114-14121, 2005.
Decanniere, Klaas et al., A single-domain antibody fragment in complex with Rnase A: non-canonical loop structures and nanomolar affinity using two CDR loops, Structure, Apr. 1999, pp. 361-370, vol. 7, No. 4, Elsevier Science Ltd. ISSN 0969-2126.
Decision of Grant by Russian Patent Office dated May 21, 2014, regarding Russian Patent Application No. 2011/142759, filed on Mar. 19, 2010.
Dekker, et al., 'Intracellularly Expressed Single-Domain Antibody against p15 Matrix Protein Prevents the Production of Porcine Retroviruses', J Virol., vol. 77, No. 22, pp. 12132-12139, 2003.
Denham, S., et al., 'Monoclonal antibodies putatively identifying porcine B cells', Veterinary Immunology and Immunopathology, vol. 60, Nos. 3-4, pp. 317-328, 1998.
Desmyter, A., et al., 'Crystal structure of a camel single-domain V.sub.H antibody fragment in complex with lysozyme', Nature Structural Biology, vol. 3, No. 9, pp. 803-811, 1996.
Dolk, E., et al., 'Isolation of Llama Antibody Fragments for Prevention of Dandruff by Phage Display in Shampoo', Applied Environmental Microbiology, vol. 71, No. 1, pp. 442-450, 2005.
Dumoulin, M., et al., Single-domain antibody fragments with high conformational stability:, Protein Science, vol. 11, No. 3, pp. 500-515, 2002.
Echelard, Y., 'Year of the ox', Nature Biotechnology, vol. 27, No. 2, pp. 146-147, 2009.
Ehlich, Andreas et al., Immunoglobulin Heavy and Light Chain Genes Rearrange Independently at Early Stages of B Cell Development, Cell, Mar. 12, 1993, pp. 695-704, vol. 72, Cell Press.
Ellyard, J.I., et al., 'Antigen-selected, immunoglobulin-secreting cells persist in human spleen and bone marrow', Blood, vol. 103, No. 10, pp. 3805-3812, 2004.
EP Communication dated Feb. 27, 2014 regarding European Patent Application No. 10179784.3.
Ewert, S., et al., 'Biophysical Properties of Camelid VHH Domains Compared to Those of Human VH3 Domains', Biochemistry, vol. 41, No. 11, pp. 3628-3636, 2002.
Fahrner, R.L., et al., Industrial purification of pharmaceutical anitbodies: development, operation, and validation of chromatography processes:, Biotechnol. Gen. Eng. Rev., vol. 18, pp. 301-327, 2001.
Ferguson, P.J., et al., 'Antigen-Based Heteropolymers', Arthritis and Rheumatism, vol. 38, pp. 190-200, 1995.
Galler, Gunther R. et al., Surface u Heavy Chain Signals Down-Regulation of the V (D)J-Recombinase Machinery in the Absence of Surrogate Light Chain Components, The Journal of Experimental Medicine, Jun. 7, 2004, pp. 1523-1532, vol. 199, No. 11, The Rockefeller Univerity Press.
Geraldes, P., et al., 'Ig heavy chain promotes mature B cell survival in the absence of light chain', Journal of Immunology, vol. 179, No. 3, pp. 1659-1668, 2007.
Geraldes, P. et al., "Immunoglobulin heavy chain and the life of memory B cells," FASEB Journal, vol. 19, No. 4, Suppl. S. Part 1., pp. A21-A22, 2005.
Ghahroudi, M. Arbabi et al., Selection and identification of single domain antibody fragments from camel heavy-chain antibodies, FEBS Letters, FEBS 19210, 1997, pp. 521-526, vol. 414, Federation of European Biochemical Societies.
Glennie, M.J., et al., 'Renaissance of cancer therapeutic antibodies', Drug Discovery Today, vol. 8, pp. 503-510, 2003.
Green, L. L. et al., Antigen-specific human monoclonal antibodies from mice engineered with human Ig heavy and light chain YACs, Nature Genetics, May 1994, pp. 13-21, vol. 7, Nature Publishing Group.
Green, Larry L., Antibody engineering via genetic engineering of the mouse: XenoMouse strains are a vehicle for the facile generation of therapeutic human monoclonal antibodies, Journal of Immunological Methods, 1999, pp. 11-23, vol. 231, Elsevier Science B.V.
Hamers-Casterman, C., et al., 'Naturally occurring antibodies devoid of light chains', Nature, vol. 363, No. 6428, pp. 446-448, 1993.
Hammer, R.E., et al., 'Spontaneous Inflammatory Disease in Transgenic Rats Expressing HLA-B27 and Human Beta2m: an Animal Model of HLA-B27-Associated Human Disorders', Cell, vol. 63, pp. 1099-1112, 1990.
Harmsen, Michiel M. et al., Llama heavy-chain V regions consist of at least four distinct subfamilies revealing novel sequence features, Molecular Immunology, 2000, pp. 579-590, vol. 37, Pergamon, Elsevier.
Hartman, S.C., et al., 'Two dominant-acting selectable markers for gene transfer studies in mammalian cells', Proc. Natl. Acad. Sci. USA, vol. 85, No. 21, pp. 8047-8051, 1988.
Hasan, Milena et al., Incomplete block of B cell development and immunoglobulin production in mice carrying the uMT mutation on the BALB/c background, European Journal of Immunology, 2002, pp. 2463-3471, vol. 32, Wiley-Vch Verlag GmbH & Co., Weinheim.
Heinrich, G., et al., Characterization of a human T cell specific chimeric antibody (CD7) with human constant and mouse variable regions, J. Immunol.,, vol. 143, No. 11, pp. 3589-3597, 1989.
Hendershot, Linda et al., Assembly and Secretion of Heavy Chains that Do Not Associate Posttranslationally with Immunoglobulin Heavy Chain-binding Protein, The Journal of Cell Biology, Mar. 1987, pp. 761-767, vol. 104, The Rockefeller University Press.
Holliger, P., et al., 'Diabodies': Small bivalent and bispecific antibody fragments', Proc. Natl. Acad. Sci. USA, vol. 90, pp. 6444-6448, Jul. 1993.
Holt, L.J. et al., "Domain Antibodies: Proteins for Therapy," Trends in Biotechnology, vol. 21, No. 11, pp. 484-490, 2003.
Hudson, P.J., 'Recombinant antibody constructs in cancer therapy', Curr. Opin. Immunol., vol. 11, pp. 548-557, 1999.
Imam, A.M.A. et al., 'Modification of human p-globin locus PAC clones by homologous recombination in *Escherichia coli*,' Nucleic Acids Research, vol. 18, No. 12, pp. e65 i-vi, 2000.
Inquiry by Japanese Patent Office dated Jun. 24, 2014, regarding Russian Patent Application No. 2011/166561, filed on Jul. 29, 2011.
International Search Report and Written Opinion dated Jul. 15, 2014 for International Application No. PCT/IB2014/059824.
International Search Report based on International Application No. PCT/GB2010/000500 dated Dec. 21, 2010.
International Search Report based on PCT/GB2005/002892 dated Apr. 7, 2006.
Ja'Kemp, Third Party Observation Filed with the European Patent Office, Jul. 1, 2015, pp. 1-7.
Ja'Kemp, Third Party Observations, The European Patent Office, Munich, Germany, Jul. 1, 2015, pp. 1-5.
Janeway, C.A. et al., 'The Development of B Lymphocytes,' Immunobiology, 3rd Edition, Garland Publishing Inc., pp. 5:1-5:33 and 8:1-8:17, 1997.
Janeway-Travers, Immunobiology The Immune System in Health and Disease, 1st Edition, 1994, 11 pp., (selected excerpts).
Jang, Y.J. et al., 'The structural basis for DNA binding by an anti-DNA autoantibody,' Molec. Immunol., vol. 35, pp. 1207-1217 (1997).

(56) References Cited

OTHER PUBLICATIONS

Janssens, R., et al., 'Generation of heavy-chain-only antibodies in mice', Proc. Natl. Acad. Sci. USA, vol. 103, No. 41, pp. 15130-15135, 2006.
Japanese Patent Office Inquiry dispatched on Mar. 11, 2014.
Japanese Patent Office Inquiry dispatched on Mar. 11, 2014. English translation.
Jaton, J.C., et al., 'Recovery of Antibody Activity upon Reoxidation of Completely Reduced Polyalanyl Heavy Chain and Its Fd Fragment Derived from Anti-2,4-dinitrophenyl Antibody', Biochemistry, vol. 7, No. 12, pp. 4185-4195, Dec. 1968.
Jendreyko, N. et al., 'Intradiabodies, Bispecific, Tetravalent Antibodies for the Simultaneous Functional Knockout of Two Cell Surface Receptors,' J. Biol. Chem., vol. 278, pp. 47812-47819 (2003).
Jespers, et al., 'Crystal structure of HEL4, a soluble, refoldable human V(H) single domain with a germ-line scaffold', J. Mol. Biol., vol. 337, No. 4, pp. 893-903, 2004.
Kandavelou, K., et al., 'Targeted manipulation of mammalian genomes using designed zinc finger nucleases', Biochem. Biophys. Res. Commun., vol. 388, No. 1, pp. 56-61, 2009.
Kellerman, S., 'Antibody discovery: the use of transgenic mice to generate human monoclonal antibodies for therapeutics', Current Opinion in Biotechnology, vol. 13, pp. 593-597, 2002.
Kim, C.W., et al., 'Members of the syndecan family of heparan sulfate proteoglycans are expressed in distinct cell-, tissue-, and development-specific patterns', Mol. Biol. Cell., vol. 5, No. 7, pp. 797-805, 1994.
Kitamura, Daisuke et al., A B cell-deficient mouse by targeted disruption of the membrane exon of the immunoglobulin u chain gene, Nature, Apr. 4, 1991, pp. 423-426, vol. 350, Nature Publishing Group.
Kitamura, Daisuke et al., Targeted disruption of u chain membrane exon causes loss of heavy-chain allelic exclusion, Nature, Mar. 12, 1992, pp. 154-156, vol. 356, Nature Publishing Group.
Klein, U., et al., Human immunoglobulin (Ig)M+IgD+ peripheral blood B-cells expressing the CD27 cell surface antigen carry somatically mutated variable region genes: CD27 as a general markerfor somatically mutated (memory) B Cells, J. Exp. Med., vol. 188, No. 9, pp. 1679-1689, 1998.
Kobayashi, H. et al., 'Tryptophan H33 plays an important role in pyrimidine (6-4) pyrimidine photoproduct binding by a high-affinity antibody,' Protein Engineering, vol. 12, pp. 879-844 (1999).
Kobayashi et al. (Protein Engineering 12:879-844 (1999)).
Kokubu, F., et al., 'Diverse Organization of Immunoglobulin VH-Gene Loci in a Primitive Vertebrate', EMBO J., vol. 7, No. 11, pp. 3413-3422, 1988.
Kriangkum, J. et al., 'Bispecific and bifunctional single chain recombinant antibodies,' Biomolecular Engineering, vol. 18, pp. 31-40 (2001).
Kumar, Ramest, "Recombinant Hemoglobins as Blood Substitutes: A Biotechnology Perspective" P.S.E.B.M. 1995, vol. 208, pp. 150-158.
Kumar, S. et al., 'Molecular Cloning and Expression of the Fabs of Human Autoantibodies in *Escherichia coli*,' J. Biol. Chem., vol. 275, pp. 35139-35136 (2000).
Kuroiwa, Y., et al., 'Cloned transchromosomic calves producing human immunoglobulin', Nature Biotechnology, vol. 20, No. 9, pp. 889-894, 2002.
Laventie, BJ "Heavy chain-only antibodies and tetravalent bispecific antibody neutralizing *Staphyloccus aureus* leukotoxins," Sep. 27, 2011, vol. 108, No. 39, pp. 16404-16409.
Leenan, P.J., et al., "Heterogeneity of Mouse Spleen Dendritic Cells: In Vivo Phagocytic Activity, Expression of Macrophage Markers, and Subpopulation Turnover", The Journal of Immunology, vol. 160, pp. 2166-2173, 1998.
Lefranc et al., 'IMGT, the international ImMunoGeneTics database,' Nucleic Acids Research, vol. 27, No. 1, pp. 209-212(1999).
Leher, et al., Monoclonal IgA antibodies protect against Acanthamoeba keratitis, Exp. Eye. Res., vol. 69, No. 1, pp. 75-84, 1999.
Lonberg, N., 'Human antibodies from transgenic animals', Nature Biotechnology, vol. 23, No. 9, pp. 1117-1125, 2005.
Lonberg, Nils et al., Antigen-specific human antibodies from mice comprising four distinct genetic modifications, Nature, Apr. 28, 1994, pp. 856-859, vol. 368. Nature Publishing Group.
Lu, D., et al., 'Di-Diabody: A Novel Tetravalent Bispecific Antibody Molecule by Design', J. Immunol. Methods, vol. 279, Nos. 1-2, pp. 219-232, 2003.
Lyden, D., et al., 'Impaired recruitment of bone-marrow-derived endothelial and hematopoietic precursor cells blocks tumor angiogenesis and growth', Nat. Med., vol. 7, No. 11, pp. 1194-1201, 2001.
Macpherson, Andrew J. et al., BLySsful interactions between DCs and B cells, Nature Immunology, Sep. 2002, pp. 798-800, vol. 3, No. 9, Nature Publishing Group.
Marian, A.J., et al., 'A transgenic rabbit model for human hypertrophic cardiomyopathy', The Journal of Clinical Investigation, vol. 104, No. 12, pp. 1683-1692, 1999.
Maruyama, M., et al., 'Memory B-cell persistence is independent of persisting immunizing antigen', Nature, vol. 407, No. 6804, pp. 636-642, 2000.
Meijer, P.J., et al., 'Human Antibody Repertoires', Therapeutic Antibodies: Methods and Protocols, vol. 525, pp. 261-277, 2009.
Mills, et al., Enhancer Complexes Located Downstream of Both Human Immunoglobulin Ca Genes, The Journal of Experimental Medicine, vol. 186, No. 6, pp. 845-858, 1997.
Morrison, S.L., et al., 'Chimeric human antibody molecules: Mouse antigen-binding domains with human constant region domains', Proc. Natl. Acad. Sci. USA, vol. 81, pp. 6851-6855, Nov. 1984.
Muller, K.M., et al., 'The first constant domain (C(H)1 and C(L)) of an antibody used as heterodimerization domain for bispecific miniantibodies', FEBS Letters, vol. 422, Issue 2, pp. 259-264, 1998.
Mullins, JH.J., et al., 'Fulminant hypertension in transgenic rats harbouring the mouse Ren-2 gene', Letters to Nature, vol. 344, pp. 541-544, 1990.
Muyldermans, S., 'Single domain camel antibodies: current status', Molecular Biotechnology, vol. 74, pp. 277-302, 2001.
Muyldermans, S., et al., 'Sequence and structure of VHdomain from naturally occurring camel heavy chain immunoglobulins lacking light chains', Protein Engineering , vol. 7, No. 9, pp. 1129-1135, 1994.
Muyldermans, Serge et al., Unique single-domain antigen binding fragments derived from naturally occurring camel heavy-chain antibodies, Journal of Molecular Recognition, 1999, pp. 131-140, vol. 12, John Wiley & Sons, Ltd.
Naessens, J., 'Surface Ig on B lymphocytes from cattle and sheep', Int. Immunol., vol. 9, No. 3, pp. 349-354, 1997.
Neuberger, M.S., et al., 'A hapten-specific chimaeric IgE antibody with Human physiological effector function', Nature, vol. 314, No. 6008, pp. 268-270, 1985.
Neuberger, M.S., et al., 'Construction of novel antibodies by use of DNA transfection: design of plasmid vectors', Phil. Trans. R. Soc. Lond., vol. 317, No. 1540, pp. 425-432, 1986.
Nguyen, V.K., et al., 'Heavy-chain only antibodies derived from dromedary are secreted and displayed by mouse B cells', Immunology, vol. 109, No. 1, pp. 93-101, 2003.
Nicholson, I.C., et al., 'Antibody Repertoires of Four- and Five-Feature Translocus Mice Carrying Human Immunoglobulin Heavy Chain and {kappa} and {lambda} Light Chain Yeast Artificial Chromosomes,' The Journal of Immunology 163 (12), pp. 6898-6906 (Dec. 15, 1999), The William and Wilkins Co, Baltimore, MD.
Notice of Opposition to a European Patent, European Patent Office, Aug. 20, 2014, Patent No. EP1776383, Title of Invention: Binding Molecules, Proprietor of Patent, Erasmus University Medical Center, Opponent: Ablynx NV, pp. 1-24.
Notice of Opposition to a European Patent, European Patent Office, Aug. 20, 2014, Patent No. EP1776383, Title of Invention: Binding Molecules, Proprietor of Patent, Erasmus University Medical Center, Opponent: Crescendo Biologies Limited, pp. 1-56.
Notice of Opposition to a European Patent, European Patent Office, Aug. 20, 2014, Patent No. EP1776383, Title of Invention: Binding Molecules, Proprietor of Patent, Erasmus University Medical Center, Opponent: Regeneron Pharmaceuticals, Inc., pp. 1-28.

(56) References Cited

OTHER PUBLICATIONS

O'Donnell, J.K., et al., 'Production of human hemoglobin in transgenic swine: an approach to a blood substitute,' vol. 17, No. 2, pp. 307-312, 1993.
O'Neill, T.P., 'HLA-B27 transgenic rats: animal model of human HLA-B27-associated disorders,' Toxicologic Pathology, vol. 25, No. 4, pp. 407-408, 1997.
O'Neill, T.P., "Apoliproprotein E-Deficient Mouse Model of Human Atherosclerosis," Toxicology Pathology, vol. 25, No. 1, 1997, pp. 20-21.
Orinska, Zane et al., Novel B cell population producing functional IgG in the absence of membrane IgM expression, European Journal of Immunology, 2002, pp. 3472-3480, vol. 32, Wiley-VCH Verlag GmbH & Co., KGaA, Weinheim.
Pharma Focus Asia, 'VelocImmune—A novel platform,' 2009, retrieved from the Internet, URL: http://www. pharmafocusasia. com/clinical_trials/human_antibody_discovery.htm, retrieved on Jul. 30, 2014.
Radbruch, A., et al., 'Competence and competition: the challenge of becoming a long-lived plasma cell', Nature Reviews Immunology, vol. 6, No. 10, pp. 741-750, 2006.
Reiter, Y. et al., "An Antibody Single-domain Phage Display Library of a Native Heavy Chain Variable Region: Isolation of Functional Single-domain VH Molecules with a Unique Interface," J. Mol. Biol., vol. 290, pp. 685-698 (1999).
Related U.S. Appl. No. 13/815,812, filed Mar. 15, 2013.
Related U.S. Appl. No. 11/658,361, filed Oct. 10, 2008, now abandoned.
Related U.S. Appl. No. 12/645,653, filed Dec. 23, 2009.
Related U.S. Appl. No. 12/645,684, filed Dec. 23, 2009.
Related U.S. Appl. No. 13/259,472, filed Feb. 22, 2012.
Related U.S. Appl. No. 13/837,402, filed Mar. 15, 2013.
Related U.S. Appl. No. 13/837,520, filed Mar. 15, 2013.
Remy, et al., 'Zinc-finger nucleases: a powerful tool for genetic engineering of animals', Transgenic Res., vol. 19, No. 3, pp. 363-371, 2010, (Sep. 26, 2009 [Epub ahead of print]).
Riechmann, L., 'Rearrangement of the Former VL Interface in the Solution Structure of a Camelised, Single Antibody VH Domain', J. Mol. Biol., vol. 259, No. 5, pp. 957-969, 1996.
Riechmann, L., et al., 'Single domain antibodies: comparison of camel VH and camelised human VH domains', J. Immunol. Methods, vol. 231, Nos. 1-2, pp. 25-38, 1999.
Riechmann, Lutz, Declaration, In the Matter of European Patent No. EP 1776383 and the opposition thereto by Crescendo Biologies Limited, May 5, 2015, pp. 1-36.
Riechmann, Lutz.Curriculum Vitae, pp. 1-4.
Rosenberg, A.S., 'Effects of protein aggregates: an immunologic perspective', The AAPS Journal, vol. 8, No. 3, Article 59, pp. E501-E507, 2006.
Sakurai, K., et al., 'Efficient integration of transgenes into a defined locus in human embryonic stem cells', Nucleic Acids Res., vol. 38, No. 7, e96., [Epub Jan. 13, 2010].
Sanderson, R.D., et al., 'B lymphocytes express and lose syndecan at specific stages of differentiation', Cell Regulation, vol. 1, No. 1, pp. 27-35, 1989.
Santerre, R.F., et al., 'Expression of Prokaryotic Genes for Hygromycin B and G418 Resistance as Dominant-Selection Markers in Mouse L Cells', Gene, vol. 30, Nos. 1-3, pp. 147-156, 1984.
Scheid, J.F. et al., "Broad Diversity of Neutralizing Antibodies Isolated from Memory B Cells in HIV-infected Individuals," Nature, vol. 458, No. 7238, pp. 636-640, 2009.
Scheid et al., Nature. Apr. 2, 2009;458(7238):636-40. doi: 10.1038/nature07930. Epub Mar. 15, 2009.
Segal, D.M., et al., 'Introduction: Bispecific Antibodies,' J. Immunol. Methods, vol. 248, pp. 1-6, 2001.
Sehgal, D., et al., 'Distinct clonal Ig diversification patterns in young appendix compared to antigen-specific clones', J. Immunol., vol. 168, No. 11, pp. 5424-5433, 2002.
Singh, N., et al., 'Biallelic germline transcription at the kappa immunoglobulin locus', J Exp. Med., vol. 197, No. 6, pp. 743-750, 2003.
Sitia, R., et al., 'Developmental regulation of IgM secretion: The role of the carboxy-terminal cysteine,' Cell, vol. 60, No. 5, pp. 781-790, 1990.
Slieker, WA. et al., "ER-MP12 antigen, a new cell surface marker on mouse bone marrow cells with thymus-repopulating ability: I. Intrathymic repopulating ability of ET-MP12-positive bone marrow cells," Int. Immunol., Sep. 1993, vol. 5, No. 9, pp. 1093-1098.
Slifka, M.K., et al., 'Humoral immunity due to long-lived plasma cells', Immunity, vol. 8, No. 3, pp. 363-372, 1998.
Smith, B., et al., Prolonged in Vivo Residence Times of antibody Fragments Associated with Albumin:, Bioconjugate Chem., vol. 12, pp. 750-756, 2001.
Smith-Gill, S. et al., 'Contributions of Immunoglobulin Heavy and Light Chains to Antibody Specificity for Lysozyme and Two Haptens,' J. Immunol., vol. 139, pp. 4135-4144 (1987).
Song, M.K. et al., 'Light Chain of Natural Antibody Plays a Dominant Role in Protein Antigen Binding,' Biochem. Biophys. Res. Comm., vol. 268, pp. 390-394 (2000).
Southern, EM., "Detection of specific sequences among DNA fragments separated by gel electrophoresis," J. Mol. Biol., Nov. 5, 1975, 98(3), pp. 503-517.
Stanfield, et al., 'Crystal Structure of a Shark Single-Domain Antibody V Region in Complex with Lysozyme', Science, vol. 305, No. 5691, pp. 1770-1773, 2004.
Sun, L.K., et al., 'Chimeric antibody with human constant regions and mouse variable regions directed against carcinoma-associated antigen 17-1A', Proc. Natl. Acad. Sci. USA, vol. 84, (No. 1), pp. 214-218, Jan. 1987.
Sung, C, et al., 'An IFN-Beta-Albumin Fusion Protein That Displays Improved Pharmacokinetic and Pharmacodynamic Properties in Nonhuman Primates', J. Interferon Cytokine Res., vol. 23, No. 1, pp. 25-36, 2003.
Suresh, M.R., et al., 'Advantages of bispecific hybridomas in one-step immunocytochemistry and immunoassays,' PNAS, vol. 83, No. 20, pp. 7989-7993, 1986.
Tacken, P.J., et al., 'Effective Targeting of Pathogens to Neutrophils via Chimeric Surfactant Protein D/Anti-CD89 Protein', The Journal of Immunology, vol. 172, No. 8, pp. 4934-4940, Apr. 15, 2004.
Tanaka, Tomoyuki et al., Single Domain Intracellular Antibodies: A Minimal Fragment for Direct In Vivo Selection of Antigen-specific Intrabodies, Journal of Molecular Biology, 2003, pp. 1109-1120, vol. 331, Elsevier Ltd.
Tangye, S.G.,, and Tarlington, D.M., 'Memory B cells: effectors of long-lived immune responses', Eur. J. Immunol., vol. 39, No. 8, pp. 2065-2075, 2009.
Tanha, et al., Selection by phage display of llama conventional VH fragments with heavy chain antibody VHH properties, Recombinant Technology, Journal of Immunological Methods, 2002, pp. 97-109, vol. 263, Published by Elsevier Science B.V.
Tanha, J., et al., 'Optimal Design Features of Camelized Human Single-domain Antibody Libraries', The Journal of Biological Chemistry, vol. 276, No. 27, pp. 24774-24780, Jul. 6, 2001.
To, R., et al., 'Isolation of Monomeric Human VHS by a Phage Selection', The Journal of Biological Chemistry, vol. 280, No. 50, pp. 41395-41403, 2005.
Van Dijk and Van Der Winkel, 'Human antibodies as next generation therapeutics', Curr. Opin. Chem. Biol., vol. 5, No. 4, pp. 368-374, 2001.
Van Spriel, A.B., et al, 'Effective Phagocytosis and Killing of Candida albicans via Targeting FcyRI (CD64) or FcaRI (CD89) on Neutrophils', Journal if Infectious Diseases, vol. 179, No. 3, pp. 661-669, 1999.
Van Spriel, et al., 'Immunotherapeutic perspective for bispecific antibodies', Immunology Today, vol. 21, No. 8, pp. 391-397, 2000.
Vara, et al., 'Expression in Mammalian Cells of a Gene from Streptomyces alboniger Conferring Puromycin Resistance', Nucleic Acids Research, vol. 14, No. 11, pp. 4617-4624, 1986.
Vranken, W., et al., 'Solution structure of a llama single-domain antibody with hydrophobic residues typical of the VH/VL interface,' Biochemistry, vol. 41, pp. 8570-8579, 2002.

(56) References Cited

OTHER PUBLICATIONS

Vu, Khoa Bang et al., Comparison of Llama VH Sequences From Conventional and Heavy Chain Antibodies, Molecular Immunology, 1997, pp. 1121-1131, vol. 34, No. 16-17, Elsevier Sciences, Ltd., Pergamon PII: S0161-5890 (97)00146-6, Great Britain.

Wang, B., et al., 'Transgenic goats produced by DNA pronuclear microinjection of in vitro derived zygotes,' Molecular Reproduction and Development, vol. 63, pp. 437-443, 2002.

Ward, et al., 'Binding activities of a repertoire of single immunoglobulin variable domains secreted from *Escherichia coli*', Nature, vol. 341, pp. 544-546, 1989.

Watson et al., Recombinant DNA, 2nd edition, Scientifican American Books, 1992, chapter 14 "The Introduction of Foreign Genes into Mice" pp. 255-272.

Wols, Heather A. Minges, Plasma Cells, Encyclopedia of Life Sciences, 2005, pp. 1-8, John Wiley & Sons, Ltd., USA.

Worn, A., and Pluckthun, A., 'Different equilibrium stability behavior of ScFv fragments: identification, classification, and improvement by protein engineering', Biochemistry, vol. 38, No. 27, pp. 8739-8750, 1999.

Wrammert, J. et al., "Rapid Cloning of High-Affinity Human Monoclonal Antibodies Against Influenza Virus," Nature, vol. 453, No. 7195, pp. 667-672, 2008.

Wright, G., et al., 'High level expression of active human alpha-1-antitrypsin in the milk of transgenic sheep,' Bio/technology, vol. 9, pp. 830-834, 1991.

Wu, Tai Te et al., Length Distribution of CDRH3 in Antibodies, Proteins: Structure, Function, and Genetics, 1993, pp. 1-7, vol. 16.Wiley-Liss, Inc.

Xu, J.L., and Davis, M.M., 'Diversity in the CDR3 region of V(H) is sufficient for most antibody specificities', Immunity, vol. 13, pp. 37-45, 2000.

Yau, et al., 'Affinity maturation of a V(H)H by mutational hotspot randomization', J. Imunol. Methods, vol. 297, Nos. 1-2, pp. 213-224, 2005.

Zou, X., et al., 'Heavy chain-only antibodies are spontaneously produced in light chain-deficient mice', J. Exp. Med., vol. 204, No. 13, pp. 3271-3283, 2007.

Zou, X., et al., "Expression of a Dromedary Heavy Chain-Only Antibody and B Cell Development in the Mouse," J. Immunology, vol. 175, pp. 3769-3779, 2005.

Zou, X. et al., "Dominant Expression of a 1.3 Mb Human IgK Locus Replacing Mouse Light Chain Production," The FASEB J., vol. 10, No. 10, pp. 1227-1232, 1996.

Navas, Patrick A., et al., "Developmental Specificity of the Interaction between the Locus Control Region and Embryonic or Fetal Globin Genes in Transgenic Mice with an HS3 Core Deletion," Molecular and Cellular Biology, Jul. 1998, vol. 18, No. 7, pp. 4188-4196.

Lu et al., "Tailoring in Vitro Selection for a Picomolar Affinity Human Antibody Directed against Vascular Endothelial Growth Factor Receptor 2 for Enhanced Neutralizing Activity", J. Biol. Chem. Oct. 31, 2003; 278(44): 43496-507. Epub Aug. 12, 2003.

Skottrup et al., "Diagnostic evaluation of a nanobody with picomolar affinity toward the protease RgpB from Porphyromonas gingivalis", Anal. Biochem. Aug. 15, 2011; 415(2): 158-167.

Janeway et al., Immunobiology, 3rd edition, 1997, Garland Press, pp. 3:1-3:11.

Rudikoff et al., Proc Natl Acad Sci USA. Mar. 1982; 79(6): 1979-83.

Ghahroudi et al., FEBS Letters, 1997, 414:521-526.

Flajnik et al. A case of convergence: Why did a simple alternative to canonical antibodies arise in sharks and camels. PLoS Biology 9(8): e1001120, 2011.†

Smolarek et al. Variable fragments of heavy chain antibodies (VHHs): a new magic bullet molecule of medicine? Postepy Hig Med Dosw 66: 348-358, 2012.†

Lefranc, Marie-Paule, and Gérard Lefranc. Immunoglobulin Facts Book. London: Academic Press, 2001. Print. (pp. 3-44, 97-428).†

Murphy, A. 2009. VelocImmune: Immunoglobulin Variable Region Humanized Mice. In M. Little (ed.), Recombinant Antibodies for Immunotherapy (pp. 100-107). New York, NY: Cambridge University Press.†

* cited by examiner
† cited by third party

Fig. 3

STARTVHLOCUSSEQUENCEATCCCTAGCTGAAGCTTCTGATGGAATTAGAACTTGGCAAAACAATACTGAGAATGA
AGTGTATGTGGAACAGAGGCTGCTGATCTCGTTCTTCAGGCTATGAAACTGACACATTTGGAAACCACAGTACTTAG
AACCACAAAGTGGGAATCAAGAGAAAAACAATGATCCCACGAGAGATCTATAGATCTATAGATCATGAGTGGGAGGA
ATGAGCTGGCCCTTAATTTGGTTTTGCTTGTTTAAATTATGATATCCAACTATGAAACATTATCATAAAGCAATAGT
AAAGAGCCTTCAGTAAAGAGCAGGCATTTATCTAATCCCACCCCACCCCCACCCCCGTAGCTCCAATCCTTCCATTC
AAAATGTAGGTACTCTGTTCTCACCCTTCTTAACAAAGTATGACAGGAAAAACTTCCATTTTAGTGGACATCTTTAT
TGTTTAATAGATCATCAATTTCTCGATTTCTCGACTATTCCTTTGCCCTCGGACGAGTGCTGGGGCGTCGGTTTCCA
CTATCGGCCAGTACTTCTACACAGCCATCGGTCCAGACGGCCGCGCTTCTGCGGGCGATTTGTGTACGCCCGACAGT
CCCGGCTCCGGATCGGACGATTGCGTCGCATCGACCCTGCGCCCAAGCTGCATCATCGAAATTGCCGTCAACCAAGC
TCTGATAGAGTTGGTCAAGACCAATGCGGAGCATATACGCCCGGAGCCGCGGCGATCCTGCAAGCTCCGGATGCCTC
CGCTCGAAGTAGCGCGTCTGCTGCTCCATACAAGCCAACCACGGCCTCCAGAAGAAGATGTTGGCGACCTCGTATTG
GGAATCCCCGAACATCGCCTCGCTCCAGTCAATGACCGCTGTTATGCGGCCATTGTCCGTCAGGACATTGTTGGAGC
CGAAATCCGCGTGCACGAGGTGCCGGACTTCGGGGCAGTCCTCGGCCCAAAGCATCAGCTCATCGAGAGCCTGCGCG
ACGGACGCACTGACGGTGTCGTCCATCACAGTTTGCCAGTGATACACATGGGGATCAGCAATCGCGCATATGAAATC
ACGCCATGTAGTGTATTGACCGATTCCTTGCGGTCCGAATGGGCCGAACCCGCTCGTCTGGCTAAGATCGGCCGCAG
CGATCGCATCCATGGCCTCCGCGACCGGCTGCAGAACAGCGGGCAGTTCGGTTTCAGGCAGGTCTTGCAACGTGACA
CCCTGTGCACGGCGGGAGATGCAATAGGTCAGGCTCTCGCTGAATTCCCCAATGTCAAGCACTTCCGGAATCGGGAG
CGCGGCCGATGCAAAGTGCCGATAAACATAACGATCTTTGTAGAAACCATCGGCGCAGCTATTTACCCGCAGGACAT
ATCCACGCCCTCNTACATCGAAGCTGAAAGCACGAGATTCTTCGCCCTCCGAGAGCTGCATCAGGTCGGAGACGCTG
TCGAACTTTTCGATCAGAAACTTCTCGACAGACGTCGCGGTGAGTTCAGGCTTTTTCATGGTGGCGGCTGGATCGGT
CGGTCGAAAGGCCCGGAGATGAGGAAGAGGAGAACAGCGCGGCAGACGTGCGCTTTTGAAGCGTGCAGAATGCCGGG
CCTCCGGAGGACCTTCGGGCGCCCGCCCCGCCCCTGAGCCCGCCCCTGAGCCCGCCCCCGGACCCACCCCTTCCCAG
CCTCTGAGCCCAGAAAGCGAAGGAGCAAAGCTGCTATTGGCCGCTGCCCCAAAGGCCTACCCGCTTCCATTGCTCAG
CGGTGCTGTCCATCTGCACGAGACTAGTGAGACGTGCTACTTCCATTTGTCACGTCCTGCACGACGCGAGCTGCGGG
GCGGGGGGGAACTTCCTGACTAGGGGAGGAGTAGAAGGTGGCGCGAAGGGGCCACCAAAGAACGGAGCCGGTTGGCG
CCTACCGGTGGATGTGGAATGTGTGCGAGGCCAGAGGCCACTTGTGTAGCGCCAAGTGCCCAGCGGGGCTGCTAAAG
CGCATGCTCCAGACTGCCTTGGGAAAAGCGCCTCCCCTACCCGGTAGAATTCATCGCTCGAGCAATTGGCTAGATAA
CTTCGTATAATGTATGCTATACGAAGTTATCTAGCTCTAGA
hygro
GTCTTGTTACACTTCATCAAGAATTAACCTCTGCTGTTTCCTCAAAGTGTTTAATTGGATAATGAATTTGTCTATAA
ATTGAAGAGTTGAAATACATCAAATATTAATTTGTAATAATCTGGCACAAATTATCTAAGCAAATTCAATAACTAGA
TGTTTTTTCATTTATTTTTATTTAAAATCAGGATCTAAGCACTGACATGCTTTAATAACATCTGTGACCCTCTCAGC
AGTTTTCTCTTCTGAGTATATGATCTGCTGTGGCAGTTTTCTTAGCTTCAATGTTACCTCTTTTGGCAATGACTACC
GTCTTTATATTTGCCAGGAATCTGGGATAAGGGAGTGCTTCTAAGAGTTCCCTAACTTGCCCATTTTGGTGGGTGTT
CCAGAACATATGAGATGCTCTGTTGTTAACAAAGCATCCCAAAGCCATGCACTGCCCTAAAATGTGTTTGTTTCCTA
GTTTGACAAATTGGAAGTTCTAATAAATACAATCACTTCTGCCATCTGGGCTGATTTTACATCAGATAGAGGGCTGT
ATTCCAAAGAAAAGCTTACATTAGTAATAGCAATTCTAGTCAGAAACCTAGAGTTTTATCATTGAGGTGCAATTCAT
AACAAATAATATTAGGTCGAGGTTCTCAGTGGCAGTGTCTAAATCTCTTAGGTGTACAGGGTCTTCCCTGTTAACAT
GAAGCATTTATAAGCACAGTCATAGTTTCCAGCTATGCTTCTCCCTGTCTCATTATCACCACAAACTATGGCCTCAC
CTGGAACTTGGGTTAATTTCCAAATAAGTAATTTTTAGTGTTTATGCCTCTAGATTATTATGTGAGAAAGTTAACA
TTCAGTAGAAAGTTAAAAAGAACATTTGAACTGACTAAACAACACAGACAATCAAGAATAAAATTCAAAGCCTAGAT
GTGAGAGGCTCCAGGCCTGGATAATGCAATAGTTCATGTATGCAGGCAGTTTCTTTGCCCAGTTCTACACTGATACA
CCCAGAATGTCAGCTTCATGCCAGATTTGACTCCTATTATGTAGAGACATGGCAATACATTCTCAAGGGTCACATGA
AATAATATGAAAATTGGTGGGAATAGGGGAGGAGACAACTCTGCAATTCTCATCTGAAGGACCAGGAAAGCCTGGAC
AGACCATCTCCCCAGCCTCCGTGACTGCACCACGTGCCCACATGGACGCTCATCCCTGATAGGGTAAGAAGACTCCA
TTGATGGGGCTGAGCATTTTATGATAGAAATTACTAGAGACTGACGTGGAGGTTTCAACAACTAATATTTATAACCA
AAATTTAATTACCCCCACATTGTTACCATTTTCTTCAGTGAAAAATTGCTTGCCATGATTAAGTTTTAAGTAGATTT
CCAATGTTCACAACTGAGCTTCCAAGAGAGTCTTGAGAACAAAAACAATGAGGGCAGAGAAATCTACCTTTTCTGCA
TTCACCACTAAACTCAAGTGGACTCAGCACTGCCTTTGATCACTGCTACTTCTCTGCAGAGTTCAGGTTTCTACTTC
TCACAATTCTGACACACATTCTACCTCTCCTCAGATGTTTGGCCTCTGCTTCTTGTAAGGTCACCCTCTGTTCTTAA
CTTCTTCTCTGAGTCATTTTGTGAGGTGGTCATGAGCCATTAAATGGATATTTTATATTTTCCCAACATGAATCACA
TGAGTGGTCATGAATTATACTTCTGATTATGGCAGTTGATTTTTCTTGGCATGTTCATGACTAGTAATATTTGAAGC
CATTTCATTCAAATCTTCGGGGCTTCGTTTTTGTTGCTATGACATTTTTTCTTCTATTGAGTCTTTCCACTAGTATT
ATAACATGACCTAGTATCCAGGCTCAGTTGTCATTAATAATAACCACATATGTCAAAAATCATGCATTCTTTTCACA

Fig. 3 (cont.)

GCAGACATAATTTCCTCTTTTCTGCAGATGAAGACACACTGCTGAGCTACCCCCACTTACAAGAATATATGCACAAT
TATGATATCTTCATTTATTTGACTAATAAGCTATATCATTCTCCCTTCAAATTCTTTACCCCCCAGAAGTCCTGGAC
AAATTTCTGCATCTGCTCAAACGATAAACTCAGAACTACATGGTGAGTAAAAGTCACCTGGTTCTGGATATTGGGTC
CATCTCTTCCCCTCCAATGTCCCAGAGCACCTCAGCACACCCGTCCAGGTTCTATCAAGAAAGAGTAGCTCCTGCAC
ACTGAAGGAAACAATTGAGTTAAGAGAGGACCTGCAGATGATAGACAATATTGAAAACTGTTAATATGACAAAGGAT
TACTACCAAGCATGTGAAATAAGCTCAACGGGTGCGGTGGTTCATGTCTGTAGTACCAGCAATTTGGGAGGCAAGTT
GCGCAGATCACCTGAGGTTAGGAGCTCGACACCAGCCTGACCAACATAAAGAACACCCTGTCTCTACTAAAAGTACA
AAATTAGCCGGGCATGGTGGCATGCGCCTGTAATCCCAGCTACTCGGGAGGCTGAGGCAGGAGCATCACTTGAACCT
GGGAAGTGGAGGTTGCGGTGAGCTGAGATGGCACCATTGCACTCCAGCCTGGGCAACAAGAGGGAAACTCCATCTCA
AAAAAAAAATTACAAAAAATTAGCTGAGCGTGGTGGTGGGCGCCTGTATACCCAGCTGCTAGGGAGACTGAGGCAGG
AGAATGGCTTGAACCCAGGAGGTGAAGGTTGCAGTGAGCTGAGATTGCGCCATTGCACTCCATCCTGGGCAACAAGA
GTGAAACTCCATCTCAAAAAAAAAAAAAAGAGACTTGCAAAGGGCAAATAGATCATAGACAGACAGATAGATAGATAG
ACCTATTAGTATACATACATACATATATATACACTAATATTCAGGAAAATGCAAATTCATAATGAGATGTCTTTTCA
CCCTTCATCTCTGCTAGAAAGTTTGTTATCTGAAAAACAAATACATACATACATACTTATTAAAAGCTGGCCAGGAT
GCCTAGAAAGTAAAACTCATAGACCACTGGTGGAAATGTAAATTAGTGCAGCCATCAAGGGAAAAAAATAGAACTAC
CATATATTCCAGCAATCCAACTGCTAAGTATATATCTATTTAAATATTTAAAAGAAAAAACTAATATTGAAGAGATA
CCTGTACACCCATGTTTATTGCAGCACTAATCACAATTTCTAGGATATGAAATCAACATATGTGTCCATCAACAGAT
GAATGGATACATAAAATGTGATATATTTACACAATGGAATATTATTCAGCCTTAACAATGAAATTCTGCCGTTTGAA
GCAACATGGATGGAATGGGACACCTCTATGTTGAGTGAAATGAGTCAGACACAGAAAAATAAATACCGCATTTCTCA
GCGTTACTTCTAGAAGTAAATAGTAGAGTAGTGGTGATGAGATGCCAGGAATGAGAGAAGGCTGAGATAAGAAGAGG
TTTGTTAACAAACACACAATTACAGGTAGACAGGAGGGATGTGCTCTAGTGTTCTACAGCACAGTAGGGTGACTACA
GTTAACAATATATTGTACGTTTTCTGTTTACAAGAAGCCAGAAGAGAGAATTTTCTATGCTACCAACACAAATAAAT
GTTAGTGTCTGAACTGACGAATTTGCTCATTGTTCTGATTTTAGTCATACCAAGTGGCACACATGTATTCAAATATC
ACACTGTACCCCATAAACATAAGCAGTTATTATGTGCCAAATTTGAAAAATCCTTTAATTAGAAGGAATTATATTGG
CGTACATTACAAATGATTCAACACAGAGACAGGAATAAATACCATTTTTCTTTGAAATAGTTAATTAACTAACAATG
TAGTTACATTCATTTGCACCAAATCGTGTATTTGATAATGGTATGCATAGACAGATTTATGCATAGGATAATATCTT
TTAATTTTAGACTACTACTTAATACTATAAATATAAATAATTTTAAAACAACTAAGTAAAAAGAATAAAGCTGAGAA
AATGTGTGTGTGGTGTGTGATGTGTGAGCTTTTTCTTGTGCACCACTGTGTCCTTGGTGGATGTGTGGTTCATGTGT
TTGTTTTTATTTACTCTGTTTGGGGTTCTCTTTGCTTCTAGGATCTGTAGTTCAGTTTCTTTCACAAAATTGGGAAC
ATTCTTCGCTATTATCTTTTTCAAATAGTTTCTGTGTATTTATAATTTCTCCTTCTCAGATTTAAAATATACACATA
CTATAATTTTGATATTAATGTTTAGTTTCTTTCTTCACTCTCTTTTCGTTTGCAATTTACTTTGTGAAATTTCTAAT
GACATACTAATCACATGGTTTTATTGAAAAGCTGAGCCAGCTCTACTGAGGTGTGTGCCAAAAGATTGCTCGATGTT
TATACAGCATTGCTTTTGATTTCTTATGCATTTCCATTTGATTTATTCTTAGTATTTTCATATTTCAGTTCCCTATC
TATGTCCACGATTTCTTTAAGAGATTCTTGCGTGTGAATTATAGTTACTTTACATATCTTGTTTAATTAGATATTTA
TAACATCTGTTTCATCTACAAATCTCATGCTGATCATTTGTTTATTACAACTTTGGTACTTCTCATTAATGTATGTA
ATAATTGTTGATAGCCACAGATACTGGGATGGACAGTGGATACTGGCCTTATTATTTCATTTTATGCATTTCTGCCT
GTATTTGACCACACTTTACCTTTGCCAGGCCTTTACTGTGGAAGTATCTGTGAATCTTCTCAGAACTATATTTGACA
TTCACTTTTGCAGTGGACATCAAAGTTGAAGTCTGTTCTTCTGTGTCCACCAGAGACTTCAGTTCCTCCAGTGATAC
CTTGTTTTTCTTTCCTGCTTGGCTTTGTCTCTTCACCTGTTCCCTCCTCCAGAGAATCATGTTCAGCTCCCTCAGGT
GGATTAAAATGTTATCTAACTGACAATTGTGAAATTGGTGGAAAGCAATAGAATAAAGGGAGATTTTCTGACCTTTC
TTGGGTTCATATTGTGAACATGAGTCTGGGTGTGACCTTCCCAATGTTTCTGAACTTCCTCCAGATGAGATGTTGGT
CTGTGTGTTCTTGCTCTTTTCCCTGCTGTGGAGTCCTCTTGTTTCCCCCAGTTGTTCCCTCCCGCAGCTCCAATGTT
CTCTTTTTGTGTTATCACCTTACAGATTTGCTGACTAGAACTGCAGATTAGGGCTCTGATTAAATAAGAAGGAGGGG
AGATACTTCTCAATGGAACTTAGGTGAAGACCTCTTTTCCCATCTCAGTTCTTAAGGGATTGCCCCAGTGNNNNNNN
ACTGGTTTTGGTGGCTTGCCCCTCCAAAAAATTTCTTTGTTCTCCAGTGGGGATATGGAAGGTGGGTCTGAACACTT
TTCAGAAGGGTGGGCACTTTTTCTCTCCTAGACAGACACAATGGGACAGAACAATTTTGGTGACTGTCCCCATTTTG
GGGAAAAAGGATTCAATAGGATAGGAAAACTCTTCAGTCTGTGGTCCCTTAGAAATTCACCCTACAACACATTTACC
ACACTTGACTTCAAGAAATCCAATATATATGTGTGTTTTCATCTTGTAATAGCCTACATTTTACATGCCATACTCTG
CCTCAGTTCAGCTCATACCCCAGCTTTGTTACTCTTTACAAGAACTTGCCTCTCCCTAGATTTCACATTTGCTGTTT
ATCTTAAAACTTCAAGTATCTAAAGTATTATTTTTAAAAAATGGCCAGTTGTGGTGGCTCACACCTGTAATCCCAAC
GCTTTGGGAGGCTGAGGTATGTGGATCACCTGAGGTCAGGAGTTTGAGACCACCCTGGCCAACATGGTAAAACCTGT
CTCTACTAAAAATACAAAAAAAAAAAAAATAGCTTGGCATGGTGGCAGGCACCTGTAATCCCAGCTACTCGGGAGGCT
GATACTGGAGAATAGCTTGAACCCACGAGGCAGAGTTTGCAAGTCGTACCATTGCACTCCAGCCTGGGCGACAGAGT

Fig. 3 (cont.)

GAGACTCTGTCTCAAAAAAAAAAAATTCCAAAATTCCAGCTCCTCTGTTTATCTATTTTTGTTGATACTGTTGTTGTA
AAACATAAGTAAAATATATTATTCATCTATGTACATTTCCAAGCTGTGTAGAAGAATTTTTAATAAGACCCAGAGTA
AAAAAAGAATGCAAATATGTAGGGGCCAGCCCTACAGGGTCTGTGGATCTTTCTCCCCATGTGCAGAGATGAGAGAT
CATAGAAATAAAGGCACAAGACAAAGAGATAGAAGAAAAAACAGCCGGGCCCAGGGGACCACTACCACCAAGACACA
GACTAGAAGTGGCCCCAAATGCCTGGCTCTGCTGTTATTTATTGGATACAAGGCAAAAGGGGAAGGGTAAGGAGTGT
GAGTCATCTGCAATGATTGATAAGGTCATGTGTGTCACGTGTCCGCCAGACAGAGGGCACTTCCCTGTTTGGCAGCC
GAGGCGGAGAGAGAGAGAGGACAGCTTAGGTCATTATTTCTTCCATTCTCTTCTCAGAAAGATCAAAGACTTTAATA
CTTTCACTAATTCTGCTACTGCTATCTAGAGGGCGGAGCAAGTGTACAGAGTGGAACATGAGAGTGAAACAGGAGTG
TGACCGCTGAAGCACAGCATCACAGAGAGACGTTTAGGCCTCTGGAGGGCTGCGGGCAGGTTTGACTGATGTCAGGC
CTTCCACAAGAGGTGGTGGAGCAGAGTCTTCTCTAACTCCCCCGGGGAAAGGGAGACTCCCTTTCCAGGTCTTCTAA
GTAATGGGTGCCTTCCCAGGCACTGGCGCTACCGCTAGACTGAGGAGCCCTCTAGTGGCCCTGTCCGGGCGTGACAG
AGGCTCACACTCCTGTCTTCTGGTCACTTCTCACCGTGTCCCTTCAGCTCCTATTGCTGTATGGCCTGGTTTTTCCT
AGGTTATAATTGTAGAGCAAGGATTGTTATAATGTTGGAATAAAGAGTAATGCTACAGACTGATGATTAATGATATT
CATATATAAACATATCTATAACCTATTACTAGTACAACTATTCTTATTTTACATATTCTCTTCATTACACTGGAACA
GCTTGTGCCCTCAGTCTCTTGCCTCAGCACCTGGGTGGCTTGCCGCCCAGACAAATATTGTTAAGCTTCTTAATAGA
AAAACAAATTATGGTAAATGTGTTCACTGGAATACTACCCGTCATTTATAATAAATTAATGCCTGATACACAGAGCA
ACAAGGTAAAATATCTAAGTATTTATGTTGAGTAAAATAAGCTAAACAAATAAGAATATATACTATGTAATTTCATT
TTTATAAATTCTGATAAATAAAAATGCATCTGAAGTAAAATAATGAAGATAAGTAGTTGCCTGGGGAAATGGTAGAA
GAAGGGAGGGGGAGAGGAGGAGGAATACAGCAGAACAAAGGGAAAATGTTGAGAAGAATTCACTTGTCCACTTTCTT
GATAATGATAGCAGTTACATCATTTTTATTAGTTGTACATTTTAAATATGTGAAGTTTATCATCTTTCAATTAAGCC
TCATAAAATGTCTTACAAGCAAACAAATGGAAACTTAGACAAGGAAAGAGTAATAGAAAGATAGAAAAAATAAGTTC
AATGTCAGAAGTACCTGAAAATTAATGTGCCTGGATCCTAGTTCTCTCCATATTTTCAGAAGAGTGCTGGAGGGCAG
CAAAACCACACATGCTCTTATTACGCAAAGTGGGTTCTGATAAAAACACTAGACACATCCAGCTTTGTCCTGGAGTT
GGTTTAGGGGGATGTCAGAGACAGTGATGAAGAGCACAGGGCCAGATACCGGGGTTCACTCATCCCAGACATGAGCT
CCTAGATGCATACAGAGCCCCCCCATGTGTGGGTTTACTTCCACTTCTGTAAATGGAGAAAATATTGTCTCCTACAG
AACATAGTTTACATGAATACTTAAAATGAAATAGGGTGATTAGTGCAAAGTGTTTATCACAGCACAATTTCATAATA
AGACAGCATATTTTCCAAATGCAATCATTGCCAGCAAACTTCTACAGGGCACCGTCGTCTTATCTGGGTACAGCCTA
CTCCTCAAGGGTCCCACCCTAGAGCTTGCTATATAGTAGGAGATATGCAAATAGGGCCCTCCCTCTACTGATGAAAA
CCAACCCAACCCTGACCCTGCAGCTCTCAGAGAGGTGCCTTAGCCCTGGATTCCAAGGCATTTCCACTTGGTGATCA
GCACTGAACACAGAGGACTCACC[redacted]
CACAGTGAGGGGAGGTCAGTGTGAGCCCAGACACAAACCTCCCTGCAGGGGTCCGCAGGA
VH 3-48
CCACCAGGGGGCGACAGGACACTGAGCACGGGGCTGTCTCCAGGGCAGGTGCAGGTGCTGCTGAGGGCTGGCTTCCT
GTCATGGCCTGGGGCGGCCTCATTGTCAAGTTTCCCCAGGGAACTTCTCCAGATTTACAATCCTGTACTAATATTTG
ATGTCTCTAAATGCAACCTTTTTTTTCCTTTTTGTGTCTGTTTTTTTTTTTTTAAAAACAGGAGGACACATCCTCAC
CTCCACAGAAGCCACAGTGTCACTTTGGGGGCGGAAATAATCCTTTCGTGGTCAACAGGGTGAGAGTTTTGAGGAAT
CCCAGGGAAACCTGGGGAATGTTTTCCAATTAGACTCAGGGCAGAGACCTCCATGGGAATCCCTGATTAGAACAGGC
TTTGAGTTCTGATGGGAGCCAAAAGAGAGGCTCACCCAGGGTCAGGGTTCTTAAAACCTGATGGTTTTCACAGCAAT
CCCCCTTCATCTTGTGAAACTGGGCACATCTGACTCAGACTGATTCAGTTGACCCTCTTTCTGCTAATCCATTTTCC
TTCCCAGTAGACTTGATTCTCACAGATCCCTTTCTTCTTCTCTTTCCTGAAAACAGAGGATGTGTTTTCTGTAGTC[redacted]
CCTTGATTGAAGTGCTGAGTAAATGGTTGCAAACATAGGTCTACATTTTTCAAATCATTCACCATAAATTTG
AATTATTTATTAATTACACTCGAATAAAGCAATAAAGAAACTGATGAGATAATATTTGACTGAATTGCATCAATAAA
TAGATCGATATTAACACAAGGAATATAACTGATTTCCAAAAACATACACATGAACCGTGGTTCACTCTGCGTATTTA
GATAAATTACAGAAAGTTGTCATAACAGATGGGGAATCCTGCAGACTTCACTAGGCATGGGCCATGCTGCCCTGGAG
TTGTCTCAGGGGAGCTGCCTCCTCCAGAGGTTAGAGCACAGGCCCAGGTAATAGGACTAAATTTTTAGATGTGTTAT
CTTAGACACACTGCACAACTGCTGTGTTCTCTATGTAAATTATCTCCTGTAAAATATAACATTGAAGCCTGCATTAA
ATATATTGTGTAAATATGTAAGAATAAAAGAAAGTTATGAGAGCTAAGTGTTAATCAAGGCACAAGCATATAAGATA
TAACTATATTTTCCTGAATGATGGAATTACTACCAGTCTCCCCCAGGACACTTCATCTGCCCTGAGCCCAGCCTCTC

Fig. 3 (cont.)

CTCAGATGTCCCACCCAGAGCTTGCTATATAGTGGGGGACATGCAAATAGGGCCCTCCCTCTACTGATGAAAACCAG
CCCAGCCCTGACCCTGCAGCTCTGGGAGAGGAGCCCAGCACTAGAAGTCGGCGGTGTTTCCATTCGGTGATCAGCAC
TGAACACAGAGGACTCACC[redacted]GACACAGTGAGGGGAGGTCATTGTGCGCCCAGACACAAACCTCCCTGCAGGAACGCTGGGGGAAATC
VH 3-30
AGCTGCAGGGGGCGCTCAGGAGCCACTGATCAGAGTCAGCCCTGGAGGCAGGTGCAGATGGAGGCTGTTTCCTGTCA
GGATGTGGGACTTTGTCTTCTTCTGACAGTTCCCCAGGGAACCTCTTAAATTTAGAAAACTGTGCCTAACAATGTCT
TCTCTATGCATATGAGGACCTTTTCTCCCTGGCACAAAATGCAGATTGACGCTGACACGGATG[redacted]GCTGCTGA
CATTCCTAGATAACTGCAGCTGTAGTTATGCCTGCTAAGGTTTGGGCGCATGGGGCTTGGCTTTTGTCAGCTCCCTG
GGATTTATTTTCCCAAACAAAGAAACCTCCAGGTTAGGGGCACCCTATTCATTCCCATCACCTGGCATGATTTAAAG
GATAATTGCTTAGAATTAAAATATTGATCCAGATTTTTTATATTCCCCATCGCTTTTTGTTTCTTCTGGGCTGTAGC
CAGAGATCATTGATTGGCGCTCAGGAATAAGCAGAGTTAGTCTAAAATGCAGGCAAATACTTAAACAACTGAAGAGA
TTAGAATTTAAAGACAAGTGTATGATATGTTTTGAAATACAATGTTTCTCTTTCCAGTTTTGGTTTTTGTCAGCAGC
AAATAATGATAAGACTGAGTTGTTTGCAAAATAAACTTTAGTCTTAAACTTGGCCTGATTATTTGCATAAAGTGCAG
CAAGAATATTAATAATAATTCTGTAGGAAAAGCCTGCAAGCACCAGGAGCTTCACAGTCTAACACTATGAGCACGTG
CATCCTCACGCAACTCACTGAATATGTCCAAGTCAGCCTGTTCCGATCTTAAATGCCATCCAGTGGCATCTGCCCCA
GGTACACTAATACATGGGTCCTGCTTCTCTCTGCAGCCGCCTCTCTCCTCAGATTTCAGGTTTTGTGTATTGTTTGT
TTTCTCTCTGACATCAACACAGATATGTTGAAGGTTTTCTTTTTTTTATTTGTAGTTGTTCAGCTTTGTTGTTAATG
AGGTCAGAATAAGCTCATAGTTTACACATTTTTACATTCCCATGCCGAGTAGCTGCTTTTCTCTATCAAATCCATTA
ACTGAGAGAACAATCACATTTCGTTACAGGTGAACAGTTAAATAGTTTGGCATATATTTCTGTGCTGGAATCTAATG
CAGCTTGAAATCAAGTCATGCCTCACTCATTGAAAAAAACATGGCTAAATTCTCAAAGAATTGTGCTGAGTGAAAGA
AACTAAGGAATGAAGAGTAAATTTTATATGATACATTTGTAGAAATTTTAGAAGATGCCACTATTATAAATTAACAT
GGAGAAGATTTAAGTGTTTCTGAGAATATGCTATTGGGAGTAATGGGGATGTGAGTTAAATTTCAGAGGAATAAGAG
AAAGATTTAGGGATTAATTTTTTCAAACCTTGATTGAAGTGCTGAGTAAATGGTTGCAAACATAGGTCTACATTTTT
CAAATCATTCACCATAAATTTGAATTATTTATTAATTACACTCGAATAAAGCAATAAAGAAACTGATGAGATAATAT
TTGACTGAATTGCATCAATAAATAGATCGATATTAACACAAGGAATATAACTGATTTCCAAAAACATACACATGAAC
CGTGGTTCACTCTGCGTATTTAGATAAATTACAGAAAGTTGTCATAACAGATGGGGAATCCTGCAGACTTCACTAGG
CATGGGCCATGCTGCCCTGGAGTTGTCTCAGGGGAGCTGCCTCCTCCAGAGGTTAGAGCACAGGCCCAGGTAATAGG
ACTAAATTTTTAGATGTGTTATCTTAGACACACTGCACAACTGCTGTGTTCTCTATGTAAATTATCTCCTGTAAAAT
ATAACATTGAAGCCTGCATTAAATATATTGTGTAAATATGTAAGAATAAAAGAAAGTTATGAGAGCTAAGTGTTAAT
CAAGGCACAAGCATATAAGATATAACTATATTTTCCTGAATGATGGAATTACTACCAGTCTCCCCCAGGACACTTCA
TCTGCCCTGAGCCCAGCCTCTCCTCAGATGTCCCACCCAGAGCTTGCTATATAGTGGGGGACATGCAAATAGGGCCC
TCCCTCTACTGATGAAAACCAGCCCAGCCCTGACCCTGCAGCTCTGGGAGAGGAGCCCAGCACTAGAAGTCGGCGGT
GTTTCCATTCGGTGATCAGCACTGAACACAGAGGACTCACC[redacted]CACAGTGAGGGGAGGTCATTGTGCGCCCAGACACAAACCTCCCT
VH 3-33
GCAGGAACGCTGGGGGAAATCAGCTGCAGGGGGCGCTCAGGAGCCACTGATCAGAGTCAGCCCTGGAGGCAGGTGC
AGATGGAGGCTGTTTCCTGTCAGGATGTGGGACTTTGTCTTCTTCTGACAGTTCCCCAGGGAACCTCTTAAATTTAG
AAAACTGTGCCTAACAATGTCTTCTCTATGCATATGAGGACCTTTTCTCCCTGGCACAAAATGCAGATTGACGCTGA
CACGGATGAAAATTCCTCAACCATGGTCACAAGGATCAGAGTCCTGAGTAACCTCAGGGCTTCCTGGTGATTCTTCT
CCAATCAGACCCAGGACAGGGACCTCCGTGAGATTCCCTGACTGGAACAGTCTTTATGGATCCTGGTCACAGACAAT
AGAGAGGCTGAACCAGGGTCAGCGTCATGTAGAACGTCACAGATTTCACGTCTGATCCTTCTCCTGACACGAAAGTA
TGCAAATCAGTATCAGCACCGATCTG[redacted]GATGGAAAGATAGATACCAACATGAGAAATGTATGACACTCAAGA

Fig. 3 (cont.)

AAATAAAACTGTAGGAAACTTGCTTTTCTTTATATTTGTTAGGTAATCACCACAGTGTGTACACATCACACCATGTT
CCCATTACAGAGAAAAGGTTCTGCGAACCTCACGAGCTGTGACCCCTGTGTGCTGGGCTTGGTTCAGGGAGAAGTCA
GGTCCAGTGGTGAGAAGCACAGGCCCAGATGCCCAGGCTCACTCTGACCAAAAGTGAGCACTGGGGACATTGTAAAA
CCCACCTGTGCTTTTGCTGATAATTTTTCATCTTTAACATGGAAATAATATTGATACTATATACCATGGTTTCTCTG
CGTATGTAAAAATAAAAGATGATTGGTGCTAACTTTAAAAATATGCAGTTTATGTAGATCTATGGTACCTCAATAAA
ACTGTTTTAAAATAAAAATTACAAAATTATAAGATTTTTAGGTTTTAAGGTTTAAGTTTATCACAAAACAAACTGAC
AATAGGAAAGCACAATTTCCCAATGCTTTCAATATCACAGATCTCCCCGAGGACATTCTGACATGCTCTGAGCCCCA
CTATCTCCAAAGGCCTCTCACCCCAGAGCTTACTATATAGTAGGAGATATGCAAATAGAGCCCTCCGTCTGCTGATG
AAAACCAGCCCAGCCCTGACCCTGCAGCTCTGAGAGAGGAGCCCAGCCCTGGGATTTTCAGGTGTTTTCATTTGGTG
ATCAGGACTGAACAGAGAGAACTCACC[redacted]
CACAGTGAGGGGAAGTCATTGTGAGCCCAGACACAAACCTCCCTGCAGGAACGATG
VH 3-23
GGGGGGAAATCAGCGGCAGGGGGCGCTCAGGACCCGCTGATCAGAGTCATCCGCAGAGGCAGGTGCAGATGGAGGCT
GTTTCCTGTCAGGGTGTGGGACTTCATCTTCTTCTGACAGTTTCTCTAGTGAACCTCTCTAACCTCAGAATTCTGTG
CTTACTAATGTCATCTCTACGTATTTTTTAAAAGATCATTTTAATATGAGCACCTATTCTCACACGCACCAAATGCA
GATTGACGCTTACAGAGATG[redacted]GAGGAATGCTGAGGGGAGTTGACTTGTCACCTTCTTAAAAATAGAGATTTT
ATTTTTCAAAGTTTACTATTGTACAGAATAAATATGTGAATTTTCTTATCTGTCAATTAAACCTCATAAAATTTATT
ACAAAAAAACTGAAATTTTAGACAAAAAGAGGGTGATAGGAAGGAACAAATAAATATGTTAAATGTCAAATATACCT
AAAAATTTATTTGTCTGACCCCTAGTTTTCTCCGTATTTTTAGGTAAATGCAGCAAAATCACACAAGTTGTCGTGGC
AGGAAGTGGATTCTGCAAACCACACTAGGCCCGTTTATCTCTGTCCTAGAGTTGGTTAAAAGAGCAACTGAGGCCAG
CTGTGAGGAGCATAGGCCCGGGTACTAGGACTCACTCATGCCAGATATAAGCCCTTAGACACATACATAGCCCCTCC
ATGTGTGGGTTCACTTTTACATCTGTACATGAAGAAACCACTGATTCCTAAATAACATAATTTATACACATAGGTAA
AAATAATTAAAAATGTGATAGTTATTAAGTGTTTATCACACAACAATTTCACAATAAAACAGCATTTTCCCAAATGT
AATCATTGTCATCGAAATCCCCAAGGCACACTCTCATCTGCCCTGGGCCCTGCCCTCTCCTCAGGCATCTCACCCCAG
AGCTTGCTATATAGTAGGAGACATGCAAATAGGTCCCTCCCTCTCCTGATGAAAACCAGCCCAGCCCTGACTCCGCA
GCTCTGGGAGAGGAGCCCCCGCCCTGGGATTCCCAGGTGTTTTCATTTGGTGATCAGCACTGAACACAGAAGAGTC[redacted]
CACA
VH3-64
GTGAGGAGAAGTTAATGTGGGACCATGCAGAAACCTCCCTGCGGGAACGCTGGGGAAAGTCATCTGCAGGGGGCGCT
CAGGAGCCACTGATCAGAGTCAGCCCCAGCGGCAGGTGCAGATGAAGGCTGATTTCCTGTCACGATGTGGGACTTCA
TCTTCTTAAAGTTTCTCTACTGAACCTAAGTTCGGAATTCTGTGATTACTAGGGTCATTTCTA[redacted]GAAGTTGA
GGCAATTTCACTTGTCCACCTTCCTTATAATGGTAATAGTTATGCCATGATTATCAGTTTTACACTTTAAATATGTA
AAGTTTATAATCTGTCAATCAAATCTTATAAAATGTATTATGAGGAAACAAGTTGAAAATTAGACAATGTAGGAGTG
ACAGAAAGATAGATATGAGTATGTTGAATGTCAGAGATACCTGAAAGTTTATCTACCTGAACCCTAGTTCTCTCCAT
AGTTTAAGGTAAACAGGAGAGTGCAGGAAAATCATCCATATTCTGATTAGGCAGTGGCTTCTGCAAACCACACTAGG
CCTGGCCGGCTGTGTCCTGGAGTTGGCTAAGGGAGGAGTCAGGGCCAGTGGTGAGAAGTGCAGGCCCAGATACCAGA
ACTCACTCATCCCAGACATGAGCTCTTAGATACACAGAGAGCCCATCCATGTGTGGATTTATCTTACATCTGTAAGT
AGAGAACATTGACTCTTACAGAACATAATTTACACACATAGGTAAATCTGAAATAAGGTGATCAGTGTGAAGATTTT
ATCACAGCACAGTTTCATAATAAGCACAATTTCTCAAATCCCATTGTTGTCACCCATCTTCCTCAGGACACTTTCAT
CTGCCCTGGGTCCTGCTCTTTCTTCAGGTGTCTCACCCCAGAGCTTGATATATAGTAGGAGACATGCAAATAGGGCC
CTCACTCTGCTGAAGAAAACCAGCCCTGCAGCTCTGGGAGAGGAGCCCCAGCCCTGGGATTCCCAGCTGTTTCTGCT
TGCTGATCAGGACTGCACACAGAGAACTCACC[redacted]

Fig. 3 (cont.)

[illegible]CACAGTGAGGGGAAGTCAATGTGAGCCCAGACACAAACCTCGCTGCAGGGG
VH3-74
CATCTGAGACCACGAGGGGGTGTCCTGGGCCCTGTGAACTGGGCTGCTCTCCGTGGCAGCGGCTGGTGGTGCTAAAG
GCTGATTTTCTCTCAGCATCTGGGGCTGATTCATCAAGTTTCCTCAGAGACCTTTCAGATTACAATTCTGTACTTAC
GTTTAATGTCTCTGAATGTGACACTTTCCTTCCCTGGTGTGTCTTTGTTTTTGTGACAAGAGGACACATTCTCACCT
CCACAG[illegible]GAAGTGCCGAGTGAATGGCTGCAAACATAGCTCTACATTTTTCAAATCATTCCCTATAAATCTGA
ATTAATTATTTATTTATTATACTTGAATAAAGCAATAACGAAGAAATAAATGAATATTTTTGCTAAAATGGAGCAAT
AAAAAGACTGATATTGACAGAAGAAATATGACTGACTTCTGAAAACACACATGAACCATGGTTCTCTCTGCATATTT
AGGTGAATTACAGAAAGTTGTCATAACAGATGGGGAATCCTGCAGACTTCACTAGGCATGGTCCACGCTGCCCTGGA
GTTGTCTCAGGGGAGCTGCCTCCTCCGGTGATTAGAGCACAGGCCCAGATAATAGGATTACATTTTTTTAGATGTGT
AAACTTAGACGCACTGCACAGCTGCTGTATTCTCTATGTAAATTATCTTCTGTAAAATACAACATTAAAGGCTGCAT
TAAATATATTGTGTAAATATGTAAAAATAAAATCAGATTATGAGAGCTAAATGTTAATCAAGGCACAATCACATAAT
ATAAAATTATATTTTCCTGAATGATGGAATTACTACCAATCTCCCCCAGGAGACTTCATCTGCACTGGGCCCGGCCT
CTCCTCAGATGTCCCATCACAGAGCTTGCTATATAATGGGGGACATGCAAATAGGGCCCTCCCTCTGCTGATGAAAA
CCAGCCCAGCCCTGACCCTGCAGCTCTGGGAGAGGAGCCCAGCACTGGGATTCCGAGGTGTTTCCATTCAGTGATCT
GCACTGAACACAGAGGACTCGCC[illegible]CACAGTGAGGGGAGGCCATTGTGCGCCCAGACACAAACCTCCCTGCAGGAACGTTGGGGGAATCA
VH3-66
GCGGCAGGGGGCGCTCAGGAGCCACTGATCAGAGTCAGCCCCGGAGGCAGGTGCAGGTGGAGGCTGTTTCCTGTCAG
GATGTGGGACTTCATCTTCTTCCAACAGTTTCTCTAATGAACCTCTCTAATTTTAGAATTCTGTGGTTCCTAATGTC
ATCTCTAC[illegible]GTCGAGGATGCCGATGTGATTTAAGTTTCAGAGGAATAAGAAAAAAGATTTAGGGATTAATTT
AATTATTCAAAACTTGATTGAAGTGCCGAGTGAATGGCTCCAAACATAGTCTACATTTTTCAAATCATTCCCTATAA
ATTTGAATTAATTATTTATTTTTATACTTGAATAAAGCAATAACAAAGAAATAAATGAATATTTTTGCTAAAATGGA
GCAATAAAAAGACTGATATTGACAGAAGAAATATGACTGACTTCTGAAAATACACACACATGAGCCGTGGTTCTCTC
TACATATTTAGATAAATTACAGAAAGTTGTCATAACTGATGGGGAATCCTGCAGACTTCACTAGGCATAGTCCACAC
TGCCCTGGAGTTGTCTCAGGGGAGCTGCCTCCTCCAGTGGTTAGAGCACAGGCCCAGGTAATAGGACTCATTTTTTT
AGATGTGTAATTTTAGACACACTGCACAACTGCTGTGTTCTCTGTGCAAATTATCTCCTGTAAAATGTAACATTGAA
ACCTGCCTTAAATATATTGTGTAAATATGTAAAAATAAAATCAGATTGTGAGAGCTAAATGCTAATCAAGGCGCAAT
CACGTAATATACAATTATATTTTCCTGAATGATGGAATTAATACCAATCTCCCCCAGGACACTTCATCTGCACGGAG
CCCGGCCTCTCCTCAGATGTCCCACCCCAGAGCTTGCTATATAGTCGGGGACATCCAAATAGGGCCCTCCCTCTGCT
GATGAAAACCAGCCCAGCTGACCCTGCAGCTCTGGGAGAGGAGCCCAGCACTGGGATTCCGAGGTGTTTCCATTCGG
TGATCAGCACTGAACACAGAGGACTCACC[illegible]CACAGTGAGGGGAAGTCATTGTGCGCCCAGACACAAACCTCCCTGCAGGAACGCTGGGG
VH3-53
GGAAATCAGCGGCAGGGGGCGCTCAGGAGCCACTGATCAGAGTCAGCCCCGGAGGCAGGTGCAGATGGAGGCTGATT
TCCTGTCAGGATGTGGGACTTTGTCTTCTTCTGACGGTTCCCCAGGGAACCTCTCTAAGTTTAGCATTCTGTGCCTA
TGAACGTCTTCTCTAAGTATTTGAAAGAGATTATTTTAATATGAAGAGCAGTTCTCACTCGCC[illegible]GAGCATGT
GCACATTTCATTAAACCCACTGTGTATGCAGCCCCTCCCAAGTGCTGGCAGGCCACTGTACATGTGGGCAGCCCACT

Fig. 3 (cont.)

CCAAGGGAAGAATCAAGGGAGAAGAAATACAAACCCCAGAACCATGTCAATGTATAAAACCCCAAGTCAAGGGCCGG
ACAGAGCACTTAGATCTCTCAAGTCGCCCACTTAGCCCTCTTCCAAGTGTACTTTACTTCCTTTAGTTCCCACTTTA
AAACTTTAATAAACATTTACTCCTGCTCTAAAACTTGCTTGGGTCTCTCACTCTTCTGTATGCCCCTTGGCCAAATT
CTTTCCTCCAAGGAGGCGAGAATCAAGTTGCTGCAGACCTGTATGGATTCGCTCCTGCTAACAGATAGCTGGATGGG
TGGACAGATGCATGAATTAGTGGATGGACGTTTGGATGTGTGGGTGGGTGGGTGGATTGTGGGATGGCTGGATGAAT
GCATGGCTGGATGGGTGGACAGATGCATGAATTAGTGGATGGATGTTTGGATGTGTGAGTGGGTGGGTGGATTGTGG
GATGGCTGGATGAATGCATGGCTGGATGGGTGGACAGATGCATGAATTCGTGGATGGACGTTTGGATGTGTGGGTGG
GTGGGTGGATTGTGGGATGGCTGGATGAATGCATGGCTGGATGGGTGGACAGATGCATGAATTCGTGGATGGACGTT
TGGATGTGTGGGTGGGTGGGTGGATTGTGGGATGGCTGGATGAATGCATGGCTGGATGGGTGGACAGATGCATGAAT
TCGTGGATGGACGTTTGGATGTGTGGGTGGGTGGGTGGATTGTGGGATGGCTGGATGAATGCATGGCTGGGTGGGTG
GATGGATGCATGGATAAGTGGTGGACGGATGGACGGGTGAGTGGATGGGTGGATGTGTGTGTGGATGGGTGGATAGG
AAAGCCCTCTAATTGATTACAGGGCTCAGTGTGTGCTTCAACATCATGATGGCATCATCACATTGGTCCCTGTATGA
AGCAGTGGGGGAGGAGAGTGTACCAGGGGAGCAGGAATGACTCTTCTCCAGAATCGACCTCTCCCACCCTGCAGCCT
GGGCTGTGCAGGCCACATTGGAGAAGGTGCGGTCGACTACTCCTAAATGTTGTTGTGTCCAATGGCTTTTTGACGTT
GATGTAGGAATGAGCCTACATCTCCACCATAGATGGAACTGTTTGGGTCCCCAAAGCAGAAAGCCTCTTCTGTTGCA
GGTGCTGAAGTTTCCATCTTCTTCTGCTTATACGGAAGCTCACGCATCCCTTGGATGGCAGGCGTCAGGTTCCTGTG
CGCACTGAGTTCCCCCCTTACATGCTTTGGACAGAAGTGTGAGACACACAAGATTGCTGCAGGAAGTCCACCTGTGG
GGATGCTGCGACTTCTCCAGCAAGAACACGAGTCTGCTCATTGACCATCACCACACATAACAAATTAAGTGTCCCTT
TTTTGATAACACGTCATTGTTTCACAGAGTATTCTTTTAAAGTGTATAAGTTGACTGCAGTTATTATTTTTTACTTC
TGTTACTAATTTACTCATAATTAGGCACAATTTACACTTAAGAAATTTCTTAATAGTTTTTTCCTCCTTAAGGTGAA
CTACAGTCAGATAACATACTTATCAATTGTCTCTAGCTCTTGTCAGAAAAGCATATAGATGTGTGTGTGCGTGTGTC
TTGGCCTTTCCAATGATGAATTAAGATGTGCATTGAGAAGGCATTCACTTTATTTGACGTTAAGGAAGTACCAAGAA
GACGCTCTCCACAGACCCTGGGAAAGCCAGCAGCTGCACCCCGAGGCTGTGCCAGGCAGGGAACAAGGAGGCAGCAC
CACCTGCTGGGCAGGGAAAATGTCCTCCCAGTCCCTGCCGCTTCTCTGCAGAGGCACAAAGAGCTGCCCCTTCTCCT
GGGCCTTCTCCTGGGCTGATGAGATTGCTCCCCGATATGCCAAATCAGGGTTGTGCATCTGAGGCTCTGTCTAGACT
CTCAGCTCCTTCCTACTCCTGCAAAGTGAAGAAAACAATGCCAAGGGGTCCTGGAGGCGTCTCTACCCCTGGAGAGT
TTTGACTCTCTTCAATAGTCTCCACTACCCTGCCCTCACTCCATGTCCTCCGTTTCTCCCTAAAGCGGTGCCCAGTC
TGATTGCACTGTGGCAGGGATAACGAGGGGCCAGGACATCAGGGGAGAGAAGTTTCTACCTGAGTCACAGCAGCGGC
TGCCCTGCAGACTCCTGAAGACACAAGACACATTTCCATCCCAGAGACCCAGCGAAATGCAACCTCAGGCTAGAGAC
AGCCAGTTATTTTTTCTTGTTCTGTCCTGGAGAGGCCACTGAGAAAGTCGAGCCCCTTGTTGAGGAAAACATGAGAT
CTCTGTGTGTCGTCCTCTGCCTGATGGCTGTACCTCCATGTGAGTGTCTCAGAGATTTCAGAACGGGGGCTGTGGGC
TGTGGTGTCCGCTTGTGACTCATCTCTTTGCTTCTTGTCCCTGAGTGTCCTGCATCAGATGCAGCTACTGGAGTCAT
GCCCAGGGCTGGTGAGGTCCTCACAGACCTCTGGGCCTGGACCCAGCAGCCCTCTGGGAAGGCGCTGGGGCACCTCA
GCTCCAGGGGCAGCACACACTTCAGCCCAGCCTTTCTGGGCCAACTCTCCATCTGTAGAGACACATCCAAGGCCCAG
TTATCCCTGCAGCTGAGCTCCGTGATGGCCAAGGGCAGGGCCGCACATTCCCGTGGGAGACAGAATGGGGACCTCAG
CGTGAGCCCAGACACAAACCTCCCTGCAGGGAAGCACAAGACCACCAGGCGGCGCTCCAGACCACACAGCGGCCCCA
GAAGCAGGTTTTAGGGGGCGGGGCAGACGTGTCCGCGTTGAGTCAGGTCACTGGTTTTACTTTCCCTGAACAAACGG
CCTCTGCCAAGGACTCACTGCACCTCTCACCTTCACAGTTGTTTTTTTTTTTTTTTTAATCACCCTGTAGGGTTTTG
CTAGCTAATTTAGATATTGAGGAGTGCTTCATACTTCCTTGGGCCTCTGCTTGCAGAAACATAGCAATTGTAAGGAG
GCACGTGGGAAAGCCCCGGCTCGGTGACCCGGGGGATGCTGCTGTAGCCCTGGCAAGAGGGCGTCGGGCCGCAGTAA
CAAAGGTGCAGACGGCTCTCAGCCTGCGCCCGCGGAGTACAACACATAAGGGCTGTAACCTAACGAAAAAGAATCG
CAGTGCAACTGTCCTGCATTTGAGTTTGTGATCAGTTTTGCCCTTTGTCTTTAACAGGTTCTAACATAAAATTTTGA
ATGCTGGTTCAAGCCCTGTGGGTAAAATGCACTTACCCACATTCCTTAAACAAATAGAACACTGAGGTGGAAATGTT
TTGAAAAAGTAGTTTTCAGACATTTGGAAACAAGCATCACAGGATCATAACCCCTGAGAAAGAAAAACAAATGAAC
GAATCCTGCTATTGCCTGAAAGCAGCTGCCAGGACACACGGAAAGGCTTAGTGAGCTGAGCGGACAGAGAGCAGAGT
TCAAGGCAGCAGCAGCCCGAGGGGAGGAGCACCGGGGAGCAGGCTGCTGTGCAGCCAGGATGGGCCGGGGTGGGGCG
GGGGGAGAACAGCTGGAGACTTGCCGCAGGGAGGGGGATCCCTCAGGTTTGGGGCTGAGAACTGACTTATGCCTGAC
TTATGCCTGCATGAAAAGAAACTACTCGATATCAGGGGGAAATCACCAGAAACCTGTGGACCCAAAACTACACAGAG
CCTACACAAGGAAAGCATTGTTTGTGTTCTCCCAGCCAGGGTGGAAAGACCTTGAGATATGTAAAGCTTCAAGCAAT
CTTCCGAAGTAATCTCGTGAGTAGTGGTGCCACATTAATTCAGGACTAAAGACTGCTCTGAACTGAACCTAAGAAAT
GCTTCAAGTGTAGCCTGGAGCCCGGGTGCAGTGGCTCACACCTGTAATCCCAGCACTGTGGGAGGCCGAGGCAGGCG
GATCACTTGAGGTCAGGACTTTGAGACCAGCCTGGCCAACATGGCAAAACCTGTCTCTACTAAAAACACAAAAATTA
GCTGGGCATGGTGGCAGATGCCTGTAATCACCTCCCACCTGGACCCTTCCTTGATACATCAGAATTACAACTAGAGA

Fig. 3 (cont.)

```
TGAGATTGGGGTGGGGACACAGAGCCAGACCGTATCACATAGGAACCTAAAAGGATAATAAAGTAGGAAAACTTCCC
ACATCAGTAACCCTTTATCCGATAGTAATCCCAATCTGCAAAGTAAAACTGTGTGATTTTACTAAGATAACGGAATC
TTCTCTACAGAAGGACTTTCCAGTGCAAAAGCTCCCCACCCTCACCATGAAATGCACGTGACCATTTCCAATTTGTG
TAAAGTCCTCAGTTAGTACTGAGACTTCGGAAGGTTAGAAATCCCTTTGCTCATGCTGCATGGTCCGGATGAGATGT
AAGAATCATTAGCTAATAGACATGCAACAGCTTTTGTGCGAAAGATGTTATGAGACATTTAAGGTATTTGCTTGTGC
TTACTAAGCATTCATTGTATCATTGGAGCACATGTGCTTTTATACCCTGGAGAAATTCCAGTAATTGAATTGCTGGG
TTGAATGGGATTTTGATTTGGATTAAATTTAAACTATAGATTTTATTTAGGGAAAACTGGCATCTTAATTATGTTAT
TGGGGGGCCCTTGCTCCCAGAGCTCCCAAGATGGTGGCAGGCCGCTTCCAAAATGACCGCAGGCCACTTCCAAGATG
GTGGCAAGCCTCATGTTCTCTGACCTGGGGTTCTTGGCCTCACGGATTCCAAGGAATGGAAGCTTGGGCCATGCAGT
GAGTGTTATAGCTCTATTAGAAGCCGTGGGTCACGGAAGAGAACCGTGGAACCCAGTGACTAGTGTTCAGCTCGATT
AGGACGAACCCAGGCACTTAGCCGTGCAGGAACAATGGCGAGCATTTGGCCCGATCGAGAGTGGCAATGGGCGCCTC
GCCGGATCAGGAGCACAGCGGATACCCTGATGGATCCGGAGGGATGGAAGCCAGCGGTGGGTCTCCCACGGGGGCAA
ACAGCAGTGGTGGACGGTGAGCGAAAGCGAAGCTCGAGCCGTAACAAACATGGACCAGAAGAGTGCAGTTGCAAGAT
TTAGTAGAGTGAAGACAGAGCTCCCATACAAAGGGAGGGGACCCAAAGAGGGTAGCTGTTACCGGCTCGAATGCCTG
GGTTTATATCCCGATCATTGTCCCTCCCGCTGTGCTCTCAGGTGATAGATGATTGGCTATTTCTTTACCTCCTGCTT
TTGCCTAATTAGCATTTTAGTGAACTCTCTTTACTATCTGATTGGTCGGGTGTGAGCTGAGTTGCAAGCCCCGTGTT
TAAAGGTGGAAGTGGTCACCTTCCCAGCTGGGCTTAGGGATTCTTAGTCGGCCTAGGAAATCCAGCTAGTCCTGTCT
CTCAATTACACTGAGTTTTCCAATCCATGCATCCAATATGTGGTGTATCTCTTCATATGTTCATAGCCTCTGAGCAA
TGTTTTACAATTTTCTGTGTAAAGAACTCCACATCGTTTTATGTTTCTTCTAAGGTATATCCTGATTGCTTTTTATG
TCTTCACAAGTTTTTCCCTTTCAAAATTAATTTTCCAATTGTTTGGTGCTAATATGCTCAAATGTCCTTGATTTTCT
TAGTTTGAACAGTCCGTTTTCGTTTTGGGGATTTATTTTTTTTTCAGATTCTTTAAGATTTTCTATGTCTATAACCA
TATAATCTCTGAACAGAGACAGTTTTGCTTTTCCCTTTCAACTTGAGGTAGGTTTTCTGGGTAGTTCAGGACGCGCA
GGCACTGGGTGGGTGGTGTTAGCAGCTGCACGATGCCTTGGAGAGGACACTCTCGGGGGACTGTGGCCGCTGCTCAG
CTGTGACTGTTCTTATAGCACCAGCAGCTGCGGCCACCATTCTTATCCAATTTCCAAAGCCACACCACAGGCCCTCT
CAAGAACGAGGCGTGGAGGCTATGCCCTCTCCTGGACACATCATCATTCCCAAGCCCCACGATGTGGGCCCCATGGG
ACGCACACCTTTGTCTGTCCAGACCTCAGCCCCACCTCCTCATCCTGCACCAGAACTCTTCAGAGCCCAGTGCATGA
AATGGGCTACCAAGGAAATGAGGGTAGGTTCCTGAGAGGAAACTGGCCCTGCATTTGGGAGCTAAGAGTCTGCTAAT
TCGCCTGGCAGCCCTGTGCAGCCCTCCGTGGCTACAGTCCACCCCGTGCCCATCAGTGCCTCCTTCCTGTGCAAGCC
TGGACCTCGCCCTGGGCTCAGGATGGGCTGTAGACCGAGAATGCAGGCGGGAAAGTCGTTGTCTATCGGGGCCATAG
TCAGGTTCTACAGTGAGTCAGGGAAAGACCTGTGGAGGTGTGGATGAGGACAATGGGTCCACCATCAACAGGAGGAC
ACGGGTTCGACCCCTTGCAGAGGCACAGTCCCACATCACTGGGAGGCAGCCACACTCACTGCCTCGCCCTCTCCTCA
CACAGTGCAGTTTCCACGTTCACAGCCCCAGCCAGTCACCAGGAATGCCCTGGGGGCGGCCTTTCCCCAGTGCACCC
CGAGCCCTCCCTTGGCTGTGCGGTGAGCTCCATGCCCAGGAGATATCCACCCATAGTCCTCCGGAAAGCAGCTGACC
TGCCATGCCCTGGAACCACAAATCCCCACAGATCAGCCAGCCTGCAGTGGGCCTTGGATGTGGTGAGGAGTGGTGGC
ACCCCCGTTCCCACCCCACAGATGCAACGCCTGTGGGTGACGCATGTGAGTACTGAGGAGTAGAGGGTAGAACTGTA
GGCCCCGAGAACCACAGAAACTCGGGTGTTACACTCTGGGGCCATGTAAGGAGAAAGTGTCACTGGACAGAAACAGG
CCCCTCCTAGACACTGTGTGCGCCATAGTCACCTGTCATTAGCTCTCACTCTTGCAGATTCATGATTGAGGTGGTTA
AAAAAAAAAAAGCTCCTACTCACCCATCCAACCCCATCCTGGGGTGTTTCCACCACCCTTGGGGTTTGGGATGAGCT
GCCCTTGCCCACTGTGCTCTGTGGACCTCCCTTTAGAAGCTCACAGCTCCCTGCACTCGGCTCCATCCTGCCCCACC
ACACAGAAGCAAAACCCCTCTCCTTTCCACTGCAGGCTTTTCCTGGACCAGAATGCTGACCTGCTGCCCTTCACTCC
CGAAGTGGTGGGACTGCCTGGGGTGGTGTGGGTGTTGAGCCTTCTTACTCTAGGGACCTGGCACCTGGCCCCAGGGG
CACAGGGATGGTGCATCTGCCTAGGGATGCCTCCTCATGCCAGGGGGTGGGGGTTAGTACCATCGGCCCTCAGGATT
TGTTGCATGAATGAGTGAATGGGTGAATAAATGAAGGGGATCTGATCTATGAATAAGGGTATATGGACTTTGGTTGA
TGTAGGACGCCAAATGCTGGAATTTCGGAGTCATCACACCCAGGGGCCCTGCCTCTGAGCTCCTCTTTGCATCCAAT
CTGCTGAAGAACATGGCTCTAGGGAAACCCAGTTGTAGACCTGAGGGCCCCGGCTCTTCAATGAGCCATCTCCGTCC
CGGGGCCTTATATCAGCAAGTGACGCACACAGGCAAATGCCAGGGTGTGGTTTCCTGTTTAAATGTAGCCTCCCCCG
CTGCAGAGCTGCAGAGCCTGCTGAATTCTGGCTGACCAGGGCAGTCACCCGAGCTCCAGACA
```

Fig. 3 (cont.)

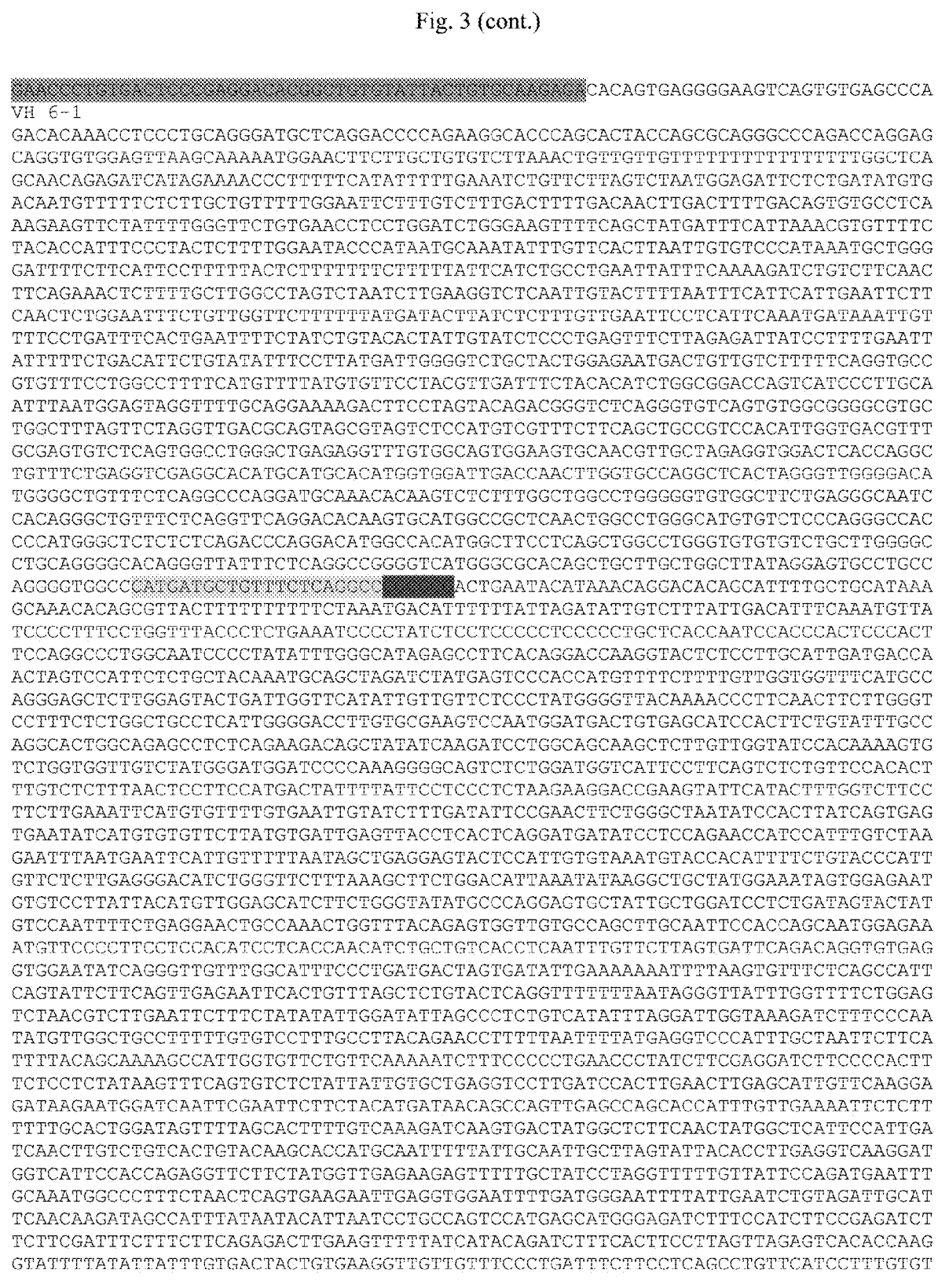

[illegible]CACAGTGAGGGGAAGTCAGTGTGAGCCCA
VH 6-1
GACACAAACCTCCCTGCAGGGATGCTCAGGACCCCAGAAGGCACCCAGCACTACCAGCGCAGGGCCCAGACCAGGAG
CAGGTGTGGAGTTAAGCAAAAATGGAACTTCTTGCTGTGTCTTAAACTGTTGTTGTTTTTTTTTTTTTTTTGGCTCA
GCAACAGAGATCATAGAAAACCCTTTTTCATATTTTTGAAATCTGTTCTTAGTCTAATGGAGATTCTCTGATATGTG
ACAATGTTTTTCTCTTGCTGTTTTTGGAATTCTTTGTCTTTGACTTTTGACAACTTGACTTTTGACAGTGTGCCTCA
AAGAAGTTCTATTTTGGGTTCTGTGAACCTCCTGGATCTGGGAAGTTTTCAGCTATGATTTCATTAAACGTGTTTTC
TACACCATTTCCCTACTCTTTTGGAATACCCATAATGCAAATATTTGTTCACTTAATTGTGTCCCATAAATGCTGGG
GATTTTCTTCATTCCTTTTTACTCTTTTTTTCTTTTTATTCATCTGCCTGAATTATTTCAAAAGATCTGTCTTCAAC
TTCAGAAACTCTTTTGCTTGGCCTAGTCTAATCTTGAAGGTCTCAATTGTACTTTTAATTTCATTCATTGAATTCTT
CAACTCTGGAATTTCTGTTGGTTCTTTTTTATGATACTTATCTCTTTGTTGAATTCCTCATTCAAATGATAAATTGT
TTTCCTGATTTCACTGAATTTTCTATCTGTACACTATTGTATCTCCCTGAGTTTCTTAGAGATTATCCTTTTGAATT
ATTTTTCTGACATTCTGTATATTTCCTTATGATTGGGGTCTGCTACTGGAGAATGACTGTTGTCTTTTTCAGGTGCC
GTGTTTCCTGGCCTTTTCATGTTTTATGTGTTCCTACGTTGATTTCTACACATCTGGCGGACCAGTCATCCCTTGCA
ATTTAATGGAGTAGGTTTTGCAGGAAAAGACTTCCTAGTACAGACGGGTCTCAGGGTGTCAGTGTGGCGGGGCGTGC
TGGCTTTAGTTCTAGGTTGACGCAGTAGCGTAGTCTCCATGTCGTTTCTTCAGCTGCCGTCCACATTGGTGACGTTT
GCGAGTGTCTCAGTGGCCTGGGCTGAGAGGTTTGTGGCAGTGGAAGTGCAACGTTGCTAGAGGTGGACTCACCAGGC
TGTTTCTGAGGTCGAGGCACATGCATGCACATGGTGGATTGACCAACTTGGTGCCAGGCTCACTAGGGTTGGGGACA
TGGGGCTGTTTCTCAGGCCCAGGATGCAAACACAAGTCTCTTTGGCTGGCCTGGGGGTGTGGCTTCTGAGGGCAATC
CACAGGGCTGTTTCTCAGGTTCAGGACACAAGTGCATGGCCGCTCAACTGGCCTGGGCATGTGTCTCCCAGGGCCAC
CCCATGGGCTCTCTCTCAGACCCAGGACATGGCCACATGGCTTCCTCAGCTGGCCTGGGTGTGTGTCTGCTTGGGGC
CTGCAGGGGCACAGGGTTATTTCTCAGGCCGGGGTCATGGGCGCACAGCTGCTTGCTGGCTTATAGGAGTGCCTGCC
AGGGGTGGCCCATGATGCTGTTTCTCAGCC[illegible]ACTGAATACATAAACAGGACACAGCATTTTGCTGCATAAA
GCAAACACAGCGTTACTTTTTTTTTTCTAAATGACATTTTTTATTAGATATTGTCTTTATTGACATTTCAAATGTTA
TCCCCTTTCCTGGTTTACCCTCTGAAATCCCCTATCTCCTCCCCCTCCCCCTGCTCACCAATCCACCCACTCCCACT
TCCAGGCCCTGGCAATCCCCTATATTTGGGCATAGAGCCTTCACAGGACCAAGGTACTCTCCTTGCATTGATGACCA
ACTAGTCCATTCTCTGCTACAAATGCAGCTAGATCTATGAGTCCCACCATGTTTTCTTTTGTTGGTGGTTTCATGCC
AGGGAGCTCTTGGAGTACTGATTGGTTCATATTGTTGTTCTCCCTATGGGGTTACAAAACCCTTCAACTTCTTGGGT
CCTTTCTCTGGCTGCCTCATTGGGGACCTTGTGCGAAGTCCAATGGATGACTGTGAGCATCCACTTCTGTATTTGCC
AGGCACTGGCAGAGCCTCTCAGAAGACAGCTATATCAAGATCCTGGCAGCAAGCTCTTGTTGGTATCCACAAAAGTG
TCTGGTGGTTGTCTATGGGATGGATCCCCAAAGGGGCAGTCTCTGGATGGTCATTCCTTCAGTCTCTGTTCCACACT
TTGTCTCTTTAACTCCTTCCATGACTATTTTATTCCTCCCTCTAAGAAGGACCGAAGTATTCATACTTTGGTCTTCC
TTCTTGAAATTCATGTGTTTTGTGAATTGTATCTTTGATATTCCGAACTTCTGGGCTAATATCCACTTATCAGTGAG
TGAATATCATGTGTGTTCTTATGTGATTGAGTTACCTCACTCAGGATGATATCCTCCAGAACCATCCATTTGTCTAA
GAATTTAATGAATTCATTGTTTTTAATAGCTGAGGAGTACTCCATTGTGTAAATGTACCACATTTTCTGTACCCATT
GTTCTCTTGAGGGACATCTGGGTTCTTTAAAGCTTCTGGACATTAAATATAAGGCTGCTATGGAAATAGTGGAGAAT
GTGTCCTTATTACATGTTGGAGCATCTTCTGGGTATATGCCCAGGAGTGCTATTGCTGGATCCTCTGATAGTACTAT
GTCCAATTTTCTGAGGAACTGCCAAACTGGTTTACAGAGTGGTTGTGCCAGCTTGCAATTCCACCAGCAATGGAGAA
ATGTTCCCCTTCCTCCACATCCTCACCAACATCTGCTGTCACCTCAATTTGTTCTTAGTGATTCAGACAGGTGTGAG
GTGGAATATCAGGGTTGTTTGGCATTTCCCTGATGACTAGTGATATTGAAAAAAATTTTAAGTGTTTCTCAGCCATT
CAGTATTCTTCAGTTGAGAATTCACTGTTTAGCTCTGTACTCAGGTTTTTTTAATAGGGTTATTTGGTTTTCTGGAG
TCTAACGTCTTGAATTCTTTCTATATATTGGATATTAGCCCTCTGTCATATTTAGGATTGGTAAAGATCTTTCCCAA
TATGTTGGCTGCCTTTTTGTGTCCTTTGCCTTACAGAACCTTTTTAATTTTATGAGGTCCCATTTGCTAATTCTTCA
TTTTACAGCAAAAGCCATTGGTGTTCTGTTCAAAAATCTTTCCCCCTGAACCCTATCTTCGAGGATCTTCCCCACTT
TCTCCTCTATAAGTTTCAGTGTCTCTATTATTGTGCTGAGGTCCTTGATCCACTTGAACTTGAGCATTGTTCAAGGA
GATAAGAATGGATCAATTCGAATTCTTCTACATGATAACAGCCAGTTGAGCCAGCACCATTTGTTGAAAATTCTCTT
TTTTGCACTGGATAGTTTTAGCACTTTTGTCAAAGATCAAGTGACTATGGCTCTTCAACTATGGCTCATTCCATTGA
TCAACTTGTCTGTCACTGTACAAGCACCATGCAATTTTTATTGCAATTGCTTAGTATTACACCTTGAGGTCAAGGAT
GGTCATTCCACCAGAGGTTCTTCTATGGTTGAGAAGAGTTTTTGCTATCCTAGGTTTTTGTTATTCCAGATGAATTT
GCAAATGGCCCTTTCTAACTCAGTGAAGAATTGAGGTGGAATTTTGATGGGAATTTTATTGAATCTGTAGATTGCAT
TCAACAAGATAGCCATTTATAATACATTAATCCTGCCAGTCCATGAGCATGGGAGATCTTTCCATCTTCCGAGATCT
TCTTCGATTTCTTTCTTCAGAGACTTGAAGTTTTTATCATACAGATCTTTCACTTCCTTAGTTAGAGTCACACCAAG
GTATTTTATATTATTTGTGACTACTGTGAAGGTTGTTGTTTCCCTGATTTCTTCCTCAGCCTGTTCATCCTTTGTGT

Fig. 3 (cont.)

AGAGAAAGGCCACTGATTTATTTGAGTTAATATTGTATCCAGCTAATTCACTGAAGTTGTTTATCAGGTTTAGGAGT
TCTCTTGTGGAATTTTTGGAATCACATGTGTATACTATTATATCATCTGCAATTAGTGATATTTTGACTTCTTCTTT
CCCAAATTGTATCCCTTTGATCTCCTTTTGTTGTCTAATTGCCCACACTAGGACTCGGGCAGCCTTAGTGCCTAGTC
CCTGATTTTAGTGTGATTTGTTCAAGTTTCTCTCCACTTAGTCGGATGTTGGCTACTGATTTGCTGTATATTGCTTT
TATTATGTTTAGGTATGGGCCTTGAATTCCTGATCTTTCCAATACTTTTATCATGAATGGGTGTTGAATTTTGTCAA
ATGCTTTCTCAACACCTACAAAGATGATCATGTAGATTTTGTCTTTCAGTTTGATTATATAGTGTATTATGTTGATG
GATTTCCATATATTAAACCATCCCTGCATCCCTGGGATGAAGCCTACTTGGTCATGATAGACGATTGTTTTGATGTG
TTCTTGGATTCAGTTAGTGAGAAATATATTGAGTATTTTTACATCGATATTCATAAGGGAAATTGGTCTGAAGTTCT
CTTTCTTTGTTGGGTCTTTATGTGGTTTAGTTATCAGAGTCATCGTAGCTTCATAGAACAAATTGAGTAGAGTACCT
TCTGTCTCTATTTTGTGGTATAGTTTGAGGAGATTTGGAAATATGTCTTCTTGGGACGTCTGAGAGAATTCTGCACT
AAACCCATCTGATCCTGGGCTTCTTTGGGGGGGGGGGACTATTAATGACTGCTTCTATTTCTTTAGGGGAAATGGGA
CTGTTTAGATTGTTAATATGATCCTGAATAGAAATCTGATCTGATCTAGAAAATTGTCCATTTTATTCAGGTTTTCC
AGTTTTGTTGAGTATTGCCTTTTGTGGTAGGGTCTGATGATGTTTTGGATTTCCTTAGGTTCTGTTGTTATGTCTTC
TTTTCCATTTCTCATTTTGTTAATTAGGATACTGTCCCTGTGTCCTCTAGTTACTCTGGCTAAGCGTTTATCTATCT
TATTGATTTTCTCAAAGAACCAGCTCCTGGTTTGGTTGATTCTTTGTATAGTTCTTTTTGTTTCCACTTGATTGATT
TCTGCCCTAAGTTTGATTGTTTCCTGCTGTCTACTCCTCTTGGGTGAATTTGCTTCCTTTTGTTCTAGAGCTTTTAG
GTGTGCTGTCAAGCTGATAGGGTATGCTCTCTCTAGTTTCTTTTTGGCGGCACTCATAGCTAGGAGTTTTCCTCTTA
GCAGTGCTTTCATTACGTCCTGTAAGTTTGGGTATGTTGTGGCTTCATTTGCATTAAATTCTAATAAGTCTTTAATC
TCTTTCCTTCTTTCTTCCTTGACCGAGTTATCATTGACTAGAGTGTTCATCAGCTTCCACATCAATGTTGGCTTTTA
ATTATTTATGTTTTTATTGAGGATCAGCCTTTGTCGGTGGTGATCTTCTAGGATGCACGGGAAATTTTCAATATTTT
TGTATCTATTGAGGCCTGTTTTGTGACCAATTATACGGTCAATTTTGGAGAAAGTACCGTGAGGTACTGAGAAGATG
GTATATCTTTTTGTTTTAGGATAAAATGTTCTGTAGATATCTGTTAAATCCATTTGTTTCATAACTTCTGTTAGTTT
CACTGTGTCTCTGCTTAGTTTCTGATTCCAGAATCTGTCCAATGATAAGAGTAGGGTATTAAATTCTCCCACTACTA
TTGTGTGAGGTACAATGTGTGGTTTGAGCTTTAAAAGAGTTTCCTTAATGAATGTGGATGGCCTTGCATTTGGAGCA
TAGTTATTCAGAATTGAGAGTTCCTCTTGGAAGATTTTACCTTTGATGAGTATAAAATGCCCCTCCTTGTCTTTTTT
GATACCTTTGGGTTAGAAGTGGATTTTATTCGATATTAGAATGGCTAATCCATCTTGTTTCTTTGAGATGTTTGCTT
GGAAAATTATTTTCCTGCCCTTTACTCGGTGGTAGTGTCTGTCTTAGTCCCTGAGGTGGGTTTCCTGTATACAGCAA
AATGTTGGGTCCTGGTTATGTAGCCAGTCTGTTAGTCTGTCTTTTTATCAGGTAATTGAGTCCATTGATATTAAGAG
CTATTAAGGAAAAGTAATTGGTGCTTCCTGTTATTTTTGTTGTTAGACTTGGGATTCTGTTCTTGTGGCTATCTTCT
TTTAGGTTTGTTGAAGGATTACTTTCTTGCTTTTTTTAGGGTGTAATTTCCCTCTTTGTGTTGGAGTTTTCTCTTTA
TTATCCTTTGAAGGGCTGGATTCATGGAAAGATGTTGGGTGAATTTGGTTTTGTCATGGAATTCTTTGGTTTCTCCA
TCTATAATTGAGAGTTTTGCTGGGTATAGTAGCCTAAGCTGGCATTTGTGCTCTCTTAGTGTCTATAACATCTGTCC
AGGATCTTCTGGCTTTCATAATCTCTGGTGAGAAGTCTGGTGTAATTCTGATAGGCCTGCCTTTATATGTTACTTGA
CCTTTTTCCCTTACTGCTTTAAATATTCTATCTTCATTTAGTGCATTTTTTTTCTGATTTTTTATGTGTCAGGAGGA
ATTTCTTTTCTGCTCCAGTCTATTCGGATTCTGTAGGCTACTTCTATGTTCATGGGCATCTCCTTCTTTAGGTTACG
GACGTTTTCTTCTATAATTTTGTTGAAGATATTTACTGGCCCTTTAAGTTGAAAATCTCCATTCTCATCTATACCTA
TTATCTTTAGGTTTGGTCTTCTCATTGTGTCCTGGATTTCCTGGATGTTTTGAGTTAGGATCTTTTTTGCATTTTGC
ATTTTTTTTTATTGTTGTGCCCATGTTTTCTACGGAATCTTATGCACCTGAGACTCTCTCTTCTACCTCTTGTATTC
TATTGGCTGATGCTTCCACCTATGTTTCTCGATTTCTTTCCTAGGATTTCTATCCCCAGAGTTGTCTCCCCTTTGTGA
TTTCTTTATTGTTTCTACTTCCATTTTTAGATTTTGAATGGTTCTGTTCGATTCCATCGCCTGTTGGGTTGTGTTTT
TCTGTATTTCTTTGAGGGATTTTTGTGCTTCATCTTTAAGGTCTTCTACCTGTTTAGGAGTGTTTTCCTATAATTCT
TTGAGGGATTTTTGTGTTTTCTCTTTAAGGGCTTCTAGCAATTTAGCAGTGTTCTCCTGTATTTCTTTAAGTGAGTT
ATTAATGCCCTTCTTAAAATCCTCTACCAACATCATTAGATATGATTTTAAATCCGAATCTTGCTTTTCAGGTGTGT
TGGGGTATCCAGGACTCACTGTGGGGGGAGTACTGGGTTCTGATGATGAAAACTGGTCTTGGTTTTTATTAGTAAGA
TTCCTACTTTTGCCTTCCACCATCTGATAATATCTGTTGTTAGATATTCTAGCTGTCTCTGGCTGGAGCTTGTTCCT
CCTGTGATTCTGTCAGCCTCTGTCAGCACTCCTGGGAGTACAACTCTTTTCTGAGTCCCAATGTTCAGAGCATTCTC
TGCAGGCAAGCTCTCCTCTGGCAGGTAAGGTGCCCAGAGCTCTTGAGCTCAGCTCCACCTCCTGACTGCAGATGAAG
ACCCAAAGGGACCCTGTCCAATAAGCTCTGTTGCTTCTGCCACCCACATGCTCTCCTGTGCGAACTGGTCTCTGAGA
GACCCGGGATACAAGATGGTACTCTCACCTGAATCCCAGGGTCAAAGCCCTCCCTGGAGGCTGACTCTCCTCTTGTG
GGAAGGTGCACAGAGGTCTGGAGCTCAGCTCTGCCTCCTGGCTGAAGATGAAGGCCCGAAGGGACCCTGTCCAAGAA
GCTTTGTTGCTTCTGGGACCCACATGCTCTCCTACATGGACTGGTCTCTGAGAGACCAGGGATTCAAGATGGTGCTC
TCACCTGAGTCCCAGGGTCAGAGCCCTCTCTGGAGGCCAACTCTCCTCAGTGATCCTAAGATCCTGGGTATGCTAGG
GTGCCTATGGCATGGAGAGTCCTCTGAGGAATGTGGGACTGTCTGCTGAGTTTCCACCCAAGGTGGTGCTGGGCTGG

Fig. 3 (cont.)

CTCCAGTCAGAATGAACCCAGACTCTGGTTGGGCAGGTTTCCAGTCCTGTTGGCCCAAGCCCCTCTGGGTTGTTTTA
GAACAGATGTTGCTTTCCACTCACCAGTGATCCCAAGATCCTGGGCGTGCTAGGGTGCCTGCTATGTGGAGAGTCCA
CTGGGGACCTTAGGAGCATACATCAAGTTCACACCCATGGTGGCAAGGAGCTGGTGCCTACCAGAACAAACCCCGGG
CACTTTTACTGACCCTTTAAGTTGAAAATCTTCATTCTCATCTATACCTATTATCCTTAGGTTTGGTCTTCTCATTG
TGTCCTGGATTTCCTGGATGTTTTGACTTAAGATCTTTTTGCATTTTGCATTTTTTTGATTGTTGTGTCCATGTTCT
CTCTGGAATCTTCTACACCTGAGATTCTCTCCTCTGTATCTTGTATTCTGTTGGTGATGCTTGCATCTATTGCTCCT
GATCTCTTTCCTAGGGTTTCTATCTCCAGAGTTTTCTCCCTTTGTGATTTCTTTATTATTTCTACTTCCATTTTTAG
ATCCTAGATGATTTTGTTAAATTCCTTCACCTGTTTGGTTGTGTGTTCCTGTAATTCTTTAAGGGATTTTTGTATTT
CCTCTTTAAGGGCTTCTACCTGTTTAGCTGTGTTCTACTGTATTTCTTTAAAGGACTTATGAATGTCCTTCTTAAAA
ACCTCTACCAGCATCATGAGATGTGATCTTAAATGTCAATCTTCCCTTTCTGGTGTGTTGGGGTATCCAGGACTTGC
TGTGGTTGGAGTTCTGGGTTCTGGTAAACCTGCCTTAGAGGGTCACCACAGAGTAATGATAGCACTACTTTTAAACA
GGGGAAGATGATGAAATAATTGCTGTGGGAAAATGCAAGGAAGGCTCCAACACATGTAGGCATCTATGAAGGTCTCA
AATCTTCAAAATCCAAAACCACCAAGAAAGAAAGAAAGAAAGAAAGAAAGAAAGAAAGAAAGAAAGAAAGAAAGAAA
GAAAGAAAGAAAGAAAGAAAGGAAGGAAGGAAGGAAGGAAGGAAGGAAGGAAGGAAGGAAGGAAGGAAGGAAGGAAG
GAAGGAAGGAAGGAAGATTCTAAAAGTAGTCACCTGCACCAGGTGCCTGGGGAGTCACTCAGCAGCCCTAGACTGAG
AAAGCTTGAAGAAAGTAGAAATAGAGAAAGTGTACAGCCAGTATCCTCTAGCTACTCACATCCAAACAGGGCCTCCT
GACTGCTCTGAGCCTGTCCTAAGAACAGCAATGATGCCACAGAAATTTTTAGAGTGAACCCTGAAGGAACTTGAGGC
CGATATGAGAAAGCCAGTCCCAGAGGAAAGGAAAACCCGTAGAGAGAAAACAGGTGAGTTAGTGCATTAAAGGGGCT
GAGCAGGCAACGCGCCGTCGACCGGAGGAGTTTCTTCCCTGTGCGGAGTCCACGGGCCTCCTGTGAGTGTGTGCATG
GGCACAAGTGTGTGTGTGGCTCTGCTGTGTGTCTGTACACACATATGTTTTGGGTTTTTTTGTGTCTCAGACCACAG
AGTCTGCCCCTCCCACCAAAGCCCAGGCAGAAGGATGAACCCACGCCCCTGGGGCCCAGGCCTCAGCAGCCTCTGCG
GGATCATTGTTCCCAGTTGTCACTTGCCTTTGCCACAGCCCTATTTCTCCACAATTCCTTAAAGTCCTCAACATGCA
TTTAAGGCACAAAGGTGAAACTGCCCAGAAACATCTGACTCCGCCGTGGAACCCAGGAGCAAGCTGGGTTAGCTAAG
GAGCGGGGCCGTTGGCAGAGGCTGGGGATCCAGGCTGAACTTTGGAGGAGGCATGTCCCAGCATGGGCTCCTGACTA
TGTCCTCCTGGGACAAACCCAAACCCACTCTTTGAATATGGGAGGGACTTTGCTGGCCCCGGCCCTGACCGCAGCAC
TTGGAAACTGAGGAGTGGTCGCCTCCTCCGTGTCACAGCTGCCCGTTCACCATCATAGAAGCAACTCTGTCACCTCC
ATGGGCCCCTCTGTGGCTGCTGCCTGGGTCCAAGCTGAGCCCAGCTGCCCAGGCCCAGAAGGAAAGCCCAGGCCAGG
TGCCCAGCACAGAGGCAGTCACATACCCCGGGGAGAGCCACAGCAAGCAGCCAATATTGCCCAGGAGAGGAGTAGCT
GACAAGGCAGAACGTGAGCTGCCATCGGCTCGAGAGGCTTTGCTGGTCCTCCTGGGGCTCTGGACATGACCAGGAGG
AGCGAGGGAAGAAGTCGCATGGTGGTCCCATCCTGGGTGGGGCCTGATGGCAGCTGGCCACCCGTCCCAGAGTGGCA
GCCAGATGCCAGCGCCATTCCCACAGTCACATCATTGGTCACAGAATGCAGGACATAGAGTGTCTTCTTTCCATCAC
AGTGCTGTCCAGACCCATAGCCTAGGGTAGACCTGGAAGATTCAATGTCCACACCCGGGGCTGGAGCGTAGCCATGA
GCCACGCCCCCTGCCCGTGCATGGAAAGCCAGCCCAAGCTCTGCTCCATCCCTAGCCAAAGTCAGTGTCCTTTCCCC
TTCTCCCAAGTGAGCTCTAGCCACCTGCCTACCCTGCCATCTGAGGATGACAGCCTTCATTCCATTGGAACCTGGCT
CTGCCACCAGCAGGCTTGCAGTCCTGGGCAGACTCCGTCACCTCTCTATGCCTCAGCCTTTCCATCTGCACAGGAGG
AAGATGATGATGGTGGTGATGATGATGGCGATGGTTTCCTTTTGCATCTGAGGCAAGGACTAATTGAGATGATACAC
ATCAGGCACTGGGTATGGTGCTGGTCCTTCCTGAGCACTCAATCTATGTGAGCTGTCCTTGTGAAATGGGTGTCACC
ACATTTCCCCACGCAGAACATCCTTTGTCTGCCATACTTGAAACGTCTGCCCCAATACTAACAGCTCCTCATGGAAG
ATGTGCCCACCCACCCACCCTCATACTCCCAAAGGTGCCCGTGCTTTATCAAGCCAAAGTCCAGCCAGGAACTTTAC
AGCAGCATCCCTTTCCCTCTCCAAGCACCAAGGAGCAAGGCAAAGCACTACATCTTCCATCTGGAGGCAATGCCACC
CTCTTCTCCCATTTTCACTGCCATCCCTAAGAGGCAGTGCTTCCCCAAAAGGTTCCATAGCAGCCTGCCTACAGCAA
CTCTGTTCACACGAGTTTCAGCATCCTTGCAGTGGCTCCCCTGCCATGCTGTGGCTCTTCATTCACCCTCTTCTCCT
GCTCCCCGTGACAGGCATAGATTCTGAGTGATCTGGATACATTGCTTTGTTTAATAACATTACAGCTTCTGTGCTGA
AAAAGATACAGCAGATAGAGAAGGCAATTGTTGAACACAAAATAGTGACAGCAGAGATGACGGCAAGTTGGCATTTT
TCTTTTCTAGCAATAAAACTTAAAGCTGACTCAAGGAGAAATGGAAATCATAATTGGAACAGTAATCCTCAAGAAAG
CATTAAGATTATTAAATAATTGCCCTCACAGATGACTTCAGGCCAAGATGGCTTTATGGGTGAAGTTTAGACTTTCA
CAAAACTAATCAGTTCCCATAAGAACTGCTCCAGGATTTGGAGGAACATGGGAAAGTCTATTAAAGGGATCACAATT
CACAGTCCCCAGAGTAAAACATGGGCTAACTTGCATTTTGGCAAAGAGCCAAATGTTATAAATGACATCCTAGAAGG
CCAAATTCTGTCCATCTCGTTGAACAAGGACTTACACCAGGAATTTAGAACTATTTATAGCTCATCCCACCACTCAG
GCCAATGATGACCCATGATCATCTCACCAGAAATGGAAAGACTCAGATGATTAATAGAGTCTCAATTTCTCTGAGAC
ATCTAAGAGCCCAGCCCAAGCCCAGACCCAGGAGGGCACCCAGGCCTGGACAGAGAACACTGATATCACACCAGCCC
TCCAGAGGGAAGCAGAGACTCCTTCAAGCTCTGGAAACACAGGCCCAGACAGCTGCCCAAAGTTGGGCAGGCTTCAC
TGCAAACCCAAATCATGAAGCTAGGTAACACCTTTACAGATTCTTTACATTTAAAAATCATCAAAACAAGAGTAAAT

Fig. 3 (cont.)

AATAAACTCAAATAATATTAATCTAATATGTAAAGGTCTTGTACCATTATTATGCAAACAACATACATAAGCTAATA
AGAAAAAGAACAAATCCCTTAAGAAATCAGCAAAAAGGATATAACACAATTTCTAAAAGAAAACAAATGGCTAGCAC
ACATAAGGAAAACACTTTGTGAACAGACATTCTTCAGAACATTATTTATAATTATAAAATAGTTGAAAGCAAGATAG
TGCCTGAAGAAATTATGGTGCATACATTAGTGGGACTATTCTGCAAACATTCCCAATTATACTTGTCACATATCTGT
GATAACGTGACAGCCAGCATTCATGGGGTGACCTCATTTGGTAAAAGGGTGCAAAGCTCAACACGCATTGTGAGATG
ACTGTGGTGTAAAATTAGTGGGATTATTCCGCAAACATTCCCAATTATACTTACCGCATATCTGTGATAACATGACA
GCATTCATGGGGTGACCTCATTTGGTAAAAGGGTGCAAAGCTCAACACGCATTGTGAGATGACTGGTGTAAATACAA
AGACCAAACTGTGAAAAGGAGTCCATCAATTAATCGATGCTTACCTTCAGTTTTGGGCTAATTTTTAAAGTATGCTA
TAAGCATATGCTCCTGTTATAACAGAATGGAGGGATTATGAGAGATGATGCAGGTGTGTCCTGGGCCTCCCCTGGCC
CACTGGGCCCTAGAGATGCCTTCCCAGGCATCGCTGTCAGGGCTTCCCTCAGAGGGAGTCCTGTATTGACCTCACCA
CCAAGGTCTGGAGCAGGGGATCCTTAGATATTGGTTGGGGTTATCTCACCTTAGGTCTGAATATGGGGTTGTCTTAG
ACTGTTTTGTGCTGTTAGAATAGAATACCCAAGACTGGGAAATTTATACTGAACGGAAATTTATTTCTCACAGTTCT
AGAGGCTGTGAAGTCCAAGAGCACAGGTGCCAGAGCAAGTCCAAGAGCAAGGGAAAGTCCAAAGCAAGTCCAGGAGC
ATCTGGCGAGGACCTTCTTGCTGTGTCATCACATGGCGGAAGGCAAGAAAGAGAGCAAGAGGGGGCCGAACTCACCC
TTTTATAACAGCACCAATCCCACCCATGAGGTGGGGACCTTATGACCTAATCACTCTTCATACTGTTACAATGGCAA
TGAAATTTCAACATGAGTTTTGGAGGAGAGAAGCATTCAAACCACAGCAAGGGTGCTCCTACCTCCTCTCTCAGGGC
ATCTGCAGAAAGAGCTGCAACTGCACGTCCTTCCTCCGTCCATCCTCCATCCCTTCCCAATGTCCGTGCATATCCTG
TGACCCAGGAGGTCTGGCATAGGGGGTGCTCCTGCCTTAGGTCTGAGGCCCTGTCTGAAGAGGGGTAGGTGAGGAGG
CCATCTGATGGTCTGGGCCAAGACAGTCACAGGACGCATCATTTATCATCAAGGAGGCTGAGGGTTGAGTCTCCAGG
TCCAGGGAACTCCCCACAAAGTGGGAACCCTGCCCAGCTCCACACAGCCTCTGCTGGGGGACCCTGCTCTGGTGCAG
AGCCTGGGGACAGGTCTTGAGCTCAGCCAGAGTCTGCCTCCCTGTCATTTAGGAACTAAACCAAGCGGCAGGATGCT
GGAGCCCAGCCCCCATCTGACCTTACAGGGCCAAGGCTGGGGCCCTGGGTTCCCCTCAAGGCACAGCAGGACTGGAG
CCCCAGGCAGTGCAGGAGTGGCCAAAGCTGGGGCTTCCTCCAGAGCCCCCAAGCATCATGGCACCAAGAAGGGTAGG
ACCCTGGCCTGAGGAATTGGCACCAAAGCCCCAGAAACTACCCTGGACACCATGGAGAGAGGCTTGGAGGGGAAGCA
CCAGGCACTGCCTCCCCTTCTGATCCCACCTGAGGTGGCTGCCAAGCCCAGAGAGCCGCTCTGATGTCCCCCAGCCC
TGCAGCCCAGGGATACCTGTACTGTGCCCCTGGGGGACCCCTGGCCAGTCTGTGCAAAGAAGTCACCACCCTACACT
CAGAGACAGTGGGGGTCCTCGTCCCACATCCTCAGAGCATGGCCCGGCTGCTGCAGGGATGGTCTCCTTGTCCTCAG
AGCATGGCCCGGCTGCTGCAGGGATGGTCTCCTTGTCCTCAGAGCATGGCCCAGCTGCTGCAGGGATGGTCTCCTGG
AGGCCCCCCAGTGCTCTATTGTCAGGGCTCCCTCCACCCCCCCGCACCAAGAGAGAGCCAGACCCCAGCAAGGCTTC
CAGTGGCTTCAGGTCACACCCCTAGGCTGACCCCAGCCCCATTAACACCTGCCTGAGAAAGCTCCACGCACCAGAAC
TGACCGTCTGCTCCAACTCTTGACCTCCCGTTCTCAGGGCGTCTGCTGAAAAGGCTGCAACTGCACATCCTTCCTCC
GTCCGTTCCCGATGTCCGTGTGTCTCCTGTGGCCAGGAAGGTCTTTCTCGGGACCTGAGAGCCGCTCCCTGAAGTGT
CCCCATTGGGAAGGATGGGGCCTGTGTCTCCAGGCTCTGGGAGGACAGAATCCTGACCTCAACAGTGGCCGGCACGG
ACACAACTGGCCCCATCCCGGGGACGCTGACCAGCGCTGGGCAACTTTTCCCTTCCCCGACGACTGAGCCCCGAGCA
CCCTCCCTGCTCCCCTACCACCTCCCTTTACAAGGCTGTGGCCTCTGCACAGATGATAATGGAGCTTGGCTCATTCC
CCTAGAGTCGGTAGGGAGTTAAGGACAAAACTCAGTTTCCTCCACCTGAACTCAAGTCTGCCTATGTTTACCTAATC
ACACCTGGTGGACAGTTTGGACAAACTTGCACACTCAGAGACACAGACACTTCTAGAAATCATTATCTCCCTGCCCC
GGGGACCCCACTCCAGCAGAAGTCTGCTAGGCACTGGCCTGGGCCCTCCTGCTGTCCTAGGAGGCTGCTGACCTCCT
GCCTGGCTCCTGTCCCCAGGTCCAGAGTCAGAGCAGACTCCAGGGACGCTGCAGGCTAGGAAGCCGCCCCCTCCAGG
CCAGGGTCTAGTGCAGGTGCCCAGGACAAGAAAGATTGTGAATGCAGGAATGACTGGGCCACACCCCTCCCGTGCAC
GCCCCCTCCTGCCCTGCACCCCACAGCCCAGCCCCCCGTGCTGGATGCCCCCCCACAGCAGAGGTGCTGTTCTGTGA
TCCCCTGGGAAAGACGCCCTCAACCTCCACCCTGTCCCACGGCCCAAGGAAGACAAGACACAGGCCCTCTCCTCACA
GTCTCCCCACCTGGCTCCTGCTGGGACCCTCAAGGTGTGAACAGGGAGGATGGTTGTCTGGGTGGCCCCTAGGAGCC
CAGATCTTCACTCCACAGACCCCAACCCAAGCACCCCCTTCTGCAGGGCCCAGCTCATCCCCCTCCTCCTCCCTCTG
CTCTCCTCTCGTCGCCTCTACGGGAAATCCGGGACTCAGCAGTAACCCTCAGGAAGCAGGGCCCAGGCGCCGTTTAA
TAGGAGGCTTCCTCACAATGAAACTTTTAGAAAGCCTTGACTACAATGATGACCTTGGTGTGGCTGTGAACACTGTC
AGCTCCCACAGCTGCTGCAGCAAAAAATGTCCATAGACAGGGTGGGGGCCCGGGGTCGTCTGCTGTCCTGCTCAGCC
CACAGCACGCATGGAGGATCTGAGGTGCCACACCTGACGCCCAGGCCAGAACATGCCTCCCTCCAGGGTGACCTGCC
ATGTCCTGCATTGCTGGAGGGACAGGGGCAGCCTATGAGGATCTGGGGCCAGGAGATGAATCCTATTAACCCAGAGG
AAAACTAACAGGACCCAAGCACCCTCCCCGTTGAAGCTGACCTGCCCAGAGGGGCCTGGGCCCACCCCACACACCGG
GGCGGAATGTGTACAGGCCCCGGTCTCTGTGGGTGTTCCGCTAACTGGGGCTCCCAGTGCTCACCCCACAACTAAAG
CGAGCCCCAGCCTCCAGAGCCCCCGAAGGAGATGCCGCCCACAAGCCCAGCCCCCATCCAGGAGGCCCCAGAGCTCA
GGGCGCCGGGGCAGATTCTGAACAGCCCCGAGTCACGGTG[redacted]CACCGTGAGAAAAACTGTGT

CCAAAACTGTCTCCTGGCCCCTGCTGGAGGCCGCGCCAGAGAGGGGAGCAGCCGCCCCGAACCTAGGTCCTGCTCAG
CTCACACGACCCCCAGCACCCAGAGCACAGTGGAGTCCCCACTGAATGGTGAGGATGGGGACCAGGGCTCCAGGGGG
TCATGGAAGGGGCTGGACCCCATCCTACTGCTATGGTCCCAGTGCTCCTGGCCAGAAACGACCCTACCACCGACAAG
AGTCCCTCAGGGAAACGGGGGTCACTGGCACCTCCCAGCATCAACCCCAGGCAGCACAGGCATAAACCCCACATCCA
GAGCCGACTCCAGGAGCAGAGACACCCCAGTACCCTGGGGACACCGACCCTGATGACTCCCCACTGGAATCCACCC
CAGAGTCCACCAGGACCAAAGACCCCGCCCCTGTCTCTGTCCCTCACTCAGGACCTGCTGCGGGGCGGGCCATGAGA
CCAGACTCGGGCTTAGGGAACACCACTGTGGCCCCAACCTCGACCAGGCCACAGGCCCTTCCTTCCTGCCCTGCGGC
AGCACAGACTTTGGGGTCTGTGCAGAGAGGAATCACAGAGGCCCCAGGCTGAGGTGGTGGGGGTGGAAGGCCCCCAG
GAGGTGGCCCACTTCCCTTCCTCCCAGCTGGAACCCACCATGACCTTCTTAAGATAGGGGTGTCATCCGAGGCAGGT
CCTCCATGGAGCTCCCTTCAGGCTCCTCCCTGGTCCTCACTAGGCCTCAGTCCCGGCTGTGGGAATGCAGCCACCAC
AGGCACACCAGGCAGCCCAGACCCAGCCAGCCTGCAGTGCCCAAGCCCACATTCTGGAGCAGAGCAGGCTGTGTCTG
GGAGAGTCTGGGCTCCCCACCGCCCCCCCGCACACCCCACCCACCCCTGTCCAGGCCCTATGCAGGAGGGTCAGAGC
CCCCCATGGGGTATGGACTTAGGGTCTCACTCACGCGGCTCCCCTCCTGGGTGAAGGGGTCTCATGCCCAGATCCCC
ACAGCAGAGCTGGTCAAAGGTGGAGGCAGTGGCCCCAGGGCCACCCTGACCTGGACCCTCAGGCTCCTCTAGCCCTG
GCTGCCCTGCTGTCCCTGGGAGGCCTGGACTCCACCAGACCACAGGTCCAGGGCACCGCCCATAGGTGCTGCCCACA
CTCAGTTCACAGGAAGAAGATAAGCTCCAGACCCCCAAGACTGGGACCTGCCTTCCTGCCACCGCTTGTAGCTCCAG
ACCTCCGTGCCTCCCCCGACCACTTACACACGGGCCAGGGAGCTGTTCCACAAAGATCAACCCCAAACCGGACCGC
CTGGCACTCGGGCCGCTGCCACTTCCCTCTCCATTTGCTCCCAGCACCTCTGTGCTCCCTCCCTCCTCCCTCCTTCA
GGGGAACAGCCTGTGCAGCCCCTCCCTGCACCCCACACCCTGGGGAGGCCCAACCCTGCCTCCAGCCCTTTCTCCCC
CGCTGCTCTTCCTGCCCATCCAGACAACCCTGGGGTCCCATCCCTGCAGCCTACACCCTGGTCTCCACCCAGACCCC
TGTCTCTCCCTCCAGATACCCCTCCCAGGCCAACCCTGCACATGCAGGCCCTCCCCTTTTCTGCTGCCAGAGCCTCA
GTTTCTACCCTCTGTGCCTACCCCCTGCCTCCTCCTGCCCACAACTCGAGCTCTTCCTCTCCTGGGGCCCCTGAGCC
ATGGCACTGACCGTGCACTCCCACCCCCACACTGCCCATGCCCTCACCTTCCTCCTGGACACTCTGACCCCGCTCCC
CTCTTGGACCCAGCCCTGGTATTTCCAGGACAAAGGCTCACCCAAGTCTTCCCCATGCAGGCCCTTGCCCTCACTGC
CCGGTTACACGGCAGCCTCCTGTGCACAGAAGCAGGGAGCTCAGCCCTTCCACAGGCAGAAGGCACTGAAAGAAATC
GGCCTCCAGCACCCTGATGCACGTCCGCCTGTGTCTCTCACTGCCCGCACCTGCAGGGAGGCTCGGCACTCCCTGTA
AAGACGAGGGATCCAGGCAGCAACATCATGGGAGAATGCAGGGCTCCCAGACAGCCCAGCCCTCTCGCAGGCCTCTC
CTGGGAAGAGACCTGCAGCCACCACTGAACAGCCACGGAGCCCGCTGGATAGTAACTGAGTCAGTGACCGACCTGGA
GGGCAGGGGAGCAGTGAACCGGAGCCCAGACCATAGGGACAGAGACCAGCCGCTGACATCCCGAGCCCCTCACTGGC
GGCCCCAGAACACCGCGTGGAAACAGAACAGACCCACATTCCCACCTGGAACAGGGCAGACACTGCTGAGCCCCCAG
CACCAGCCCTGAGAAACACCAGGCAACGGCATCAGAGGGGGCTCCTGAGAAAGAAAGGAGGGGAGGTCTCCTTCACC
AGCAAGTACTTCCCTTGACCAAAAACAGGGTCCACGCAACTCCCCCAGGACAAAGGAGGAGCCCCCTGTACAGCACT
GGGCTCAGAGTCCTCTCCAACACACCCTGAGTTTCAGACAAAAACCCCCTGGAAATCATAGTATCAGCAGGAGAACT
AGCCAGAGACAGCAAGAGGGGACTCAGTGACTCCCGCGGGGACAGGAGGATTTTGTGGGGGCTCGTGTCACTGTG[redacted]CACAGTGACACAGCCCCATTCCCAAAGCCCTGCTGTAAACGCTTCCAC

D2-2

TTCTGGAGCTGAGGGGCTGGGGGGAGCGTCTGGGAAGTAGGGCCTAGGGGTGGCCATCAATGCCCAAAACGCACCAG
ACTCCCCCCCAGACATCACCCCACTGGCCAGTGAGCAGAGTAAACAGAAAATGAGAAGCAGCTGGGAAGCTTGCACA
GGCCCCAAGGAAAGAGCTTTGGCGGGTGTGCAAGAGGGGATGCGGGCAGAGCCTGAGCAGGGCCTTTTGCTGTTTCT
GCTTTCCTGTGCAGATAGTTCCATAAACTGGTGTTCAAGATCGATGGCTGGGAGTGAGCCCAGGAGGACAGTGTGGG
AAGGGCACAGGGAAGGAGAAGCAGCCGCTATCCTACACTGTCATCTTTCAAGAGTTTGCCCTGTGCCCACAATGCTG
CATCATGGGATGCTTAACAGCTGATGTAGACACAGCTAAAGAGAGAATCAGTGAAATGGATTTGCAGCACAGATCTG
AATAAATTCTCCAGAATGTGGAGCCACACAGAAGCAAGCACAAGGAAAGTGCCTGATGCAAGGGCAAAGTACAGTGT
GTACCTTCAGGCTGGGCACAGACACTCTGAAAAGCCTTGGCAGGAACTCCCTGCAACAAAGCAGAGCCCTGCAGGCA
ATGCCAGCTCCAGAGCCCTCCCTGAGAGCCTCATGGGCAAAGATGTGCAGAACATATGTTTGTCATAGCCCCAAACT
GAGAATGAAGCAAACAGCCATCTGAAGGAAAACAGGCAAATAAACGATGGCAGGTTCATGAAATGCAAACCCAGACA
GCCAGAAGGACAACAGTGAGGGTTACAGGTGACTCTGTGGTTGAGTTCATGACAATGCTGAGTAATTGGAGTAACAA
AGGAAAGTCCAAAAAATACTTTCAATGTGATTTCTTCTAAATAAAATTTACAGCCGGCAAAATGAACTATCTTCTTA
AGGGATAAACTTTCCACTAGGAAAACTATAAGGAAAATCAAGAAAAGGATGATCACATAAACACAGTGGTCGTTACT
TCTACTGGGGAAGGAAGAGGGTATGAACTGAGACACACAGGGTTGGCAAGTCTCCTAACAAGAAGAGAACAAATACA
TTACAGTACCTTGAAAACAGCAGTTAAAATTCTAAATTGCAAGAAGAGGAAAATGCACACAGCTGTGTTTAGAAAAT
TCTCAGTCCAGCACTGTTCATAATAGCAAAGACATTAACCCAGGTTGGATAAATAAACGATGACACAGGCAATTGCA
CAATGATACAGACATACATTCAGTATATGAGACATTGATGATGTATCCCCAAAGAAATGACTTTAAAGAGAAAAGGC

Fig. 3 (cont.)

CTGATATGTGGTGGCACTCACCTCCCTGGGCATCCCCGGACAGGCTGCAGGCACACTGTGTGGCAGGGCAGGCTGGT
ACCTGCTGGCAGCTCCTGGGGCCTGATGTGGAGCAGGCACAGAGCCGTATCCCCCCGAGGACATATACCCCCAAGGA
CGGCACAGTTGGTACATTCCGGAGACAAGCAACTCAGCCACACTCCCAGGCCAGAGCCCGAGAGGGACGCCCATGCA
CAGGGAGGCAGAGCCCAGCTCCTCCACAGCCAGCAGCACCTGTGCAGGGGCCGCCATCTGGCAGGCACAGAGCATGG
GCTGGGAGGAGGGGCAGGGACACCAGGCAGGGTTGGCACCAACTGAAAATTACAGAAGTCTCATACATCTACCTCAG
CCTTGCCTGACCTGGGCCTCACCTGACCTGGACCTCACCTGGCCTGGACCTCACCTGGCCTAGACCTCACCTCTGGG
CTTCACCTGAGCTCGGCCTCACCTGACTTGGACCTTGCCTGTCCTGAGCTCACATGATCTGGGCCTCACCTGACCTG
GGTTTCACCTGACCTGGGCTTCACCTGACCTGGGCCTCATCTGACCTGGGCCTCACTGGCCTGGACCTCACCTGGCC
TGGGCTTCACCTGGCCTCAGGCCTCATCTGCACCTGCTCCAGGTCTTGCTGGAACCTCAGTAGCACTGAGGCTGCAG
GGGCTCATCCAGGGTTGCAGAATGACTCTAGAACCTCCCACATCTCAGCTTTCTGGGTGGAGGCACCTGGTGGCCCA
GGGAATATAAAAAGCCTGAATGATGCCTGCGTGATTTGGGGGCAATTTATAAACCCAAAAGGACATGGCCATGCAGC
GGGTAGGGACAATACAGACAGATATCAGCCTGAAATGGAGCCTCAGGGCACAGGTGGGCACGGACACTGTCCACCTA
AGCCAGGGGCAGACCCGAGTGTCCCCGCAGTAGACCTGAGAGCGCTGGGCCCACAGCCTCCCCTCGGTGCCCTGCTA
CCTCCTCAGGTCAGCCCTGGACATCCCGGGTTTCCCCAGGCCTGGCGGTAGGTTTGGGGTGAGGTCTGTGTCACTGT
G[redacted]CACAGTGTCACAGAGTCCATCAAAAACCCATCCCTGGGAACCTGC
D3-3
TGCCACAGCCCTCCCTGTGGGGCACCGCCGCGTGCCATGTTAGGATTTTGACTGAGGACACAGCACCATGGGTATGG
TGGCTACCGCAGCAGTGCAGCCTGTGACCCAAACACACAGGGCAGCAGGCACAACAGACAAGCCCACAAGTGACCAC
CCTGAGCTCCTGCCTGCCAGCCCTGGAGACCATGAAACAGATGGCCAGGATTATCCCATAGGTCAGCCAGACCTCAG
TCCAACAGGTCTGCATCGCTGCTGCCCTCCAATACCAGTCCGGATGGGGACAGGGCCGGCCCACATTACCATTTGCT
GCCATCCGGCCAACAGTCCCAGAAGCCCCTCCCTCAAGGCTGGGCCACATGTGTGGACCCTGAGAGCCCCCCATGTC
TGAGTAGGGGCACCAGGAAGGTGGGGCTGGCCCTGTGCACTGTCACTGCCCCTGTGGTCCCTGGCCTGCCTGGCCCT
GACACCTGGGCCTCTCCTGGGTCATTTCCAAGACAGAAGACATTCCCAGGACAGCTGGAGCTGGGAGTCCATCATCC
TGCCTGGCCATCCTGAGTCCTGCGCCTTTCCAAACCTCACCCGGGAAGCCAACAGAGGAATCACCTCCCACAGGCAG
AGACAAAGACCTTCCAGAAATCTCTGTCTCTCTCCCCAGTGGGCACCCTCTTCCAGGGCAGTCCTCAGTGATATCAC
AGTGGGAACCCACATCTGGATCGGGACTGCCCCCAGAACACAAGATGGCCCACAGGGACAGCCCCACAGCCCAGCCC
TTCCCAGACCCCTAAAAGGCGTCCCACCCCCTGCATCTGCCCCAGGGCTCAAACTCCAGGAGGACTGACTCCTGCAC
ACCCTCCTGCCAGACATCACCTCAGCCCCTCCTGGAAGGGACAGGAGCGCGCAAGGGTGAGTCAGACCCTCCTGCCC
TCGATGGCAGGCGGAGAAGATTCAGAAAGGTCTGAGATCCCCAGGACGCAGCACCACTGTCAATGGGGGCCCCAGAC
GCCTGGACCAGGGCCTGCGTGGGAAAGGCCTCTGGGCACACTCAGGGGCTTTTTGTGAAGGGTCCTCCTACTGTG[redacted]CACAGTGATGAACCCAGCAGCAAAAACTGACCGGACTCCCAAGGTTTATGCACACTTCTCCGC
D4-4
TCAGAGCTCTCCAGGATCAGAAGAGCCGGGCCCAAGGGTTTCTGCCCAGACCCTCGGCCTCTAGGGACATCTTGGCC
ATGACAGCCCATGGGCTGGTGCCCCACACATCGTCTGCCTTCAAACAAGGGCTTCAGAGGGCTCTGAGGTGACCTCA
CTGATGACCACAGGTGCCCTGGCCCCTTCCCCGCCAGCTGCACCAGACCCCGTCCTGACAGATGCCCCGATTCCAAC
AGCCAATTCCTGGGGCCAGGAATCGCTGTAGACACCAGCCTCCTTCCAACACCTCTTGCCAATTGCCTGGATTCCCA
TCCCGGTTGGAATCAAGAGGACAGCATCCCCCAGGCTCCCAACAGGCAGGACTCCCACACCCTCCTCTGAGAGGCCG
CTGTGTTCCGTAGGGCCAGGCTGCAGACAGTCCCCCTCACCTGCCACTAGACAAATGCCTGCTGTAGATGTCCCCAC
CTGGAAAAGACCACTCATGGAGCCCCCAGCCCCAGGTACAGCCATAGAGAGAGTCTCTGAGGCCCCTAAGAAGTAGC
CATGCCCAGTTCTGCCGGGACCCTCGGCCAGGCTGACAGGAGTGGACGCTGGAGCTGGGCCCACACTGGGCCACATA
GGAGCTCACCAGTGAGGGCAGGAGAGCACATGCCGGGGAGCACCCAGCCTCCTGCTGACCAGAGGCCCGTCCCAGAG
CCCAGGAGGCTGCAGAGGCCTCTCCAGGGGGACACTGTGCATGTCTGGTCCCTGAGCAGCCCCCCATGTCCCCAGTC
CTGGGGGCCCCTGGCACAGCTGTCTGGACCCTCTCTATTCCCTGGGAAGCTCCTCCTGACAGCCCCGCCTCCAGTTC
CAGGTGTGGTTATTGTCAGGGGGTGTCAGACTGTG[redacted]CACAGTGGTGCTGCCCATAGCA
D5-5
GCAACCAGGCCAAGTAGACAGGCCCCTGCTGTGCAGCCCCAGGCCTCCAGCTCACCTGCTTCTCCTGGGGCTCTCAA
GGCTGCTGTTTCTGCACTCTCCCCTCTGTGGGGAGGGTTCCCTCAGTGGGAGATCTGTTCTCAACATCCCAGGGCC
TCATTCCTGCAAGGAAGGCCAATGGATGGGCAACCTCACATGCCGCGGCTAAGATAGGGTGGGCAGCCTGGCGGGGA
CAGGACATCCTGCTGGGGTATCTGTCACTGTGCCTAGTGGGGCACTGGCTCCCAAACAACGCAGTCCTCGCCAAAAT
CCCCACGGCCTCCCCCGCTAGGGGCTGGCCTGATCTCCTGCAGTCCTAGGAGGCTGCTGACCTCCAGAATGGCTCCG
TCCCCAGTTCCAGGGCGAGAGCAGATCCCAGGCCGGCTGCAGACTGGGAGGCCACCCCCTCCTTCCCAGGGTTCACT
GCAGGTGACCAGGGCAGGAAATGGCCTGAACACAGGGATAACCGGGCCATCCCCCAACAGAGTCCACCCCCTCCTGC
TCTGTACCCCGCACCCCCAAGGCCAGCCCATGACATCCGACAACCCCACACCAGAGTCACTGCCCGGTGCTGCCCTA

Fig. 3 (cont.)

GGGAGGACCCCTCAGCCCCCACCCTGTCTAGAGGACTGGGGAGGACAGGACACGCCCTCTCCTTATGGTTCCCCCAC
CTGGCTCTGGCTGGGACCCTTGGGGTGTGGACAGAAAGGACGCTTGCCTGATTGGCCCCCAGGAGCCCAGAACTTCT
CTCCAGGGACCCCAGCCCGAGCACCCCCTTACCCAGGACCCAGCCCTGCCCCTCCTCCCATCTGCTCTCCTCTCATC
ACCCCATGGGAATCCAGAATCCCCAGGAAGCCATCAGGAAGGGCTGAGGGAGGAAGTGGGGCCACTGCACCACCAGG
CAGGAGGCTCCGTCTTTGTGAACCCAGGGAGGTGCCAGCCTCCTAGAGGGTATGGTCCACCCTGCCTATGGCTCCCA
CAGTGGCAGGCTGCAGGGAAGGACCAGGGACGGTGTGGGGGAGGGCTCAGGGCCCCGCGGGTGCTCCATCTTGGATG
AGCCCATCTCTCTCACCCACGGACTCACCCACCTCCTCTCCACCCTGGCCACACGTCGTCCACACCATCCTAAGTCC
CACCTACACCAGAGCCGGCACAGCCAGTGCAGACAGAGGCTGGGGTGCAGGGGGGCCGCCAGGGCAGCTTTGGGGAG
GGAAGGATGGAGGAAGGGGAGTTCAGTGAAGAGGCCCCCCTCCCCTGGGTCCAGGATCCTCCTCTGGGACCCCCGGA
TCCCATCCCCTCCAGGCTCTGGGAGGAGAAGCAGGATGGGAGAATCTGTGCGGGACCCTCTCACAGTGGAATACCTC
CACAGCGGCTCAGGCAAGACCCAAAAGCCCCTCAGTGAGCCCTCCACTGCAGTCCTGGGCCTGGGTAGCAGCCCCTC
CCACAGAGGATGAACCCAGCACCCCGAGGATGTCCTGCCAGGGGGAGCTCAGAGCCATGAAGGAGCAGGATATGGGA
CCCCCGATACAGGCACAGACCTCAGCTCCATTCAGGACTGCCACGTCCTGCCCTGGGAGGAACCCCTTTCTCTAGTC
CCTGCAGGCCAGGAGGCAGCTGACTCCTGACTTGGACGCCTATTCCAGACACCAGACAGAGGGGCAGGCCCCCCAGA
ACCAGGGATGAGGACGCCCCGTCAAGGCCAGAAAAGACCAAGTTGTGCTGAGCCCAGCAAGGGAAGGTCCCCAAACA
AACCAGGAAGTTTCTGAAGGTGTCTGTGTCACAGTG[redacted]CACAGTGACACTCGCCAGGCCAG
D6-6
AAACCCCATCCCAAGTCAGCGGAATGCAGAGAGAGCAGGGAGGACATGTTTAGGATCTGAGGCCGCACCTGACACCC
AGGCCAGCAGACGTCTCCTGTCCATGGCACCCTGCCATGTCCTGCATTTCTGGAAGAACAAGGGCAGGCTGAAGGGG
GTCCAGGACCAGGAGATGGGTCCCCTCTACCCAGAGAAGGAGCCAGGCAGGACACAAGCCCCCTCCCCATTGAGGCT
GACCTGCCCAGAGGGTCCTGGGCCCACCCCACACACCGGGGCGGAATGTGTGCAGGCCTCGGTCTCTGTGGGTGTTC
CGCTAGCTGGGGCTCACAGTGCTCACCCCACACCTAAAACGAGCCACAGCCTCAGAGCCCCTGAAGGAGACCCCGCC
CACAAGCCCAGCCCCCACCCAGGAGGCCCCAGAGCACAGGGCGCCCCGTCGGATTCTGAACAGCCCCGAGTCACAGT
G[redacted]CACTGTGAGAAAAGCTTCGTCCAAAACGGTCTCCTGGCCACAGTCGGAGGCCCCGCCAG
D1-7
AGAGGGGAGCAGCCACCCCAAACCCATGTTCTGCCGGCTCCCATGACCCCGTGCACCTGGAGCCCCACAGTGTCCCC
ACTGGATGGGAGGACAAGGGCCGGGGGCTCCGGCGGGTCGGGGCAGGGGCTTGATGGCTTCCTTCTGCCGTGGCTCC
AGTGCCCCTGGCTGGAGTTGACCCTTCTGACAAGTGTCCTCAGAGAGTCAGGGATCAGTGGCACCTCCCTAACATCA
ACCCCACGCAGCGCAGGCACAAACCCCACATCCAGGGCCAACTCCAGGAACAGAGACACCCCAATACCCTGGGGGAC
CCCAACCCTGATGACTCCCGTCCCATCTCTGTCCCTCACTTGGGGCCTGCTGCGGGGCGAGCACCTGGGAGCAAACT
CAGGATTAGGGGACACCACTGTGGGCCTGACCTCGAGCAGGCCACAGACCCTTCCCTCCTGCCCTGGTGCAGCACAG
ACTTTGGGGTCTGGGCAGGGAGGAACTTCTGGCAGGTCACCAAGCACAGAGCCCCCAGGCTGAGGTGGCCCCAGGGG
GAACCCCAGCAGGTGGCCCACTACCCTTCCTCCCAGCTGGACCCCATGTCTTCCCCAAGATAGGGGTGCCATCCAAG
GCAGGTCCTCCATGGAGCCCCCTTCAGGCTCCTCTCCAGACCCCACTGGGCCTCAGTCCCCACTCTAGGAATGCAGC
CACCACGGGCACACCAGGCAGCCCAGGCCCAGCCACCCTGCAGTGCCCAAGCCCACACCCTGGAGGAGAGCAGGGTG
CGTCTGGGAGGGGCTGGGCTCCCCACCCCCACCCCCACCTGCACACCCCACCCACCCTTGCCCGGGCCCCCTGCAGG
AGGGTCAGAGCCCCCATGGGATATGGACTTAGGGTCTCACTCACGCACCTCCCCTCCTGGGAGAAGGGGTCTCATGC
CCAGATCCCCCCAGCAGCGCTGGTCACAGGTAGAGGCAGTGGCCCCAGGGCCACCCTGACCTGGCCCCTCAGGCTCC
TCTAGCCCTGGCTGCCCTGCTGTCCCTGGGAGGCCTGGGCTCCACCAGACCACAGGTCTAGGGCACCGCCCACACTG
GGGCCGCCCACACACAGCTCACAGGAAGAAGATAAGCTCCAGACCCCCAGGCCCGGGACCTGCCTTGCTGCTACGAC
TTCCTGCCCCAGACCTCGTTGCCCTCCCCCGTCCACTTACACACAGGCCAGGAAGCTGTTCCCACACAGACCAACCC
CAGACGGGGACCACCTGGCACTCAGGTCACTGCCATTTCCTTCTCCATTCACTTCCAATGCCTCTGTGCTTCCTCCC
TCCTCCTTCCTTCGGGGGAGCACCCTGTGCAGCTCCTCCCTGCAGTCCACACCCTGGGGAGACCCGACCCTGCAGCC
CACACCCTGGGGAGACCTGACCCTCCTCCAGCCCTTTCTCCCCCGCTGCTCTTGCCACCCACCAAGACAGCCCTGGG
GTCCTGTCCCTACAGCCCCCACCCAGTTCTCTACCTAGACCCGTCTTCCTCCCTCTAAACACCTCTCCCAGGCCAAC
CCTACACCTGCAGGCCCTCCCCTCCACTGCCAAAGACCCTCAGTTTCTCCTGCCTGTGCCCACCCCCGTGCTCCTCC
TGCCCACAGCTCGAGCTCTTCCTCTCCTAGGGCCCCTGAGGGATGGCATTGACCGTGCCCTCGCACCCACACACTGC
CCATGCCCTCACATTCCTCCTGGCCACTCCAGCCCCACTCCCCTCTCAGGCCTGGCTCTGGTATTTCTGGGACAAAG
CCTTACCCAAGTCTTTCCCATGCAGGCCTGGGCCCTTACCCTCACTGCCCGGTTACAGGGCAGCCTCCTGTGCACAG
AAGCAGGGAGCTCAGCCCTTCCACAGGCAGAAGGCACTGAAAGAAATCGGCCTCCAGCGCCTTGACACACGTCTGCC
TGTGTCTCTCACTGCCCGCACCTGCAGGGAGGCTCGGCACTCCCTCTAAAGACGAGGGATCCAGGCAGCAGCATCAC
AGGAGAATGCAGGGCTACCAGACATCCCAGTCCTCTCACAGGCCTCTCCTGGGAAGAGACCTGAAGACGCCCAGTCA
ACGGAGTCTAACACCAAACCTCCCTGGAGGCCGATGGGTAGTAACGGAGTCATTGCCAGACCTGGAGGCAGGGGAGC

Fig. 3 (cont.)

AGTGAGCCCGAGCCCACACCATAGGGCCAGAGGACAGCCACTGACATCCCAAGCCACTCACTGGTGGTCCCACAACA
CCCCATGGAAAGAGGACAGACCCACAGTCCCACCTGGACCAGGGCAGAGACTGCTGAGACCCAGCACCAGAACCAAC
CAAGAAACACCAGGCAACAGCATCAGAGGGGGCTCTGGCAGAACAGAGGAGGGGAGGTCTCCTTCACCAGCAGGCGC
TTCCCTTGACCGAAGACAGGATCCATGCAACTCCCCCAGGACAAAGGAGGAGCCCCTTGTTCAGCACTGGGCTCAGA
GTCCTCTCCAAGACACCCAGAGTTTCAGACAAAAACCCCCTGGAATGCACAGTCTCAGCAGGAGAGCCAGCCAGAGC
CAGCAAGATGGGGCTCAGTGACACCCGCAGGGACAGGAGGATTTTGTGGGGGCTCGTGTCACTGTG[redacted]
CACAGTGACACAGCCCCATTCCCAAAGCCCTACTGCAAACGCATTCCACTTCTGGGG
D2-8
CTGAGGGGCTGGGGGAGCGTCTGGGAAATAGGGCTCAGGGGTGTCCATCAATGCCCAAAACGCACCAGACTCCCCTC
CATACATCACACCCACCAGCCAGCGAGCAGAGTAAACAGAAAATGAGAAGCAAGCTGGGAAGCTTGCACAGGCCCC
AAGGAAAGAGCTTTGGCGGGTGTGTAAGAGGGGATGCGGGCAGAGCCTGAGCAGGGCCTTTTGCTGTTTCTGCTTTC
CTGTGCAGAGAGTTCCATAAACTGGTGTTCGAGATCAATGGCTGGGAGTGAGCCCAGGAGGACAGCGTGGGAAGAGC
ACAGGGAAGGAGGACCAGCCGCTATCCTACACTGTCATCTTTCGAAAGTTTGCCTTGTGCCCACACTGCTGCATCAT
GGGATGCTTAACAGCTGATGTAGACACAGCTAAAGAGAGAATCAGTGAGATGGATTTGCAGCACAGATCTGAATAAA
TTCTCCAGAATGTGGAGCAGCACAGAAGCAAGCACACAGAAAGTGCCTGATGCAAGGACAAAGTTCAGTGGGCACCT
TCAGGCATTGCTGCTGGGCACAGACACTCTGAAAAGCCCTGGCAGGAACTCCCTGTGACAAAGCAGAACCCTCAGGC
AATGCCAGCCCCAGAGCCCTCCCTGAGAGCCTCATGGGCAAAGATGTGCACAACAGGTGTTTCTCATAGCCCCAAAC
TGAGAGCAAAGCAAACGTCCATCTGAAGGAGAACAGGCAAATAAACGATGGCAGGTTCATGAAATGCAAACCCAGAC
AGCCACAAGCACAAAAGTACAGGGTTATAAGCGACTCTGGTTGAGTTCATGACAATGCTGAGTAATTGGAGTAACAA
AGTAAACTCCAAAAAATACTTTCAATGTGATTTCTTCTAAATAAAATTTACACCCTGCAAAATGAACTGTCTTCTTA
AGGGATACATTTCCCAGTTAGAAAACCATAAAGAAAACCAAGAAAAGGATGATCACATAAACACAGTGGTGGTTACT
TCTGCTGGGGAAGGAAGAGGGTATGAACTGAGATACACAGGGTGGGCAAGTCTCCTAACAAGAACAGAACGAATACA
TTACAGTACCTTGAAAACAGCAGTTAAACTTCTAAATTGCAAGAAGAGGAAAATGCACACAGTTGTGTTTAGAAAAT
TCTCAGTCCAGCACTGTTCATAATAGCAAAGACATTAACCCAGGTCGGATAAATAAGCGATGACACAGGCAATTGCA
CAATGATACAGACATATATTTAGTATATGAGACATCGATGATGTATCCCCAAATAAACGACTTTAAAGAGATAAAGG
GCTGATGTGTGGTGGCATTCACCTCCCTGGGATCCCCGGACAGGTTGCAGGCTCACTGTGCAGCAGGGCAGGCGGGT
ACCTGCTGGCAGTTCCTGGGGCCTGATGTGGAGCAAGCGCAGGGCCATATATCCCGGAGGACGGCACAGTCAGTGAA
TTCCAGAGAGAAGCAACTCAGCCACACTCCCCAGGCAGAGCCCGAGAGGGACGCCCACGCACAGGGAGGCAGAGCCC
AGCACCTCCGCAGCCAGCACCACCTGTGCACGGGCCACCACCTTGCAGGCACAGAGTGGGTGCTGAGAGGAGGGGCA
GGGACACCAGGCAGGGTGAGCACCCAGAGAAAACTGCAGACGCCTCACACATCCACCTCAGCCTCCCCTGACCTGGA
CCTCACTGGCCTGGGCCTCACTTAACCTGGGCTTCACCTGACCTTGGCCTCACCTGACTTGGACCTCGCCTGTCCCA
AGCTTTACCTGACCTGGGCCTCAACTCACCTGAACGTCTCCTGACCTGGGTTTAACCTGTCCTGGAACTCACCTGGC
CTTGGCTTCCCCTGACCTGGACCTCATCTGGCCTGGGCTTCACCTGGCCTGGGCCTCACCTGACCTGGACCTCATCT
GGCCTGGACCTCACCTGGCCTGGACTTCACCTGGCCTGGGCTTCACCTGACCTGGACCTCACCTGGCCTCAGGCCTC
ACCTGCACCTGCTCCAGGTCTTGCTGGAGCCTGAGTAGCACTGAGGGTGCAGAAGCTCATCCAGGGTTGGGAATGA
CTCTAGAAGTCTCCCACATCTGACCTTTCTGGGTGGAGGCAGCTGGTGGCCCTGGGAATATAAAAATCTCCAGAATG
ATGACTCTGTGATTTGTGGGCAACTTATGAACCCGAAAGGACATGGCCATGGGGTGGGTAGGGACATAGGGACAGAT
GCCAGCCTGAGGTGGAGCCTCAGGACACAGGTGGGCACGGACACTATCCACATAAGCGAGGGATAGACCCGAGTGTC
CCCACAGCAGACCTGAGAGCGCTGGGCCCACAGCCTCCCCTCAGAGCCCTGCTGCCTCCTCCGGTCAGCCCTGGACA
TCCCAGGTTTCCCCAGGCCTGGCGGTAGGTTTAGAATGAGGTCTGTGTCACTGTG[redacted]
CACAGTGTCACAGAGTCCATCAAAAACCCATGCCTGGAAGCTTCCCGCCACAGCCCTCCCCATGGGGC
D3-9
CCTGCTGCCTCCTCAGGTCAGCCCCGGACATCCTGGGTTTCCCCAGGCTGGGCGGTAGGTTTGGGGTGAGGTCTGTG
TCACTGTG[redacted]CACAGTGTCACAGAGTCCATCAAAAACCCATCCCTGGG
D3-10
AGCCTCCCGCCACAGCCCTCCCTGCAGGGGACCGGTACGTGCCATGTTAGGATTTTGATCGAGGAGACAGCACCATG
GGTATGGTGGCTACCACAGCAGTGCAGCCTGTGACCCAAACCCGCAGGGCAGCAGGCACGATGGACAGGCCCGTGAC
TGACCACGCTGGGCTCCAGCCTGCCAGCCCTGGAGATCATGAAACAGATGGCCAAGGTCACCCTACAGGTCATCCAG
ATCTGGCTCCGAGGGGTCTGCATCGCTGCTGCCCTCCCAACGCCAGTCCAAATGGGACAGGGACGGCCTCACAGCAC
CATCTGCTGCCATCAGGCCAGCGATCCCAGAAGCCCCTCCCTCAAGGCTGGCCACATGTGTGGACACTGAGAGCCCT
CATATCTGAGTAGGGGCACCAGGAGGGAGGGGCTGGCCCTGTGCACTGTCCCTGCTCCTGTGGTCTCTGGCCTGCCT
GGCCCTGACACCTGAGCCTCTCCTGGGTCATTTCCAAGACAGAAGACATTCCTGGGGACAGCCGGAGCTGGGCGTCG
CTCATCCTGCCCGGCCGTCCTGAGTCCTGCTCATTTCCAGACCTCACCGGGGAAGCCAACAGAGGACTCGCCTCCCA

Fig. 3 (cont.)

CATTCAGAGACAAAGAACCTTCCAGAAATCCCTGCCTCTCTCCCCAGTGGACACCCTCTTCCAGGACAGTCCTCAGT
GGCATCACAGCGGCCTGAGATCCCCAGGACGCAGCACCGCTGTCAATAGGGGCCCCAAATGCCTGGACCAGGGCCTG
CGTGGGAAAGGCCTCTGGCCACACTCGGGCTTTTTGTGAAGGGCCCTCCTGCTGTG[redacted]CATAG
D4-11
TGATGAACCCAGTGGCAAAAACTGGCTGGAAACCCAGGGGCTGTGTGCACGCCTCAGCTTGGAGCTCTCCAGGAGCA
CAAGAGCCGGGCCCAAGGATTTGTGCCCAGACCCTCAGCCTCTAGGGACACCTGGGCCATCTCAGCCTGGGCTGGTG
CCCTGCACACCATCTTCCTCCAAATAGGGGCTTCAGAGGGCTCTGAGGTGACCTCACTCATGACCACAGGTGACCTG
GCCCTTCCCTGCCAGCTATACCAGACCCTGTCTTGACAGATGCCCCGATTCCAACAGCCAATTCCTGGGACCCTGAA
TAGCTGTAGACACCAGCCTCATTCCAGTACCTCCTGCCAATTGCCTGGATTCCCATCCTGGCTGGAATCAAGAAGGC
AGCATCCGCCAGGCTCCCAACAGGCAGGACTCCCGCACACCCTCCTCTGAGAGGCCGCTGTGTTCCGCAGGGCCAGG
CCCTGGACAGTTCCCCTCACCTGCCACTAGAGAAACACCTGCCATTGTCGTCCCCACCTGGAAAAGACCACTCGTGG
AGCCCCCAGCCCCAGGTACAGCTGTAGAGACAGTCCTCGAGGCCCCTAAGAAGGAGCCATGCCCAGTTCTGCCGGGA
CCCTCGGCCAGGCCGACAGGAGTGGACGCTGGAGCTGGGCCCACACTGGGCCACATAGGAGCTCACCAGTGAGGGCA
GGAGAGCACATGCCGGGGAGCACCCAGCCTCCTGCTGACCAGAGGCCTGCCCCAGAGCCCAGGAGGCTGCAGAGGCC
TCTCCAGGGAGACACTGTGCATGTCTGGTACCTAAGCAGCCCCCCACGTCCCCAGTCCTGGGGGCCCCTGGCTCAGC
TGTCTGGGCCCTCCCTGCTCCCTGGGAAGCTCCTCCTGACAGCCCCGCCTCCAGTTCCAGGTGTGGTTATTGTCAGG
CGATGTCAGACTGTG[redacted]CACAGTGGTGCCGCCCATAGCAGCAACCAGGCCAAGTAG
D5-12
ACAGGCCCCTGCTGCGCAGCCCCAGGCATCCACTTCACCTGCTTCTCCTGGGGCTCTCAAGGCTGCTGTCTGTCCTC
TGGCCCTCTGTGGGGAGGGTTCCCTCAGTGGGAGGTCTGTGCTCCAGGGCAGGGATGATTGAGATAGAAATCAAAGG
CTGGCAGGGAAAGGCAGCTTCCCGCCCTGAGAGGTGCAGGCAGCACCACGGAGCCACGGAGTCACAGAGCCACGGAG
CCCCCATTGTGGGCATTTGAGAGTGCTGTGCCCCCGGCAGGCCCAGCCCTGATGGGGAAGCCTGTCCCATCCCACAG
CCCGGGTCCCACGGGCAGCGGGCACAGAAGCTGCCAGGTTGTCCTCTATGATCCTCATCCCTCCAGCAGCATCCCCT
CCACAGTGGGGAAACTGAGGCTTGGAGCACCACCCGGCCCCCTGGAAATGAGGCTGTGAGCCCAGACAGTGGGCCCA
GAGCACTGTGAGTACCCCGGCAGTACCTGGCTGCAGGGATCAGCCAGAGATGCCAAACCCTGAGTGACCAGCCTACA
GGAGGATCCGGCCCCACCCAGGCCACTCGATTAATGCTCAACCCCCTGCCCTGGAGACCTCTTCCAGTACCACCAGC
AGCTCAGCTTCTCAGGGCCTCATCCCTGCAAGGAAGGTCAAGGGCTGGGCCTGCCAGAAACACAGCACCCTCCCTAG
CCCTGGCTAAGACAGGGTGGGCAGACGGCTGTGGACGGGACATATTGCTGGGGCATTTCTCACTGTCACTTCTGGGT
GGTAGCTCTGACAAAAACGCAGACCCTGCCAAAATCCCCACTGCCTCCCGCTAGGGGCTGGCCTGGAATCCTGCTGT
CCTAGGAGGCTGCTGACCTCCAGGATGGCTCCGTCCCCAGTTCCAGGGCGAGAGCAGATCCCAGGCAGGCTGTAGGC
TGGGAGGCCACCCCTGCCCTTGCCGGGGTTGAATGCAGGTGCCCAAGGCAGGAAATGGCATGAGCACAGGGATGACC
GGGACATGCCCCACCAGAGTGCGCCCCTTCCTGCTCTGCACCCTGCACCCCCCAGGCCAGCCCACGACGTCCAACAA
CTGGGCCTGGGTGGCAGCCCCACCCAGACAGGACAGACCCAGCACCCTGAGGAGGTCCTGCCAGGGGGAGCTAAGAG
CCATGAAGGAGCAAGATATGGGGCCCCCGATACAGGCACAGATGTCAGCTCCATCCAGGACCACCCAGCCCACACCC
TGAGAGGAACGTCTGTCTCCAGCCTCTGCAGGTCGGGAGGCAGCTGACCCCTGACTTGGACCCCTATTCCAGACACC
AGACAGAGGCGCAGGCCCCCCAGAACCAGGGTTGAGGGACGCCCCGTCAAAGCCAGACAAAACCAAGGGGTGTTGAG
CCCAGCAAGGGAAGGCCCCCAAACAGACCAGGAGGTTTCTGAAGGTGTCTGTGTCACAGTG[redacted]CACAGTGACACTCACCCAGCCAGAAACCCCATTCCAAGTCAGCGGAAGCAGAGAGAGCAGGGAGGACACGTT
D6-13
TAGGATCTGAGACTGCACCTGACACCCAGGCCAGCAGACGTCTCCCCTCCAGGGCACCCCACCCTGTCCTGCATTTC
TGCAAGATCAGGGGCGGCCTGAGGGGGGGTCTAGGGTGAGGAGATGGGTCCCCTGTACACCAAGGAGGAGTTAGGCA
GGTCCCGAGCACTCTCCCCATTGAGGCTGACCTGCCCAGAGAGTCCTGGGCCCACCCCACACACCGGGGCGGAATGT
GTGCAGGCCTCGGTCTCTGTGGGTGTTCCGCTAGCTGGGGCTCACAGTGCTCACCCCACACCTAAAATGAGCCACAG
CCTCCGGAGCCCCCGCAGGAGACCCCGCCCACAAGCCCAGCCCCCACCCAGGAGGCCCCAGAGCTCAGGGCGCCCCG
TCGGATTCCGAACAGCCCCGAGTCACAGCG[redacted]CACTGTCAGAATAGCTACGTCAAAAACTGT
D1-14
CCAGTGGCCACTGCCGGAGGCCCCGCCAGAGAGGGCAGCAGCCACTCTGATCCCATGTCCTGCCGGCTCCCATGACC
CCCAGCACGCGGAGCCCCACAGTGTCCCCACTGGATGGGAGGACAAGAGCTGGGGATTCCGGCGGGTCGGGGCAGGG
GCTTGATCGCATCCTTCTGCCGTGGCTCCAGTGCCCCTGGCTGGAGTTGACCCTTCTGACAAGTGTCCTCAGAGAGA
CAGGCATCACCGGCGCCTCCCAACATCAACCCCAGGCAGCACAGGCACAAACCCCACATCCAGAGCCAACTCCAGGA
GCAGAGACACCCCAATACCCTGGGGGACCCCGACCCTGATGACTTCCCACTGGAATTCGCCGTAGAGTCCACCAGGA
CCAAAGACCCTGCCTCTGCCTCTGTCCCTCACTCAGGACCTGCTGCCGGGCGAGGCCTTGGGAGCAGACTTGGGCTT
AGGGGACACCAGTGTGACCCCGACCTTGACCAGGACGCAGACCTTTCCTTCCTTTCCTGGGGCAGCACAGACTTTGG

Fig. 3 (cont.)

GGTCTGGGCCAGGAGGAACTTCTGGCAGGTCGCCAAGCACAGAGGCCACAGGCTGAGGTGGCCCTGGAAAGACCTCC
AGGAGGTGGCCACTCCCCTTCCTCCCAGCTGGACCCCATGTCCTCCCCAAGATAAGGGTGCCATCCAAGGCAGGTGC
TCCTTGGAGCCCCATTCAGACTCCTCCCTGGACCCCACTGGGCCTCAGTCCCAGCTCTGGGGATGAAGCCACCACAA
GCACACCAGGCAGCCCAGGCCCAGCCACCCTGCAGTGCCCAAGCACACACTCTGGAGCAGAGCAGGGTGCCTCTGGG
AGGGGCTGAGCTCCCCACCCCACCCCCACCTGCACACCCCACCCACCCCTGCCCAGCGGCTCTGCAGGAGGGTCAGA
GCCCCACATGGGGTATGGACTTAGGGTCTCACTCACGTGGCTCCCATCATGAGTGAAGGGGCCTCAAGCCCAGGTTC
CCACAGCAGCGCCTGTCGCAAGTGGAGGCAGAGGCCCGAGGGCCACCCTGACCTGGTCCCTGAGGTTCCTGCAGCCC
AGGCTGCCCTGCTGTCCCTGGGAGGCCTGGGCTCCACCAGACCACAGGTCCAGGGCACCGGGTGCAGGAGCCACCCA
CACACAGCTCACAGGAAGAAGATAAGCTCCAGACCCCCAGGGCCAGAACCTGCCTTCCTGCTACTGCTTCCTGCCCC
AGACCTGGGCGCCCTCCCCCGTCCACTTACACACAGGCCAGGAAGCTGTTCCCACACAGAACAACCCCAAACCAGGA
CCGCCTGGCACTCAGGTGGCTGCCATTTCCTTCTCCATTTGCTCCCAGCGCCTCTGTCCTCCCTGGTTCCTCCTTCG
GGGGAACAGCCTGTGCAGCCAGTCCCTGCAGCCCACACCCTGGGGAGACCCAACCCTGCCTGGGGCCCTTCCAACCC
TGCTGCTCTTACTGCCCACCCAGAAAACTCTGGGGTCCTGTCCCTGCAGTCCCTACCCTGGTCTCCACCCAGACCCC
TGTGTATCACTCCAGACACCCCTCCCAGGCAAACCCTGCACCTGCAGGCCCTGTCCTCTTCTGTCGCTAGAGCCTCA
GTTTCTCCCCCCTGTGCCCACACCCTACCTCCTCCTGCCCACAACTCTAACTCTTCTTCTCCTGCAGCCCCTGAGCC
ATGGCATTGACCCTGCCCTCCCACCACCCACAGCCCATGCCCTCACCTTCCTCCTGGCCACTCCGACCCCGCCCCCT
CTCAGGCCAAGCCCTGGTATTTCCAGGACAAAGGCTCACCCAAGTCTTTCCCAGGCAGGCCTGGGCTCTTGCCCTCA
CTTCCCGGTTACACGGGAGCCTCCTGTGCACAGAAGCAGGGAGCTCAGCCCTTCCACAGGCAGAAGGCACTGAAAGA
AATCGGCCTCCAGCACCTTGACACACGTCCGCCCGTGTCTCTCACTGCCCGCACCTGCAGGGAGGCTCCGCACTCCC
TCTAAAGACAAGGGATCCAGGCAGCAGCATCACGGGAGAATGCAGGGCTCCCAGACATCCCAGTCCTCTCACAGGCC
TCTCCTGGGAAGAGACCTGCAGCCACCACCAAACAGCCACAGAGGCTGCTGGATAGTAACTGAGTCAATGACCGACC
TGGAGGGCAGGGGAGCAGTGAGCCGGAGCCCATACCATAGGGACAGAGACCAGCCGCTGACATCCCGAGCTCCTCAA
TGGTGGCCCCATAACACACCTAGGAAACATAACACACCCACAGCCCCACCTGGAACAGGGCAGAGACTGCTGAGCCC
CCAGCACCAGCCCCAAGAAACACCAGGCAACAGTATCAGAGGGGGCTCCCGAGAAAGAGAGGAGGGGAGATCTCCTT
CACCATCAAATGCTTCCCTTGACCAAAAACAGGGTCCACGCAACTCCCCCAGGACAAAGGAGGAGCCCCCTATACAG
CACTGGGCTCAGAGTCCTCTCTGAGACACCCTGAGTTTCAGACAACAACCCGCTGGAATGCACAGTCTCAGCAGGAG
AACAGACCAAAGCCAGCAAAAGGGACCTCGGTGACACCAGTAGGGACAGGAGGATTTTGTGGGGGCTCGTGTCACTG
TG[redacted]CACAGTGACACAGACCCATTCCCAAAGCCCTACTGCAAACACAC
D2-15
CCACTCCTGGGGCTGAGGGGCTGGGGGAGCATCTGGGAAGTAGGGTCCAGGGGTGTCTATCAATGTCCAAAATGCAC
CAGACTCCCCGCCAAACACCACCCCACCAGCCAGCGAGCAGGGTAAACAGAAAATGAGAGGCTCTGGGAAGCTTGCA
CAGGCCCCAAGGAAAGAGCTTTGGCAGGTGTGCAAGAGGGGATGCAGGCAGAGCCTGAGCAGGGCCTTTTGCTGTTT
CTGCTTTCCTGTGCAGAGAGTTCCATAAACTGGTGTTCAAGATCAGTGGCTGGGAATGAGCCCAGGAGGGCAGTCTG
TGGGAAGAGCACAGGGAAGGAGGACCAGCCGCTATCCTACACTGTCATCTTTCAAAAGTTTGCCTTGTGACCACACT
ATTGCATCATGGGATGCTTAAGAGCTGATGTAGACACAGCTAAAGAGAGAATCAGTGAGATGAATTTGCAGCATAGA
TCTGAATAAACTCTCCAGAATGTGGAGCAGTACAGAAGCAAACACACAGAAAGTGCCTGATGCAAGGACAAAGTTCA
GTGGGCACCTTCAGGCATTGCTGCTGGGCACAGACACTCTGAAAAGCCCTGGCAGGATCTCCCTGCGACAAAGCAGA
ACCCTCAGGCAATGCCAGCCCCAGAGCCCTCCCTGAGAGCGTCATGGGGAAAGATGTGCAGAACAGCTGATTATCAT
AGACTCAAACTGAGAACAGAGCAAACGTCCATCTGAAGAACAGTCAAATAAGCAATGGTAGGTTCATGCAATGCAAA
CCCAGACAGCCAGGGGACAACAGTAGAGGGCTACAGGCGGCTTTGCGGTTGAGTTCATGACAATGCTGAGTAATTGG
AGTAACAGAGGAAAGCCCAAAAAATACTTTTAATGTGATTTCTTCTAAATAAAATTTACACCAGGCAAAATGAACTG
TCTTCTTAAGGGATAAACTTTCCCCTGGAAAAACTACAAGGAAAATTAAGAAAACGATGATCACATAAACACAGTTG
TGGTTACTTCTACTGGGGAAGGAAGAGGGTATGAGCTGAGACACACAGAGTCGGCAAGTCTCCAAGCAAGCACAGAA
CGAATACATTACAGTACCTTGAATACAGCAGTTAAACTTCTAAATCGCAAGAAGAGGAAAATGCACACAGCTGTGTT
TAGAAAATTCTCAGTCCAGCACTATTCATAATAGCAAAGACATTAACCCAGGTTGGATAAATAAATGATGACACAGG
CAATTGCACAATGATACAGACATACATTTAGTACATGAGACATCGATGATGTATCCCCAAAGAAATGACTTTAAAGA
GAAAAGGCCTGATGTGTGGTGGCACTCACCTCCCTGGGATCCCCGGACAGGTTGCAGGCACACTGTGTGGCAGGGCA
GGCTGGTACATGCTGGCAGCTCCTGGGGCCTGATGTGGAGCAAGCGCAGGGCTGTATACCCCCAAGGATGGCACAGT
CAGTGAATTCCAAAGAGAAGCAGCTCAGCCACACTGCCCAGGCAGAGCCCGAGAGGGACGCCCACGCACAGGGAGGC
AGAGCCCAGCTCCTCCACAGCCACCACCACCTGTGCACGGGCCACCACCTTGCAGGCACAGAGTGGGTGCTGAGAGG
AGGGGCAGGGACACCAGGCAGGGTGAGCACCCAGAGAAAACTGCAGAAGCCTCACACATCCACCTCAGCCTCCCCTG
ACCTGGACCTCACCTGGTCTGGACCTCACCTGGCCTGGGCCTCACCTGACCTGGACCTCACCTGGCCTGGGCTTCAC
CTGACCTGGACCTCACCTGGCCTCCGGCCTCACCTGCACCTGCTCCAGGTCTTGCTGGAACCTGAGTAGCACTGAGG

Fig. 3 (cont.)

CTGCAGAAGCTCATCCAGGGTTGGGGAATGACTCTGGAACTCTCCCACATCTGACCTTTCTGGGTGGAGGCATCTGG
TGGCCCTGGGAATATAAAAAGCCCCAGAATGGTGCCTGCGTGATTTGGGGGCAATTTATGAACCCGAAAGGACATGG
CCATGGGGTGGGTAGGGACATAGGGACAGATGCCAGCCTGAGGTGGAGCCTCAGGACACAGTTGGACGCGGACACTA
TCCACATAAGCGAGGGACAGACCCGAGTGTTCCTGCAGTAGACCTGAGAGCGCTGGGCCCACAGCCTCCCCTCGGTG
CCCTGCTGCCTCCTCAGGTCAGCCCTGGACATCCCGGGTTTCCCCAGGCCAGATGGTAGG[redacted]CACAGCATCACACGGTCCATCAGAAACCCAT
D3-16
GCCACAGCCCTCCCCGCAGGGGACCGCCGCGTGCCATGTTACGATTTTGATCGAGGACACAGCGCCATGGGTATGGT
GGCTACCACAGCAGTGCAGCCCATGACCCAAACACACAGGGCAGCAGGCACAATGGACAGGCCTGTGAGTGACCATG
CTGGGCTCCAGCCCGCCAGCCCCGGAGACCATGAAACAGATGGCCAAGGTCACCCCACAGTTCAGCCAGACATGGCT
CCGTGGGGTCTGCATCGCTGCTGCCCTCTAACACCAGCCCAGATGGGGACAAGGCCAACCCCACATTACCATCTCCT
GCTGTCCACCCAGTGGTCCCAGAAGCCCCTCCCTCATGGCTGAGCCACATGTGTGAACCCTGAGAGCACCCCATGTC
AGAGTAGGGGCAGCAGAAGGGCGGGGCTGGCCCTGTGCACTGTCCCTGCACCCATGGTCCCTCGCCTGCCTGGCCCT
GACACCTGAGCCTCTTCTGAGTCATTTCTAAGATAGAAGACATTCCCGGGGACAGCCGGAGCTGGGCGTCGCTCATC
CTGCCCGGCCGTCCTGAGTCCTGCTTGTTTCCAGACCTCACCAGGGAAGCCAACAGAGGACTCACCTCACACAGTCA
GAGACAAAGAACCTTCCAGAAATCCCTGTCTCACTCCCCAGTGGGCACCTTCTTCCAGGACATTCCTCGGTCGCATC
ACAGCAGGCACCCACATCTGGATCAGGACGGCCCCCAGAACACAAGATGGCCCATGGGGACAGCCCCACAACCCAGG
CCTTCCCAGACCCCTAAAAGGCGTCCCACCCCCTGCACCTGCCCCAGGGCTAAAAATCCAGGAGGCTTGACTCCCGC
ATACCCTCCAGCCAGACATCACCTCAGCCCCCTCCTGGAGGGGACAGGAGCCCGGGAGGGTGAGTCAGACCCACCTG
CCCTCGATGGCAGGCGGGGAAGATTCAGAAAGGCCTGAGATCCCCAGGACGCAGCACCACTGTCAATGGGGGCCCCA
GACGCCTGGACCAGGGCCTGCGTGGGAAAGGCCGCTGGGCACACTCAGGGGCTTTTTGTGAAGGCCCCTCCTACTGT
G[redacted]CACAGTGATGAAACTAGCAGCAAAAACTGGCCGGACACCCAGGGACCATGCACACTTCTC
D3-17
AGCTTGGAGCTCTCCAGGACCAGAAGAGTCAGGTCTGAGGGTTTGTAGCCAGACCCTCGGCCTCTAGGGACACCCTG
GCCATCACAGCGGATGGGCTGGTGCCCCACATGCCATCTGCTCCAAACAGGGGCTTCAGAGGGCTCTGAGGTGACTT
CACTCATGACCACAGGTGCCCTGGCCCCTTCCCCGCCAGCTACACCGAACCCTGTCCCAACAGCTGCCCCAGTTCCA
ACAGCCAATTCCTGGGGCCCAGAATTGCTGTAGACACCAGCCTCGTTCCAGCACCTCCTGCCAATTGCCTGGATTCA
CATCCTGGCTGGAATCAAGAGGGCAGCATCCGCCAGGCTCCCAACAGGCAGGACTCCCGCACACCCTCCTCTGAGAG
GCCGCTGTGTTCCGCAGGGCCAGGCCCTGGACAGTTCCCCTCACCTGCCACTAGAGAAACACCTGCCATTGTCGTCC
CCACCTGGAAAAGACCACTCGTGGAGCCCCCAGCCCCAGGTACAGCTGTAGAGAGACTCCCCGAGGGATCTAAGAAG
GAGCCATGCGCAGTTCTGCCGGGACCCTCGGCCAGGCCGACAGGAGTGGACACTGGAGCTGGGCCCACACTGGGCCA
CATAGGAGCTCACCAGTGAGGGCAGGAGAGCACATGCCGGGGAGCACCCAGCCTCCTGCTGACCAGAGGCCTGCCCC
AGAGCCCAGGAGGCTGCAGAGGCCTCTCCAGGGGGACACTGTGCATGTCTGGTCCCTGAGCAGCCCCCCACGTCCCC
AGTCCTGGGGGCCCCTAGCACAGCTGTCTGGACCCTCCCTGTTCCCTGGGAAGCTCCTCCTGACAGCCCCGCCTCCA
GTTCCAGGTGTGGTTATTGTCAGGGGGTGTCAGACTGTG[redacted]CACAGTGGTGCTGCCCAT
D5-18
AGCAGCAACCAGGCCAAGTAGACAGGCCCCTGCTGTGCAGCCCCAGGCCTCCAGCTCACCTGCTTCTCCTGGGGCTC
TCAAGGTCACTGTTGTCTGTACTCTGCCCTCTGTGGGGAGGGTTCTCTCAGTGGGAGGTCTGTTCTCAACATCCCAG
GGCCTCATGTCTGCACGGAAGGCCAATGGATGGGCAACCTCACATGCCGCGGCTAAGATAGGGTGGGCAGCCTGGCG
GGGGACAGTACATACTGCTGGGGTGTCTGTCACTGTGCCTAGTGGGGCACTGGCTCCCAAACAACGCAGTCCTCACC
AAAATCCCCACAGCCTCCCCTGCTAGGGGCTGGCCTGATCTCCTGCAGTCCTAGGAGGCTGCTGACCTCCAGAATGT
CTCCGTCCCCAGTTCCAGGGCGAGAGCAGATCCCAGGCCGGCTGCAGACTGGGAGGCCACCCCCTCCTTCCCAGGGT
TCACTGGAGGTGACCAAGGTAGGAAATGGCCTTAACACAGGGATGACTGCGCCATCCCCCAACAGAGTCAGCCCCCT
CCTGCTCTGTACCCCGCACCCCCCAGGCCAGTCCACGAAAACCAGGGCCCCACATCAGAGTCACTGCCTGGCCCGGC
CCTGGGGCGGACCCCTCAGCCCCCACCCTGTCTAGAGGACTTGGGGGGACAGGACACAGGCCCTCTCCTTATGGTTC
CCCCACCTGCCTCCGGCCGGGACCCTTGGGGTGTGGACAGAAAGGACACCTGCCTAATTGGCCCCCAGGAACACAGA
ACTTCTCTCCAGGGACCCCAGCCCGAGCACCCCCTTACCCAGGACCCAGCCCTGCCCCTCCTCCCCTCTGCTCTCCT
CTCATCACCCCATGGGAATCCGGTATCCCCAGGAAGCCATCAGGAAGGGCTGAAGGAGGAAGCGGGGCCGTGCACCA
CCGGGCAGGAGGCTCCGTCTTCGTGAACCCAGGGAAGTGCCAGCCTCCTAGAGGGTATGGTCCACCCTGCCTGGGGC
TCCCACCGTGGCAGGCTGCGGGGAAGGACCAGGGACGGTGTGGGGGAGGGCTCAGGGCCCTGCGGGTGCTCCTCCAT
CTTCGGTGAGCCTCCCCCTTCACCCACCGTCCCGCCCACCTCCTCTCCACCCTGGCTGCACGTCTTCCACACCATCC
TGAGTCCTACCTACACCAGAGCCAGCAAAGCCAGTGCAGACAAAGGCTGGGGTGCAGGGGGGCTGCCAGGGCAGCTT
CGGGGAGGGAAGGATGGAGGGAGGGGAGGTCAGTGAAGAGGCCCCCTTCCCCTGGGTCCAGGATCCTCCTCTGGGAC

Fig. 3 (cont.)

CCCCGGCTCCCATCCCCTCCTGGCTCTGGGAGGAGAAGCAGGATGGGAGAATCTGTGCGGGACCCTCTCACAGTGGA
ATATCCCCACAGCGGCTCAGGCCAGACCCAAAAGCCCCTCAGTGAGCCCTCCACTGCAGTCCTGGGCCTGGGTAGCA
GCCCCTCCCACAGAGGACAGACCCAGCACCCCGAAGAAGTCCTGCCAGGGGGAGCTCAGAGCCATGAAAGAGCAGGA
TATGGGGTCCCCGATACAGGCACAGACCTCAGCTCCATCCAGGCCCACCGGGACCCACCATGGGAGGAACACCTGTC
TCCGGGTTGTGAGGTGGCTGGCCTCTGTCTCGGACCCCACTCCAGACACCAGACAGAGGGGCAGGCCCCCCAAAACC
AGGGTTGAGGGATGATCCGTCAAGGCAGACAAGACCAAGGGGCACTGACCCCAGCAAGGGAAGGCTCCCAAACAGAC
GAGGAGGTTTCTGAAGCTGTCTGTATCACAGTG[redacted]CACAGTGACACTCGCCAGGCCAG
D6-19
AAACCCCGTCCCAAGTCAGCGGAAGCAGAGAGAGCAGGGAGGACACGTTTAGGATCTGAGGCCGCACCTGACACCCA
GGGCAGCAGACGTCTCCCCTCCAGGGCACCCTCCACCGTCCTGCGTTTCTTCAAGAATAGGGGCGGCCTGAGGGGGT
CCAGGGCCAGGCGATAGGTCCCCTCTACCCCAAGGAGGAGCCAGGCAGGACCCGAGCACCGTCCCCATTGAGGCTGA
CCTGCCCAGACGGGCCTGGGCCCACCCCACACACCGGGGCGGAATGTGTGCAGGCCCCAGTCTCTGTGGGTGTTCCG
CTAGCTGGGGCCCCCAGTGCTCACCCCACACCTAAAGCGAGCCCCAGCCTCCAGAGCCCCCTAAGCATTCCCCGCCC
AGCAGCCCAGCCCCTGCCCCCACCCAGGAGGCCCCAGAGCTCAGGGCGCCTGGTCGGATTCTGAACAGCCCCGAGTC
ACAGTG[redacted]CACCGTGAGAAAAACTGTGTCCAAAACTGACTCCTGGCAGCAGTCGGAGGCCCC
D1-20
GCCAGAGAGGGGAGCAGCCGCCCTGAACCCATGTCCTGCCGGTTCCCATGACCCCCAGCACCCAGAGCCCCACGGTG
TCCCCGTTGGATAATGAGGACAAGGGCTGGGGGCTCCGGTGGTTTGCGGCAGGGACTTGATCACATCCTTCTGCTGT
GGCCCCATTGCCTCTGGCTGGAGTTGACCCTTCTGACAAGTGTCCTCAGAAAGACAGGGATCACCGGCACCTCCCAA
TATCAACCCCAGGCAGCACAGACACAAACCCCACATCCAGAGCCAACTCCAGGAGCAGAGACACCCCAACACTCTGG
GGGACCCCAACCGTGATAACTCCCCACTGGAATCCGCCCCAGAGTCTACCAGGACCAAAGGCCCTGCCCTGTCTCTG
TCCCTCACTCAGGGCCTCCTGCAGGGCGAGCGCTTGGGAGCAGACTCGGTCTTAGGGGACACCACTGTGGGCCCCAA
CTTTGATGAGGCCACTGACCCTTCCTTCCTTTCCTGGGGCAGCACAGACTTTGGGGTCTGGGCAGGGAAGAACTACT
GGCTGGTGGCCAATCACAGAGCCCCCAGGCCGAGGTGGCCCCAAGAAGGCCCTCAGGAGGTGGCCACTCCACTTCCT
CCCAGCTGGACCCCAGGTCCTCCCCAAGATAGGGGTGCCATCCAAGGCAGGTCCTCCATGGAGCCCCCTTCAGACTC
CTCCCGGGACCCCACTGGACCTCAGTCCCTGCTCTGGGAATGCAGCCACCACAAGCACACCAGGAAGCCCAGGCCCA
GCCACCCTGCAGTGGGCAAGCCCACACTCTGGAGCAGAGCAGGGTGCGTCTGGGAGGGGCTAACCTCCCCACCCCCC
ACCCCCCATCTGCACACAGCCACCTACCACTGCCCAGACCCTCTGCAGGAGGGCCAAGCCACCATGGGGTATGGACT
TAGGGTCTCACTCACGTGCCTCCCCTCCTGGGAGAAGGGGCCTCATGCCGAGATCCCTGCAGCACTAGACACAGCTG
GAGGCAGTGGCCCCAGGGCCACCCTGACCTGGCATCTAAGGCTGCTCCAGCCCAGACAGCACTGCCGTTCCTGGGAA
GCCTGGGCTCCACCAGACCACAGGTCCAGGGCACAGCCCACAGGAGCCACCCACACACAGCTCACAGGAAGAAGATA
AGCTCCAGACCCCAGGGCGGGACCTGCCTTCCTGCCACCACTTACACACAGGCCAGGGAGCTGTTCCCACACAGATC
AACCCCAAACCGGGACTGCCTGGCACTAGGGTCACTGCCATTTCCCTCTCCATTCCCTCCCAGTGCCTCTGTGCTCC
CTCCTTCTGGGGAACACCCTGTGCAGCCCCTCCCTGCAGCCCACACGCTGGGGAGACCCCACCCTGCCTCGGGCCTT
TTCTACCTGCTGCACTTGCCGCCCACCCAAACAACCCTGGGTACGTGACCCTGCAGTCCTCACCCTGATCTGCAACC
AGACCCCTGTCCCTCCCTCTAAACACCCCTCCCAGGCCAACTCTGCACCTGCAGGCCCTCCGCTCTTCTGCCACAAG
AGCCTCAGGTTTTCCTACCTGTGCCCACCCCCTAACCCCTCCTGCCCACAACTTGAGTTCTTCCTCTCCTGGAGCCC
TTGAGCCATGGCACTGACCCTACACTCCCACCCACACACTGCCCATGCCATCACCTTCCTCCTGGACACTCTGACCA
CGCTCCCCTCCCTCTCAGACCCGGCCCTGGTATTTCCAGGACAAAGGCTCACCCAAGTCTTCCCCATGCAGGCCCTT
GCCCTCACTGCCTGGTTACACGGGAGCCTCCTGTGCGCAGAAGCAGGGAGCTCAGCTCTTCCACAGGCAGAAGGCAC
TGAAAGAAATCGGCCTCCAGTGCCTTGACACACGTCCGCCTGTGTCTCTCACTGCCTGCACCTGCAGGGAGGCTCCG
CACTCCCTCTAAAGATGAGGGATCCAGGCAGCAACATCACGGGAGAATGCAGGGCTCCCAGACAGCCCAGCCCTCTC
GCAGGCCTCTCCTGGGAAGAGACCTGCAGCCACCACTGAACAGCCACGGAGGTCGCTGGATAGTAACCGAGTCAGTG
ACCGACCTGGAGGGCAGGGGAGCAGTGAACCGGAGCCCATACCATAGGGACAGACACCAGCCGCTAACATCCCGAGC
CCCTCACTGGCGGCCCCAGAACACCCCGTGGAAACAGAACAGACCCACAGTCCCACCTGGAACAGGGCAGACACTGC
TGAGCCCCCAGCACCAGCCCCAAGAAACACTAGGCAACAGCATCAGAGGGGGCTCCTGAGAAAGAGAGGAGGGGAGG
TCTCCTTCACCATCAAATGCTTCCCTTGACCAAAAACAGGGTCCACGCAACTCCCCCAGGACAAAGGAGGAGCCCCC
TGTACAGCACTGGGCTCAGAGTCCTCTCTGAGACAGGCTCAGTTTCAGACAACAACCCGCTGGAATGCACAGTCTCA
GCAGGAGAGCCAGGCCAGAGCCAGCAAGAGGAGACTCGGTGACACCAGTCTCCTGTAGGGACAGGAGGATTTTGTGG
GGGTTCGTGTCACTGTG[redacted]CACAGTGACACAACCCCATTCCTAAAGCCCTA
D2-21
CTGCAAACGCACCCACTCCTGGGGCTGAGGGGCTGGGGGAGCATCTGGGAAGTATGGCCTAGGGGTGTCCATCAATG
CCCAAAATGCACCAGACTCTCCCCAAGACATCACCCCACCAGCCAGTGAGCAGAGTAAACAGAAAATGAGAAGCAGC

Fig. 3 (cont.)

TGGGAAGCTTGCACAGGCCCCAAGGAAAGAGCTTTGGCAGGTGTGCAAGAGGGGATGTGGGCAGAGCCTGAGCAGGG
CCTTTTGCTGTTTCTGCTTTCCTGTGCAGAGAGTTCCATAAACTGGTATTCAGGATCAATGGCTGGGAGTGAGCCCA
GGAGGACAGTGTGGGAAGAGCACAGGGAAGGAGGACCAGCCGCTATCCTACACTGTCATCTTTTGAAAGTTTGCCCT
GTGCCCACAATGCTGCATCATGGGATGCTTAACAGCTGATGTAGACACAGCTAAAGAGAGAATCAGTGAAATGCATT
TGCAGCACAGATCTGAATAAATCCTCCAGAATGTGGAGCAGCACAGAAGCAAGCACACAGAAAGTGCCTGATGCCAA
GGCAAAGTTCAGTGGGCACCTTCAGGCATTGCTGCTGGGCACAGACACTCTGAAAAGCACTGGCAGGAACTGCCTGT
GACAAAGCAGAACCCTCAGGCAATGCCAGCCCTAGAGCCCTTCCTGAGAACCTCATGGGCAAAGATGTGCAGAACAG
CTGTTTGTCATAGCCCCAAACTATGGGGCTGGACAAAGCAAACGTCCATCTGAAGGACAACAGACAAATAAACGATG
GCAGGTTCATGAAATGCAAACTAGGACAGCCAGAGGACAACAGTAGAGAGCTACAGGCGGCTTTGCGGTTGAGTTCA
TGACAATGCTGAGTAATTGGAGTAACAGAGGAAAGCCCAAAAAATACTTTTAATGTGATTTCTTCTAAATAAAATTT
ACACCCGGCAAAATGAACTATCTTCTTAAGGGATAAACTTTCCCCTGGAAAAACTATAAGGAAAATCAAGAAAACGA
TGATCACATAAACACAGTGGTGGTTACTTCTACTGGGGAAGGAAGAGGGTATGAGCTGAGACACACAGAGTCGGCAA
GTCTCCTAACAAGAACAGAACAAATACATTACAGTACCTTGAAAACAGCAGTTAAACTTCTAAATCGCAAGAAGAGG
AAAATGCACACACCTGTGTTTAGAAAATTCTCAGTCCAGCACTGTTCATAATAGCAAAGACATTAACCCAGGTTGGA
TAAATAAGCGATGACACAGGCAATTGCACAATGATACAGACATACATTCAGTATATGAGACATCGATGATGTATCCC
CAAAGAAATGACTTTAAAGAGAAAAGGCCTGATGTGTGGTGGCAATCACCTCCCTGGGCATCCCCGGACAGGCTGCA
GGCTCACTGTGTGGCAGGGCAGGCAGGCACCTGCTGGCAGCTCCTGGGGCCTGATGTGGAGCAGGCACAGAGCTGTA
TATCCCCAAGGAAGGTACAGTCAGTGCATTCCAGAGAGAAGCAACTCAGCCACACTCCCTGGCCAGAACCCAAGATG
CACACCCATGCACAGGGAGGCAGAGCCCAGCACCTCCGCAGCCACCACCACCTGCGCACGGGCCACCACCTTGCAGG
CACAGAGTGGGTGCTGAGAGGAGGGGCAGGGACACCAGGCAGGGTGAGCACCCAGAGAAAACTGCAGAAGCCTCACA
CATCCACCTCAGCCTCCCCTGACCTGGACCTCACCTGGCCTGGGCCTCACCTGACCTGGACCTCACCTGGCCTGGGC
TTCACCTGGCCTGGGCTTCACCTGACCTGGACCTCACCTGGCCTCGGGCCTCACCTGGCCTGGGCTTCACCTGGCCT
GGGCTTCACCTGACCTGGACCTCACCTGGCCTGGGCCTCACCTGACCTGGACCTCACCTGGCCTGGGCTTCACCTGG
CCTGGGCTTCACCTGGCCTGGGCTTCACCTGACCTGGACCTCACCTGGCCTGGGCTTCACCTGACCTGGACCTCACC
TGGCCTCAGGCCTCACCTGCACCTGCTCCAGGTCTTGCTGGAGCCTGAGTAGCACTGAGGCTGTAGGGACTCATCCA
GGGTTGGGGAATGACTCTGCAACTCTCCCACATCTGACCTTTCTGGGTGGAGGCACCTGGTGGCCCAGGGAATATAA
AAAGCCCCAGAATGATGCCTGTGTGATTTGGGGGCAATTTATGAACCCGAAAGGACATGGCCATGGGGTGGGTAGGG
ACAGTAGGGACAGATGTCAGCCTGAGGTGAAGCCTCAGGACACAGGTGGGCATGGACAGTGTCCACCTAAGCGAGGG
ACAGACCCGAGTGTCCCTGCAGTAGACCTGAGAGCGCTGGGCCCACAGCCTCCCCTCGGGGCCCTGCTGCCTCCTCA
GGTCAGCCCTGGACATCCCGGGTTTCCCCAGGCCTGGCGGTAGGTTTGAAGTGAGGTCTGTGTCACTGTG[redacted]CACAGTGTCACAGAGTCCATCAAAAACTCATGCCTGGGAGCCTCCCACCACAG
D3-22
CCCTCCCTGCGGGGGACCGCTGCATGCCGTGTTAGGATTTTGATCGAGGACACGGCGCCATGGGTATGGTGGCTACC
ACAGCAGTGCAGCCCATGACCCAAACACACGGGGCAGCAGAAACAATGGACAGGCCCACAAGTGACCATGATGGGCT
CCAGCCCACCAGCCCCAGAGACCATGAAACAGATGGCCAAGGTCACCCTACAGGTCATCCAGATCTGGCTCCAAGGG
GTCTGCATCGCTGCTGCCCTCCCAACGCCAAACCAGATGGAGACAGGGCCGGCCCCATAGCACCATCTGCTGCCGTC
CACCCAGCAGTCCCGGAAGCCCCTCCCTGAACGCTGGGCCACGTGTGTGAACCCTGCGAGCCCCCCATGTCAGAGTA
GGGGCAGCAGGAGGGCGGGGCTGGCCCTGTGCACTGTCACTGCCCCTGTGGTCCCTGGCCTGCCTGGCCCTGACACC
TGAGCCTCTCCTGGGTCATTTCCAAGACATTCCCAGGGACAGCCGGAGCTGGGAGTCGCTCATCCTGCCTGGCTGTC
CTGAGTCCTGCTCATTTCCAGACCTCACCAGGGAAGCCAACAGAGGACTCACCTCACACAGTCAGAGACAACGAACC
TTCCAGAAATCCCTGTTTCTCTCCCCAGTGAGAGAAACCCTCTTCCAGGGTTTCTCTTCTCTCCCACCCTCTTCCAG
GACAGTCCTCAGCAGCATCACAGCGGGAACGCACATCTGGATCAGGACGGCCCCCAGAACACGCGATGGCCCATGGG
GACAGCCCAGCCCTTCCCAGACCCCTAAAAGGTATCCCCACCTTGCACCTGCCCCAGGGCTCAAACTCCAGGAGGCC
TGACTCCTGCACACCCTCCTGCCAGATATCACCTCAGCCCCCTCCTGGAGGGGACAGGAGCCCGGGAGGGTGAGTCA
GACCCACCTGCCCTCAATGGCAGGCGGGGAAGATTCAGAAAGGCCTGAGATCCCCAGGACGCAGCACCACTGTCAAT
GGGGGCCCCAGACGCCTGGACCAGGGCCTGTGTGGGAAAGGCCTCTGGCCACACTCAGGGGCTTTTGTGAAGGGCC
CTCCTGCTGTG[redacted]CACAGTGATGAAACCAGCAGCAAAAACTGACTGGACTCGCAGGGTTT
D4-23
ATGCACACTTCTCGGCTCGGAGCTCTCCAGGAGCACAAGAGCCAGGCCCGAGGGTTTCTGCCCAGACCCTCGGCCTC
TAGGGACACCCGGGCCATCTTAGCCGATGGGCTGGTGCCCTGCACACCGTGTGCTGCCAAACAGGGGCTTCAGAGGG
CTCTGAGGTGACTTCACTCATGACCACAGGTGCCCTGGTCCCTTCACTGCCAGCTGCACCAGACCCTGTTCCGAGAG
ATGCCCCAGTTCCAAAAGCCAATTCCTGGGGCCGGGAATTACTGTAGACACCAGCCTCATTCCAGTACCTCCTGCCA
ATTGCCTGGATTCCCATCCTGGCTGGAATCAAGAGGGCAGCATCCGCCAGGCTCCCAACAGGCAGGACTCCCACACA

Fig. 3 (cont.)

CCCTCCTCTGAGAGGCCGCTGTGTTCCGCAGGGCCAGGCCGCAGACAGTTCCCCTCACCTGCCCATGTAGAAACACC
TGCCATTGTCGTCCCCACCTGGAAAAGACCACTTGTGGAGCCCCCAGCCCCAGGTACAGCTGTAGAGAGAGTCCTCG
AGGCCCCTAAGAAGGAGCCATGCCCAGTTCTGCCGGGACCCTCGGCCAGGCCGACAGGAGTGGACGCTGGAGCTGGG
CCCACACTGGGCCACATAGGAGCTCACCAGTGAGGGCAGGAGAGCACATGCCGGGGAGCACCCAGCCTCCTGCTGAC
CAGAGACCCGTCCCAGAGCCCAGGAGGCTGCAGAGGCCTCTCCAGGGGGACACAGTGCATGTCTGGTCCCTGAGCAG
CCCCCAGGCTCTCTAGCACTGGGGGCCCCTAGCACAGCTGTCTGGACCCTCCCTGTTCCCTGGGAAGCTCCTCCTGA
CAGCCCCGCCTCCAGTTCCAGGTGTGGTTATTGTCAGGGGGTGCCAGGCCGTG[redacted]CACA
D5-24
GTGGTGCCGCCCATAGCAGCAACCAGGCCAAGTAGACAGACCCCTGCCACGCAGCCCCAGGCCTCCAGCTCACCTGC
TTCTCCTGGGGCTCTCAAGGCTGCTGTCTGCCCTCTGGCCCTCTGTGGGGAGGGTTCCCTCAGTGGGAGGTCTGTGC
TCCAGGGCAGGGATGACTGAGATAGAAATCAAAGGCTGGCAGGGAAAGGCAGCTTCCCGCCCTGAGAGGTGCAGGCA
GCACCACAGAGCCATGGAGTCACAGAGCCACGGAGCCCCCAGTGTGGGCGTGTGAGGGTGCTGGGCTCCCGGCAGGC
CCAGCCCTGATGGGGAAGCCTGCCCCGTCCCACAGCCCAGGTCCCCAGGGGCAGCAGGCACAGAAGCTGCCAAGCTG
TGCTCTACGATCCTCATCCCTCCAGCAGCATCCACTCCACAGTGGGGAAACTGAGCCTTGGAGAACCACCCAGCCCC
CTGGAAACAAGGCGGGGAGCCCAGACAGTGGGCCCAGAGCACTGTGTGTATCCTGGCACTAGGTGCAGGGACCACCC
GGAGATCCCCATCACTGAGTGGCCAGCCTGCAGAAGGACCCAACCCCAACCAGGCCGCTTGATTAAGCTCCATCCCC
CTGTCCTGGGAACCTCTTCCCAGCGCCACCAACAGCTCGGCTTCCCAGGCCCTCATCCCTCCAAGGAAGGCCAAAGG
CTGGGCCTGCCAGGGGCACAGTACCCTCCCTTGCCCTGGCTAAGACAGGGTGGGCAGACGGCTGCAGATAGGACATA
TTGCTGGGGCATCTTGCTCTGTGACTACTGGGTACTGGCTCTCAACGCAGACCCTACCAAAATCCCCACTGCCTCCC
CTGCTAGGGGCTGGCCTGGTCTCCTCCTGCTGTCCTAGGAGGCTGCTGACCTCCAGGATGGCTTCTGTCCCCAGTTC
TAGGGCCAGAGCAGATCCCAGGCAGGCTGTAGGCTGGGAGGCCACCCCTGTCCTTGCCGAGGTTCAGTGCAGGCACC
CAGGACAGGAAATGGCCTGAACACAGGGATGACTGTGCCATGCCCTACCTAAGTCCGCCCCTTTCTACTCTGCAACC
CCCACTCCCCAGGTCAGCCCATGACGACCAACAACCCAACACCAGAGTCACTGCCTGGCCCTGCCCTGGGGAGGACC
CCTCAGCCCCCACCCTGTCTAGAGGACTTGGGGGGACAGGACACAGGCCCTCTCCTTATGGTTCCCCCACCTGGCTC
CTGCCGGGACCCTTGGGGTGTGGACAGAAAGGACGCCTGCCTAATTGGCCCCCAGGAACACAGAACTTCTCTCCAGG
GACCCCAGCCCGAGCACCCCCTTACCCAGGACCCAGCCCTGCCCCTCCTCCCCTCTGCTCTCCTCTCATCACTCCAT
GGGAATCCAGAATCCCCAGGAAGCCATCAGGAAGGGCTGAAGGAGGAAGCGGGGCCGCTGCACCACCGGGCAGGAGG
CTCCGTCTTCGTGAACCCAGGGAAGTGCCAGCCTCCTAGAGGGTATGGTCCACCCTGCCTGGGGCTCCCACCGTGGC
AGGCTGCGGGGAAGGACCAGGGACGGTGTGGGGGAGGGCTCAGGGCCCTGCAGGTGCTCCATCTTGGATGAGCCCAT
CCCTCTCACCCACCGACCCGCCCACCTCCTCTCCACCCTGGCCACACGTCGTCCACACCATCCTGAGTCCCACCTAC
ACCAGAGCCAGCAGAGCCAGTGCAGACAGAGGCTGGGGTGCAGGGGGGCCGCCAGGGCAGCTTTGGGGAGGGAGGAA
TGGAGGAAGGGGAGGTCAGTGAAGAGGCCCCCCTCCCCTGGGTCTAGGATCCACCTTTGGGACCCCCGGATCCCATC
CCCTCCAGGCTCTGGGAGGAGAAGCAGGATGGGAGATTCTGTGCAGGACCCTCTCACAGTGGAATACCTCCACAGCG
GCTCAGGCCAGATACAAAAGCCCCTCAGTGAGCCCTCCACTGCAGTGCTGGGCCTGGGGCAGCCCCTCCCACAGAG
GACAGACCCAGCACCCCGAAGAAGTCCTGCCAGGGGGAGCTCAGAGCCATGAAGGAGCAAGATATGGGGACCCCAAT
ACTGGCACAGACCTCAGCTCCATCCAGGCCCACCAGGACCCACCATGGGTGGAACACCTGTCTCCGGCCCCTGCTGG
CTGTGAGGCAGCTGGCCTCTGTCTCGGACCCCCATTCCAGACACCAGACAGAGGGACAGGCCCCCCAGAACCAGTGT
TGAGGGACACCCCTGTCCAGGGCAGCCAAGTCCAAGAGGCGCGCTGAGCCCAGCAAGGGAAGGCCCCCAAACAAACC
AGGAGGTTTCTGAAGCTGTCTGTGTCACAGTC[redacted]CACAATGACACTGGCAGGACAGAAAC
D6-25
CCCATCCCAAGTCAGCCGAAGGCAGAGAGAGCAGGCAGGACACATTTAGGATCTGAGGCCACACCTGACACTCAAGC
CAACAGATGTCTCCCCTCCAGGGCGCCCTGCCCTGTTCAGTGTTCCTGAGAAAACAGGGGCAGCCTGAGGGGATCCA
GGGCCAGGAGATGGGTCCCCTCTACCCCGAGGAGGAGCCAGGCGGGAATCCCAGCCCCCTCCCCATTGAGGCCATCC
TGCCCAGAGGGGCCCGGACCCACCCCACACACCCAGGCAGAATGTGTGCAGGCCTCAGGCTCTGTGGGTGCCGCTAG
CTGGGGCTGCCAGTCCTCACCCCACACCTAAGGTGAGCCACAGCCGCCAGAGCCTCCACAGGAGACCCCACCCAGCA
GCCCAGCCCCTACCCAGGAGGCCCCAGAGCTCAGGGCGCCTGGGTGGATTCTGAACAGCCCCGAGTCACGGTG[redacted]
[redacted]CACTGTGAGAAAAGCTATGTCCAAAACTGTCTCCCGGCCACTGCTGGAGGCCCAGCCAGAG
D1-26
AAGGGACCAGCCGCCCGAACATACGACCTTCCCAGCCCTCATGACCCCCAGCACTTGGAGCTCCACAGTGTCCCCAT
TGGATGGTGAGGATGGGGGCCGGGGCCATCTGCACCTCCCAACATCACCCCCAGGCAGCACAGGCACAAACCCCAAA
TCCAGAGCCGACACCAGGAACACAGACACCCCAATACCCTGGGGGACCCTGGCCCTGGTGACTTCCCACTGGGATCC
ACCCCCGTGTCCACCTGGATCAAAGACCCCACCGCTGTCTCTGTCCCTCACTCAGGGCCTGCTGAGGGGCGGGTGCT
TTGGAGCAGACTCAGGTTTAGGGGCCACCATTGTGGGGCCCAACCTCGACCAGGACACAGATTTTTCTTTCCTGCCC

Fig. 3 (cont.)

TGGGGCAACACAGACTTTGGGGTCTGGGCAGGGAGGACCTTCTGGAAAGTCACCAAGCACAGAGCCCTGACTGAGGT
GGTCTCAGGAAGACCCCCAGGAGGGGGCTTGTGCCCCTTCCTCTCATGTGGACCCCATGCCCCCCAAGATAGGGGCA
TCATGCAGGGCAGGTCCTCCATGCAGCCACCACTAGGCAACTCCCTGGCGCCGGTCCCCACTGCGCCTCCATCCCGG
CTCTGGGGATGCAGCCACCATGGCCACACCAGGCAGCCCGGGTCCAGCAACCCTGCAGTGCCCAAGCCCTTGGCAGG
ATTCCCAGAGGCTGGAGCCCACCCCTCCTCATCCCCCCACACCTGCACACACACACCTACCCCCTGCCCAGTCCCCC
TCCAGGAGGGTTGGAGCCACCCATAGGGTGGGCGCTCCAGGTCTCACTCACTCGCTTCCCTTCCTGGGCAAAGGAGC
CTCGTGCCCCGGTCCCCCCTGACGGCGCTGGGCACAGGTGTGGGTACTGGGCCCCAGGGCTCCTCCAGCCCCAGCTG
CCCTGCTCTCCCTGGGAGGCCTGGGCACCACCAGACCACCAGTCCAGGGCACAGCCCCAGGGAGCCGCCCACTGCCA
GCTCACAGGAAGAAGATAAGCTTCAGACCCTCAGGGCCGGGAGCTGCCTTCCTGCCACCCCTTCCTGCCCCAGACCT
CCATGCCCTCCCCCAACCACTTACACACAAGCCAGGGAGCTGTTTCCACACAGTTCAACCCCAAACCAGGACGGCCT
GGCACTCGGGTCACTGCCATTTCTGTCTGCATTCGCTCCCAGCGCCCCTGTGTTCCCTCCCTCCTCCCTCCTTCCTT
TCTTCCTGCATTGGGTTCATGCCGCAGAGTGCCAGGTGCAGGTCAGCCCTGAGCTTGGGGTCACCTCCTCACTGAAG
GCAGCCTCAGGGTGCCCAGGGGCAGGCAGGGTGGGGGTGAGGCTTCCAGCTCCAACCGCTCCACTAGCCGAGACTAA
GGAAGTGAGAGGCAGCCAGAAATCCAGACCATTCCATAGCAAATGGATTTCATTAAAGTTACCAGACTTCAGTGTAA
GTAACATGAGCCCCATGCACAACAATCCCTTATGAAGGGGAAGTCAGTGTCGCCTCGGATTTCTTGAAAAACACAAA
AACTTATCAATGCCTGTAAAAGTCTGTTGGAAAGAAAATATGATTCAAGAATGTTATGCCCAACAAAGCTGGCATAT
TTTCTACCCGGACACACTCAGGGAATGTGGTCCCTTGAGTGCTTCTCTCACTGCGTAAATCCTACGTGGTGTTTAAG
CATATTCATAAATGTGTATGTCTATTTTTATGTGTAAGATGGTTCATTTTTATTTTATTTATTCAATATGTACAATA
AAGAATATTGACAAATAGGCTGGACATGGTGGCTCCCACCTGTAATCCCAGCCCTTTGGGAGGCCGAGGCGGGCAGA
TCACCTGAGGTCTGGAGTTCGAGACCAGCCTGGCCAACATGATGAAAACCCATCTCTACTAAAAATACAAAGATTAG
CCAGGCATGGTGGTGCATGCCTGTAATCCCAGCCACTCAGGAGGCTGAGACAGGAGAAATGCGTGAACCCGGAAGGC
GGAGGTTGCAGTGAGCCGAGATCACACCACTGCACTCCAGCCTGGCGACAGAGCAAGATTCCATCTCAAAAAAAAAA
AAAGACAAAGAAATTTGTTTTTTTGAATAAAGACAAATTTCATCACACGAAGATAAAGATGCAAAGCTCCAGACAGG
AAGGCACGGACAGCACAGTGAAGCCCGGAGCGGGCGCTGGGGGGCCAGGGGCATGGCGGGGGTGCCAGCGTCTCTCG
GTGCCTACCATGGCCACTCCAGCCTGTGTTCTCACGAGGATGGCTGTGCAATGCTAGGAGCGTGTTCGAAGCTCTAG
GGCAACCACTGGAAGTGAGGCTGAGGAGCAGAGCCCAGAGGCCCGTGGAGCTGATGAAAAGAAAGCTGGAGAAAGTG
TTTGCTGCCTCCCAACATGGTAAGAAAAGATAGAAAGAGAGAGCACACGGCAAAGGGAGCTTGCTGAGGGACTCTTT
ACAATGGCTTGCACAGAGCTCAGGGGGTCTGGGAGGCTAGGGCCCTGCGCAGGGCAGTCACCCCAGCCTGCTGACCA
AGGTTTGCTGCAGGCAGCTCTGGGGGTGGTTGAGGCGCGGTCCCTGGAGCCACCCCTCAAGGGAACGAGGCAGCAGA
GTGGGCCAAGGCCCAGGTCGGCTGCAAGGCTGCCCAGGACTTGGGGTCCTTACATCAGCAGCCACTGATGCAGCTGG
CCCAGAGAGAGGCGCCGAGCAGGTTGCCTCCAGGGGACAAACCAGGTCGGAGAGGGTGAGGCAGTGGATGGAGCCAC
AACAACCCCGGGCACGGGTGACACGCACGTTCATGCACATCTGACCCTTCCTCCCTCACCAAACAGGTCCCCCTGCC
TTCCCCATGGTTGCGAAAAAGCAAAATGTAGACGTTTTTTCTTTTTTAATTCATGTTTTAATTGACAAATGAAGCCG
TATATATTTATTGTGTACAACATGATGCTTTAAAATATGTATACATCGTGGAACAGCAACGTTGAGCTAATTTAACA
CGCATTACTTCACATACTTGTCATCTTTTGTGGCGAGAATGCTTAAAATCCACTCTCTTAGTATTTTTTAAGAATGC
AATACATTGTTGTCAACTGTGGTCACCGTCATGCATAGCCAAGCTCCCGACCTCACCCTCCTGCCAGCTCAGGCTGT
GCATCCTTTCACCAGCATCCCCCACCCCGGCCCCTGGCCCTGGTAACTACCACTCTATACTCTACGTATGAGTTCAG
CTTTTTAAGATTCCACAGATGAATGAGATCATACAGTATTTGCTTTCTATGCCTGGCTTATTTTAGTTAACACACTG
TCCTCCAGATCCATCCGTTGTTGCAAATGACAGGGTTTCATTCTTTTTAAAGTCTAAAGAGTATTCCATTGTGTCAA
TGGACCTCATTTGCTTTATCCATGCATCAACTATGGACATTTAGGTTGATTCCATTTCTTAGCTGTTGTGGATGGTG
CTGCAGTAAACATGGGGCTGCAGATGTCTCTTCAACATACTGACATCATGTCCTTTGGATAAATACCCAGTAGTGGG
ATCGCTGGATCACAATGTACAGTTTGTTTTTTAATGGAAACTTTCATTTTTTGGTGAAATTAGGAAAACAGATAAAA
CCCACAGAATCCAAAATATATGTGAAGATGCCAAAAACAGTTGACATTGGGCAGAGGTCACATGGAAGGAAGTGAAT
ACATGACGGGGTGTGAGGGCCCAGAGGCAGCTGAAATACGCTTTCTAAACACAAGGACCTCTTCTGAGAGGGCAGAA
GTTTTATCCTGCACATGCAATGACCAGCACAGCTAAAATACACTTTCTAAACATGAGGACCTCTTCTGAGAGGGCAG
CTTTATCCTGCAAATGCAATGACCAGCACAGGACCCAGAATAAAGAGAGTTGCCAGCGGACGCCTGGTGTCCATGTG
TCCAGGTGAGTTCGAGATGCGGACGGCGCTGGCCAGCCAGTCACACCCTAAGTCAATCTGCTGCATGCATTTGTCCT
TGCCACAGCAGAAAACGAGAAAGCCTTTGGGCTGCAAAGCTTCACAGGCTCCTCTTCTCCCGACTCCATGGAAACAG
CTACAAAGAGCAGGCCCAGTAGAGCTTAATTCATGAAAATGAGTAATAAACTTGAACTGGAACAGTATCGACTTTTT
AGAAACGGCAGCAAAGTGTATAAAAAATATTCACCAGAACAATATTTCCAAACGATGAGATGAGAATTTCAGCCAAG
TAATCCTCCATGGATAGAAAATAATGAAGGGATTGGATTTATGAAGGAAAATCATGGAGCTCAAATACAAGAGAAGA
GAATCAAAAATGAACAGGAGGAGATAAAATATGGTTTGGCCAAAGTTACAAAATAAATTTTTTAAAAACCCTTCATC
ATGGCAAGTAGAAAGAGCGAGAGGAAAAACAGATCCCGTGGAAGACACAAATAGGACATGGGGAGAAAAATGAATGA

Fig. 3 (cont.)

GATGAAACAGAGCAGAAATAAAATTTTACGGAACTAAAGACAAGTGATCTGAACCTGCCTGGGGCCTGGGGGACCTC
GCCACCCTGAAGGGAAAGAACATGCCTGGCTGGCTTTGCCACCTGCTCATTGCAGAGCCCCACAGCTTGCAACAAAC
ATAGGCGGTAGCCAGGGAGTGGTTACAGCAGGCCTTGAGCAAGACCCAGTGTTGTGCTGACTTCAGGTCTGACCCAG
CACTGTCATAGTGGTGGTGTCCATAGTGGTAGTGGGGGTGCTTGTGTCACTCCACCCCCATCTCCAGGAGGCTCAGA
ACAGACAGAGAGAGACTCCATTTGTTTGGGAGAAAGTAAGGGATGAGAACAAGAGTCTCTGCCTGGTAATCCAGAGA
ATTATTCTAGATCTTGGCCAAGATTATCAAAGCAGTACCTCTATGAGTCTTTTGGGCTTGGAGTCCCCCTAAAGCAG
ATATAGCTAAGATCACAACACCCAAGTCCTTTTGAATATGTGGGAAGACTTCCCAAGGACAGGAGCAAACAAACAAG
CCCAGACTGCAAAAAAACAAGCCCAGACTGCAATAAACACCTCACTCTTCAATGCCCAGGCACTGAAGAACATCTCC
TAGCAGCAACACCATCCAGGAAAACATGGCCTCAACCAGTGAACTAAATAAGGCACCAGGGACCAGTCTCGGAGAAA
TAGAGGTATGTTATCTTTCAGAGAATTCAAAGTAGCTTTGTTGAGGAAACTCAAAGAAATTCAAGATAACACAGTGA
AGGAATTCAGAATCCTATCCGATAAATTTAACAGAGATTGAAGCAATTAAAAAGAATTAAGCAGAAATTATGGAGCT
GAAAAATGCAATTGGCATACTGAAAAATGCATCAGAGTATTTTCATAGCCTCTTATATCAAGTAGAAGAAAGAATTA
GTGAGCTTGAAAACAGGCTATTTGGAAAAGCACGATAAAAGGAGACAAAAGAGAAAAGAATAAATAACAATGAAGCA
TATCTACAGGATCTAGAAAATAGCCTCAAAAGGCCAAATCTAAGAATTATTAGCCTTAAAGAGGAGGTAGAGAAAGA
GGGATGGAGAGTTTATTCAAAGGGATAATAACAGAAAACTTCCCAAACCTAGAGAAAGATATCAATATCCAAATGCA
AGAAGGATGTAGTACACCAAGGAGATTTAATGCAAAGAAGACTACCTCAAGGCATTCAATACTCAAACTCCCATATG
ACAAGGACTTTAAAAAGATCCTAAAAGCAGCAAAAGAAAAGAAATGAATAAAATACTATGGAGCTCCAATATGTCTG
GCAGCAGACTTTTCAGTGAAGACTTTATATGCCAGGAGAGAGTGTCATAATGGATTTAAAGTGCTGAAGGAAAAAAC
TTTTACCCTCGAACAGTATAGCTGGTGAAATTATCCTTCAAACATGAAGGAGAAATAATTTGTTTCCAGACAAATGT
TGAGGGATTTCATGAACACCAGACCTGTCTTTTAAGAAATGCTAAAGGGAGTACTTCAATCAGAAAGAAACACGTTA
GTGAACAATAAGAAATCATCTGAAGGCACAAAACTCACCGGTAATAGTAAGTACACAGAAAAACACAGAATATTATA
ACACTGTAACTGTGGTGTGTAAACTCCTTTTGTTTGTTTGTTTGTTTGTTTGTTTGTTTTTGTTTTTAGACGGAGTT
TTGCTCCAGCCCAGGCTGGAGTGCAATGGCACAATCTCAGCTCACTGCAACTTCCACCTCCCGGGTTCAAGCAATTC
TCCTGCCTCAGCCTCCCAAGTAGCTGGGATTACAGGCATGTGCTACCATGTCCAGCTAATTTTGTATTTTAGTAGAG
ACGGTGTTTCACCATGTTGGTCAGGCTAGCCTTATCTTGAGTAGAAAAACTAAATGATGAAGCAATGAAAAATAATA
ACTACAACTTTTCAAGACATAGTACAATAAGATATAAATCATAACAAAAAGTTAAAAGGTGGAGGGATGAAGTTAAG
GCAAAGAGTCTTTATTAGTTTTCTTTTTACTTGTCTGTTTATGCAAACAGTGTTAAGTTGTCATCAGTTTAAAATAA
TGGGTCATAAGATACTATTTGCAAGCCTCATGGTAACGTCAAACCAAAAGCAATACAACAGATACACAAAAAACAAA
AAGCAAGAAGCTAAATTACGTCATCAGAGAAAATCACCTTCACTAAAAGGAAGACGGAGAAAAGAATGAAGAGAGAG
AAGACCAAAAGCAAATAGCAATATGGCAGGAGTAAGTCCTTACTTATCAATAATACCATTGAATGTAAATGGACTAA
ACTCTCCAATCAAAAGACATAGAGTGGCTGAATCAATTAAAGAAAAAACAAGACCCATTGATCTGTTGTCCACAAGA
AACACACTTTATCTATAAAGACACACATAGACTGAAAACAAAGGGATGGAAAAAGATACTCCACGCCAATGGAAACC
AAAGAAAGAGCAGGAGTAGCTACACTTATATCAGGCAAAATAGATTTCAAGACAAAAACTATAAGAAGAGACAAGGT
CACTAATGATAAACAGGTCAATTCAGCAAGAGGATATAACAATTGTAAATATATATGCACCCAATGCTGGAGCACCC
AGATATATAAAGCAAGTATTTACTAGAGCTAAAGAGAGAAATAGACTCCAATGCAATAATAGCTGGAGATTTCAACA
TCCCACTTTCAACATTGAACAGATCCTCCAGATAGAAAATCAACAAAGAAATATTGGACTTAATCTGCACTATCGAC
CAAATGGATCTAACAGATATTTACAGAACATTTCATCCAACAGCTGCAGAACACACATTCTTTTCCTCAGCACATAG
ATCATTCTCAAGGATAGACCATATGTTGGGTCACAAAACAAGTTTTAAAATATTCAAATACATTGAAATAATATCAA
GCATCTTCTGTGACCACAATGGACTAAAACTAGAAATCAATAACAAGAGGAATTTTGGAAACTATATAAATATATGG
AAATTAATGAATGCTGAGTGGGTCAATGAAGCAATTAAGAAGGAAACTGAAATTTTTCTTGGAACGAATGATCATGG
AAACAGAAAATACCAAAACCTATGGGATACAGCAAAAGCAGTACTAAGAGGGAAGTTTACAGCTACAAATGCTTACA
TTAAAAAAGAAGAAAAACTTCAATAAAAAAACCTAACAATGCATCTTAAAGAACTAGAAAAGCAAGAGGAAATCAAA
TCCAAAATTAGTAGAAGAAAACAGTAAAGGTCAGAGCAGAAATAAGTAAAATTGAAATGAAGAAAACAATACAAAAG
ATCAATAAAACAACAGGTTGTTTTCTTGAAAAGTTAAACAAAATTGACAAACCTTTAGCCAGACTAAGAAAAAAAGA
CAGAAGATCCAAATAAATAAAATCAGAGATGAAAAAGGTGACATTACAACTTACACCACAGAAATTCAAAGGATCAT
TAGTGGCTACTATAAGCAACTATATGCCAATAAATTGGAAAATCTAGAAGAAATGCAGAAATTCCTAGACACATACA
ACCTCCCAAGATTAAACCAAGAAGAAATTCAAAACCTGAACAGACTGATAACAAGTAATGAGATCAAAGCCGTAATA
AAAAGCCTCCCAGTAAAGAGAAGCCCAGGACCCGACGGCTTCACTGCTGAATTCTACCAAACATTTAAAGTAGAACT
AATACCAATCCTACTCAAACTATTCCAAAAAATAGAGGTGGAAGGAATACTTCAAAACTCATTATACGAGGCCAGTA
TTAACCTGACACCAAAACTAGACAAAGACACATGAAAAAAAGAAAACTACAGGCCAATATGTCTGATGAATATTGAC
ACAAAAATCCTCAACAAAATACTAGCAAACCAAATTCAACTACACATTAGAAAGTTCACTCATCATGACCAAGTGGA
ATTTATCTAACTTGGGATGCAAAGATGGTTCAACATATGCAAATCAATCAATGTGATACATCATATCAACAGAATGA
ACAACAAAAACCATTTGATCATTTAATTGATACTGAAAAAGCATTTGATAAAATTCAACATTCCTTCATAATAAAAA

Fig. 3 (cont.)

TTCTCTTCTATACTAGGTACAAAAGAAACTTACCTCAACATAATAAAGCCATATATGACAGTCCCACAGTATGATAC
TAAATGAGGAAAAACTGAGAGCCTTTCCTCTACGATCTGGAACATGACAAAGATGCCCACTTTCATCACTGTTATTC
AACATAGTACTGGAAGTCCTAGCTGGAGCGATCAGACAAGAGAAAGATATAAAAGACATCCAAATTGGAAAGGAATA
AGTCAAATTATCCTCATTTGCATATGGTATGATCTTCTATTTAGAGCTAACTAAAGACTCCACCAAAAAAAGTTATT
AGAACTGACGAACAAATTCAGTAAAGCTGCAGGATACAAAATCAACATACAAAAATCAGTAGCATTTCTATATGCCA
ACAATGACCAATGTGAAAAAGAAATTAAAAAGTAACCCTATTTACAATAACCACAAATAAACACCTAGGAATTAACC
AAAGAGGTAAAAGATTTCTGTAATGAAAACTATAAAAAACTGATGAAAGAAATTGAAGAGTACACCAAAAAATGGAA
AGCAATTGCATGTTCATGGATTAGAAGAATCAGTGTTGTTATAATGTCCATACTATCCAAAGCAATCTACAGATTCA
ATGCAATCCTTATCAAAATACCAATGACATCATTCACAGAAATAGAAAAAAAAAATCCTAAAATTTACGTGGAACCA
CAAAGACCCAGAATAGCCAAAGCTCTCCTAAGCAAAAAGAACGAAACTGTAGGAATGACATTGCCTGTCTTCAAATT
CTACTACAGAGCTATAGATAGTAACCAAAACAGCGTGGTACTAGCATAAAAACAGACACAGAGACAAACAGAACAAA
ATTTAAAAACCCAGAAATAAATCCACACACCTACAGCAAATTCATTTTTGACAAAGTTGCCAAGAACATACTCTGGG
GAATAGATAATGATATCTCTTCAATAAATAATGTGGGGAAAACTGGATATCCATATACATAACAGTGAAACTAGACC
CCTCTCTCTCTCACTATATACAAAAATCAAATCAAAATTGTTTAAGGACTTAAATCTAAGACCTCATACTATGAAAC
CACTGCAAGACAACCTTGGCGGAAACTCTCCAAGACATCAGTCCAGGCAAAGATTTCTTGAGTAATATCCCACAAGC
ACAGACAACCAAAGCAAAAATGGACAAATGGGATCACATCAAGTTAAAAAGCTTCTGCACAGTAAGGGAAACAACCA
ACAAAATGAAGAGACAACCCACAGAATGGGAGAAAATATTTGAAAAATACCCATCTGGCAAGGGATTAAAAACCAGA
ATATATGCAGAATATATAAGGAGCTCAAACAGTGCTATAGAAAAAAAAATCTAATAATCTGATTTAAAAATGGGAAA
AATGTTAGAATAGACATTTCTTAAAATAAGACATACAGATGGCAAACCGACATGGAACGGTGCTCAACATCATGGAT
TATCACAGAAACACAATCAATCAAAACTAAAACTAAAATGTGCTATCATCTCACCCCAGTTAAAATGGCTGATATCC
AGAAGACAGGCAATAACAAATGCTGGCAAGGATGTGGGGAAAAGGGAGCCCCCATACACTGTTGCTGGGATTGTAAA
TTAGTACAACCACTGTGGAGAGCAGCATGAAAGTTCCTCAAAAAACTGAAAGAAAGCTACCATAGGATCCAGCAATC
CCACTGCTGTGTATATACTACAAAAGAAAGGAAGTCAGTATATGAAGAGGTATCTGCACTCCCATGTTTGTTGCAGC
CCTGTTCACAACAGCCAAGATTTGGAAGCAACCTAAGTGTCCATCAGCAGTTGAATGTATAAAGAAAATGTGGTGCA
TATACACAATGGAGTATTATTCAATAATAAAAAGGAATGAGATTGAGTCATTTGCAACAACATGGATGGAACTGGAG
ATCATTATGTGAAGTGAAATAAGCCAGGCACAGAAAGACAAACATTACAATGTTCTTACTTATTAATGAGATCTAAA
AATCAAAACAATTGCACCCATGTTCATAAAGAGTAAAAGGATGGTTACCAGATGCTGAGAACGGTGGTGGGGGGATA
GGGAAAGGTGGCAGTGGTTAACGGGTACAAAAAAATAGAAAGAATGAATAAGACTTACTACTTGATAGCACAGCAAG
GTGGCTATAGTCAGTAATTTAGTTGTATATTTTTAATAATGAAAGGTGTATAATTGGATTGTTTCTAACACAAAGGA
TAATGCTTAAGAGGATGGATACCCCATTTTCCATGATGTGATTATTTCACATTGCACGCCTAGATCAAAACATCCAA
TGTACCCCATAAATATATACATCTTCTATGTACCCATAAAAATTCTGTAAAATAAAATATATAAAAAGAGGTGACAG
ATATGGAAGACAGGCAAAGAAGAGACGACATCCACATAATCCGAGTACCTAAGAAAGAATGGAGTCCAGTGCATCTC
AGGAGCCACCATTCTAAGCCAATTTTCTCTGGTTCTCTCAGTCACCCTACCAATACGTGGGCAATCTTGTTTTATTT
CAGGATAGAGTTTTTGAAATTATAGATTTAAGTATGCTTTCTGTTCTATTACTTTTGGTAATTAATTTTAGAAAGAA
CTAATTTGGGCACAAATTTGAAAAAATTCTAAATCCAAAAAAAAAAAGAAAAAAACACACACACAATCATCTATAAG
GGGGATGATGACCAGTCCTAGATTTCTCACCAGCCACATTCAAGATCAGTAAATGGTAGGACAAAACCTGTAGGGTC
CTTAAGGGGGAAAGAAGTAGTGGATAGTCCAGAGTCTATATACAGCCAACTGTTCTTGAAGAAAAAAGGCTGCTGAA
AAGGAGTTCCAAACATTCTATAATCCATAATCTCATGATGAAACTACTAGAGGAAGACCACCAGCCATCAAAAGGTG
CTTGGAGAACCCAGGGCCAAGAACCAAAAGTAAATATTAAGTGTCCTTAACTGCGAGACTAAGATAGAAATGACTGT
GGGGGACCATGTGGCCTCAACAGAGGTGAAATGGTGTCTGCCTGACAAAGTGGACATTTTACAATGATCAAAACACA
GAATATGAGATAGAGAGCACTTCTGAATTACTGCCTCACTCCAAATAACTCTCAGCCAAAGGACTTCAGTAAAACCA
AATTGGGCATATTAGACAGTACAAACAAATTCTAAGAAAATAATATTACTGATTACAATCACATGATGCTAGAGATG
GAGGGGAAAAGGAAGAGGAAACCAGGTAATTTCATACTCGTATATAGTAAAGAACTAAAGTACATTGTCCAAAGAAG
AACAAAGAATATTTTGGAAAGTTATAAAGGTAGCCACTACACATAGAAGATAGCAAAGAACAAGAAAACTTAAGATG
GAAAACTTTTTGGAAGCATAAAAATAGAAAATATAAACTACTAAGATAAGATTGAAGCCAAACAGATCTATGAAAAC
AACAAACATCAATGGCCTTAACTTGCCTATTAAAAGGAAGAGACTTTCAAATTGGACCACAAGATAAAACCCAACTC
TATATAGCATATGAGTATTACACACAAAATGGGAAAAGCTGAAAAAACTTGGGCAAAATTCACCCCAAGCAAATTCC
ACTGTTTCCTTTGGGACAAAATGCCAAGCTCCATGCCAGGGAAGATGATTCTCCTCAGACCTTCTCCTCACTCTCCC
AGTCCTCTTAGGGAAGGAATTGGGTGTTAGAGGAGGGAGACTCTGTCGATTATCAGCTGAAGCAGTGGTGTGCTCCT
GCGTTGCTTCTGACCTGGGAAATGAAGCAGCAAGACTCTTTCTGCTGTGTCTTTGCCCAGAAGGGCCATCCCCCCAG
AGCAGAGTACCCAGGCCGGCAGGAGCAGTGGTGGAAGCGTGGAAACCACGTCTCCTACAGCAGAGACCATCAGAAGC
GGAGCCTCGGGTATAAGGGAAACAACGCGTTCTCCCTAACCTGGGAGTGACAGACAGCGTCATTCCTCACAGTGATA
CCCTGTGTTCTAGCCATCTGGCCCATGACAGAGCCAGCCCAGAGCCAGCCCAGAGCCAGCCCCTGACCATCCTGGAG

Fig. 3 (cont.)

CCTGGCCAGCTCGCCAAGCTGCACCATAGGCCTGGAAGGCGTGGAGACCTGCGGCAGTGCCCTGTCCTCCCGTGAGG
CCTGCCATCCCTGCCAGGGGTCGCCTCTGGCTTCTCCTTCTCCAGGACCGCACGGTCCAGAGGCTCAGTGCCTGGAG
TAGGTGTTGCCTCCCTGCTTCTAGGCCCAGACCCTCCCTTGTTCCTGACCCCGGGCCTTTCCCTCTGGCTTGGACAT
CCAGGGCCCTGTCTCAGCTGGGGAGCTGCTCCTGCTCAAGGACTGTCTTCCGCGGGATCGAAAGGCCGCGTCCTGAA
CAATGCGTGGGCCACGTGAGCGGAGCAGGCTCTAAAGGCCGCGTCCTAAACAGTGCGTGGGCCACGTGAGCGGAGCA
GGCTCTAAAGGCCGCGTCCTAAACAGTGCGTGGGCCACGTGAGCGGAGCAGGCTCTAAAGGCCGCGTCCTAAACAGT
GCGTGGGCCACGTGAGCGGAGCAGGCTCTAAAGGCCGCGTCCTAAACAGTGCGTGGGCCACGTGAGCGGAGCAGGCT
CTAAAGGCCGCGTCCTAAACAGTGCGTGGGCCACGTGAGCGGAGCAGGCTCTAAAGGCCGCGTCCTAAACAGTGCGT
GGGCCACGTGAGCGGAGCAGGCTCTAAAGGCCGCGTCCTAAACAGTGCGTGGGCCACGTGAGCGGAGCAGGCTCTAA
AGGCCGCGTCCTAAACAGTGCGTGGGCCACGTGAGCGGAGCAGGCTCTAAAGGCCGCGTCCTAAACAGTGCGTGGGC
CACGGGAGCGGAGCAGACTCTAAAGGCCGCGTCCTAAACAGTGTGTGGGCCACGTGAGCGAAGCGCCCTCTCCACTG
CCCTCGGGGCCGCAGCTCCCAGCTCAGCTCCCAGCCCTGCTCAGGGCAGCCAGGCCAGGAGGTACCATCCAGGCTAA
GTGACCCTCAGGGGGGACAGGTGCCCCAGGAGATGCCAGCTGTTGGGAGAGGCTGGGGGACCAACTCGACCTGGCCT
GTGGGCCCTGCCCTGGCCACCCATTGTAGGATCCAGCCGCCACGCCTGTGACACTCGTGTGCTTTCCCTGGTGTGTG
CTTGTGGCAGGTGGGGGCAGAGGGTCCTCAGGCCAGAGAGCCACTCCCCCAGCGCCAGACCACCCTCTTCCTCACTC
CCCCACCTCACCCCCTCACAGGTGCCTCCCAGGCCATCAGGGCCCAACCACCCCTAAACAAATGGGTTCTCGGCCCC
TCGTGGCTGGAGGTGGGTTCTCTCACCATTCCCAGCCTAAGACTCCATCCCCATGCTGGCAGCTGTTCAACCATGTC
TAGAGAGATCCACTGTCCCAGACAGCACCTCAGGGTCCCCCGTCCTGCCTGGAACCCTGTAGGAAACTCCACAAACC
GCCGCCATTCTGTCCACACCCCTACAGGAGCCCCAACCCTCTCCCCACATCCAGGCTTCCCTCCCAGACCCCTCATC
CCTGCCCGCACGGTGCCTGAGGGGGCCTTCTTGGGCAGCGCCTAAGCAAGCCCCCAGCACCCTTCGGCCCCTTCAAG
GCACACAGGCCCCCTTTCCACCCAGCCTCAGGAAACCACCTGTGTCCTCCAACGACAGGTCCCAGCCTCCCAGCCTT
TGCCTTGCCTGTTCCTCTCCCTGGAACTCTGCCCCGACACAGACCCTCCCCAGCAAGCCCGCAGGGGCACCTCCCCT
GCCCCCAGACACCCTGTGCCCGTCAGTTCATCCCCAGCAGAGGCCCTCACCAGGCACACCCCCATGCTCACACCTGG
CCCCAGGCCTCAGCCTCCCTGAGGGCCCCACCCAGCCCGCGTCTGGCCAGTGGTGCGTGCAAAGCCCCTCACCCAGA
CTCGGCGGAAGGCAGCCAGTGCAGGCCTGGGGAGGGGCTCTCCTTAGACCACCTTGCACCTTCCCTGGCACCCACCA
TGGGAAGAGCTGAGACTCACTGAGGACCAGCTGAGGCTCAGAGAAGGGACCCAGCACTGGTGGACACGCAGGGAGCC
CACGCCAGGGCGCCGTGGTGAGTGAGGCCCAGTGCCACCCACTGAGGCCTCCCGTTCAGTGGGACGACGGTGAACAG
GTGGAACCAACCAGGCAACCCCCGCCGGGCCCCACAGACGGGATCAGAGCAGGAAAGGCTTCCTGCCCCTGCAGGCC
AGCGAGGAGCCCTGGCGGGGGCCGTGGCCCTCCAGGCGAGGAGGCTCCCCTGGCCACCGCCACCCGGGCCTCTCTGC
TGCTGGGAAAACAAGTCAGAAAGCAAGTGGATGAGAGGTGGCGTGACAGACCCAGCTTCAGATCTGCTCTAATTTAC
AAAAGAAAAGGAAAAACACACTTGGCAGCCTTCAGCACTCTAATGATTCTTAACAGCAGCAAATTATTGGCACAAGA
CTCCAGAGTGACTGGCAGGGTTGAGGGCTGGGGTCTCCCACGTGTTTTGGGGCTAACAGCGGAAGGGAGAGCACTGG
CAAAGGTGCTGGGGGCCCCTGGACCCGACCCGCCCTGGAGACCGCAGCCACATCAGCCCCCAGCCCCACAGGCCCCC
TACCAGCCGCAGGGTTTTGGCTGAGCTGAGAACCACTGTG[redacted]CACAGTGATTGGCAGCTCTACAAAAA
D7-27
CCATGCTCCCCCGGGACCCCGGGCTGTGGGTTTCTGTAGCCCCTGGCTCAGGGCTGACTCACCGTG[redacted]
GTGAGTCTGCTGTCTJ1GGGGATAGCGGGGAGCCAG
JH1
GTGTACTGGGCCAGGCAAGGGCTTTGGCTTCAGACTTGGGGACAGGTGCTCAGCAAAGGAGGTCGGCAGGAGGGCGG
AGGGTGTGTTTTTGTATGGGAGAAGCAGGAGGGCAGAGGCTGTG[redacted]
GTGAGTCCCACTGCAGCCCCCTCCCAGTCTTCTCTGTCCAGGCACCAJ2GGCCAGGT
JH2
ATCTGGGGTCTGCAGCCGGCCTGGGTCTGGCCTGAGGCCACACCAGCTGCCATCCCTGGGGTCTCCGCCATGGGCTG
CATGCCAGAGCCCTGCTGTCACTTAGCCCTGGGGCCAGCTGGAGCCCCCAAGGACAGGCAGGGACCCCGCTGGGCTT
CAGCCCCGTCAGGGACCCTCCACAGGTAGCAAGCAGGCCGAGGGCAGGGACGGGAAGGAGAAGTTGTGGGCAGAGCC
TGGGCTGGGGCTGGGCGCTGGCTGTTCATGTGCCGGGGACCAGGCCTGCGCTTTAGTGTGGCTACAAGTGCTTGGAG
CACTGGGGCCAGGGCAGCCCGGCCACCGTCTCCCTGGGAACGTCACCCCTCCCTGCCTGGGTCTCAGCCCGGGGGTC
TGTGTGGCTGGGGACAGGGACGCCGGCTGCCTCTGCTCTGTGCTTGGGCCATGTGACCCATTCGAGTGTCCTGCACG
GGCACAGGTTTGTGTCTGGGCAGGAACAGGGACTGTGTCCCTGTG[redacted]
GTAAGATGGCTTTCCTTCTGCCTCCTTTCTCTGGGCCCAGCGTCCTCTGTCCTGGAGCT
JH3
GGGAGATAATGTCCGGGGGCTCCTTGGTCTGCGCTGGGCCATGTGGGGCCCTCCGGGGCTCCTTCTCCGGCTGTTTG
GGACCACGTTCAGCAGAAGGCCTTTCTTTGGGAACTGGGACTCTGCTGCTGGGGCAAAGGGTGGGCAGAGTCATGCT

Fig. 3 (cont.)

TGTGCTGGGGACAAAATGACCTTGGGACACGGGGCTGGCTGCCACGGCCGGCCCGGGACAGTCGGAGAGTCAGGTTT
TTGTGCACCCCTTAATGGGGCCTCCCACAATGTG[redacted]
GTGAGTCCTCACAACCTCTCTCCTGCTTTAACTCTGAAGGGTTTTGCTGCATTTTTGGGGGGAAATAAGGGT
JH4
GCTGGGTCTCCTGCCAAGAGAGCCCCGGAGCAGCCTGGGGGGCTCAGGAGGATGCCCTGAGGCAACAGCGGCCACAC
AGACGAGGGGCAAGGGCTCCAGATGCTCCTTCCTCCTGAGCCCAGCAGCACGGGTCTCTCTGTGGCCAGGGCCACCC
TAGGCCTCTGGGGTCCAATGCCCAACAACCCCCGGGCCCTCCCCGGGCTCAGTCTGAGAGGGTCCCAGGGACGTAGC
GGGGCGCCAGTTCTTGCCTGGGGTCCTGGCATTGTTGTCACAATGTG[redacted]
GTGAGTCCTCACCACCCCCTCTCTGAGTCCACTTAGGGAGACTCAGCTTGCCAGGG
JH5
TCTCAGGGTCAGAGTCTTGGAGGCATTTTGGAGGTCAGGAAAGAAAGCCGGGGAGAGGGACCCTTCGAATGGGAACC
CAGCCTGTCCTCCCCAAGTCCGGCCACAGATGTCGGCAGCTGGGGGGCTCCTTCGGCTGGTCTGGGGTGACCTCTCT
CCGCTTCACCTGGAGCATTCTCAGGGGCTGTCGTGATGATTGCGTGGTGGGACTCTGTCCCGCTCCAAGGCACCCGC
TCTCTGGGACGGGTGCCCCCCGGGGTTTTTGGACTCCTGGGGGTGACTTAGCAGCCGTCTGCTTGCAGTTGGACTTC
CCAGGCCGACAGTGGTCTGGCTTCTGAGGGGTCAGGCCAGAATGTGGGGTACGTGGGAGGCCAGCAGAGGGTTCCAT
GAGAAGGGCAGGACAGGGCCACGGACAGTCAGCTTCCATGTGACGCCCGGAGACAGAAGGTCTCTGGGTGGCTGGGT
TTTTGTGGGGTGAGGATGGACATTCTGCCATTGTG[redacted]
GTAAGAATGGCCACTCTAGGGCCTTTGTTTTCTGCTACTGCCTGTG
JH6
GGGTTTCCTGAGCATTGCAGGTTGGTCCTCGGGGCATGTTCCGAGGGGACCTGGGCGGACTGGCCAGGAGGGGACGG
GCACTGGGGTGCCTTGAGGATCTGGGAGCCTCTGTGGATTTTCCGATGCCTTTGGAAAATGGGACTCAGGTTGGGTG
CGTCTGATGGAGTAACTGAGCCTGGGGGCTTGGGGAGCCACATTTGGACGAGATGCCTGAACAAACCAGGGGTCTTA
GTGATGGCTGAGGAATGTGTCTCAGGAGCGGTGTCTGTAGGACTGCAAGATCGCTGCACAGCAGCGAATCGTGAAAT
ATTTTCTTTAGAATTATGAGGTGCGCTGTGTGTCAACCTGCATCTTAAATTCTTTATTGGCTGGAAAGAGAACTGTC
GGAGTGGGTGAATCCAGCCAGGAGGGACGCGTAGCCCCGGTCTTGATGAGAGCAGGGTTGGGGGCAGGGGTAGCCCA
GAAACGGTGGCTGCCGTCCTGACAGGGGCTTAGGGAGGCTCCAGGACCTCAGTGCCTTGAAGCTGGTTTCCATGAGA
AAAGGATTGTTTATCTTAGGAGGCATGCTTACTGTTAAAAGACAGGATATGTTTGAAGTGGCTTCTGAGAAAAATGG
TTAAGAAAATTATGACTTAAAAATGTGAGAGATTTTCAAGTATATTAATTTTTTTAACTGTCCAAGTATTTGAAATT
CTTATCATTTGATTAACACCCATGAGTGATATGTGTCTGGAATTGAGGCCAAAGCAAGCTCAGCTAAGAAATACTAG
CACAGTGCTGTCGGCCCCGATGCGGGACTGCGTTTTGACCATCATAAATCAAGTTTATTTTTTTAATTAATTGGCGC
GCGCCCTCTGTGACAGCATTTATACAGTATCCGATGCATAGGGACAAAGAGTGGAGTGGGGCACTTTCTTTAGATTT
GTGAGGAATGTTCCGCACTAGATTGTTTAAAACTTCATTTGTTGGAAGGAGAGCTGTCTTAGTGATTGAGTCAAGGG
AGAAAGGCATCTAGCCTCGGTCTCAAAAGGGTAGTTGCTGTCTAGAGAGGTCTGGTGGAGCCTGCAAAAGTCCAGCT
TTCAAAGGAACACAGAAGTATGTGTATGGAATATTAGAAGATGTTGCTTTTACTCTTAAGTTGGTTCCTAGGAAAAA
TAGTTAAATACTGTGACTTTAAAATGTGAGAGGGTTTTCAAGTACTCATTTTTTTAAATGTCCAAAATTCTTGTCAA
TCAGTTTGAGGTCTTGTTTGTGTAGAACTGATATTACTTAAAGTTTAACCGAGGAATGGGAGTGAGGCTCTCTCATA
ACCTATTCAGAACTGACTTTTAACAATAATAAATTAAGTTTCAAATATTTTTAAATGAATTGAGCAATGTTGAGTTG
GAGTCAAGATGGCCGATCAGAACCAGAACACCTGCAGCAGCTGGCAGGAAGCAGGTCATGTGGCAAGGCTATTTGGG
GAAGGGAAAATAAAACCACTAGGTAAACTTGTAGCTGTGGTTTGAAGAAGTGGTTTTGAAACACTCTGTCCAGCCCC
ACCAAACCGAAAGTCCAGGCTGAGCAAAACACCACCTGGGTAATTTGCATTTCTAAAATAAGTTGAGGATTCAGCCG
AAACTGGAGAGGTCCTCTTTTAACTTATTGAGTTCAACCTTTTAATTTTAGCTTGAGTAGTTCTAGTTTCCCCAAAC
TTAAGTTTATCGACTTCTAAAATGTATTTAGAATTCATTTTCAAAATTAGGTTATGTAAGAAATTGAAGGACTTTAG
TGTCTTTAATTTCTAATATATTTAGAAAACTTCTTAAAATTACTCTATTATTCTTCCCTCTGATTATTGGTCTCCAT
TCAATTCTTTTCCAATACCCGAAGCATTTACAGTGACTTTGTTCATGATCTTTTTTAGTTGTTTGTTTTGCCTTACT
ATTAAGACTTTGACATTCTGGTCAAAACGGCTTCACAAATCTTTTTCAAGACCACTTTCTGAGTATTCATTTTAGGA
GAAAGACTTTTTTTTTAAATGAATGCAATTATCTAGACTTATTTCAGTTGAACATGCTGGTTGGTGGTTGAGAGGAC
ACTCAGTCAGTCAGTGACGTGAAGGGCTTCTAAGCCAGTCCACATGCTCTGTGTGAACTCCCTCTGGCCCTGCTTAT
TGTTGAATGGGCCAAAGGTCTGAGACCAGGCTGCTGCTGGGTAGGCCTGGACTTTGGGTCTCCCACCCAGACCTGGG
AATGTATGGTTGTGGCTTCTGCCACCCATCCACCTGGCTGCTCATGGACCAGCCAGCCTCGGTGGCTTTGAAGGAAC
AATTCCACACAAAGACTCTGGACCTCTCCGAAACCAGGCACCGCAAATGGTAAGCCAGAGGCAGCCACAGCTGTGGC
TGCTGCTCTTAAAGCTTGTAAACTGTTTCTGCTTAAGAGGGACTGAGTCTTCAGTCATTGCTTTAGGGGGAGAAAGA
GACATTTGTGTGTCTTTTGAGTACCGTTGTCTGGGTCACTCACATTTAACTTTCCTTGAAAAACTAGTAAAAGAAAA
ATGTTGCCTGTTAACCAATAATCATAGAGCTCATGGTACTTTGAGGAAATCTTAGAAAGCGTGTATACAATTGTCTG

Fig. 3 (cont.)

GAATTATTTCAGTTAAGTGTATTAGTTGAGGTACTGATGCTGTCTCTACTTCAGTTATACATGTGGGTTTGAATTTT
GAATCTATTCTGGCTCTTCTTAAGCAGAAAATTTAGATAAAATGGATACCTCAGTGGTTTTAATGGTGGGTTTAAT
ATAGAAGGAATTTAAATTGGAAGCTAATTTAGAATCAGTAAGGAGGGACCCAGGCTAAGAAGGCAATCCTGGGATTC
TGGAAGAAAAGATGTTTTTAGTTTTTATAGAAAACACTACTACATTCTTGATCTACAACTCAATGTGGTTTAATGAA
TTTGAAGTTGCCAGTAAATGTACTTCCTGGTTGTTAAAGAATGGTATCAAAGGACAGTGCTTAGATCCGAGGTGAGT
GTGAGAGGACAGGGGCTGGGGTATGGATACGCAGAAGGAAGGCCACAGCTGTACAGAATTGAGAAAGAATAGAGACC
TGCAGTTGAGGCCAGCAGGTCGGCTGGACTAACTCTCCAGCCACAGTAATGACCCAGACAGAGAAAGCCAGACTCAT
AAAGCTTGCTGAGCAAAATTAAGGGAACAAGGTTGAGAGCCCTAGTAAGCGAGGCTCTAAAAAGCACAGCTGAGCTG
AGATGGGTGGGCTTCTCTGAGTGCTTCTAAAATGCGCTAAACTGAGGTGATTACTCTGAGGTAAGCAAAGCTGGGCT
TGAGCCAAAATGAAGTAGACTGTAATGAACTGGAATGAGCTGGGCCGCTAAGCTAAACTAGGCTGGCTTAACCGAGA
TGAGCCAAACTGGAATGAACTTCATTAATCTAGGTTGAATAGAGCTAAACTCTACTGCCTACACTGGACTGTTCTGA
GCTGAGATGAGCTGGGGTGAGCTCAGCTATGCTACGCTGTGTTGGGGTGAGCTGATCTGAAATGAGATACTCTGGAG
TAGCTGAGATGGGGTGAGATGGGGTGAGCTGAGCTGGGCTGAGCTAGACTGAGCTGAGCTAGGGTGAGCTGAGCTGG
GTGAGCTGAGCTAAGCTGGGGTGAGCTGAGCTGAGCTTGGCTGAGCTAGGGTGAGCTGGGCTGAGCTGGGGTGAGCT
GAGCTGAGCTGGGGTAAGCTGGGATGAGCTGGGGTGAGCTGAGCTGAGCTGGAGTGAGCTGAGCTGGGCTGAGCTGG
GGTGAGCTGGGCTGAGCTGGGCTGAGCTGGGCTGAGCTGGGGTGAGCTGAGCTGGGGTGAGCTGAGCTGAGCTGGGG
TGAGCTGAGCTGAGCTGGGGTGAGCTGGGGTGAGCTGAGCTGGGGTGAGCTGAGCTGAGCTGGGGTGAGCTGAGCTG
GGGTGAGCTGAGCTGAGCTGGGGTGAGCTGAGCTGAGCTGAGCTGAGCTGAGCTGGGGTGAGCTGAGCTGAGCTGAG
CTGGGGTGAGCTGGGGTGAGCTGAGCTGAGCTGGAGTGAGCTGAGCTGGGCTGAGCTGGGGTGAGCTGGGCTGAGCT
GGGGTGAGCTGAGCTGAGCTGAGCTGAGCTGGGGTGAGCTGAGCTGAGCTGGGGTGAGCTGAGCTGGGGTGAGCTGG
GCTGAGCTGAGCTGAGCTGAGCTGAGCTGAGCTGAGCTGAGCTGAGCTGAGCTGAGCTGAGCTGAGCTGAGCTGAGC
TGAGCTGAGCTGGGGTGAGCTGAGCTGAGCTGGGCTGAGCTGGGGTGAGCTGGGCTGAGCTGGGCTGAGCTGGGCTG
AGCTGGGGTGAGCTGAGCTGGGGTGAGCTGAGCTGAGCTGGGCTGAGCTGAGCTGAGCTGGGGTGAGCTGAGCTGAG
CTGGGGTGAGCTGAGCTGAGCTGAGCTGGGGTGAGCTGAGCTGGGCTGAGCAGGGCTGAGCTGGGGTGAGCTGAGCT
GAGCTGGGGTGAGCTGGGCTGAGCTGGGCTGAGCTGAGCTGAGCTGGGCTGAGCTGGGCTGAGCTGGGCTGAGCTGG
GCTGAGCTGGGCTGAGCTGGGGTGAGCTGAGCTGAGCTGGGGTGAGCTGGGGTGAGCTGAGCTGGGGTGAGCTGAGC
TGGGGTGAGCTGAGCTGAGCTGGGGTGAGCTGAGCTGGGGTGAGCTGAGCTGAGCTGGGGTGAGCTGAGCTGAGCTG
GGGTGAGCTGAGCTAGGGTGAACTGGGCTGGGTGAGCTGGAGTGAGCTGAGCTGAGGTGAACTGGGGTGAGCCGGGA
TGTTTTGAGTTGAGCTGGGGTAAGATGAGCTGAACTGGGGTAAACTGGGATGAGCTGTGGTGAGCGGAGCTGGATTG
AACTGAGCTGTGTGAGCTGAGCTGGGGTCAGCTGAGCAAGAGTGAGTAGAGCTGGCTGGCCAGAACCAGAATCAATT
AGGCTAAGTGAGCCAGATTGTGCTGGGATCAGCTGTACTCAGATGAGCTGGGATGAGGTAGGCTGGGATGAGCTGGG
CTAGCTGACATGGATTATGTGAGGCTGAGCTAGCATGGGCTGGCCTAGCTGATGAGCTAAGCTTGAATGAGCGGGGC
TGAGCTGGACTCAGATGTGCTAGACTGAGCTGTACTGGATGATCTGGTGTAGGGTGATCTGGACTCAACTGGGCTGG
CTGATGGGATGCGCCAGGTTGAACTAGGCTCAGATAAGTTAGGCTGAGTAGGGCCTGGTTGAGATGGTTCGGGATGA
GCTGGGAAAAGATGGACTCGGACCATGAACTGGGCTGAGCTGGGTTGGGAGACCATGAATTGAGCTGAACTGAGTGC
AGCTGGGATAAACTGGGTTGAGCTAAGAATAGACTACCTGAATTGTGCCAAACTCGGCTGGGATCAATTGGAAATTA
TCAGGATTTAGATGAGCCGGACTAAACTATGCTGAGCTGGACTGGTTGGATGTGTTGAACTGGCCTGCTGCTGGGCT
GGCATAGCTGAGTTGAACTTAAATGAGGAAGGCTGAGCAAGGCTAGCCTGCTTGCATAGAGCTGAACTTTAGCCTAG
CCTGAGCTGGACCAGCCTGAGCTGAGTAGGTCTAAACTGAGTTAAAAATCAACAGGGATAATTTAACAGCTAATTTA
ACAAGCCTGAGGTCTGAGATTGAATGAGCAGAGCTGGGATGAACTGAATGAGTTTCACCAGGCCTGGACCAGTTAGG
CTAGGACCTCGTTCTATAGAGGCAGACTGTGTGCTACAGTGGAGTTTCAAGATGATTCCATGAGTCCTCCCCGCCCC
CAACATAACCCACCTTCCTCCTACCCTACACGCCTGTCTGGTGTGTAAATCCCAGCTTTGTGTGCTGATACAGAAGC
CTGAGCCCCTCCCCCACCTCCACCTACCTATTACTTTGGATGAGAATAGTTCTCCCAGCCAGTGTCTCAGAGGGAA
GCCAAGCAGGACAGGCCCAAGGCTACTTGAGAAGCCAGGATCTAGGCCTCTCCCTGAGAACGGGTGTTCATGCCCCT
AGAGTTGGCTGAAGGGCCAGATCCACCTACTCTAGAGGCATCTCTCCCTGTCTGTGAAGGCTTCCAAAGTCACGTTC
CTGTGGCTAGAAGGCAGCTCCATAGCCCTGCTGCAGTTTCGTCCTGTATACCAGGTTCACCTACTACCATATCTAGC
CCTGCCTGCCTTAAGAGTAGCAACAAGGCGCGTCAAACTTACCCTACCTTTATCCTGGTGGCTTCTCATCTCCAGAC
CCCAGTAACACATAGCTTTCTCTCCACA[redacted]

Fig. 3 (cont.)

[redacted]ATGATCCCAGTGTCCTTGGAGCCCTCTGGTCCTACAGGACTCTGACACCTACCTCCACCCCTCCCTGTG mouse IGHγ1 - ΔCH1

TAAATAAAGCACCCAGCACTGCCTTGGGACCCTGCAATAATGTCCTGGTGATTTCTGAGATGTAGAGTCTAGCTAGG
TCATGGAATGAGGGGTCTCCATGGTTTGAGGCCTGAGTTGTGACTAAGGAAAAACCCATAGGCCTACACTGCCACAC
CCAGCACTTTTGAATTTGCCTGACATGAAAAGAATTTACCTCTCCCTGGAAAGTGGAGCCTTATCCCTAGGCAGTTC
CCTTACCAGACCTTCCTCTAGCTTGCACTTTGTTCTGGGCACAGAATGTGTCTAACCCCCCAAAGCAAGGAAGACAC
AACCTCTACCTCCCTCACTCTGTCCTTACCCCTTTTCCTGGCTAAGCATCTCACTGAGTGCGCTGAATAGATGCATG
TGGCCACAGTCTTGCAGACAGACCCTTGCCATCTCTCCACTCAGCTTTCCAGAGGCTAAGTCTAGCCCGTATGGTGA
TAATGCAGGGAGCTCTATGCTATCTCAGTGCTATCAGACTCCCAAGTGGAGGATGAACATGGACCCATTAAAACCAA
CCTGCGCAGCAACACCCTGCCAATAAGGCCCGTATGTGAAAATGTGCACACATCTACACATGCACAGGCACACACAC
ACACACATGCATGGGCACACACACATACAGAGAGAGAGAATCACAGAAACTCCCATGAGCATCCTATACAGTACTCA
AAGATAAAAAGGTACCAGGTCTACCCACATGATCATCCTCGGCATTTACAAGTGGGCCAACTGATACAGATAAAACT
TTTCTATGCCAAGGACGCCAACATATACACAAGTCCGCTCATGACAAATCTGTCCCTGAACCTCAGACTGGCGCCCG
TGACTCATACAGTGGACACTCCTCCAAAGCTGTATAGCTTCCTTTACTTCCCTGTGTGTACTTTCTCTGAAGTACAC
TCATCACACAGAAGAGGCCCTGTGATTACTCTGGCCCTCTGTTCTTGGTCATCAGAGAATAGACAGAAGATCAGGCA
AACTACACAGACACTTCCCACAATCATCACAGGCCCTGACTCTGCTCTCCAGTCTCAAAACTGAAGGCTGGAGCACA
CAGAATAAGCTCCTGCACAGGCCAGGCCAGTATCGGGTCCAGTGTGTCTGACTGAGCCCAGGGACAAAATGGCAGCA
CTTTGGGGAACTGAGGTTTCTGGTCCAAGAAGGAGAGATGGAGGCCCAGGGAGGGTCTGCTGACCCAGCCCAGCCCA
GCCCAGCTGCAGCTTTCTCCTGGGCCTCCATACAGCCTCCTGCCACACAGGGAATGGCCCTAGCCCCACCTTATTGG
GACAAACACTGACCGCCCTCTCTGTCCAGGGCTGCAACTGGACGAGACCTGTGCTGAGGCCCAGGACGGGGAGCTGG
ACGGGCTCTGGACGACCATCACCATCTTCATCAGCCTCTTCCTGCTCAGTGTGTGCTACAGCGCTGCTGTCACACTC
TTCAAGGTCAGCCATACTGTCCCCACAGTGTCTACAATGTCCTCATACTCTTCCCCATACTGTCCCTGTGGTGACCT
ATACCCCACACTGTCCCATGCTAATGACCACAGTCTTACATGCTATGTAATGCTGTCTACCCTTCTGTATGCACAGT
CTCACAATGTCCCATGCAGTCTCCACGATGCTCCATACTGTCCCCATTCCAACCCATGCTGCCCCTTGTTCCCCGCT
ATGCTGTCCCATGCTATTGTCTGTATTTTCATGCTCTTTTCACACTGTCCCTAGTGTCACATTCTGCCCATGTTGTC
CACCACATTGTCCCCACTCTGTACACAGCCTCACACTGTACCCTGCTACCCGATAATGTTCCCTGTTGTCCCCAACT
CTCTCCCTGCACCATTTGTCAACTGTCCCCTGAATTCCCATGTTGTTCCCACACTGTTAGTGTGTAATGTGCTCTGT
CCCAGGTGTACCTTGTTCCGTGCTGTCTCACTTCATCGCCCATTCTGTCCTTGTACTAACCCCACTCTATCACCACA
CTGTCCCTATGCACTGCCCACATTGTCCTCATACTGTCCCATTTTGTATCTTCATCCTGTCCCCATAGTGTCCAATG
ATCTACCCCACACTATTCCCACTTCATGCCCCTACAATTTCCCTATTCCATTCCTCTCTGGTCACCATGCCATCCTT
CCCACTCCTGCACAGCTGGAGAGGGACTCCCGGGATGAGTCCTTGCCCAGATGAGCTACCTATCTAGAGGAGTCTTC
AGGTGGGAAGGGAATGCAGTCTTGATCTTGGTCTTATTCACCCTGTCTCACAGGTAAAGTGGATCTTCTCCTCGGTG
GTGGAGCTGAAGCAGACACTGGTTCCTGAATACAAGAACATGATTGGGCAAGCACCCTAGGCCACCTCCTGTAATGG
CATTTCCCAGGCCCCGAAGGACCCTGTCCAATATGCCAAGCAGCACAACTGAGATCACACTGTCTGCTCATCTCGCT
TTCCTCCGACCCCGAGACTCAGCTACTCTCAAATTTTCCCTCTCTGAAGGACCATGTGGACATTACATTGCTCCAGG
CCACAGCCACCAGGACCTAAAACACCATCACAGCAGCACCAAAGACACTGGATAGACCCACAAGGGCAATAGTTTCC
TCAACAGTATATCCAAACTGTTGGGACAAACGAGCAATCACTGAAGAAGTGACAAGTTCCCACAATGTCAGTGTCCA
GCTGAGAAGGGACAAAAAGTGGTACCAGCCCTGTCCACACCACCTTCTAATTCACAGGAATACGTGATAGAAGAGGC
AGGTTGTAGATCCGAAAGATGAGACAGATTTTATCAACTCCAGAAAGAGCTGGGTCCAACTGAATTATTCTAGCGAC
CTTGGCATTGTCATGACCTGCCATGACCTTCCTCCTTAACACTTCGATAAACCCTGGGATATGGAAAATGCCTGTGT
TTCTCAGGGTTTGGGAAAGAACCATCCATGTTGGGATTCTTGTGTAGATCCTCCTTCTGGTCACAGATGCAATACAC
TGGATTTTCAGGCAAAGGAGCAAATTCACAGACAACTCTGGCCCTACAGCCCTAAGACCTAGACACCACCATCTCCT
TGGAATTATCAAATTTAACACCCGGCACACAACAAAGAAGGACTGGGACTTTGAGGCCTTTGTGTAGCCCTAGAGGG
GGCAGAGGCCACTGAGCAGGGATTGGGTGATCACAAGGACCTCCTGGAGAGGGACCTGAGGAGCAGGTTCCAATTGG
GCCAAAGAAAGAAGAACAACAATAGAGATGAAGGATGCTGGAAAGAGCCATGGTACAGCAGTCTTGTCCTTCAGACA
TGACTCTTACAGCCCAGGACTCTTACAGTAGCTAGCTGGAGCAGAAGTCCAAGGGATTACCATGCCCTAGGGCCACA
GGCTACTGGAGGGTGGAGTGAGTCTACTACACAGGTCCAATGCCTGTTTCTCCATTGCTTCTCAGCCAATGAGAAT

Fig. 3 (cont.)

CAGAGTCTCCACCTCCAAGAAAAAGGAAGGTGGAAATGAAAGGTGAGCACCTGCCTTCCCGTGACTGGCAGAAAGAT
CTCCACGGACTCAAGGCTTTGACTTCAAACGGCGCGCCAATCTTCCAGAAGCCAGGCTGGGACCTCAGCAAAAGGGA
AGACATAACCCAACTCCAGGATGCCCTGTGGCTGATCACTCTTGTCTTGGCGGGGATGAAGGTTGGAGAAAGGCCTC
CACGTTTCAGAGCTAAGACCGACGTGACAACTTCCCAGCCCACTCACAGACTTTCCTGAGCAATAAATTGATGCAAA
ACCACAAATTCCTACTCTCAAAAACAAACATTAACAAAGGATTGGGGGAGGGGGTCAGGGGTAGTATGGTGGCGTTG
GGCAGGGTAAACTCAGGGTACCCATTGTCTAATGTCTGAGACATAACTTGAACATATGTGTAGCTGCAGCCAAAGAT
GAACAAGTGATGGTATTTGTGTCCTCTTCAGACCCGATACCAGGTCATTAAGCTTGAGATCTGGACCTGATTTCTAA
ACATTTGGCCTCTGTGAGCACCCTTGGCAAATACTGAACAGCAAACCCTGGTCCTGGCTGTGAACCTTGGTCCTGAT
CACTGAGCCCTATATTGGTAACTGAACCGTGATCCTGATCTCTGACCTCAGTCATGGTCATGAGGCCCTGGTCCTGG
CCACTCATTCTAATAACTGGTCCCTAGTCCTGAGCCCTGAACCTTGGTCCAGGTCACTGAATCCTAGTCATGATCAC
TGGGTTTGATCCTCATTACTGAGCCTAGTCTTGATCACCGATGACTGGTTTTGATCATAGCAATTAACCTGATCACT
AGTCCCCGTTCCTCATCACTGGGCCATGATACTGGTCACTGGGTCCTGATCCTGATCACTAAATCCTGTTTCTAAAC
AATGTGTAGTGGAATGTATAGTGAAGCCTTTGTGTCTGGCTCTGGGTGAAATGTCTCAGCAGAGCCTTTGCTAGGTT
TGGGTTAATCAGTTGGGGCTGAGAAATGTTTTTGAGGCTGTTTGAACTTCAAAAGAAGAAATGTCTCCCTGGACAAT
CTGCACATTTGCAGCTGCGCAAACCTTCATCCTAAAACTTAACTCCTGGCAAACTTAGAATTCTTACTTTTAATAAT
GGCTAGCCATGGTTGAAAGGGACTGAGATGTCTGTGGGTGGGTGGAACCTTTCCCAGCTCCAAGTAACTCTGTATAC
TGTTTGAATAAAGTAACTGAAGTGAGCTAGCTGGGGTCAATCTTCTTTCCAAGGAGAATAAAGCCCTCCGCTCCTCC
AGAAAATGAAGGCTTAGCTCCTTGGTTAGCTTCTCTCTCTACTGCGGCACCTACAACCAACTCAGCAGTCCTAGGTT
CCTGTCACCAGATCCAGTCCTGATAGCTAAGTGTCAATCCTCGTCACTAAGGCCTGATCCTTAGCAATATGCCTGGG
GTCTGATAATCAGACTGACATTCTGATAACTGGACCCAGATTCTTATCACTGGGTCTTTGTCCTGGTCATGGGCATT
TGACCCTAGTCTACAGCACTGAGTTCTGGGCATGGACCCTGGGTCCCAGTTCTAGATACTGAGTTCTGGTTCTAATA
ACTGGCTCCTGTACTGATCGATGGGTCCTGACCTAGTCATTGGGCCCTGATCCTCAACATTGACTTCAAAACCTGAA
CTCTAGCCCCATGCCTCATTCACATTAGGAGGATCCCTACAGGGGATTCCTGCAGAAGATTCCAGAATCCCCACAAC
ACTGTTCACACACTGGGCTGCAACTGGGACAGTGACCCCTTTGCTCATAGGACTTGCCCAGGCTCAGATGCACTGAA
TGGAGACAAAGCAAGCCCAGGCCCTGGGAGATGGAGCCTCTGGCCTGGGGTCTACAGATGTGGGGTCAGCATCATAG
GGAGGTTTGCAGGGCAGGTGTGGGGCAGGGCAGAAGTGGTCATGCTTGTAGATACTATTTTTCTCTCCTCTGGAGCC
TCCTTTGTCTATCACCTGCTGTCCTGGGATCTCTATCTGGGGTCAACAATGTTTGCAGTACAGGTGTGGGGGTAGGG
CAGGGATGTTCACATTAGCAACTTGTTTTTCTCTCTTCTGAAGTCTCTGTTGTCTATCACCTGCTGAAACATTCAAA
GCAGCTCTGAGCTGAGGGCAGCTGAGTCATCCTGAGCCTGTCTCAGCACAGGTGCCCCAAACCAGAGCTACTGTTCT
GAGAATCACACCACACTGGACCAGGCCAGGTGGGCCTGGGGCCTGGATGAGGGGTGGGAGCCAGGGGAGCCCTGCCA
GGGGCTGAGGAGGCCCCAACCCCCATCACCCAAGGCCATCCACACTCGTGCCTTAATGAGGCCATGTTCTGTCCCAA
TGAGAACAAGTCCAATTAAGATTAAGTATGGTCTTCCCAGGATCATCCAGAGTCAAGGGGTGTCAGCCAGGGACAAC
CCAGACCAGCCTGAGGTCAGCCAGCATCACCCAAGGCCACACAGCTATTCTGGCAGAGGACTAGAATAGTCAGCTCA
TCGAGGCCCTGGAGATGCAGAATGGAGAGTTTATCCCTGCCAGACAGGGTTCCTCAGATAGGCAGGTCCCTCACCAC
ACATGACCTCCCTGAATATTTCCCAGAGTCCAGTTGGTTCTAGACTATCACAATAGTCTTCTGTATTCCTGATAAGC
ATGCAGAAAGCTAACAGGATGACAAGAAATTTTATGCAGAAAACAGAAGCATCTACAGGATAGAACAGAGGAGAATA
GATACTGGAAGTCTGCTGGAGACCCCAGTGGAGTCTCTTTGTAGAGTCAAGCTGTAAGATCAAACCTGCACTGAGCC
TCAAGATTGAGTCAAGTACAGAGGCAACCTTCAGGACCCTAAAGACCTTACAGGCAATGGACAGGATGGAGTCCAGG
CAGACAAGTAAACGGGCAGTCATATGTAACATAATGAACCATGTCAACAGAGGGTACTGAGCCAAGGAAGGCTCTGG
GACACTTGTGGATAATCTGCCACTGGATCTCTTGATGTATATACCAGGTGATCAGATGACAGTTTAGTGGCGCCATC
GCCGTTACAGTGTTAGGTGTTGTCCTCGTCATGGGTTCACGTGAGAATGTGACACCTTTTTAGTTGGATGTGTACAG
TAAGCTCTCAGGCCTGGTGTTCCTGGTATGATTTTAATGATCCATGTGTTCCTATATCTTTAATAAGTTTATAGGGT
GACATTAAGCTTGGGGATAAGTTGTTTATCAGGCTGTGCCTTTAGAAGTTGATGTGCAGGGATTGTTGTTTACACCA
AGATGCCCAGTCTTCCTCCAGCTTCCAAACGGAGTCAAAGGCCATTTGAAAATGTGAAACCTCTCAGGGCAAGGTAC
AATCTTTTTTTTTTTTAAAGCCACTACCTCACACAACATGGAGTAATTTAAAGCAGGGTACAGCTTGATCGAAACAC
ACACACACACACACGCATACACACAATGTAAGATACCGAGAAGGGGATCAAGGGACACAGAAGTAGAGAGAGAATGA
GACAGTTCAGGGATGTAGAGATGAGAGGTAACTAGAGGAAAGGAGAAACACAAGGACTGGAGGGTAAAGAGCCAGGG
ACAGAAAGATCCATGCAAGCAAGACAGACAGACACAAGGAAGGGAAAGGTGGGAAGAGACAGACAGACAAGGTGCAG
CAATGTAGCCCACCTGAGACTCCCATGAAAGTCTGGCACCCACTCTCAGATGAAAGCCAAGTACCTACAGACACGTA
CCCACAGCACCCACACAGAGCACCTGCCTGCCTAACTCAAGCCCACCTACCCATCGCCTCTCCTCCAGGCCTCTGTC
CTCAGGAAGCACACTGAGGGTAACTCAGTCTGGACACTTCTAACTATGGCTTAGTGAACAGCCTGAGAGGCTCTGGA
TCCACAGGTCACTACCACTTGCTGGCCCTGTGCTCCATGCCATGCTTCAGGGGGGGATTCACTGAATGCATGAACCA
TAGTCTGGGGTCAACATGTACTAAGGGATAGGATCCTATCAGGATTTGTCCAAATAAGGTCCAAACAAAGTGAAGAA

Fig. 3 (cont.)

GGTGATAGGCGAGAACAGCTGGCAGCTGAGAGAACGCTGGCCAGTTCTTAGGCCAGAGCTTAGGGACAATTTCCAGA
CCTAGCCTTTCATCTCAACTCTAGGTCATGGGTAACTTCCCAGATCTCTATTTTGTTCCTGGTAACTATGCATGCTG
GTACAAGTCTAAGAACCTCGGTGAGACACAGAACCAGTAAGATGAAAGCATCCGTGGATAAGGAAGAAAGGAGAAGA
GTAGAAGGGACAGGACCCTGGACACATGAGATTCCCACACCCAGGAACTGCTCATCCAGCCCGAGAAACGGTATACC
CCTAGCACACAGAAAGAAAACAGTACCACAGGTCTAAAAGAGTAGAGTCAGTGGGAAGGGGTACTACTAGGGCGCCT
CCTGCCTGGTCCAGGAGCAGAGGCTGGGAAGGGGCACTAAACAGGGGGAAGCATGGAGACAGGGAGATGAAGGAGCC
TTTGGGACTGCATGGTGGGAACTAGACTGTTCTCTGAATGAGCCTGTGTGTGTGGCAGCTGCCTGAGAGGGAAGACA
CCCAGAGGCCAGGCAGAGGAAAAGAGTAATCAGGGCTGAGGGGACTGGGGTGGGGGTCTGAGGAAGTCAAGGTAGCT
ATCGCCCATTTATCAGGGCCATGACATGCACTTCATGGGCACATATCTAAAACCAGACCTGGCCCTCACCTACACTC
AGACAATGTCCCTTTTGTGGATTTAGGGATTTCAGTACTTCATCCCATGGCCTCTCAAACTGGAAGATCCATCTAAA
AGGCTGATGTTGTGGTATCAGGGCCCAGGACTAGAGAATGGGACACTGAGTGGCAGAGGTGCAGAGGACACATACAC
TCACTCAGATGAAAGCAATGCACAAGAAGACAGAGCCATGTATGAACACTCCTCAGACTCAGACCCACAGCACTCAC
ACCCAGCTCCCCACAGACACACACAGCCCCTGCCTGCCTGTTCCAAAAATCAAACCCATCTACCCACTCCCTCTCCT
GCAGGCCTTTGTCCTCAGAGTGGCACACTGAAGGTAGCTCAGCCTGAACACTTCCCATGGGACCTGGTGAACAGCAG
GAGCCTCTGGTCCACACTCCCCACCTCTTGTTAGCCCTGTAGTCTATGTGATGCTGTTGAGAACAGGGTACATGGCC
TCTGCCTGGTACAGTCTGGGGTGCAGGCTTCAGGTGAGGCCCAAGTGTGAAGAGTGCAGAAGACAGTGGGCAGAGCT
GAGAGACTGCTAGCCAGTTTTGTTCAAAGGACTGTGATGGCTGCTCCAGGCTACTGAACATTCCAGGACTGCTTCCT
ACCCTCCTCAAAGATGCTGGAACACAACCAATCCTCAACACAATCCAATGTAGTTGCCTGTAGCAGGGCATGCCTCT
GTACAGCAGGGAGTCACACAGAGCCACATGAGACTCTAGACCTGGGGACTGCAGAGGGGAAGGCATGTCCAAGACGG
CCTCCTCCTTGTTACCCTAGGTTTTCAGGCCTCAGGATAACCACTGAACAACATATGCTGAGTCCTGTTCCCCAGGA
TGCTGATGGACACCAGGTCACAGGGCTAGAGGCCAGGAGGGCTAGAGCCTGTGGGCAGGGGGGCTATATTCATTCTT
CCTGTGCTTGCCCAGGAGCAGGTGCTGGGCAGGGGCACAGGACAGGGTGAGGCAGGGAGACAGGGGCATGAAGGGGC
CTCTGGGACCACAAGGTGGGAACTAGGCTGTGCCTGACTGAGCCTGTGTGTGTGACAGCTGATTCATGGGGAAGACA
CCCAGAGACCAGGCAGAGGAAAAGAGTAATCAGGGCTGAGGTGACTGGGGGTTGGGAGGTCTGAGGAGGTAGAGGCA
GCTATGTCCCATTTGTCAGGGTATGGGGACATGTACTTCATAGACACAGATCTAAGAACCAGGCGTGGTTCCCACCT
ACCCCCAGACAGTGTCCCTCATATGGGCTTAGGGATTTCAGTACTTCATCCCACGGCCTCACACCTTGGAAGATCCA
CCTCAAAGGCTGATGTTGTGGTGTGGGGGTCCAGGACTGGGGCCAGGGACACTGGTTGGCAGAGGTGCCCAGGACAT
AGAGTGCTCAGAGTGTAGTTGGGGACATGCTGAGCACTGTTCCTCTGTGAGGGGACAGGCTGAGACAGGGACTGAAG
TCCATCCATAGGCTCAGCACATACCAGGCTCTGGATGGGAACACTGAGCTCTGCCACCCTCCAACATCTGGCACAGC
AGCCTCCTGTGCCAGGGAAGCTAGTCAGCAGGGACAGAGTTCCTGTCCGGGCTGGATGGAGTCTTCTCTGCTAGCAT
CCAAAATAAGTGCATCTTCAGCAATAAGGTCCAGTCATGGTGGACGGCCAGGAACAAAGGCAGTAAACAGCCTGGTT
TGTGTTTGGTTATCTACAGTCTCTCTCACTAAAGCATCAAGACTTCTTTTAATAAATTTAGAAGTTGTTTTCTTTTG
AAACACGGTCTCTCTATGTAGTCCTGGGGGTCCTGGAACTCCCTGTGTAGAAGACCAGACTGTCTTCAAACTTAAGG
AGATCCTCCTGTCTCTGCTTCCTGAATGCTGGGATTAAAAGCATGTGCCACCACACCCAACCTAACCCTTTCTTCTG
AGAGCAACATGCATACAATTTCCCCTCTTATTTCCCCAGATTTTCAATCCTTTTATCCACACTTAAATCTTTAATGC
TAAAATCTCCCTCCCTCCATTTCCAAGCTGCATGTGTTCTACTATTCCCTCAAATTATTTTTCCTTGTGTGCAGGTT
TTAGATTTGAATGCAGGAAGCCTTCACTCTGGCAAAGCCTCCCCCAACCCAGCCTTTCCCATTTCCACACCTCCTAA
CACGTGATTTAGCCCACATCCCCTCATGTGTATGGTGTTTCCCTTCAGTCTGAGGTATTACCCCCAGTGTCCCCTTA
CAGCTGCCTATGGTCACAAATACCTTTCATCTGTTTTTGCTGTGGAAAGCGTTTATTTCCCCTTGAATTTTAATAGC
TTTCTGGGTATACTACCCTGGGTTGAGAGTTTAGATTTTTCAGATCTTGGAATATGTCTTTCTAGACATCTAGCCTT
AAATGTTTCTACTGGGGGCTACAGAAATGGCTTGGTGGTTGACAACACATGATGTTCTTGCAGAGGAGTGGGTTTTG
ATTCCTAGTACCCCATATCAGCTAAGAGCTATGGAAGACACAAATGGAAGAGGGGACTCTGAGATTCTGAGAAAAGC
CTCATGGTTAAGGGTACACTGAGATACTGAGAGAGAAAGACAGAGACACTGAGAAAGACAGAAGCACAGACCACTAA
AAGAGACAGGGAAACAGAGAGAGACAGTGATGAGATGCAGGGACAGAGCAACCCAGAGAGACAGACAGAGACATAGA
CACTGATAGAGACACAAAGAAGAGAGGGGTCGTGGAAGTTTTGAGAGAAACTGGTAGGAGGTGAGAGAGACACAGAG
CCAATACAGACACAGAAAGACAGAGACTCCAGAGAGACAGAGACTGAGAGAGACAGAGACTGGGAGAGACAAAGATA
CTGAGACAGTCAGAGACACCAATGGGTGCTTTTCCAGGGGATCCAGATTCAATTCCCAGCACCCACATGGCAGCTCT
CTACTGTAATCCCAGTTCCAGGGTGCCCTGAAAAATCCTTCATGCATGTGAAGCTTAGAAGCTCACACACAAACACA
CAGACAGACAGACAGACAGACAGACAGACAGACACACACACACACACACTCAAATGAAGAGTGTGGTTCTCTTTC
TCTCTCTCTGATGAAAGCCATGCACCAGAAGACAGAGCCATGTGTGAACACTCCTCAGACTCAGACCCACAGCACTC
ACACCCAGCTCCCCACAGACACACACAGCCCTGCCTGCCTGCCTGTTCCAAAACTCAAACCCATCTACCCACTCCCT
CTCCTGCAGGCCTTTGTCCTCAGAGTGGCACACTGAAGGTAGCTCAGCCTGGACACTTCCCATGGGACCTGGTGAAC
AGCAGGAGCCTCTGGTCCACACTCCCCACCTCTTGTTAGCCCTGTAGTCTATGTGATGCTGTTGAGAACAGGGTACA

Fig. 3 (cont.)

TGGCCTCTGCCTGGTACAGTCTGGGGTGCAGGCTTCAGGGGAGGCCCAAGTGTGAAGAGTTCAGAAGACAGTAGGCA
GATCTGAGAGACTGCTAACCAATTTTGTTCAAAGGACAGTGATGGCTGCTCCAGGCTACTGAACATCCCAGGTCTGC
TTCCTACCCTCCTCCAAGCTGTTGGAGCACAACCAACCATCTTTGTAATTGCCCAGTTGTTTGTTATTGCCTATAGC
AGGGCATGCCTCTGCACACCAGGGAGTCACACAGAGCCACATGAGACTCTAGACCTGGGGACTGCAGAGGGAAAGGC
ATGTCCAAGAGGGCCTCCTCCTTGGGACACTGGGATTCCAGGTCTCAGGATAACCACTGAACAACATCTGCTGAGTC
CTGTTCCCCAGGATCCTGATGGACCCCAGGAGGTCACAGAGCTAGAGGCCAGGAGGGCTAGAGCCTTTGGGAAGGGG
GAATGTTAGGGTTTCTCCCATCCTGGTCCAGGAGCTGCTCACCTGACAGTGATACAGGACAGGGTAAGGCAGAGACA
GGGGGATGAAGGAAACTTTGGGAGCACATGGTGGGAGTGTAGGTTGTGCTTTTGCTTAGCCTGTGTATATAGCAGCT
GCATCATTGGGAAGACACTCAGAGGCCCGACAGAGGAAGAGTAATCAAGGCTGAGGGGACAGCAGTGTCTAAGGAAG
TGGAGGCAGCTATGGTCCATTTGTCATAGTATTGGGACATGTACTTCATGAACACTGATCTATGGACCAAGCCTGGT
TGTCATCTGCCCTCAGTCAGTGTCCCTCATGTGGGTTTAGGAATTTCAGTACTTCATCCCACAAGCCAGTCACATTG
GAACATAAATGAAATGCTGATGCTGTGGTGCTGGGGCCCAGGAGTGCGGGGTTAGTATACTGGGTGACAGAGGGTGT
CCAGTAAATAGATTGCTTAGAGTGTAGGTGGGGACAAGCTGTGCAGTGTTCCTCCATGAGGGGAAAGACTGGTACAG
GTTTTGACATCTCTTTCGTATCCATAGGCCCTGCCATACTGCCCTTGTCCATGGTCCCTGTGGGGTCACATACTTAG
TGTCAAGTAAACCATACCACAAACTGGAAGGGTCTACACTATCCTTGTAGGTTCTACACTCTCCATGACTTCTCCCA
ACTCACACAGACTGTTCCAATACACTACTCTCTTCAGTGGGCAATCATGCCATGAACAGAGAGTGGAGGGTTATGGT
TGCCCTATATTCTGACACATCCAACAGTCTTGTGCATTTGACTCTCATGTGTACAAGCGTGCTCAGGCCTGCTGTAG
TCCCCTCGAGACAGTGATGCCTTCCTTGAGAGCCGATTCTCACTGTCAGCATCTCCTCAGACCAAAGCCCTATAGAT
CCAGCCTCTTTGAGGAGCTAATGTAGTCAGTCACAGGGCTTGATGTTGGTGGCTATAGCTGCTGTCCCCATGGCTGC
CAGAGATGCTTGACCACCATAATCCCAGACTTGAGCATAGGAATAACCTGGAATCAACAGCATCCAGACACTGTAGG
GACTGGCCAGAGATGTGCATAGACCCTATGTCATGTGACCAAGACCTCTTTTTCTAGTATCTTATTTCATGAAAGTC
TACAAAATACGATCTTCTATTCCTTTTATTCCTCTTTGCCTGCTAACATGGAACCTTCTAGAAAGAGGGTCCCCTCT
CTGTCTACTGACTGTGAAGATAGATCCTGTAGGTGTGATCACAGAGTAATGTTTCATTTCTTGGCCAGTCTCAAGCC
AGGGGACTCAGGGAGAGAGACAGGAGAAGGAGAGATGGGGAGAGAGACAGAAAGACAGAAAAACAAAGCAAGGGAGA
GACAGAAGCAGGCAGACCTGGAGACTGGGTGCTTAGGAAAGAGATAAATGTGGATACAGGGAGTGAAAGATAGGGAA
TTGAAGACAGAGGTGGAGATAAAGACCAGAATATGGGAGTCAGAGACAGACAAGAGATATAGAGATCAATATAGGCA
AACAGAGACTGAGAAAGACAGTGATGAGACAGAGAGACATGGAGACAGACAAGGAGACAGACATGGAGACAGACAAG
GAGACAGAGATAGAAATAGGGAGAGAAAATAATACATAATTAGTGGTTGATTAAGGAAGAGATAATGAATGGCAAGA
AGAGACAGAGGCAGGGAGAGACATATACAGGTAGAGAAAAAGATGAAGACAGACAGAGAGAGACTGAAAGAGGGAGA
AAGATACAGAGAGAAGAGAGACTATGAAACAGGCAGAGATATAAAGACAGTGAGAGAAAAACAGAGAGACAGAGATG
GAAGAGAGACAGAGAGACAGGGAGATAGAGAAATGGGAAGACAGGAGGACCAAGAGAAGAGACACACGGCGAGGCAA
GATGTAGTAGAGAGACCTCTGATGGAATCGGCATAGGTGGAGGCAAACATAGATAGACTCTCTCCAACTGCAGTTGA
CAGACTGAGCAGAGAGAATACCATTCAGAGAGAAACAGAGGCTAAGGCTAGGAAAGGCAAGAGTAGCCAGAGGAGAC
AGAGTTGAGCCTGTGGGACAGGACCAGACGCCATCTTGGAAGAGGCAGTGACAAGCCAGGGAGGTGACAGGCTGGTA
CAGTTTCTATCCCACAGTCCACAGGCTGGTGTCACAGGCCTGTCTCCTCGTGGCCACAGTCTATCCCTGCCTGCCAA
GCCTGTCTGTGGAGGGATGGGGGGGGGGGGGGCTGGGCTGAGGCAGGCCAGGACTTTTCCAGTGGAGTGGCCAGGCA
CTGGGCTGAGGGCATGATCCCTGCCCACCATCCCAGTGGGTCTGGGTAATGGATGGCCTTGATTATTTTCCTTCGTG
TTTAGGGTGGAACCTGCTTAGAGGCAGCTAGGGCTCTCCATGATGGCCTAGCCTGTGGTGAGTTAATGAACCCCTAA
GGGTAGTTCTTCCACATGGGCTAGGGTTACAATCTGGGGGTTGGGGGCTCAGATATCAGTACCAGAAACAAGGCTTA
CTCCCAACATGTCACACTCGCACACACACAGCTGCCGAGTTACTCATTCTGTGCAGAGTTGGCTCACAAGGGCACAT
GCAAATGGATGTTTGTTTCATACAGAAAAACATGTTTCTCACTTTCTGAGGTTGTTTCCAGAAATAGCATCAGTGAC
TCCCCCACCTGCAGCTGCAGGTTCACCCCAACCTGGCCAGGCTGACCAGCCTTGGGGATGGGGGACTCCCAGCATAG
GCCACTGGGACTGGGGGTCCATGACCCCTATTGATGATGTTGAATTCAGTGTTTCCCAGTTATCACCACTGCTGGAA
TCTGACCCACCAAGAGGACATGACAGGAGATGGGCAAGGATGGGTGGCTCAACACCCCAGGGAAGTGAGAGAGGCAG
GAAGGCTGTAGGTGTGCTCCAGATCCTGGGTCTACCCAGAACCATGGGAATGGTGGGCAGTGATCATGCCCTCAGCC
CAGTCCCTGGCCACTCCACTGGAAAAGTCTTGGCCTGCCTCAGCCCAGACCCCCTCCCCCACCCCTTCTCAGACAGA
CTTGGCAGACAGGGAGCTAGCCTGTGGCCACATGGAGACAGGCCTGTGACTCCAACCTGTGGACTGTGGGATAGAAA
CTGTACCAGCCTGTCACCTCCCTGCTTGTCACTGGCTCTTTCAAGATGGTGTCTGACCCTGGCTCCATCTCTGGCCA
ACCCTGCCTTTCCCAGCCTTAGCCTCTGCCTCTTTCTCTCTCTCTCAGTGTGATTCTTGCTCAGTCTGTCCCTCAGT
TACTGTCTCTCCATCTCTAACAAAACATAAGAGCTGTCTCTATTAACACCTTGTCTCTCCTCTTTCTTCTTCTCCTT
CTCCTTCTCCTTCTCCTTCCTCTCTCTCTCTCTCTCTCTCTCTCTCTCTCTCTCTCTCTCTCTCTCTCTCTCTCTCT
CTCTCTCTCATCTCTGCTTGTGCCCCCTTTCTCTAGGTGCACATCTCCTACCTCTGTCTGTCTATCTGTGTCTCTTC
CTTCTGTCATCTCCTCTCTATCATTCTTTCAGTCCTTCTCTATGTCTCTTTTCTGTTGATGTCTGTCTTTGTGTGTC

Fig. 3 (cont.)

TCTCTCTCCATCCCATTCCTTTTATGACTCTGGCTCCCCTTATCTCTCTGTCTGTATTTCTGCCCCACTTCTCTGTC
TTCCTATCTTTTTGTCTTTTCTCTGTTTCTGATTTTTCTCTCCATGTCTTTCTCTCCACTTTTCTCTCTCCCTTTCT
GAGTCTTCCTGCATCTGTCTCATTGCTTCTCCATCTCGCTCTCTCTTTCTCTGTTTTCTGTCTCTGTTCTTGTATCT
CTGTGTGCCTCTCCATGTCTCTCTGCTGTCTCTTTTTCTCCATACAGCAATTTACTAAAAGAACAAACATCAAGGCA
GGAAAGTATATATATTTCAAATAAAAGTTCTTCAAATTGCTATGTCCTATACTCCAAGAAGCATTTCCAAAGTATAG
ATTAATTTAACCCTTTTAAATGAAAAGATACATTTTTAACTTCTAAAGTGTCTCCACAAAGAAATGAATGTTTTTAA
TTAAGAAATGTTGTAATTTAGTGTTGGGCTCCTGTCTTATAATGTACACTTCCTTATAAATCTAGCCATGTGGCTTA
TATCCATTTGGTATGCTCGGAGCTTTATGTAATAAACGTCTTCCCGATAGGTGCAAGGATTGGTGTTTTGTACTGCT
TACTACATACATGCTTTTAATCATTCCAGGACATACCGTCCCTCTGCTGCTGCTTCTCACCGTCTTTGCCTTTCTCT
CACCCTGTCCATCTTTCTCTCTCCCCATCTCTCTGTTTCTGTCCCTTCCTGTTTCAGTCTCTCTCCAATCTCCCTGT
GTTTCTCTCTCTCTCTCTCTCCTGATGTCTCTTTCTCTGTGGGCTTGTCTCCCCATCTGTCCTCTTCATTTCTGTAT
TTCTCCTTATCTTTCTATCTCTGTCCATGACTCTGTCTCTTTCTGCCTCGTTCATCCCCTGCCCCCCTGAAGGCACA
ATGACACTTTTATCAGGGTTTAATAGGAAAGTTTCAGGGCAGGAAAGTTGTAAGACTCAAGCAGCTGCCCCGAGGAG
GCCAGTGGGGGAGATTGGTAAAAAGCCATGACATCTAATCTGACATGGAGGTCAGGCACATGTCCCACAAGCAGCCA
CATGGCGAGAAGGGGGCAGTTAGAGAACAAGTAAGAAAGCCCAGCATGTTGGGGAGGAAGCCAAGGTGTTAAGGAAA
ACTTGCTCAGAGGGAGACAGAAAGAAGGAAGCTACAATTCTGTGAATTCAGAAAGGAAGCTGACTTACAGCCCCACA
TGGCTATAGCCCCTAAGCTTCTGGCCCTTCCTCTTCTGTCTCTTCCTGTTCTCTGTCACCCCTGTTTCTCCCTATTC
TCTGTCACACCTGTCTCTGTGCTCCCATTAATCTCTCTCTGTCTCTACACATCTCCACCTCTGCCTCCTTCATCTCT
GTCTTTTCCGGAACCCTGTCTGTCTCTGTCAGGCTTCTCCTTGTCTCCCCCTGCAGACTTGCAGTTTCTCCCTTTGT
CTTCCTCTGTCTTACCTTTATTATGTCTCCCCGTCTTTCCTACCTTCCTGACTTTCTGTCTCTTACCCTGAGTCCCC
TGGCCTGAAACTGGCCAAGAAGGAAAACATCAGTCTGTGATCACTCCTACAGGGTCTGTCTCCATAGCCAGCAGAGA
GGGGACCCTCTTTCTAGAAGGTTCCCTGTTCGCAGGCAATGAAGAATAAAAGGAATAGAAGATCCCGTTGCATTAAG
GTTTCATGAGATAACATACTAGGAAAAGAGACCTTGGTCTACGTAGAAGTCTGGTCAGTCCCTGAAGTGTCTAGACG
CACTTGATCCCTAGGCCATCACTATGTCTGAGGTCATGGTGGTCAAGCATCTCTGGCAGTCACAGTGAAAGCAGCTG
TGGTCACCAACATCAAGCCCTGTGACTACAATAGCTCCTCAAAGAGGCTGGGTCTGTGGGGTTTTGTTTTGAGGGTC
AGCTAGAAATGGGAGTGAGTCCAAGGAAGACCCACTGCCCCCGCCCCCGAGAGATAGGGGAATGAGCATGCTTGCAC
ACGTGGACATGAAAGGCACAAGAGTGTTGTATGTGACAGTTTGAGGTGACCACATTCTGCCCTCTCTGTGCCTGTCA
TGGTTACAACTGAGGACAGTGGTGGATTTGGGCAGAGTCTGTGTGAGCTGGGAGAAGCTGTGGAGAGTTGCAAGCAT
GGCATGTAGATATCAGAAGCCCTGGTCTTCCAGCAGTCCTCATGGTGATGGTTCAGTAGGACACTGGATGTGTGGCC
CATGCTAGGGTCATGGGCAAGGCTGGTATGGGTTGACTCTATGGCTGGACAAAGAGCTTTAACCTCGTCAGCTTCCG
CAATATGGAGGAACACTGCACAGCTTGCCCCCACCTGCACTCTGAGCACTCTGTACACTGGACATGCTCTACTACCC
AGTGTCTCAGACTCCAGTCCTGGGCCCCAGCCCCATAGCACAACCATGTTTATAATCCCTCCAGTGTGAGAGGCCAT
GAAATGTTGTGGAGCTCAGTCTGAAGGCAGGTGGGAGACAGGCATGCTTTTGGATCCATGTCCATGAAGTATATGTC
CACATTCCATGACAAAGGAGCCGAAGCCACCTCTATTTTCTCAAGGACCCCCTCAGTCCTCATTACTCTTCCTCTGC
CTGGCCTCTGGATGTCTTCCCCATGAATCAGCTGTCACAAACACAGGCTCAGTCAGAGCACAGTCTAGTTCCCACCT
TGTGGTCCCAAAGGCTCTTTCACGCCAGTGTCTCCCTGCCTTACCCTGTCATGCACCTCTGGCCAGCCAGCTGCTCC
TGGGCAAGGACGAGAAGAAGCCAAGTAGTTCCTCTTCTCACAGACTCTAGTCCTGCTGGCCTCTAACTCTGTAACCT
TCTGGTGTCCATCAGGATCCTGGGGCCACATCACTCTGAGTGTGTTTATCACCGGCAATCCTGAGGGCTAAGATTTC
AGATTCTAAAGGAGGAGGCCCCCGTGGACATGCCTTCCCCTCTGCAGTCCCCAGGTCTAGAGTCTCATGTGGCTCTG
TGTGACTCCCTGATGTACAGAGGCATGCCCTGCTACAGGCAATTACAATGGATTGGGTAGAGGGTTGGTTGTGCTCC
AACATCTTTGAGGAGGGTAGGAAGCAGACCTGGGATGTTCAGTAGCCTGGAGCAGCCATCACTGTCCTTTGAACAAA
ACTGGCCAGCACTCTCTCAGCTCTGCCCACTGTCTTCTGTACTCTTCACACTTGGGCCTCACCTGAAGCCTGCACCC
CAGACTGTACCAGGCAGAGGCCATGTACCCTGCTCTCAGATGATGTTTCATACAGATTACAGAGCTAACAAGAGGTG
TGGTGTGTGGACCAGAGGCTCATGCTGTGTAGTCACCCATGGTCCTGCTGAAAAGCAGGCTGGGGCTAAAAAGAGAA
TAGAGTATGAGACACACCAAGACAAATGCTGATCAAAGCCCAATGTTTACTAAAAATCTGTGCTTATATAAAAGGAA
AGCCCTTCTCCTGCAGATCCACTTTTGATGTCTGTTGCCAGCCTGTAAGCAATTTGTCTGACAGCACTAGTTTGACA
AGAAGGTGTCAATCACTGCTGTCTTTGGAATCTCTCAGCCTCTCAGCAGGTATCAGTGTCTTGGAGAAGAAGAGCAA
TGGTGACAGAACAATAGAATCATCTAGGTGGGAAGGCTCTACCCCAGGTGGTCTCATTCTCAGTGGCAGCAAGGTCT
GAGCCAGCCTGCTCAAGGCTGGGGGAGGCTACAATGTTATTCAACAGGTCCCATGGGAAGTGTCCAGGCTGAGCTAC
TCAGTGTGCCACTCTGAGGACAAAGGCCTGCAGGAGAGGGAATGGGTAGATGGGTTTGAGGTTTGGAACAGGCAGGC
AGGGGCTGTGTGTGTGTCTGTGGGGAGCTGGGTGTGAGTGCTGTGGGTCTGAGTCTGAGGGGTGTTCACACATGGCTCT
GTCTTCTGGTGCATGGCTTTCATCTGAGAGAGAGAAAGAGAACCACACTCTTCATTAGAGTGTGTGTGTGTGTGTGT
GTGTGTGTGTGTGTGTGTGTGTGTGTGTGTGTTTGTATGTGAGTCTGTCTGCTGTCTGTGTGTAAATGTGAGCTTCT

Fig. 3 (cont.)

ATGCTTCACATGCATGAAGGATCCTTCAGGGCACCCTGGAACTGGGATTACAGTAGAGAGCTGCCATGTGGGTGCTG
GGAATTGAATCTGGATCCCCTGGAAAAGCAGCCAGTGCTCTTAATCCTTTTGGTGTCTCTGCCTGTCTCAGTATCTC
TGTCTCTCTCAGTCTCTGTCTCTCTGGAGTCTCTGTCTTTCTGTGTCTGTACTGCCTCTGTGTCTCCCACACCTCCT
ACCAGTTGCTCTCAAAACTTCCACGTCCCCCCTCTTCTTCATGTCTCTATCAGTGTCTGTGTCTCTGTCTGTCTCTC
TGTGTCTCTCTGTCCCTGCAGCTCATGACTGTTTCTCTCTAAGTGTTTCCCTGTCTCTTTCAGTGGTCTGTGCTTCT
GTCTTTCTCAGTGTCTCTGTCTTTCTACTTCAGAATCTCAGAGTCCCCTCTTCCATTTGTGTCCCTTCTTGGGCTCA
TTCACTCTGCCTCCAGTGTCATCACTTGTGAGACCAGAACCTACTATGAGTCCAGAGGACTGTCCTTCATGGTCTGT
GACCAGCTGTGATCTGGGGAACACTGGGGAAGGCATGAACAGGGAGGGACCTGCCTGTCTGTGGAGCCCTGCCTGTC
AGCATGAACTCCCCATTCTGCACCACCAGAGCCCTGCTGAGCTGACTATTCCACACCACCTCCAGAAAAGGGCATTG
AATCCTGTGGAACCGATGGCTCTTAGCTGATACGGGGTACTAGGAATCAAAACCCACTCCTCTGCAAGAACATCATG
TGTTGTCAACCACCAAGCCATTTCTGTAGCCCCACAGTAGAAACATTTAAGGCTAGATGTCTAGAAAGACATATTCC
AAGATCTGAAAAATCTAAACTCTCAACCCAGGGTAGTATACCCAGAAAGCTATTAAATTTCAGGAGAAAATAAAAAA
GCTTTCCACAGCAAAAACAGATGAAAGGTATTTGTGACCATAGACAGCTGTAAGGGGACACTGGGGGTAATACCTCA
GACTGAAGGGAAACACCATACACATGAGGGGACGTGGGCTAAATCACGTGTTAGGAGGTGTGGAGATGGGAAAGGCT
GGGTGGGGGGAGGCTTTGCCAGAGTGAAGGCTTCCTGCACTCAAATCTAAAACCTGCACACAAGGAAAAATAATTTG
AGGGAATAGTAGAACACATGCAGCTTGGAAATGGAGGGAGGGAGATTTTAGCATTAAAGTTTTAAGTGTGGATAAAA
GGATTGGAAATCTGGGGAAATAAGAGGGGAAATTGTATGCATGTTGTTCTCAGAAGAAAGGGTTAGGTTGGGTGTGG
TGGCACATGCTTTTAATCCCAGCATTCAGGAAGCAGAGACAGGAGGATCTCCTTAAGTTTGAAGACAGCCTGGTCTT
CTACACAGGGAGTTCCAGGACACCCAGGACTACATAGAGAGACCGTGTTTCAAAAGAAAACAGTTTCTAAATTTATT
AAAAGAAGTCTTGATGCTTTAGTGAGGGAGACTGTAGATAACCAAACACAAACCAGGCTGTTTACTGCCTTTGATCC
TGGCCCTCCACCATGACTGGACCTTATTGCTGAAGATGCACTTATTTTGGATGCAGAGCAAAGAAGACTCCATCCAG
CCTGGACAGGAACTCTGTCCCTGCTGACTAGCTTCCCTGGCACGGGAGGCTGCTGTGCCAGCTGTTGGAGGGTGGCA
GAGCTTAGTGTTCCCATCCAGAGCCTGGTATGTGCTGAGCCTATGAATGGACTTCAGTCCCTGTCTCAGCCTGTCCC
CTCACAGAGGAACAGTGCTCAGCATGTCCCCAACTACACTCTGAGCACTCTATGTCCTGGGTACCTCTGCCAACCAG
TGTCCCTGACCCCAGTCCTGGACCCCCACACCACAACATCAGCCTTTGAGGTGGATCTTCCAAAGTGTGAGGCCGTG
GGATGAAGTACTGAAATCCCTAAGCCCATATGAGGGACACTGTTTGGGGGTAGGTGGGAACCACGCCTGGTTCTTAG
ATCTGTGTCTATGAAGTACATGTCCCAATACCCTAACAAATGGGACATAGCTGCCTCTACCTCCTCAGACCCCCCAA
ACCGCAGTCCCCTCAGCCCTGATTACTCTTTTCCTCTGCCTGGTCTCTGGGTGTCTTCCCCATGAATCAGCTGTCAC
ACACACACAGGCTCAGTCAGGCACAGCCTAGTCCCCACCTTGTGGTCCCAAAGGCCCCTTCATGCCCCTGTCTCCCT
GCCTCACCCTGTCCTGTGCCCCTGCCCAGCACCTGCTCCTGGGCAAGCACAGGAAGAATGAATATAGTCCCCCTGCC
CACAGGCTCTAGCCTTCCTGGCCTCTAGCCCTGTGACCTGGTGTCCATCAGCATCCTGCACAACAGGACTCAGCATA
TGTTGTTCAGTGGTTATCCTGAGGCCTGAAAACCTAGGGTAACAAGGAGGAGGCCCTCTTGGACATGCCTTCCCCTC
TGCAGTCCCCAGGTCTAGAGTCTCATGTGGCTCTGTGTGACTCCCTGCTGTACAGAGGCATGCCCTGCTATAGGCAA
CTACAATGGATTGTGTTGAGGGTTGGTTGTGTTTCAGCAGCTTGGAGGAGGGTAGGAAGCAGACCTGGGATGTTCAG
TAGCCTGGAGCAGCCATCACTGTCCTTTGAACAAAACTGGCCAGCACTCTCTCAGCTCTGCCCACTGTCTTCTGCAC
TCTTCACACTTGGGCATCCCCTGAAGCCTGCACCCCAGACTGTACCAGGCAGAGGCCATGTACCCTGCTCTCAACAG
CATCACATAGACTACAGGGCTAACAAGAGGTGGGGAGTGTGGACCAGAGGCTCCTGCTGTTCACCAGGTCCCATGGG
AAGTGTCCAGGCTGAGCTACCTTCAGTGTGCCACTCTGAGGACAAAGGCCTGCAGGAGAGGGAGTGGGCAGATGGGT
TTGAGGTTTGGAACAGGCAGGCAGGCAGGCAGGGGCTGTGTGTGTCTGTGGGGAGCTGGGTGTGAGTACTGTGGGTC
TGAGTCTGAGGAGTGTTCACACATGGCTCTGTCTTCTGGTGCATGGCTTCCATCTGAGGGGGTGTGTGTGTGTGTGT
GTGTGTGTGTGTGTGTGTGTGTGTGTGTGTGAGCTTCTAAGCTTCGCATGCATGAATGATCCTTCAGAGCACCCTGGAA
CTGGGATTACAGAGGTGAGCTGCCATGTGGGTGCTGGGAATTGAATCTGGATCCCCTGGAAATCAGCCAGTGCTCTT
AATCCTTTTTGTGTCTCTGCCTGTCTCAGTATCTCTGTCTCTCTCAGTCTCTGTCTCTCTGGAGTCTCTGTCTTTCT
ATGTCTGTACTGCCTCTGTGTCTCCCTCACCTCCTACCAGTTGCTCTCAAAACTTCCATGTCCCCCCCTTCTCTGAG
TTTCTATCAGTGTCTGTGTCTCCGTCTGTCTCTCTGTGTCTCTCTGTCCCTGCAGCCCATGACTGTTTCTCTCTAAG
TGTTTCCCTGTCTCTTTCAGTGGTCTGTGCTTCTGTCTTTCTCAGTGTCTCTGTCTTTCTCTCTCAGAATCTCAGTG
TCCCCTCTTCCATTTGTGTCCCTTCTTGGGCTCATTCACTCTGCCTTCAGTGTCATCACTTGTGAGACCAGAACCTA
CTATGAGTCCAGAGGACTGTCCTTCATGGTCTGTGACCAGCTGTGATCTGGGGAACACTGGGGAAGGCATGAGCAGG
GAGGGACCTGCCTGTCTGTGGAGCCCTGCCTGTCCGCATGAACTCCCCATTCTGCACCACCAGAGCCCTGCTGAGCT
GACTATTCCACACCACCTCCAGAAAGGGGCATTGAATCACGTGGAACCTAAGAACACCGTGTTGTCAACCACCAAGC
CATTTCTGTAGCCCCACAGTAGAAACATTTAAGGCTAGATGTCTAGAAAGACATATTCCAAGATCTGAAAAAAATCT
AAACTCTCAACCCAGGGTAGTATACCCAGAAAGCTATTAAATTTCAGGAGAAAATAAAAAAGCTTTCCACAGCAAAA
ACAGATGAAAGGTATTTGTGACCATAGACAGCTGTAAGGGGACACTGGGGGTAATACCTCAGACTGAAGGGAAACAC

Fig. 3 (cont.)

CATACACATGAGGGGACGTGGGCTAAATCACGTGTTAGGAGGTGTGGAGATGGGAAAGGCTGGGTGGGGGGAGGCTT
TGCCAGAGTGAAGGCTTCCTGCACTCAAATCTAAAACCTGCACACAAGGAAAAATAATTTGAGGGAATAGTAGAACA
CATGCAGCTTGGAAATGGAGGGAGGGAGATTTTAGCATTAAAGTTTTAAGTGTGGATAAAAGGATTGGAAATCTGGG
GAAATAAGAGGGGAAATTGTATGCATGTTGTTCTCAGAAGAAAGGGTTAGGTTGGGTGTGGTGGCACATGCTTTTAA
TCCCAGCATTCAGGAAGCAGAGACAGGAGGATCTCCTTAAGTTTGAAGACAGCTTGGTCTTCTACACAGGGAGTTCC
AGGACACCCAGGACTACATAGAGAGACCGTGTTTTAAAAGAAAACAGTTTCTAAATTTATTAAAAGAAGTCTTGATG
CTTTAGTGAGGGAGACTGTAGATAACCAAACACAAACCAGGCTGTTTACTGCCTTTGATCCTGGCCCTCCACCATGA
CTGGACCTTATTGCTGAAGATGCACTTATTTTGGATGCAGAGCAGAGAAGACTCCATCCAGCCTGGACAGGAACTCT
GTCCCTGCTGACTAGCTTCCCTGGCACGGGAGGCTGCTGTGCCAGCTGTTGGAGGGTGGCAGAGCTCAGTGTTCCCA
TCCAGAGCCTGGTATGTGCTGAGCCTATGGATGGACTTCAGTCCCTGTCTCAGCCTGTCCCCTCACAGAGGAACAGT
GCTCAGCATGTCCCCAACTGCACTCTGAGCACTCTATGTCCTGGGTACCTCTGCCAACCAGTGTCCCTGACCCCAGT
CCTAGACCCCCACACCACAACATCAGCCTTTGAGGTGGATCTTCCAAAGTGTGAGGCCGTGGGATGAAGTACTGAAA
TCCCTAAGCCCATATGAGGGACACTGTCTGGGGGTAGGTGGGAACCACGCCTGGTTCTTAGATCTGTGTCTATGAAG
TACATGTCCCCATACCCTGACAAATGGGACATAGCTGCCTCTACCTCCTCAGACCTCCCCAACCCCCAGTCCCCTCA
GCCCTGATTACTCTTTTCCTCTGCCTGGTCTCTGGGTGTCTTCCCCATGAATCAGCTGTCACACACACACAGGCTCA
GTCAGGCACAGCCTAGTTCCCACCTTGTGGTCCCAGAGGCCCCTTCATGCCCCTGTCTCCCTGCCTCACCCTGTCCT
GTGCCCCTGCCCAGCACCTGCTCCTGGGCAAGCACAGGAAGAATGAATATAGTCCCCCTGCCCACAGGCTCTAGCCC
TCCTGGCCTCTAGCCCTGTGACCTGGTGTCCATCAGCATCCTGGGGAACAGGACTCAGCATATGTTGTTCAGTGGTT
ATCCTGAGGCCTGAAAACCTAGGGTAACAAGGAGGAGGCCCTCTTGGACATGCCTTCCCCTCTGCAGTCCCCAGGTC
TAGAGTCTCATGTGGCTCTGTGTGACTCCCTGATGTACAGAGGCATGCCCTGCTATAGGCAACTACAATGGATTATG
TTGAGGGTTGGTTGTGTTTCAGCAGCTTTGAGGAGGGTAGGAAGCAGTCCTGGAATGTTCAGTAGCCTGGAGCAGCC
ATCACTGTCCTTTGAACAAAACTGGCCAGCACTCTCTCAGCTCTGCCCACTGTCTTCTGCACTCTTCACACTTGGGC
ATCCCCTGAAGCCTGCACCCCAGACTGTACCAGGCAGAGGCCATGTACCCTGCTCTCAACAGCATCACATAGACTAC
AGGGCTAGCAAAGAGGTGGGGAGTGTGGACCAGAGGCTCCTACTGTTCACCAGGTCCCATGGGAAGTGTCCAGGCTG
AGCTACCTTCAGTGTGCCACTCTGAGGACAAAGGCCTGCAGGAGAGGGAATGGGTAGATGGGTTTGATGTTTGGAAC
AGGCAGGCAGGGGCTGTGTGTGTCTGTGGGGAGCTGGGTGTGAGTGCTATGGGTCTGAGTCTGAGGGGTGTTCACAC
ATGGCTCTGGTGCATGGCTCTCATCTGTGTGTGTGTGTGCCACAGGCTCCATTTGAGTGCTCGGTTGGCTCCATTGC
TGTACCTCTGTCTCCCTTGTTTTCTATCTGTCTGTCCTCCCTGTCTGTCTGTCTCTCCTTTCCTATGCCTCCTCCTC
ATATCCATGTCTGCATCTCTTTCTATCAGTCTCTATCCCTGTGACCCCTGGTTTCCATTTCTGTCTTTCTGCATATC
TTTCCATCTTTCTCTCTGTGTGTCTGTCCTCATCTCTTCCAGTGTCCGTGTTTCTGTTTCCCTCTGTTCCCATGCGG
AGGTATGTTCTCACAATCCTTAAGTTCCCTGGTCCCCTGTCCCCCATTTCTTGTCATATTATCCCATCAGTGTCTCT
GTGCCTCTCTGTCTGTGTCTCTGTGTTGTCTCTGTGTGTGTCTCTCAGTATCTCTCTCTCTCTCTCTCTCTCTCTCT
CTCTCAGTATCTGTATTTCTTTTAGTAACTTTGCTATCTTTTTAAGTATCTCTGTCTTTCTTCATCTCTGTCTCTCT
TGAGGTCTCTGTCTTTCTGCATGTCTAATGTTTCTGTATCTCTCTCACCTCATCTCTGCCTCTCTCAATATTCAGTA
GATCCATGCCCCTTTATTCTTTGTGCCTCTGTCTCTGTTTGTCTCTTTCTCTGTCTCTCTGTCTTTCTCTCTCTCAG
AATCTGTGTCCCTCATGTTATTTCTCAAAATGCCTCCCTAACTCTTTCAATAACAGTTTCTGCCTCTTCTTTCTGGG
CCTGGCTCAATCTTCCTTCTTGGACCTCAGTTTCATTGGTTGTGAGACCATACCCTGCTATGAGTCCAGAGGACTGT
CCTCCATAGTCTAGAACCACATGCTATCTAAGGGATATTGGGGCAATACATGTGTAGTGAGATACCTGCCTTTCTGA
TGAGCCCTGTCTGGCAGGGATAAATTCTCCATTCTGCATCTCCAGGGCCTTGCTGAGCTGACTATTCTAGTCCTCTG
CCAGAATAGCTGTGTGGCCTTGGGTGATGCTGGCTGACCTCAGGCTGGTCTGGGTTGTCTCTGGCTGACACCCCTTG
ACTCTGGATGACCCTGGGAAGACCATACTTAATCTTAATTGGACTTGTTCTCATTGGGACAGAACATGGCCTCACTA
AGGCACGAGTGTGGATGGCCTTGGGTGATGGGGGTTGGGGCCTCCTCAGCCCCTGGCAGGGCTCCCCTGGCTCCCAC
CCCTCATCCAGGTCCCAGGCCCACCTGGCCTGGTCCAGTGTGGTGTGATTCTCAGAACAGTAGCTCTGGTTTGGGGC
ACCTGTGCTGAGAAAGGCTCAGGATGACTCAGCTGCCCTCAGCTCAGAGCTGCTTTGAATGTTTCAGCAGGTGATAG
ACAACAGAGACTTCAGAAGAGAGAAAAACAAGTTGCTAATGTGAACATCCCTGCCCTACCCCCACACCTGTACTGCA
AACATTGTTGACCCCAGATAGAGATCCCAGGACAGCAAGTGATAGACAAAGGAGGCTCCAGAGGAGAGAAAAATAGT
ATCTACAAGCATGACCACTTCTGCCCTGCCCCACACCTGCCCTGCAAAGCTCCCCAGGATGCTGACCCCACATCTGT
AGACCCCAGGCCAGAGGCTCCATCTCCCAGGGCCTGGGCTTGCTTTGTCTCCATTCTGTGCCTCTGAGCCTGGGCAA
GGCCAATGAGCAAAGGGGTCACTGTCCCAGTTGCAGCCCAGTGTGTGAACAGTGTTGTGGGGATTCTGGAATCTTCT
GCAGGAATCCCCTGTAGGGATCCTCCTAATGTGAATGAGGCTTGGAATAGCAAAGGGACGTCTTGTAAAATACCACT
GATTCCTTGGGCCTCAGACAATGGATTTGAGATGAGGACCAAGGTCCAGGGCCAGTGTTGGTAAGCAGAATTTGGGG
CTAGAGTTCAGGCTTAGAAGTCAATGATGAGGGCCAGGGCCCAGTGACTAGGTCAGGGCCCATTGATCAGTACAGGA
CCCAGTTGTTAGAGCCGGAGCTCAATGATCTGGACCAAGTCACAAGGCCAAATGATCAGGATCAGTAGCCAGTTACC

Fig. 3 (cont.)

AGGACCGAGATCCAGGTTTCACAGCCAAAGCCAGGTTACCCCAACCAGAGACCATTCATCGGAATCTGGGTCTGTTG
ATCGGAGCCCAAGCACGCTGCTGTAAACCAGAGCTGCTCTAAAGCAGAACTCAGTGCTGAGCACCAGAGATAAGTGA
TGAGACCAGGATTCAGTGATTAAGGAAACAAAACCAAAGGTCAATAGGATATTATGTGGAGAGAGGGGAGAGAGAGA
GAGAGAGAGGACAGAGAGAGAAAGAGCGGTAGGTTCAGGACTAAGTCTCAGTGAGGAGGGTCAGGAGTCAGTGGTTT
GAACCCAGACACACTGCTCAGGTCCACAGTTCAACGGTGAGAGCCAGGGGTCAGCTATCAGAACCAGGTCCAGTAAC
TACAACCAAAAACCAGTGGCCCCAACCAAAAACCAGTTACTAAAACCCGAATAGAATAGAAACTAGCCAGGCAGTGA
TAGCTTTAATCCCAATACTCAGGAGTCAGAGGCAGGTGGATCTCTGAGTTCAAGGTCAGCCTGGTCTACACAATGAG
TTCTAAGACAGCCAGGGCTACACAGAGAAACCCTGTCTGGAAAACAAGCAAAAGCCTAGAAACCGTGGACTCAGTGG
TCAGTGGCAGTTCTTGGTGACTAAGACCATGGTCAAGAGGTCAAGCAGGACTCAGCGGTTAGAATCAGGGCATGGGT
GATGACAGCCTGTTCCAGGGATCAGAACCAGGTCTAAGGGCAAAGGCCATGACTGAGTCATCAAACAGTGTCTCTTC
ATAAGTCCTAGCCAGGCCCAACCAGGCCTAGGGTGTCAGATCAGGCAAGACTGATGCGGTATGTGTGAGGTGGTATG
ACAATACATCTCAGTATCTCTGGGACCCCACCACCATCTTCCCTGCCTCGGTCCACTCACAAATCTCTGGCTCTCTC
ACTGTCTTTGTCTCATTCTTGTCTAGCTTTCTACCGTGTCCCCTCTCCCCACATTTGTCTCTCCCAGTATCTGTCTC
TCTGAAAGTCTCTGTGTCCCCTCTGACTTTCTCAGTGCTTATGTTCCCTGCCCCTTGATCATTTGAGAGGGGGATGG
TAAGTAGAGAATTATGGAACAGTGAGTGTGTGTCTCTATATGTGTGTGTGTGTCTGTGGGGCTGGCAGTGGGTATGT
GTGAGTATGTGTGTGTCTGTGTGAGTGTGTGTCTGTGGGGTGACAGTATGTATGAGTGTCAGTGTGTGTGTGTGTGT
GTGTGTGTGTGTGTGTGTGTGTGTGTGTGTGTCTGTGTGTCTGTGTGTCTGTGTGTCTGTGTGTCTGTGTGTCTGTG
GGGTGGCAGTGTACATGTGTGAGTGTGTGAATCAAAATGTGTGAGCATGTGTGTGTGGAGGTGGTAATGTATGTATG
TATGTCTGTGTGTATGAGTGTGTGTCTATGGGAGTGGCAGTGTATATGTGTGAGTATATTGTGTATTGTGGGTACGG
GTGTGTGTCTGTGTGAGTGTGTGTTTCTATGTGTCTGTGGAGGTAACAGTGTGTATGTGTGAGTGTGTGTCTATATG
AGTGTCTGTATGTGTGTGTGTATGAGAGAGAGAGAGAGAGAAAGAGAGAGTGTGTGCAGGGTGATAGTGTATATATG
TGAGTTTGTGTGTATGTGAGTGTGTGTTTGTGTGTATGAATGTGTGTGTTTATGGGGTGACAGTATGTATGTATGAG
TGCATGTGTCTGTGGGGTAGCAGTGTGTATGTGTGAGTGTGTGTGTGTGTGTGTGTGTGTGTGTGGTATGTGTGTGT
GTGAGAGAGAGAGTGCAGGGTGATAGTGTATATATGTGAGTGTGTGTGTCTGTTTGTGAGAGTGTGTGTTTGTGTGT
ATGAGTGTGTGTGTCTATGGAGTGACACTATGTATGCATGAGTGCATGTGTCTGTGGGATAGCAGTGTATATGTGGG
AGTGTGTGTGTGTGTGTATGTGCAGGGTGGTAGTGTATATATGTGAGAGTGTGTGTTTGTGTGTATGAGTGTGTATG
TCTATGGGGTGACAGTATGGATGGATGTATGAGTGCCTGTGGGGCAGCAGTGTGTATATGTGAGTGTGTGTGTGTGT
GTGTGTGTGTGTGTGTGTGTGTGTGCAGTGTGAGAGTGTATATATGTGAGTGTGTGTGTCTGTGTGTGTGAGTGTGT
GTGTTTGTGTGTATGAGTGTGTGTGTCTATGGGATGACAGTATGTATGTATGAGTGCATGTGTCTGTGGGGCAGCAG
TGTGTATGGTGAGTGTGTGTGTGAGTGTGTGTGTCTGTGTGTGTGTGTGTGTGTGTGTGTGTGTGTGTGTGTGTGTG
TGTGCCACTTCCCTAATATGTTCTCTTCCAGCTATGGCTTCTGCTTCATCCTTCACTCAAGGCCAGACCTCACTGGC
CAGTCCACAGCATAATACCAGCCATGCCTCTACCCAATAATTGTATGTGTCAGGGAGCCAAGAGGATGGACAGGGAT
CTTGTTCTTGGGGTGAGAATGTGAGAACTTTTGGGGAGCCCTTCCACACACCCATGCAGTAGTAGACACCTCTGCAA
AGCTATGCACATCCTCACACTAGCACACTGCACAACCATGCACTCTCTGCAGACTCACTGTTCACCATGAACCCAGC
TAGTCAGATTCATATGTGAAACTCATATCAGCCTCTGCACACACATACACACATATTACACCCATGCACACACATGT
ACACATACATACACATGTACACATACATGTGTACACACACATATAGAGAAGGCATTGGTGGGGAAAACATTAGGCCA
TGGCTACAGTACAGGGCACAAGGATGGTGGTACAGAATGAGGTCAGGCTGGGTCAGCATAACAAGAACACTTGGACA
AAGTGAGGGTAGTGTGTGTGTGTGTGTGTGTGTGTGTGTGTGTGTGTGTATGTGTGTGTGTGTGTACACGTTGAAAG
TCTTCAGTAGACTGGTATCACTAGCCCTGATATGGGCAACACAGCAAGCCTGGGTCACACTCAAGCTGAGTATCAGG
GTAACCAGGGCCTTCTAACCAAGGGTAGATGCAGCCTGTGTTCCGTTTACTGACCAGTGAGAAGCCATGAGCTGAAC
CAGACCAGAAGACCCTTACTGTTCCCACCCAACCCCCACCCAGTTTAGTCTCAGCAAGACCCTGTACTGTGGGCCAC
AGCTCTCCCCCACACCCCACCTGTAGCACAAACACTATTTGCAAACATTTCTAAAAATGATGAGAACAGGAACCACA
GAGCAGAGGGGGGGACTGGCGTGGAAAGCCCCATTCACCCATGGGACTGAAACTCGGGGAACCAGAACCGTAAGGAG
ATTTGCATGGTGCTGGGGGAGGTTGGCCCTGGATCAGTGAGCCCAGAGAGTTACTGGTTTCTCACTTCCATCAGGTC
AACCTCCTCAACCCCCAAAAATGGCCAGGCCTAGGCTATGGATGAGTTTCAATGACCAGGCCCTAAGGACGAGTCAC
AGAGGACTTCCTGGTGGGCTCAGGCAGCAGACCTGCCCAGATGGATTGCAGAACCAGGGGGAGCCATGGCCAGGAAG
GCCAGACGCCTTAGGGGTGTGCTGTCTCTGCATCCTTTGCCCTCTCTGCTCCTCACAGTCCATCTGCCATCTCACAA
TCCCTCCTGTCGCTCTGGGGCCCAGACCTGGCCAGTCTGGGTACCTGTGGAATACACCCAAAGAAGCAATCCCCAGC
CTCAGGACCCACAACTACTTCCCCTACAGACATGAGTGATCTCAGCCCACATGTCTGGGGGCCACAGAAGCCCCTAA
GACCCTACTCTGCTAATAGGCCCTCCTCCCACCAGCCAAGACAATACACAGGCAAGGTGATGTGGATGAGTCACCCC
ATGGGTACCTGTGTCTGAGATACACCCTGTGGGTATCCTGGCCAGAATCTGGTGACCAACCCAACCTGTGTCCCTAG
AGGAGAACTCTGTGCCTGCACTCACCTACCCACCTAACTCCAAGCTTGGTATGATGCAGAGCCCCTGTGTAGACCTA
AAAGTCAGCCATAGGACAGGGTCAAGAATGACTCTTCCTACACATAAAGTCTTCTACTAAGACAGTAAGGTAGACAC

Fig. 3 (cont.)

ACAAACATACCCGGATGCAGAGACACACAGGCATGCAGAGAAGGCATGTAGACACAAACGCATGCATAAACGCACAA
ACATACAGATATATGCTGACAAATATACACAGCAACTTACAAGTACACAGACACACAAACAGACAAACATGCACAGA
CAGAAACACACAGAGCTCAAAATCAAGTATACACAGACAAATTTACACAGAGACTTACAGATACACAGATATATGAG
ACACACCCAAACAGACACACACATGGGGGCACAGAAAAACATACAAGCAGACACATGCAGACTTAAAGACCCACAAG
ACATGGAGAGATACAAAAACACACAACACAGACACAGAGATATAGAGACACACAGACCCACAAATATGAACAGACAC
AGAGACACCCAGAAACAAAAACACACTCAGGCATTCCACTCCCAATGGGCGTACACATGGGCATACACAGCCCAGTC
ACACAGACAAACATAACACATACAGAAGTGCAGGCATACATATCACACAATACACGCTGGTATTCACACACAGGTGT
GCTCACAAACCCCACACACTCACACATAAAAGTTGACACTGGCACTCCCACTCCGAGGCACATGCTTAGCCACAGCC
GGCTGACACTGCACACCCCACACACGTTCCAGAGACTCCCACAGAACTGGAAGCTCACCCAGGCCCACCCAGGCTCT
CAGGCCACACACATGGGACATCTCAGAGACATGTGGGATACAGTTGCTCACAGGTTTCATGAGGACTCACAGGCCTG
TCCTTGAACATTCCCCTGAGCAGGGGCTCCCTTCTTAAAGCACAGGGATCCCATTCTTTACAGATAAGCACCCAGAC
AGAGGCACTACCAGGCCCAGACCACACTAGACACACACAGCTCTGCATTGTCCCACACTCAAACACAGCTCTGTCGC
CTGAGCTCATGCCAGTCACACAGAACACAGACATGGGCTCGTGTGCTAGAGAGACATAAGCAATGGTAGCCAAGGTG
CTCACATCATGCCCATACACACACACACACACACACACACACACACACACACACACACACACACACACCCTGTGAAC
AGGCCTGCAGTCCTGACTGAAGCCCTGCTCTACCCAATTTAGTGAGTCCTGCACCTGAACCCTCTTACCCTCACAGC
CCCTGACCTCTCCCTGTGTGCTGCTCAGCTATGGCCCCTTCCCATTCCTAACGTGCCACCCTAAGATGTCGGTTCCG
TGCATCACCGCACACATGCTCTTGGGATAAGGCCTTAGAAGGCTCTGTACCATCTGCAGCTCATGCCACTGCCTTCC
CTGGTAACCCTCTCCTGCATACAAGGGCTGCAAGGGTCAATGATATGAATCCATCCATGCTCTGACCCCAGCTTGGC
CCAGGGCAGCCATGATGGGAGGACAACCCCTGACCCCAGCCTAAGATAGTTGTTGCACAGAGCAGTCCCTTAACGCA
GGATAACTGTTGGAGGTAGGCAGCACTTGACCCCTGCCCAAGCTAGATGATGGGAGAGGATAGGTCCAGCCATTGAC
AGCTGCTGTAGCAAGGCAGGCCCTGGTCCCAGGTTAACTCAAGGCTGCTGCTTAGGCAACCCCTGACTCCAGCTCCA
GAAGTCTGCTGGGGGTGTATCCTCTGGCTACAGGAGCTGAACAAATGGCGCGCCGCGGCCGCTCGACCAATTCTCAT
GTTTGACAGCTTATCATCGAATTTCTGCCATTCATCCGCTTATTATCACTTATTCAGGCGTAGCAACCAGGCGTTTA
AGGGCACCAATAACTGCCTTAAAAAAATTACGCCCCGCCCTGCCACTCATCGCAGTACTGTTGTAATTCATTAAGCA
TTCTGCCGACATGGAAGCCATCACAAACGGCATGATGAACCTGAATCGCCAGCGGCATCAGCACCTTGTCGCCTTGC
GTATAATATTTGCCCATGGTGAAAACGGGGGCGAAGAAGTTGTCCATATTGGCCACGTTTAAATCAAAACTGGTGAA
ACTCACCCAGGGATTGGCTGAGACGAAAAACATATTCTCAATAAACCCTTTAGGGAAATAGGCCAGGTTTTCACCGT
AACACGCCACATCTTGCGAATATATGTGTAGAAACTGCCGGAAATCGTCGTGGTATTCACTCCAGAGCGATGAAAAC
GTTTCAGTTTGCTCATGGAAAACGGTGTAACAAGGGTGAACACTATCCCATATCACCAGCTCACCGTCTTTCATTGC
CATACGGAACTCCGGATGAGCATTCATCAGGCGGGCAAGAATGTGAATAAAGGCCGGATAAAACTTGTGCTTATTTT
TCTTTACGGTCTTTAAAAAGGCCGTAATATCCAGCTGAACGGTCTGGTTATAGGTACATTGAGCAACTGACTGAAAT
GCCTCAAAATGTTCTTTACGATGCCATTGGGATATATCAACGGTGGTATATCCAGTGATTTTTTTCTCCATTTTAGC
TTCCTTAGCTCCTGAAAATCTCGATAACTCAAAAAATACGCCCGGTAGTGATCTTATTTCATTATGGTGAAAGTTGG
AACCTCTTACGTGCCGATCAACGTCTCATTTTCGCCAAAAGTTGGCCCAGGGCTTCCCGGTATCAACAGGGACACCA
GGATTTATTTATTCTGCGAAGTGATCTTCCGTCACAGGTATTTATTCGCGATAAGCTCATGGAGCGGCGTAACCGTC
GCACAGGAAGGACAGAGAAAGCGCGGATCTGGGAAGTGACGGACAGAACGGTCAGGACCTGGATTGGGGAGGCGGTT
GCCGCCGCTGCTGCTGACGGTGTGACGTTCTCTGTTCCGGTCACACCACATACGTTCCGCCATTCCTATGCGATGCA
CATGCTGTATGCCGGTATACCGCTGAAAGTTCTGCAAAGCCTGATGGGACATAAGTCCATCAGTTCAACGGAAGTCT
ACACGAAGGTTTTTGCGCTGGATGTGGCTGCCCGGCACCGGGTGCAGTTTGCGATGCCGGAGTCTGATGCGGTTGCG
ATGCTGAAACAATTATCCTGAGAATAAATGCCTTGGCCTTTATATGGAAATGTGGAACTGAGTGGATATGCTGTTTT
TGTCTGTTAAACAGAGAAGCTGGCTGTTATCCACTGAGAAGCGAACGAAACAGTCGGGAAAATCTCCCATTATCGTA
GAGATCCGCATTATTAATCTCAGGAGCCTGTGTAGCGTTTATAGGAAGTAGTGTTCTGTCATGATGCCTGCAAGCGG
TAACGAAAACGATTTGAATATGCCTTCAGGAACAATAGAAATCTTCGTGCGGTGTTACGTTGAAGTGGAGCGGATTA
TGTCAGCAATGGACAGAACAACCTAATGAACACAGAACCATGATGTGGTCTGTCCTTTTACAGCCAGTAGTGCTCGC
CGCAGTTGAGCGACAGGGCGAAGCCCTCGAGTGAGCGAGGAAGCACCAGGGAACAGCACTTATATATTCTGCTTACA
CACGATGCCTGAAAAAACTTCCCTTGGGGTTATCCACTTATCCACGGGGATATTTTTATAATTATTTTTTTTATAGT
TTTTAGATCTTCTTTTTTAGAGCGCCTTGTAGGCCTTTATCCATGCTGGTTCTAGAGAAGGTGTTGTGACAAATTGC
CCTTTCAGTGTGACAAATCACCCTCAAATGACAGTCCTGTCTGTGACAAATTGCCCTTAACCCTGTGACAAATTGCC
CTCAGAAGAAGCTGTTTTTTCACAAAGTTATCCCTGCTTATTGACTCTTTTTTATTTAGTGTGACAATCTAAAAACT
TGTCACACTTCACATGGATCTGTCATGGCGGAAACAGCGGTTATCAATCACAAGAAACGTAAAAATAGCCCGCGAAT
CGTCCAGTCAAACGACCTCACTGAGGCGGCATATAGTCTCTCCCGGGATCAAAAACGTATGCTGTATCTGTTCGTTG
ACCAGATCAGAAAATCTGATGGCACCCTACAGGAACATGACGGTATCTGCGAGATCCATGTTGCTAAATATGCTGAA
ATATTCGGATTGACCTCTGCGGAAGCCAGTAAGGATATACGGCAGGCATTGAAGAGTTTCGCGGGGAAGGAAGTGGT

Fig. 3 (cont.)

TTTTTATCGCCCTGAAGAGGATGCCGGCGATGAAAAAGGCTATGAATCTTTTCCTTGGTTTATCAAACGTGCGCACA
GTCCATCCAGAGGGCTTTACAGTGTACATATCAACCCATATCTCATTCCCTTCTTTATCGGGTTACAGAACCGGTTT
ACGCAGTTTCGGCTTAGTGAAACAAAAGAAATCACCAATCCGTATGCCATGCGTTTATACGAATCCCTGTGTCAGTA
TCGTAAGCCGGATGGCTCAGGCATCGTCTCTCTGAAAATCGACTGGATCATAGAGCGTTACCAGCTGCCTCAAAGTT
ACCAGCGTATGCCTGACTTCCGCCGCCGCTTCCTGCAGGTCTGTGTTAATGAGATCAACAGCAGAACTCCAATGCGC
CTCTCATACATTGAGAAAAAGAAAGGCCGCCAGACGACTCATATCGTATTTTCCTTCCGCGATATCACTTCCATGAC
GACAGGATAGTCTGAGGGTTATCTGTCACAGATTTGAGGGTGGTTCGTCACATTTGTTCTGACCTACTGAGGGTAAT
TTGTCACAGTTTTGCTGTTTCCTTCAGCCTGCATGGATTTTCTCATACTTTTTGAACTGTAATTTTTAAGGAAGCCA
AATTTGAGGGCAGTTTGTCACAGTTGATTTCCTTCTCTTTCCCTTCGTCATGTGACCTGATATCGGGGGTTAGTTCG
TCATCATTGATGAGGGTTGATTATCACAGTTTATTACTCTGAATTGGCTATCCGCGTGTGTACCTCTACCTGGAGTT
TTTCCCACGGTGGATATTTCTTCTTGCGCTGAGCGTAAGAGCTATCTGACAGAACAGTTCTTCTTTGCTTCCTCGCC
AGTTCGCTCGCTATGCTCGGTTACACGGCTGCGGCGAGCGCTAGTGATAATAAGTGACTGAGGTATGTGCTCTTCTT
ATCTCCTTTTGTAGTGTTGCTCTTATTTTAAACAACTTTGCGGTTTTTTGATGACTTTGCGATTTTGTTGTTGCTTT
GCAGTAAATTGCAAGATTTAATAAAAAAACGCAAAGCAATGATTAAAGGATGTTCAGAATGAAACTCATGGAAACAC
TTAACCAGTGCATAAACGCTGGTCATGAAATGACGAAGGCTATCGCCATTGCACAGTTTAATGATGACAGCCCGGAA
GCGAGGAAAATAACCCGGCGCTGGAGAATAGGTGAAGCAGCGGATTTAGTTGGGGTTTCTTCTCAGGCTATCAGAGA
TGCCGAGAAAGCAGGGCGACTACCGCACCCGGATATGGAAATTCGAGGACGGGTTGAGCAACGTGTTGGTTATACAA
TTGAACAAATTAATCATATGCGTGATGTGTTTGGTACGCGATTGCGACGTGCTGAAGACGTATTTCCACCGGTGATC
GGGGTTGCTGCCCATAAAGGTGGCGTTTACAAAACCTCAGTTTCTGTTCATCTTGCTCAGGATCTGGCTCTGAAGGG
GCTACGTGTTTTGCTCGTGGAAGGTAACGACCCCCAGGGAACAGCCTCAATGTATCACGGATGGGTACCAGATCTTC
ATATTCATGCAGAAGACACTCTCCTGCCTTTCTATCTTGGGGAAAAGGACGATGTCACTTATGCAATAAAGCCCACT
TGCTGGCCGGGGCTTGACATTATTCCTTCCTGTCTGGCTCTGCACCGTATTGAAACTGAGTTAATGGGCAAATTTGA
TGAAGGTAAACTGCCCACCGATCCACACCTGATGCTCCGACTGGCCATTGAAACTGTTGCTCATGACTATGATGTCA
TAGTTATTGACAGCGCGCCTAACCTGGGTATCGGCACGATTAATGTCGTATGTGCTGCTGATGTGCTGATTGTTCCC
ACGCCTGCTGAGTTGTTTGACTACACCTCCGCACTGCAGTTTTTCGATATGCTTCGTGATCTGCTCAAGAACGTTGA
TCTTAAAGGGTTCGAGCCTGATGTACGTATTTTGCTTACCAAATACAGCAATAGTAATGGCTCTCAGTCCCCGTGGA
TGGAGGAGCAAATTCGGGATGCCTGGGGAAGCATGGTTCTAAAAAATGTTGTACGTGAAACGGATGAAGTTGGTAAA
GGTCAGATCCGGATGAGAACTGTTTTTGAACAGGCCATTGATCAACGCTCTTCAACTGGTGCCTGGAGAAATGCTCT
TTCTATTTGGGAACCTGTCTGCAATGAAATTTTCGATCGTCTGATTAAACCACGCTGGGAGATTAGATAATGAAGCG
TGCGCCTGTTATTCCAAAACATACGCTCAATACTCAACCGGTTGAAGATACTTCGTTATCGACACCAGCTGCCCCGA
TGGTGGATTCGTTAATTGCGCGCGTAGGAGTAATGGCTCGCGGTAATGCCATTACTTTGCCTGTATGTGGTCGGGAT
GTGAAGTTTACTCTTGAAGTGCTCCGGGGTGATAGTGTTGAGAAGACCTCTCGGGTATGGTCAGGTAATGAACGTGA
CCAGGAGCTGCTTACTGAGGACGCACTGGATGATCTCATCCCTTCTTTTCTACTGACTGGTCAACAGACACCGGCGT
TCGGTCGAAGAGTATCTGGTGTCATAGAAATTGCCGATGGGAGTCGCCGTCGTAAAGCTGCTGCACTTACCGAAAGT
GATTATCGTGTTCTGGTTGGCGAGCTGGATGATGAGCAGATGGCTGCATTATCCAGATTGGGTAACGATTATCGCCC
AACAAGTGCTTATGAACGTGGTCAGCGTTATGCAAGCCGATTGCAGAATGAATTTGCTGGAAATATTTCTGCGCTGG
CTGATGCGGAAAATATTTCACGTAAGATTATTACCCGCTGTATCAACACCGCCAAATTGCCTAAATCAGTTGTTGCT
CTTTTTTCTCACCCCGGTGAACTATCTGCCCGGTCAGGTGATGCACTTCAAAAAGCCTTTACAGATAAAGAGGAATT
ACTTAAGCAGCAGGCATCTAACCTTCATGAGCAGAAAAAAGCTGGGGTGATATTTGAAGCTGAAGAAGTTATCACTC
TTTTAACTTCTGTGCTTAAAACGTCATCTGCATCAAGAACTAGTTTAAGCTCACGACATCAGTTTGCTCCTGGAGCG
ACAGTATTGTATAAGGGCGATAAAATGGTGCTTAACCTGGACAGGTCTCGTGTTCCAACTGAGTGTATAGAGAAAAT
TGAGGCCATTCTTAAGGAACTTGAAAAGCCAGCACCCTGATGCGACCACGTTTTAGTCTACGTTTATCTGTCTTTAC
TTAATGTCCTTTGTTACAGGCCAGAAAGCATAACTGGCCTGAATATTCTCTCTGGGCCCACTGTTCCACTTGTATCG
TCGGTCTGATAATCAGACTGGGACCACGGTCCCACTCGTATCGTCGGTCTGATTATTAGTCTGGGACCACGGTCCCA
CTCGTATCGTCGGTCTGATTATTAGTCTGGGACCACGGTCCCACTCGTATCGTCGGTCTGATAATCAGACTGGGACC
ACGGTCCCACTCGTATCGTCGGTCTGATTATTAGTCTGGGACCATGGTCCCACTCGTATCGTCGGTCTGATTATTAG
TCTGGGACCACGGTCCCACTCGTATCGTCGGTCTGATTATTAGTCTGGAACCACGGTCCCACTCGTATCGTCGGTCT
GATTATTAGTCTGGGACCACGGTCCCACTCGTATCGTCGGTCTGATTATTAGTCTGGGACCACGATCCCACTCGTGT
TGTCGGTCTGATTATCGGTCTGGGACCACGGTCCCACTTGTATTGTCGATCAGACTATCAGCGTGAGACTACGATTC
CATCAATGCCTGTCAAGGGCAAGTATTGACATGTCGTCGTAACCTGTAGAACGGAGTAACCTCGGTGTGCGGTTGTA
TGCCTGCTGTGGATTGCTGCTGTGTCCTGCTTATCCACAACATTTTGCGCACGGTTATGTGGACAAAATACCTGGTT
ACCCAGGCCGTGCCGGCACGTTAACCGGGCTGCATCCGATGCAAGTGTGTCGCTGTCGAGCGGCCGC

*End of Figure 3*

The antibodies were purified using a standard proteinA pull down
All V18 and 8V3 mice were endogenous heavy and kappa light chain null

*Fig. 7*

STARTVHLOCUSSEQUENCEATCCCTAGCTGAAGCTTCTGATGGAATTAGAACTTGGCAAAACAATACTGAGAATGA
AGTGTATGTGGAACAGAGGCTGCTGATCTCGTTCTTCAGGCTATGAAACTGACACATTTGGAAACCACAGTACTTAG
AACCACAAAGTGGGAATCAAGAGAAAAACAATGATCCCACGAGAGATCTATAGATCTATAGATCATGAGTGGGAGGA
ATGAGCTGGCCCTTAATTTGGTTTTGCTTGTTTAAATTATGATATCCAACTATGAAACATTATCATAAAGCAATAGT
AAAGAGCCTTCAGTAAAGAGCAGGCATTTATCTAATCCCACCCCACCCCCACCCCCGTAGCTCCAATCCTTCCATTC
AAAATGTAGGTACTCTGTTCTCACCCTTCTTAACAAAGTATGACAGGAAAAACTTCCATTTTAGTGGACATCTTTAT
TGTTTAATAGATCATCAATTTCTCGATTTCTCGACTATTCCTTTGCCCTCGGACGAGTGCTGGGGCGTCGGTTTCCA
CTATCGGCGAGTACTTCTACACAGCCATCGGTCCAGACGGCCGCGCTTCTGCGGGCGATTTGTGTACGCCCGACAGT
CCCGGCTCCGGATCGGACGATTGCGTCGCATCGACCCTGCGCCCAAGCTGCATCATCGAAATTGCCGTCAACCAAGC
TCTGATAGAGTTGGTCAAGACCAATGCGGAGCATATACGCCCGGAGCCGCGGCGATCCTGCAAGCTCCGGATGCCTC
CGCTCGAAGTAGCGCGTCTGCTGCTCCATACAAGCCAACCACGGCCTCCAGAAGAAGATGTTGGCGACCTCGTATTG
GGAATCCCCGAACATCGCCTCGCTCCAGTCAATGACCGCTGTTATGCGGCCATTGTCCGTCAGGACATTGTTGGAGC
CGAAATCCCCGTGCACCAGGTCCCGCACTTCGGGGCAGTCCTCGGCCCAAAGCATCAGCTCATCGAGAGCCTGCGCG
ACGGACGCACTGACGGTGTCGTCCATCACAGTTTGCCAGTGATACACATGGGGATCAGCAATCGCGCATATGAAATC
ACGCCATGTAGTGTATTGACCGATTCCTTGCGGTCCGAATGGGCCGAACCCGCTCGTCTGGCTAAGATCGGCCGCAG
CGATCGCATCCATGGCCTCCGCGACCGGCTGCAGAACAGCGGGCAGTTCGGTTTCAGGCAGGTCTTGCAACGTGACA
CCCTGTGCACGGCGGGAGATGCAATAGGTCAGGCTCTCGCTGAATTCCCCAATGTCAAGCACTTCCGGAATCGGGAG
CGCGGCCGATGCAAAGTGCCGATAAACATAACGATCTTTGTAGAAACCATCGGCGCAGCTATTTACCCGCAGGACAT
ATCCACGCCCTCNTACATCGAAGCTGAAAGCACGAGATTCTTCGCCCTCCGAGAGCTGCATCAGGTCGGAGACGCTG
TCGAACTTTTCGATCAGAAACTTCTCGACAGACGTCGCGGTGAGTTCAGGCTTTTTCATGGTGGCGGCTGGATCGGT
CGGTCGAAAGGCCCGGAGATGAGGAAGAGGAGAACAGCGCGGCAGACGTGCGCTTTTGAAGCGTGCAGAATGCCGGG
CCTCCGGAGGACCTTCGGGCGCCCGCCCCGCCCCTGAGCCCGCCCCTGAGCCCGCCCCCGGACCCACCCCTTCCCAG
CCTCTGAGCCCAGAAAGCGAAGGAGCAAAGCTGCTATTGGCCGCTGCCCCAAAGGCCTACCCGCTTCCATTGCTCAG
CGGTGCTGTCCATCTGCACGAGACTAGTGAGACGTGCTACTTCCATTTGTCACGTCCTGCACGACGCGAGCTGCGGG
GCGGGGGGGAACTTCCTGACTAGGGGAGGAGTAGAAGGTGGCGCGAAGGGGCCACCAAAGAACGGAGCCGGTTGGCG
CCTACCGGTGGATGTGGAATGTGTGCGAGGCCAGAGGCCACTTGTGTAGCGCCAAGTGCCCAGCGGGGCTGCTAAAG
CGCATGCTCCAGACTGCCTTGGGAAAAGCGCCTCCCCTACCCGGTAGAATTCATCGCTCGAGCAATTGGCTAGATAA
CTTCGTATAATGTATGCTATACGAAGTTATCTAGCTCTAGAGTCG[redacted]GATTGAAGAGTGTGATAAGTGCCCAGACCA
hygro
AGCAGAACAGAAATCAGCATGTAAAGATGATGATCTATGGATATGATCTAAAACCATGTAAATACTTCAAATAATTC
TATTTAATGCAGTTTGAAATAAAACACAAACTTATTCAAAATACAAATTACTTGGTAATTATTTTGGGAGCTATGAG
TTCACCAAGAAACTCAAATTCCTATTTCTATTTCAACCCCTGATTCCTACTGTCAATGGGAGGGAAGTCTCAGAACC
AATCACACATCAGACGGCAAATCTGTCAACCAAGAGTCTTTCCACTGAAGGACCTGGGAGGTCAGGACCCTCAGGAA
AGTGCTGGGGACCCTGTCTTGGGAGTGCCCAGCAGATCTCAGAACTCTCCATGGGTCCTGCTGGACACTCATGTAGG
GTAACGAGTGGCCACCTTTTCAGTGTTACCAGTGAGCTCTGAGTGTTCCTAACGGGACCAGGATGGGTCTAGGTGCC
TGCTCAATGTCAGAGACAGCAATGGTCCCACAAAAAACCCAGGTAATCTTTAGGCCAATAAAATGTGGGTTCACAGT
GAGGAGTGCATCCTGGGGTTGGGGTTTGTTCTGCAGCGGGAAGAGCGCTGTGCACAGAAAGCTTAGAAATGGGGCAA
GAGATGCTTTTCCTCAGGCAGGATTTAGGGCTTGGTCTCTCAGCATCCCACACTTGTACAGCTGATGTGGCATCTGT
GTTTTCTTTCTCATCCTAGATCAGGCTTTGAGCTGTGAAATACCCTGCCTCATGCATATGCAAATAACCTGAGGTCT
TCTGAGATAAATATAGATATATTGGTGCCCTGAGAGCATCACATAACAACCACATTCCTCCTCTGAAGAAGCCCCTG
GGAGCACAGCTCATCACC[redacted]CACAG
VH 1-69
TGTGAAAACCCACATCCTGAGAGTGTCAGAAACCCTGAGGGAGAAGGCAGCTGTGCCGGGCTGAGGAGATGACAGGG
GTTATTACGTTTAAGGCTGTTTACAAAATGGGTTATATATTTGAGAAAAAAAGAACAGTAGAAACAAGTACATACTC
TAATTTTAAGATAAATATTCCATTCAAGAGTCGTAATATAAGCCAAATTCACAGAGTGGAAAAGGCCACACTCTATA
ACGTTGATACAAACATTCCATGAAGGTGCTACTGTGAACAAGTTTTCAAATTGGATGAATACATGATTTGGAGCAAG
GTTATTTGATCATGTGCTGAGACTAAGAATG[redacted]TCTGGACTTGAGTGTCATTGTCCAGCCATGTTGCACAAGT
GTGTCCTGTCAGGGAAGGATCAGAGTTCCTTGTGCTCTCAGAGGGAAGGGGTCACAGAGTTCCTCTCTGGTTCCCAG

Fig. 7 (cont.)

GAAAGGTAATCGCACTAATCTTCATGATCTTCATGAGACTATCCTCCAGTGCTGACCTGTTATAGAGTTTTTGTCTG
AAGTTCTCACTGCAATCCCCAATCTACATATTTTCAATCAGAAGTGTTTAGAGGCCAGGACACATCTTCAAGGTCAC
ACATTGAGAAGGATGTAGATATGTCCCACTACCTTCTCCTGAGATCTCAGACAGAATCCCAGATTTCAAAAGGACAC
AGAAGGACAGCTCTCAGGTGCTTTTAAAAAATGACCCACTTCCAGGGACAGGGAGCTTCCCTATAACCATGGTGGAT
GTTCTGAACTACAATAAACATTGGATGGATCCAGGATTGTTTGAAGTCACTGTCATTATTACATTCAGCTGCTGTTT
CAATGTGTCTGAAGTAGTAAATGACAATTTAGATGACAATTTATATGAATCTTCAAGGGTAGAACAATATTGACCAT
ATTCCAAAATCTGTCCTTGATCCATGATCACACTCATCTCCCAGACCAGGTCCTTCAGCACGTCTCTTTACCTGAAA
GAAGAGGACTCTGGGCTTGGAGAGGGGAGACCCCAAGAAGACAACTGAGTTCTCAAAGGGCACAGCCAGCATCCTAC
TCCCAGGGCGAGCCCAAAAGACTGGGGCCTCCCTCCTCCTTTTTCACCTCTCCATACAAAGGCACCACCCACATGCA
AATCCTCACTTAAGCACCCACAGGAAACCACCACACATTTCCTTAAATTCAGGTTCCAGCTCACATGGGAAATACTT
TCTGAGAGTCCTGGACCTCCTGTGCAAGAAC[illegible]
[illegible]CACAGTGAGGGGAGGTGAGTGTGAGCCCAGACAAAAACCTCCGTGCAGGGAGGCGGAGGGGACCGGCGCAGGTGCT
VH 4-59
GCTCAGAGCCAGCAGGGGGCGCGCGGGGCCCACAGAGCAGGAGGCCCGGTCAGGAGCAGGTGCAGGGAGGGCGGGGC
TTCCTCATCTGCTCAGTGGTCTCCCTCCTCGCCAGCACCTCAGCTGTCCCCAGGGGTCCTCTTTCTTTATTATCTGT
GGTTCTGCTTCCTCACATTCTTGTGCCAAGAAAGAAATGAGGAAGACAAATTTTCGTCTGTAGTTGAAGTTTCACCA
AT[illegible]ACGATGCGGATGTGATTTAAGTTTCAGAGGAATAAAAAAAAAGATTTAGGGATTAATTTAATTATTCAA
AAGTTGATTGAAGTGCCGAGTGAATGGCTGCAAACATAGTCTACATTTTTCAAATCATTCCCTATAAATTTGAATTA
ATTATTTATTTTTATACTTGAATAAAGCAATAACAAAGAAATAAATGAATATTTTTGCTAAAATGGAGCAATAAAAA
GACTGATATTGACAGAAGAAATATGACTGACTTCTGAAAATACACACACATGAGCCGTGGTTCTCTCTACATATTTA
GATAAATTACAGAAAGTTGTCATAACTGATGGGGAATCCTGCAGACTTCACTAGGCATAGTCCACACTGCCCTGGAG
TTGTCTCAGGGGAGCTGCCTCCTCCAGTGGTTAGAGCACAGGCCCAGGTAATAGGACTCATTTTTTTAGATGTGTAA
TTTTAGACACACTGCACAACTGCTGTGTTCTCTGCGCAAATTATCTCCTGTAAAATGCAACATTGAAACCTGCCTTA
AATATATTGTGTAAATATGTAAAAATAAAATCAGATTGTGAGAGCTAAATGCTAATCAAGGCGCAATCACGTAATAT
ACAATTATATTTTCCTGAATGATGGAATTAATACCAATCTCCCCCAGGACACTTCATCTGCACGGAGCCCGGCCTCT
CCTCAGATGTCCCACCCCAGAGCTTGCTATATAGTCGGGGACATGCAAATAGGGCCCTCCCTCTGCTGATGAAAACC
AGCCCAGCTGACCCTGCAGCTCTGGGAGAGGAGCCCAGCACTGGGATTCCGAGGTGTTTCCATTCGGTGATCAGCAC
TGAACACAGAGGACTCACC[illegible]
[illegible]AGTGAGGGGAAGTCATTGTGCGCCCAGACACAAACCTCCCTGCAGGAACGCTGGGGGGAAATCAGC
VH 3-53
TGCAGGGGGCGCTCAGGAGCCACTGATCAGAGTCAGCCCCGGAGGCAGGTGCAGATGGAGGCTGATTTCCTGTCAGG
ATGTGGGACTCTGTCTTCTTCTGACGGTTCCCCAGGGAACCTCTCTAAGTTTAGCATTCTGTGCCTATGAACGTCTT
CTCTAAGTATTTGAAAGAGATTATTTTAATATGAAGAGCAGTTCTCACTC[illegible]CTCTTCTGAAGGACCATGAAT
GCCTCAACCAACCATCTCCCCTGCCTCCATGACCAGAAATGCACCACGTGCCCACACGGATATTCATCCCTCATGGG
GATAAGACTCCATTGATGAGGCTGACTATTTTATCATATAAAATTACTAAAGACTGATTTAAGGGTTTCAAAAACTA
ATTGAACTCTGTTGTTCTATGTCCACCAGAGATTACAAATCTTCCAATGATGCCTTCTTTGTTTTTTGTCTGCTTGA
CTTTGTCTCTTCAACTTGTTCTGTACCCCAGAGAATCTCTTTCAGCTCCCTCAGGTGCATTCAATTGTTTTATTTAA
CTGACAATTTCTAAATCAGTTAAAGACATTACGCTAAAGACTCCATATTCCTAGGTCCATATTCCTTTTTCCATATT
CCTAGGAAGGCATTGTGACCCAGAGTCTGGGCATGACCTTGTGAGTGTTCCTGACCCTCCTCCATATGAGATGCTGG
TCTGGGTGTTCTTGCCCCTTTCCCTGGGGTAGAGTCCTCCTGTTTTCCCCAGGTGCTCCCTCCCACAGCTCTAGTGT
TCTCAATCAGTGTCATCACCTTCCAGATCTTCTGCCCTGCCCTGCAGACTAAGGCTCTGATTCCATAAGCAAGATAG
GGGAGCTGCTCCTCAATAGATCTTTGGTGAGGATCTCTGTTCCCATCTCAATTCCTGTAGGGTGGAACCAGTGTTCC
TAGGATTCTGGTTTCAGTAGCTTGTCCCTGCAGAGTAAATTCTTAGTTCTGTAGGGGGATTAAGGGAGTTGGGTCTG

Fig. 7 (cont.)

AATACATTTTAGATGTCGAGGATCTTGTTCTCTCCCAGAAAGACACTTCGGGAAAGTAAGACTTTGGTAACTGTCCC
CTTTCTTGGGGAAAGGGATTCAAGAGGATAGGTTGCTTTTGGGCATGTGGTCCCTTAAAATTTCACACTAAAAAGCG
TTTCCCACACTCAATTTCAAGCAGCCCAATATATATTTGTATTTTTTCTTGGAACAGACAATATTTTATATTCCAGA
CTCTGCCTTAGGTAATTTCAAACCCCGGCTTTGTTACTCTCTACAAGAAATTGCTTCTCCATAAGCTTCAGATTTGT
TGTGTGTTTTGAAATTTTATCAGAAATATTAAAGAAAATTGGCAAAATTCCATCCTCCATGTTTATCTGTTATTGTT
GATGCAGTTGTAAAAAATAAGAAAAATATATTCCTTTTTTCTGTACATTTCCAAGCTTAGTAGCAAATTTTTAGTAA
CACCCAGAATAATAAAAAATTCAAATATTGTTTAGCTGCTTAATAGGAAAACAAATTATAGTAAATTTGTTTGCTAG
AATGCTACCCAGCATTTATAATAAGTAAACATTTGATATACCCAACTACAAGGTAAAATATCCATTTATGCTAACTA
AAATAAGCCAAACAAATGAGAATATATACTGTTATTTCATTTTTATAAATTCTGAAAAATTAAAATGAATTTGCAGC
AATGTAAAGATCAGTAGTTGCCAGGGAAATGGTAGAAGAAAGAAAGGAAAAGGAGAAAGAATACAGAAAAACAAAAG
GAAATGTTAAGAATTCTCTTGTCCAACTTGATAAGGATGACGGTTACATCATTTTTATCAACTGTAATCTTTAAATA
TGTGAAAGTTTATTATCCGTAAACTAAACGTTATAAACTTTATTACAAGCAAAAATTGAAAGTTAGACAACAAGGAG
TGATAGAAAGAGAAAATGTATATTAAATTTCAGAAATATTTAAGAATGTATCTGCCTGAACCCTAGTTCTCACCATA
TCTTTAGGTGAATGCTAAAATGCAGCAAAATCACGCATGTTCTCACTACAGAAAGTGGGTTCTACAAACCACACTCG
GCACATTTAGCTTTGTCCTGGAGTTGGTGCAGGGAGTTATTGGGGCCAGTGATGAGGAGCACAGGCCAAGATACCAG
CGATTACTTATCCCAAACATGAGCTCTAACATACACACTTAGTCCCTTTTCCGTGTGTGGTTTACTTCCACATCTGT
ACATGGAGAGACCACTGACTGACAAAATATAATTTATACAAATATGTAAAATTAAATAGGGTGATCAGTTCAAGGTG
TTTATCACAGCATAATTTACAATAAGACAGCATATTTCCCAAATACCATCATTGTCACCAAACTCCTTCAAGGCAC
AGTCATCTTATCTGGGCCCCGTCCTCTCCTCAGGTGTCCCACCCCAGAGCTTGGTATATAGTAGGAGACATGCAAAT
AAGGCCCTCCCTCTGCTGATGAAAATGAGCCCAGCCCTGACCCTGCAGCTCTGGGAGAGGAGCCCCAGCCGTGAGAT
TCCCAGGAGTTTCCACTTGGTGATCAGCACTGAACACAGACCACCAACC[redacted]ACTAGAGACACAGTGAGGGGAGGTCAATGTGAGCCC

VH 3-49

AGACACAAACCTCCCTGCAGGGGCGCACAGAGCCACCAGGGGGCGCTAGGGACCGACTGAGTACGGGACAGGTCCCA
GGAGCAGGTGCAGGGGGAGGTTTCCTTTTTCCTTGGCTGGAAAAGTCACCTTTATCTTCCCAGGA[redacted]GATGAG
ACTATCCTCCAGTGCTGATGTACTATAGAGTTTTCATCTGAAGCTGTCACTGCTATCCCCAATGTACATCTTTTCAC
ACAGAAATGTTTAGAGGTCAGGCCATATTCTCAGGGTTACACATTGAGAAGGATGGAGATATATTCTACTACCTTCT
CCTGAGATCTCACACACAATCTCAAATTTCAAAAGGTCTCAGAAGGGCAGCTCTCAGGTACTATTTAAAAATAACCC
ACTTCCTGGGACAGGTAGCATCCTTCTAACCATGATGGATGTTCTGAACTACAGTACACATTGCATGGATCCGGGTT
TGTCTCAATTCACTGTGATTATTACACTCAGCAGCTGTTTCAATATGTCTGAAGGGGTAAATGACAATTTAGGTGAC
CTGGGTGTATGGTTGGTGTTATATGAATCTTTAAATGTAGAACAGTATTAACTGTATTCCAAAATCTGTCTTTGATC
CATGATCACACTTGTCTCCCAGACCAGCTCCTTCAGCACATTTCCTACCTGGAAGAAGAGGACTCTGGGTTTGGTGA
GGGGAGGCCACAGGAAGAGAACTGAGTTCTCAGAGGGCACAGCCAGCATACACCTCCCAGGGTGAGCCCAAAAGACT
GGGGCCTCCCTCATCCCTTTTTACCTATCCATACAAAGGCACCACCCACATGCAAATCCTCACTTAGGCACCCACAG
GAAATGACTACACATTTCCTTAAATTCAGGGTCCAGCTCACATGGGAAGTGCTTTCTGAGAGTCATGGACCTCCTGC
ACAAGAAC[redacted]GCACAGTGAGGGGAGGTGAGTG

VH 4-34

TGAGCCCAGACAAAAACCCCCCTGCAGGTAGGCAGAGGGGCGGGCGCAGGTACTGCTCAAGACCAGCAGGTGGCGC
GCGGCGCCCACAGATCCCGAGGCCGGGTCCGGAGCAGGTGCAAGGAGGGCGGGGCTTCCTCAACAGCTCAGTGGTCT
GTCTCCTCGCCAGCACCTCAGATGTCCCCAGGACTCTCTTTCTTTATTATCTGTGGTTCTGCTTCCTCACATCCTTG
TGGCAGGGAAGAAAGGAGGAAGACAATTTTTCTGTTTACTGTTGAGGTTTCACCAATTAC[redacted]GTCTTGTTACA
CTTCATCAAGAATTAACCTCTGCTGTTTCCTCAAAGTGTTTAATTGGATAATGAATTTGTCTATAAATTGAAGAGTT
GAAATACATCAAATATTAATTTGTAATAATCTGGCACAAATTATCTAAGCAAATTCAATAACTAGATGTTTTTTCAT

Fig. 7 (cont.)

TTATTTTTATTTAAAATCAGGATCTAAGCACTGACATGCTTTAATAACATCTGTGACCCTCTCAGCAGTTTTCTCTT
CTGAGTATATGATCTGCTGTGGCAGTTTTCTTAGCTTCAATGTTACCTCTTTTGGCAATGACTACCGTCTTTATATT
TGCCAGGAATCTGGGATAAGGGAGTGCTTCTAAGAGTTCCCTAACTTGCCCATTTTGGTGGGTGTTCCAGAACATAT
GAGATGCTCTGTTGTTAACAAAGCATCCCAAAGCCATGCACTGCCCTAAAATGTGTTTGTTTCCTAGTTTGACAAAT
TGGAAGTTCTAATAAATACAATCACTTCTGCCATCTGGGCTGATTTTACATCAGATAGAGGGCTGTATTCCAAAGAA
AAGCTTACATTAGTAATAGCAATTCTAGTCAGAAACCTAGAGTTTTATCATTGAGGTGCAATTCATAACAAATAATA
TTAGGTCGAGGTTCTCAGTGGCAGTGTCTAAATCTCTTAGGTGTACAGGGTCTTCCCTGTTAACATGAAGCATTTAT
AAGCACAGTCATAGTTTCCAGCTATGCTTCTCCCTGTCTCATTATCACCACAAACTATGGCCTCACCTGGAACTTGG
GTTAATTTCCAAATAAGTAATTTTTTAGTGTTTATGCCTCTAGATTATTATGTGAGAAAGTTAACATTCAGTAGAAA
GTTAAAAAGAACATTTGAACTGACTAAACAACACAGACAATCAAGAATAAAATTCAAAGCCTAGATGTGAGAGGCTC
CAGGCCTGGATAATGCAATAGTTCATGTATGCAGGCAGTTTCTTTGCCCAGTTCTACACTGATACACCCAGAATGTC
AGCTTCATGCCAGATTTGACTCCTATTATGTAGAGACATGGCAATACATTCTCAAGGGTCACATGAAATAATATGAA
AATTGGTGGGAATAGGGGAGGAGACAACTCTGCAATTCTCATCTGAAGGACCAGGAAAGCCTGGACAGACCATCTCC
CCAGCCTCCGTGACTGCACCACGTGCCCACATGGACGCTCATCCCTGATAGGGTAAGAAGACTCCATTGATGGGGCT
GAGCATTTTATGATAGAAATTACTAGAGACTGACGTGGAGGTTTCAACAACTAATATTTATAACCAAAATTTAATTA
CCCCCACATTGTTACCATTTTCTTCAGTGAAAAATTGCTTGCCATGATTAAGTTTTAAGTAGATTTCCAATGTTCAC
AACTGAGCTTCCAAGAGAGTCTTGAGAACAAAAACAATGAGGGCAGAGAAATCTACCTTTTCTGCATTCACCACTAA
ACTCAAGTGGACTCAGCACTGCCTTTGATCACTGCTACTTCTCTGCAGAGTTCAGGTTTCTACTTCTCACAATTCTG
ACACACATTCTACCTCTCCTCAGATGTTTGGCCTCTGCTTCTTGTAAGGTCACCCTCTGTTCTTAACTTCTTCTCTG
AGTCATTTTGTGAGGTGGTCATGAGCCATTAAATGGATATTTTATATTTTCCCAACATGAATCACATGAGTGGTCAT
GAATTATACTTCTGATTATGGCAGTTGATTTTTCTTGGCATGTTCATGACTAGTAATATTTGAAGCCATTTCATTCA
AATCTTCGGGGCTTCGTTTTTGTTGCTATGACATTTTTTCTTCTATTGAGTCTTTCCACTAGTATTATAACATGACC
TAGTATCCAGGCTCAGTTGTCATTAATAATAACCACATATGTCAAAAATCATGCATTCTTTTCACAGCAGACATAAT
TTCCTCTTTTCTGCAGATGAAGACACACTGCTGAGCTACCCCCACTTACAAGAATATATGCACAATTATGATATCTT
CATTTATTTGACTAATAAGCTATATCATTCTCCCTTCAAATTCTTTACCCCCCAGAAGTCCTGGACAAATTTCTGCA
TCTGCTCAAACGATAAACTCAGAACTACATGGTGAGTAAAAGTCACCTGGTTCTGGATATTGGGTCCATCTCTTCCC
CTCCAATGTCCCAGAGCACCTCAGCACACCCGTCCAGGTTCTATCAAGAAAGAGTAGCTCCTGCACACTGAAGGAAA
CAATTGAGTTAAGAGAGGACCTGCAGATGATAGACAATATTGAAAACTGTTAATATGACAAAGGATTACTACCAAGC
ATGTGAAATAAGCTCAACGGGTGCGGTGGTTCATGTCTGTAGTACCAGCAATTTGGGAGGCAAGTTGCGCAGATCAC
CTGAGGTTAGGAGCTCGACACCAGCCTGACCAACATAAAGAACACCCTGTCTCTACTAAAAGTACAAAATTAGCCGG
GCATGGTGGCATGCGCCTGTAATCCCAGCTACTCGGGAGGCTGAGGCAGGAGCATCACTTGAACCTGGGAAGTGGAG
GTTGCGGTGAGCTGAGATGGCACCATTGCACTCCAGCCTGGGCAACAAGAGGGAAACTCCATCTCAAAAAAAAAATT
ACAAAAAAATTAGCTGAGCGTGGTGGTGGGCGCCTGTATACCCAGCTGCTAGGGAGACTGAGGCAGGAGAATGGCTTG
AACCCAGGAGGTGAAGGTTGCAGTGAGCTGAGATTGCGCCATTGCACTCCATCCTGGGCAACAAGAGTGAAACTCCA
TCTCAAAAAAAAAAAAAGAGACTTGCAAAGGGCAAATAGATCATAGACAGACAGATAGATAGATAGACCTATTAGTA
TACATACATACATATATATACACTAATATTCAGGAAAATGCAAATTCATAATGAGATGTCTTTTCACCCTTCATCTC
TGCTAGAAAGTTTGTTATCTGAAAAACAAATACATACATACATACTTATTAAAAGCTGGCCAGGATGCCTAGAAAGT
AAAACTCATAGACCACTGGTGGAAATGTAAATTAGTGCAGCCATCAAGGGAAAAAAATAGAACTACCATATATTCCA
GCAATCCAACTGCTAAGTATATATCTATTTAAATATTTAAAAGAAAAAACTAATATTGAAGAGATACCTGTACACCC
ATGTTTATTGCAGCACTAATCACAATTTCTAGGATATGAAATCAACATATGTGTCCATCAACAGATGAATGGATACA
TAAAATGTGATATATTTACACAATGGAATATTATTCAGCCTTAACAATGAAATTCTGCCGTTTGAAGCAACATGGAT
GGAATGGGACACCTCTATGTTGAGTGAAATGAGTCAGACACAGAAAAATAAATACCGCATTTCTCAGCGTTACTTCT
AGAAGTAAATAGTAGAGTAGTGGTGATGAGATGCCAGGAATGAGAGAAGGCTGAGATAAGAAGAGGTTTGTTAACAA
ACACACAATTACAGGTAGACAGGAGGGATGTGCTCTAGTGTTCTACAGCACAGTAGGGTGACTACAGTTAACAATAT
ATTGTACGTTTTCTGTTTACAAGAAGCCAGAAGAGAGAATTTTCTATGCTACCAACACAAATAAATGTTAGTGTCTG
AACTGACGAATTTGCTCATTGTTCTGATTTTAGTCATACCAAGTGGCACACATGTATTCAAATATCACACTGTACCC
CATAAACATAAGCAGTTATTATGTGCCAAATTTGAAAAATCCTTTAATTAGAAGGAATTATATTGGCGTACATTACA
AATGATTCAACACAGAGACAGGAATAAATACCATTTTTCTTTGAAATAGTTAATTAACTAACAATGTAGTTACATTC
ATTTGCACCAAATCGTGTATTTGATAATGGTATGCATAGACAGATTTATGCATAGGATAATATCTTTTAATTTTAGA
CTACTACTTAATACTATAAATATAAATAATTTTAAAACAACTAAGTAAAAAGAATAAAGCTGAGAAAATGTGTGTGT
GGTGTGTGATGTGTGAGCTTTTTCTTGTGCACCACTGTGTCCTTGGTGGATGTGTGGTTCATGTGTTTGTTTTTATT
TACTCTGTTTGGGGTTCTCTTTGCTTCTAGGATCTGTAGTTCAGTTTCTTTCACAAAATTGGGAACATTCTTCGCTA
TTATCTTTTTCAAATAGTTTCTGTGTATTTATAATTTCTCCTTCTCAGATTTAAAATATACACATACTATAATTTTG
ATATTAATGTTTAGTTTCTTTCTTCACTCTCTTTTCGTTTGCAATTTACTTTGTGAAATTTCTAATGACATACTAAT

Fig. 7 (cont.)

CACATGGTTTTATTGAAAAGCTGAGCCAGCTCTACTGAGGTGTGTGCCAAAAGATTGCTCGATGTTTATACAGCATT
GCTTTTGATTTCTTATGCATTTCCATTTGATTTATTCTTAGTATTTTCATATTTCAGTTCCCTATCTATGTCCACGA
TTTCTTTAAGAGATTCTTGCGTGTGAATTATAGTTACTTTACATATCTTGTTTAATTAGATATTTATAACATCTGTT
TCATCTACAAATCTCATGCTGATCATTTGTTTATTACAACTTTGGTACTTCTCATTAATGTATGTAATAATTGTTGA
TAGCCACAGATACTGGGATGGACAGTGGATACTGGCCTTATTATTTCATTTTATGCATTTCTGCCTGTATTTGACCA
CACTTTACCTTTGCCAGGCCTTTACTGTGGAAGTATCTGTGAATCTTCTCAGAACTATATTTGACATTCACTTTTGC
AGTGGACATCAAAGTTGAAGTCTGTTCTTCTGTGTCCACCAGAGACTTCAGTTCCTCCAGTGATACCTTGTTTTTCT
TTCCTGCTTGGCTTTGTCTCTTCACCTGTTCCCTCCTCCAGAGAATCATGTTCAGCTCCCTCAGGTGGATTAAAATG
TTATCTAACTGACAATTGTGAAATTGGTGGAAAGCAATAGAATAAAGGGAGATTTTCTGACCTTTCTTGGGTTCATA
TTGTGAACATGAGTCTGGGTGTGACCTTCCCAATGTTTCTGAACTTCCTCCAGATGAGATGTTGGTCTGTGTGTTCT
TGCTCTTTTCCCTGCTGTGGAGTCCTCTTGTTTCCCCCAGTTGTTCCCTCCCGCAGCTCCAATGTTCTCTTTTTGTG
TTATCACCTTACAGATTTGCTGACTAGAACTGCAGATTAGGGCTCTGATTAAATAAGAAGGAGGGGAGATACTTCTC
AATGGAACTTAGGTGAAGACCTCTTTTCCCATCTCAGTTCTTAAGGGATTGCCCCAGTGNNNNNNNACTGGTTTTGG
TGGCTTGCCCCTCCAAAAAATTTCTTTGTTCTCCAGTGGGGATATGGAAGGTGGGTCTGAACACTTTTCAGAAGGGT
GGGCACTTTTTCTCTCCTAGACAGACACAATGGGACAGAACAATTTTGGTGACTGTCCCCATTTTGGGGAAAAAGGA
TTCAATAGGATAGGAAAACTCTTCAGTCTGTGGTCCCTTAGAAATTCACCCTACAACACATTTACCACACTTGACTT
CAAGAAATCCAATATATATGTGTGTTTTCATCTTGTAATAGCCTACATTTTACATGCCATACTCTGCCTCAGTTCAG
CTCATACCCCAGCTTTGTTACTCTTTACAAGAACTTGCCTCTCCCTAGATTTCACATTTGCTGTTTATCTTAAAACT
TCAAGTATCTAAAGTATTATTTTTAAAAAATGGCCAGTTGTGGTGGCTCACACCTGTAATCCCAACGCTTTGGGAGG
CTGAGGTATGTGGATCACCTGAGGTCAGGAGTTTGAGACCACCCTGGCCAACATGGTAAAACCTGTCTCTACTAAAA
ATACAAAAAAAAAAAAATAGCTTGGCATGGTGGCAGGCACCTGTAATCCCAGCTACTCGGGAGGCTGATACTGGAGA
ATAGCTTGAACCCACGAGGCAGAGTTTGCAAGTCGTACCATTGCACTCCAGCCTGGGCGACAGAGTGAGACTCTGTC
TCAAAAAAAAAAATTCCAAAATTCCAGCTCCTCTGTTTATCTATTTTTGTTGATACTGTTGTTGTAAAACATAAGTA
AAATATATTATTCATCTATGTACATTTCCAAGCTGTGTAGAAGAATTTTTAATAAGACCCAGAGTAAAAAAAGAATG
CAAATATGTAGGGGCCAGCCCTACAGGGTCTGTGGATCTTTCTCCCCATGTGCAGAGATGAGAGATCATAGAAATAA
AGGCACAAGACAAAGAGATAGAAGAAAAAACAGCCGGGCCCAGGGGACCACTACCACCAAGACACAGACTAGAAGTG
GCCCCAAATGCCTGGCTCTGCTGTTATTTATTGGATACAAGGCAAAAGGGGAAGGGTAAGGAGTGTGAGTCATCTGC
AATGATTGATAAGGTCATGTGTGTCACGTGTCCGCCAGACAGAGGGCACTTCCCTGTTTGGCAGCCGAGGCGGAGAG
AGAGAGAGGACAGCTTAGGTCATTATTTCTTCCATTCTCTTCTCAGAAAGATCAAAGACTTTAATACTTTCACTAAT
TCTGCTACTGCTATCTAGAGGGCGGAGCAAGTGTACAGAGTGGAACATGAGAGTGAAACAGGAGTGTGACCGCTGAA
GCACAGCATCACAGAGAGACGTTTAGGCCTCTGGAGGGCTGCGGGCAGGTTTGACTGATGTCAGGCCTTCCACAAGA
GGTGGTGGAGCAGAGTCTTCTCTAACTCCCCCGGGGAAAGGGAGACTCCCTTTCCAGGTCTTCTAAGTAATGGGTGC
CTTCCCAGGCACTGGCGCTACCGCTAGACTGAGGAGCCCTCTAGTGGCCCTGTCCGGGCGTGACAGAGGCTCACACT
CCTGTCTTCTGGTCACTTCTCACCGTGTCCCTTCAGCTCCTATTGCTGTATGGCCTGGTTTTTCCTAGGTTATAATT
GTAGAGCAAGGATTGTTATAATGTTGGAATAAAGAGTAATGCTACAGACTGATGATTAATGATATTCATATATAAAC
ATATCTATAACCTATTACTAGTACAACTATTCTTATTTTACATATTCTCTTCATTACACTGGAACAGCTTGTGCCCT
CAGTCTCTTGCCTCAGCACCTGGGTGGCTTGCCGCCCAGACAAATATTGTTAAGCTTCTTAATAGAAAAACAAATTA
TGGTAAATGTGTTCACTGGAATACTACCCGTCATTTATAATAAATTAATGCCTGATACACAGAGCAACAAGGTAAAA
TATCTAAGTATTTATGTTGAGTAAAATAAGCTAAACAAATAAGAATATATACTATGTAATTTCATTTTTATAAATTC
TGATAAATAAAAATGCATCTGAAGTAAAATAATGAAGATAAGTAGTTGCCTGGGGAAATGGTAGAAGAAGGGAGGGG
GAGAGGAGGAGGAATACAGCAGAACAAAGGGAAAATGTTGAGAAGAATTCACTTGTCCACTTTCTTGATAATGATAG
CAGTTACATCATTTTTATTAGTTGTACATTTTAAATATGTGAAGTTTATCATCTTTCAATTAAGCCTCATAAAATGT
CTTACAAGCAAACAAATGGAAACTTAGACAAGGAAAGAGTAATAGAAAGATAGAAAAAATAAGTTCAATGTCAGAAG
TACCTGAAAATTAATGTGCCTGGATCCTAGTTCTCTCCATATTTTCAGAAGAGTGCTGGAGGGCAGCAAAACCACAC
ATGCTCTTATTACGGAAAGTGGGTTCTGATAAAAACACTAGACACATCCAGCTTTGTCCTGGAGTTGGTTTAGGGGG
ATGTCAGAGACAGTGATGAAGAGCACAGGGCCAGATACCGGGGTTCACTCATCCCAGACATGAGCTCCTAGATGCAT
ACAGAGCCCCCCCATGTGTGGGTTTACTTCCACTTCTGTAAATGGAGAAAATATTGTCTCCTACAGAACATAGTTTA
CATGAATACTTAAAATGAAATAGGGTGATTAGTGCAAAGTGTTTATCACAGCACAATTTCATAATAAGACAGCATAT
TTTCCAAATGCAATCATTGCCAGCAAACTTCTACAGGGCACCGTCGTCTTATCTGGGTACAGCCTACTCCTCAAGGG
TCCCACCCTAGAGCTTGCTATATAGTAGGAGATATGCAAATAGGGCCCTCCCTCTACTGATGAAAACCAACCCAACC
CTGACCCTGCAGCTCTCAGAGAGGTGCCTTAGCCCTGGATTCCAAGGCATTTCCACTTGGTGATCAGCACTGAACAC
AGAGGACTCACC[redacted]

Fig. 7 (cont.)

[redacted]CACAGTGAGGGGAGGTCAGTGTGAGCCCAGACACAAACCTCCCTGCAGGGGTCCGCAGGACCACCAGGGGG
VH 3-48
CGACAGGACACTGAGCACGGGGCTGTCTCCAGGGCAGGTGCAGGTGCTGCTGAGGGCTGGCTTCCTGTCATGGCCTG
GGGCGGCCTCATTGTCAAGTTTCCCCAGGGAACTTCTCCAGATTTACAATCCTGTACTAATATTTGATGTCTCTAAA
TGCAACCTTTTTTTCCTTTTTGTGTCTGTTTTTTTTTTTTAAAAACAGGAGGACACATCCTCACCTCCACAGAAG
CCACAGTGTCACTTTGGGGGCGGAAATAATCCTTTCGTGGTCAACAGGGTGAGAGTTTTGAGGAATCCCAGGGAAAC
CTGGGGAATGTTTTCCAATTAGACTCAGGGCAGAGACCTCCATGGGAATCCCTGATTAGAACAGGCTTTGAGTTCTG
ATGGGAGCCAAAAGAGAGGCTCACCCAGGGTCAGGGTTCTTAAAACCTGATGGTTTTCACAGCAATCCCCCTTCATC
TTGTGAAACTGGGCACATCTGACTCAGACTGATTCAGTTGACCCTCTTTCTGCTAATCCATTTTCCTTCCCAGTAGA
CTTGATTCTCACAGATCCCTTTCTTCTTCTCTTTCCTGAAAACAGAGGATGTGTTTTCTGTAGTC[redacted]CCTTGA
TTGAAGTGCTGAGTAAATGGTTGCAAACATAGGTCTACATTTTTCAAATCATTCACCATAAATTTGAATTATTTATT
AATTACACTCGAATAAAGCAATAAAGAAACTGATGAGATAATATTTGACTGAATTGCATCAATAAATAGATCGATAT
TAACACAAGGAATATAACTGATTTCCAAAAACATACACATGAACCGTGGTTCACTCTGCGTATTTAGATAAATTACA
GAAAGTTGTCATAACAGATGGGGAATCCTGCAGACTTCACTAGGCATGGGCCATGCTGCCCTGGAGTTGTCTCAGGG
GAGCTGCCTCCTCCAGAGGTTAGAGCACAGGCCCAGGTAATAGGACTAAATTTTTAGATGTGTTATCTTAGACACAC
TGCACAACTGCTGTGTTCTCTATGTAAATTATCTCCTGTAAAATATAACATTGAAGCCTGCATTAAATATATTGTGT
AAATATGTAAGAATAAAAGAAAGTTATGAGAGCTAAGTGTTAATCAAGGCACAAGCATATAAGATATAACTATATTT
TCCTGAATGATGGAATTACTACCAGTCTCCCCCAGGACACTTCATCTGCCCTGAGCCCAGCCTCTCCTCAGATGTCC
CACCCAGAGCTTGCTATATAGTGGGGGACATGCAAATAGGGCCCTCCCTCTACTGATGAAAACCAGCCCAGCCCTGA
CCCTGCAGCTCTGGGAGAGGAGCCCAGCACTAGAAGTCGGCGGTGTTTCCATTCGGTGATCAGCACTGAACACAGAG
GACTCACC[redacted]GA
VH 3-30
CACAGTGAGGGGAGGTCATTGTGCGCCCAGACACAAACCTCCCTGCAGGAACGCTGGGGGGAAATCAGCTGCAGGGG
GCGCTCAGGAGCCACTGATCAGAGTCAGCCCTGGAGGCAGGTGCAGATGGAGGCTGTTTCCTGTCAGGATGTGGGAC
TTTGTCTTCTTCTGACAGTTCCCCAGGGAACCTCTTAAATTTAGAAAACTGTGCCTAACAATGTCTTCTCTATGCAT
ATGAGGACCTTTTCTCCCTGGCACAAAATGCAGATTGACGCTGACACGGATG[redacted]GCTGCTGACATTCCTAGAT
AACTGCAGCTGTAGTTATGCCTGCTAAGGTTTGGGCGCATGGGGCTTGGCTTTTGTCAGCTCCCTGGGATTTATTTT
CCCAAACAAAGAAACCTCCAGGTTAGGGGCACCCTATTCATTCCCATCACCTGGCATGATTTAAAGGATAATTGCTT
AGAATTAAAATATTGATCCAGATTTTTTATATTCCCCATCGCTTTTTGTTTCTTCTGGGCTGTAGCCAGAGATCATT
GATTGGCGCTCAGGAATAAGCAGAGTTAGTCTAAAATGCAGGCAAATACTTAAACAACTGAAGAGATTAGAATTTAA
AGACAAGTGTATGATATGTTTTGAAATACAATGTTTCTCTTTCCAGTTTTGGTTTTTGTCAGCAGCAAATAATGATA
AGACTGAGTTGTTTGCAAAATAAACTTTAGTCTTAAACTTGGCCTGATTATTTGCATAAAGTGCAGCAAGAATATTA
ATAATAATTCTGTAGGAAAAGCCTGCAAGCACCAGGAGCTTCACAGTCTAACACTATGAGCACGTGCATCCTCACGC
AACTCACTGAATATGTCCAAGTCAGCCTGTTCCGATCTTAAATGCCATCCAGTGGCATCTGCCCCAGGTACACTAAT
ACATGGGTCCTGCTTCTCTCTGCAGCCGCCTCTCTCCTCAGATTTCAGGTTTTGTGTATTGTTTGTTTTCTCTCTGA
CATCAACACAGATATGTTGAAGGTTTTCTTTTTTTTATTTGTAGTTGTTCAGCTTTGTTGTTAATGAGGTCAGAATA
AGCTCATAGTTTACACATTTTTACATTCCCATGCCGAGTAGCTGCTTTTCTCTATCAAATCCATTAACTGAGAGAAC
AATCACATTTCGTTACAGGTGAACAGTTAAATAGTTTGGCATATATTTCTGTGCTGGAATCTAATGCAGCTTGAAAT
CAAGTCATGCCTCACTCATTGAAAAAAACATGGCTAAATTCTCAAAGAATTGTGCTGAGTGAAAGAAACTAAGGAAT
GAAGAGTAAATTTTATATGATACATTTGTAGAAATTTTAGAAGATGCCACTATTATAAATTAACATGGAGAAGATTT
AAGTGTTTCTGAGAATATGCTATTGGGAGTAATGGGGATGTGAGTTAAATTTCAGAGGAATAAGAGAAAGATTTAGG
GATTAATTTTTTCAAACCTTGATTGAAGTGCTGAGTAAATGGTTGCAAACATAGGTCTACATTTTTCAAATCATTCA
CCATAAATTTGAATTATTTATTAATTACACTCGAATAAAGCAATAAAGAAACTGATGAGATAATATTTGACTGAATT
GCATCAATAAATAGATCGATATTAACACAAGGAATATAACTGATTTCCAAAAACATACACATGAACCGTGGTTCACT
CTGCGTATTTAGATAAATTACAGAAAGTTGTCATAACAGATGGGGAATCCTGCAGACTTCACTAGGCATGGGCCATG
CTGCCCTGGAGTTGTCTCAGGGGAGCTGCCTCCTCCAGAGGTTAGAGCACAGGCCCAGGTAATAGGACTAAATTTTT

Fig. 7 (cont.)

AGATGTGTTATCTTAGACACACTGCACAACTGCTGTGTTCTCTATGTAAATTATCTCCTGTAAAATATAACATTGAA
GCCTGCATTAAATATATTGTGTAAATATGTAAGAATAAAAGAAAGTTATGAGAGCTAAGTGTTAATCAAGGCACAAG
CATATAAGATATAACTATATTTTCCTGAATGATGGAATTACTACCAGTCTCCCCCAGGACACTTCATCTGCCCTGAG
CCCAGCCTCTCCTCAGATGTCCCACCCAGAGCTTGCTATATAGTGGGGGACATGCAAATAGGGCCCTCCCTCTACTG
ATGAAAACCAGCCCAGCCCTGACCCTGCAGCTCTGGGAGAGGAGCCCAGCACTAGAAGTCGGCGGTGTTTCCATTCG
GTGATCAGCACTGAACACAGAGGACTCACC[illegible]
[illegible]CACAGTGAGGGGAGGTCATTGTGCGCCCAGACACAAACCTCCCTGCAGGAACGCT
VH 3-33
GGGGGGAAATCAGCTGCAGGGGGCGCTCAGGAGCCACTGATCAGAGTCAGCCCTGGAGGCAGGTGCAGATGGAGGCT
GTTTCCTGTCAGGATGTGGGACTTTGTCTTCTTCTGACAGTTCCCCAGGGAACCTCTTAAATTTAGAAAACTGTGCC
TAACAATGTCTTCTCTATGCATATGAGGACCTTTTCTCCCTGGCACAAAATGCAGATTGACGCTGACACGGATGAAA
ATTCCTCAACCATGGTCACAAGGATCAGAGTCCTGAGTAACCTCAGGGCTTCCTGGTGATTCTTCTCCAATCAGACC
CAGGACAGGGACCTCCGTGAGATTCCCTGACTGGAACAGTCTTTATGGATCCTGGTCACAGACAATAGAGAGGCTGA
ACCAGGGTCAGCGTCATGTAGAACGTCACAGATTTCACGTCTGATCCTTCTCCTGACACGAAAGTATGCAAATCAGT
ATCAGCACCGATCTG[redacted]GATGGAAAGATAGATACCAACATGAGAAATGTATGACACTCAAGAAAATAAAACTG
TAGGAAACTTGCTTTTCTTTATATTTGTTAGGTAATCACCACAGTGTGTACACATCACACCATGTTCCCATTACAGA
GAAAAGGTTCTGCGAACCTCACGAGCTGTGACCCCTGTGTGCTGGGCTTGGTTCAGGGAGAAGTCAGGTCCAGTGGT
GAGAAGCACAGGCCCAGATGCCCAGGCTCACTCTGACCAAAAGTGAGCACTGGGGACATTGTAAAACCCACCTGTGC
TTTTGCTGATAATTTTTCATCTTTAACATGGAAATAATATTGATACTATATACCATGGTTTCTCTGCGTATGTAAAA
ATAAAAGATGATTGGTGCTAACTTTAAAAATATGCAGTTTATGTAGATCTATGGTACCTCAATAAAACTGTTTTAAA
ATAAAAATTACAAAATTATAAGATTTTTAGGTTTTAAGGTTTAAGTTTATCACAAAACAAACTGACAATAGGAAAGC
ACAATTTCCCAATGCTTTCAATATCACAGATCTCCCCGAGGACATTCTGACATGCTCTGAGCCCCACTATCTCCAAA
GGCCTCTCACCCCAGAGCTTACTATATAGTAGGAGATATGCAAATAGAGCCCTCCGTCTGCTGATGAAAACCAGCCC
AGCCCTGACCCTGCAGCTCTGAGAGAGGAGCCCAGCCCTGGGATTTTCAGGTGTTTTCATTTGGTGATCAGGACTGA
ACAGAGAGAACTCACC[illegible]
[illegible]CACAGTGAGGGGAAGTCATTGTGAGCCCAGACACAAACCTCCCTGCAGGAACGATGGGGGGGAAATC
VH 3-23
AGCGGCAGGGGGCGCTCAGGACCCGCTGATCAGAGTCATCCGCAGAGGCAGGTGCAGATGGAGGCTGTTTCCTGTCA
GGGTGTGGGACTTCATCTTCTTCTGACAGTTTCTCTAGTGAACCTCTCTAACCTCAGAATTCTGTGCTTACTAATGT
CATCTCTACGTATTTTTTAAAAGATCATTTTAATATGAGCACCTATTCTCACACGCACCAAATGCAGATTGACGCTT
ACAGAGATG[redacted]CACTGGGATTCCTAAGGCCAATTCAGTATTTCAAAAGATGGTGTGAGAAGCACAGGCTGTCA
CTAAAGGAGAATTCTGAGCCAGGGCACAGCCACTTTATACTTGGCTGGGGACACTGGTAGGAATATACTCTGTGAGA
TCAGACACAGGAACCTCCTTGCAGGGGCAGGGCAGGGCTGCAGGGGGCGCTCAGGACACACAGAGCACAGGCTTCCGCC
CCAGAGCAGGTGAAGGAGGCTGGGGAGGGGTTCCTCTCAGGGCCTGGGACTTCCTTTAAAAAATCTAAAATAAGTAT
TTCACAAGGACTGCCGATGTTTATATAAATATCCTATTCAATTGTGAGCATTTATGAAACTCGATGTTGTAATGAGA
ACCACTTTTACAATGGGAATTTCAAACTTCCCTAGACATCTTAATAGTAAGCAGCTGGAGGTCAGGAGGAGATCCTT
TCTTATAAATAAGTGCAATTTTTGGAGAAACACACTCATTCCCAAAATAGCACATTCACATATTAAGGTCTAGAAAT
GATTCGAGTTGCCCCTGAGACAGTCAAATGTGGGTTCTAAGTGAGGTGCGTGTCCTGGGGGAGCTTGTTCTCCAGTG
GGGGAAGCTCTGTCAACACAGAGTTCAGGGATGGATAGGGGATGCGTGGCCTCTAACAGGATTACGGCTTTAACCCT
CAGCTTCTACAATTGTGTCGTCCATGTGTCATGTATTTGCTCTTTCTCATCCTGGGTCAGGAATTGGGCTATTAAAT
AGCATCCTTCATGAATATGCAAATAACTGAGGTGAATATAGATATCTGTGTGCCCTGAGAGCATCACCCAAAAACCA
CACCCCTCCTTGGGAGAATCCCCTAGATCACAGCTCCTCACC[illegible]

Fig. 7 (cont.)

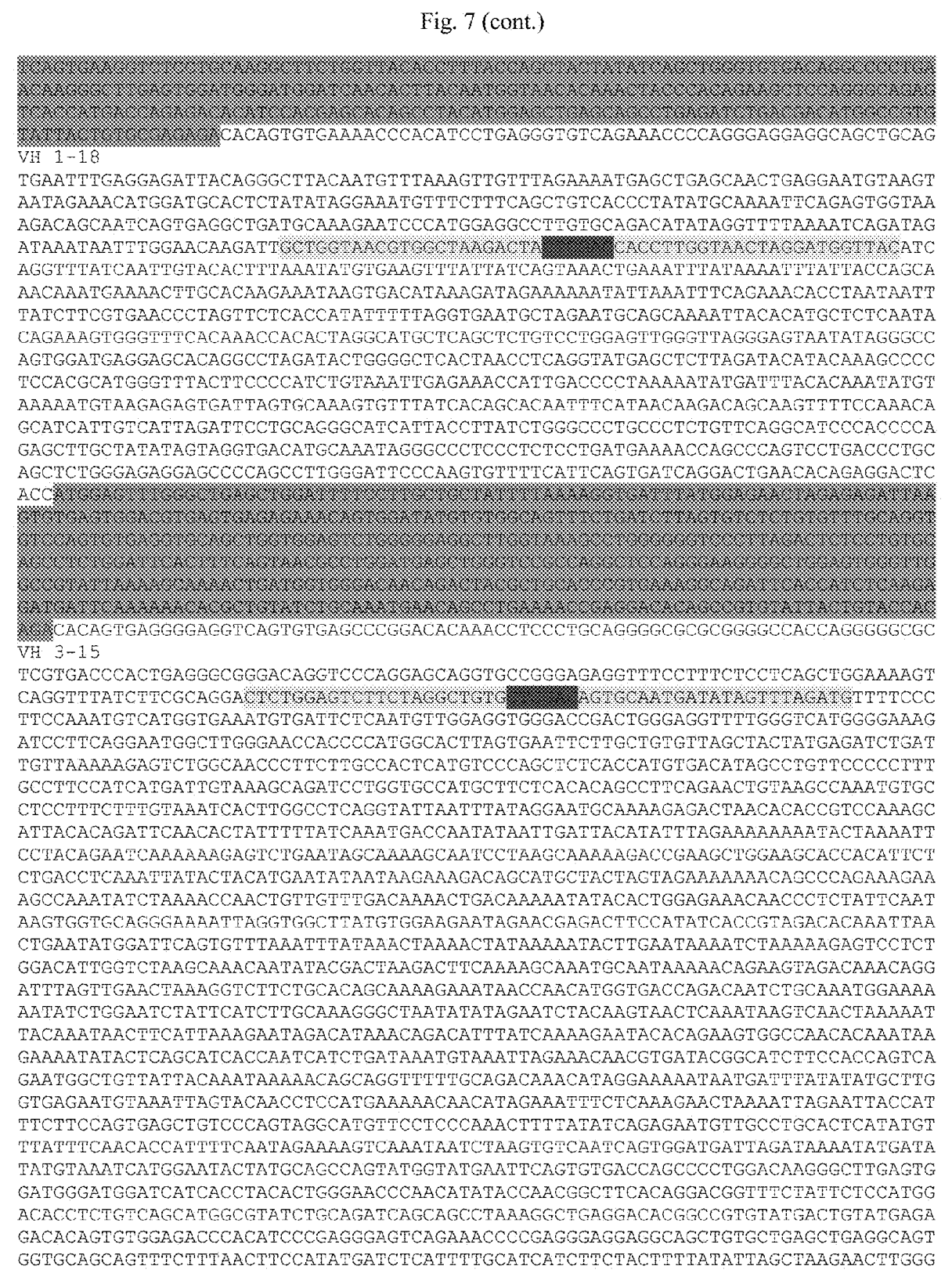

[illegible]CACAGTGTGAAAACCCACATCCTGAGGGTGTCAGAAACCCCAGGGAGGAGGCAGCTGCAG
VH 1-18
TGAATTTGAGGAGATTACAGGGCTTACAATGTTTAAAGTTGTTTAGAAAATGAGCTGAGCAACTGAGGAATGTAAGT
AATAGAAACATGGATGCACTCTATATAGGAAATGTTTCTTTCAGCTGTCACCCTATATGCAAAATTCAGAGTGGTAA
AGACAGCAATCAGTGAGGCTGATGCAAAGAATCCCATGGAGGCCTTGTGCAGACATATAGGTTTTAAAATCAGATAG
ATAAATAATTTGGAACAAGATTGCTGGTAACGTGGCTAAGACTA[redacted]CACCTTGGTAACTAGGATGGTTACATC
AGGTTTATCAATTGTACACTTTAAATATGTGAAGTTTATTATCAGTAAACTGAAATTTATAAAATTTATTACCAGCA
AACAAATGAAAACTTGCACAAGAAATAAGTGACATAAAGATAGAAAAAATATTAAATTTCAGAAACACCTAATAATT
TATCTTCGTGAACCCTAGTTCTCACCATATTTTTAGGTGAATGCTAGAATGCAGCAAAATTACACATGCTCTCAATA
CAGAAAGTGGGTTTCACAAACCACACTAGGCATGCTCAGCTCTGTCCTGGAGTTGGGTTAGGGAGTAATATAGGGCC
AGTGGATGAGGAGCACAGGCCTAGATACTGGGGCTCACTAACCTCAGGTATGAGCTCTTAGATACATACAAAGCCCC
TCCACGCATGGGTTTACTTCCCCATCTGTAAATTGAGAAACCATTGACCCCTAAAAATATGATTTACACAAATATGT
AAAAATGTAAGAGAGTGATTAGTGCAAAGTGTTTATCACAGCACAATTTCATAACAAGACAGCAAGTTTTCCAAACA
GCATCATTGTCATTAGATTCCTGCAGGGCATCATTACCTTATCTGGGCCCTGCCCTCTGTTCAGGCATCCCACCCCA
GAGCTTGCTATATAGTAGGTGACATGCAAATAGGGCCCTCCCTCTCCTGATGAAAACCAGCCCAGTCCTGACCCTGC
AGCTCTGGGAGAGGAGCCCCAGCCTTGGGATTCCCAAGTGTTTTCATTCAGTGATCAGGACTGAACACAGAGGACTC
ACC[illegible]CACAGTGAGGGGAGGTCAGTGTGAGCCCGGACACAAACCTCCCTGCAGGGGCGCGCGGGGCCACCAGGGGGCGC
VH 3-15
TCGTGACCCACTGAGGGCGGGACAGGTCCCAGGAGCAGGTGCCGGGAGAGGTTTCCTTTCTCCTCAGCTGGAAAAGT
CAGGTTTATCTTCGCAGGACTCTGGAGTCTTCTAGGCTGTG[redacted]AGTGCAATGATATAGTTTAGATGTTTTCCC
TTCCAAATGTCATGGTGAAATGTGATTCTCAATGTTGGAGGTGGGACCGACTGGGAGGTTTTGGGTCATGGGGAAAG
ATCCTTCAGGAATGGCTTGGGAACCACCCCATGGCACTTAGTGAATTCTTGCTGTGTTAGCTACTATGAGATCTGAT
TGTTAAAAAGAGTCTGGCAACCCTTCTTGCCACTCATGTCCCAGCTCTCACCATGTGACATAGCCTGTTCCCCCTTT
GCCTTCCATCATGATTGTAAAGCAGATCCTGGTGCCATGCTTCTCACACAGCCTTCAGAACTGTAAGCCAAATGTGC
CTCCTTTCTTTGTAAATCACTTGGCCTCAGGTATTAATTTATAGGAATGCAAAAGAGACTAACACACCGTCCAAAGC
ATTACACAGATTCAACACTATTTTTATCAAATGACCAATATAATTGATTACATATTTAGAAAAAAAATACTAAAATT
CCTACAGAATCAAAAAAGAGTCTGAATAGCAAAAGCAATCCTAAGCAAAAAGACCGAAGCTGGAAGCACCACATTCT
CTGACCTCAAATTATACTACATGAATATAATAAGAAAGACAGCATGCTACTAGTAGAAAAAAACAGCCCAGAAAGAA
AGCCAAATATCTAAAACCAACTGTTGTTTGACAAAACTGACAAAAATATACACTGGAGAAACAACCCTCTATTCAAT
AAGTGGTGCAGGGAAAATTAGGTGGCTTATGTGGAAGAATAGAACGAGACTTCCATATCACCGTAGACACAAATTAA
CTGAATATGGATTCAGTGTTTAAATTTATAAACTAAAACTATAAAAATACTTGAATAAAATCTAAAAAGAGTCCTCT
GGACATTGGTCTAAGCAAACAATATACGACTAAGACTTCAAAAGCAAATGCAATAAAAACAGAAGTAGACAAACAGG
ATTTAGTTGAACTAAAGGTCTTCTGCACAGCAAAAGAAATAACCAACATGGTGACCAGACAATCTGCAAATGGAAAA
AATATCTGGAATCTATTCATCTTGCAAAGGGCTAATATATAGAATCTACAAGTAACTCAAATAAGTCAACTAAAAAT
TACAAATAACTTCATTAAAGAATAGACATAAACAGACATTTATCAAAAGAATACACAGAAGTGGCCAACACAAATAA
GAAAATATACTCAGCATCACCAATCATCTGATAAATGTAAATTAGAAACAACGTGATACGGCATCTTCCACCAGTCA
GAATGGCTGTTATTACAAATAAAAACAGCAGGTTTTTGCAGACAAACATAGGAAAAATAATGATTTATATATGCTTG
GTGAGAATGTAAATTAGTACAACCTCCATGAAAAACAACATAGAAATTTCTCAAAGAACTAAAATTAGAATTACCAT
TTCTTCCAGTGAGCTGTCCCAGTAGGCATGTTCCTCCCAAACTTTTATATCAGAGAATGTTGCCTGCACTCATATGT
TTATTTCAACACCATTTTCAATAGAAAAGTCAAATAATCTAAGTGTCAATCAGTGGATGATTAGATAAAATATGATA
TATGTAAATCATGGAATACTATGCAGCCAGTATGGTATGAATTCAGTGTGACCAGCCCCTGGACAAGGGCTTGAGTG
GATGGGATGGATCATCACCTACACTGGGAACCCAACATATACCAACGGCTTCACAGGACGGTTTCTATTCTCCATGG
ACACCTCTGTCAGCATGGCGTATCTGCAGATCAGCAGCCTAAAGGCTGAGGACACGGCCGTGTATGACTGTATGAGA
GACACAGTGTGGAGACCCACATCCCGAGGGAGTCAGAAACCCCGAGGGAGGAGGCAGCTGTGCTGAGCTGAGGCAGT
GGTGCAGCAGTTTCTTTAACTTCCATATGATCTCATTTTGCATCATCTTCTACTTTTATATTAGCTAAGAACTTGGG

Fig. 7 (cont.)

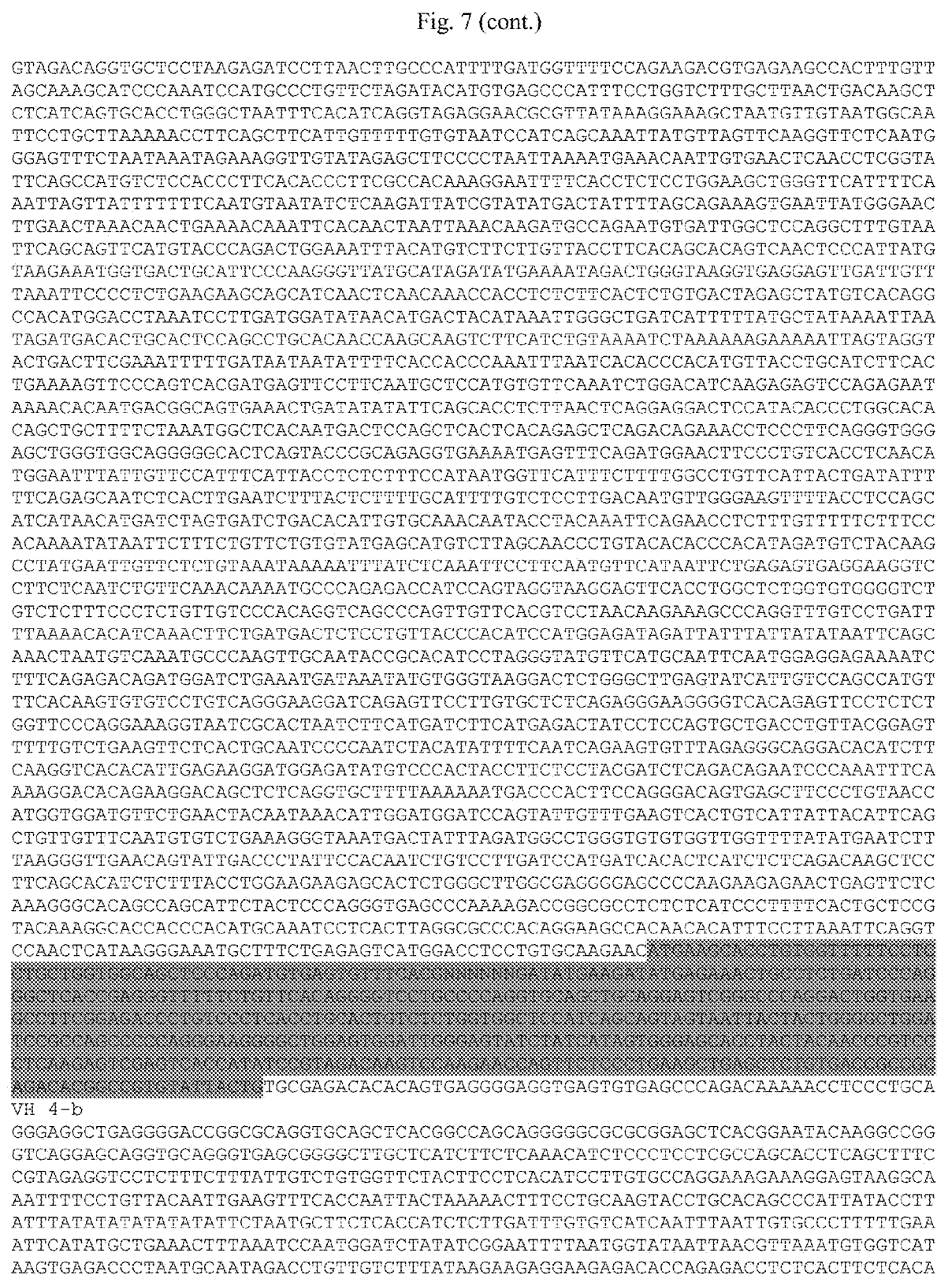

GTAGACAGGTGCTCCTAAGAGATCCTTAACTTGCCCATTTTGATGGTTTTCCAGAAGACGTGAGAAGCCACTTTGTT
AGCAAAGCATCCCAAATCCATGCCCTGTTCTAGATACATGTGAGCCCATTTCCTGGTCTTTGCTTAACTGACAAGCT
CTCATCAGTGCACCTGGGCTAATTTCACATCAGGTAGAGGAACGCGTTATAAAGGAAAGCTAATGTTGTAATGGCAA
TTCCTGCTTAAAAACCTTCAGCTTCATTGTTTTTGTGTAATCCATCAGCAAATTATGTTAGTTCAAGGTTCTCAATG
GGAGTTTCTAATAAATAGAAAGGTTGTATAGAGCTTCCCCTAATTAAAATGAAACAATTGTGAACTCAACCTCGGTA
TTCAGCCATGTCTCCACCCTTCACACCCTTCGCCACAAAGGAATTTTCACCTCTCCTGGAAGCTGGGTTCATTTTCA
AATTAGTTATTTTTTTCAATGTAATATCTCAAGATTATCGTATATGACTATTTTAGCAGAAAGTGAATTATGGGAAC
TTGAACTAAACAACTGAAAACAAATTCACAACTAATTAAACAAGATGCCAGAATGTGATTGGCTCCAGGCTTTGTAA
TTCAGCAGTTCATGTACCCAGACTGGAAATTTACATGTCTTCTTGTTACCTTCACAGCACAGTCAACTCCCATTATG
TAAGAAATGGTGACTGCATTCCCAAGGGTTATGCATAGATATGAAAATAGACTGGGTAAGGTGAGGAGTTGATTGTT
TAAATTCCCCTCTGAAGAAGCAGCATCAACTCAACAAACCACCTCTCTTCACTCTGTGACTAGAGCTATGTCACAGG
CCACATGGACCTAAATCCTTGATGGATATAACATGACTACATAAATTGGGCTGATCATTTTTATGCTATAAAATTAA
TAGATGACACTGCACTCCAGCCTGCACAACCAAGCAAGTCTTCATCTGTAAAATCTAAAAAAGAAAAATTAGTAGGT
ACTGACTTCGAAATTTTTGATAATAATATTTTCACCACCCAAATTTAATCACACCCCACATGTTACCTGCATCTTCAC
TGAAAAGTTCCCAGTCACGATGAGTTCCTTCAATGCTCCATGTGTTCAAATCTGGACATCAAGAGAGTCCAGAGAAT
AAAACACAATGACGGCAGTGAAACTGATATATATTCAGCACCTCTTAACTCAGGAGGACTCCATACACCCTGGCACA
CAGCTGCTTTTCTAAATGGCTCACAATGACTCCAGCTCACTCACAGAGCTCAGACAGAAACCTCCCTTCAGGGTGGG
AGCTGGGTGGCAGGGGGCACTCAGTACCCGCAGAGGTGAAAATGAGTTTCAGATGGAACTTCCCTGTCACCTCAACA
TGGAATTTATTGTTCCATTTCATTACCTCTCTTTCCATAATGGTTCATTTCTTTTGGCCTGTTCATTACTGATATTT
TTCAGAGCAATCTCACTTGAATCTTTACTCTTTTGCATTTTGTCTCCTTGACAATGTTGGGAAGTTTTACCTCCAGC
ATCATAACATGATCTAGTGATCTGACACATTGTGCAAACAATACCTACAAATTCAGAACCTCTTTGTTTTTCTTTCC
ACAAAATATAATTCTTTCTGTTCTGTGTATGAGCATGTCTTAGCAACCCTGTACACACCCACATAGATGTCTACAAG
CCTATGAATTGTTCTCTGTAAATAAAAATTTATCTCAAATTCCTTCAATGTTCATAATTCTGAGAGTGAGGAAGGTC
CTTCTCAATCTGTTCAAACAAAATGCCCAGAGACCATCCAGTAGGTAAGGAGTTCACCTGGCTCTGGTGTGGGGTCT
GTCTCTTTCCCTCTGTTGTCCCACAGGTCAGCCCAGTTGTTCACGTCCTAACAAGAAAGCCCAGGTTTGTCCTGATT
TTAAAACACATCAAACTTCTGATGACTCTCCTGTTACCCACATCCATGGAGATAGATTATTTATTATATAATTCAGC
AAACTAATGTCAAATGCCCAAGTTGCAATACCGCACATCCTAGGGTATGTTCATGCAATTCAATGGAGGAGAAAATC
TTTCAGAGACAGATGGATCTGAAATGATAAATATGTGGGTAAGGACTCTGGGCTTGAGTATCATTGTCCAGCCATGT
TTCACAAGTGTGTCCTGTCAGGGAAGGATCAGAGTTCCTTGTGCTCTCAGAGGGAAGGGGTCACAGAGTTCCTCTCT
GGTTCCCAGGAAAGGTAATCGCACTAATCTTCATGATCTTCATGAGACTATCCTCCAGTGCTGACCTGTTACGGAGT
TTTTGTCTGAAGTTCTCACTGCAATCCCCAATCTACATATTTTCAATCAGAAGTGTTTAGAGGGCAGGACACATCTT
CAAGGTCACACATTGAGAAGGATGGAGATATGTCCCACTACCTTCTCCTACGATCTCAGACAGAATCCCAAATTTCA
AAAGGACACAGAAGGACAGCTCTCAGGTGCTTTTAAAAAATGACCCACTTCCAGGGACAGTGAGCTTCCCTGTAACC
ATGGTGGATGTTCTGAACTACAATAAACATTGGATGGATCCAGTATTGTTTGAAGTCACTGTCATTATTACATTCAG
CTGTTGTTTCAATGTGTCTGAAAGGGTAAATGACTATTTAGATGGCCTGGGTGTGTGGTTGGTTTTATATGAATCTT
TAAGGGTTGAACAGTATTGACCCTATTCCACAATCTGTCCTTGATCCATGATCACACTCATCTCTCAGACAAGCTCC
TTCAGCACATCTCTTTACCTGGAAGAAGAGCACTCTGGGCTTGGCGAGGGCAGCCCCAAGAAGAGAACTGAGTTCTC
AAAGGGCACAGCCAGCATTCTACTCCCAGGGTGAGCCCAAAAGACCGGCGCCTCTCTCATCCCTTTTCACTGCTCCG
TACAAAGGCACCACCCACATGCAAATCCTCACTTAGGCGCCCACAGGAAGCCACAACACATTTCCTTAAATTCAGGT
CCAACTCATAAGGGAAATGCTTTCTGAGAGTCATGGACCTCCTGTGCAAGAAC[illegible]
[illegible]TGCGAGACACACAGTGAGGGGAGGTGAGTGTGAGCCCAGACAAAAACCTCCCTGCA
VH 4-b
GGGAGGCTGAGGGGACCGGCGCAGGTGCAGCTCACGGCCAGCAGGGGGCGCGGAGCTCACGGAATACAAGGCCGG
GTCAGGAGCAGGTGCAGGGTGAGCGGGGCTTGCTCATCTTCTCAAACATCTCCCTCCTCGCCAGCACCTCAGCTTTC
CGTAGAGGTCCTCTTTCTTTATTGTCTGTGGTTCTACTTCCTCACATCCTTGTGCCAGGAAAGAAAGGAGTAAGGCA
AATTTTCCTGTTACAATTGAAGTTTCACCAATTACTAAAAACTTTCCTGCAAGTACCTGCACAGCCCATTATACCTT
ATTTATATATATATATATTCTAATGCTTCTCACCATCTCTTGATTTGTGTCATCAATTTAATTGTGCCCTTTTTGAA
ATTCATATGCTGAAACTTTAAATCCAATGGATCTATATCGGAATTTTAATGGTATAATTAACGTTAAATGTGGTCAT
AAGTGAGACCCTAATGCAATAGACCTGTTGTCTTTATAAGAAGAGGAAGAGACACCAGAGACCTCTCACTTCTCACA

Fig. 7 (cont.)

TGCACACAGAGAAGAGGCCACGTGGAGACATAGTGCACTAGAAGGTGGGCCTCTGCAAGCCAGGAAGAAGCCGCACC
AAGAACCAACCCTGCCAGCACCTTGATCTTCTACATTCAGACTGCAGAATTGTAAGAAAACCAATATTTGTTGTTTA
AGCCACCCACTCCTTTTGTCTTCTTACGAAGACCCAGACAGGCTAATACCACACAACTCTGTTAGCTCCATCTCCTG
GAGGGAGAAGCAGCCCCCTGAGGCTGGGCACATCGCTCAGATTTTCACATGAATTAGGCAAAAACAGTAGCTCTCAT
ATAAAAACTGTCACGTCCCTGTTGGGACAAGGTCTTCTAAACAACCCCTGGGGCTTTGTCACAAATGTTGCATTTTA
TCCTTTATTAGGACTTAACTAATTGACAATGAGTACCAGCTGGATGGAAACTGACCACTGACCATCTTCTGCTGTCT
CCTTATTATATCACAGAAAACCACAGCAACATTACTCTATGTCTTCAACTTTCTAAATTTGTACTGAATCTATTGCT
AAATGAGGAGCTACATGGGGTCTGAGTTTTGTTATCTTCTCCCCAGTCTTCCCCAATTACCAAGCACAGAAGATACT
TTCAGTGAAATTTAGCTGTCAATGCCCCCAACACCACATCATGTTTTAAGGTCCAAGGACTTTCTTTGGGGGGCTAT
TTAAAAACACTTTTGAATGGAAAATCCTAAAGCATACAACAGCTGAAAGAATGGCCCCTGTGCACGTGAAGGCTGAA
GGGATGGATGATAGGGTACGTTCCTCCAAGGTGTTCCTGGGCATGTGATGGTTGGATACCTCATG[redacted]CTATGG
ATGTGAACTACAAGTATGTAAGTACTTCAAGTAATTCTATTTAATGGAGTTTGAAATAAAACTCAAACTTATTCAAA
ACACTAATTACTTGGTATTTATTTTGAGATCTATGAGTTTATCAAGAAATTCAAATTCCTATTTCTATTTAAACTCC
CGATTCCTACTCTCAGTGGGAGGGAAAACTCACAGCCAATCACACATCACAGGACAAATCTGTAAACGAAGAGTCAT
TCCTCTGAAGGTCCTGGGTGTTCAGGACTCTCAGGCAGGTGCTGAGGACCCTGTCTTGGGAGTGCCCAGCAGATCTC
AGAACCCTACATGGGGCCTGCTGGACACTCATGTGGGATAACTAGTCGCCACTTATTCAGAGTTACCAGTGAGCTTT
GACTGTTCCGAATGGGACCAGCATGGAGTCAAGGTGCCTGCTCAATGTCAGAGACAGCGATGGTCTCAGAAACAATC
CAGGTAATCTCTAGGCCAATAAAATGTGGATTCACAGTGAGAAGTACATCCTGGAGGTGGAGCTTGTTCTTCAGTGG
GAAGAGTGCTGTGCACAGAAAGCTTAGAAATGGGGAAGGGGGTGCGTTTCCTCAGGCAGGATTAGGGCTTCGTCCCT
CAGCGTCCCACTCTTGTATGGCTGATGTGGCATCTGTGTTTTCTTTTTCATACTAGATAAGGCTTTGAGCTGTGAAA
TACCCTGCCTCATGAATATGCAAATAACCTGAGCTCTTCTGAGGTAAATATAGGTATATTGGTGCCCTGAGAGCATC
ACTCAACAACCACATCTGTCCTCTAGAGAAAACCCTGTGAGCACAGCTCCTCACC[redacted]
CACAGTGTGAAAAACCACATCCTCAGAGAGTCAGAAACCCTAGGG

VH 1-8

GAGAAGGCAGCTGTGCTGGCTGAGCAGATGACAGGGGTTATCAGGTTTAAGGCTTTTTGAAAATGGGTTATATAT
TTGAGAAAAAAATAACAATAGAAACAAGTACACACTCTAATTTTAAGAGATATATTCAATTCAAGAATTGTAGAAGC
CGAATTCACAGTGGGAAAGGCCACACTCAATAAAGTTGATAAAAACATTCCAGGAAGGTGCTACTG[redacted]CCTGT
GTTTATCTGTTATGTTCATGCTGTAAAACAGTAAGTAAAATATACTCCTCATCTATGTACATTTTGAAGCTGAGTTG
CAGGTTTTTTGGTAAGACCCAGAGTCACAGAGAATTCAAATATTGTTAAGCTGCTTAATAGAAAAACAAATTATGGT
AAATGTGTTCACTGGAATACTACCCATGATTTATAATAAATAAATGCCTGACACACAGAACAGCAGCAAAACCACAC
ATGCTCTTATTACAGAAAGTGGCTTCTGAAAACCACACCGGGCACGTACAGCTTTGTCCTGGAGTTGGTTTAGGGGG
ATGTCAGAGCCAGTGACGAGAAGCACAGGGCCAGATGGCAGCGTTCACTCATCCCAGACATGAGCTCCTGGATGCAT
ACAGAGCCCCCCCATGTGTGGGTTTACTTCCACTTCTGTAAAAGGAGAAAATACTGACTCCTACAGAGCATAATTTA
CACATTTTTTAAAAAATGTAATAGGGTGATCAGGGCAAAGTGTTTATCACAGCACAATTTCATAAGACAGCATATTT
TCCAAATACCATCATTGTCAGCAAACTTCTGCAGAGCACCGTCTTCTTATATGGGTACAGCCTATTCCTCCAGCATC
CCACTAGAGCTTCTTATATAGTAGGAGACATGCAAATAGGGCCCTCCCTCTACTGATGAAAACCAACCCAACCCTGA
CCCTGCAGGTCTCAGAGAGGAGCCTTAGCCCTGGACTCCAAGGCCTTTCCACTTGGTGATCAGCACTGAGCACAGAG
GACTCACT[redacted]
CACAGTGAGGGGAAGTCAGTGTGAGCCCAGACACAAACCTCCCTGCAGGGGTCCCTTGGGACCACCAGGGGGCGA

VH 3-7

CAGGGCATTGAGCACTGGGCTGTCTCCAGGGCAGGTGCAGGTGCTGCTGAGGGCTGGCTTCCTGTCGCGGTCTGGGG
CTGCCTCGTCGTCAAATTTCCCCAGGAACTTCTCCAGATTTACAATTCTGTACTGACATTTCATGTCTCTAAATGCA
ATACTTTTTTTGTCCTTTTTGTTTCTTTGTTTTTTTGCAACAGGAGTACATATCCTCAGCTCCACAGAAGCCAGGC[redacted]
CATGGTCAGTGTCATATAGAATATGGGGACCCTCACAAGTTTTTGTCTGACCCTTCTCCTGACACTAAATT

Fig. 7 (cont.)

ATGCAAATTAATAACACTGATCTGGTGCTTCTTTTGATTCTAATTTATTTTATTTTAGTTGTCGTTCTCACTTTTC
CTTTGGATTTTCCTGCTCCCTGGAAAAGGTAAATGTGGTCTCCGTGACCTCAATTCAAGGGCTGAAGCCCTTTCCCT
GTAGCTCAGCTGGGGCTCAGGCTGTGGCTACTGCAGCCATGTGGAAGAGGCTGAAGGGACTTTCTTCACTCTCCTTG
CTCAGGACCATCCACTGTATTGTGTATAGGCTTCTCTGGAAATGCAAGTGGCCATTTGTAGTGAAAGAAATATGTTT
GTCTGGTTAAAATGGGAGGTGGATGTAGAGTTAATTGGCTGCTACATAAACTGTCCTTCTCCACCAGTGCTTTTAGG
ATGAGATTGTGAAATTTGTAAGAATCAAAATGGAGTCACATATGTTAAAACCCTGACAAATGGATTCAGGAAGTGTA
GGGAGAATTCTTACACACATATCCCTGACAACAAGAACTATCATAAAATAGTTCTTGCAAAAAGACCAACATGACCT
CATAATCATGACTTCTGCAAAGACTTCTACTCAGAATCTACTTGCCCAGCCTTAGATTAATGCCATCTGAATTACAC
TGATCATGTTACTATCACTGCTCCTCACCACAGATGCAACACCCTCCTGAGTCCTGAAACCTGACTCCATCCCATAG
AGTAGGGCACAGATGAGGGGAATGCAAATCTCCACCAGCTCCACCCTCCTCTGGGTTGAAAAAGCCGAGCACAGGTC
CCAGCTCAGTGACTCCTGTGCCCCACC[redacted]CACAAAGACACAGCCCAGGGCACCTCCTGTACAAAAACCCAGGCTGCTTCTCATTGGTGCTCCCTCCC
VH 2-5
CACCTTTGCAGAACAGGAAAGTGCAGCTGAGATACGTTTTCCTGCCAGGGCCTGCATTTCCCATCCCCATTAGACTC
AGAGCCCTGTCTTCCTCCTTCTTCTTTAATAATAAATGGCATGACTCCTGTTAATAGTTCATAGAAGCAGAAGCTGA
GTCCTGTTTGTCAAACATTCAGCATGAAATGTTCATGTTACCTGGGCCAGATGCATCACTGGTATGTGGCCGCCAG[redacted]GGTCACACATTGAGAATGATGAAGATATGTCCCACGAGTTTTTCCTAAGGTCTCAGAAAGAATTCCAGGACT
CAAAAGGTCTCAGAGGGCAGCTCCCAGTGCCTTAATTAAAATGGTGGCTCAGGCCTGTAATCCCAGCATTTTGGGAG
GCTAAGGCAAGTGGATCACCTGAGGTCGGGACATTGAGACTAGCTTGGCCAACATGGTGAAACCTTATCTCTACTAA
AAATATAAAAATTAGACGGGGGTGGTTGTGCGTGCCTGTACTCCCAGCTACTCGGGAGGCTGAGGCAGGAGAATCAC
TTGAACCCAGGAGGCGGAGGTTGCGGTGAGCCGAGATCGGGACACTGCACTCTAGCCTGGGCAAAGGAGCAAAAGTT
CATCTAAAAAATTTATTTTAATTTAAAAATTTTGAAAAAATGGCCCACTCCCTAGAACAGAGAGATTCCCTCTAAAC
ATGATGGAGGTCCCGAACTATACATTAAGTGAATCCTGGTGTGTCTGAACTCACATGATTATTACGTTAAGCTGCTG
TTCCAATCTACTTCCTCACCTGGGAAAAGAGGAGCCAGGGCATGGCTAGTTGAGGCCCCAGGAAGAGAACTGAGTTC
TCAAAGGACAAAGCAAGCATCCTCATCCCAGGGCGAGCCTAAAAGACTGGGGCCTCCCTCATCCCTTTTCACCTCTT
TATACAAAGGCACCACCTACATGCAAATCCTCACTTAGGCACCCACAGGAAACCACCACACATTTCCTTAAATTCAG
GGTCCAGCTCACATGGGAAATACTTTCTGAGAGTCATGGACCTCCTGCACAAGAAC[redacted]CACAGTGAGGGGAGGTGAGTGTGAGCCCAGACACAAACCTCCCTGCAGGGA
VH 4-4
GGCTGAGGGGACCGGCGCAGGTGCAGCTCAAAGCCAGCAGGGGGCGCGCGGGGCCCACAGAGCAAGAGGCCGGGTCT
GGAGCAGGTGCAGGGAGGGCGGGGCTTCCTCATCAGCTCAGTGCTCTCCCTCCTCGCCAGGACCTCAGCTGTCCCCA
GGCCTCCTCTTTCTTTATTATCTGTGGTTCTGCTTCCTCAC[redacted]GTCACTGAAGGAGCATTCTGAGCCAGGGCA
CAGTCACTTCCTAGTGAGCTACAGAGGCTGAGAGAAAAATGCTCTGTGAGACCCAATGGGAAGCTCCCTGCAGTGCA
AGGTCTGGGTGGCAGGGAGCGCTAGGGCCTCGCCCAGCACAGGCTGCAGCCCTGGAGCAGGTGCAAGGGAGGCTGGG
GAGGGGTTCCTCCCAGGGTCTGATGTCTTCCTTTTCTCGGACAAACATGCTTTAATAAGTTAAACAAGACTTTAGTA
AAGACTATTGATGTGTCTTTGTGTCTTTCAGTATACAGTTCTATTTGTAGGATTTATCTAACCTAACAAGTCAATGA
GAATCACATGTAAAAGGAGAAATTTCTAGGATTTTCAGATATCTTAATAGGTAGGAGATGGAGAAAAGGGATGGTTT
TATTAATTCAGTGCTTGCCAATCTTAACAGAGACAGTAGTAAGACATGCAGAAAGCAAAGCCCAGAAAAGTATGAAG
GTGTCAAAGTGCCATTTAAGTATGGGTTCACTTGGAGGACCATGTTCTGCGGGAACTTGTTTTCAGCAGACAATCTA
TTTTAGCAGAGTTCTGGGCATACAAGGGGACACACATCATTAAACAAGGATTGGGACAGGGACTTCAGCGTCCCACT
GTTGCATGGCCCATAAATTATGTGTGTTCTCTTTCTCATCTTGGATCAAGTCTAGAGCTATGAAATAGTATCCCTCA
TGAATATGCAAATAACCTGAGATTTACTGAAGTAAATACAGACCTGTCCTGTGCCCTGAGAGCATCACCCAGCAACC
ACATCTGTCCTCTAGAGAATCCCCTGAGAGCTCCGTTCCTCACC[redacted]

Fig. 7 (cont.)

[redacted]CACAGTGTGAAAACCCACATCCTGAGGGTGTCAGAAACCCAAGGGAGGAGGCAGCTG
VH 1-2
TGCTGGGGCTGAGAAATGAAAGGGATTATTATTTTTAATGTTGTTTACAGTATGTCATTAATAAATTGAAAAAAAGT
AACAATAGAAGTATATACTCTAATTATATGGGAACTTTGTTTTTTCAGTTTTTTCATTTTTTTTTTTTTTTTTGGTT
TGTTTGTGACAGAGTCTCACTCTGCCACCCAGGCTGGAGTGTAACGGCACAAT[redacted]GAGCATGTGCACATTTCA
TTAAACCCACTGTGTATGCAGCCCCTCCCAAGTGCTGGCAGGCCACTGTACATGTGGGCAGCCCACTCCAAGGGAAG
AATCAAGGGAGAAGAAATACAAACCCCAGAACCATGTCAATGTATAAAACCCCAAGTCAAGGGCCGGACAGAGCACT
TAGATCTCTCAAGTCGCCCACTTAGCCCTCTTCCAAGTGTACTTTACTTCCTTTAGTTCCCACTTTAAAACTTTAAT
AAACATTTACTCCTGCTCTAAAACTTGCTTGGGTCTCTCACTCTTCTGTATGCCCCTTGGCCAAATTCTTTCCTCCA
AGGAGGCGAGAATCAAGTTGCTGCAGACCTGTATGGATTCGCTCCTGCTAACAGATAGCTGGATGGGTGGACAGATG
CATGAATTAGTGGATGGACGTTTGGATGTGTGGGTGGGTGGGTGGATTGTGGGATGGCTGGATGAATGCATGGCTGG
ATGGGTGGACAGATGCATGAATTAGTGGATGGATGTTTGGATGTGTGAGTGGGTGGGTGGATTGTGGGATGGCTGGA
TGAATGCATGGCTGGATGGGTGGACAGATGCATGAATTCGTGGATGGACGTTTGGATGTGTGGGTGGGTGGGTGGAT
TGTGGGATGGCTGGATGAATGCATGGCTGGATGGGTGGACAGATGCATGAATTCGTGGATGGACGTTTGGATGTGTG
GGTGGGTGGGTGGATTGTGGGATGGCTGGATGAATGCATGGCTGGATGGGTGGACAGATGCATGAATTCGTGGATGG
ACGTTTGGATGTGTGGGTGGGTGGGTGGATTGTGGGATGGCTGGATGAATGCATGGCTGGGTGGGTGGATGGATGCA
TGGATAAGTGGTGGACGGATGGACGGGTGAGTGGATGGGTGGATGTGTGTGTGGATGGGTGGATAGGAAAGCCCTCT
AATTGATTACAGGGCTCAGTGTGTGCTTCAACATCATGATGGCATCATCACATTGGTCCCTGTATGAAGCAGTGGGG
GAGGAGAGTGTACCAGGGGAGCAGGAATGACTCTTCTCCAGAATCGACCTCTCCCACCCTGCAGCCTGGGCTGTGCA
GGCCACATTGGAGAAGGTGCGGTCGACTACTCCTAAATGTTGTTGTGTCCAATGGCTTTTTGACGTTGATGTAGGAA
TGAGCCTACATCTCCACCATAGATGGAACTGTTTGGGTCCCCAAAGCAGAAAGCCTCTTCTGTTGCAGGTGCTGAAG
TTTCCATCTTCTTCTGCTTATACGGAAGCTCACGCATCCCTTGGATGGCAGGCGTCAGGTTCCTGTGCGCACTGAGT
TCCCCCCTTACATGCTTTGGACAGAAGTGTGAGACACACAAGATTGCTGCAGGAAGTCCACCTGTGGGGATGCTGCG
ACTTCTCCAGCAAGAACACGAGTCTGCTCATTGACCATCACCACACATAACAAATTAAGTGTCCCTTTTTTGATAAC
ACGTCATTGTTTCACAGAGTATTCTTTTAAAGTGTATAAGTTGACTGCAGTTATTATTTTTTACTTCTGTTACTAAT
TTACTCATAATTAGGCACAATTTACACTTAAGAAATTTCTTAATAGTTTTTTCCTCCTTAAGGTGAACTACAGTCAG
ATAACATACTTATCAATTGTCTCTAGCTCTTGTCAGAAAAGCATATAGATGTGTGTGTGCGTGTGTCTTGGCCTTTC
CAATGATGAATTAAGATGTGCATTGAGAAGGCATTCACTTTATTTGACGTTAAGGAAGTACCAAGAAGACGCTCTCC
ACAGACCCTGGGAAAGCCAGCAGCTGCACCCCGAGGCTGTGCCAGGCAGGGAACAAGGAGGCAGCACCACCTGCTGG
GCAGGGAAAATGTCCTCCCAGTCCCTGCCGCTTCTCTGCAGAGGCACAAAGAGCTGCCCCTTCTCCTGGGCCTTCTC
CTGGGCTGATGAGATTGCTCCCCGATATGCCAAATCAGGGTTGTGCATCTGAGGCTCTGTCTAGACTCTCAGCTCCT
TCCTACTCCTGCAAAGTGAAGAAAACAATGCCAAGGGGTCCTGGAGGCGTCTCTACCCCTGGAGAGTTTTGACTCTC
TTCAATAGTCTCCACTACCCTGCCCTCACTCCATGTCCTCCGTTTCTCCCTAAAGCGGTGCCCAGTCTGATTGCACT
GTGGCAGGGATAACGAGGGGCCAGGACATCAGGGGAGAGAAGTTTCTACCTGAGTCACAGCAGCGGCTGCCCTGCAG
ACTCCTGAAGACACAAGACACATTTCCATCCCAGAGACCCAGCGAAATGCAACCTCAGGCTAGAGACAGCCAGTTAT
TTTTTCTTGTTCTGTCCTGGAGAGGCCACTGAGAAAGTCGAGCCCCTTGTTGAGGAAAACATGAGATCTCTGTGTGT
CGTCCTCTGCCTGATGGCTGTACCTCCATGTGAGTGTCTCAGAGATTTCAGAACGGGGGCTGTGGGCTGTGGTGTCC
GCTTGTGACTCATCTCTTTGCTTCTTGTCCCTGAGTGTCCTGCATCAGATGCAGCTACTGGAGTCATGCCCAGGGCT
GGTGAGGTCCTCACAGACCTCTGGGCCTGGACCCAGCAGCCCTCTGGGAAGGCGCTGGGGCACCTCAGCTCCAGGGG
CAGCACACACTTCAGCCCAGCCTTTCTGGGCCAACTCTCCATCTGTAGAGACACATCCAAGGCCCAGTTATCCCTGC
AGCTGAGCTCCGTGATGGCCAAGGGCAGGGCCGCACATTCCCGTGGGAGACAGAATGGGGACCTCAGCGTGAGCCCA
GACACAAACCTCCCTGCAGGGAAGCACAAGACCACCAGGCGGCGCTCCAGACCACACAGCGGCCCCAGAAGCAGGTT
TTAGGGGGCGGGGCAGACGTGTCCGCGTTGAGTCAGGTCACTGGTTTTACTTTCCCTGAACAAACGGCCTCTGCCAA
GGACTCACTGCACCTCTCACCTTCACAGTTGTTTTTTTTTTTTTTTTAATCACCCTGTAGGGTTTTGCTAGCTAATT
TAGATATTGAGGAGTGCTTCATACTTCCTTGGGCCTCTGCTTGCAGAAACATAGCAATTGTAAGGAGGCACGTGGGA
AAGCCCCGGCTCGGTGACCCGGGGGATGCTGCTGTAGCCCTGGCAAGAGGGCGTCGGGCCGCAGTAACAAAGGTGCA
GACGGCTCTCAGCCTGCGCCCGCGGAGTACAACACATAAGGGCTGTAACCTAACGAAAAAAGAATCGCAGTGCAACT
GTCCTGCATTTGAGTTTGTGATCAGTTTTGCCCTTTGTCTTTAACAGGTTCTAACATAAAATTTTGAATGCTGGTTC
AAGCCCTGTGGGTAAAATGCACTTACCCACATTCCTTAAACAAATAGAACACTGAGGTGGAAATGTTTTGAAAAAGT
AGTTTTCAGACATTTGGAAACAAGCATCACAGGATCATAACCCCTGAGAAAAGAAAAACAAATGAACGAATCCTGCT

Fig. 7 (cont.)

ATTGCCTGAAAGCAGCTGCCAGGACACACGGAAAGGCTTAGTGAGCTGAGCGGACAGAGAGCAGAGTTCAAGGCAGC
AGCAGCCCGAGGGGAGGAGCACCGGGGAGCAGGCTGCTGTGCAGCCAGGATGGGCCGGGGTGGGGCGGGGGGAGAAC
AGCTGGAGACTTGCCGCAGGGAGGGGGATCCCTCAGGTTTGGGGCTGAGAACTGACTTATGCCTGACTTATGCCTGC
ATGAAAAGAAACTACTCGATATCAGGGGGAAATCACCAGAAACCTGTGGACCCAAAACTACACAGAGCCTACACAAG
GAAAGCATTGTTTGTGTTCTCCCAGCCAGGGTGGAAAGACCTTGAGATATGTAAAGCTTCAAGCAATCTTCCGAAGT
AATCTCGTGAGTAGTGGTGCCACATTAATTCAGGACTAAAGACTGCTCTGAACTGAACCTAAGAAATGCTTCAAGTG
TAGCCTGGAGCCCGGGTGCAGTGGCTCACACCTGTAATCCCAGCACTGTGGGAGGCCGAGGCAGGCGGATCACTTGA
GGTCAGGACTTTGAGACCAGCCTGGCCAACATGGCAAAACCTGTCTCTACTAAAAACACAAAAATTAGCTGGGCATG
GTGGCAGATGCCTGTAATCACCTCCCACCTGGACCCTTCCTTGATACATCAGAATTACAACTAGAGATGAGATTGGG
GTGGGGACACAGAGCCAGACCGTATCACATAGGAACCTAAAAGGATAATAAAGTAGGAAAACTTCCCACATCAGTAA
CCCTTTATCCGATAGTAATCCCAATCTGCAAAGTAAAACTGTGTGATTTTACTAAGATAACGGAATCTTCTCTACAG
AAGGACTTTCCAGTGCAAAAGCTCCCCACCCTCACCATGAAATGCACGTGACCATTTCCAATTTGTGTAAAGTCCTC
AGTTAGTACTGAGACTTCGGAAGGTTAGAAATCCCTTTGCTCATGCTGCATGGTCCGGATGAGATGTAAGAATCATT
AGCTAATAGACATGCAACAGCTTTTGTGCGAAAGATGTTATGAGACATTTAAGGTATTTGCTTGTGCTTACTAAGCA
TTCATTGTATCATTGGAGCACATGTGCTTTTATACCCTGGAGAAATTCCAGTAATTGAATTGCTGGGTTGAATGGGA
TTTTGATTTGGATTAAATTTAAACTATAGATTTTATTTAGGGAAAACTGGCATCTTAATTATGTTATTGGGGGGCCC
TTGCTCCCAGAGCTCCCAAGATGGTGGCAGGCCGCTTCCAAAATGACCGCAGGCCACTTCCAAGATGGTGGCAAGCC
TCATGTTCTCTGACCTGGGGTTCTTGGCCTCACGGATTCCAAGGAATGGAAGCTTGGGCCATGCAGTGAGTGTTATA
GCTCTATTAGAAGCCGTGGGTCACGGAAGAGAACCGTGGAACCCAGTGACTAGTGTTCAGCTCGATTAGGACGAACC
CAGGCACTTAGCCGTGCAGGAACAATGGCGAGCATTTGGCCCGATCGAGAGTGGCAATGGGCGCCTCGCCGGATCAG
GAGCACAGCGGATACCCTGATGGATCCGGAGGGATGGAAGCCAGCGGTGGGTCTCCCACGGGGGCAAACAGCAGTGG
TGGACGGTGAGCGAAAGCGAAGCTCGAGCCGTAACAAACATGGACCAGAAGAGTGCAGTTGCAAGATTTAGTAGAGT
GAAGACAGAGCTCCCATACAAAGGGAGGGGACCCAAAGAGGGTAGCTGTTACCGGCTCGAATGCCTGGGTTTATATC
CCGATCATTGTCCCTCCCGCTGTGCTCTCAGGTGATAGATGATTGGCTATTTCTTTACCTCCTGCTTTTGCCTAATT
AGCATTTTAGTGAACTCTCTTTACTATCTGATTGGTCGGGTGTGAGCTGAGTTGCAAGCCCCGTGTTTAAAGGTGGA
AGTGGTCACCTTCCCAGCTGGGCTTAGGGATTCTTAGTCGGCCTAGGAAATCCAGCTAGTCCTGTCTCTCAATTACA
CTGAGTTTTCCAATCCATGCATCCAATATGTGGTGTATCTCTTCATATGTTCATAGCCTCTGAGCAATGTTTTACAA
TTTTCTGTGTAAAGAACTCCACATCGTTTTATGTTTCTTCTAAGGTATATCCTGATTGCTTTTTATGTCTTCACAAG
TTTTTCCCTTTCAAAATTAATTTTCCAATTGTTTGGTGCTAATATGCTCAAATGTCCTTGATTTTCTTAGTTTGAAC
AGTCCGTTTTCGTTTTGGGGATTTATTTTTTTTTCAGATTCTTTAAGATTTTCTATGTCTATAACCATATAATCTCT
GAACAGAGACAGTTTTGCTTTTCCCTTTCAACTTGAGGTAGGTTTTCTGGGTAGTTCAGGACGCGCAGGCACTGGGT
GGGTGGTGTTAGCAGCTGCACGATGCCTTGGAGAGGACACTCTCGGGGGACTGTGGCCGCTGCTCAGCTGTGACTGT
TCTTATAGCACCAGCAGCTGCGGCCACCATTCTTATCCAATTTCCAAAGCCACACCACAGGCCCTCTCAAGAACGAG
GCGTGGAGGCTATGCCCTCTCCTGGACACATCATCATTCCCAAGCCCCACGATGTGGGCCCCATGGGACGCACACCT
TTGTCTGTCCAGACCTCAGCCCCACCTCCTCATCCTGCACCAGAACTCTTCAGAGCCCAGTGCATGAAATGGGCTAC
CAAGGAAATGAGGGTAGGTTCCTGAGAGGAAACTGGCCCTGCATTTGGGAGCTAAGAGTCTGCTAATTCGCCTGGCA
GCCCTGTGCAGCCCTCCGTGGCTACAGTCCACCCCGTGCCCATCAGTGCCTCCTTCCTGTGCAAGCCTGGACCTCGC
CCTGGGCTCAGGATGGGCTGTAGACCGAGAATGCAGGCGGGAAAGTCGTTGTCTATCGGGGCCATAGTCAGGTTCTA
CAGTGAGTCAGGGAAAGACCTGTGGAGGTGTGGATGAGGACAATGGGTCCACCATCAACAGGAGGACACGGGTTCGA
CCCCTTGCAGAGGCACAGTCCCACATCACTGGGAGGCAGCCACACTCACTGCCTCGCCCTCTCCTCACACAGTGCAG
TTTCCACGTTCACAGCCCCAGCCAGTCACCAGGAATGCCCTGGGGGCGGCCTTTCCCCAGTGCACCCCGAGCCCTCC
CTTGGCTGTGCGGTGAGCTCCATGCCCAGGAGATATCCACCCATAGTCCTCCGGAAAGCAGCTGACCTGCCATGCCC
TGGAACCACAAATCCCCACAGATCAGCCAGCCTGCAGTGGGCCTTGGATGTGGTGAGGAGTGGTGGCACCCCCGTTC
CCACCCCACAGATGCAACGCCTGTGGGTGACGCATGTGAGTACTGAGGAGTAGAGGGTAGAACTGTAGGCCCCGAGA
ACCACAGAAACTCGGGTGTTACACTCTGGGGCCATGTAAGGAGAAAGTGTCACTGGACAGAAACAGGCCCCTCCTAG
ACACTGTGTGCGCCATAGTCACCTGTCATTAGCTCTCACTCTTGCAGATTCATGATTGAGGTGGTTAAAAAAAAAAA
AGCTCCTACTCACCCATCCAACCCCATCCTGGGGTGTTTCCACCACCCTTGGGGTTTGGGATGAGCTGCCCTTGCCC
ACTGTGCTCTGTGGACCTCCCTTTAGAAGCTCACAGCTCCCTGCACTCGGCTCCATCCTGCCCCACCACACAGAAGC
AAAACCCCTCTCCTTTCCACTGCAGGCTTTTCCTGGACCAGAATGCTGACCTGCTGCCCTTCACTCCCGAAGTGGTG
GGACTGCCTGGGGTGGTGTGGGTGTTGAGCCTTCTTACTCTAGGGACCTGGCACCTGGCCCCAGGGGCACAGGGATG
GTGCATCTGCCTAGGGATGCCTCCTCATGCCAGGGGGTGGGGGTTAGTACCATCGGCCCTCAGGATTTGTTGCATGA
ATGAGTGAATGGGTGAATAAATGAAGGGGATCTGATCTATGAATAAGGGTATATGGACTTTGGTTGATGTAGGACGC
CAAATGCTGGAATTTCGGAGTCATCACACCCAGGGGCCCTGCCTCTGAGCTCCTCTTTGCATCCAATCTGCTGAAGA
ACATGGCTCTAGGGAAACCCAGTTGTAGACCTGAGGGCCCCGGCTCTTCAATGAGCCATCTCCGTCCCGGGGCCTTA

Fig. 7 (cont.)

TATCAGCAAGTGACGCACACAGGCAAATGCCAGGGTGTGGTTTCCTGTTTAAATGTAGCCTCCCCCGCTGCAGAGCT
GCAGAGCCTGCTGAATTCTGGCTGACCAGGGCAGTCACCCGAGCTCCAGACA[redacted]CACAGTGAGGGGAAGTCAGTGTGAGCCCAGACACAAACC
VH 6-1
TCCCTGCAGGGATGCTCAGGACCCCAGAAGGCACCCAGCACTACCAGCGCAGGGCCCAGACCAGGAGCAGGTGTGGA
GTTAAGCAAAAATGGAACTTCTTGCTGTGTCTTAAACTGTTGTTTTTTTTTTTTTTTTTGGCTCAGCAACAGAGA
TCATAGAAAACCCTTTTTCATATTTTTGAAATCTGTTCTTAGTCTAATGGAGATTCTCTGATATGTGACAATGTTTT
TCTCTTGCTGTTTTTGGAATTCTTTGTCTTTGACTTTTGACAACTTGACTTTTGACAGTGTGCCTCAAAGAAGTTCT
ATTTTGGGTTCTGTGAACCTCCTGGATCTGGGAAGTTTTCAGCTATGATTTCATTAAACGTGTTTTCTACACCATTT
CCCTACTCTTTTGGAATACCCATAATGCAAATATTTGTTCACTTAATTGTGTCCCATAAATGCTGGGGATTTTCTTC
ATTCCTTTTTACTCTTTTTTTCTTTTTATTCATCTGCCTGAATTATTTCAAAAGATCTGTCTTCAACTTCAGAAACT
CTTTTGCTTGGCCTAGTCTAATCTTGAAGGTCTCAATTGTACTTTTAATTTCATTCATTGAATTCTTCAACTCTGGA
ATTTCTGTTGGTTCTTTTTTATGATACTTATCTCTTTGTTGAATTCCTCATTCAAATGATAAATTGTTTTCCTGATT
TCACTGAATTTTCTATCTGTACACTATTGTATCTCCCTGAGTTTCTTAGAGATTATCCTTTTGAATTATTTTTCTGA
CATTCTGTATATTTCCTTATGATTGGGGTCTGCTACTGGAGAATGACTGTTGTCTTTTTCAGGTGCCGTGTTTCCTG
GCCTTTTCATGTTTTATGTGTTCCTACGTTGATTTCTACACATCTGGCGGACCAGTCATCCCTTGCAATTTAATGGA
GTAGGTTTTGCAGGAAAAGACTTCCTAGTACAGACGGGTCTCAGGGTGTCAGTGTGGCGGGGCGTGCTGGCTTTAGT
TCTAGGTTGACGCAGTAGCGTAGTCTCCATGTCGTTTCTTCAGCTGCCGTCCACATTGGTGACGTTTGCGAGTGTCT
CAGTGGCCTGGGCTGAGAGGTTTGTGGCAGTGGAAGTGCAACGTTGCTAGAGGTGGACTCACCAGGCTGTTTCTGAG
GTCGAGGCACATGCATGCACATGGTGGATTGACCAACTTGGTGCCAGGCTCACTAGGGTTGGGGACATGGGGCTGTT
TCTCAGGCCCAGGATGCAAACACAAGTCTCTTTGGCTGGCCTGGGGGTGTGGCTTCTGAGGGCAATCCACAGGGCTG
TTTCTCAGGTTCAGGACACAAGTGCATGGCCGCTCAACTGGCCTGGGCATGTGTCTCCCAGGGCCACCCCATGGGCT
CTCTCTCAGACCCAGGACATGGCCACATGGCTTCCTCAGCTGGCCTGGGTGTGTGTCTGCTTGGGGCCTGCAGGGGC
ACAGGGTTATTTCTCAGGCCGGGGTCATGGGCGCACAGCTGCTTGCTGGCTTATAGGAGTGCCTGCCAGGGGTGGCC
CATGATGCTGTTTCTCAGGCC[redacted]ACTGAATACATAAACAGGACACAGCATTTTGCTGCATAAAGCAAACACAG
CGTTACTTTTTTTTTTCTAAATGACATTTTTTATTAGATATTGTCTTTATTGACATTTCAAATGTTATCCCCTTTCC
TGGTTTACCCTCTGAAATCCCCTATCTCCTCCCCCTCCCCCTGCTCACCAATCCACCCACTCCCACTTCCAGGCCCT
GGCAATCCCCTATATTTGGGCATAGAGCCTTCACAGGACCAAGGTACTCTCCTTGCATTGATGACCAACTAGTCCAT
TCTCTGCTACAAATGCAGCTAGATCTATGAGTCCCACCATGTTTTCTTTTGTTGGTGGTTTCATGCCAGGGAGCTCT
TGGAGTACTGATTGGTTCATATTGTTGTTCTCCCTATGGGGTTACAAAACCCTTCAACTTCTTGGGTCCTTTCTCTG
GCTGCCTCATTGGGGACCTTGTGCGAAGTCCAATGGATGACTGTGAGCATCCACTTCTGTATTTGCCAGGCACTGGC
AGAGCCTCTCAGAAGACAGCTATATCAAGATCCTGGCAGCAAGCTCTTGTTGGTATCCACAAAAGTGTCTGGTGGTT
GTCTATGGGATGGATCCCCAAAGGGGCAGTCTCTGGATGGTCATTCCTTCAGTCTCTGTTCCACACTTTGTCTCTTT
AACTCCTTCCATGACTATTTTATTCCTCCCTCTAAGAAGGACCGAAGTATTCATACTTTGGTCTTCCTTCTTGAAAT
TCATGTGTTTTGTGAATTGTATCTTTGATATTCCGAACTTCTGGGCTAATATCCACTTATCAGTGAGTGAATATCAT
GTGTGTTCTTATGTGATTGAGTTACCTCACTCAGGATGATATCCTCCAGAACCATCCATTTGTCTAAGAATTTAATG
AATTCATTGTTTTTAATAGCTGAGGAGTACTCCATTGTGTAAATGTACCACATTTTCTGTACCCATTGTTCTCTTGA
GGGACATCTGGGTTCTTTAAAGCTTCTGGACATTAAATATAAGGCTGCTATGGAAATAGTGGAGAATGTGTCCTTAT
TACATGTTGGAGCATCTTCTGGGTATATGCCCAGGAGTGCTATTGCTGGATCCTCTGATAGTACTATGTCCAATTTT
CTGAGGAACTGCCAAACTGGTTTACAGAGTGGTTGTGCCAGCTTGCAATTCCACCAGCAATGGAGAAATGTTCCCCT
TCCTCCACATCCTCACCAACATCTGCTGTCACCTCAATTTGTTCTTAGTGATTCAGACAGGTGTGAGGTGGAATATC
AGGGTTGTTTGGCATTTCCCTGATGACTAGTGATATTGAAAAAAATTTTAAGTGTTTCTCAGCCATTCAGTATTCTT
CAGTTGAGAATTCACTGTTTAGCTCTGTACTCAGGTTTTTTTAATAGGGTTATTTGGTTTTCTGGAGTCTAACGTCT
TGAATTCTTTCTATATATTGGATATTAGCCCTCTGTCATATTTAGGATTGGTAAAGATCTTTCCCAATATGTTGGCT
GCCTTTTTGTGTCCTTTGCCTTACAGAACCTTTTTAATTTTATGAGGTCCCATTTGCTAATTCTTCATTTTACAGCA
AAAGCCATTGGTGTTCTGTTCAAAAATCTTTCCCCCTGAACCCTATCTTCGAGGATCTTCCCCACTTTCTCCTCTAT
AAGTTTCAGTGTCTCTATTATTGTGCTGAGGTCCTTGATCCACTTGAACTTGAGCATTGTTCAAGGAGATAAGAATG
GATCAATTCGAATTCTTCTACATGATAACAGCCAGTTGAGCCAGCACCATTTGTTGAAAATTCTCTTTTTTGCACTG
GATAGTTTTAGCACTTTTGTCAAAGATCAAGTGACTATGGCTCTTCAACTATGGCTCATTCCATTGATCAACTTGTC

Fig. 7 (cont.)

TGTCACTGTACAAGCACCATGCAATTTTTATTGCAATTGCTTAGTATTACACCTTGAGGTCAAGGATGGTCATTCCA
CCAGAGGTTCTTCTATGGTTGAGAAGAGTTTTTGCTATCCTAGGTTTTTGTTATTCCAGATGAATTTGCAAATGGCC
CTTTCTAACTCAGTGAAGAATTGAGGTGGAATTTTGATGGGAATTTTATTGAATCTGTAGATTGCATTCAACAAGAT
AGCCATTTATAATACATTAATCCTGCCAGTCCATGAGCATGGGAGATCTTTCCATCTTCCGAGATCTTCTTCGATTT
CTTTCTTCAGAGACTTGAAGTTTTTATCATACAGATCTTTCACTTCCTTAGTTAGAGTCACACCAAGGTATTTTATA
TTATTTGTGACTACTGTGAAGGTTGTTGTTTCCCTGATTTCTTCCTCAGCCTGTTCATCCTTTGTGTAGAGAAAGGC
CACTGATTTATTTGAGTTAATATTGTATCCAGCTAATTCACTGAAGTTGTTTATCAGGTTTAGGAGTTCTCTTGTGG
AATTTTTGGAATCACATGTGTATACTATTATATCATCTGCAATTAGTGATATTTTGACTTCTTCTTTCCCAAATTGT
ATCCCTTTGATCTCCTTTTGTTGTCTAATTGCCCACACTAGGACTCGGGCAGCCTTAGTGCCTAGTCCCTGATTTTA
GTGTGATTTGTTCAAGTTTCTCTCCACTTAGTCGGATGTTGGCTACTGATTTGCTGTATATTGCTTTTATTATGTTT
AGGTATGGGCCTTGAATTCCTGATCTTTCCAATACTTTTATCATGAATGGGTGTTGAATTTTGTCAAATGCTTTCTC
AACACCTACAAAGATGATCATGTAGATTTTGTCTTTCAGTTTGATTATATAGTGTATTATGTTGATGGATTTCCATA
TATTAAACCATCCCTGCATCCCTGGGATGAAGCCTACTTGGTCATGATAGACGATTGTTTTGATGTGTTCTTGGATT
CAGTTAGTGAGAAATATATTGAGTATTTTTACATCGATATTCATAAGGGAAATTGGTCTGAAGTTCTCTTTCTTTGT
TGGGTCTTTATGTGGTTTAGTTATCAGAGTCATCGTAGCTTCATAGAACAAATTGAGTAGAGTACCTTCTGTCTCTA
TTTTGTGGTATAGTTTGAGGAGATTTGGAAATATGTCTTCTTGGGACGTCTGAGAGAATTCTGCACTAAACCCATCT
GATCCTGGGCTTCTTTGGGGGGGGGGGACTATTAATGACTGCTTCTATTTCTTTAGGGGAAATGGGACTGTTTAGAT
TGTTAATATGATCCTGAATAGAAATCTGATCTGATCTAGAAAATTGTCCATTTTATTCAGGTTTTCCAGTTTTGTTG
AGTATTGCCTTTTGTGGTAGGGTCTGATGATGTTTTGGATTTCCTTAGGTTCTGTTGTTATGTCTTCTTTTCCATTT
CTCATTTTGTTAATTAGGATACTGTCCCTGTGTCCTCTAGTTACTCTGGCTAAGCGTTTATCTATCTTATTGATTTT
CTCAAAGAACCAGCTCCTGGTTTGGTTGATTCTTTGTATAGTTCTTTTTGTTTCCACTTGATTGATTTCTGCCCTAA
GTTTGATTGTTTCCTGCTGTCTACTCCTCTTGGGTGAATTTGCTTCCTTTTGTTCTAGAGCTTTTAGGTGTGCTGTC
AAGCTGATAGGGTATGCTCTCTCTAGTTTCTTTTTGGCGGCACTCATAGCTAGGAGTTTTCCTCTTAGCAGTGCTTT
CATTACGTCCTGTAAGTTTGGGTATGTTGTGGCTTCATTTGCATTAAATTCTAATAAGTCTTTAATCTCTTTCCTTC
TTTCTTCCTTGACCGAGTTATCATTGACTAGAGTGTTCATCAGCTTCCACATCAATGTTGGCTTTTAATTATTTATG
TTTTTATTGAGGATCAGCCTTTGTCGGTGGTGATCTTCTAGGATGCACGGGAAATTTTCAATATTTTTGTATCTATT
GAGGCCTGTTTTGTGACCAATTATACGGTCAATTTTGGAGAAAGTACCGTGAGGTACTGAGAAGATGGTATATCTTT
TTGTTTTAGGATAAAATGTTCTGTAGATATCTGTTAAATCCATTTGTTTCATAACTTCTGTTAGTTTCACTGTGTCT
CTGCTTAGTTTCTGATTCCAGAATCTGTCCAATGATAAGAGTAGGGTATTAAATTCTCCCACTACTATTGTGTGAGG
TACAATGTGTGGTTTGAGCTTTAAAAGAGTTTCCTTAATGAATGTGGATGGCCTTGCATTTGGAGCATAGTTATTCA
GAATTGAGAGTTCCTCTTGGAAGATTTTACCTTTGATGAGTATAAAATGCCCCTCCTTGTCTTTTTTGATACCTTTG
GGTTAGAAGTGGATTTTATTCGATATTAGAATGGCTAATCCATCTTGTTTCTTTGAGATGTTTGCTTGGAAAATTAT
TTTCCTGCCCTTTACTCGGTGGTAGTGTCTGTCTTAGTCCCTGAGGTGGGTTTCCTGTATACAGCAAAATGTTGGGT
CCTGGTTATGTAGCCAGTCTGTTAGTCTGTCTTTTTATCAGGTAATTGAGTCCATTGATATTAAGAGCTATTAAGGA
AAAGTAATTGGTGCTTCCTGTTATTTTTGTTGTTAGACTTGGGATTCTGTTCTTGTGGCTATCTTCTTTTAGGTTTG
TTGAAGGATTACTTTCTTGCTTTTTTTAGGGTGTAATTTCCCTCTTTGTGTTGGAGTTTTCTCTTTATTATCCTTTG
AAGGGCTGGATTCATGGAAAGATGTTGGGTGAATTTGGTTTTGTCATGGAATTCTTTGGTTTCTCCATCTATAATTG
AGAGTTTTGCTGGGTATAGTAGCCTAAGCTGGCATTTGTGCTCTCTTAGTGTCTATAACATCTGTCCAGGATCTTCT
GGCTTTCATAATCTCTGGTGAGAAGTCTGGTGTAATTCTGATAGGCCTGCCTTTATATGTTACTTGACCTTTTTCCC
TTACTGCTTTAAATATTCTATCTTCATTTAGTGCATTTTTTTTCTGATTTTTTATGTGTCAGGAGGAATTTCTTTTC
TGCTCCAGTCTATTCGGATTCTGTAGGCTACTTCTATGTTCATGGGCATCTCCTTCTTTAGGTTACGGACGTTTTCT
TCTATAATTTTGTTGAAGATATTTACTGGCCCTTTAAGTTGAAAATCTCCATTCTCATCTATACCTATTATCTTTAG
GTTTGGTCTTCTCATTGTGTCCTGGATTTCCTGGATGTTTTGAGTTAGGATCTTTTTTGCATTTTGCATTTTTTTTT
ATTGTTGTGCCCATGTTTTCTACGGAATCTTATGCACCTGAGACTCTCTCTTCTACCTCTTGTATTCTATTGGCTGA
TGCTTCCACCTATGTTTCTCGATTTCTTTCCTAGGATTTCTATCCCCAGAGTTGTCTCCCTTTGTGATTTCTTTATT
GTTTCTACTTCCATTTTTAGATTTTGAATGGTTCTGTTCGATTCCATCGCCTGTTGGGTTGTGTTTTTCTGTATTTC
TTTGAGGGATTTTTGTGCTTCATCTTTAAGGTCTTCTACCTGTTTAGGAGTGTTTTCCTATAATTCTTTGAGGGATT
TTTGTGTTTTCTCTTTAAGGGCTTCTAGCAATTTAGCAGTGTTCTCCTGTATTTCTTTAAGTGAGTTATTAATGCCC
TTCTTAAAATCCTCTACCAACATCATTAGATATGATTTTAAATCCGAATCTTGCTTTTCAGGTGTGTTGGGGTATCC
AGGACTCACTGTGGGGGGAGTACTGGGTTCTGATGATGAAAACTGGTCTTGGTTTTTATTAGTAAGATTCCTACTTT
TGCCTTCCACCATCTGATAATATCTGTTGTTAGATATTCTAGCTGTCTCTGGCTGGAGCTTGTTCCTCCTGTGATTC
TGTCAGCCTCTGTCAGCACTCCTGGGAGTACAACTCTTTTCTGAGTCCCAATGTTCAGAGCATTCTCTGCAGGCAAG
CTCTCCTCTGGCAGGTAAGGTGCCCAGAGCTCTTGAGCTCAGCTCCACCTCCTGACTGCAGATGAAGACCCAAAGGG
ACCCTGTCCAATAAGCTCTGTTGCTTCTGCCACCCACATGCTCTCCTGTGCGAACTGGTCTCTGAGAGACCCGGGAT

Fig. 7 (cont.)

ACAAGATGGTACTCTCACCTGAATCCCAGGGTCAAAGCCCTCCCTGGAGGCTGACTCTCCTCTTGTGGGAAGGTGCA
CAGAGGTCTGGAGCTCAGCTCTGCCTCCTGGCTGAAGATGAAGGCCCGAAGGGACCCTGTCCAAGAAGCTTTGTTGC
TTCTGGGACCCACATGCTCTCCTACATGGACTGGTCTCTGAGAGACCAGGGATTCAAGATGGTGCTCTCACCTGAGT
CCCAGGGTCAGAGCCCTCTCTGGAGGCCAACTCTCCTCAGTGATCCTAAGATCCTGGGTATGCTAGGGTGCCTATGG
CATGGAGAGTCCTCTGAGGAATGTGGGACTGTCTGCTGAGTTTCCACCCAAGGTGGTGCTGGGCTGGCTCCAGTCAG
AATGAACCCAGACTCTGGTTGGGCAGGTTTCCAGTCCTGTTGGCCCAAGCCCCTCTGGGTTGTTTTAGAACAGATGT
TGCTTTCCACTCACCAGTGATCCCAAGATCCTGGGCGTGCTAGGGTGCCTGCTATGTGGAGAGTCCACTGGGGACCT
TAGGAGCATACATCAAGTTCACACCCATGGTGGCAAGGAGCTGGTGCCTACCAGAACAAACCCCGGGCACTTTTACT
GACCCTTTAAGTTGAAAATCTTCATTCTCATCTATACCTATTATCCTTAGGTTTGGTCTTCTCATTGTGTCCTGGAT
TTCCTGGATGTTTTGACTTAAGATCTTTTTGCATTTTGCATTTTTTTGATTGTTGTGTCCATGTTCTCTCTGGAATC
TTCTACACCTGAGATTCTCTCCTCTGTATCTTGTATTCTGTTGGTGATGCTTGCATCTATTGCTCCTGATCTCTTTC
CTAGGGTTTCTATCTCCAGAGTTTTCTCCCTTTGTGATTTCTTTATTATTTCTACTTCCATTTTTAGATCCTAGATG
ATTTTGTTAAATTCCTTCACCTGTTTGGTTGTGTGTTCCTGTAATTCTTTAAGGGATTTTTGTATTTCCTCTTTAAG
GGCTTCTACCTGTTTAGCTGTGTTCTACTGTATTTCTTTAAAGGACTTATGAATGTCCTTCTTAAAAACCTCTACCA
GCATCATGAGATGTGATCTTAAATGTCAATCTTCCCTTTCTGGTGTGTTGGGGTATCCAGGACTTGCTGTGGTTGGA
GTTCTGGGTTCTGGTAAACCTGCCTTAGAGGGTCACCACAGAGTAATGATAGCACTACTTTTAAACAGGGGAAGATG
ATGAAATAATTGCTGTGGGAAAATGCAAGGAAGGCTCCAACACATGTAGGCATCTATGAAGGTCTCAAATCTTCAAA
ATCCAAAACCACCAAGAAAGAAAGAAAGAAAGAAAGAAAGAAAGAAAGAAAGAAAGAAAGAAAGAAAGAAAGAAAGA
AAGAAAGAAAGGAAGGAAGGAAGGAAGGAAGGAAGGAAGGAAGGAAGGAAGGAAGGAAGGAAGGAAGGAAGGAAGGA
AGGAAGATTCTAAAAGTAGTCACCTGCACCAGGTGCCTGGGGAGTCACTCAGCAGCCCTAGACTGAGAAAGCTTGAA
GAAAGTAGAAATAGAGAAAGTGTACAGCCAGTATCCTCTAGCTACTCACATCCAAACAGGGCCTCCTGACTGCTCTG
AGCCTGTCCTAAGAACAGCAATGATGCCACAGAAATTTTTAGAGTGAACCCTGAAGGAACTTGAGGCCGATATGAGA
AAGCCAGTCCCAGAGGAAAGGAAAACCCGTAGAGAGAAAACAGGTGAGTTAGTGCATTAAAGGGGCTGAGCAGGCAA
CGCGCCGTCGACCGGAGGAGTTTCTTCCCTGTGCGGAGTCCACGGGCCTCCTGTGAGTGTGTGCATGGGCACAAGTG
TGTGTGTGGCTCTGCTGTGTGTCTGTACACACATATGTTTTGGGTTTTTTTGTGTCTCAGACCACAGAGTCTGCCCC
TCCCACCAAAGCCCAGGCAGAAGGATGAACCCACGCCCCTGGGGCCCAGGCCTCAGCAGCCTCTGCGGGATCATTGT
TCCCAGTTGTCACTTGCCTTTGCCACAGCCCTATTTCTCCACAATTCCTTAAAGTCCTCAACATGCATTTAAGGCAC
AAAGGTGAAACTGCCCAGAAACATCTGACTCCGCCGTGGAACCCAGGAGCAAGCTGGGTTAGCTAAGGAGCGGGGCC
GTTGGCAGAGGCTGGGGATCCAGGCTGAACTTTGGAGGAGGCATGTCCCAGCATGGGCTCCTGACTATGTCCTCCTG
GGACAAACCCAAACCCACTCTTTGAATATGGGAGGGACTTTGCTGGCCCCGGCCCTGACCGCAGCACTTGGAAACTG
AGGAGTGGTCGCCTCCTCCGTGTCACAGCTGCCCGTTCACCATCATAGAAGCAACTCTGTCACCTCCATGGCCCCT
CTGTGGCTGCTGCCTGGGTCCAAGCTGAGCCCAGCTGCCCAGGCCCAGAAGGAAAGCCCAGGCCAGGTGCCCAGCAC
AGAGGCAGTCACATACCCCGGGGAGAGCCACAGCAAGCAGCCAATATTGCCCAGGAGAGGAGTAGCTGACAAGGCAG
AACGTGAGCTGCCATCGGCTCGAGAGGCTTTGCTGGTCCTCCTGGGGCTCTGGACATGACCAGGAGGAGCGAGGGAA
GAAGTCGCATGGTGGTCCCATCCTGGGTGGGGCCTGATGGCAGCTGGCCACCCGTCCCAGAGTGGCAGCCAGATGCC
AGCGCCATTCCCACAGTCACATCATTGGTCACAGAATGCAGGACATAGAGTGTCTTCTTTCCATCACAGTGCTGTCC
AGACCCATAGCCTAGGGTAGACCTGGAAGATTCAATGTCCACACCCGGGGCTGGAGCGTAGCCATGAGCCACGCCCC
CTGCCCGTGCATGGAAAGCCAGCCCAAGCTCTGCTCCATCCCTAGCCAAAGTCAGTGTCCTTTCCCCTTCTCCCAAG
TGAGCTCTAGCCACCTGCCTACCCTGCCATCTGAGGATGACAGCCTTCATTCCATTGGAACCTGGCTCTGCCACCAG
CAGGCTTGCAGTCCTGGGCAGACTCCGTCACCTCTCTATGCCTCAGCCTTTCCATCTGCACAGGAGGAAGATGATGA
TGGTGGTGATGATGATGGCGATGGTTTCCTTTTGCATCTGAGGCAAGGACTAATTGAGATGATACACATCAGGCACT
GGGTATGGTGCTGGTCCTTCCTGAGCACTCAATCTATGTGAGCTGTCCTTGTGAAATGGGTGTCACCACATTTCCCC
ACGCAGAACATCCTTTGTCTGCCATACTTGAAACGTCTGCCCCAATACTAACAGCTCCTCATGGAAGATGTGCCCAC
CCACCCACCCTCATACTCCCAAAGGTGCCCGTGCTTTATCAAGCCAAAGTCCAGCCAGGAACTTTACAGCAGCATCC
CTTTCCCTCTCCAAGCACCAAGGAGCAAGGCAAAGCACTACATCTTCCATCTGGAGGCAATGCCACCCTCTTCTCCC
ATTTTCACTGCCATCCCTAAGAGGCAGTGCTTCCCCAAAAGGTTCCATAGCAGCCTGCCTACAGCAACTCTGTTCAC
ACGAGTTTCAGCATCCTTGCAGTGGCTCCCCTGCCATGCTGTGGCTCTTCATTCACCCTCTTCTCCTGCTCCCCGTG
ACAGGCATAGATTCTGAGTGATCTGGATACATTGCTTTGTTTAATAACATTACAGCTTCTGTGCTGAAAAAGATACA
GCAGATAGAGAAGGCAATTGTTGAACACAAAATAGTGACAGCAGAGATGACGGCAAGTTGGCATTTTTCTTTTCTAG
CAATAAAACTTAAAGCTGACTCAAGGAGAAATGGAAATCATAATTGGAACAGTAATCCTCAAGAAAGCATTAAGATT
ATTAAATAATTGCCCTCACAGATGACTTCAGGCCAAGATGGCTTTATGGGTGAAGTTTAGACTTTCACAAAACTAAT
CAGTTCCCATAAGAACTGCTCCAGGATTTGGAGGAACATGGGAAAGTCTATTAAAGGGATCACAATTCACAGTCCCC
AGAGTAAAACATGGGCTAACTTGCATTTTGGCAAAGAGCCAAATGTTATAAATGACATCCTAGAAGGCCAAATTCTG
TCCATCTCGTTGAACAAGGACTTACACCAGGAATTTAGAACTATTTATAGCTCATCCCACCACTCAGGCCAATGATG

Fig. 7 (cont.)

ACCCATGATCATCTCACCAGAAATGGAAAGACTCAGATGATTAATAGAGTCTCAATTTCTCTGAGACATCTAAGAGC
CCAGCCCAAGCCCAGACCCAGGAGGGCACCCAGGCCTGGACAGAGAACACTGATATCACACCAGCCCTCCAGAGGGA
AGCAGAGACTCCTTCAAGCTCTGGAAACACAGGCCCAGACAGCTGCCCAAAGTTGGGCAGGCTTCACTGCAAACCCA
AATCATGAAGCTAGGTAACACCTTTACAGATTCTTTACATTTAAAAATCATCAAAACAAGAGTAAATAATAAACTCA
AATAATATTAATCTAATATGTAAAGGTCTTGTACCATTATTATGCAAACAACATACATAAGCTAATAAGAAAAAGAA
CAAATCCCTTAAGAAATCAGCAAAAAGGATATAACACAATTTCTAAAAGAAAACAAATGGCTAGCACACATAAGGAA
AACACTTTGTGAACAGACATTCTTCAGAACATTATTTATAATTATAAAATAGTTGAAAGCAAGATAGTGCCTGAAGA
AATTATGGTGCATACATTAGTGGGACTATTCTGCAAACATTCCCAATTATACTTGTCACATATCTGTGATAACGTGA
CAGCCAGCATTCATGGGGTGACCTCATTTGGTAAAAGGGTGCAAAGCTCAACACGCATTGTGAGATGACTGTGGTGT
AAAATTAGTGGGATTATTCCGCAAACATTCCCAATTATACTTACCGCATATCTGTGATAACATGACAGCATTCATGG
GGTGACCTCATTTGGTAAAAGGGTGCAAAGCTCAACACGCATTGTGAGATGACTGGTGTAAATACAAAGACCAAACT
GTGAAAAGGAGTCCATCAATTAATCGATGCTTACCTTCAGTTTTGGGCTAATTTTTAAAGTATGCTATAAGCATATG
CTCCTGTTATAACAGAATGGAGGGATTATGAGAGATGATGCAGGTGTGTCCTGGGCCTCCCCTGGCCCACTGGGCCC
TAGAGATGCCTTCCCAGGCATCGCTGTCAGGGCTTCCCTCAGAGGGAGTCCTGTATTGACCTCACCACCAAGGTCTG
GAGCAGGGGATCCTTAGATATTGGTTGGGGTTATCTCACCTTAGGTCTGAATATGGGGTTGTCTTAGACTGTTTTGT
GCTGTTAGAATAGAATACCCAAGACTGGGAAATTTATACTGAACGGAAATTTATTTCTCACAGTTCTAGAGGCTGTG
AAGTCCAAGAGCACAGGTGCCAGAGCAAGTCCAAGAGCAAGGGAAAGTCCAAAGCAAGTCCAGGAGCATCTGGCGAG
GACCTTCTTGCTGTGTCATCACATGGCGGAAGGCAAGAAAGAGAGCAAGAGGGGGCCGAACTCACCCTTTTATAACA
GCACCAATCCCACCCATGAGGTGGGGACCTTATGACCTAATCACTCTTCATACTGTTACAATGGCAATGAAATTTCA
ACATGAGTTTTGGAGGAGAGAAGCATTCAAACCACAGCAAGGGTGCTCCTACCTCCTCTCTCAGGGCATCTGCAGAA
AGAGCTGCAACTGCACGTCCTTCCTCCGTCCATCCTCCATCCCTTCCCAATGTCCGTGCATATCCTGTGACCCAGGA
GGTCTGGCATAGGGGGTGCTCCTGCCTTAGGTCTGAGGCCCTGTCTGAAGAGGGGTAGGTGAGGAGGCCATCTGATG
GTCTGGGCCAAGACAGTCACAGGACGCATCATTTATCATCAAGGAGGCTGAGGGTTGAGTCTCCAGGTCCAGGGAAC
TCCCCACAAAGTGGGAACCCTGCCCAGCTCCACACAGCCTCTGCTGGGGGACCCTGCTCTGGTGCAGAGCCTGGGGA
CAGGTCTTGAGCTCAGCCAGAGTCTGCCTCCCTGTCATTTAGGAACTAAACCAAGCGGCAGGATGCTGGAGCCCAGC
CCCCATCTGACCTTACAGGGCCAAGGCTGGGGCCCTGGGTTCCCCTCAAGGCACAGCAGGACTGGAGCCCCAGGCAG
TGCAGGAGTGGCCAAAGCTGGGGCTTCCTCCAGAGCCCCCAAGCATCATGGCACCAAGAAGGGTAGGACCCTGGCCT
GAGGAATTGGCACCAAAGCCCCAGAAACTACCCTGGACACCATGGAGAGAGGCTTGGAGGGGAAGCACCAGGCACTG
CCTCCCCTTCTGATCCCACCTGAGGTGGCTGCCAAGCCCAGAGAGCCGCTCTGATGTCCCCCAGCCCTGCAGCCCAG
GGATACCTGTACTGTGCCCCTGGGGGACCCCTGGCCAGTCTGTGCAAAGAAGTCACCACCCTACACTCAGAGACAGT
GGGGGTCCTCGTCCCACATCCTCAGAGCATGGCCCGGCTGCTGCAGGGATGGTCTCCTTGTCCTCAGAGCATGGCCC
GGCTGCTGCAGGGATGGTCTCCTTGTCCTCAGAGCATGGCCCAGCTGCTGCAGGGATGGTCTCCTGGAGGCCCCCCA
GTGCTCTATTGTCAGGGCTCCCTCCACCCCCCCGCACCAAGAGAGAGCCAGACCCCAGCAAGGCTTCCAGTGGCTTC
AGGTCACACCCCTAGGCTGACCCCAGCCCCATTAACACCTGCCTGAGAAAGCTCCACGCACCAGAACTGACCGTCTG
CTCCAACTCTTGACCTCCCGTTCTCAGGGCGTCTGCTGAAAAGGCTGCAACTGCACATCCTTCCTCCGTCCGTTCCC
GATGTCCGTGTGTCTCCTGTGGCCAGGAAGGTCTTTCTCGGGACCTGAGAGCCGCTCCCTGAAGTGTCCCCATTGGG
AAGGATGGGGCCTGTGTCTCCAGGCTCTGGGAGGACAGAATCCTGACCTCAACAGTGGCCGGCACGGACACAACTGG
CCCCATCCCGGGGACGCTGACCAGCGCTGGGCAACTTTTCCCTTCCCCGACGACTGAGCCCCGAGCACCCTCCCTGC
TCCCCTACCACCTCCCTTTACAAGGCTGTGGCCTCTGCACAGATGATAATGGAGCTTGGCTCATTCCCCTAGAGTCG
GTAGGGAGTTAAGGACAAAACTCAGTTTCCTCCACCTGAACTCAAGTCTGCCTATGTTTACCTAATCACACCTGGTG
GACAGTTTGGACAAACTTGCACACTCAGAGACACAGACACTTCTAGAAATCATTATCTCCCTGCCCCGGGGACCCCA
CTCCAGCAGAAGTCTGCTAGGCACTGGCCTGGGCCCTCCTGCTGTCCTAGGAGGCTGCTGACCTCCTGCCTGGCTCC
TGTCCCCAGGTCCAGAGTCAGAGCAGACTCCAGGGACGCTGCAGGCTAGGAAGCCGCCCCCTCCAGGCCAGGGTCTA
GTGCAGGTGCCCAGGACAAGAAAGATTGTGAATGCAGGAATGACTGGGCCACACCCCTCCCGTGCACGCCCCCTCCT
GCCCTGCACCCCACAGCCCAGCCCCCCGTGCTGGATGCCCCCCCACAGCAGAGGTGCTGTTCTGTGATCCCCTGGGA
AAGACGCCCTCAACCTCCACCCTGTCCCACGGCCCAAGGAAGACAAGACACAGGCCCTCTCCTCACAGTCTCCCCAC
CTGGCTCCTGCTGGGACCCTCAAGGTGTGAACAGGGAGGATGGTTGTCTGGGTGGCCCCTAGGAGCCCAGATCTTCA
CTCCACAGACCCCAACCCAAGCACCCCCTTCTGCAGGGCCCAGCTCATCCCCCTCCTCCTCCCTCTGCTCTCCTCTC
GTCGCCTCTACGGGAAATCCGGGACTCAGCAGTAACCCTCAGGAAGCAGGGCCCAGGCGCCGTTTAATAGGAGGCTT
CCTCACAATGAAACTTTTAGAAAGCCTTGACTACAATGATGACCTTGGTGTGGCTGTGAACACTGTCAGCTCCCACA
GCTGCTGCAGCAAAAAATGTCCATAGACAGGGTGGGGGCCCGGGGTCGTCTGCTGTCCTGCTCAGCCCACAGCACGC
ATGGAGGATCTGAGGTGCCACACCTGACGCCCAGGCCAGAACATGCCTCCCTCCAGGGTGACCTGCCATGTCCTGCA
TTGCTGGAGGGACAGGGGCAGCCTATGAGGATCTGGGGCCAGGAGATGAATCCTATTAACCCAGAGGAAAACTAACA
GGACCCAAGCACCCTCCCCGTTGAAGCTGACCTGCCCAGAGGGGCCTGGGCCCACCCCACACACCGGGGCGGAATGT

Fig. 7 (cont.)

GTACAGGCCCCGGTCTCTGTGGGTGTTCCGCTAACTGGGGCTCCCAGTGCTCACCCCACAACTAAAGCGAGCCCCAG
CCTCCAGAGCCCCCGAAGGAGATGCCGCCCACAAGCCCAGCCCCCATCCAGGAGGCCCCAGAGCTCAGGGCGCCGGG
GCAGATTCTGAACAGCCCCGAGTCACGGTG[redacted]CACCGTGAGAAAAACTGTGT

D1-1

CCAAAACTGTCTCCTGGCCCCTGCTGGAGGCCGCGCCAGAGAGGGGAGCAGCCGCCCCGAACCTAGGTCCTGCTCAG
CTCACACGACCCCCAGCACCCAGAGCACAGTGGAGTCCCCACTGAATGGTGAGGATGGGGACCAGGGCTCCAGGGGG
TCATGGAAGGGGCTGGACCCCATCCTACTGCTATGGTCCCAGTGCTCCTGGCCAGAAACGACCCTACCACCGACAAG
AGTCCCTCAGGGAAACGGGGGTCACTGGCACCTCCCAGCATCAACCCCAGGCAGCACAGGCATAAACCCCACATCCA
GAGCCGACTCCAGGAGCAGAGACACCCCAGTACCCTGGGGACACCGACCCTGATGACTCCCCACTGGAATCCACCC
CAGAGTCCACCAGGACCAAAGACCCCGCCCCTGTCTCTGTCCCTCACTCAGGACCTGCTGCGGGGCGGGCCATGAGA
CCAGACTCGGGCTTAGGGAACACCACTGTGGCCCCAACCTCGACCAGGCCACAGGCCCTTCCTTCCTGCCCTGCGGC
AGCACAGACTTTGGGGTCTGTGCAGAGAGGAATCACAGAGGCCCCAGGCTGAGGTGGTGGGGGTGGAAGGCCCCCAG
GAGGTGGCCCACTTCCCTTCCTCCCAGCTGGAACCCACCATGACCTTCTTAAGATAGGGGTGTCATCCGAGGCAGGT
CCTCCATGGAGCTCCCTTCAGGCTCCTCCCTGGTCCTCACTAGGCCTCAGTCCCGGCTGTGGGAATGCAGCCACCAC
AGGCACACCAGGCAGCCCAGACCCAGCCAGCCTGCAGTGCCCAAGCCCACATTCTGGAGCAGAGCAGGCTGTGTCTG
GGAGAGTCTGGGCTCCCCACCGCCCCCCCGCACACCCCACCCACCCCTGTCCAGGCCCTATGCAGGAGGGTCAGAGC
CCCCCATGGGGTATGGACTTAGGGTCTCACTCACGCGGCTCCCCTCCTGGGTGAAGGGGTCTCATGCCCAGATCCCC
ACAGCAGAGCTGGTCAAAGGTGGAGGCAGTGGCCCCAGGGCCACCCTGACCTGGACCCTCAGGCTCCTCTAGCCCTG
GCTGCCCTGCTGTCCCTGGGAGGCCTGGACTCCACCAGACCACAGGTCCAGGGCACCGCCCATAGGTGCTGCCCACA
CTCAGTTCACAGGAAGAAGATAAGCTCCAGACCCCCAAGACTGGGACCTGCCTTCCTGCCACCGCTTGTAGCTCCAG
ACCTCCGTGCCTCCCCCGACCACTTACACACGGGCCAGGGAGCTGTTCCACAAAGATCAACCCCAAACCGGACCGC
CTGGCACTCGGGCCGCTGCCACTTCCCTCTCCATTTGCTCCCAGCACCTCTGTGCTCCCTCCCTCCTCCCTCCTTCA
GGGGAACAGCCTGTGCAGCCCCTCCCTGCACCCCACACCCTGGGGAGGCCCAACCCTGCCTCCAGCCCTTTCTCCCC
CGCTGCTCTTCCTGCCCATCCAGACAACCCTGGGGTCCCATCCCTGCAGCCTACACCCTGGTCTCCACCCAGACCCC
TGTCTCTCCCTCCAGATACCCCTCCCAGGCCAACCCTGCACATGCAGGCCCTCCCCTTTTCTGCTGCCAGAGCCTCA
GTTTCTACCCTCTGTGCCTACCCCCTGCCTCCTCCTGCCCACAACTCGAGCTCTTCCTCTCCTGGGGCCCCTGAGCC
ATGGCACTGACCGTGCACTCCCACCCCCACACTGCCCATGCCCTCACCTTCCTCCTGGACACTCTGACCCCGCTCCC
CTCTTGGACCCAGCCCTGGTATTTCCAGGACAAAGGCTCACCCAAGTCTTCCCCATGCAGGCCCTTGCCCTCACTGC
CCGGTTACACGGCAGCCTCCTGTGCACAGAAGCAGGGAGCTCAGCCCTTCCACAGGCAGAAGGCACTGAAAGAAATC
GGCCTCCAGCACCCTGATGCACGTCCGCCTGTGTCTCTCACTGCCCGCACCTGCAGGGAGGCTCGGCACTCCCTGTA
AAGACGAGGGATCCAGGCAGCAACATCATGGGAGAATGCAGGGCTCCCAGACAGCCCAGCCCTCTCGCAGGCCTCTC
CTGGGAAGAGACCTGCAGCCACCACTGAACAGCCACGGAGCCCGCTGGATAGTAACTGAGTCAGTGACCGACCTGGA
GGGCAGGGGAGCAGTGAACCGGAGCCCAGACCATAGGGACAGAGACCAGCCGCTGACATCCCGAGCCCCTCACTGGC
GGCCCCAGAACACCGCGTGGAAACAGAACAGACCCACATTCCCACCTGGAACAGGGCAGACACTGCTGAGCCCCCAG
CACCAGCCCTGAGAAACACCAGGCAACGGCATCAGAGGGGGCTCCTGAGAAAGAAAGGAGGGAGGTCTCCTTCACC
AGCAAGTACTTCCCTTGACCAAAAACAGGGTCCACGCAACTCCCCCAGGACAAAGGAGGAGCCCCCTGTACAGCACT
GGGCTCAGAGTCCTCTCCAACACACCCTGAGTTTCAGACAAAAACCCCCTGGAAATCATAGTATCAGCAGGAGAACT
AGCCAGAGACAGCAAGAGGGGACTCAGTGACTCCCGCGGGGACAGGAGGATTTTGTGGGGGCTCGTGTCACTGTG[redacted]
CACAGTGACACAGCCCCATTCCCAAAGCCCTGCTGTAAACGCTTCCAC

D2-2

TTCTGGGGGTGTGTAAGAGGGGATGCGGGCAGAGCCTGAGCAGGGCCTTTTGCTGTTTCTGCTTTCCTGTGCAGAGA
GTTCCATAAACTGGTGTTCGAGATCAATGGCTGGGAGTGAGCCCAGGAGGACAGCGTGGGAAGAGCACAGGGAAGGA
GGACCAGCCGCTATCCTACACTGTCATCTTTCGAAAGTTTGCCTTGTGCCCACACTGCTGCATCATGGGATGCTTAA
CAGCTGATGTAGACACAGCTAAAGAGAGAATCAGTGAGATGGATTTGCAGCACAGATCTGAATAAATTCTCCAGAAT
GTGGAGCAGCACAGAAGCAAGCACACAGAAAGTGCCTGATGCAAGGACAAAGTTCAGTGGGCACCTTCAGGCATTGC
TGCTGGGCACAGACACTCTGAAAAGCCCTGGCAGGAACTCCCTGTGACAAAGCAGAACCCTCAGGCAATGCCAGCCC
CAGAGCCCTCCCTGAGAGCCTCATGGGCAAAGATGTGCACAACAGGTGTTTCTCATAGCCCCAAACTGAGAGCAAAG
CAAACGTCCATCTGAAGGAGAACAGGCAAATAAACGATGGCAGGTTCATGAAATGCAAACCCAGACAGCCACAAGCA
CAAAAGTACAGGGTTATAAGCGACTCTGGTTGAGTTCATGACAATGCTGAGTAATTGGAGTAACAAAGTAAACTCCA
AAAAATACTTTCAATGTGATTTCTTCTAAATAAAATTTACACCCTGCAAAATGAACTGTCTTCTTAAGGGATACATT
TCCCAGTTAGAAAACCATAAAGAAAACCAAGAAAAGGATGATCACATAAACACAGTGGTGGTTACTTCTGCTGGGGA
AGGAAGAGGGTATGAACTGAGATACACAGGGTGGGCAAGTCTCCTAACAAGAACAGAACGAATACATTACAGTACCT
TGAAAACAGCAGTTAAACTTCTAAATTGCAAGAAGAGGAAAATGCACACAGTTGTGTTTAGAAAATTCTCAGTCCAG
CACTGTTCATAATAGCAAAGACATTAACCCAGGTCGGATAAATAAGCGATGACACAGGCAATTGCACAATGATACAG

Fig. 7 (cont.)

ACATATATTTAGTATATGAGACATCGATGATGTATCCCCAAATAAACGACTTTAAAGAGATAAAGGGCTGATGTGTG
GTGGCATTCACCTCCCTGGGATCCCCGGACAGGTTGCAGGCTCACTGTGCAGCAGGGCAGGCGGGTACCTGCTGGCA
GTTCCTGGGGCCTGATGTGGAGCAAGCGCAGGGCCATATATCCCGGAGGACGGCACAGTCAGTGAATTCCAGAGAGA
AGCAACTCAGCCACACTCCCCAGGCAGAGCCCGAGAGGGACGCCCACGCACAGGGAGGCAGAGCCCAGCACCTCCGC
AGCCAGCACCACCTGTGCACGGGCCACCACCTTGCAGGCACAGAGTGGGTGCTGAGAGGAGGGGCAGGGACACCAGG
CAGGGTGAGCACCCAGAGAAAACTGCAGACGCCTCACACATCCACCTCAGCCTCCCCTGACCTGGACCTCACTGGCC
TGGGCCTCACTTAACCTGGGCTTCACCTGACCTTGGCCTCACCTGACTTGGACCTCGCCTGTCCCAAGCTTTACCTG
ACCTGGGCCTCAACTCACCTGAACGTCTCCTGACCTGGGTTTAACCTGTCCTGGAACTCACCTGGCCTTGGCTTCCC
CTGACCTGGACCTCATCTGGCCTGGGCTTCACCTGGCCTGGGCCTCACCTGACCTGGACCTCATCTGGCCTGGACCT
CACCTGGCCTGGACTTCACCTGGCCTGGGCTTCACCTGACCTGGACCTCACCTGGCCTCAGGCCTCACCTGCACCTG
CTCCAGGTCTTGCTGGAGCCTGAGTAGCACTGAGGGTGCAGAAGCTCATCCAGGGTTGGGGAATGACTCTAGAAGTC
TCCCACATCTGACCTTTCTGGGTGGAGGCAGCTGGTGGCCCTGGGAATATAAAAATCTCCAGAATGATGACTCTGTG
ATTTGTGGGCAACTTATGAACCCGAAAGGACATGGCCATGGGGTGGGTAGGGACATAGGGACAGATGCCAGCCTGAG
GTGGAGCCTCAGGACACAGGTGGGCACGGACACTATCCACATAAGCGAGGGATAGACCCGAGTGTCCCCACAGCAGA
CCTGAGAGCGCTGGGCCCACAGCCTCCCCTCAGAGCCCTGCTGCCTCCTCCGGTCAGCCCTGGACATCCCAGGTTTC
CCCAGGCCTGGCGGTAGGTTTAGAATGAGGTCTGTGTCACTGTG[redacted]CA
CAGTGTCACAGAGTCCATCAAAAACCCATGCCTGGAAGCTTCCCGCCACAGCCCTCCCCATGGGGC D3-9
CCTGCTGCCTCCTCAGGTCAGCCCCGGACATCCTGGGTTTCCCCAGGCTGGGCGGTAGGTTTGGGGTGAGGTCTGTG
TCACTGTG[redacted]CACAGTGTCACAGAGTCCATCAAAAACCCATCCCTGGG
D3-10
AGCCTCCCGCCACAGCCCTCCCTGCAGGGGACCGGTACGTGCCATGTTAGGATTTTGATCGAGGAGACAGCACCATG
GGTATGGTGGCTACCACAGCAGTGCAGCCTGTGACCCAAACCCGCAGGGCAGCAGGCACGATGGACAGGCCCGTGAC
TGACCACGCTGGGCTCCAGCCTGCCAGCCCTGGAGATCATGAAACAGATGGCCAAGGTCACCCTACAGGTCATCCAG
ATCTGGCTCCGAGGGGTCTGCATCGCTGCTGCCCTCCCAACGCCAGTCCAAATGGGACAGGGACGGCCTCACAGCAC
CATCTGCTGCCATCAGGCCAGCGATCCCAGAAGCCCCTCCCTCAAGGCTGGCCACATGTGTGGACACTGAGAGCCCT
CATATCTGAGTAGGGGCACCAGGAGGGAGGGGCTGGCCCTGTGCACTGTCCCTGCTCCTGTGGTCTCTGGCCTGCCT
GGCCCTGACACCTGAGCCTCTCCTGGGTCATTTCCAAGACAGAAGACATTCCTGGGGACAGCCGGAGCTGGGCGTCG
CTCATCCTGCCCGGCCGTCCTGAGTCCTGCTCATTTCCAGACCTCACCGGGGAAGCCAACAGAGGACTCGCCTCCCA
CATTCAGAGACAAAGAACCTTCCAGAAATCCCTGCCTCTCTCCCCAGTGGACACCCTCTTCCAGGACAGTCCTCAGT
GGCATCACAGCGGCCTGAGATCCCCAGGACGCAGCACCGCTGTCAATAGGGGCCCCAAATGCCTGGACCAGGGCCTG
CGTGGGAAAGGCCTCTGGCCACACTCGGGCTTTTTGTGAAGGGCCCTCCTGCTGTG[redacted]CATAG
D4-11
TGATGAACCCAGTGGCAAAAACTGGCTGGAAACCCAGGGGCTGTGTGCACGCCTCAGCTTGGAGCTCTCCAGGAGCA
CAAGAGCCGGGCCCAAGGATTTGTGCCCAGACCCTCAGCCTCTAGGGACACCTGGGCCATCTCAGCCTGGGCTGGTG
CCCTGCACACCATCTTCCTCCAAATAGGGGCTTCAGAGGGCTCTGAGGTGACCTCACTCATGACCACAGGTGACCTG
GCCCTTCCCTGCCAGCTATACCAGACCCTGTCTTGACAGATGCCCCGATTCCAACAGCCAATTCCTGGGACCCTGAA
TAGCTGTAGACACCAGCCTCATTCCAGTACCTCCTGCCAATTGCCTGGATTCCCATCCTGGCTGGAATCAAGAAGGC
AGCATCCGCCAGGCTCCCAACAGGCAGGACTCCCGCACACCCTCCTCTGAGAGGCCGCTGTGTTCCGCAGGGCCAGG
CCCTGGACAGTTCCCCTCACCTGCCACTAGAGAAACACCTGCCATTGTCGTCCCCACCTGGAAAAGACCACTCGTGG
AGCCCCCAGCCCCAGGTACAGCTGTAGAGACAGTCCTCGAGGCCCCTAAGAAGGAGCCATGCCCAGTTCTGCCGGGA
CCCTCGGCCAGGCCGACAGGAGTGGACGCTGGAGCTGGGCCCACACTGGGCCACATAGGAGCTCACCAGTGAGGGCA
GGAGAGCACATGCCGGGGAGCACCCAGCCTCCTGCTGACCAGAGGCCTGCCCCAGAGCCCAGGAGGCTGCAGAGGCC
TCTCCAGGGAGACACTGTGCATGTCTGGTACCTAAGCAGCCCCCCACGTCCCCAGTCCTGGGGGCCCCTGGCTCAGC
TGTCTGGGCCCTCCCTGCTCCCTGGGAAGCTCCTCCTGACAGCCCCGCCTCCAGTTCCAGGTGTGGTTATTGTCAGG
CGATGTCAGACTGTG[redacted]CACAGTGGTGCCGCCCATAGCAGCAACCAGGCCAAGTAG
D5-12
ACAGGCCCCTGCTGCGCAGCCCCAGGCATCCACTTCACCTGCTTCTCCTGGGGCTCTCAAGGCTGCTGTCTGTCCTC
TGGCCCTCTGTGGGGAGGGTTCCCTCAGTGGGAGGTCTGTGCTCCAGGGCAGGGATGATTGAGATAGAAATCAAAGG
CTGGCAGGGAAAGGCAGCTTCCCGCCCTGAGAGGTGCAGGCAGCACCACGGAGCCACGGAGTCACAGAGCCACGGAG
CCCCCATTGTGGGCATTTGAGAGTGCTGTGCCCCCGGCAGGCCCAGCCCTGATGGGGAAGCCTGTCCCATCCCACAG
CCCGGGTCCCACGGGCAGCGGGCACAGAAGCTGCCAGGTTGTCCTCTATGATCCTCATCCCTCCAGCAGCATCCCCT
CCACAGTGGGGAAACTGAGGCTTGGAGCACCACCCGGCCCCCTGGAAATGAGGCTGTGAGCCCAGACAGTGGGCCCA
GAGCACTGTGAGTACCCCGGCAGTACCTGGCTGCAGGGATCAGCCAGAGATGCCAAACCCTGAGTGACCAGCCTACA
GGAGGATCCGGCCCCACCCAGGCCACTCGATTAATGCTCAACCCCCTGCCCTGGAGACCTCTTCCAGTACCACCAGC

Fig. 7 (cont.)

AGCTCAGCTTCTCAGGGCCTCATCCCTGCAAGGAAGGTCAAGGGCTGGGCCTGCCAGAAACACAGCACCCTCCCTAG
CCCTGGCTAAGACAGGGTGGGCAGACGGCTGTGGACGGACATATTGCTGGGGCATTTCTCACTGTCACTTCTGGGT
GGTAGCTCTGACAAAAACGCAGACCCTGCCAAAATCCCCACTGCCTCCCGCTAGGGGCTGGCCTGGAATCCTGCTGT
CCTAGGAGGCTGCTGACCTCCAGGATGGCTCCGTCCCCAGTTCCAGGGCGAGAGCAGATCCCAGGCAGGCTGTAGGC
TGGGAGGCCACCCCTGCCCTTGCCGGGGTTGAATGCAGGTGCCCAAGGCAGGAAATGGCATGAGCACAGGGATGACC
GGGACATGCCCCACCAGAGTGCGCCCCTTCCTGCTCTGCACCCTGCACCCCCCAGGCCAGCCCACGACGTCCAACAA
CTGGGCCTGGGTGGCAGCCCCACCCAGACAGGACAGACCCAGCACCCTGAGGAGGTCCTGCCAGGGGGAGCTAAGAG
CCATGAAGGAGCAAGATATGGGGCCCCCGATACAGGCACAGATGTCAGCTCCATCCAGGACCACCCAGCCCACACCC
TGAGAGGAACGTCTGTCTCCAGCCTCTGCAGGTCGGGAGGCAGCTGACCCCTGACTTGGACCCCTATTCCAGACACC
AGACAGAGGCGCAGGCCCCCCAGAACCAGGGTTGAGGGACGCCCCGTCAAAGCCAGACAAAACCAAGGGGTGTTGAG
CCCAGCAAGGGAAGGCCCCCAAACAGACCAGGAGGTTTCTGAAGGTGTCTGTGTCACAGTG[redacted]CACAGTGACACTCACCCAGCCAGAAACCCCATTCCAAGTCAGCGGAAGCAGAGAGAGCAGGGAGGACACGTT
D6-13
TAGGATCTGAGACTGCACCTGACACCCAGGCCAGCAGACGTCTCCCCTCCAGGGCACCCCACCCTGTCCTGCATTTC
TGCAAGATCAGGGGCGGCCTGAGGGGGGGTCTAGGGTGAGGAGATGGGTCCCCTGTACACCAAGGAGGAGTTAGGCA
GGTCCCGAGCACTCTCCCCATTGAGGCTGACCTGCCCAGAGAGTCCTGGGCCCACCCCACACACCGGGGCGGAATGT
GTGCAGGCCTCGGTCTCTGTGGGTGTTCCGCTAGCTGGGGCTCACAGTGCTCACCCCACACCTAAAATGAGCCACAG
CCTCCGGAGCCCCCGCAGGAGACCCCGCCCACAAGCCCAGCCCCCACCCAGGAGGCCCCAGAGCTCAGGGCGCCCCG
TCGGATTCCGAACAGCCCCGAGTCACAGCG[redacted]CACTGTCAGAATAGCTACGTCAAAAACTGT
D1-14
CCAGTGGCCACTGCCGGAGGCCCCGCCAGAGAGGGCAGCAGCCACTCTGATCCCATGTCCTGCCGGCTCCCATGACC
CCCAGCACGCGGAGCCCCACAGTGTCCCCACTGGATGGGAGGACAAGAGCTGGGGATTCCGGCGGTCGGGGCAGGG
GCTTGATCGCATCCTTCTGCCGTGGCTCCAGTGCCCCTGGCTGGAGTTGACCCTTCTGACAAGTGTCCTCAGAGAGA
CAGGCATCACCGGCGCCTCCCAACATCAACCCCAGGCAGCACAGGCACAAACCCCACATCCAGAGCCAACTCCAGGA
GCAGAGACACCCCAATACCCTGGGGGACCCCGACCCTGATGACTTCCCACTGGAATTCGCCGTAGAGTCCACCAGGA
CCAAAGACCCTGCCTCTGCCTCTGTCCCTCACTCAGGACCTGCTGCCGGGCGAGGCCTTGGGAGCAGACTTGGGCTT
AGGGGACACCAGTGTGACCCCGACCTTGACCAGGACGCAGACCTTTCCTTCCTTTCCTGGGCAGCACAGACTTTGG
GGTCTGGGCCAGGAGGAACTTCTGGCAGGTCGCCAAGCACAGAGGCCACAGGCTGAGGTGGCCCTGGAAAGACCTCC
AGGAGGTGGCCACTCCCCTTCCTCCCAGCTGGACCCCATGTCCTCCCCAAGATAAGGGTGCCATCCAAGGCAGGTGC
TCCTTGGAGCCCCATTCAGACTCCTCCCTGGACCCCACTGGGCCTCAGTCCCAGCTCTGGGGATGAAGCCACCACAA
GCACACCAGGCAGCCCAGGCCCAGCCACCCTGCAGTGCCCAAGCACACACTCTGGAGCAGAGCAGGGTGCCTCTGGG
AGGGGCTGAGCTCCCCACCCCACCCCCACCTGCACACCCCACCCACCCCTGCCCAGCGGCTCTGCAGGAGGGTCAGA
GCCCCACATGGGGTATGGACTTAGGGTCTCACTCACGTGGCTCCCATCATGAGTGAAGGGGCCTCAAGCCCAGGTTC
CCACAGCAGCGCCTGTCGCAAGTGGAGGCAGAGGCCCGAGGGCCACCCTGACCTGGTCCCTGAGGTTCCTGCAGCCC
AGGCTGCCCTGCTGTCCCTGGGAGGCCTGGGCTCCACCAGACCACAGGTCCAGGGCACCGGGTGCAGGAGCCACCCA
CACACAGCTCACAGGAAGAAGATAAGCTCCAGACCCCCAGGGCCAGAACCTGCCTTCCTGCTACTGCTTCCTGCCCC
AGACCTGGGCGCCCTCCCCCGTCCACTTACACACAGGCCAGGAAGCTGTTCCCACACAGAACAACCCCAAACCAGGA
CCGCCTGGCACTCAGGTGGCTGCCATTTCCTTCTCCATTTGCTCCCAGCGCCTCTGTCCTCCCTGGTTCCTCCTTCG
GGGGAACAGCCTGTGCAGCCAGTCCCTGCAGCCCACACCCTGGGGAGACCCAACCCTGCCTGGGCCCCTTCCAACCC
TGCTGCTCTTACTGCCCACCCAGAAAACTCTGGGGTCCTGTCCCTGCAGTCCCTACCCTGGTCTCCACCCAGACCCC
TGTGTATCACTCCAGACACCCCTCCCAGGCAAACCCTGCACCTGCAGGCCCTGTCCTCTTCTGTCGCTAGAGCCTCA
GTTTCTCCCCCCTGTGCCCACACCCTACCTCCTCCTGCCCACAACTCTAACTCTTCTTCTCCTGGAGCCCCTGAGCC
ATGGCATTGACCCTGCCCTCCCACCACCCACAGCCCATGCCCTCACCTTCCTCCTGGCCACTCCGACCCCGCCCCCT
CTCAGGCCAAGCCCTGGTATTTCCAGGACAAAGGCTCACCCAAGTCTTTCCCAGGCAGGCCTGGGCTCTTGCCCTCA
CTTCCCGGTTACACGGGAGCCTCCTGTGCACAGAAGCAGGGAGCTCAGCCCTTCCACAGGCAGAAGGCACTGAAAGA
AATCGGCCTCCAGCACCTTGACACACGTCCGCCCGTGTCTCTCACTGCCCGCACCTGCAGGGAGGCTCCGCACTCCC
TCTAAAGACAAGGGATCCAGGCAGCAGCATCACGGGAGAATGCAGGGCTCCCAGACATCCCAGTCCTCTCACAGGCC
TCTCCTGGGAAGAGACCTGCAGCCACCACCAAACAGCCACAGAGGCTGCTGGATAGTAACTGAGTCAATGACCGACC
TGGAGGGCAGGGGAGCAGTGAGCCGGAGCCCATACCATAGGGACAGAGACCAGCCGCTGACATCCCGAGCTCCTCAA
TGGTGGCCCCATAACACACCTAGGAAACATAACACACCCACAGCCCCACCTGGAACAGGGCAGAGACTGCTGAGCCC
CCAGCACCAGCCCCAAGAAACACCAGGCAACAGTATCAGAGGGGGCTCCCGAGAAAGAGAGGAGGGGAGATCTCCTT
CACCATCAAATGCTTCCCTTGACCAAAAACAGGGTCCACGCAACTCCCCCAGGACAAAGGAGGAGCCCCCTATACAG
CACTGGGCTCAGAGTCCTCTCTGAGACACCCTGAGTTTCAGACAACAACCCGCTGGAATGCACAGTCTCAGCAGGAG
AACAGACCAAAGCCAGCAAAAGGACCTCGGTGACACCAGTAGGGACAGGAGGATTTTGTGGGGGCTCGTGTCACTG

Fig. 7 (cont.)

TG[redacted]CACAGTGACACAGACCCATTCCCAAAGCCCTACTGCAAACACAC
D2-15
CCACTCCTGGGGCTGAGGGGCTGGGGGAGCATCTGGGAAGTAGGGTCCAGGGGTGTCTATCAATGTCCAAAATGCAC
CAGACTCCCCGCCAAACACCACCCCACCAGCCAGCGAGCAGGGTAAACAGAAAATGAGAGGCTCTGGGAAGCTTGCA
CAGGCCCCAAGGAAAGAGCTTTGGCAGGTGTGCAAGAGGGGATGCAGGCAGAGCCTGAGCAGGGCCTTTTGCTGTTT
CTGCTTTCCTGTGCAGAGAGTTCCATAAACTGGTGTTCAAGATCAGTGGCTGGGAATGAGCCCAGGAGGGCAGTCTG
TGGGAAGAGCACAGGGAAGGAGGACCAGCCGCTATCCTACACTGTCATCTTTCAAAAGTTTGCCTTGTGACCACACT
ATTGCATCATGGGATGCTTAAGAGCTGATGTAGACACAGCTAAAGAGAGAATCAGTGAGATGAATTTGCAGCATAGA
TCTGAATAAACTCTCCAGAATGTGGAGCAGTACAGAAGCAAACACACAGAAAGTGCCTGATGCAAGGACAAAGTTCA
GTGGGCACCTTCAGGCATTGCTGCTGGGCACAGACACTCTGAAAAGCCCTGGCAGGATCTCCCTGCGACAAAGCAGA
ACCCTCAGGCAATGCCAGCCCCAGAGCCCTCCCTGAGAGCGTCATGGGGAAAGATGTGCAGAACAGCTGATTATCAT
AGACTCAAACTGAGAACAGAGCAAACGTCCATCTGAAGAACAGTCAAATAAGCAATGGTAGGTTCATGCAATGCAAA
CCCAGACAGCCAGGGGACAACAGTAGAGGGCTACAGGCGGCTTTGCGGTTGAGTTCATGACAATGCTGAGTAATTGG
AGTAACAGAGGAAAGCCCAAAAAATACTTTTAATGTGATTTCTTCTAAATAAAATTTACACCAGGCAAAATGAACTG
TCTTCTTAAGGGATAAACTTTCCCCTGGAAAAACTACAAGGAAAATTAAGAAAACGATGATCACATAAACACAGTTG
TGGTTACTTCTACTGGGGAAGGAAGAGGGTATGAGCTGAGACACACAGAGTCGGCAAGTCTCCAAGCAAGCACAGAA
CGAATACATTACAGTACCTTGAATACAGCAGTTAAACTTCTAAATCGCAAGAAGAGGAAAATGCACACAGCTGTGTT
TAGAAAATTCTCAGTCCAGCACTATTCATAATAGCAAAGACATTAACCCAGGTTGGATAAATAAATGATGACACAGG
CAATTGCACAATGATACAGACATACATTTAGTACATGAGACATCGATGATGTATCCCCAAAGAAATGACTTTAAAGA
GAAAAGGCCTGATGTGTGGTGGCACTCACCTCCCTGGGATCCCCGGACAGGTTGCAGGCACACTGTGTGGCAGGGCA
GGCTGGTACATGCTGGCAGCTCCTGGGGCCTGATGTGGAGCAAGCGCAGGGCTGTATACCCCCAAGGATGGCACAGT
CAGTGAATTCCAAAGAGAAGCAGCTCAGCCACACTGCCCAGGCAGAGCCCGAGAGGGACGCCCACGCACAGGGAGGC
AGAGCCCAGCTCCTCCACAGCCACCACCACCTGTGCACGGGCCACCACCTTGCAGGCACAGAGTGGGTGCTGAGAGG
AGGGGCAGGGACACCAGGCAGGGTGAGCACCCAGAGAAAACTGCAGAAGCCTCACACATCCACCTCAGCCTCCCCTG
ACCTGGACCTCACCTGGTCTGGACCTCACCTGGCCTGGGCCTCACCTGACCTGGACCTCACCTGGCCTGGGCTTCAC
CTGACCTGGACCTCACCTGGCCTCCGGCCTCACCTGCACCTGCTCCAGGTCTTGCTGGAACCTGAGTAGCACTGAGG
CTGCAGAAGCTCATCCAGGGTTGGGGAATGACTCTGGAACTCTCCCACATCTGACCTTTCTGGGTGGAGGCATCTGG
TGGCCCTGGGAATATAAAAAGCCCCAGAATGGTGCCTGCGTGATTTGGGGGCAATTTATGAACCCGAAAGGACATGG
CCATGGGGTGGGTAGGGACATAGGGACAGATGCCAGCCTGAGGTGGAGCCTCAGGACACAGTTGGACGCGGACACTA
TCCACATAAGCGAGGGACAGACCCGAGTGTTCCTGCAGTAGACCTGAGAGCGCTGGGCCCACAGCCTCCCCTCGGTG
CCCTGCTGCCTCCTCAGGTCAGCCCTGGACATCCCGGGTTTCCCCAGGCCAGATGGTAGG[redacted]CACAGCATCACACGGTCCATCAGAAACCCAT
D3-16
GCCACAGCCCTCCCCGCAGGGGACCGCCGCGTGCCATGTTACGATTTTGATCGAGGACACAGCGCCATGGGTATGGT
GGCTACCACAGCAGTGCAGCCCATGACCCAAACACACAGGGCAGCAGGCACAATGGACAGGCCTGTGAGTGACCATG
CTGGGCTCCAGCCCGCCAGCCCCGGAGACCATGAAACAGATGGCCAAGGTCACCCCACAGTTCAGCCAGACATGGCT
CCGTGGGGTCTGCATCGCTGCTGCCCTCTAACACCAGCCCAGATGGGGACAAGGCCAACCCCACATTACCATCTCCT
GCTGTCCACCCAGTGGTCCCAGAAGCCCCTCCCTCATGGCTGAGCCACATGTGTGAACCCTGAGAGCACCCCATGTC
AGAGTAGGGGCAGCAGAAGGGCGGGGCTGGCCCTGTGCACTGTCCCTGCACCCATGGTCCCTCGCCTGCCTGGCCCT
GACACCTGAGCCTCTTCTGAGTCATTTCTAAGATAGAAGACATTCCCGGGGACAGCCGGAGCTGGGCGTCGCTCATC
CTGCCCGGCCGTCCTGAGTCCTGCTTGTTTCCAGACCTCACCAGGGAAGCCAACAGAGGACTCACCTCACACAGTCA
GAGACAAAGAACCTTCCAGAAATCCCTGTCTCACTCCCCAGTGGGCACCTTCTTCCAGGACATTCCTCGGTCGCATC
ACAGCAGGCACCCACATCTGGATCAGGACGGCCCCCAGAACACAAGATGGCCCATGGGGACAGCCCCACAACCCAGG
CCTTCCCAGACCCCTAAAAGGCGTCCCACCCCCTGCACCTGCCCCAGGGCTAAAAATCCAGGAGGCTTGACTCCCGC
ATACCCTCCAGCCAGACATCACCTCAGCCCCCTCCTGGAGGGGACAGGAGCCCGGGAGGGTGAGTCAGACCCACCTG
CCCTCGATGGCAGGCGGGGAAGATTCAGAAAGGCCTGAGATCCCCAGGACGCAGCACCACTGTCAATGGGGGCCCCA
GACGCCTGGACCAGGGCCTGCGTGGGAAAGGCCGCTGGGCACACTCAGGGGCTTTTTGTGAAGGCCCCTCCTACTGT
G[redacted]CACAGTGATGAAACTAGCAGCAAAAACTGGCCGGACACCCAGGGACCATGCACACTTCTC
D3-17
AGCTTGGAGCTCTCCAGGACCAGAAGAGTCAGGTCTGAGGGTTTGTAGCCAGACCCTCGGCCTCTAGGGACACCCTG
GCCATCACAGCGGATGGGCTGGTGCCCCACATGCCATCTGCTCCAAACAGGGGCTTCAGAGGGCTCTGAGGTGACTT
CACTCATGACCACAGGTGCCCTGGCCCCTTCCCCGCCAGCTACACCGAACCCTGTCCCAACAGCTGCCCCAGTTCCA
ACAGCCAATTCCTGGGGCCCAGAATTGCTGTAGACACCAGCCTCGTTCCAGCACCTCCTGCCAATTGCCTGGATTCA
CATCCTGGCTGGAATCAAGAGGGCAGCATCCGCCAGGCTCCCAACAGGCAGGACTCCCGCACACCCTCCTCTGAGAG

Fig. 7 (cont.)

GCCGCTGTGTTCCGCAGGGCCAGGCCCTGGACAGTTCCCCTCACCTGCCACTAGAGAAACACCTGCCATTGTCGTCC
CCACCTGGAAAAGACCACTCGTGGAGCCCCCAGCCCCAGGTACAGCTGTAGAGAGACTCCCCGAGGGATCTAAGAAG
GAGCCATGCGCAGTTCTGCCGGGACCCTCGGCCAGGCCGACAGGAGTGGACACTGGAGCTGGGCCCACACTGGGCCA
CATAGGAGCTCACCAGTGAGGGCAGGAGAGCACATGCCGGGGAGCACCCAGCCTCCTGCTGACCAGAGGCCTGCCCC
AGAGCCCAGGAGGCTGCAGAGGCCTCTCCAGGGGGACACTGTGCATGTCTGGTCCCTGAGCAGCCCCCCACGTCCCC
AGTCCTGGGGGCCCCTAGCACAGCTGTCTGGACCCTCCCTGTTCCCTGGGAAGCTCCTCCTGACAGCCCCGCCTCCA
GTTCCAGGTGTGGTTATTGTCAGGGGGTGTCAGACTGTG[redacted]CACAGTGGTGCTGCCCAT
D5-18
AGCAGCAACCAGGCCAAGTAGACAGGCCCCTGCTGTGCAGCCCCAGGCCTCCAGCTCACCTGCTTCTCCTGGGGCTC
TCAAGGTCACTGTTGTCTGTACTCTGCCCTCTGTGGGGAGGGTTCTCTCAGTGGGAGGTCTGTTCTCAACATCCCAG
GGCCTCATGTCTGCACGGAAGGCCAATGGATGGGCAACCTCACATGCCGCGGCTAAGATAGGGTGGGCAGCCTGGCG
GGGGACAGTACATACTGCTGGGGTGTCTGTCACTGTGCCTAGTGGGGCACTGGCTCCCAAACAACGCAGTCCTCACC
AAAATCCCCACAGCCTCCCCTGCTAGGGGCTGGCCTGATCTCCTGCAGTCCTAGGAGGCTGCTGACCTCCAGAATGT
CTCCGTCCCCAGTTCCAGGGCGAGAGCAGATCCCAGGCCGGCTGCAGACTGGGAGGCCACCCCCTCCTTCCCAGGGT
TCACTGGAGGTGACCAAGGTAGGAAATGGCCTTAACACAGGGATGACTGCGCCATCCCCCAACAGAGTCAGCCCCCT
CCTGCTCTGTACCCCGCACCCCCCAGGCCAGTCCACGAAAACCAGGGCCCCACATCAGAGTCACTGCCTGGCCCGGC
CCTGGGGCGGACCCCTCAGCCCCCACCCTGTCTAGAGGACTTGGGGGGACAGGACACAGGCCCTCTCCTTATGGTTC
CCCCACCTGCCTCCGGCCGGGACCCTTGGGGTGTGGACAGAAAGGACACCTGCCTAATTGGCCCCCAGGAACACAGA
ACTTCTCTCCAGGGACCCCAGCCCGAGCACCCCCTTACCCAGGACCCAGCCCTGCCCCTCCTCCCCTCTGCTCTCCT
CTCATCACCCCATGGGAATCCGGTATCCCCAGGAAGCCATCAGGAAGGGCTGAAGGAGGAAGCGGGGCCGTGCACCA
CCGGGCAGGAGGCTCCGTCTTCGTGAACCCAGGGAAGTGCCAGCCTCCTAGAGGGTATGGTCCACCCTGCCTGGGGC
TCCCACCGTGGCAGGCTGCGGGGAAGGACCAGGGACGGTGTGGGGGAGGGCTCAGGGCCCTGCGGGTGCTCCTCCAT
CTTCGGTGAGCCTCCCCCTTCACCCACCGTCCCGCCCACCTCCTCTCCACCCTGGCTGCACGTCTTCCACACCATCC
TGAGTCCTACCTACACCAGAGCCAGCAAAGCCAGTGCAGACAAAGGCTGGGGTGCAGGGGGGCTGCCAGGGCAGCTT
CGGGGAGGGAAGGATGGAGGGAGGGGAGGTCAGTGAAGAGGCCCCCTTCCCCTGGGTCCAGGATCCTCCTCTGGGAC
CCCCGGCTCCCATCCCCTCCTGGCTCTGGGAGGAGAAGCAGGATGGGAGAATCTGTGCGGGACCCTCTCACAGTGGA
ATATCCCCACAGCGGCTCAGGCCAGACCCAAAAGCCCCTCAGTGAGCCCTCCACTGCAGTCCTGGGCCTGGGTAGCA
GCCCCTCCCACAGAGGACAGACCCAGCACCCCGAAGAAGTCCTGCCAGGGGGAGCTCAGAGCCATGAAAGAGCAGGA
TATGGGGTCCCCGATACAGGCACAGACCTCAGCTCCATCCAGGCCCACCGGGACCCACCATGGGAGGAACACCTGTC
TCCGGGTTGTGAGGTGGCTGGCCTCTGTCTCGGACCCCACTCCAGACACCAGACAGAGGGGCAGGCCCCCCAAAACC
AGGGTTGAGGGATGATCCGTCAAGGCAGACAAGACCAAGGGGCACTGACCCCAGCAAGGGAAGGCTCCCAAACAGAC
GAGGAGGTTTCTGAAGCTGTCTGTATCACAGTG[redacted]CACAGTGACACTCGCCAGGCCAG
D6-19
AAACCCCGTCCCAAGTCAGCGGAAGCAGAGAGAGCAGGGAGGACACGTTTAGGATCTGAGGCCGCACCTGACACCCA
GGGCAGCAGACGTCTCCCCTCCAGGGCACCCTCCACCGTCCTGCGTTTCTTCAAGAATAGGGGCGGCCTGAGGGGGT
CCAGGGCCAGGCGATAGGTCCCCTCTACCCCAAGGAGGAGCCAGGCAGGACCCGAGCACCGTCCCCATTGAGGCTGA
CCTGCCCAGACGGGCCTGGGCCCACCCCACACACCGGGGCGGAATGTGTGCAGGCCCCAGTCTCTGTGGGTGTTCCG
CTAGCTGGGGCCCCCAGTGCTCACCCCACACCTAAAGCGAGCCCCAGCCTCCAGAGCCCCCTAAGCATTCCCCGCCC
AGCAGCCCAGCCCCTGCCCCCACCCAGGAGGCCCCAGAGCTCAGGGCGCCTGGTCGGATTCTGAACAGCCCCGAGTC
ACAGTG[redacted]CACCGTGAGAAAAACTGTGTCCAAAACTGACTCCTGGCAGCAGTCGGAGGCCCC
D1-20
GCCAGAGAGGGGAGCAGCCGCCCTGAACCCATGTCCTGCCGGTTCCCATGACCCCCAGCACCCAGAGCCCCACGGTG
TCCCCGTTGGATAATGAGGACAAGGGCTGGGGGCTCCGGTGGTTTGCGGCAGGGACTTGATCACATCCTTCTGCTGT
GGCCCCATTGCCTCTGGCTGGAGTTGACCCTTCTGACAAGTGTCCTCAGAAAGACAGGGATCACCGGCACCTCCCAA
TATCAACCCCAGGCAGCACAGACACAAACCCCACATCCAGAGCCAACTCCAGGAGCAGAGACACCCCAACACTCTGG
GGGACCCCAACCGTGATAACTCCCCACTGGAATCCGCCCCAGAGTCTACCAGGACCAAAGGCCCTGCCCTGTCTCTG
TCCCTCACTCAGGGCCTCCTGCAGGGCGAGCGCTTGGGAGCAGACTCGGTCTTAGGGGACACCACTGTGGGCCCCAA
CTTTGATGAGGCCACTGACCCTTCCTTCCTTTCCTGGGGCAGCACAGACTTTGGGGTCTGGGCAGGGAAGAACTACT
GGCTGGTGGCCAATCACAGAGCCCCCAGGCCGAGGTGGCCCCAAGAAGGCCCTCAGGAGGTGGCCACTCCACTTCCT
CCCAGCTGGACCCCAGGTCCTCCCCAAGATAGGGGTGCCATCCAAGGCAGGTCCTCCATGGAGCCCCCTTCAGACTC
CTCCCGGGACCCCACTGGACCTCAGTCCCTGCTCTGGGAATGCAGCCACCACAAGCACACCAGGAAGCCCAGGCCCA
GCCACCCTGCAGTGGGCAAGCCCACACTCTGGAGCAGAGCAGGGTGCGTCTGGGAGGGGCTAACCTCCCCACCCCCC
ACCCCCCATCTGCACACAGCCACCTACCACTGCCCAGACCCTCTGCAGGAGGGCCAAGCCACCATGGGGTATGGACT
TAGGGTCTCACTCACGTGCCTCCCCTCCTGGGAGAAGGGGCCTCATGCCGAGATCCCTGCAGCACTAGACACAGCTG

Fig. 7 (cont.)

GAGGCAGTGGCCCCAGGGCCACCCTGACCTGGCATCTAAGGCTGCTCCAGCCCAGACAGCACTGCCGTTCCTGGGAA
GCCTGGGCTCCACCAGACCACAGGTCCAGGGCACAGCCCACAGGAGCCACCCACACACAGCTCACAGGAAGAAGATA
AGCTCCAGACCCCAGGGCGGGACCTGCCTTCCTGCCACCACTTACACACAGGCCAGGGAGCTGTTCCCACACAGATC
AACCCCAAACCGGGACTGCCTGGCACTAGGGTCACTGCCATTTCCCTCTCCATTCCCTCCCAGTGCCTCTGTGCTCC
CTCCTTCTGGGGAACACCCTGTGCAGCCCCTCCCTGCAGCCCACACGCTGGGGAGACCCCACCCTGCCTCGGGCCTT
TTCTACCTGCTGCACTTGCCGCCCACCCAAACAACCCTGGGTACGTGACCCTGCAGTCCTCACCCTGATCTGCAACC
AGACCCCTGTCCCTCCCTCTAAACACCCCTCCCAGGCCAACTCTGCACCTGCAGGCCCTCCGCTCTTCTGCCACAAG
AGCCTCAGGTTTTCCTACCTGTGCCCACCCCCTAACCCCTCCTGCCCACAACTTGAGTTCTTCCTCTCCTGGAGCCC
TTGAGCCATGGCACTGACCCTACACTCCCACCCACACACTGCCCATGCCATCACCTTCCTCCTGGACACTCTGACCA
CGCTCCCCTCCCTCTCAGACCCGGCCCTGGTATTTCCAGGACAAAGGCTCACCCAAGTCTTCCCCATGCAGGCCCTT
GCCCTCACTGCCTGGTTACACGGGAGCCTCCTGTGCGCAGAAGCAGGGAGCTCAGCTCTTCCACAGGCAGAAGGCAC
TGAAAGAAATCGGCCTCCAGTGCCTTGACACACGTCCGCCTGTGTCTCTCACTGCCTGCACCTGCAGGGAGGCTCCG
CACTCCCTCTAAAGATGAGGGATCCAGGCAGCAACATCACGGGAGAATGCAGGGCTCCCAGACAGCCCAGCCCTCTC
GCAGGCCTCTCCTGGGAAGAGACCTGCAGCCACCACTGAACAGCCACGGAGGTCGCTGGATAGTAACCGAGTCAGTG
ACCGACCTGGAGGGCAGGGGAGCAGTGAACCGGAGCCCATACCATAGGGACAGACACCAGCCGCTAACATCCCGAGC
CCCTCACTGGCGGCCCCAGAACACCCCGTGGAAACAGAACAGACCCACAGTCCCACCTGGAACAGGGCAGACACTGC
TGAGCCCCCAGCACCAGCCCCAAGAAACACTAGGCAACAGCATCAGAGGGGGCTCCTGAGAAAGAGAGGAGGGGAGG
TCTCCTTCACCATCAAATGCTTCCCTTGACCAAAAACAGGGTCCACGCAACTCCCCCAGGACAAAGGAGGAGCCCCC
TGTACAGCACTGGGCTCAGAGTCCTCTCTGAGACAGGCTCAGTTTCAGACAACAACCCGCTGGAATGCACAGTCTCA
GCAGGAGAGCCAGGCCAGAGCCAGCAAGAGGAGACTCGGTGACACCAGTCTCCTGTAGGGACAGGAGGATTTTGTGG
GGGTTCGTGTCACTGTG[redacted]CACAGTGACACAACCCCATTCCTAAAGCCCTA
D2-21
CTGCAAACGCACCCACTCCTGGGGCTGAGGGGCTGGGGGAGCATCTGGGAAGTATGGCCTAGGGGTGTCCATCAATG
CCCAAAATGCACCAGACTCTCCCCAAGACATCACCCCACCAGCCAGTGAGCAGAGTAAACAGAAAATGAGAAGCAGC
TGGGAAGCTTGCACAGGCCCCAAGGAAAGAGCTTTGGCAGGTGTGCAAGAGGGGATGTGGGCAGAGCCTGAGCAGGG
CCTTTTGCTGTTTCTGCTTTCCTGTGCAGAGAGTTCCATAAACTGGTATTCAGGATCAATGGCTGGGAGTGAGCCCA
GGAGGACAGTGTGGGAAGAGCACAGGGAAGGAGGACCAGCCGCTATCCTACACTGTCATCTTTTGAAAGTTTGCCCT
GTGCCCACAATGCTGCATCATGGGATGCTTAACAGCTGATGTAGACACAGCTAAAGAGAGAATCAGTGAAATGCATT
TGCAGCACAGATCTGAATAAATCCTCCAGAATGTGGAGCAGCACAGAAGCAAGCACACAGAAAGTGCCTGATGCCAA
GGCAAAGTTCAGTGGGCACCTTCAGGCATTGCTGCTGGGCACAGACACTCTGAAAAGCACTGGCAGGAACTGCCTGT
GACAAAGCAGAACCCTCAGGCAATGCCAGCCCTAGAGCCCTTCCTGAGAACCTCATGGGCAAAGATGTGCAGAACAG
CTGTTTGTCATAGCCCCAAACTATGGGGCTGGACAAAGCAAACGTCCATCTGAAGGACAACAGACAAATAAACGATG
GCAGGTTCATGAAATGCAAACTAGGACAGCCAGAGGACAACAGTAGAGAGCTACAGGCGGCTTTGCGGTTGAGTTCA
TGACAATGCTGAGTAATTGGAGTAACAGAGGAAAGCCCAAAAAATACTTTTAATGTGATTTCTTCTAAATAAAATTT
ACACCCGGCAAAATGAACTATCTTCTTAAGGGATAAACTTTCCCCTGGAAAAACTATAAGGAAAATCAAGAAAACGA
TGATCACATAAACACAGTGGTGGTTACTTCTACTGGGGAAGGAAGAGGGTATGAGCTGAGACACACAGAGTCGGCAA
GTCTCCTAACAAGAACAGAACAAATACATTACAGTACCTTGAAAACAGCAGTTAAACTTCTAAATCGCAAGAAGAGG
AAAATGCACACACCTGTGTTTAGAAAATTCTCAGTCCAGCACTGTTCATAATAGCAAAGACATTAACCCAGGTTGGA
TAAATAAGCGATGACACAGGCAATTGCACAATGATACAGACATACATTCAGTATATGAGACATCGATGATGTATCCC
CAAAGAAATGACTTTAAAGAGAAAAGGCCTGATGTGTGGTGGCAATCACCTCCCTGGGCATCCCCGGACAGGCTGCA
GGCTCACTGTGTGGCAGGGCAGGCAGGCACCTGCTGGCAGCTCCTGGGGCCTGATGTGGAGCAGGCACAGAGCTGTA
TATCCCCAAGGAAGGTACAGTCAGTGCATTCCAGAGAGAAGCAACTCAGCCACACTCCCTGGCCAGAACCCAAGATG
CACACCCATGCACAGGGAGGCAGAGCCCAGCACCTCCGCAGCCACCACCACCTGCGCACGGGCCACCACCTTGCAGG
CACAGAGTGGGTGCTGAGAGGAGGGGCAGGGACACCAGGCAGGGTGAGCACCCAGAGAAAACTGCAGAAGCCTCACA
CATCCACCTCAGCCTCCCCTGACCTGGACCTCACCTGGCCTGGGCCTCACCTGACCTGGACCTCACCTGGCCTGGGC
TTCACCTGGCCTGGGCTTCACCTGACCTGGACCTCACCTGGCCTCGGGCCTCACCTGGCCTGGGCTTCACCTGGCCT
GGGCTTCACCTGACCTGGACCTCACCTGGCCTGGGCCTCACCTGACCTGGACCTCACCTGGCCTGGGCTTCACCTGG
CCTGGGCTTCACCTGGCCTGGGCTTCACCTGACCTGGACCTCACCTGGCCTGGGCTTCACCTGACCTGGACCTCACC
TGGCCTCAGGCCTCACCTGCACCTGCTCCAGGTCTTGCTGGAGCCTGAGTAGCACTGAGGCTGTAGGGACTCATCCA
GGGTTGGGGAATGACTCTGCAACTCTCCCACATCTGACCTTTCTGGGTGGAGGCACCTGGTGGCCCAGGGAATATAA
AAAGCCCCAGAATGATGCCTGTGTGATTTGGGGGCAATTTATGAACCCGAAAGGACATGGCCATGGGGTGGGTAGGG
ACAGTAGGGACAGATGTCAGCCTGAGGTGAAGCCTCAGGACACAGGTGGGCATGGACAGTGTCCACCTAAGCGAGGG
ACAGACCCGAGTGTCCCTGCAGTAGACCTGAGAGCGCTGGGCCCACAGCCTCCCCTCGGGGCCCTGCTGCCTCCTCA
GGTCAGCCCTGGACATCCCGGGTTTCCCCAGGCCTGGCGGTAGGTTTGAAGTGAGGTCTGTGTCACTGTG[redacted]

Fig. 7 (cont.)

[redacted]CACAGTGTCACAGAGTCCATCAAAAACTCATGCCTGGGAGCCTCCCACCACAG
D3-22
CCCTCCCTGCGGGGGACCGCTGCATGCCGTGTTAGGATTTTGATCGAGGACACGGCGCCATGGGTATGGTGGCTACC
ACAGCAGTGCAGCCCATGACCCAAACACACGGGGCAGCAGAAACAATGGACAGGCCCACAAGTGACCATGATGGGCT
CCAGCCCACCAGCCCCAGAGACCATGAAACAGATGGCCAAGGTCACCCTACAGGTCATCCAGATCTGGCTCCAAGGG
GTCTGCATCGCTGCTGCCCTCCCAACGCCAAACCAGATGGAGACAGGGCCGGCCCCATAGCACCATCTGCTGCCGTC
CACCCAGCAGTCCCGGAAGCCCCTCCCTGAACGCTGGGCCACGTGTGTGAACCCTGCGAGCCCCCCATGTCAGAGTA
GGGGCAGCAGGAGGGCGGGGCTGGCCCTGTGCACTGTCACTGCCCCTGTGGTCCCTGGCCTGCCTGGCCCTGACACC
TGAGCCTCTCCTGGGTCATTTCCAAGACATTCCCAGGGACAGCCGGAGCTGGGAGTCGCTCATCCTGCCTGGCTGTC
CTGAGTCCTGCTCATTTCCAGACCTCACCAGGGAAGCCAACAGAGGACTCACCTCACACAGTCAGAGACAACGAACC
TTCCAGAAATCCCTGTTTCTCTCCCCAGTGAGAGAAACCCTCTTCCAGGGTTTCTCTTCTCTCCCACCCTCTTCCAG
GACAGTCCTCAGCAGCATCACAGCGGGAACGCACATCTGGATCAGGACGGCCCCCAGAACACGCGATGGCCCATGGG
GACAGCCCAGCCCTTCCCAGACCCCTAAAAGGTATCCCCACCTTGCACCTGCCCCAGGGCTCAAACTCCAGGAGGCC
TGACTCCTGCACACCCTCCTGCCAGATATCACCTCAGCCCCCTCCTGGAGGGGACAGGAGCCCGGGAGGGTGAGTCA
GACCCACCTGCCCTCAATGGCAGGCGGGGAAGATTCAGAAAGGCCTGAGATCCCCAGGACGCAGCACCACTGTCAAT
GGGGGCCCCAGACGCCTGGACCAGGGCCTGTGTGGGAAAGGCCTCTGGCCACACTCAGGGGCTTTTTGTGAAGGGCC
CTCCTGCTGTG[redacted]CACAGTGATGAAACCAGCAGCAAAAACTGACTGGACTCGCAGGGTTT
D4-23
ATGCACACTTCTCGGCTCGGAGCTCTCCAGGAGCACAAGAGCCAGGCCCGAGGGTTTCTGCCCAGACCCTCGGCCTC
TAGGGACACCCGGGCCATCTTAGCCGATGGGCTGGTGCCCTGCACACCGTGTGCTGCCAAACAGGGGCTTCAGAGGG
CTCTGAGGTGACTTCACTCATGACCACAGGTGCCCTGGTCCCTTCACTGCCAGCTGCACCAGACCCTGTTCCGAGAG
ATGCCCCAGTTCCAAAAGCCAATTCCTGGGGCCGGGAATTACTGTAGACACCAGCCTCATTCCAGTACCTCCTGCCA
ATTGCCTGGATTCCCATCCTGGCTGGAATCAAGAGGGCAGCATCCGCCAGGCTCCCAACAGGCAGGACTCCCACACA
CCCTCCTCTGAGAGGCCGCTGTGTTCCGCAGGGCCAGGCCGCAGACAGTTCCCCTCACCTGCCCATGTAGAAACACC
TGCCATTGTCGTCCCCACCTGGAAAAGACCACTTGTGGAGCCCCCAGCCCCAGGTACAGCTGTAGAGAGAGTCCTCG
AGGCCCCTAAGAAGGAGCCATGCCCAGTTCTGCCGGGACCCTCGGCCAGGCCGACAGGAGTGGACGCTGGAGCTGGG
CCCACACTGGGCCACATAGGAGCTCACCAGTGAGGGCAGGAGAGCACATGCCGGGGAGCACCCAGCCTCCTGCTGAC
CAGAGACCCGTCCCAGAGCCCAGGAGGCTGCAGAGGCCTCTCCAGGGGGACACAGTGCATGTCTGGTCCCTGAGCAG
CCCCCAGGCTCTCTAGCACTGGGGGCCCCTAGCACAGCTGTCTGGACCCTCCCTGTTCCCTGGGAAGCTCCTCCTGA
CAGCCCCGCCTCCAGTTCCAGGTGTGGTTATTGTCAGGGGGTGCCAGGCCGTG[redacted]CACA
D5-24
GTGGTGCCGCCCATAGCAGCAACCAGGCCAAGTAGACAGACCCCTGCCACGCAGCCCCAGGCCTCCAGCTCACCTGC
TTCTCCTGGGGCTCTCAAGGCTGCTGTCTGCCCTCTGGCCCTCTGTGGGGAGGGTTCCCTCAGTGGGAGGTCTGTGC
TCCAGGGCAGGGATGACTGAGATAGAAATCAAAGGCTGGCAGGGAAAGGCAGCTTCCCGCCCTGAGAGGTGCAGGCA
GCACCACAGAGCCATGGAGTCACAGAGCCACGGAGCCCCCAGTGTGGGCGTGTGAGGGTGCTGGGCTCCCGGCAGGC
CCAGCCCTGATGGGGAAGCCTGCCCCGTCCCACAGCCCAGGTCCCCAGGGGCAGCAGGCACAGAAGCTGCCAAGCTG
TGCTCTACGATCCTCATCCCTCCAGCAGCATCCACTCCACAGTGGGGAAACTGAGCCTTGGAGAACCACCCAGCCCC
CTGGAAACAAGGCGGGGAGCCCAGACAGTGGGCCCAGAGCACTGTGTGTATCCTGGCACTAGGTGCAGGGACCACCC
GGAGATCCCCATCACTGAGTGGCCAGCCTGCAGAAGGACCCAACCCCAACCAGGCCGCTTGATTAAGCTCCATCCCC
CTGTCCTGGGAACCTCTTCCCAGCGCCACCAACAGCTCGGCTTCCCAGGCCCTCATCCCTCCAAGGAAGGCCAAAGG
CTGGGCCTGCCAGGGGCACAGTACCCTCCCTTGCCCTGGCTAAGACAGGGTGGGCAGACGGCTGCAGATAGGACATA
TTGCTGGGGCATCTTGCTCTGTGACTACTGGGTACTGGCTCTCAACGCAGACCCTACCAAAATCCCCACTGCCTCCC
CTGCTAGGGGCTGGCCTGGTCTCCTCCTGCTGTCCTAGGAGGCTGCTGACCTCCAGGATGGCTTCTGTCCCCAGTTC
TAGGGCCAGAGCAGATCCCAGGCAGGCTGTAGGCTGGGAGGCCACCCCTGTCCTTGCCGAGGTTCAGTGCAGGCACC
CAGGACAGGAAATGGCCTGAACACAGGGATGACTGTGCCATGCCCTACCTAAGTCCGCCCCTTTCTACTCTGCAACC
CCCACTCCCCAGGTCAGCCCATGACGACCAACAACCCAACACCAGAGTCACTGCCTGGCCCTGCCCTGGGGAGGACC
CCTCAGCCCCCACCCTGTCTAGAGGACTTGGGGGGACAGGACACAGGCCCTCTCCTTATGGTTCCCCCACCTGGCTC
CTGCCGGGACCCTTGGGGTGTGGACAGAAAGGACGCCTGCCTAATTGGCCCCCAGGAACACAGAACTTCTCTCCAGG
GACCCCAGCCCGAGCACCCCCTTACCCAGGACCCAGCCCTGCCCCTCCTCCCCTCTGCTCTCCTCTCATCACTCCAT
GGGAATCCAGAATCCCCAGGAAGCCATCAGGAAGGGCTGAAGGAGGAAGCGGGGCCGCTGCACCACCGGGCAGGAGG
CTCCGTCTTCGTGAACCCAGGGAAGTGCCAGCCTCCTAGAGGGTATGGTCCACCCTGCCTGGGGCTCCCACCGTGGC
AGGCTGCGGGGAAGGACCAGGGACGGTGTGGGGGAGGGCTCAGGGCCCTGCAGGTGCTCCATCTTGGATGAGCCCAT
CCCTCTCACCCACCGACCCGCCCACCTCCTCTCCACCCTGGCCACACGTCGTCCACACCATCCTGAGTCCCACCTAC
ACCAGAGCCAGCAGAGCCAGTGCAGACAGAGGCTGGGGTGCAGGGGGGCCGCCAGGGCAGCTTTGGGGAGGGAGGAA

Fig. 7 (cont.)

TGGAGGAAGGGGAGGTCAGTGAAGAGGCCCCCCTCCCCTGGGTCTAGGATCCACCTTTGGGACCCCCGGATCCCATC
CCCTCCAGGCTCTGGGAGGAGAAGCAGGATGGGAGATTCTGTGCAGGACCCTCTCACAGTGGAATACCTCCACAGCG
GCTCAGGCCAGATACAAAAGCCCCTCAGTGAGCCCTCCACTGCAGTGCTGGGCCTGGGGGCAGCCCCTCCCACAGAG
GACAGACCCAGCACCCCGAAGAAGTCCTGCCAGGGGGAGCTCAGAGCCATGAAGGAGCAAGATATGGGGACCCCAAT
ACTGGCACAGACCTCAGCTCCATCCAGGCCCACCAGGACCCACCATGGGTGGAACACCTGTCTCCGGCCCCTGCTGG
CTGTGAGGCAGCTGGCCTCTGTCTCGGACCCCCATTCCAGACACCAGACAGAGGGACAGGCCCCCCAGAACCAGTGT
TGAGGGACACCCCTGTCCAGGGCAGCCAAGTCCAAGAGGCGCGCTGAGCCCAGCAAGGGAAGGCCCCCAAACAAACC
AGGAGGTTTCTGAAGCTGTCTGTGTCACAGTC[redacted]CACAATGACACTGGCAGGACAGAAAC
D6-25
CCCATCCCAAGTCAGCCGAAGGCAGAGAGAGCAGGCAGGACACATTTAGGATCTGAGGCCACACCTGACACTCAAGC
CAACAGATGTCTCCCCTCCAGGGCGCCCTGCCCTGTTCAGTGTTCCTGAGAAAACAGGGGCAGCCTGAGGGGATCCA
GGGCCAGGAGATGGGTCCCCTCTACCCCGAGGAGGAGCCAGGCGGGAATCCCAGCCCCCTCCCCATTGAGGCCATCC
TGCCCAGAGGGGCCCGGACCCACCCCACACACCCAGGCAGAATGTGTGCAGGCCTCAGGCTCTGTGGGTGCCGCTAG
CTGGGGCTGCCAGTCCTCACCCCACACCTAAGGTGAGCCACAGCCGCCAGAGCCTCCACAGGAGACCCCACCCAGCA
GCCCAGCCCCTACCCAGGAGGCCCCAGAGCTCAGGGCGCCTGGGTGGATTCTGAACAGCCCCGAGTCACGGTG[redacted]CACTGTGAGAAAAGCTATGTCCAAAACTGTCTCCCGGCCACTGCTGGAGGCCCAGCCAGAG
D1-26
AAGGGACCAGCCGCCCGAACATACGACCTTCCCAGCCCTCATGACCCCCAGCACTTGGAGCTCCACAGTGTCCCCAT
TGGATGGTGAGGATGGGGGCCGGGGCCATCTGCACCTCCCAACATCACCCCCAGGCAGCACAGGCACAAACCCCAAA
TCCAGAGCCGACACCAGGAACACAGACACCCCAATACCCTGGGGGACCCTGGCCCTGGTGACTTCCCACTGGGATCC
ACCCCCGTGTCCACCTGGATCAAAGACCCCACCGCTGTCTCTGTCCCTCACTCAGGGCCTGCTGAGGGGCGGGTGCT
TTGGAGCAGACTCAGGTTTAGGGGCCACCATTGTGGGGCCCAACCTCGACCAGGACACAGATTTTTCTTTCCTGCCC
TGGGGCAACACAGACTTTGGGGTCTGGGCAGGGAGGACCTTCTGGAAAGTCACCAAGCACAGAGCCCTGACTGAGGT
GGTCTCAGGAAGACCCCCAGGAGGGGGCTTGTGCCCCTTCCTCTCATGTGGACCCCATGCCCCCCAAGATAGGGGCA
TCATGCAGGGCAGGTCCTCCATGCAGCCACCACTAGGCAACTCCCTGGCGCCGGTCCCCACTGCGCCTCCATCCCGG
CTCTGGGGATGCAGCCACCATGGCCACACCAGGCAGCCCGGGTCCAGCAACCCTGCAGTGCCCAAGCCCTTGGCAGG
ATTCCCAGAGGCTGGAGCCCACCCCTCCTCATCCCCCCACACCTGCACACACACACCTACCCCCTGCCCAGTCCCCC
TCCAGGAGGGTTGGAGCCACCCATAGGGTGGGCGCTCCAGGTCTCACTCACTCGCTTCCCTTCCTGGGCAAAGGAGC
CTCGTGCCCCGGTCCCCCCTGACGGCGCTGGGCACAGGTGTGGGTACTGGGCCCCAGGGCTCCTCCAGCCCCAGCTG
CCCTGCTCTCCCTGGGAGGCCTGGGCACCACCAGACCACCAGTCCAGGGCACAGCCCCAGGGAGCCGCCCACTGCCA
GCTCACAGGAAGAAGATAAGCTTCAGACCCTCAGGGCCGGGAGCTGCCTTCCTGCCACCCCTTCCTGCCCCAGACCT
CCATGCCCTCCCCCAACCACTTACACACAAGCCAGGGAGCTGTTTCCACACAGTTCAACCCCAAACCAGGACGGCCT
GGCACTCGGGTCACTGCCATTTCTGTCTGCATTCGCTCCCAGCGCCCCTGTGTTCCCTCCCTCCTCCCTCCTTCCTT
TCTTCCTGCATTGGGTTCATGCCGCAGAGTGCCAGGTGCAGGTCAGCCCTGAGCTTGGGGTCACCTCCTCACTGAAG
GCAGCCTCAGGGTGCCCAGGGGCAGGCAGGGTGGGGGTGAGGCTTCCAGCTCCAACCGCTCCACTAGCCGAGACTAA
GGAAGTGAGAGGCAGCCAGAAATCCAGACCATTCCATAGCAAATGGATTTCATTAAAGTTACCAGACTTCAGTGTAA
GTAACATGAGCCCCATGCACAACAATCCCTTATGAAGGGGAAGTCAGTGTCGCCTCGGATTTCTTGAAAAACACAAA
AACTTATCAATGCCTGTAAAAGTCTGTTGGAAAGAAAATATGATTCAAGAATGTTATGCCCAACAAAGCTGGCATAT
TTTCTACCCGGACACACTCAGGGAATGTGGTCCCTTGAGTGCTTCTCTCACTGCGTAAATCCTACGTGGTGTTTAAG
CATATTCATAAATGTGTATGTCTATTTTTATGTGTAAGATGGTTCATTTTTATTTTATTTATTCAATATGTACAATA
AAGAATATTGACAAATAGGCTGGACATGGTGGCTCCCACCTGTAATCCCAGCCCTTTGGGAGGCCGAGGCGGGCAGA
TCACCTGAGGTCTGGAGTTCGAGACCAGCCTGGCCAACATGATGAAAACCCATCTCTACTAAAAATACAAAGATTAG
CCAGGCATGGTGGTGCATGCCTGTAATCCCAGCCACTCAGGAGGCTGAGACAGGAGAAATGCGTGAACCCGGAAGGC
GGAGGTTGCAGTGAGCCGAGATCACACCACTGCACTCCAGCCTGGCGACAGAGCAAGATTCCATCTCAAAAAAAAAA
AAAGACAAAGAAATTTGTTTTTTTGAATAAAGACAAATTTCATCACACGAAGATAAAGATGCAAAGCTCCAGACAGG
AAGGCACGGACAGCACAGTGAAGCCCGGAGCGGGCGCTGGGGGGCCAGGGGCATGGCGGGGGTGCCAGCGTCTCTCG
GTGCCTACCATGGCCACTCCAGCCTGTGTTCTCACGAGGATGGCTGTGCAATGCTAGGAGCGTGTTCGAAGCTCTAG
GGCAACCACTGGAAGTGAGGCTGAGGAGCAGAGCCCAGAGGCCCGTGGAGCTGATGAAAAGAAAGCTGGAGAAAGTG
TTTGCTGCCTCCCAACATGGTAAGAAAAGATAGAAAGAGAGAGCACACGGCAAAGGGAGCTTGCTGAGGGACTCTTT
ACAATGGCTTGCACAGAGCTCAGGGGGTCTGGGAGGCTAGGGCCCTGCGCAGGGCAGTCACCCCAGCCTGCTGACCA
AGGTTTGCTGCAGGCAGCTCTGGGGGTGGTTGAGGCGCGGTCCCTGGAGCCACCCCTCAAGGGAACGAGGCAGCAGA
GTGGGCCAAGGCCCAGGTCGGCTGCAAGGCTGCCCAGGACTTGGGGTCCTTACATCAGCAGCCACTGATGCAGCTGG
CCCAGAGAGAGGCGCCGAGCAGGTTGCCTCCAGGGGACAAACCAGGTCGGAGAGGGTGAGGCAGTGGATGGAGCCAC
AACAACCCCGGGCACGGGTGACACGCACGTTCATGCACATCTGACCCTTCCTCCCTCACCAAACAGGTCCCCCTGCC

Fig. 7 (cont.)

TTCCCCATGGTTGCGAAAAAGCAAAATGTAGACGTTTTTTCTTTTTTAATTCATGTTTTAATTGACAAATGAAGCCG
TATATATTTATTGTGTACAACATGATGCTTTAAAATATGTATACATCGTGGAACAGCAACGTTGAGCTAATTTAACA
CGCATTACTTCACATACTTGTCATCTTTTGTGGCGAGAATGCTTAAAATCCACTCTCTTAGTATTTTTTAAGAATGC
AATACATTGTTGTCAACTGTGGTCACCGTCATGCATAGCCAAGCTCCCGACCTCACCCTCCTGCCAGCTCAGGCTGT
GCATCCTTTCACCAGCATCCCCCACCCCGGCCCCTGGCCCTGGTAACTACCACTCTATACTCTACGTATGAGTTCAG
CTTTTTAAGATTCCACAGATGAATGAGATCATACAGTATTTGCTTTCTATGCCTGGCTTATTTTAGTTAACACACTG
TCCTCCAGATCCATCCGTTGTTGCAAATGACAGGGTTTCATTCTTTTTAAAGTCTAAAGAGTATTCCATTGTGTCAA
TGGACCTCATTTGCTTTATCCATGCATCAACTATGGACATTTAGGTTGATTCCATTTCTTAGCTGTTGTGGATGGTG
CTGCAGTAAACATGGGGCTGCAGATGTCTCTTCAACATACTGACATCATGTCCTTTGGATAAATACCCAGTAGTGGG
ATCGCTGGATCACAATGTACAGTTTGTTTTTTAATGGAAACTTTCATTTTTTGGTGAAATTAGGAAAACAGATAAAA
CCCACAGAATCCAAAATATATGTGAAGATGCCAAAAACAGTTGACATTGGGCAGAGGTCACATGGAAGGAAGTGAAT
ACATGACGGGGTGTGAGGGCCCAGAGGCAGCTGAAATACGCTTTCTAAACACAAGGACCTCTTCTGAGAGGGCAGAA
GTTTTATCCTGCACATGCAATGACCAGCACAGCTAAAATACACTTTCTAAACATGAGGACCTCTTCTGAGAGGGCAG
CTTTATCCTGCAAATGCAATGACCAGCACAGGACCCAGAATAAAGAGAGTTGCCAGCGGACGCCTGGTGTCCATGTG
TCCAGGTGAGTTCGAGATGCGGACGGCGCTGGCCAGCCAGTCACACCCTAAGTCAATCTGCTGCATGCATTTGTCCT
TGCCACAGCAGAAAACGAGAAAGCCTTTGGGCTGCAAAGCTTCACAGGCTCCTCTTCTCCCGACTCCATGGAAACAG
CTACAAAGAGCAGGCCCAGTAGAGCTTAATTCATGAAAATGAGTAATAAACTTGAACTGGAACAGTATCGACTTTTT
AGAAACGGCAGCAAAGTGTATAAAAAATATTCACCAGAACAATATTTCCAAACGATGAGATGAGAATTTCAGCCAAG
TAATCCTCCATGGATAGAAAATAATGAAGGGATTGGATTTATGAAGGAAAATCATGGAGCTCAAATACAAGAGAAGA
GAATCAAAAATGAACAGGAGGAGATAAAATATGGTTTGGCCAAAGTTACAAAATAAATTTTTTAAAAACCCTTCATC
ATGGCAAGTAGAAAGAGCGAGAGGAAAAACAGATCCCGTGGAAGACACAAATAGGACATGGGGAGAAAAATGAATGA
GATGAAACAGAGCAGAAATAAAATTTTACGGAACTAAAGACAAGTGATCTGAACCTGCCTGGGGCCTGGGGGACCTC
GCCACCCTGAAGGGAAAGAACATGCCTGGCTGGCTTTGCCACCTGCTCATTGCAGAGCCCCACAGCTTGCAACAAAC
ATAGGCGGTAGCCAGGGAGTGGTTACAGCAGGCCTTGAGCAAGACCCAGTGTTGTGCTGACTTCAGGTCTGACCCAG
CACTGTCATAGTGGTGGTGTCCATAGTGGTAGTGGGGGTGCTTGTGTCACTCCACCCCCATCTCCAGGAGGCTCAGA
ACAGACAGAGAGAGACTCCATTTGTTTGGGAGAAAGTAAGGGATGAGAACAAGAGTCTCTGCCTGGTAATCCAGAGA
ATTATTCTAGATCTTGGCCAAGATTATCAAAGCAGTACCTCTATGAGTCTTTTGGGCTTGGAGTCCCCCTAAAGCAG
ATATAGCTAAGATCACAACACCCAAGTCCTTTTGAATATGTGGGAAGACTTCCCAAGGACAGGAGCAAACAAACAAG
CCCAGACTGCAAAAAAACAAGCCCAGACTGCAATAAACACCTCACTCTTCAATGCCCAGGCACTGAAGAACATCTCC
TAGCAGCAACACCATCCAGGAAAACATGGCCTCAACCAGTGAACTAAATAAGGCACCAGGGACCAGTCTCGGAGAAA
TAGAGGTATGTTATCTTTCAGAGAATTCAAAGTAGCTTTGTTGAGGAAACTCAAAGAAATTCAAGATAACACAGTGA
AGGAATTCAGAATCCTATCCGATAAATTTAACAGAGATTGAAGCAATTAAAAAGAATTAAGCAGAAATTATGGAGCT
GAAAAATGCAATTGGCATACTGAAAAATGCATCAGAGTATTTTCATAGCCTCTTATATCAAGTAGAAGAAAGAATTA
GTGAGCTTGAAAACAGGCTATTTGGAAAAGCACGATAAAAGGAGACAAAAGAGAAAAGAATAAATAACAATGAAGCA
TATCTACAGGATCTAGAAAATAGCCTCAAAAGGCCAAATCTAAGAATTATTAGCCTTAAAGAGGAGGTAGAGAAAGA
GGGATGGAGAGTTTATTCAAAGGGATAATAACAGAAAACTTCCCAAACCTAGAGAAAGATATCAATATCCAAATGCA
AGAAGGATGTAGTACACCAAGGAGATTTAATGCAAAGAAGACTACCTCAAGGCATTCAATACTCAAACTCCCATATG
ACAAGGACTTTAAAAAGATCCTAAAAGCAGCAAAAGAAAAGAAATGAATAAAATACTATGGAGCTCCAATATGTCTG
GCAGCAGACTTTTCAGTGAAGACTTTATATGCCAGGAGAGAGTGTCATAATGGATTTAAAGTGCTGAAGGAAAAAAC
TTTTACCCTCGAACAGTATAGCTGGTGAAATTATCCTTCAAACATGAAGGAGAAATAATTTGTTTCCAGACAAATGT
TGAGGGATTTCATGAACACCAGACCTGTCTTTTAAGAAATGCTAAAGGGAGTACTTCAATCAGAAAGAAACACGTTA
GTGAACAATAAGAAATCATCTGAAGGCACAAAACTCACCGGTAATAGTAAGTACACAGAAAAACACAGAATATTATA
ACACTGTAACTGTGGTGTGTAAACTCCTTTTGTTTGTTTGTTTGTTTGTTTGTTTGTTTTTGTTTTTAGACGGAGTT
TTGCTCCAGCCCAGGCTGGAGTGCAATGGCACAATCTCAGCTCACTGCAACTTCCACCTCCCGGGTTCAAGCAATTC
TCCTGCCTCAGCCTCCCAAGTAGCTGGGATTACAGGCATGTGCTACCATGTCCAGCTAATTTTGTATTTTAGTAGAG
ACGGTGTTTCACCATGTTGGTCAGGCTAGCCTTATCTTGAGTAGAAAAACTAAATGATGAAGCAATGAAAAATAATA
ACTACAACTTTTCAAGACATAGTACAATAAGATATAAATCATAACAAAAAGTTAAAAGGTGGAGGGATGAAGTTAAG
GCAAAGAGTCTTTATTAGTTTTCTTTTTACTTGTCTGTTTATGCAAACAGTGTTAAGTTGTCATCAGTTTAAAATAA
TGGGTCATAAGATACTATTTGCAAGCCTCATGGTAACGTCAAACCAAAAGCAATACAACAGATACACAAAAAACAAA
AAGCAAGAAGCTAAATTACGTCATCAGAGAAAATCACCTTCACTAAAAGGAAGACGGAGAAAAGAATGAAGAGAGAG
AAGACCAAAAGCAAATAGCAATATGGCAGGAGTAAGTCCTTACTTATCAATAATACCATTGAATGTAAATGGACTAA
ACTCTCCAATCAAAAGACATAGAGTGGCTGAATCAATTAAAGAAAAAACAAGACCCATTGATCTGTTGTCCACAAGA
AACACACTTTATCTATAAAGACACACATAGACTGAAAACAAAGGGATGGAAAAAGATACTCCACGCCAATGGAAACC
AAAGAAAGAGCAGGAGTAGCTACACTTATATCAGGCAAAATAGATTTCAAGACAAAAACTATAAGAAGAGACAAGGT

Fig. 7 (cont.)

CACTAATGATAAACAGGTCAATTCAGCAAGAGGATATAACAATTGTAAATATATATGCACCCAATGCTGGAGCACCC
AGATATATAAAGCAAGTATTTACTAGAGCTAAAGAGAGAAATAGACTCCAATGCAATAATAGCTGGAGATTTCAACA
TCCCACTTTCAACATTGAACAGATCCTCCAGATAGAAAATCAACAAAGAAATATTGGACTTAATCTGCACTATCGAC
CAAATGGATCTAACAGATATTTACAGAACATTTCATCCAACAGCTGCAGAACACACATTCTTTTCCTCAGCACATAG
ATCATTCTCAAGGATAGACCATATGTTGGGTCACAAAACAAGTTTTAAAATATTCAAATACATTGAAATAATATCAA
GCATCTTCTGTGACCACAATGGACTAAAACTAGAAATCAATAACAAGAGGAATTTTGGAAACTATATAAATATATGG
AAATTAATGAATGCTGAGTGGGTCAATGAAGCAATTAAGAAGGAAACTGAAATTTTTCTTGGAACGAATGATCATGG
AAACAGAAAATACCAAAACCTATGGGATACAGCAAAAGCAGTACTAAGAGGGAAGTTTACAGCTACAAATGCTTACA
TTAAAAAAGAAGAAAAACTTCAATAAAAAAACCTAACAATGCATCTTAAAGAACTAGAAAAGCAAGAGGAAATCAAA
TCCAAAATTAGTAGAAGAAAACAGTAAAGGTCAGAGCAGAAATAAGTAAAATTGAAATGAAGAAAACAATACAAAAG
ATCAATAAAACAACAGGTTGTTTTCTTGAAAAGTTAAACAAAATTGACAAACCTTTAGCCAGACTAAGAAAAAAAGA
CAGAAGATCCAAATAAATAAAATCAGAGATGAAAAAGGTGACATTACAACTTACACCACAGAAATTCAAAGGATCAT
TAGTGGCTACTATAAGCAACTATATGCCAATAAATTGGAAAATCTAGAAGAAATGCAGAAATTCCTAGACACATACA
ACCTCCCAAGATTAAACCAAGAAGAAATTCAAAACCTGAACAGACTGATAACAAGTAATGAGATCAAAGCCGTAATA
AAAAGCCTCCCAGTAAAGAGAAGCCCAGGACCCGACGGCTTCACTGCTGAATTCTACCAAACATTTAAAGTAGAACT
AATACCAATCCTACTCAAACTATTCCAAAAAATAGAGGTGGAAGGAATACTTCAAAACTCATTATACGAGGCCAGTA
TTAACCTGACACCAAAACTAGACAAAGACACATGAAAAAAAGAAAACTACAGGCCAATATGTCTGATGAATATTGAC
ACAAAAATCCTCAACAAAATACTAGCAAACCAAATTCAACTACACATTAGAAAGTTCACTCATCATGACCAAGTGGA
ATTTATCTAACTTGGGATGCAAAGATGGTTCAACATATGCAAATCAATCAATGTGATACATCATATCAACAGAATGA
ACAACAAAAACCATTTGATCATTTAATTGATACTGAAAAAGCATTTGATAAAATTCAACATTCCTTCATAATAAAAA
TTCTCTTCTATACTAGGTACAAAAGAAACTTACCTCAACATAATAAAGCCATATATGACAGTCCCACAGTATGATAC
TAAATGAGGAAAAACTGAGAGCCTTTCCTCTACGATCTGGAACATGACAAAGATGCCCACTTTCATCACTGTTATTC
AACATAGTACTGGAAGTCCTAGCTGGAGCGATCAGACAAGAGAAAGATATAAAAGACATCCAAATTGGAAAGGAATA
AGTCAAATTATCCTCATTTGCATATGGTATGATCTTCTATTTAGAGCTAACTAAAGACTCCACCAAAAAAAGTTATT
AGAACTGACGAACAAATTCAGTAAAGCTGCAGGATACAAAATCAACATACAAAAATCAGTAGCATTTCTATATGCCA
ACAATGACCAATGTGAAAAAGAAATTAAAAAGTAACCCTATTTACAATAACCACAAATAAACACCTAGGAATTAACC
AAAGAGGTAAAAGATTTCTGTAATGAAAACTATAAAAAACTGATGAAAGAAATTGAAGAGTACACCAAAAAATGGAA
AGCAATTGCATGTTCATGGATTAGAAGAATCAGTGTTGTTATAATGTCCATACTATCCAAAGCAATCTACAGATTCA
ATGCAATCCTTATCAAAATACCAATGACATCATTCACAGAAATAGAAAAAAAAAATCCTAAAATTTACGTGGAACCA
CAAAGACCCAGAATAGCCAAAGCTCTCCTAAGCAAAAAGAACGAAACTGTAGGAATGACATTGCCTGTCTTCAAATT
CTACTACAGAGCTATAGATAGTAACCAAAACAGCGTGGTACTAGCATAAAAACAGACACAGAGACAAACAGAACAAA
ATTTAAAAACCCAGAAATAAATCCACACACCTACAGCAAATTCATTTTTGACAAAGTTGCCAAGAACATACTCTGGG
GAATAGATAATGATATCTCTTCAATAAATAATGTGGGGAAAACTGGATATCCATATACATAACAGTGAAACTAGACC
CCTCTCTCTCTCACTATATACAAAAATCAAATCAAAATTGTTTAAGGACTTAAATCTAAGACCTCATACTATGAAAC
CACTGCAAGACAACCTTGGCGGAAACTCTCCAAGACATCAGTCCAGGCAAAGATTTCTTGAGTAATATCCCACAAGC
ACAGACAACCAAAGCAAAAATGGACAAATGGGATCACATCAAGTTAAAAAGCTTCTGCACAGTAAGGGAAACAACCA
ACAAAATGAAGAGACAACCCACAGAATGGGAGAAAATATTTGAAAAATACCCATCTGGCAAGGGATTAAAAACCAGA
ATATATGCAGAATATATAAGGAGCTCAAACAGTGCTATAGAAAAAAAAATCTAATAATCTGATTTAAAAATGGGAAA
AATGTTAGAATAGACATTTCTTAAAATAAGACATACAGATGGCAAACCGACATGGAACGGTGCTCAACATCATGGAT
TATCACAGAAACACAATCAATCAAAACTAAAACTAAAATGTGCTATCATCTCACCCCAGTTAAAATGGCTGATATCC
AGAAGACAGGCAATAACAAATGCTGGCAAGGATGTGGGGAAAAGGGAGCCCCCATACACTGTTGCTGGGATTGTAAA
TTAGTACAACCACTGTGGAGAGCAGCATGAAAGTTCCTCAAAAAACTGAAAGAAAGCTACCATAGGATCCAGCAATC
CCACTGCTGTGTATATACTACAAAAGAAAGGAAGTCAGTATATGAAGAGGTATCTGCACTCCCATGTTTGTTGCAGC
CCTGTTCACAACAGCCAAGATTTGGAAGCAACCTAAGTGTCCATCAGCAGTTGAATGTATAAAGAAAATGTGGTGCA
TATACACAATGGAGTATTATTCAATAATAAAAAGGAATGAGATTGAGTCATTTGCAACAACATGGATGGAACTGGAG
ATCATTATGTGAAGTGAAATAAGCCAGGCACAGAAAGACAAACATTACAATGTTCTTACTTATTAATGAGATCTAAA
AATCAAAACAATTGCACCCATGTTCATAAAGAGTAAAAGGATGGTTACCAGATGCTGAGAACGGTGGTGGGGGGATA
GGGAAAGGTGGCAGTGGTTAACGGGTACAAAAAAATAGAAAGAATGAATAAGACTTACTACTTGATAGCACAGCAAG
GTGGCTATAGTCAGTAATTTAGTTGTATATTTTTAATAATGAAAGGTGTATAATTGGATTGTTTCTAACACAAAGGA
TAATGCTTAAGAGGATGGATACCCCATTTTCCATGATGTGATTATTTCACATTGCACGCCTAGATCAAAACATCCAA
TGTACCCCATAAATATATACATCTTCTATGTACCCATAAAAATTCTGTAAAATAAAATATATAAAAAGAGGTGACAG
ATATGGAAGACAGGCAAAGAAGAGACGACATCCACATAATCCGAGTACCTAAGAAAGAATGGAGTCCAGTGCATCTC
AGGAGCCACCATTCTAAGCCAATTTTCTCTGGTTCTCTCAGTCACCCTACCAATACGTGGGCAATCTTGTTTTATTT
CAGGATAGAGTTTTTGAAATTATAGATTTAAGTATGCTTTCTGTTCTATTACTTTTGGTAATTAATTTAGAAAGAA

Fig. 7 (cont.)

CTAATTTGGGCACAAATTTGAAAAAATTCTAAATCCAAAAAAAAAAAGAAAAAAACACACACACAATCATCTATAAG
GGGGATGATGACCAGTCCTAGATTTCTCACCAGCCACATTCAAGATCAGTAAATGGTAGGACAAAACCTGTAGGGTC
CTTAAGGGGGAAAGAAGTAGTGGATAGTCCAGAGTCTATATACAGCCAACTGTTCTTGAAGAAAAAAGGCTGCTGAA
AAGGAGTTCCAAACATTCTATAATCCATAATCTCATGATGAAACTACTAGAGGAAGACCACCAGCCATCAAAAGGTG
CTTGGAGAACCCAGGGCCAAGAACCAAAAGTAAATATTAAGTGTCCTTAACTGCGAGACTAAGATAGAAATGACTGT
GGGGGACCATGTGGCCTCAACAGAGGTGAAATGGTGTCTGCCTGACAAAGTGGACATTTTACAATGATCAAAACACA
GAATATGAGATAGAGAGCACTTCTGAATTACTGCCTCACTCCAAATAACTCTCAGCCAAAGGACTTCAGTAAAACCA
AATTGGGCATATTAGACAGTACAAACAAATTCTAAGAAAATAATATTACTGATTACAATCACATGATGCTAGAGATG
GAGGGGAAAAGGAAGAGGAAACCAGGTAATTTCATACTCGTATATAGTAAAGAACTAAAGTACATTGTCCAAAGAAG
AACAAAGAATATTTTGGAAAGTTATAAAGGTAGCCACTACACATAGAAGATAGCAAAGAACAAGAAAACTTAAGATG
GAAAACTTTTTGGAAGCATAAAAATAGAAAATATAAACTACTAAGATAAGATTGAAGCCAAACAGATCTATGAAAAC
AACAAACATCAATGGCCTTAACTTGCCTATTAAAAGGAAGAGACTTTCAAATTGGACCACAAGATAAAACCCAACTC
TATATAGCATATGAGTATTACACACAAAATGGGAAAAGCTGAAAAAACTTGGGCAAAATTCACCCCAAGCAAATTCC
ACTGTTTCCTTTGGACAAAATGCCAAGCTCCATGCCAGGGAAGATGATTCTCCTCAGACCTTCTCCTCACTCTCCC
AGTCCTCTTAGGGAAGGAATTGGGTGTTAGAGGAGGGAGACTCTGTCGATTATCAGCTGAAGCAGTGGTGTGCTCCT
GCGTTGCTTCTGACCTGGGAAATGAAGCAGCAAGACTCTTTCTGCTGTGTCTTTGCCCAGAAGGGCCATCCCCCCAG
AGCAGAGTACCCAGGCCGGCAGGAGCAGTGGTGGAAGCGTGGAAACCACGTCTCCTACAGCAGAGACCATCAGAAGC
GGAGCCTCGGGTATAAGGGAAACAACGCGTTCTCCCTAACCTGGGAGTGACAGACAGCGTCATTCCTCACAGTGATA
CCCTGTGTTCTAGCCATCTGGCCCATGACAGAGCCAGCCCAGAGCCAGCCCAGAGCCAGCCCCTGACCATCCTGGAG
CCTGGCCAGCTCGCCAAGCTGCACCATAGGCCTGGAAGGCGTGGAGACCTGCGGCAGTGCCCTGTCCTCCCGTGAGG
CCTGCCATCCCTGCCAGGGGTCGCCTCTGGCTTCTCCTTCTCCAGGACCGCACGGTCCAGAGGCTCAGTGCCTGGAG
TAGGTGTTGCCTCCCTGCTTCTAGGCCCAGACCCTCCCTTGTTCCTGACCCCGGGCCTTTCCCTCTGGCTTGGACAT
CCAGGGCCCTGTCTCAGCTGGGGAGCTGCTCCTGCTCAAGGACTGTCTTCCGCGGGATCGAAAGGCCGCGTCCTGAA
CAATGCGTGGGCCACGTGAGCGGAGCAGGCTCTAAAGGCCGCGTCCTAAACAGTGCGTGGGCCACGTGAGCGGAGCA
GGCTCTAAAGGCCGCGTCCTAAACAGTGCGTGGGCCACGTGAGCGGAGCAGGCTCTAAAGGCCGCGTCCTAAACAGT
GCGTGGGCCACGTGAGCGGAGCAGGCTCTAAAGGCCGCGTCCTAAACAGTGCGTGGGCCACGTGAGCGGAGCAGGCT
CTAAAGGCCGCGTCCTAAACAGTGCGTGGGCCACGTGAGCGGAGCAGGCTCTAAAGGCCGCGTCCTAAACAGTGCGT
GGGCCACGTGAGCGGAGCAGGCTCTAAAGGCCGCGTCCTAAACAGTGCGTGGGCCACGTGAGCGGAGCAGGCTCTAA
AGGCCGCGTCCTAAACAGTGCGTGGGCCACGTGAGCGGAGCAGGCTCTAAAGGCCGCGTCCTAAACAGTGCGTGGGC
CACGGGAGCGGAGCAGACTCTAAAGGCCGCGTCCTAAACAGTGTGTGGGCCACGTGAGCGAAGCGCCCTCTCCACTG
CCCTCGGGGCCGCAGCTCCCAGCTCAGCTCCCAGCCCTGCTCAGGGCAGCCAGGCCAGGAGGTACCATCCAGGCTAA
GTGACCCTCAGGGGGGACAGGTGCCCCAGGAGATGCCAGCTGTTGGGAGAGGCTGGGGGACCAACTCGACCTGGCCT
GTGGGCCCTGCCCTGGCCACCCATTGTAGGATCCAGCCGCCACGCCTGTGACACTCGTGTGCTTTCCCTGGTGTGTG
CTTGTGGCAGGTGGGGGCAGAGGGTCCTCAGGCCAGAGAGCCACTCCCCCAGCGCCAGACCACCCTCTTCCTCACTC
CCCCACCTCACCCCCTCACAGGTGCCTCCCAGGCCATCAGGGCCCAACCACCCCTAAACAAATGGGTTCTCGGCCCC
TCGTGGCTGGAGGTGGGTTCTCTCACCATTCCCAGCCTAAGACTCCATCCCCATGCTGGCAGCTGTTCAACCATGTC
TAGAGAGATCCACTGTCCCAGACAGCACCTCAGGGTCCCCCGTCCTGCCTGGAACCCTGTAGGAAACTCCACAAACC
GCCGCCATTCTGTCCACACCCCTACAGGAGCCCCAACCCTCTCCCCACATCCAGGCTTCCCTCCCAGACCCCTCATC
CCTGCCCGCACGGTGCCTGAGGGGGCCTTCTTGGGCAGCGCCTAAGCAAGCCCCCAGCACCCTTCGGCCCCTTCAAG
GCACACAGGCCCCCTTTCCACCCAGCCTCAGGAAACCACCTGTGTCCTCCAACGACAGGTCCCAGCCTCCCAGCCTT
TGCCTTGCCTGTTCCTCTCCCTGGAACTCTGCCCCGACACAGACCCTCCCCAGCAAGCCCGCAGGGGCACCTCCCCT
GCCCCCAGACACCCTGTGCCCGTCAGTTCATCCCCAGCAGAGGCCCTCACCAGGCACACCCCCATGCTCACACCTGG
CCCCAGGCCTCAGCCTCCCTGAGGGCCCCACCCAGCCCGCGTCTGGCCAGTGGTGCGTGCAAAGCCCCTCACCCAGA
CTCGGCGGAAGGCAGCCAGTGCAGGCCTGGGGAGGGGCTCTCCTTAGACCACCTTGCACCTTCCCTGGCACCCACCA
TGGGAAGAGCTGAGACTCACTGAGGACCAGCTGAGGCTCAGAGAAGGGACCCAGCACTGGTGGACACGCAGGGAGCC
CACGCCAGGGCGCCGTGGTGAGTGAGGCCCAGTGCCACCCACTGAGGCCTCCCGTTCAGTGGACGACGGTGAACAG
GTGGAACCAACCAGGCAACCCCCGCCGGGCCCCACAGACGGGATCAGAGCAGGAAAGGCTTCCTGCCCCTGCAGGCC
AGCGAGGAGCCCTGGCGGGGGCCGTGGCCCTCCAGGCGAGGAGGCTCCCCTGGCCACCGCCACCCGGGCCTCTCTGC
TGCTGGGAAAACAAGTCAGAAAGCAAGTGGATGAGAGGTGGCGTGACAGACCCAGCTTCAGATCTGCTCTAATTTAC
AAAAGAAAAGGAAAAACACACTTGGCAGCCTTCAGCACTCTAATGATTCTTAACAGCAGCAAATTATTGGCACAAGA
CTCCAGAGTGACTGGCAGGGTTGAGGGCTGGGGTCTCCCACGTGTTTTGGGGCTAACAGCGGAAGGGAGAGCACTGG
CAAAGGTGCTGGGGGCCCCTGGACCCGACCCGCCCTGGAGACCGCAGCCACATCAGCCCCCAGCCCCACAGGCCCCC
TACCAGCCGCAGGGTTTTGGCTGAGCTGAGAACCACTGTG[redacted]CACAGTGATTGGCAGCTCTACAAAAA
D7-27

Fig. 7 (cont.)

CCATGCTCCCCCGGGACCCCGGGCTGTGGGTTTCTGTAGCCCCTGGCTCAGGGCTGACTCACCGTG[redacted]
GTGAGTCTGCTGTCTJ1GGGGATAGCGGGGAGCCAG
JH1
GTGTACTGGGCCAGGCAAGGGCTTTGGCTTCAGACTTGGGGACAGGTGCTCAGCAAAGGAGGTCGGCAGGAGGGCGG
AGGGTGTGTTTTTGTATGGGAGAAGCAGGAGGGCAGAGGCTGTG[redacted]
GTGAGTCCCACTGCAGCCCCCTCCCAGTCTTCTCTGTCCAGGCACCAJ2GGCCAGGT
JH2
ATCTGGGGTCTGCAGCCGGCCTGGGTCTGGCCTGAGGCCACACCAGCTGCCATCCCTGGGGTCTCCGCCATGGGCTG
CATGCCAGAGCCCTGCTGTCACTTAGCCCTGGGGCCAGCTGGAGCCCCCAAGGACAGGCAGGGACCCCGCTGGGCTT
CAGCCCCGTCAGGGACCCTCCACAGGTAGCAAGCAGGCCGAGGGCAGGGACGGGAAGGAGAAGTTGTGGGCAGAGCC
TGGGCTGGGGCTGGGCGCTGGCTGTTCATGTGCCGGGGACCAGGCCTGCGCTTTAGTGTGGCTACAAGTGCTTGGAG
CACTGGGGCCAGGGCAGCCCGGCCACCGTCTCCCTGGGAACGTCACCCCTCCCTGCCTGGGTCTCAGCCCGGGGGTC
TGTGTGGCTGGGGACAGGGACGCCGGCTGCCTCTGCTCTGTGCTTGGGCCATGTGACCCATTCGAGTGTCCTGCACG
GGCACAGGTTTGTGTCTGGGCAGGAACAGGGACTGTGTCCCTGTG[redacted]
GTAAGATGGCTTTCCTTCTGCCTCCTTTCTCTGGGCCCAGCGTCCTCTGTCCTGGAGCT
JH3
GGGAGATAATGTCCGGGGGCTCCTTGGTCTGCGCTGGGCCATGTGGGGCCCTCCGGGGCTCCTTCTCCGGCTGTTTG
GGACCACGTTCAGCAGAAGGCCTTTCTTTGGGAACTGGGACTCTGCTGCTGGGGCAAAGGGTGGGCAGAGTCATGCT
TGTGCTGGGGACAAAATGACCTTGGGACACGGGGCTGGCTGCCACGGCCGGCCCGGGACAGTCGGAGAGTCAGGTTT
TTGTGCACCCCTTAATGGGGCCTCCCACAATGTG[redacted]
GTGAGTCCTCACAACCTCTCTCCTGCTTTAACTCTGAAGGGTTTTGCTGCATTTTTGGGGGGAAATAAGGGT
JH4
GCTGGGTCTCCTGCCAAGAGAGCCCCGGAGCAGCCTGGGGGGCTCAGGAGGATGCCCTGAGGCAACAGCGGCCACAC
AGACGAGGGGCAAGGGCTCCAGATGCTCCTTCCTCCTGAGCCCAGCAGCACGGGTCTCTCTGTGGCCAGGGCCACCC
TAGGCCTCTGGGGTCCAATGCCCAACAACCCCCGGGCCCTCCCCGGGCTCAGTCTGAGAGGGTCCCAGGGACGTAGC
GGGGCGCCAGTTCTTGCCTGGGGTCCTGGCATTGTTGTCACAATGTG[redacted]
GTGAGTCCTCACCACCCCCTCTCTGAGTCCACTTAGGGAGACTCAGCTTGCCAGGG
JH5
TCTCAGGGTCAGAGTCTTGGAGGCATTTTGGAGGTCAGGAAAGAAAGCCGGGGAGAGGGACCCTTCGAATGGGAACC
CAGCCTGTCCTCCCCAAGTCCGGCCACAGATGTCGGCAGCTGGGGGGCTCCTTCGGCTGGTCTGGGGTGACCTCTCT
CCGCTTCACCTGGAGCATTCTCAGGGGCTGTCGTGATGATTGCGTGGTGGGACTCTGTCCCGCTCCAAGGCACCCGC
TCTCTGGGACGGGTGCCCCCCGGGGTTTTTGGACTCCTGGGGGTGACTTAGCAGCCGTCTGCTTGCAGTTGGACTTC
CCAGGCCGACAGTGGTCTGGCTTCTGAGGGGTCAGGCCAGAATGTGGGGTACGTGGGAGGCCAGCAGAGGGTTCCAT
GAGAAGGGCAGGACAGGGCCACGGACAGTCAGCTTCCATGTGACGCCCGGAGACAGAAGGTCTCTGGGTGGCTGGGT
TTTTGTGGGGTGAGGATGGACATTCTGCCATTGTG[redacted]
GTAAGAATGGCCACTCTAGGGCCTTTGTTTTCTGCTACTGCCTGTG
JH6
GGGTTTCCTGAGCATTGCAGGTTGGTCCTCGGGGCATGTTCCGAGGGGACCTGGGCGGACTGGCCAGGAGGGGACGG
GCACTGGGGTGCCTTGAGGATCTGGGAGCCTCTGTGGATTTTCCGATGCCTTTGGAAAATGGGACTCAGGTTGGGTG
CGTCTGATGGAGTAACTGAGCCTGGGGGCTTGGGGAGCCACATTTGGACGAGATGCCTGAACAAACCAGGGGTCTTA
GTGATGGCTGAGGAATGTGTCTCAGGAGCGGTGTCTGTAGGACTGCAAGATCGCTGCACAGCAGCGAATCGTGAAAT
ATTTTCTTTAGAATTATGAGGTGCGCTGTGTGTCAACCTGCATCTTAAATTCTTTATTGGCTGGAAAGAGAACTGTC
GGAGTGGGTGAATCCAGCCAGGAGGGACGCGTAGCCCCGGTCTTGATGAGAGCAGGGTTGGGGGCAGGGGTAGCCCA
GAAACGGTGGCTGCCGTCCTGACAGGGGCTTAGGGAGGCTCCAGGACCTCAGTGCCTTGAAGCTGGTTTCCATGAGA
AAAGGATTGTTTATCTTAGGAGGCATGCTTACTGTTAAAAGACAGGATATGTTTGAAGTGGCTTCTGAGAAAAATGG
TTAAGAAAATTATGACTTAAAAATGTGAGAGATTTTCAAGTATATTAATTTTTTTAACTGTCCAAGTATTTGAAATT
CTTATCATTTGATTAACACCCATGAGTGATATGTGTCTGGAATTGAGGCCAAAGCAAGCTCAGCTAAGAAATACTAG
CACAGTGCTGTCGGCCCCGATGCGGGACTGCGTTTTGACCATCATAAATCAAGTTTATTTTTTTAATTAATTGGCGC
GCGCCCTCTGTGACAGCATTTATACAGTATCCGATGCATAGGGACAAAGAGTGGAGTGGGGCACTTTCTTTAGATTT
GTGAGGAATGTTCCGCACTAGATTGTTTAAAACTTCATTTGTTGGAAGGAGAGCTGTCTTAGTGATTGAGTCAAGGG
AGAAAGGCATCTAGCCTCGGTCTCAAAAGGGTAGTTGCTGTCTAGAGAGGTCTGGTGGAGCCTGCAAAAGTCCAGCT
TTCAAAGGAACACAGAAGTATGTGTATGGAATATTAGAAGATGTTGCTTTTACTCTTAAGTTGGTTCCTAGGAAAAA
TAGTTAAATACTGTGACTTTAAAATGTGAGAGGGTTTTCAAGTACTCATTTTTTTAAATGTCCAAAATTCTTGTCAA
TCAGTTTGAGGTCTTGTTTGTGTAGAACTGATATTACTTAAAGTTTAACCGAGGAATGGAGTGAGGCTCTCTCATA

Fig. 7 (cont.)

ACCTATTCAGAACTGACTTTTAACAATAATAAATTAAGTTTCAAATATTTTTAAATGAATTGAGCAATGTTGAGTTG
GAGTCAAGATGGCCGATCAGAACCAGAACACCTGCAGCAGCTGGCAGGAAGCAGGTCATGTGGCAAGGCTATTTGGG
GAAGGGAAAATAAAACCACTAGGTAAACTTGTAGCTGTGGTTTGAAGAAGTGGTTTTGAAACACTCTGTCCAGCCCC
ACCAAACCGAAAGTCCAGGCTGAGCAAAACACCACCTGGGTAATTTGCATTTCTAAAATAAGTTGAGGATTCAGCCG
AAACTGGAGAGGTCCTCTTTTAACTTATTGAGTTCAACCTTTTAATTTTAGCTTGAGTAGTTCTAGTTTCCCCAAAC
TTAAGTTTATCGACTTCTAAAATGTATTTAGAATTCATTTTCAAAATTAGGTTATGTAAGAAATTGAAGGACTTTAG
TGTCTTTAATTTCTAATATATTTAGAAAACTTCTTAAAATTACTCTATTATTCTTCCCTCTGATTATTGGTCTCCAT
TCAATTCTTTTCCAATACCCGAAGCATTTACAGTGACTTTGTTCATGATCTTTTTTAGTTGTTTGTTTTGCCTTACT
ATTAAGACTTTGACATTCTGGTCAAAACGGCTTCACAAATCTTTTTCAAGACCACTTTCTGAGTATTCATTTTAGGA
GAAAGACTTTTTTTTTAAATGAATGCAATTATCTAGACTTATTTCAGTTGAACATGCTGGTTGGTGGTTGAGAGGAC
ACTCAGTCAGTCAGTGACGTGAAGGGCTTCTAAGCCAGTCCACATGCTCTGTGTGAACTCCCTCTGGCCCTGCTTAT
TGTTGAATGGGCCAAAGGTCTGAGACCAGGCTGCTGCTGGGTAGGCCTGGACTTTGGGTCTCCCACCCAGACCTGGG
AATGTATGGTTGTGGCTTCTGCCACCCATCCACCTGGCTGCTCATGGACCAGCCAGCCTCGGTGGCTTTGAAGGAAC
AATTCCACACAAAGACTCTGGACCTCTCCGAAACCAGGCACCGCAAATGGTAAGCCAGAGGCAGCCACAGCTGTGGC
TGCTGCTCTTAAAGCTTGTAAACTGTTTCTGCTTAAGAGGGACTGAGTCTTCAGTCATTGCTTTAGGGGGAGAAAGA
GACATTTGTGTGTCTTTTGAGTACCGTTGTCTGGGTCACTCACATTTAACTTTCCTTGAAAAACTAGTAAAAGAAAA
ATGTTGCCTGTTAACCAATAATCATAGAGCTCATGGTACTTTGAGGAAATCTTAGAAAGCGTGTATACAATTGTCTG
GAATTATTTCAGTTAAGTGTATTAGTTGAGGTACTGATGCTGTCTCTACTTCAGTTATACATGTGGGTTTGAATTTT
GAATCTATTCTGGCTCTTCTTAAGCAGAAAATTTAGATAAAATGGATACCTCAGTGGTTTTTAATGGTGGGTTTAAT
ATAGAAGGAATTTAAATTGGAAGCTAATTTAGAATCAGTAAGGAGGGACCCAGGCTAAGAAGGCAATCCTGGGATTC
TGGAAGAAAAGATGTTTTTAGTTTTTATAGAAAACACTACTACATTCTTGATCTACAACTCAATGTGGTTTAATGAA
TTTGAAGTTGCCAGTAAATGTACTTCCTGGTTGTTAAAGAATGGTATCAAAGGACAGTGCTTAGATCCGAGGTGAGT
GTGAGAGGACAGGGGCTGGGGTATGGATACGCAGAAGGAAGGCCACAGCTGTACAGAATTGAGAAAGAATAGAGACC
TGCAGTTGAGGCCAGCAGGTCGGCTGGACTAACTCTCCAGCCACAGTAATGACCCAGACAGAGAAAGCCAGACTCAT
AAAGCTTGCTGAGCAAAATTAAGGGAACAAGGTTGAGAGCCCTAGTAAGCGAGGCTCTAAAAAGCACAGCTGAGCTG
AGATGGGTGGGCTTCTCTGAGTGCTTCTAAAATGCGCTAAACTGAGGTGATTACTCTGAGGTAAGCAAAGCTGGGCT
TGAGCCAAAATGAAGTAGACTGTAATGAACTGGAATGAGCTGGGCCGCTAAGCTAAACTAGGCTGGCTTAACCGAGA
TGAGCCAAACTGGAATGAACTTCATTAATCTAGGTTGAATAGAGCTAAACTCTACTGCCTACACTGGACTGTTCTGA
GCTGAGATGAGCTGGGGTGAGCTCAGCTATGCTACGCTGTGTTGGGGTGAGCTGATCTGAAATGAGATACTCTGGAG
TAGCTGAGATGGGGTGAGATGGGGTGAGCTGAGCTGGGCTGAGCTAGACTGAGCTGAGCTAGGGTGAGCTGAGCTGG
GTGAGCTGAGCTAAGCTGGGGTGAGCTGAGCTGAGCTTGGCTGAGCTAGGGTGAGCTGGGCTGAGCTGGGGTGAGCT
GAGCTGAGCTGGGGTAAGCTGGGATGAGCTGGGGTGAGCTGAGCTGAGCTGGAGTGAGCTGAGCTGGGCTGAGCTGG
GGTGAGCTGGGCTGAGCTGGGCTGAGCTGGGCTGAGCTGGGGTGAGCTGAGCTGGGGTGAGCTGAGCTGAGCTGGGG
TGAGCTGAGCTGAGCTGGGGTGAGCTGGGGTGAGCTGAGCTGGGGTGAGCTGAGCTGAGCTGGGGTGAGCTGAGCTG
GGGTGAGCTGAGCTGAGCTGGGGTGAGCTGAGCTGAGCTGAGCTGAGCTGAGCTGGGGTGAGCTGAGCTGAGCTGAG
CTGGGGTGAGCTGGGGTGAGCTGAGCTGAGCTGGAGTGAGCTGAGCTGGGCTGAGCTGGGGTGAGCTGGGCTGAGCT
GGGGTGAGCTGAGCTGAGCTGAGCTGAGCTGGGGTGAGCTGAGCTGAGCTGGGGTGAGCTGAGCTGGGGTGAGCTGG
GCTGAGCTGAGCTGAGCTGAGCTGAGCTGAGCTGAGCTGAGCTGAGCTGAGCTGAGCTGAGCTGAGCTGAGCTGAGC
TGAGCTGAGCTGGGGTGAGCTGAGCTGAGCTGGGCTGAGCTGGGGTGAGCTGGGCTGAGCTGGGCTGAGCTGGGCTG
AGCTGGGGTGAGCTGAGCTGGGGTGAGCTGAGCTGAGCTGGGCTGAGCTGAGCTGAGCTGGGGTGAGCTGAGCTGAG
CTGGGGTGAGCTGAGCTGAGCTGAGCTGGGGTGAGCTGAGCTGGGCTGAGCAGGGCTGAGCTGGGGTGAGCTGAGCT
GAGCTGGGGTGAGCTGGGCTGAGCTGGGCTGAGCTGAGCTGAGCTGGGCTGAGCTGGGCTGAGCTGGGCTGAGCTGG
GCTGAGCTGGGCTGAGCTGGGGTGAGCTGAGCTGAGCTGGGGTGAGCTGGGGTGAGCTGAGCTGGGGTGAGCTGAGC
TGGGGTGAGCTGAGCTGAGCTGGGGTGAGCTGAGCTGGGGTGAGCTGAGCTGAGCTGGGGTGAGCTGAGCTGAGCTG
GGGTGAGCTGAGCTAGGGTGAACTGGGCTGGGTGAGCTGGAGTGAGCTGAGCTGAGGTGAACTGGGGTGAGCCGGGA
TGTTTTGAGTTGAGCTGGGGTAAGATGAGCTGAACTGGGGTAAACTGGGATGAGCTGTGGTGAGCGGAGCTGGATTG
AACTGAGCTGTGTGAGCTGAGCTGGGGTCAGCTGAGCAAGAGTGAGTAGAGCTGGCTGGCCAGAACCAGAATCAATT
AGGCTAAGTGAGCCAGATTGTGCTGGGATCAGCTGTACTCAGATGAGCTGGGATGAGGTAGGCTGGGATGAGCTGGG
CTAGCTGACATGGATTATGTGAGGCTGAGCTAGCATGGGCTGGCCTAGCTGATGAGCTAAGCTTGAATGAGCGGGGC
TGAGCTGGACTCAGATGTGCTAGACTGAGCTGTACTGGATGATCTGGTGTAGGGTGATCTGGACTCAACTGGGCTGG
CTGATGGGATGCGCCAGGTTGAACTAGGCTCAGATAAGTTAGGCTGAGTAGGGCCTGGTTGAGATGGTTCGGGATGA
GCTGGGAAAAGATGGACTCGGACCATGAACTGGGCTGAGCTGGGTTGGGAGACCATGAATTGAGCTGAACTGAGTGC
AGCTGGGATAAACTGGGTTGAGCTAAGAATAGACTACCTGAATTGTGCCAAACTCGGCTGGGATCAATTGGAAATTA
TCAGGATTTAGATGAGCCGGACTAAACTATGCTGAGCTGGACTGGTTGGATGTGTTGAACTGGCCTGCTGCTGGGCT

Fig. 7 (cont.)

GGCATAGCTGAGTTGAACTTAAATGAGGAAGGCTGAGCAAGGCTAGCCTGCTTGCATAGAGCTGAACTTTAGCCTAG
CCTGAGCTGGACCAGCCTGAGCTGAGTAGGTCTAAACTGAGTTAAAAATCAACAGGGATAATTTAACAGCTAATTTA
ACAAGCCTGAGGTCTGAGATTGAATGAGCAGAGCTGGGATGAACTGAATGAGTTTCACCAGGCCTGGACCAGTTAGG
CTAGGACCTCGTTCTATAGAGGCAGACTGTGTGCTACAGTGGAGTTTCAAGATGATTCCATGAGTCCTCCCCGCCCC
CAACATAACCCACCTTCCTCCTACCCTACACGCCTGTCTGGTGTGTAAATCCCAGCTTTGTGTGCTGATACAGAAGC
CTGAGCCCCTCCCCCACCTCCACCTACCTATTACTTTGGGATGAGAATAGTTCTCCCAGCCAGTGTCTCAGAGGGAA
GCCAAGCAGGACAGGCCCAAGGCTACTTGAGAAGCCAGGATCTAGGCCTCTCCCTGAGAACGGGTGTTCATGCCCCT
AGAGTTGGCTGAAGGGCCAGATCCACCTACTCTAGAGGCATCTCTCCCTGTCTGTGAAGGCTTCCAAAGTCACGTTC
CTGTGGCTAGAAGGCAGCTCCATAGCCCTGCTGCAGTTTCGTCCTGTATACCAGGTTCACCTACTACCATATCTAGC
CCTGCCTGCCTTAAGAGTAGCAACAAGGCGCGTCAAACTTACCCTACCTTTATCCTGGTGGCTTCTCATCTCCAGAC
CCCAGTAACACATAGCTTTCTCTCCACA[redacted]ATGATCCCAGTGTCCTTGGAGCCCTCTGGTCCTACAGGACTCTGACACCTACCTCCACCCCTCCCTGTG mouse IGHγ1 - ΔCH1

TAAATAAAGCACCCAGCACTGCCTTGGGACCCTGCAATAATGTCCTGGTGATTTCTGAGATGTAGAGTCTAGCTAGG
TCATGGAATGAGGGGTCTCCATGGTTTGAGGCCTGAGTTGTGACTAAGGAAAAACCCATAGGCCTACACTGCCACAC
CCAGCACTTTTGAATTTGCCTGACATGAAAAGAATTTACCTCTCCCTGGAAAGTGGAGCCTTATCCCTAGGCAGTTC
CCTTACCAGACCTTCCTCTAGCTTGCACTTTGTTCTGGGCACAGAATGTGTCTAACCCCCCAAAGCAAGGAAGACAC
AACCTCTACCTCCCTCACTCTGTCCTTACCCCTTTTCCTGGCTAAGCATCTCACTGAGTGCGCTGAATAGATGCATG
TGGCCACAGTCTTGCAGACAGACCCTTGCCATCTCTCCACTCAGCTTTCCAGAGGCTAAGTCTAGCCCGTATGGTGA
TAATGCAGGGAGCTCTATGCTATCTCAGTGCTATCAGACTCCCAAGTGGAGGATGAACATGGACCCATTAAAACCAA
CCTGCGCAGCAACACCCTGCCAATAAGGCCCGTATGTGAAAATGTGCACACATCTACACATGCACAGGCACACACAC
ACACACATGCATGGGCACACACACATACAGAGAGAGAGAATCACAGAAACTCCCATGAGCATCCTATACAGTACTCA
AAGATAAAAAGGTACCAGGTCTACCCACATGATCATCCTCGGCATTTACAAGTGGGCCAACTGATACAGATAAAACT
TTTCTATGCCAAGGACGCCAACATATACACAAGTCCGCTCATGACAAATCTGTCCCTGAACCTCAGACTGGCGCCCG
TGACTCATACAGTGGACACTCCTCCAAAGCTGTATAGCTTCCTTTACTTCCCTGTGTGTACTTTCTCTGAAGTACAC
TCATCACACAGAAGAGGCCCTGTGATTACTCTGGCCCTCTGTTCTTGGTCATCAGAGAATAGACAGAAGATCAGGCA
AACTACACAGACACTTCCCACAATCATCACAGGCCCTGACTCTGCTCTCCAGTCTCAAAACTGAAGGCTGGAGCACA
CAGAATAAGCTCCTGCACAGGCCAGGCCAGTATCGGGTCCAGTGTGTCTGACTGAGCCCAGGGACAAAATGGCAGCA
CTTTGGGGAACTGAGGTTTCTGGTCCAAGAAGGAGAGATGGAGGCCCAGGGAGGGTCTGCTGACCCAGCCCAGCCCA
GCCCAGCTGCAGCTTTCTCCTGGGCCTCCATACAGCCTCCTGCCACACAGGGAATGGCCCTAGCCCCACCTTATTGG
GACAAACACTGACCGCCCTCTCTGTCCAGGGCTGCAACTGGACGAGACCTGTGCTGAGGCCCAGGACGGGGAGCTGG
ACGGGCTCTGGACGACCATCACCATCTTCATCAGCCTCTTCCTGCTCAGTGTGTGCTACAGCGCTGCTGTCACACTC
TTCAAGGTCAGCCATACTGTCCCCACAGTGTCTACAATGTCCTCATACTCTTCCCCATACTGTCCCTGTGGTGACCT
ATACCCCACACTGTCCCATGCTAATGACCACAGTCTTACATGCTATGTAATGCTGTCTACCCTTCTGTATGCACAGT
CTCACAATGTCCCATGCAGTCTCCACGATGCTCCATACTGTCCCCATTCCAACCCATGCTGCCCCTTGTTCCCCGCT
ATGCTGTCCCATGCTATTGTCTGTATTTTCATGCTCTTTTCACACTGTCCCTAGTGTCACATTCTGCCCATGTTGTC
CACCACATTGTCCCCACTCTGTACACAGCCTCACACTGTACCCTGCTACCCGATAATGTTCCCTGTTGTCCCCAACT
CTCTCCCTGCACCATTTGTCAACTGTCCCCTGAATTCCCATGTTGTTCCCACACTGTTAGTGTGTAATGTGCTCTGT
CCCAGGTGTACCTTGTTCCGTGCTGTCTCACTTCATCGCCCATTCTGTCCTTGTACTAACCCCACTCTATCACCACA
CTGTCCCTATGCACTGCCCACATTGTCCTCATACTGTCCCATTTTGTATCTTCATCCTGTCCCCATAGTGTCCAATG
ATCTACCCCACACTATTCCCACTTCATGCCCCTACAATTTCCCTATTCCATTCCTCTCTGGTCACCATGCCATCCTT
CCCACTCCTGCACAGCTGGAGAGGGACTCCCGGGATGAGTCCTTGCCCAGATGAGCTACCTATCTAGAGGAGTCTTC
AGGTGGGAAGGGAATGCAGTCTTGATCTTGGTCTTATTCACCCTGTCTCACAGGTAAAGTGGATCTTCTCCTCGGTG

Fig. 7 (cont.)

GTGGAGCTGAAGCAGACACTGGTTCCTGAATACAAGAACATGATTGGGCAAGCACCCTAGGCCACCTCCTGTAATGG
CATTTCCCAGGCCCCGAAGGACCCTGTCCAATATGCCAAGCAGCACAACTGAGATCACACTGTCTGCTCATCTCGCT
TTCCTCCGACCCCGAGACTCAGCTACTCTCAAATTTTCCCTCTCTGAAGGACCATGTGGACATTACATTGCTCCAGG
CCACAGCCACCAGGACCTAAAACACCATCACAGCAGCACCAAAGACACTGGATAGACCCACAAGGGCAATAGTTTCC
TCAACAGTATATCCAAACTGTTGGGACAAACGAGCAATCACTGAAGAAGTGACAAGTTCCCACAATGTCAGTGTCCA
GCTGAGAAGGGACAAAAAGTGGTACCAGCCCTGTCCACACCACCTTCTAATTCACAGGAATACGTGATAGAAGAGGC
AGGTTGTAGATCCGAAAGATGAGACAGATTTTATCAACTCCAGAAAGAGCTGGGTCCAACTGAATTATTCTAGCGAC
CTTGGCATTGTCATGACCTGCCATGACCTTCCTCCTTAACACTTCGATAAACCCTGGGATATGGAAAATGCCTGTGT
TTCTCAGGGTTTGGGAAAGAACCATCCATGTTGGGATTCTTGTGTAGATCCTCCTTCTGGTCACAGATGCAATACAC
TGGATTTTCAGGCAAAGGAGCAAATTCACAGACAACTCTGGCCCTACAGCCCTAAGACCTAGACACCACCATCTCCT
TGGAATTATCAAATTTAACACCCGGCACACAACAAAGAAGGACTGGGACTTTGAGGCCTTTGTGTAGCCCTAGAGGG
GGCAGAGGCCACTGAGCAGGGATTGGGTGATCACAAGGACCTCCTGGAGAGGGACCTGAGGAGCAGGTTCCAATTGG
GCCAAAGAAAGAAGAACAACAATAGAGATGAAGGATGCTGGAAAGAGCCATGGTACAGCAGTCTTGTCCTTCAGACA
TGACTCTTACAGCCCAGGACTCTTACAGTAGCTAGCTGGAGCAGAAGTCCAAGGGATTACCATGCCCTAGGGCCACA
GGCTACTGGAGGGTGGAGTGAGTCTACTACACAGGTCCAATGCCTGTTTCTCCATTGCTTCTCAGCCAATGAGAAAT
CAGAGTCTCCACCTCCAAGAAAAAGGAAGGTGGAAATGAAAGGTGAGCACCTGCCTTCCCGTGACTGGCAGAAAGAT
CTCCACGGACTCAAGGCTTTGACTTCAAACGGCGCGCCAATCTTCCAGAAGCCAGGCTGGGACCTCAGCAAAAGGGA
AGACATAACCCAACTCCAGGATGCCCTGTGGCTGATCACTCTTGTCTTGGCGGGGATGAAGGTTGGAGAAAGGCCTC
CACGTTTCAGAGCTAAGACCGACGTGACAACTTCCCAGCCCACTCACAGACTTTCCTGAGCAATAAATTGATGCAAA
ACCACAAATTCCTACTCTCAAAAACAAACATTAACAAAGGATTGGGGGAGGGGGTCAGGGGTAGTATGGTGGCGTTG
GGCAGGGTAAACTCAGGGTACCCATTGTCTAATGTCTGAGACATAACTTGAACATATGTGTAGCTGCAGCCAAAGAT
GAACAAGTGATGGTATTTGTGTCCTCTTCAGACCCGATACCAGGTCATTAAGCTTGAGATCTGGACCTGATTTCTAA
ACATTTGGCCTCTGTGAGCACCCTTGGCAAATACTGAACAGCAAACCCTGGTCCTGGCTGTGAACCTTGGTCCTGAT
CACTGAGCCCTATATTGGTAACTGAACCGTGATCCTGATCTCTGACCTCAGTCATGGTCATGAGGCCCTGGTCCTGG
CCACTCATTCTAATAACTGGTCCCTAGTCCTGAGCCCTGAACCTTGGTCCAGGTCACTGAATCCTAGTCATGATCAC
TGGGTTTGATCCTCATTACTGAGCCTAGTCTTGATCACCGATGACTGGTTTTGATCATAGCAATTAACCTGATCACT
AGTCCCCGTTCCTCATCACTGGGCCATGATACTGGTCACTGGGTCCTGATCCTGATCACTAAATCCTGTTTCTAAAC
AATGTGTAGTGGAATGTATAGTGAAGCCTTTGTGTCTGGCTCTGGGTGAAATGTCTCAGCAGAGCCTTTGCTAGGTT
TGGGTTAATCAGTTGGGGCTGAGAAATGTTTTTGAGGCTGTTTGAACTTCAAAAGAAGAAATGTCTCCCTGGACAAT
CTGCACATTTGCAGCTGCGCAAACCTTCATCCTAAAACTTAACTCCTGGCAAACTTAGAATTCTTACTTTTAATAAT
GGCTAGCCATGGTTGAAAGGGACTGAGATGTCTGTGGGTGGGTGGAACCTTTCCCAGCTCCAAGTAACTCTGTATAC
TGTTTGAATAAAGTAACTGAAGTGAGCTAGCTGGGGTCAATCTTCTTTCCAAGGAGAATAAAGCCCTCCGCTCCTCC
AGAAAATGAAGGCTTAGCTCCTTGGTTAGCTTCTCTCTCTACTGCGGCACCTACAACCAACTCAGCAGTCCTAGGTT
CCTGTCACCAGATCCAGTCCTGATAGCTAAGTGTCAATCCTCGTCACTAAGGCCTGATCCTTAGCAATATGCCTGGG
GTCTGATAATCAGACTGACATTCTGATAACTGGACCCAGATTCTTATCACTGGGTCTTTGTCCTGGTCATGGGCATT
TGACCCTAGTCTACAGCACTGAGTTCTGGGCATGGACCCTGGGTCCCAGTTCTAGATACTGAGTTCTGGTTCTAATA
ACTGGCTCCTGTACTGATCGATGGGTCCTGACCTAGTCATTGGGCCCTGATCCTCAACATTGACTTCAAAACCTGAA
CTCTAGCCCCATGCCTCATTCACATTAGGAGGATCCCTACAGGGGATTCCTGCAGAAGATTCCAGAATCCCCACAAC
ACTGTTCACACACTGGGCTGCAACTGGGACAGTGACCCCTTTGCTCATAGGACTTGCCCAGGCTCAGATGCACTGAA
TGGAGACAAAGCAAGCCCAGGCCCTGGGAGATGGAGCCTCTGGCCTGGGGTCTACAGATGTGGGGTCAGCATCATAG
GGAGGTTTGCAGGGCAGGTGTGGGGCAGGGCAGAAGTGGTCATGCTTGTAGATACTATTTTTCTCTCCTCTGGAGCC
TCCTTTGTCTATCACCTGCTGTCCTGGGATCTCTATCTGGGGTCAACAATGTTTGCAGTACAGGTGTGGGGGTAGGG
CAGGGATGTTCACATTAGCAACTTGTTTTTCTCTCTTCTGAAGTCTCTGTTGTCTATCACCTGCTGAAACATTCAAA
GCAGCTCTGAGCTGAGGGCAGCTGAGTCATCCTGAGCCTGTCTCAGCACAGGTGCCCCAAACCAGAGCTACTGTTCT
GAGAATCACACCACACTGGACCAGGCCAGGTGGGCCTGGGGCCTGGATGAGGGGTGGAGCCAGGGGAGCCCTGCCA
GGGGCTGAGGAGGCCCCAACCCCCATCACCCAAGGCCATCCACACTCGTGCCTTAATGAGGCCATGTTCTGTCCCAA
TGAGAACAAGTCCAATTAAGATTAAGTATGGTCTTCCCAGGATCATCCAGAGTCAAGGGGTGTCAGCCAGGGACAAC
CCAGACCAGCCTGAGGTCAGCCAGCATCACCCAAGGCCACACAGCTATTCTGGCAGAGGACTAGAATAGTCAGCTCA
TCGAGGCCCTGGAGATGCAGAATGGAGAGTTTATCCCTGCCAGACAGGGTTCCTCAGATAGGCAGGTCCCTCACCAC
ACATGACCTCCCTGAATATTTCCCAGAGTCCAGTTGGTTCTAGACTATCACAATAGTCTTCTGTATTCCTGATAAGC
ATGCAGAAAGCTAACAGGATGACAAGAAATTTTATGCAGAAAACAGAAGCATCTACAGGATAGAACAGAGGAGAATA
GATACTGGAAGTCTGCTGGAGACCCCAGTGGAGTCTCTTTGTAGAGTCAAGCTGTAAGATCAAACCTGCACTGAGCC
TCAAGATTGAGTCAAGTACAGAGGCAACCTTCAGGACCCTAAAGACCTTACAGGCAATGGACAGGATGGAGTCCAGG
CAGACAAGTAAACGGGCAGTCATATGTAACATAATGAACCATGTCAACAGAGGGTACTGAGCCAAGGAAGGCTCTGG

Fig. 7 (cont.)

GACACTTGTGGATAATCTGCCACTGGATCTCTTGATGTATATACCAGGTGATCAGATGACAGTTTAGTGGCGCCATC
GCCGTTACAGTGTTAGGTGTTGTCCTCGTCATGGGTTCACGTGAGAATGTGACACCTTTTTAGTTGGATGTGTACAG
TAAGCTCTCAGGCCTGGTGTTCCTGGTATGATTTTAATGATCCATGTGTTCCTATATCTTTAATAAGTTTATAGGGT
GACATTAAGCTTGGGGATAAGTTGTTTATCAGGCTGTGCCTTTAGAAGTTGATGTGCAGGGATTGTTGTTTACACCA
AGATGCCCAGTCTTCCTCCAGCTTCCAAACGGAGTCAAAGGCCATTTGAAAATGTGAAACCTCTCAGGGCAAGGTAC
AATCTTTTTTTTTTTTTAAAGCCACTACCTCACACAACATGGAGTAATTTAAAGCAGGGTACAGCTTGATCGAAACAC
ACACACACACACACGCATACACACAATGTAAGATACCGAGAAGGGGATCAAGGGACACAGAAGTAGAGAGAGAATGA
GACAGTTCAGGGATGTAGAGATGAGAGGTAACTAGAGGAAAGGAGAAACACAAGGACTGGAGGGTAAAGAGCCAGGG
ACAGAAAGATCCATGCAAGCAAGACAGACAGACACAAGGAAGGGAAAGGTGGGAAGAGACAGACAGACAAGGTGCAG
CAATGTAGCCCACCTGAGACTCCCATGAAAGTCTGGCACCCACTCTCAGATGAAAGCCAAGTACCTACAGACACGTA
CCCACAGCACCCACACAGAGCACCTGCCTGCCTAACTCAAGCCCACCTACCCATCGCCTCTCCTCCAGGCCTCTGTC
CTCAGGAAGCACACTGAGGGTAACTCAGTCTGGACACTTCTAACTATGGCTTAGTGAACAGCCTGAGAGGCTCTGGA
TCCACAGGTCACTACCACTTGCTGGCCCTGTGCTCCATGCCATGCTTCAGGGGGGGATTCACTGAATGCATGAACCA
TAGTCTGGGGTCAACATGTACTAAGGGATAGGATCCTATCAGGATTTGTCCAAATAAGGTCCAAACAAAGTGAAGAA
GGTGATAGGCGAGAACAGCTGGCAGCTGAGAGAACGCTGGCCAGTTCTTAGGCCAGAGCTTAGGGACAATTTCCAGA
CCTAGCCTTTCATCTCAACTCTAGGTCATGGGTAACTTCCCAGATCTCTATTTTGTTCCTGGTAACTATGCATGCTG
GTACAAGTCTAAGAACCTCGGTGAGACACAGAACCAGTAAGATGAAAGCATCCGTGGATAAGGAAGAAAGGAGAAGA
GTAGAAGGGACAGGACCCTGGACACATGAGATTCCCACACCCAGGAACTGCTCATCCAGCCCGAGAAACGGTATACC
CCTAGCACACAGAAAGAAAACAGTACCACAGGTCTAAAAGAGTAGAGTCAGTGGGAAGGGGTACTACTAGGGCGCCT
CCTGCCTGGTCCAGGAGCAGAGGCTGGGAAGGGGCACTAAACAGGGGGAAGCATGGAGACAGGGAGATGAAGGAGCC
TTTGGGACTGCATGGTGGGAACTAGACTGTTCTCTGAATGAGCCTGTGTGTGTGGCAGCTGCCTGAGAGGGAAGACA
CCCAGAGGCCAGGCAGAGGAAAAGAGTAATCAGGGCTGAGGGGACTGGGGTGGGGGTCTGAGGAAGTCAAGGTAGCT
ATCGCCCATTTATCAGGGCCATGACATGCACTTCATGGGCACATATCTAAAACCAGACCTGGCCCTCACCTACACTC
AGACAATGTCCCTTTTGTGGATTTAGGGATTTCAGTACTTCATCCCATGGCCTCTCAAACTGGAAGATCCATCTAAA
AGGCTGATGTTGTGGTATCAGGGCCCAGGACTAGAGAATGGGACACTGAGTGGCAGAGGTGCAGAGGACACATACAC
TCACTCAGATGAAAGCAATGCACAAGAAGACAGAGCCATGTATGAACACTCCTCAGACTCAGACCCACAGCACTCAC
ACCCAGCTCCCCACAGACACACACAGCCCCTGCCTGCCTGTTCCAAAAATCAAACCCATCTACCCACTCCCTCTCCT
GCAGGCCTTTGTCCTCAGAGTGGCACACTGAAGGTAGCTCAGCCTGAACACTTCCCATGGGACCTGGTGAACAGCAG
GAGCCTCTGGTCCACACTCCCCACCTCTTGTTAGCCCTGTAGTCTATGTGATGCTGTTGAGAACAGGGTACATGGCC
TCTGCCTGGTACAGTCTGGGGTGCAGGCTTCAGGTGAGGCCCAAGTGTGAAGAGTGCAGAAGACAGTGGGCAGAGCT
GAGAGACTGCTAGCCAGTTTTGTTCAAAGGACTGTGATGGCTGCTCCAGGCTACTGAACATTCCAGGACTGCTTCCT
ACCCTCCTCAAAGATGCTGGAACACAACCAATCCTCAACACAATCCAATGTAGTTGCCTGTAGCAGGGCATGCCTCT
GTACAGCAGGGAGTCACACAGAGCCACATGAGACTCTAGACCTGGGGACTGCAGAGGGGAAGGCATGTCCAAGACGG
CCTCCTCCTTGTTACCCTAGGTTTTCAGGCCTCAGGATAACCACTGAACAACATATGCTGAGTCCTGTTCCCCAGGA
TGCTGATGGACACCAGGTCACAGGGCTAGAGGCCAGGAGGGCTAGAGCCTGTGGGCAGGGGGGCTATATTCATTCTT
CCTGTGCTTGCCCAGGAGCAGGTGCTGGGCAGGGGCACAGGACAGGGTGAGGCAGGGAGACAGGGGCATGAAGGGGC
CTCTGGGACCACAAGGTGGGAACTAGGCTGTGCCTGACTGAGCCTGTGTGTGTGACAGCTGATTCATGGGGAAGACA
CCCAGAGACCAGGCAGAGGAAAAGAGTAATCAGGGCTGAGGTGACTGGGGGTTGGGAGGTCTGAGGAGGTAGAGGCA
GCTATGTCCCATTTGTCAGGGTATGGGGACATGTACTTCATAGACACAGATCTAAGAACCAGGCGTGGTTCCCACCT
ACCCCCAGACAGTGTCCCTCATATGGGCTTAGGGATTTCAGTACTTCATCCCACGGCCTCACACCTTGGAAGATCCA
CCTCAAAGGCTGATGTTGTGGTGTGGGGGTCCAGGACTGGGGCCAGGGACACTGGTTGGCAGAGGTGCCCAGGACAT
AGAGTGCTCAGAGTGTAGTTGGGGACATGCTGAGCACTGTTCCTCTGTGAGGGGACAGGCTGAGACAGGGACTGAAG
TCCATCCATAGGCTCAGCACATACCAGGCTCTGGATGGGAACACTGAGCTCTGCCACCCTCCAACATCTGGCACAGC
AGCCTCCTGTGCCAGGGAAGCTAGTCAGCAGGGACAGAGTTCCTGTCCGGGCTGGATGGAGTCTTCTCTGCTAGCAT
CCAAAATAAGTGCATCTTCAGCAATAAGGTCCAGTCATGGTGGACGGCCAGGAACAAAGGCAGTAAACAGCCTGGTT
TGTGTTTGGTTATCTACAGTCTCTCTCACTAAAGCATCAAGACTTCTTTTAATAAATTTAGAAGTTGTTTTCTTTTG
AAACACGGTCTCTCTATGTAGTCCTGGGGGTCCTGGAACTCCCTGTGTAGAAGACCAGACTGTCTTCAAACTTAAGG
AGATCCTCCTGTCTCTGCTTCCTGAATGCTGGGATTAAAAGCATGTGCCACCACACCCAACCTAACCCTTTCTTCTG
AGAGCAACATGCATACAATTTCCCCTCTTATTTCCCCAGATTTTCAATCCTTTTATCCACACTTAAATCTTTAATGC
TAAAATCTCCCTCCCTCCATTTCCAAGCTGCATGTGTTCTACTATTCCCTCAAATTATTTTTCCTTGTGTGCAGGTT
TTAGATTTGAATGCAGGAAGCCTTCACTCTGGCAAAGCCTCCCCCAACCCAGCCTTTCCCATTTCCACACCTCCTAA
CACGTGATTTAGCCCACATCCCCTCATGTGTATGGTGTTTCCCTTCAGTCTGAGGTATTACCCCCAGTGTCCCCTTA
CAGCTGCCTATGGTCACAAATACCTTTCATCTGTTTTTGCTGTGGAAAGCGTTTATTTCCCCTTGAATTTTAATAGC
TTTCTGGGTATACTACCCTGGGTTGAGAGTTTAGATTTTTCAGATCTTGGAATATGTCTTTCTAGACATCTAGCCTT

Fig. 7 (cont.)

AAATGTTTCTACTGGGGGCTACAGAAATGGCTTGGTGGTTGACAACACATGATGTTCTTGCAGAGGAGTGGGTTTTG
ATTCCTAGTACCCCATATCAGCTAAGAGCTATGGAAGACACAAATGGAAGAGGGGACTCTGAGATTCTGAGAAAAGC
CTCATGGTTAAGGGTACACTGAGATACTGAGAGAGAAAGACAGAGACACTGAGAAAGACAGAAGCACAGACCACTAA
AAGAGACAGGGAAACAGAGAGAGACAGTGATGAGATGCAGGGACAGAGCAACCCAGAGAGACAGACAGAGACATAGA
CACTGATAGAGACACAAAGAAGAGAGGGGTCGTGGAAGTTTTGAGAGAAACTGGTAGGAGGTGAGAGAGACACAGAG
CCAATACAGACACAGAAAGACAGAGACTCCAGAGAGACAGAGACTGAGAGAGACAGAGACTGGGAGAGACAAAGATA
CTGAGACAGTCAGAGACACCAATGGGTGCTTTTCCAGGGGATCCAGATTCAATTCCCAGCACCCACATGGCAGCTCT
CTACTGTAATCCCAGTTCCAGGGTGCCCTGAAAAATCCTTCATGCATGTGAAGCTTAGAAGCTCACACACAAACACA
CAGACAGACAGACAGACAGACAGACAGACAGACACACACACACACACACTCAAATGAAGAGTGTGGTTCTCTTTC
TCTCTCTCTGATGAAAGCCATGCACCAGAAGACAGAGCCATGTGTGAACACTCCTCAGACTCAGACCCACAGCACTC
ACACCCAGCTCCCCACAGACACACACAGCCCTGCCTGCCTGCCTGTTCCAAAACTCAAACCCATCTACCCACTCCCT
CTCCTGCAGGCCTTTGTCCTCAGAGTGGCACACTGAAGGTAGCTCAGCCTGGACACTTCCCATGGGACCTGGTGAAC
AGCAGGAGCCTCTGGTCCACACTCCCCACCTCTTGTTAGCCCTGTAGTCTATGTGATGCTGTTGAGAACAGGGTACA
TGGCCTCTGCCTGGTACAGTCTGGGGTGCAGGCTTCAGGGGAGGCCCAAGTGTGAAGAGTTCAGAAGACAGTAGGCA
GATCTGAGAGACTGCTAACCAATTTTGTTCAAAGGACAGTGATGGCTGCTCCAGGCTACTGAACATCCCAGGTCTGC
TTCCTACCCTCCTCCAAGCTGTTGGAGCACAACCAACCATCTTTGTAATTGCCCAGTTGTTTGTTATTGCCTATAGC
AGGGCATGCCTCTGCACACCAGGGAGTCACACAGAGCCACATGAGACTCTAGACCTGGGGACTGCAGAGGGAAAGGC
ATGTCCAAGAGGGCCTCCTCCTTGGGACACTGGGATTCCAGGTCTCAGGATAACCACTGAACAACATCTGCTGAGTC
CTGTTCCCCAGGATCCTGATGGACCCCAGGAGGTCACAGAGCTAGAGGCCAGGAGGGCTAGAGCCTTTGGGAAGGGG
GAATGTTAGGGTTTCTCCCATCCTGGTCCAGGAGCTGCTCACCTGACAGTGATACAGGACAGGGTAAGGCAGAGACA
GGGGGATGAAGGAAACTTTGGGAGCACATGGTGGGAGTGTAGGTTGTGCTTTTGCTTAGCCTGTGTATATAGCAGCT
GCATCATTGGGAAGACACTCAGAGGCCCGACAGAGGAAGAGTAATCAAGGCTGAGGGGACAGCAGTGTCTAAGGAAG
TGGAGGCAGCTATGGTCCATTTGTCATAGTATTGGGACATGTACTTCATGAACACTGATCTATGGACCAAGCCTGGT
TGTCATCTGCCCTCAGTCAGTGTCCCTCATGTGGGTTTAGGAATTTCAGTACTTCATCCCACAAGCCAGTCACATTG
GAACATAAATGAAATGCTGATGCTGTGGTGCTGGGGCCCAGGAGTGCGGGGTTAGTATACTGGGTGACAGAGGGTGT
CCAGTAAATAGATTGCTTAGAGTGTAGGTGGGGACAAGCTGTGCAGTGTTCCTCCATGAGGGGAAAGACTGGTACAG
GTTTTGACATCTCTTTCGTATCCATAGGCCCTGCCATACTGCCCTTGTCCATGGTCCCTGTGGGGTCACATACTTAG
TGTCAAGTAAACCATACCACAAACTGGAAGGGTCTACACTATCCTTGTAGGTTCTACACTCTCCATGACTTCTCCCA
ACTCACACAGACTGTTCCAATACACTACTCTCTTCAGTGGGCAATCATGCCATGAACAGAGAGTGGAGGGTTATGGT
TGCCCTATATTCTGACACATCCAACAGTCTTGTGCATTTGACTCTCATGTGTACAAGCGTGCTCAGGCCTGCTGTAG
TCCCCTCGAGACAGTGATGCCTTCCTTGAGAGCCGATTCTCACTGTCAGCATCTCCTCAGACCAAAGCCCTATAGAT
CCAGCCTCTTTGAGGAGCTAATGTAGTCAGTCACAGGGCTTGATGTTGGTGGCTATAGCTGCTGTCCCCATGGCTGC
CAGAGATGCTTGACCACCATAATCCCAGACTTGAGCATAGGAATAACCTGGAATCAACAGCATCCAGACACTGTAGG
GACTGGCCAGAGATGTGCATAGACCCTATGTCATGTGACCAAGACCTCTTTTTCTAGTATCTTATTTCATGAAAGTC
TACAAAATACGATCTTCTATTCCTTTTATTCCTCTTTGCCTGCTAACATGGAACCTTCTAGAAAGAGGGTCCCCTCT
CTGTCTACTGACTGTGAAGATAGATCCTGTAGGTGTGATCACAGAGTAATGTTTCATTTCTTGGCCAGTCTCAAGCC
AGGGGACTCAGGGAGAGAGACAGGAGAAGGAGAGATGGGGAGAGAGACAGAAAGACAGAAAAACAAAGCAAGGGAGA
GACAGAAGCAGGCAGACCTGGAGACTGGGTGCTTAGGAAAGAGATAAATGTGGATACAGGGAGTGAAAGATAGGGAA
TTGAAGACAGAGGTGGAGATAAAGACCAGAATATGGGAGTCAGAGACAGACAAGAGATATAGAGATCAATATAGGCA
AACAGAGACTGAGAAAGACAGTGATGAGACAGAGAGACATGGAGACAGACAAGGAGACAGACATGGAGACAGACAAG
GAGACAGAGATAGAAATAGGGAGAGAAAATAATACATAATTAGTGGTTGATTAAGGAAGAGATAATGAATGGCAAGA
AGAGACAGAGGCAGGGAGAGACATATACAGGTAGAGAAAAAGATGAAGACAGACAGAGAGAGACTGAAAGAGGGAGA
AAGATACAGAGAGAAGAGAGACTATGAAACAGGCAGAGATATAAAGACAGTGAGAGAAAAACAGAGAGACAGAGATG
GAAGAGAGACAGAGAGACAGGGAGATAGAGAAATGGGAAGACAGGAGGACCAAGAGAAGAGACACACGGCGAGGCAA
GATGTAGTAGAGAGACCTCTGATGGAATCGGCATAGGTGGAGGCAAACATAGATAGACTCTCTCCAACTGCAGTTGA
CAGACTGAGCAGAGAGAATACCATTCAGAGAGAAACAGAGGCTAAGGCTAGGAAAGGCAAGAGTAGCCAGAGGAGAC
AGAGTTGAGCCTGTGGGACAGGACCAGACGCCATCTTGGAAGAGGCAGTGACAAGCCAGGGAGGTGACAGGCTGGTA
CAGTTTCTATCCCACAGTCCACAGGCTGGTGTCACAGGCCTGTCTCCTCGTGGCCACAGTCTATCCCTGCCTGCCAA
GCCTGTCTGTGGAGGGATGGGGGGGGGGGGGCTGGGCTGAGGCAGGCCAGGACTTTTCCAGTGGAGTGGCCAGGCA
CTGGGCTGAGGGCATGATCCCTGCCCACCATCCCAGTGGGTCTGGGTAATGGATGGCCTTGATTATTTTCCTTCGTG
TTTAGGGTGGAACCTGCTTAGAGGCAGCTAGGGCTCTCCATGATGGCCTAGCCTGTGGTGAGTTAATGAACCCCTAA
GGGTAGTTCTTCCACATGGGCTAGGGTTACAATCTGGGGGTTGGGGGCTCAGATATCAGTACCAGAAACAAGGCTTA
CTCCCAACATGTCACACTCGCACACACACAGCTGCCGAGTTACTCATTCTGTGCAGAGTTGGCTCACAAGGGCACAT
GCAAATGGATGTTTGTTTCATACAGAAAAACATGTTTCTCACTTTCTGAGGTTGTTTCCAGAAATAGCATCAGTGAC

Fig. 7 (cont.)

TCCCCCACCTGCAGCTGCAGGTTCACCCCAACCTGGCCAGGCTGACCAGCCTTGGGGATGGGGGACTCCCAGCATAG
GCCACTGGGACTGGGGGTCCATGACCCCTATTGATGATGTTGAATTCAGTGTTTCCCAGTTATCACCACTGCTGGAA
TCTGACCCACCAAGAGGACATGACAGGAGATGGGCAAGGATGGGTGGCTCAACACCCCAGGGAAGTGAGAGAGGCAG
GAAGGCTGTAGGTGTGCTCCAGATCCTGGGTCTACCCAGAACCATGGGAATGGTGGGCAGTGATCATGCCCTCAGCC
CAGTCCCTGGCCACTCCACTGGAAAAGTCTTGGCCTGCCTCAGCCCAGACCCCCTCCCCCACCCCTTCTCAGACAGA
CTTGGCAGACAGGGAGCTAGCCTGTGGCCACATGGAGACAGGCCTGTGACTCCAACCTGTGGACTGTGGGATAGAAA
CTGTACCAGCCTGTCACCTCCCTGCTTGTCACTGGCTCTTTCAAGATGGTGTCTGACCCTGGCTCCATCTCTGGCCA
ACCCTGCCTTTCCCAGCCTTAGCCTCTGCCTCTTTCTCTCTCTCTCAGTGTGATTCTTGCTCAGTCTGTCCCTCAGT
TACTGTCTCTCCATCTCTAACAAAACATAAGAGCTGTCTCTATTAACACCTTGTCTCTCCTCTTTCTTCTTCTCCTT
CTCCTTCTCCTTCTCCTTCCTCTCTCTCTCTCTCTCTCTCTCTCTCTCTCTCTCTCTCTCTCTCTCTCTCTCTCTCT
CTCTCTCTCATCTCTGCTTGTGCCCCCTTTCTCTAGGTGCACATCTCCTACCTCTGTCTGTCTATCTGTGTCTCTTC
CTTCTGTCATCTCCTCTCTATCATTCTTTCAGTCCTTCTCTATGTCTCTTTTCTGTTGATGTCTGTCTTTGTGTGTC
TCTCTCTCCATCCCATTCCTTTTATGACTCTGGCTCCCCTTATCTCTCTGTCTGTATTTCTGCCCCACTTCTCTGTC
TTCCTATCTTTTTGTCTTTTCTCTGTTTCTGATTTTTCTCTCCATGTCTTTCTCTCCACTTTTCTCTCTCCCTTTCT
GAGTCTTCCTGCATCTGTCTCATTGCTTCTCCATCTCGCTCTCTCTTTCTCTGTTTTCTGTCTCTGTTCTTGTATCT
CTGTGTGCCTCTCCATGTCTCTCTGCTGTCTCTTTTTCTCCATACAGCAATTTACTAAAAGAACAAACATCAAGGCA
GGAAAGTATATATATTTCAAATAAAAGTTCTTCAAATTGCTATGTCCTATACTCCAAGAAGCATTTCCAAAGTATAG
ATTAATTTAACCCTTTTAAATGAAAAGATACATTTTTAACTTCTAAAGTGTCTCCACAAAGAAATGAATGTTTTTAA
TTAAGAAATGTTGTAATTTAGTGTTGGGCTCCTGTCTTATAATGTACACTTCCTTATAAATCTAGCCATGTGGCTTA
TATCCATTTGGTATGCTCGGAGCTTTATGTAATAAACGTCTTCCCGATAGGTGCAAGGATTGGTGTTTTGTACTGCT
TACTACATACATGCTTTTAATCATTCCAGGACATACCGTCCCTCTGCTGCTGCTTCTCACCGTCTTTGCCTTTCTCT
CACCCTGTCCATCTTTCTCTCTCCCCATCTCTCTGTTTCTGTCCCTTCCTGTTTCAGTCTCTCTCCAATCTCCCTGT
GTTTCTCTCTCTCTCTCTCTCCTGATGTCTCTTTCTCTGTGGGCTTGTCTCCCCATCTGTCCTCTTCATTTCTGTAT
TTCTCCTTATCTTTCTATCTCTGTCCATGACTCTGTCTCTTTCTGCCTCGTTCATCCCCTGCCCCCCTGAAGGCACA
ATGACACTTTTATCAGGGTTTAATAGGAAAGTTTCAGGGCAGGAAAGTTGTAAGACTCAAGCAGCTGCCCCGAGGAG
GCCAGTGGGGGAGATTGGTAAAAAGCCATGACATCTAATCTGACATGGAGGTCAGGCACATGTCCCACAAGCAGCCA
CATGGCGAGAAGGGGGCAGTTAGAGAACAAGTAAGAAAGCCCAGCATGTTGGGGAGGAAGCCAAGGTGTTAAGGAAA
ACTTGCTCAGAGGGAGACAGAAAGAAGGAAGCTACAATTCTGTGAATTCAGAAAGGAAGCTGACTTACAGCCCCACA
TGGCTATAGCCCCTAAGCTTCTGGCCCTTCCTCTTCTGTCTCTTCCTGTTCTCTGTCACCCCTGTTTCTCCCTATTC
TCTGTCACACCTGTCTCTGTGCTCCCATTAATCTCTCTCTGTCTCTACACATCTCCACCTCTGCCTCCTTCATCTCT
GTCTTTTCCGGAACCCTGTCTGTCTCTGTCAGGCTTCTCCTTGTCTCCCCCTGCAGACTTGCAGTTTCTCCCTTTGT
CTTCCTCTGTCTTACCTTTATTATGTCTCCCCGTCTTTCCTACCTTCCTGACTTTCTGTCTCTTACCCTGAGTCCCC
TGGCCTGAAACTGGCCAAGAAGGAAAACATCAGTCTGTGATCACTCCTACAGGGTCTGTCTCCATAGCCAGCAGAGA
GGGGACCCTCTTTCTAGAAGGTTCCCTGTTCGCAGGCAATGAAGAATAAAAGGAATAGAAGATCCCGTTGCATTAAG
GTTTCATGAGATAACATACTAGGAAAAGAGACCTTGGTCTACGTAGAAGTCTGGTCAGTCCCTGAAGTGTCTAGACG
CACTTGATCCCTAGGCCATCACTATGTCTGAGGTCATGGTGGTCAAGCATCTCTGGCAGTCACAGTGAAAGCAGCTG
TGGTCACCAACATCAAGCCCTGTGACTACAATAGCTCCTCAAAGAGGCTGGGTCTGTGGGGTTTTGTTTTGAGGGTC
AGCTAGAAATGGGAGTGAGTCCAAGGAAGACCCACTGCCCCCGCCCCCGAGAGATAGGGGAATGAGCATGCTTGCAC
ACGTGGACATGAAAGGCACAAGAGTGTTGTATGTGACAGTTTGAGGTGACCACATTCTGCCCTCTCTGTGCCTGTCA
TGGTTACAACTGAGGACAGTGGTGGATTTGGGCAGAGTCTGTGTGAGCTGGGAGAAGCTGTGGAGAGTTGCAAGCAT
GGCATGTAGATATCAGAAGCCCTGGTCTTCCAGCAGTCCTCATGGTGATGGTTCAGTAGGACACTGGATGTGTGGCC
CATGCTAGGGTCATGGGCAAGGCTGGTATGGGTTGACTCTATGGCTGGACAAAGAGCTTTAACCTCGTCAGCTTCCG
CAATATGGAGGAACACTGCACAGCTTGCCCCCACCTGCACTCTGAGCACTCTGTACACTGGACATGCTCTACTACCC
AGTGTCTCAGACTCCAGTCCTGGGCCCCAGCCCCATAGCACAACCATGTTTATAATCCCTCCAGTGTGAGAGGCCAT
GAAATGTTGTGGAGCTCAGTCTGAAGGCAGGTGGGAGACAGGCATGCTTTTGGATCCATGTCCATGAAGTATATGTC
CACATTCCATGACAAAGGAGCCGAAGCCACCTCTATTTTCTCAAGGACCCCCTCAGTCCTCATTACTCTTCCTCTGC
CTGGCCTCTGGATGTCTTCCCCATGAATCAGCTGTCACAAACACAGGCTCAGTCAGAGCACAGTCTAGTTCCCACCT
TGTGGTCCCAAAGGCTCTTTCACGCCAGTGTCTCCCTGCCTTACCCTGTCATGCACCTCTGGCCAGCCAGCTGCTCC
TGGGCAAGGACGAGAAGAAGCCAAGTAGTTCCTCTTCTCACAGACTCTAGTCCTGCTGGCCTCTAACTCTGTAACCT
TCTGGTGTCCATCAGGATCCTGGGGCCACATCACTCTGAGTGTGTTTATCACCGGCAATCCTGAGGGCTAAGATTTC
AGATTCTAAAGGAGGAGGCCCCCGTGGACATGCCTTCCCCTCTGCAGTCCCCAGGTCTAGAGTCTCATGTGGCTCTG
TGTGACTCCCTGATGTACAGAGGCATGCCCTGCTACAGGCAATTACAATGGATTGGGTAGAGGGTTGGTTGTGCTCC
AACATCTTTGAGGAGGGTAGGAAGCAGACCTGGGATGTTCAGTAGCCTGGAGCAGCCATCACTGTCCTTTGAACAAA
ACTGGCCAGCACTCTCTCAGCTCTGCCCACTGTCTTCTGTACTCTTCACACTTGGGCCTCACCTGAAGCCTGCACCC

Fig. 7 (cont.)

CAGACTGTACCAGGCAGAGGCCATGTACCCTGCTCTCAGATGATGTTTCATACAGATTACAGAGCTAACAAGAGGTG
TGGTGTGTGGACCAGAGGCTCATGCTGTGTAGTCACCCATGGTCCTGCTGAAAAGCAGGCTGGGGCTAAAAAGAGAA
TAGAGTATGAGACACACCAAGACAAATGCTGATCAAAGCCCAATGTTTACTAAAAATCTGTGCTTATATAAAAGGAA
AGCCCTTCTCCTGCAGATCCACTTTTGATGTCTGTTGCCAGCCTGTAAGCAATTTGTCTGACAGCACTAGTTTGACA
AGAAGGTGTCAATCACTGCTGTCTTTGGAATCTCTCAGCCTCTCAGCAGGTATCAGTGTCTTGGAGAAGAAGAGCAA
TGGTGACAGAACAATAGAATCATCTAGGTGGGAAGGCTCTACCCCAGGTGGTCTCATTCTCAGTGGCAGCAAGGTCT
GAGCCAGCCTGCTCAAGGCTGGGGGAGGCTACAATGTTATTCAACAGGTCCCATGGGAAGTGTCCAGGCTGAGCTAC
TCAGTGTGCCACTCTGAGGACAAAGGCCTGCAGGAGAGGGAATGGGTAGATGGGTTTGAGGTTTGGAACAGGCAGGC
AGGGGCTGTGTGTGTCTGTGGGGAGCTGGGTGTGAGTGCTGTGGGTCTGAGTCTGAGGGGTGTTCACACATGGCTCT
GTCTTCTGGTGCATGGCTTTCATCTGAGAGAGAGAAAGAGAACCACACTCTTCATTAGAGTGTGTGTGTGTGTGTGT
GTGTGTGTGTGTGTGTGTGTGTGTGTGTGTGTTTGTATGTGAGTCTGTCTGCTGTCTGTGTGTAAATGTGAGCTTCT
ATGCTTCACATGCATGAAGGATCCTTCAGGGCACCCTGGAACTGGGATTACAGTAGAGAGCTGCCATGTGGGTGCTG
GGAATTGAATCTGGATCCCCTGGAAAAGCAGCCAGTGCTCTTAATCCTTTTGGTGTCTCTGCCTGTCTCAGTATCTC
TGTCTCTCTCAGTCTCTGTCTCTCTGGAGTCTCTGTCTTTCTGTGTCTGTACTGCCTCTGTGTCTCCCACACCTCCT
ACCAGTTGCTCTCAAAACTTCCACGTCCCCCCTCTTCTTCATGTCTCTATCAGTGTCTGTGTCTCTGTCTGTCTCTC
TGTGTCTCTCTGTCCCTGCAGCTCATGACTGTTTCTCTCTAAGTGTTTCCCTGTCTCTTTCAGTGGTCTGTGCTTCT
GTCTTTCTCAGTGTCTCTGTCTTTCTACTTCAGAATCTCAGAGTCCCCTCTTCCATTTGTGTCCCTTCTTGGGCTCA
TTCACTCTGCCTCCAGTGTCATCACTTGTGAGACCAGAACCTACTATGAGTCCAGAGGACTGTCCTTCATGGTCTGT
GACCAGCTGTGATCTGGGGAACACTGGGGAAGGCATGAACAGGGAGGGACCTGCCTGTCTGTGGAGCCCTGCCTGTC
AGCATGAACTCCCCATTCTGCACCACCAGAGCCCTGCTGAGCTGACTATTCCACACCACCTCCAGAAAAGGGCATTG
AATCCTGTGGAACCGATGGCTCTTAGCTGATACGGGGTACTAGGAATCAAAACCCACTCCTCTGCAAGAACATCATG
TGTTGTCAACCACCAAGCCATTTCTGTAGCCCCACAGTAGAAACATTTAAGGCTAGATGTCTAGAAAGACATATTCC
AAGATCTGAAAAATCTAAACTCTCAACCCAGGGTAGTATACCCAGAAAGCTATTAAATTTCAGGAGAAAATAAAAAA
GCTTTCCACAGCAAAAACAGATGAAAGGTATTTGTGACCATAGACAGCTGTAAGGGGACACTGGGGGTAATACCTCA
GACTGAAGGGAAACACCATACACATGAGGGGACGTGGGCTAAATCACGTGTTAGGAGGTGTGGAGATGGGAAAGGCT
GGGTGGGGGGAGGCTTTGCCAGAGTGAAGGCTTCCTGCACTCAAATCTAAAACCTGCACACAAGGAAAAATAATTTG
AGGGAATAGTAGAACACATGCAGCTTGGAAATGGAGGGAGGGAGATTTTAGCATTAAAGTTTTAAGTGTGGATAAAA
GGATTGGAAATCTGGGGAAATAAGAGGGGAAATTGTATGCATGTTGTTCTCAGAAGAAAGGGTTAGGTTGGGTGTGG
TGGCACATGCTTTTAATCCCAGCATTCAGGAAGCAGAGACAGGAGGATCTCCTTAAGTTTGAAGACAGCCTGGTCTT
CTACACAGGGAGTTCCAGGACACCCAGGACTACATAGAGAGACCGTGTTTCAAAAGAAAACAGTTTCTAAATTTATT
AAAAGAAGTCTTGATGCTTTAGTGAGGGAGACTGTAGATAACCAAACACAAACCAGGCTGTTTACTGCCTTTGATCC
TGGCCCTCCACCATGACTGGACCTTATTGCTGAAGATGCACTTATTTTGGATGCAGAGCAAAGAAGACTCCATCCAG
CCTGGACAGGAACTCTGTCCCTGCTGACTAGCTTCCCTGGCACGGGAGGCTGCTGTGCCAGCTGTTGGAGGGTGGCA
GAGCTTAGTGTTCCCATCCAGAGCCTGGTATGTGCTGAGCCTATGAATGGACTTCAGTCCCTGTCTCAGCCTGTCCC
CTCACAGAGGAACAGTGCTCAGCATGTCCCCAACTACACTCTGAGCACTCTATGTCCTGGGTACCTCTGCCAACCAG
TGTCCCTGACCCCAGTCCTGGACCCCCACACCACAACATCAGCCTTTGAGGTGGATCTTCCAAAGTGTGAGGCCGTG
GGATGAAGTACTGAAATCCCTAAGCCCATATGAGGGACACTGTTTGGGGGTAGGTGGGAACCACGCCTGGTTCTTAG
ATCTGTGTCTATGAAGTACATGTCCCAATACCCTAACAAATGGGACATAGCTGCCTCTACCTCCTCAGACCCCCCAA
ACCGCAGTCCCCTCAGCCCTGATTACTCTTTTCCTCTGCCTGGTCTCTGGGTGTCTTCCCCATGAATCAGCTGTCAC
ACACACACAGGCTCAGTCAGGCACAGCCTAGTCCCCACCTTGTGGTCCCAAAGGCCCCTTCATGCCCCTGTCTCCCT
GCCTCACCCTGTCCTGTGCCCCTGCCCAGCACCTGCTCCTGGGCAAGCACAGGAAGAATGAATATAGTCCCCCTGCC
CACAGGCTCTAGCCTTCCTGGCCTCTAGCCCTGTGACCTGGTGTCCATCAGCATCCTGCACAACAGGACTCAGCATA
TGTTGTTCAGTGGTTATCCTGAGGCCTGAAAACCTAGGGTAACAAGGAGGAGGCCCTCTTGGACATGCCTTCCCCTC
TGCAGTCCCCAGGTCTAGAGTCTCATGTGGCTCTGTGTGACTCCCTGCTGTACAGAGGCATGCCCTGCTATAGGCAA
CTACAATGGATTGTGTTGAGGGTTGGTTGTGTTTCAGCAGCTTGGAGGAGGGTAGGAAGCAGACCTGGGATGTTCAG
TAGCCTGGAGCAGCCATCACTGTCCTTTGAACAAAACTGGCCAGCACTCTCTCAGCTCTGCCCACTGTCTTCTGCAC
TCTTCACACTTGGGCATCCCCTGAAGCCTGCACCCCAGACTGTACCAGGCAGAGGCCATGTACCCTGCTCTCAACAG
CATCACATAGACTACAGGGCTAACAAGAGGTGGGGAGTGTGGACCAGAGGCTCCTGCTGTTCACCAGGTCCCATGGG
AAGTGTCCAGGCTGAGCTACCTTCAGTGTGCCACTCTGAGGACAAAGGCCTGCAGGAGAGGGAGTGGGCAGATGGGT
TTGAGGTTTGGAACAGGCAGGCAGGCAGGCAGGGGCTGTGTGTGTCTGTGGGGAGCTGGGTGTGAGTACTGTGGGTC
TGAGTCTGAGGAGTGTTCACACATGGCTCTGTCTTCTGGTGCATGGCTTCCATCTGAGGGGGTGTGTGTGTGTGTGT
GTGTGTGTGTGTGTGTGTGTGTGTGTGTGTGAGCTTCTAAGCTTCGCATGCATGAATGATCCTTCAGAGCACCCTGGAA
CTGGGATTACAGAGGTGAGCTGCCATGTGGGTGCTGGGAATTGAATCTGGATCCCCTGGAAATCAGCCAGTGCTCTT
AATCCTTTTTGTGTCTCTGCCTGTCTCAGTATCTCTGTCTCTCTCAGTCTCTGTCTCTCTGGAGTCTCTGTCTTTCT

Fig. 7 (cont.)

ATGTCTGTACTGCCTCTGTGTCTCCCTCACCTCCTACCAGTTGCTCTCAAAACTTCCATGTCCCCCCCTTCTCTGAG
TTTCTATCAGTGTCTGTGTCTCCGTCTGTCTCTCTGTGTCTCTCTGTCCCTGCAGCCCATGACTGTTTCTCTCTAAG
TGTTTCCCTGTCTCTTTCAGTGGTCTGTGCTTCTGTCTTTCTCAGTGTCTCTGTCTTTCTCTCTCAGAATCTCAGTG
TCCCCTCTTCCATTTGTGTCCCTTCTTGGGCTCATTCACTCTGCCTTCAGTGTCATCACTTGTGAGACCAGAACCTA
CTATGAGTCCAGAGGACTGTCCTTCATGGTCTGTGACCAGCTGTGATCTGGGGAACACTGGGGAAGGCATGAGCAGG
GAGGGACCTGCCTGTCTGTGGAGCCCTGCCTGTCCGCATGAACTCCCCATTCTGCACCACCAGAGCCCTGCTGAGCT
GACTATTCCACACCACCTCCAGAAAGGGGCATTGAATCACGTGGAACCTAAGAACACCGTGTTGTCAACCACCAAGC
CATTTCTGTAGCCCCACAGTAGAAACATTTAAGGCTAGATGTCTAGAAAGACATATTCCAAGATCTGAAAAAAATCT
AAACTCTCAACCCAGGGTAGTATACCCAGAAAGCTATTAAATTTCAGGAGAAAATAAAAAAGCTTTCCACAGCAAAA
ACAGATGAAAGGTATTTGTGACCATAGACAGCTGTAAGGGGACACTGGGGGTAATACCTCAGACTGAAGGGAAACAC
CATACACATGAGGGGACGTGGGCTAAATCACGTGTTAGGAGGTGTGGAGATGGGAAAGGCTGGGTGGGGGGAGGCTT
TGCCAGAGTGAAGGCTTCCTGCACTCAAATCTAAAACCTGCACACAAGGAAAAATAATTTGAGGGAATAGTAGAACA
CATGCAGCTTGGAAATGGAGGGAGGGAGATTTTAGCATTAAAGTTTTAAGTGTGGATAAAAGGATTGGAAATCTGGG
GAAATAAGAGGGGAAATTGTATGCATGTTGTTCTCAGAAGAAAGGGTTAGGTTGGGTGTGGTGGCACATGCTTTTAA
TCCCAGCATTCAGGAAGCAGAGACAGGAGGATCTCCTTAAGTTTGAAGACAGCTTGGTCTTCTACACAGGGAGTTCC
AGGACACCCAGGACTACATAGAGAGACCGTGTTTTAAAAGAAAACAGTTTCTAAATTTATTAAAAGAAGTCTTGATG
CTTTAGTGAGGGAGACTGTAGATAACCAAACACAAACCAGGCTGTTTACTGCCTTTGATCCTGGCCCTCCACCATGA
CTGGACCTTATTGCTGAAGATGCACTTATTTTGGATGCAGAGCAGAGAAGACTCCATCCAGCCTGGACAGGAACTCT
GTCCCTGCTGACTAGCTTCCCTGGCACGGGAGGCTGCTGTGCCAGCTGTTGGAGGGTGGCAGAGCTCAGTGTTCCCA
TCCAGAGCCTGGTATGTGCTGAGCCTATGGATGGACTTCAGTCCCTGTCTCAGCCTGTCCCCTCACAGAGGAACAGT
GCTCAGCATGTCCCCAACTGCACTCTGAGCACTCTATGTCCTGGGTACCTCTGCCAACCAGTGTCCCTGACCCCAGT
CCTAGACCCCCACACCACAACATCAGCCTTTGAGGTGGATCTTCCAAAGTGTGAGGCCGTGGGATGAAGTACTGAAA
TCCCTAAGCCCATATGAGGGACACTGTCTGGGGGTAGGTGGGAACCACGCCTGGTTCTTAGATCTGTGTCTATGAAG
TACATGTCCCCATACCCTGACAAATGGGACATAGCTGCCTCTACCTCCTCAGACCTCCCCAACCCCCAGTCCCCTCA
GCCCTGATTACTCTTTTCCTCTGCCTGGTCTCTGGGTGTCTTCCCCATGAATCAGCTGTCACACACACACAGGCTCA
GTCAGGCACAGCCTAGTTCCCACCTTGTGGTCCCAGAGGCCCCTTCATGCCCCTGTCTCCCTGCCTCACCCTGTCCT
GTGCCCCTGCCCAGCACCTGCTCCTGGGCAAGCACAGGAAGAATGAATATAGTCCCCCTGCCCACAGGCTCTAGCCC
TCCTGGCCTCTAGCCCTGTGACCTGGTGTCCATCAGCATCCTGGGGAACAGGACTCAGCATATGTTGTTCAGTGGTT
ATCCTGAGGCCTGAAAACCTAGGGTAACAAGGAGGAGGCCCTCTTGGACATGCCTTCCCCTCTGCAGTCCCCAGGTC
TAGAGTCTCATGTGGCTCTGTGTGACTCCCTGATGTACAGAGGCATGCCCTGCTATAGGCAACTACAATGGATTATG
TTGAGGGTTGGTTGTGTTTCAGCAGCTTTGAGGAGGGTAGGAAGCAGTCCTGGAATGTTCAGTAGCCTGGAGCAGCC
ATCACTGTCCTTTGAACAAAACTGGCCAGCACTCTCTCAGCTCTGCCCACTGTCTTCTGCACTCTTCACACTTGGGC
ATCCCCTGAAGCCTGCACCCCAGACTGTACCAGGCAGAGGCCATGTACCCTGCTCTCAACAGCATCACATAGACTAC
AGGGCTAGCAAAGAGGTGGGGAGTGTGGACCAGAGGCTCCTACTGTTCACCAGGTCCCATGGGAAGTGTCCAGGCTG
AGCTACCTTCAGTGTGCCACTCTGAGGACAAAGGCCTGCAGGAGAGGGAATGGGTAGATGGGTTTGATGTTTGGAAC
AGGCAGGCAGGGGCTGTGTGTGTCTGTGGGGAGCTGGGTGTGAGTGCTATGGGTCTGAGTCTGAGGGGTGTTCACAC
ATGGCTCTGGTGCATGGCTCTCATCTGTGTGTGTGTGTGCCACAGGCTCCATTTGAGTGCTCGGTTGGCTCCATTGC
TGTACCTCTGTCTCCCTTGTTTTCTATCTGTCTGTCCTCCCTGTCTGTCTGTCTCTCCTTTCCTATGCCTCCTCCTC
ATATCCATGTCTGCATCTCTTTCTATCAGTCTCTATCCCTGTGACCCCTGGTTTCCATTTCTGTCTTTCTGCATATC
TTTCCATCTTTCTCTCTGTGTGTCTGTCCTCATCTCTTCCAGTGTCCGTGTTTCTGTTTCCCTCTGTTCCCATGCGG
AGGTATGTTCTCACAATCCTTAAGTTCCCTGGTCCCCTGTCCCCCATTTCTTGTCATATTATCCCATCAGTGTCTCT
GTGCCTCTCTGTCTGTGTCTCTGTGTTGTCTCTGTGTGTGTCTCTCAGTATCTCTCTCTCTCTCTCTCTCTCTCTCT
CTCTCAGTATCTGTATTTCTTTTAGTAACTTTGCTATCTTTTTAAGTATCTCTGTCTTTCTTCATCTCTGTCTCTCT
TGAGGTCTCTGTCTTTCTGCATGTCTAATGTTTCTGTATCTCTCTCACCTCATCTCTGCCTCTCTCAATATTCAGTA
GATCCATGCCCCTTTATTCTTTGTGCCTCTGTCTCTGTTTGTCTCTTTCTCTGTCTCTCTGTCTTTCTCTCTCTCAG
AATCTGTGTCCCTCATGTTATTTCTCAAAATGCCTCCCTAACTCTTTCAATAACAGTTTCTGCCTCTTCTTTCTGGG
CCTGGCTCAATCTTCCTTCTTGGACCTCAGTTTCATTGGTTGTGAGACCATACCCTGCTATGAGTCCAGAGGACTGT
CCTCCATAGTCTAGAACCACATGCTATCTAAGGGATATTGGGGCAATACATGTGTAGTGAGATACCTGCCTTTCTGA
TGAGCCCTGTCTGGCAGGGATAAATTCTCCATTCTGCATCTCCAGGGCCTTGCTGAGCTGACTATTCTAGTCCTCTG
CCAGAATAGCTGTGTGGCCTTGGGTGATGCTGGCTGACCTCAGGCTGGTCTGGGTTGTCTCTGGCTGACACCCCTTG
ACTCTGGATGACCCTGGGAAGACCATACTTAATCTTAATTGGACTTGTTCTCATTGGGACAGAACATGGCCTCACTA
AGGCACGAGTGTGGATGGCCTTGGGTGATGGGGGTTGGGGCCTCCTCAGCCCCTGGCAGGGCTCCCCTGGCTCCCAC
CCCTCATCCAGGTCCCAGGCCCACCTGGCCTGGTCCAGTGTGGTGTGATTCTCAGAACAGTAGCTCTGGTTTGGGGC
ACCTGTGCTGAGAAAGGCTCAGGATGACTCAGCTGCCCTCAGCTCAGAGCTGCTTTGAATGTTTCAGCAGGTGATAG

Fig. 7 (cont.)

ACAACAGAGACTTCAGAAGAGAGAAAAACAAGTTGCTAATGTGAACATCCCTGCCCTACCCCCACACCTGTACTGCA
AACATTGTTGACCCCAGATAGAGATCCCAGGACAGCAAGTGATAGACAAAGGAGGCTCCAGAGGAGAGAAAAATAGT
ATCTACAAGCATGACCACTTCTGCCCTGCCCCACACCTGCCCTGCAAAGCTCCCCAGGATGCTGACCCCACATCTGT
AGACCCCAGGCCAGAGGCTCCATCTCCCAGGGCCTGGGCTTGCTTTGTCTCCATTCTGTGCCTCTGAGCCTGGGCAA
GGCCAATGAGCAAAGGGGTCACTGTCCCAGTTGCAGCCCAGTGTGTGAACAGTGTTGTGGGGATTCTGGAATCTTCT
GCAGGAATCCCCTGTAGGGATCCTCCTAATGTGAATGAGGCTTGGAATAGCAAAGGGACGTCTTGTAAAATACCACT
GATTCCTTGGGCCTCAGACAATGGATTTGAGATGAGGACCAAGGTCCAGGGCCAGTGTTGGTAAGCAGAATTTGGGG
CTAGAGTTCAGGCTTAGAAGTCAATGATGAGGGCCAGGGCCCAGTGACTAGGTCAGGGCCCATTGATCAGTACAGGA
CCCAGTTGTTAGAGCCGGAGCTCAATGATCTGGACCAAGTCACAAGGCCAAATGATCAGGATCAGTAGCCAGTTACC
AGGACCGAGATCCAGGTTTCACAGCCAAAGCCAGGTTACCCCAACCAGAGACCATTCATCGGAATCTGGGTCTGTTG
ATCGGAGCCCAAGCACGCTGCTGTAAACCAGAGCTGCTCTAAAGCAGAACTCAGTGCTGAGCACCAGAGATAAGTGA
TGAGACCAGGATTCAGTGATTAAGGAAACAAAACCAAAGGTCAATAGGATATTATGTGGAGAGAGGGGAGAGAGAGA
GAGAGAGAGGACAGAGAGAGAAAGAGCGGTAGGTTCAGGACTAAGTCTCAGTGAGGAGGGTCAGGAGTCAGTGGTTT
GAACCCAGACACACTGCTCAGGTCCACAGTTCAACGGTGAGAGCCAGGGGTCAGCTATCAGAACCAGGTCCAGTAAC
TACAACCAAAAACCAGTGGCCCCAACCAAAAACCAGTTACTAAAACCCGAATAGAATAGAAACTAGCCAGGCAGTGA
TAGCTTTAATCCCAATACTCAGGAGTCAGAGGCAGGTGGATCTCTGAGTTCAAGGTCAGCCTGGTCTACACAATGAG
TTCTAAGACAGCCAGGGCTACACAGAGAAACCCTGTCTGGAAAACAAGCAAAAGCCTAGAAACCGTGGACTCAGTGG
TCAGTGGCAGTTCTTGGTGACTAAGACCATGGTCAAGAGGTCAAGCAGGACTCAGCGGTTAGAATCAGGGCATGGGT
GATGACAGCCTGTTCCAGGGATCAGAACCAGGTCTAAGGGCAAAGGCCATGACTGAGTCATCAAACAGTGTCTCTTC
ATAAGTCCTAGCCAGGCCCAACCAGGCCTAGGGTGTCAGATCAGGCAAGACTGATGCGGTATGTGTGAGGTGGTATG
ACAATACATCTCAGTATCTCTGGGACCCCACCACCATCTTCCCTGCCTCGGTCCACTCACAAATCTCTGGCTCTCTC
ACTGTCTTTGTCTCATTCTTGTCTAGCTTTCTACCGTGTCCCCTCTCCCCACATTTGTCTCTCCCAGTATCTGTCTC
TCTGAAAGTCTCTGTGTCCCCTCTGACTTTCTCAGTGCTTATGTTCCCTGCCCCTTGATCATTTGAGAGGGGGATGG
TAAGTAGAGAATTATGGAACAGTGAGTGTGTGTCTCTATATGTGTGTGTGTGTCTGTGGGGCTGGCAGTGGGTATGT
GTGAGTATGTGTGTGTCTGTGTGAGTGTGTGTCTGTGGGGTGACAGTATGTATGAGTGTCAGTGTGTGTGTGTGTGT
GTGTGTGTGTGTGTGTGTGTGTGTGTGTGTGTGTCTGTGTGTCTGTGTGTCTGTGTGTCTGTGTGTCTGTGTGTCTGTG
GGGTGGCAGTGTACATGTGTGAGTGTGTGAATCAAAATGTGTGAGCATGTGTGTGTGGAGGTGGTAATGTATGTATG
TATGTCTGTGTGTATGAGTGTGTGTCTATGGGAGTGGCAGTGTATATGTGTGAGTATATTGTGTATTGTGGGTACGG
GTGTGTGTCTGTGTGAGTGTGTGTTTCTATGTGTCTGTGGAGGTAACAGTGTGTATGTGTGAGTGTGTGTCTATATG
AGTGTCTGTATGTGTGTGTGTATGAGAGAGAGAGAGAGAGAGAAAGAGAGAGTGTGTGCAGGGTGATAGTGTATATATG
TGAGTTTGTGTGTATGTGAGTGTGTGTTTGTGTGTATGAATGTGTGTGTTTATGGGGTGACAGTATGTATGTATGAG
TGCATGTGTCTGTGGGGTAGCAGTGTGTATGTGTGAGTGTGTGTGTGTGTGTGTGTGTGTGTGTGGTATGTGTGTGT
GTGAGAGAGAGAGTGCAGGGTGATAGTGTATATATGTGAGTGTGTGTGTCTGTTTGTGAGAGTGTGTGTTTGTGTGT
ATGAGTGTGTGTGTCTATGGAGTGACACTATGTATGCATGAGTGCATGTGTCTGTGGGATAGCAGTGTATATGTGGG
AGTGTGTGTGTGTGTGTATGTGCAGGGTGGTAGTGTATATATGTGAGAGTGTGTGTTTGTGTGTATGAGTGTGTATG
TCTATGGGGTGACAGTATGGATGGATGTATGAGTGCCTGTGGGGCAGCAGTGTGTATATGTGAGTGTGTGTGTGTGT
GTGTGTGTGTGTGTGTGTGTGTGTGTGCAGTGTGAGAGTGTATATATGTGAGTGTGTGTGTCTGTGTGTGTGAGTGTGT
GTGTTTGTGTGTATGAGTGTGTGTGTCTATGGGATGACAGTATGTATGTATGAGTGCATGTGTCTGTGGGGCAGCAG
TGTGTATGGTGAGTGTGTGTGTGAGTGTGTGTGTCTGTGTGTGTGTGTGTGTGTGTGTGTGTGTGTGTGTGTGTGTG
TGTGCCACTTCCCTAATATGTTCTCTTCCAGCTATGGCTTCTGCTTCATCCTTCACTCAAGGCCAGACCTCACTGGC
CAGTCCACAGCATAATACCAGCCATGCCTCTACCCAATAATTGTATGTGTCAGGGAGCCAAGAGGATGGACAGGGAT
CTTGTTCTTGGGGTGAGAATGTGAGAACTTTTGGGGAGCCCTTCCACACACCCATGCAGTAGTAGACACCTCTGCAA
AGCTATGCACATCCTCACACTAGCACACTGCACAACCATGCACTCTCTGCAGACTCACTGTTCACCATGAACCCAGC
TAGTCAGATTCATATGTGAAACTCATATCAGCCTCTGCACACACATACACACATATTACACCCATGCACACACATGT
ACACATACATACACATGTACACATACATGTGTACACACACATATAGAGAAGGCATTGGTGGGGAAAACATTAGGCCA
TGGCTACAGTACAGGGCACAAGGATGGTGGTACAGAATGAGGTCAGGCTGGGTCAGCATAACAAGAACACTTGGACA
AAGTGAGGGTAGTGTGTGTGTGTGTGTGTGTGTGTGTGTGTGTGTGTGTGTGTATGTGTGTGTGTGTGTACACGTTGAAAG
TCTTCAGTAGACTGGTATCACTAGCCCTGATATGGGCAACACAGCAAGCCTGGGTCACACTCAAGCTGAGTATCAGG
GTAACCAGGGCCTTCTAACCAAGGGTAGATGCAGCCTGTGTTCCGTTTACTGACCAGTGAGAAGCCATGAGCTGAAC
CAGACCAGAAGACCCCTTACTGTTCCCACCCAACCCCCACCCAGTTTAGTCTCAGCAAGACCCTGTACTGTGGGCCAC
AGCTCTCCCCCACACCCCACCTGTAGCACAAACACTATTTGCAAACATTTCTAAAAATGATGAGAACAGGAACCACA
GAGCAGAGGGGGGGACTGGCGTGGAAAGCCCCATTCACCCATGGGACTGAAACTCGGGGAACCAGAACCGTAAGGAG
ATTTGCATGGTGCTGGGGGAGGTTGGCCCTGGATCAGTGAGCCCAGAGAGTTACTGGTTTCTCACTTCCATCAGGTC
AACCTCCTCAACCCCCCAAAAATGGCCAGGCCTAGGCTATGGATGAGTTTCAATGACCAGGCCCTAAGGACGAGTCAC

Fig. 7 (cont.)

AGAGGACTTCCTGGTGGGCTCAGGCAGCAGACCTGCCCAGATGGATTGCAGAACCAGGGGGAGCCATGGCCAGGAAG
GCCAGACGCCTTAGGGGTGTGCTGTCTCTGCATCCTTTGCCCTCTCTGCTCCTCACAGTCCATCTGCCATCTCACAA
TCCCTCCTGTCGCTCTGGGGCCCAGACCTGGCCAGTCTGGGTACCTGTGGAATACACCCAAAGAAGCAATCCCCAGC
CTCAGGACCCACAACTACTTCCCCTACAGACATGAGTGATCTCAGCCCACATGTCTGGGGGCCACAGAAGCCCCTAA
GACCCTACTCTGCTAATAGGCCCTCCTCCCACCAGCCAAGACAATACACAGGCAAGGTGATGTGGATGAGTCACCCC
ATGGGTACCTGTGTCTGAGATACACCCTGTGGGTATCCTGGCCAGAATCTGGTGACCAACCCAACCTGTGTCCCTAG
AGGAGAACTCTGTGCCTGCACTCACCTACCCACCTAACTCCAAGCTTGGTATGATGCAGAGCCCCTGTGTAGACCTA
AAAGTCAGCCATAGGACAGGGTCAAGAATGACTCTTCCTACACATAAAGTCTTCTACTAAGACAGTAAGGTAGACAC
ACAAACATACCCGGATGCAGAGACACACAGGCATGCAGAGAAGGCATGTAGACACAAACGCATGCATAAACGCACAA
ACATACAGATATATGCTGACAAATATACACAGCAACTTACAAGTACACAGACACACAAACAGACAAACATGCACAGA
CAGAAACACACAGAGCTCAAAATCAAGTATACACAGACAAATTTACACAGAGACTTACAGATACACAGATATATGAG
ACACACCCAAACAGACACACACATGGGGGCACAGAAAAACATACAAGCAGACACATGCAGACTTAAAGACCCACAAG
ACATGGAGAGATACAAAAACACACAACACAGACACAGAGATATAGAGACACACAGACCCACAAATATGAACAGACAC
AGAGACACCCAGAAACAAAAACACACTCAGGCATTCCACTCCCAATGGGCGTACACATGGGCATACACAGCCCAGTC
ACACAGACAAACATAACACATACAGAAGTGCAGGCATACATATCACACAATACACGCTGGTATTCACACACAGGTGT
GCTCACAAACCCCACACACTCACACATAAAAGTTGACACTGGCACTCCCACTCCGAGGCACATGCTTAGCCACAGCC
GGCTGACACTGCACACCCCACACACGTTCCAGAGACTCCCACAGAACTGGAAGCTCACCCAGGCCCACCCAGGCTCT
CAGGCCACACACATGGGACATCTCAGAGACATGTGGGATACAGTTGCTCACAGGTTTCATGAGGACTCACAGGCCTG
TCCTTGAACATTCCCCTGAGCAGGGGCTCCCTTCTTAAAGCACAGGGATCCCATTCTTTACAGATAAGCACCCAGAC
AGAGGCACTACCAGGCCCAGACCACACTAGACACACACAGCTCTGCATTGTCCCACACTCAAACACAGCTCTGTCGC
CTGAGCTCATGCCAGTCACACAGAACACAGACATGGGCTCGTGTGCTAGAGAGACATAAGCAATGGTAGCCAAGGTG
CTCACATCATGCCCATACACACACACACACACACACACACACACACACACACACACACACACACACACCCTGTGAAC
AGGCCTGCAGTCCTGACTGAAGCCCTGCTCTACCCAATTTAGTGAGTCCTGCACCTGAACCCTCTTACCCTCACAGC
CCCTGACCTCTCCCTGTGTGCTGCTCAGCTATGGCCCCTTCCCATTCCTAACGTGCCACCCTAAGATGTCGGTTCCG
TGCATCACCGCACACATGCTCTTGGGATAAGGCCTTAGAAGGCTCTGTACCATCTGCAGCTCATGCCACTGCCTTCC
CTGGTAACCCTCTCCTGCATACAAGGGCTGCAAGGGTCAATGATATGAATCCATCCATGCTCTGACCCCAGCTTGGC
CCAGGGCAGCCATGATGGGAGGACAACCCCTGACCCCAGCCTAAGATAGTTGTTGCACAGAGCAGTCCCTTAACGCA
GGATAACTGTTGGAGGTAGGCAGCACTTGACCCCTGCCCAAGCTAGATGATGGGAGAGGATAGGTCCAGCCATTGAC
AGCTGCTGTAGCAAGGCAGGCCCTGGTCCCAGGTTAACTCAAGGCTGCTGCTTAGGCAACCCCTGACTCCAGCTCCA
GAAGTCTGCTGGGGGTGTATCCTCTGGCTACAGGAGCTGAACAAATGGCGCGCCGCGGCCGCTCGACCAATTCTCAT
GTTTGACAGCTTATCATCGAATTTCTGCCATTCATCCGCTTATTATCACTTATTCAGGCGTAGCAACCAGGCGTTTA
AGGGCACCAATAACTGCCTTAAAAAAATTACGCCCCGCCCTGCCACTCATCGCAGTACTGTTGTAATTCATTAAGCA
TTCTGCCGACATGGAAGCCATCACAAACGGCATGATGAACCTGAATCGCCAGCGGCATCAGCACCTTGTCGCCTTGC
GTATAATATTTGCCCATGGTGAAAACGGGGGCGAAGAAGTTGTCCATATTGGCCACGTTTAAATCAAAACTGGTGAA
ACTCACCCAGGGATTGGCTGAGACGAAAAACATATTCTCAATAAACCCTTTAGGGAAATAGGCCAGGTTTTCACCGT
AACACGCCACATCTTGCGAATATATGTGTAGAAACTGCCGGAAATCGTCGTGGTATTCACTCCAGAGCGATGAAAAC
GTTTCAGTTTGCTCATGGAAAACGGTGTAACAAGGGTGAACACTATCCCATATCACCAGCTCACCGTCTTTCATTGC
CATACGGAACTCCGGATGAGCATTCATCAGGCGGGCAAGAATGTGAATAAAGGCCGGATAAAACTTGTGCTTATTTT
TCTTTACGGTCTTTAAAAAGGCCGTAATATCCAGCTGAACGGTCTGGTTATAGGTACATTGAGCAACTGACTGAAAT
GCCTCAAAATGTTCTTTACGATGCCATTGGGATATATCAACGGTGGTATATCCAGTGATTTTTTTCTCCATTTTAGC
TTCCTTAGCTCCTGAAAATCTCGATAACTCAAAAAATACGCCCGGTAGTGATCTTATTTCATTATGGTGAAAGTTGG
AACCTCTTACGTGCCGATCAACGTCTCATTTTCGCCAAAAGTTGGCCCAGGGCTTCCCGGTATCAACAGGGACACCA
GGATTTATTTATTCTGCGAAGTGATCTTCCGTCACAGGTATTTATTCGCGATAAGCTCATGGAGCGGCGTAACCGTC
GCACAGGAAGGACAGAGAAAGCGCGGATCTGGGAAGTGACGGACAGAACGGTCAGGACCTGGATTGGGGAGGCGGTT
GCCGCCGCTGCTGCTGACGGTGTGACGTTCTCTGTTCCGGTCACACCACATACGTTCCGCCATTCCTATGCGATGCA
CATGCTGTATGCCGGTATACCGCTGAAAGTTCTGCAAAGCCTGATGGGACATAAGTCCATCAGTTCAACGGAAGTCT
ACACGAAGGTTTTTGCGCTGGATGTGGCTGCCCGGCACCGGGTGCAGTTTGCGATGCCGGAGTCTGATGCGGTTGCG
ATGCTGAAACAATTATCCTGAGAATAAATGCCTTGGCCTTTATATGGAAATGTGGAACTGAGTGGATATGCTGTTTT
TGTCTGTTAAACAGAGAAGCTGGCTGTTATCCACTGAGAAGCGAACGAAACAGTCGGGAAAATCTCCCATTATCGTA
GAGATCCGCATTATTAATCTCAGGAGCCTGTGTAGCGTTTATAGGAAGTAGTGTTCTGTCATGATGCCTGCAAGCGG
TAACGAAAACGATTTGAATATGCCTTCAGGAACAATAGAAATCTTCGTGCGGTGTTACGTTGAAGTGGAGCGGATTA
TGTCAGCAATGGACAGAACAACCTAATGAACACAGAACCATGATGTGGTCTGTCCTTTTACAGCCAGTAGTGCTCGC
CGCAGTTGAGCGACAGGGCGAAGCCCTCGAGTGAGCGAGGAAGCACCAGGGAACAGCACTTATATATTCTGCTTACA
CACGATGCCTGAAAAAACTTCCCTTGGGGTTATCCACTTATCCACGGGGATATTTTTATAATTATTTTTTTTATAGT

Fig. 7 (cont.)

TTTTAGATCTTCTTTTTTAGAGCGCCTTGTAGGCCTTTATCCATGCTGGTTCTAGAGAAGGTGTTGTGACAAATTGC
CCTTTCAGTGTGACAAATCACCCTCAAATGACAGTCCTGTCTGTGACAAATTGCCCTTAACCCTGTGACAAATTGCC
CTCAGAAGAAGCTGTTTTTTCACAAAGTTATCCCTGCTTATTGACTCTTTTTTATTTAGTGTGACAATCTAAAAACT
TGTCACACTTCACATGGATCTGTCATGGCGGAAACAGCGGTTATCAATCACAAGAAACGTAAAAATAGCCCGCGAAT
CGTCCAGTCAAACGACCTCACTGAGGCGGCATATAGTCTCTCCCGGGATCAAAAACGTATGCTGTATCTGTTCGTTG
ACCAGATCAGAAAATCTGATGGCACCCTACAGGAACATGACGGTATCTGCGAGATCCATGTTGCTAAATATGCTGAA
ATATTCGGATTGACCTCTGCGGAAGCCAGTAAGGATATACGGCAGGCATTGAAGAGTTTCGCGGGGAAGGAAGTGGT
TTTTTATCGCCCTGAAGAGGATGCCGGCGATGAAAAAGGCTATGAATCTTTTCCTTGGTTTATCAAACGTGCGCACA
GTCCATCCAGAGGGCTTTACAGTGTACATATCAACCCATATCTCATTCCCTTCTTTATCGGGTTACAGAACCGGTTT
ACGCAGTTTCGGCTTAGTGAAACAAAAGAAATCACCAATCCGTATGCCATGCGTTTATACGAATCCCTGTGTCAGTA
TCGTAAGCCGGATGGCTCAGGCATCGTCTCTCTGAAAATCGACTGGATCATAGAGCGTTACCAGCTGCCTCAAAGTT
ACCAGCGTATGCCTGACTTCCGCCGCCGCTTCCTGCAGGTCTGTGTTAATGAGATCAACAGCAGAACTCCAATGCGC
CTCTCATACATTGAGAAAAAGAAAGGCCGCCAGACGACTCATATCGTATTTTCCTTCCGCGATATCACTTCCATGAC
GACAGGATAGTCTGAGGGTTATCTGTCACAGATTTGAGGGTGGTTCGTCACATTTGTTCTGACCTACTGAGGGTAAT
TTGTCACAGTTTTGCTGTTTCCTTCAGCCTGCATGGATTTTCTCATACTTTTTGAACTGTAATTTTTAAGGAAGCCA
AATTTGAGGGCAGTTTGTCACAGTTGATTTCCTTCTCTTTCCCTTCGTCATGTGACCTGATATCGGGGGTTAGTTCG
TCATCATTGATGAGGGTTGATTATCACAGTTTATTACTCTGAATTGGCTATCCGCGTGTGTACCTCTACCTGGAGTT
TTTCCCACGGTGGATATTTCTTCTTGCGCTGAGCGTAAGAGCTATCTGACAGAACAGTTCTTCTTTGCTTCCTCGCC
AGTTCGCTCGCTATGCTCGGTTACACGGCTGCGGCGAGCGCTAGTGATAATAAGTGACTGAGGTATGTGCTCTTCTT
ATCTCCTTTTGTAGTGTTGCTCTTATTTTAAACAACTTTGCGGTTTTTTGATGACTTTGCGATTTTGTTGTTGCTTT
GCAGTAAATTGCAAGATTTAATAAAAAAACGCAAAGCAATGATTAAAGGATGTTCAGAATGAAACTCATGGAAACAC
TTAACCAGTGCATAAACGCTGGTCATGAAATGACGAAGGCTATCGCCATTGCACAGTTTAATGATGACAGCCCGGAA
GCGAGGAAAATAACCCGGCGCTGGAGAATAGGTGAAGCAGCGGATTTAGTTGGGGTTTCTTCTCAGGCTATCAGAGA
TGCCGAGAAAGCAGGGCGACTACCGCACCCGGATATGGAAATTCGAGGACGGGTTGAGCAACGTGTTGGTTATACAA
TTGAACAAATTAATCATATGCGTGATGTGTTTGGTACGCGATTGCGACGTGCTGAAGACGTATTTCCACCGGTGATC
GGGGTTGCTGCCCATAAAGGTGGCGTTTACAAAACCTCAGTTTCTGTTCATCTTGCTCAGGATCTGGCTCTGAAGGG
GCTACGTGTTTTGCTCGTGGAAGGTAACGACCCCCAGGGAACAGCCTCAATGTATCACGGATGGGTACCAGATCTTC
ATATTCATGCAGAAGACACTCTCCTGCCTTTCTATCTTGGGGAAAAGGACGATGTCACTTATGCAATAAAGCCCACT
TGCTGGCCGGGGCTTGACATTATTCCTTCCTGTCTGGCTCTGCACCGTATTGAAACTGAGTTAATGGGCAAATTTGA
TGAAGGTAAACTGCCCACCGATCCACACCTGATGCTCCGACTGGCCATTGAAACTGTTGCTCATGACTATGATGTCA
TAGTTATTGACAGCGCGCCTAACCTGGGTATCGGCACGATTAATGTCGTATGTGCTGCTGATGTGCTGATTGTTCCC
ACGCCTGCTGAGTTGTTTGACTACACCTCCGCACTGCAGTTTTTCGATATGCTTCGTGATCTGCTCAAGAACGTTGA
TCTTAAAGGGTTCGAGCCTGATGTACGTATTTTGCTTACCAAATACAGCAATAGTAATGGCTCTCAGTCCCCGTGGA
TGGAGGAGCAAATTCGGGATGCCTGGGGAAGCATGGTTCTAAAAAATGTTGTACGTGAAACGGATGAAGTTGGTAAA
GGTCAGATCCGGATGAGAACTGTTTTTGAACAGGCCATTGATCAACGCTCTTCAACTGGTGCCTGGAGAAATGCTCT
TTCTATTTGGGAACCTGTCTGCAATGAAATTTTCGATCGTCTGATTAAACCACGCTGGGAGATTAGATAATGAAGCG
TGCGCCTGTTATTCCAAAACATACGCTCAATACTCAACCGGTTGAAGATACTTCGTTATCGACACCAGCTGCCCCGA
TGGTGGATTCGTTAATTGCGCGCGTAGGAGTAATGGCTCGCGGTAATGCCATTACTTTGCCTGTATGTGGTCGGGAT
GTGAAGTTTACTCTTGAAGTGCTCCGGGGTGATAGTGTTGAGAAGACCTCTCGGGTATGGTCAGGTAATGAACGTGA
CCAGGAGCTGCTTACTGAGGACGCACTGGATGATCTCATCCCTTCTTTTCTACTGACTGGTCAACAGACACCGGCGT
TCGGTCGAAGAGTATCTGGTGTCATAGAAATTGCCGATGGGAGTCGCCGTCGTAAAGCTGCTGCACTTACCGAAAGT
GATTATCGTGTTCTGGTTGGCGAGCTGGATGATGAGCAGATGGCTGCATTATCCAGATTGGGTAACGATTATCGCCC
AACAAGTGCTTATGAACGTGGTCAGCGTTATGCAAGCCGATTGCAGAATGAATTTGCTGGAAATATTTCTGCGCTGG
CTGATGCGGAAAATATTTCACGTAAGATTATTACCCGCTGTATCAACACCGCCAAATTGCCTAAATCAGTTGTTGCT
CTTTTTTCTCACCCCGGTGAACTATCTGCCCGGTCAGGTGATGCACTTCAAAAAGCCTTTACAGATAAAGAGGAATT
ACTTAAGCAGCAGGCATCTAACCTTCATGAGCAGAAAAAAGCTGGGGTGATATTTGAAGCTGAAGAAGTTATCACTC
TTTTAACTTCTGTGCTTAAAACGTCATCTGCATCAAGAACTAGTTTAAGCTCACGACATCAGTTTGCTCCTGGAGCG
ACAGTATTGTATAAGGGCGATAAAATGGTGCTTAACCTGGACAGGTCTCGTGTTCCAACTGAGTGTATAGAGAAAAT
TGAGGCCATTCTTAAGGAACTTGAAAAGCCAGCACCCTGATGCGACCACGTTTTAGTCTACGTTTATCTGTCTTTAC
TTAATGTCCTTTGTTACAGGCCAGAAAGCATAACTGGCCTGAATATTCTCTCTGGGCCCACTGTTCCACTTGTATCG
TCGGTCTGATAATCAGACTGGGACCACGGTCCCACTCGTATCGTCGGTCTGATTATTAGTCTGGGACCACGGTCCCA
CTCGTATCGTCGGTCTGATTATTAGTCTGGGACCACGGTCCCACTCGTATCGTCGGTCTGATAATCAGACTGGGACC
ACGGTCCCACTCGTATCGTCGGTCTGATTATTAGTCTGGGACCATGGTCCCACTCGTATCGTCGGTCTGATTATTAG
TCTGGGACCACGGTCCCACTCGTATCGTCGGTCTGATTATTAGTCTGGAACCACGGTCCCACTCGTATCGTCGGTCT

Fig. 7 (cont.)

GATTATTAGTCTGGGACCACGGTCCCACTCGTATCGTCGGTCTGATTATTAGTCTGGGACCACGATCCCACTCGTGT
TGTCGGTCTGATTATCGGTCTGGGACCACGGTCCCACTTGTATTGTCGATCAGACTATCAGCGTGAGACTACGATTC
CATCAATGCCTGTCAAGGGCAAGTATTGACATGTCGTCGTAACCTGTAGAACGGAGTAACCTCGGTGTGCGGTTGTA
TGCCTGCTGTGGATTGCTGCTGTGTCCTGCTTATCCACAACATTTTGCGCACGGTTATGTGGACAAAATACCTGGTT
ACCCAGGCCGTGCCGGCACGTTAACCGGGCTGCATCCGATGCAAGTGTGTCGCTGTCGAGCGGCCGC

*Fig. 10*

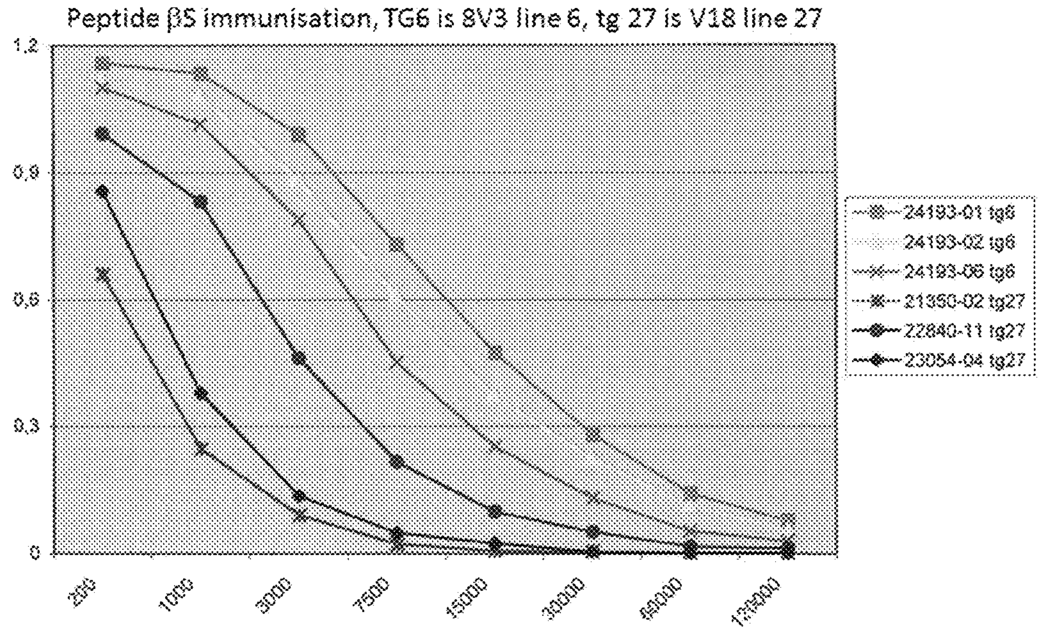

PRODUCTION OF HEAVY CHAIN ONLY ANTIBODIES IN TRANSGENIC MAMMALS

FIELD OF THE INVENTION

The present invention relates to the improved manufacture of a diverse repertoire of functional heavy chain-only antibodies that undergo affinity maturation, and uses thereof. The present invention also relates to a method for the generation of heavy chain-only antibodies by mature B-cells in transgenic animals, such as mice. In particular, the present invention relates to a method for efficiently generating human antigen-specific, high affinity, heavy chain-only antibodies of class VH3 and the isolation and expression of fully functional VH3 antigen-binding domains through the use of human VH genes belonging to subclass 3 and preferably excluding those from other subclasses.

BACKGROUND TO THE INVENTION

Before the advent of gene cloning technology, it was established in a number of laboratories that antibody heavy chains retained the ability to bind antigen when stripped of light chains (see Jaton et al. (1968) *Biochemistry* 7, 4185-4195). With the advent of new molecular biology techniques, the presence of heavy chain-only antibody (devoid of light chain) was identified in B-cell proliferative disorders in man (Heavy Chain Disease) and in murine model systems. Analysis of heavy chain disease at the molecular level showed that mutations and deletions at the level of the genome could result in inappropriate expression of the heavy chain CH1 domain, giving rise to the expression of heavy chain-only antibody lacking the ability to bind light chain (see Hendershot et al. (1987) *J. Cell Biol.* 104, 761-767; Brandt et al. (1984) *Mol. Cell. Biol.* 4, 1270-1277). Separate studies on isolated human VH domains derived from phage libraries demonstrated antigen-specific binding of VH domains but that the VH domains proved to be of low solubility. Furthermore it was suggested that the selection of human VH domains with specific binding characteristics displayed on phage arrays could form the building blocks for engineered antibodies (Ward et al. (1989) *Nature* 341, 544-546).

Studies using other vertebrate species have shown that camelids, as a result of a gene mutation, produce functional IgG2 and IgG3 heavy chain-only dimers which are unable to bind light chain due to the absence of the CH1 light chain-binding region (Hamers-Casterman et al. (1993) *Nature,* 363, 446-448) and that species such as shark produce a heavy chain like binding protein family, probably related to the mammalian T-cell receptor or immunoglobulin light chain (Stanfield et al. (2004) *Science,* 305, 1770-1773).

A characterising feature of the camelid heavy chain-only antibody is the camelid VH region (VHH), which provides improved solubility relative to the human VH region. Human VH may be engineered for improved solubility characteristics (see Davies and Riechmann (1996) *Protein Eng.* 9(6), 531-537; Lutz and Muyldermans (1999) *J. Immuno. Methods* 231, 25-38); or solubility maybe be acquired by natural selection in vivo (see Tanha et al., (2001) *J. Biol. Chem.* 276, 24774-24780). However, where VH binding domains have been derived from phage libraries, intrinsic affinities for antigen remain in the low micromolar/high nanomolar range, in spite of the application of affinity improvement strategies involving, for example, affinity hot spot randomisation (Yau et al., (2005) *J. Immunol. Methods* 297, 213-224).

Camelid VHH antibodies are also characterised by a CDR3 loop that is on average larger than VH antibodies. This CDR3 loop is a feature considered to be a major influence on overall antigen affinity and specificity that compensates for the absence of a VL domain with the camelid heavy chain only antibody species (see Desmyter et al., (1996) *Nat. Struct. Biol.* 3, 803-811), Riechmann and Muyldermans (1999) *J. Immunological Methods* 23, 25-28) Recent structural studies on camelid antibody suggests that antibody diversity is largely driven by in vivo maturation processes with dependency on V(D)J recombination events and somatic mutation (De Genst et al. (2005) *J. Biol. Chem.* 280 (14) 14114-14121).

An important and common feature of natural camelid VH (VHH) and engineered human VH regions is that each region binds as a monomer with no dependency on dimerisation with a VL region for optimal solubility and binding affinity. These features are particularly suited to the production of blocking agents and tissue penetration agents with improved characteristics over whole antibodies. Exploitation of this technology, however, has limitations.

Human VH produced by phage display technology lacks the advantage of improved characteristics as a result of somatic mutations and the additional diversity provided by D and J region recombination in the CDR3 region of the normal antibody binding site (see Xu and Davies (2000) *Immunity* 13, 37-45). Camelid VH (VHH), (whilst showing benefits in solubility relative to human VH) is antigenic in man, and must be generated by immunisation of camelids or phage display technology.

It seems likely that the optimal production and selection of heavy chain-only antibodies comprising high affinity VH binding domains (whether of human or camelid or other origin) will benefit from alternative approaches.

Thus there remains a need in the art to maximise heavy chain-only antibody generation and B-cell response in vivo and, in particular, to generate a functional repertoire of human heavy chain-only antibodies and functional VH heavy chain binding domains which retain maximum antigen-binding potential for use in diverse clinical, industrial and research applications.

SUMMARY OF THE INVENTION

The present invention provides a transgenic non-human mammal comprising a heterologous immunoglobulin heavy chain locus comprising human VH gene segments of the subclass VH3, human D gene segments, human J gene segments and a mouse constant region gene segment lacking CH1.

When compared to human VH domains, camelid VHH domains show the highest homology with human VH domains belonging to subclass 3. Camelid VHH domains (Janssens et al. 2006 Proc Natl Acad Sci USA. 103:15130-5, incorporated herein by reference in its entirety) and human VH domains (Janssens, Drabek and Grosveld, unpubl., U.S. Patent Publication 20090307787) can be generated in non-human animals. However, using a combination of all subclasses of human VH genes from loci where the constant region is devoid of CH1, did not allow the efficient generation of high affinity soluble heavy chain only antibodies (HCAbs) (Janssens, Drabek and Grosveld, unpubl. and .S. Patent Publication 20120151610, incorporated by reference herein in its entirety). We noticed that the antibodies that were produced in these animals were almost exclusively of the VH3 subclass and, to a lesser extent, VH4 subclasses. This suggested that the inefficiency may be a result of the intrinsic insolubility of the other human VH subclass domains. Optimizing the number of VH3 genes and reducing the number of VH domains from other intrinsically less soluble subclasses, could result in a much more efficient generation of HCAbs with improved solubility.

The heterologous immunoglobulin heavy chain locus (VH heavy chain locus) comprises a variable region comprising at least one VH gene segment of the VH3 subclass, or a VH derived from any vertebrate species but homologous to human VH3, at least one D gene segment and at least one J gene segment wherein a VH gene, a D segment and a J segment are capable of recombining to form a VDJ coding sequence.

The VH heavy chain locus may comprise 1, 2, 3, 4, 5, 6, 7, 8 or more VH3 gene segments. In one embodiment, the VH3 genes may be selected from VH3-48, VH3-30, VH3-33, VH3-23, VH3-64, VH3-74, VH3-66, VH3-53, VH3-49, VH3-15, and VH3-07. The VH heavy chain locus may comprise 1, 2, 3, 4, 5, 6, 7 or 8 VH-3 genes selected from VH3-48, VH3-30, VH3-33, VH3-23, VH3-64, VH3-74, VH3-66, VH3-53. Alternatively, the VH heavy chain locus may comprise 1, 2, 3, 4, 5, 6, 7 or 8 VH-3 genes selected from VH3-53, VH3-49, VH3-48, VH3-30, VH3-33, VH3-23, VH3-15, and VH3-07.

The VH heavy chain locus may additionally comprise VH gene segments from subclasses other than VH3. For example, the VH heavy chain locus may comprise one or more VH genes such as VH4-59, VH4-34, VH4-b, VH4-39 and VH4-4.

The VH heavy chain locus may comprise one or more of VH3-6, VH3-7, VH3-9, VH3-11, VH3-13, VH3-15, VH3-16, VH3-19, VH3-20, VH3-21, VH3-22, VH3-23, VH3-25, VH3-29, VH3-30, VH3-32, VH3-33, VH3-35, VH3-37, VH3-38, VH3-41, VH3-42, VH3-43, VH3-48, VH3-49, VH3-50, VH3-52, VH3-53, VH3-54, VH3-57, VH3-60, VH3-62, VH3-63, VH3-64, VH3-65, VH3-66, VH3-71, VH3-72, VH3-73, VH3-74, VH3-75, VH3-76, VH3-79, and one or more of VH4-4, VH4-28, VH4-30, VH4-31, VH4-34, VH4-39, VH4-55, VH4-59, VH4-61, and VH4-b. The VH heavy chain locus may comprise all VH3 gene segments. The VH locus may further comprise all VH4 gene segments.

In one embodiment, the VH heavy chain locus comprises a variable region comprising VH3-48, VH3-30, VH3-33, VH3-23, VH3-64, VH3-74, VH3-66, VH3-53 and VH6-1. In particular, the invention provides that the VH heavy chain locus may comprise in the following order 5' to 3' VH3-48, VH3-30, VH3-33, VH3-23, VH3-64, VH3-74, VH3-66, VH3-53 and VH6-1.

In another embodiment, the VH heavy chain locus comprises a variable region comprising VH3-53, VH3-49, VH3-48, VH3-30, VH3-33, VH3-23, VH3-15, VH3-07, VH6-1, VH4-59, VH4-34, VH4-b, and VH4-4. In particular, the invention provides that the VH heavy chain locus may comprise in the following order 5' to 3' VH4-59, VH3-53, VH3-49, VH4-34, VH3-48, VH3-30, VH3-33, VH3-23, VH3-15, VH4-b, VH3-07, and VH4-4.

The heavy chain locus can comprise all D gene segments and all J gene segments. Preferably, the D and J gene segments are derived from human. Preferably, the heavy chain locus comprises all 27 human D segments and all 6 human J segments. Alternatively, the heavy chain locus may comprise 21 human D gene segments and all 6 J gene segments. Where the heavy chain locus comprises 21 human D gene segments, the D gene segments may comprise in the following order 5' to 3', D 1-1, D2-2, D3-9, D3-10, D 4-11, D 5-12, D 6-13, D, 1-14, D 2-15, D 3-16, D 3-17, D 5-18, D 6-19, D 1-20, D 2-21, D 3-22, D 4-23, D 5-24, D 6-25, D 1-26, and D-7-27.

The constant heavy chain region gene segments of the heavy chain locus may comprise a $C\alpha_1$ and/or a $C\alpha_2$ constant heavy chain gene, a $C\varepsilon$ constant heavy chain gene, a $C\delta$ constant heavy chain gene, a $C\gamma$ constant heavy chain gene and/or a $C\mu$ constant heavy chain gene. In particular, the constant region gene segment may comprise $C\gamma1$, lacking CH1, Furthermore, the constant heavy chain region gene segments of the heavy chain locus may comprise more than one of the following constant heavy chain regions: $C\alpha_1$, $C\alpha_2$, $C\varepsilon$, $C\delta$, $C\gamma$ $C\mu$, $C\alpha$. The constant region gene segments may be murine.

In one embodiment, the invention provides a transgenic non-human mammal comprising a heterologous immunoglobulin heavy chain locus comprising human VH gene segments, human D gene segments, human J gene segments, and a mouse constant region gene segment, wherein the human VH gene segments comprise, in the following order 5' to 3', VH1-69, VH4-59, VH3-53, VH3-49, VH4-34, VH3-48, VH3-30, VH3-33, VH3-23, VH1-18, VH3-15, VH4-b, VH1-8, VH3-07, VH2-5, VH4-4, VH1-2, and VH6-1, the human J gene segments comprise all six human J gene segments, the human D gene segments comprise 21 human D gene segments and the mouse constant region gene segment comprises $C\gamma1$, lacking CH1, optionally where the D segments comprise in the following order 5' to 3', D 1-1, D2-2, D3-9, D3-10, D 4-11, D 5-12, D 6-13, D, 1-14, D 2-15, D 3-16, D 3-17, D 5-18, D 6-19, D 1-20, D 2-21, D 3-22, D 4-23, D 5-24, D 6-25, D 1-26, and D-7-27.

The invention also provides a transgenic non-human mammal comprising a heterologous immunoglobulin heavy chain locus comprising human VH gene segments, human D gene segments, human J gene segments, and a mouse constant region gene segment, wherein the human VH gene segments comprise VH3-48, VH3-30, VH3-33, VH3-23, VH3-64, VH-74, VH3-66, VH3-53, VH6-1, the human D gene segments comprise all 27 human D gene segments, the human J gene segments comprise all six human J gene segments, and the mouse constant region gene segment comprises $C\gamma1$, lacking CH1.

The VH heavy chain locus may further comprise a recombination sequence (rss) capable of recombining a J segment directly with a constant heavy chain gene. The VH heavy chain locus may further comprise a selectable marker.

The constant heavy chain region of the heterologous heavy chain locus is of non-camelid vertebrate origin e.g. of human or mouse origin. Alternatively the constant region may not be of heavy chain origin.

According to particular aspects of the invention, there is provided a transgenic non-human mammal comprising an immunoglobulin heavy chain locus comprising the sequence of SEQ ID NO:1. and a transgenic non-human mammal comprising an immunoglobulin heavy chain locus comprising the sequence of SEQ ID NO:2.

The transgenic non-human mammal may be a rodent, optionally a mouse. Where the transgenic non-human mammal of the invention is a mouse, the endogenous mouse heavy chain locus and the endogenous mouse kappa light chain locus may be disabled.

The invention further provides a vector comprising an immunoglobulin heavy chain locus as described herein.

The invention further provides methods relating to the transgenic non-human mammal described herein. In particular, the invention provides a method of producing an antigen-specific heterologous hybrid VH heavy chain-only antibody comprising: (a) immunising a non-human transgenic mammal described herein with the antigen; (b) preparing hybridomas, B cells, plasmablasts, memory B-cells or plasma cells each of which produces a VH heavy chain-only antibody from the immunised transgenic mammal; (c) optionally selecting at least one hybridoma or B cell, plasmablast, memory B-cell or plasma cell expressing the heterologous hybrid VH heavy chain-only antibody by use of the dominant selective marker genes present in the transgenes comprising the heterologous immunoglobulin heavy chain locus; and (d) selecting at least one hybridoma or B cell, plasmablast, memory B-cell or plasma cell which produces an antibody which binds specifically to the antigen.

The invention further provides a method of deriving a human VH heavy chain-only antibody from a hybrid antibody comprising performing steps (a)-(d) above and subsequently (e) selecting at least one hybridoma or B cell, plasmablast, memory B-cell or plasma cell which produces an antibody which binds specifically to the antigen and comprises a human $V_H$ binding domain; (f) cloning and sequencing the $V_H$ domain; (g) recloning selected sequences comprising the $V_H$ binding domain coding sequences with human constant effector domains of choice from; and (h) expressing the recloned sequences encoding the human heavy chain polypeptides using an expression vector in a cell type of choice. The invention further provides methods for the production of human VH heavy chain-only antibody in a non-human transgenic mammal described herein comprising the step of expressing a human VH locus in that mammal, wherein the VH heavy chain only locus comprises one or more human VH3 gene segments, one or more D gene segments, one or more J gene segments and a at least one constant heavy chain region which does not encode a CH1 domain as described above and which locus, when expressed, is capable of forming heavy chain-only antibodies of defined class or classes, and isolating VH heavy chain-only antibody.

Preferably, the methods of the invention result in essentially normal B-cell maturation. The present invention also provides a heavy chain-only antibody, or a fragment thereof, or mixture of classes of heavy chain-only antibodies obtained or obtainable according to a method of the invention. This human VH based heavy chain-only antibody may be a monoclonal antibody, or fragment thereof, such as a VH binding domain.

The present invention also provides a vector comprising a heterologous heavy chain locus of the invention and a host cell transformed with such a vector.

The invention also provides a transgenic non-human mammal expressing a heterologous heavy chain locus described herein. Preferably, the transgenic non-human mammal of the invention has a reduced capacity to produce antibodies that include light chains.

Also provided is the heavy chain-only antibody, or fragment thereof, according to the invention, for use in the preparation of a medicament for immunotherapy. The heavy chain-only antibodies of the invention may also be used as diagnostics, reagents, abzymes, or inhibitory agents. Also provided is a pharmaceutical composition comprising the heavy chain-only antibody or fragment thereof according to the invention, and a pharmacologically appropriate carrier.

Finally, the invention provides a method of production and selection of heavy chain-only antibodies comprising the steps of:

a) injecting an antigen into the transgenic mammal as described herein;

b) isolating a cell or tissue expressing an antigen-specific heavy chain-only antibody of interest; and c) producing a hybridoma from the cell or tissue of step (b) or cloning the heavy chain only antibody mRNA from said cell or tissue for subsequent production in a heterologous expression system such as a mammalian, plant, insect, microbial, fungal or alternative system or d) sequencing the mRNA/cDNA directly from said cell or tissue for subsequent production in a heterologous expression system such as a mammalian, plant, insect, microbial, fungal or alternative system or e) obtaining the amino acid sequence directly from said cell or tissue for subsequent generation of a DNA or RNA molecule for the production of the antibody in a heterologous expression system such as a mammalian, plant, insect, microbial, fungal or alternative system. VH binding domains of the invention may be produced by:

a) injecting an antigen into the transgenic mammal described herein;
b) isolating a cell or tissue expressing an antigen-specific heavy chain-only antibody of interest;
c) cloning the VH locus from mRNA derived from the isolated cell or tissue;
d) displaying the encoded protein using a phage or similar library
e) identifying antigen-specific VH domain(s); and
f) expressing the VH domain(s) alone or as a fusion protein in bacterial, yeast or alternative expression systems.

Alternatively, after step b), c) directly cloning the VH into a mammalian HCAb expression system;
d) identifying antigen-specific VH domain expressing cells; and
e) expressing the VH domain(s) alone or as a fusion protein in bacterial, yeast or alternative expression systems.

BRIEF DESCRIPTION OF THE FIGURES

The patent or application file contains at least one drawing executed in color. Copies of this patent or patent application publication with color drawings(s) will be provided by the Office upon request and payment of the necessary fee.

FIG. 3: depicts the sequence of the 8V3 locus (SEQ ID NO:1). The human VH coding segments are in green. Red surrounded by yellow indicates the joint between genomic fragments of the relevant part of the Ig locus. Human DH and JH segments are in red, the mouse Cγ1 constant region lacking CH1 is in purple.

FIG. 7 depicts the sequence of the V18 locus (SEQ ID NO:2). The human VH coding segments are highlighted in green. Red surrounded by yellow indicates the joint between genomic fragments of the relevant part of the Ig locus. Human DH and JH segments are in red, the, mouse Cγ1 constant region lacking CH1 is in purple.

The top line shows the Cμ region of the mouse with the different exons including the two exons coding for the membrane form of IgM. To the left are the J, D and $V_H$ region of the locus, to the right the other constant regions starting with Cδ. The bottom lines show part of the amino acid sequence of the normal M1 exon before and after recombination (SEQ ID NOs: 7 and 5, respectively). The DNA sequence (SEQ ID NO: 6) shows the integration sequence. The stop codon is in red, the Spe I site in red and blue.

Figure 9:
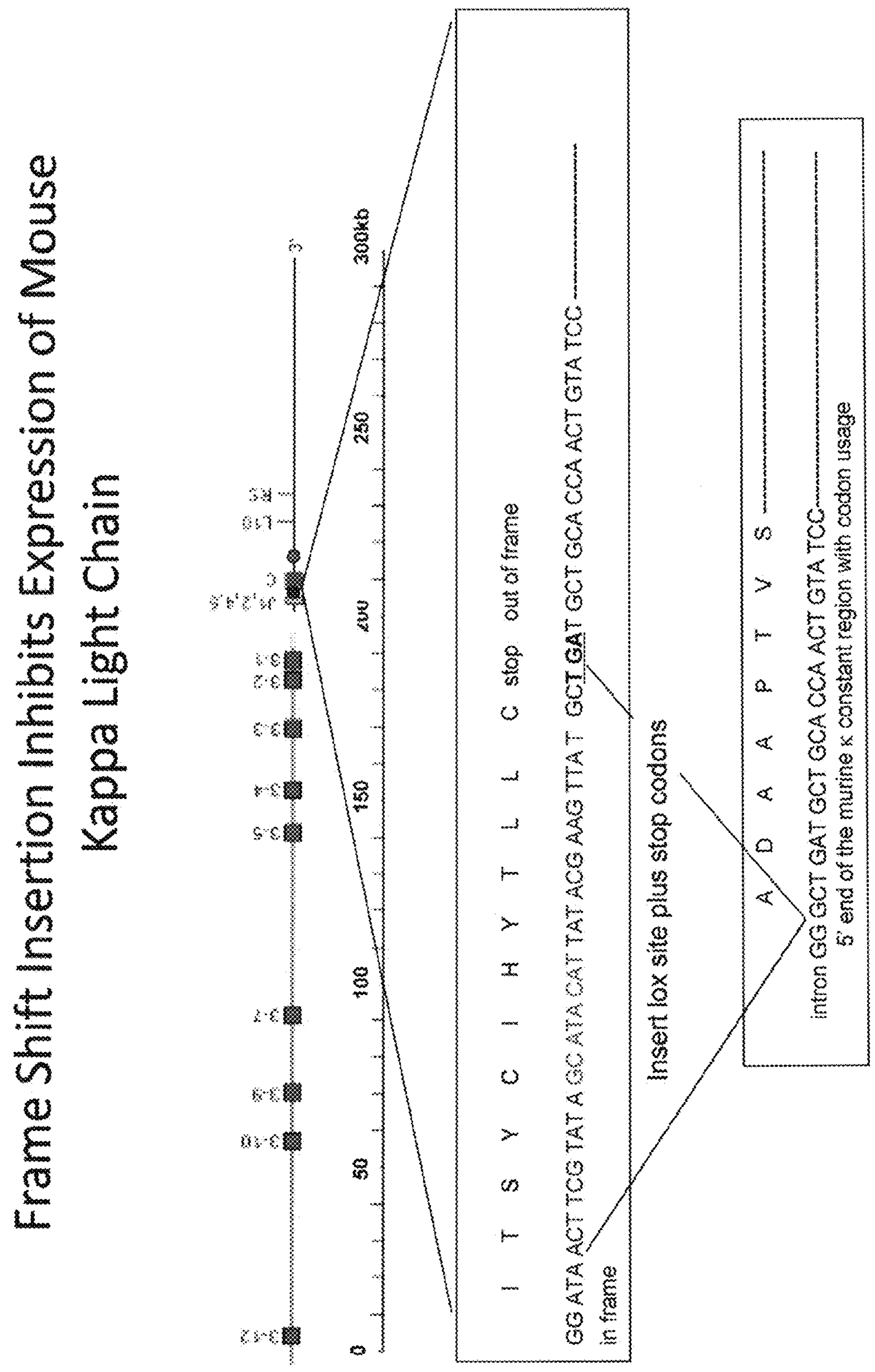

FIG. 9: depicts a mouse $C_\kappa$ insertion to inactivate the κ locus.

The locus is shown on the top line. The bottom shows the sequence at the 5' end of the $C_\kappa$ exon (blue in top line, SEQ ID NO: 11) with the amino acid coding written above the bases (SEQ ID NO:10). The GG base pair at the start is immediately flanking the splice acceptor site coding for the amino acid R after splicing. The middle line shows the insertion of a 34 basepair lox site insertion (blue and red inverted repeat sequence, SEQ ID NO: 9; amino acid sequence SEQ ID NO: 8), which puts the codon usage of the constant region out of frame and creating downstream stop codons (e.g. TGA bold print underlined). Black circle κ-enhancer and red circle κ-LCR sequences.

FIG. 10: depicts an example of results of ELISA analysis of transgenic mice immunized with a peptide (VHLTPVEKSAVTALC, SEQ ID NO: 3) specific for the $\beta^S$ form of the β-globin polypeptide. The curves represent three separate mice of a particular 8V3 line (line tg6 containing 27 human D regions) and a particular V18 line (tg27 containing 27 human D regions). Points on the line indicate the serum dilution shown at the bottom. The vertical axis is absorbance.

Figure 11:
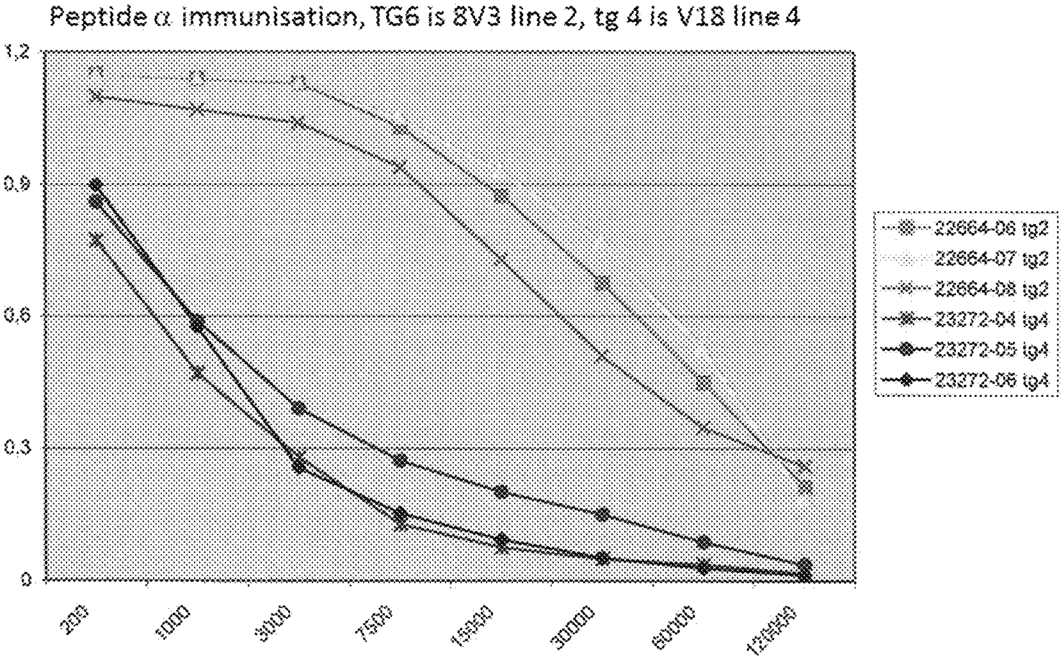

FIG. 11: depicts an example of results of ELISA analysis of transgenic mice immunized with a peptide (VLSPADKTNVKAAC, SEQ ID NO:4) form the α-globin polypeptide. The curves represent three separate mice of a particular 8V3 line (line tg2 containing 27 human D regions) and a particular V18 line (tg4 containing 21 human D regions). Points on the line indicate the serum dilution shown at the bottom. The vertical axis is absorbance.

DETAILED DESCRIPTION OF THE INVENTION

The present inventors have overcome the limitations of the prior art and shown that transgenic animals, in particular mice, can be generated to produce heavy chain only antibodies which are secreted by plasma cells much more efficiently than heavy chain only antibody loci that contain VH genes from many different subclasses and/or lack VH3 genes. These animals can then be used either to generate a reliable supply of class-specific heavy chain-only antibody using established hybridoma technology or phage display or mammalian HCAb expression technology or direct cloning technology as a source of functional soluble VH heavy chain binding domains which are free of effector functions but which retain full binding function.

Heavy chain-only antibodies (excepting camelid antibodies) which can be generated by the methods of the invention show high binding affinity resulting from VH, D and J rearrangements and somatic mutations. Essentially normal B-cell maturation is observed with high levels of heavy chain-only antibody present in isolated plasma (provided that the CH1 domain has been eliminated from all antibody classes present in the recombinant locus). B-cell maturation and the secretion of assembled dimers (e.g., IgG) has no dependency on the presence or expression of light chain genes.

Nucleotide sequence analysis of antigen-specific mRNA coding for human VH gene containing heavy chain only antibodies derived from transgenic mice has demonstrated that heavy chain antibody diversity is primarily a function of VDJ recombination. Further affinity is generated by somatic mutations in the VH domains (U.S. Patent Publication 20120151610). Using the methods described herein, functional HCAb can be cloned and expressed in mammalian systems, functional VH domains can be cloned and expressed in mammalian and bacterial systems to generate VH binding domains with full retention of antigen binding, specificity and affinity. In addition, class specific heavy chain dimers and multimers can efficiently be secreted by mammalian cell lines in culture.

By varying the number and type of constant domains (lacking a CH1 domain) the transgenic mice can be programmed to produce preferred classes of heavy chain-only antibody in response to antigen challenge, e.g., only IgG as opposed to only IgM or, for example, mixtures of IgA and IgG.

The inventors have previously described (U.S. Patent Publication 20120151610, incorporated herein by reference in its entirety) the preparation of transgenic mice expressing a minimal human IgG heavy chain constant region locus devoid of the CH1 exon and linked by human D and J segments with a concatamer of 18 human VH genes. These mice produce functional, antigen-specific IgG heavy chain-only antibody when challenged with antigen. Mixtures of heavy chain-only antibody classes can be obtained by class switching in vivo through utilisation of gene constructs incorporating heavy chain constant regions in tandem (provided that all antibodies lack a CH1 domain). However, transgenic mammals (mice) containing such loci cannot produce heavy chain only antibodies efficiently—B cell development is not efficient (low cell numbers), the heavy chain only antibody titer is low and only low numbers of high affinity antigen specific heavy chain only antibodies or VH region can be obtained after immunisation. The invention/improvements described herein show that a mouse constructed with the same constant region locus linked by human D and J segments with eight VH3 genes (rather than a mixture of VH genes of many subclasses) results in good B-cell maturation and high antigen specific heavy chain only antibody titers in the serum. The human VH3 genes (or VH genes from other vertebrates homologous to human VH3) show the best homology to camelid VHH genes which are naturally soluble as heavy chain only antibodies without association to an immunoglobulin light chain (Muyldermans, S. 2001. Single domain camel antibodies: Current status. J. Biotechnol. 74: 277-302); Davies, J., Riechmann, L., Camelising human antibody fragments: NMR studies on VH domains. FEBS Lett. (1994). 339, 285-290; Jespers L, Schon O, James L C, Veprintsev D, Winter G. Crystal structure of HEL4, a soluble, refoldable human V(H) single domain with a germ-line scaffold. J Mol Biol. 2004 Apr. 2; 337(4):893-903 and refs therein.) Moreover, the soluble HCAb (heavy chain only antibodies) generated from the V18 locus were almost exclusively of the VH3 and to a lesser extent the VH4 subclass.

The inventors have found that large heavy chain antibody loci containing many human VH genes from all or many of the subclasses of human VH genes do not efficiently result in the generation of high affinity heavy chain antibodies because such loci contain too many VH genes from subclasses that are intrinsically insoluble. As a result, during B cell differentiation and the period of heavy chain rearrangement too many VDJ rearrangements take place which result in insoluble (or weakly soluble) heavy chain only antibodies resulting in low numbers of B cells and low heavy chain only antibody titers. The inventors have found that, by restricting heavy chain antibody loci to comprise primarily VH genes of the VH3 subclass, this problem is solved through the reduction of non-productive rearrangements and that much larger numbers of B cells and antibody titers are obtained.

This observation has important implications for the improved engineering of class-specific heavy chain-only antibodies and the derivation of high affinity, soluble VH domains which incorporate affinity maturation via somatic mutation. Incorporation of selected VH3 (and optionally VH4) segments permits the production of any class of heavy chain-only antibodies or any mixture of heavy chain-only antibodies without the requirement to resort to the immunisation of large numbers of animals to obtain a few high affinity heavy chain only antibodies and soluble VH domains retaining specific antigen binding. Such VH3-derived domains can be expressed alone in bacterial (or other micro-organism systems) or mammalian systems or as functional heavy chain-only antibody incorporating effector domains secreted by hybridomas or transfected cells in culture. Antibodies and VH binding domains of human origin have wide ranging applications in the field of healthcare as medicines, diagnostics, and reagents, with parallel agricultural, environmental and industrial applications.

Thus, the present invention provides a method for the efficient production of a VH heavy chain antibody in a transgenic mammal comprising the step of expressing a heterologous VH3-based heavy chain locus in that mammal which is capable of forming a diverse repertoire of complete heavy chain-only antibodies when expressed.

The improved methods/vectors/animals for making antibodies according to the invention have the advantage over those of the prior art in that antibodies can be obtained much more efficiently and are of substantially a single subclass VH gene preferably of the human subclass of VH3 domains (or VH domains from other species representing the same human subclass) linked to human D and J regions and different mammalian constant regions or single region lacking the CH1 domain. Antibodies are of high affinity resulting from a combination of VDJ recombination and affinity maturation in vivo. Antibodies and fragments thereof may be may be isolated, characterised and manufactured using well-established methods known to those skilled in the art.

The Heterologous Heavy Chain Only Antibody (HCAb) Locus

In the context of the present invention, the term 'heterologous' means a nucleotide sequence or a locus as herein described, which is not endogenous to the mammal in which it is located.

A "VH heavy chain locus" in the context of the present invention relates to an engineered locus encoding a VH domain comprising one or more VH genes, preferably of the human VH3 subclass or homologous to the human VH3 subclass, one or more D segments and one or more J segments, operationally linked to one or more heavy chain effector regions (each devoid of a CH1 domain).

The advantage of the present invention is that the antibody repertoire generated from these VH3 loci is intrinsically more soluble than that derived from other VH subclasses and as a result that the generation of soluble high affinity HCAb occurs with much greater efficiency than those derived from a locus that contains a minority of VH3 domains, if any, amongst VH domains of different subclasses. Diversity can be maximised through the use of multiple VH3 (and VH4), D and J segments. For example, preferably the locus comprises 8VH3 segments, all 27 human D segments and all 6 human J segments. Subsequent somatic mutation is achieved without the need for the VL and LC immunoglobulin loci.

Preferably, the VH heavy chain locus comprises at least one VH subclass 3 (VH3) gene of human origin or a VH derived from any vertebrate species but homologous to human VH3 subclass. A VH from another vertebrate species is homologous to human VH3 subclass if it shows at least 60%, 70%, 75%, 80%, 85%, 90%, 95%, or greater homology with camelid VHH in the amino acid sequence. Preferably the locus should contain more VH3 genes and these should form the majority of the genes in the locus. The VH-3 genes may be selected from VH3-48, VH3-30, VH3-33, VH3-23, VH3-64, VH3-74, VH3-66, VH3-53, VH3-49, VH3-15, and VH3-07. The VH heavy chain locus may comprise 1, 2, 3, 4, 5, 6, 7 or 8 VH-3 genes selected from VH3-48, VH3-30, VH3-33, VH3-23, VH3-64, VH3-74, VH3-66, VH3-53. Alternatively, the VH heavy chain locus may comprise 1, 2, 3, 4, 5, 6, 7 or 8 VH-3 genes selected from VH3-53, VH3-49, VH3-48, VH3-30, VH3-33, VH3-23, VH3-15, and VH3-07. The VH heavy chain locus may additionally comprise VH gene segments from subclasses other than VH3. For example, the VH heavy chain locus may comprise one or more VH gene segments selected from VH1-18, VH1-69, VH1-2, VH1-8, VH6-1, VH4-59, VH4-34, VH4-b, and VH4-4. In one embodiment, the VH heavy chain locus comprises a variable region comprising VH3-48, VH3-30, VH3-33, VH3-23, VH3-64, VH3-74, VH3-66, VH3-53 and VH6-1. In particular, the invention provides that the VH heavy chain locus may comprise in the following order 5' to 3' VH3-48, VH3-30, VH3-33, VH3-23, VH3-64, VH3-74, VH3-66, VH3-53 and VH6-1. In another embodiment, the VH heavy chain locus comprises a variable region comprising VH3-53, VH3-49, VH3-48, VH3-30, VH3-33, VH3-23, VH3-15, VH3-07, VH1-18, VH1-69, VH1-2, VH1-8, VH6-1, VH4-59, VH4-34, VH4-b, and VH4-4. In particular, the invention provides that the VH heavy chain locus may comprise in the following order 5' to 3' VH1-69, VH4-59, VH3-53, VH3-49, VH4-34, VH3-48, VH3-30, VH3-33, VH3-23, VH1-18, VH3-15, VH4-b, VH1-8, VH3-07, VH2-5, H-4, VH1-2 and VH1-6.

Preferably, the VH heavy chain locus comprises from two to forty (2, 3, 4, 5, 6, 7, 8, 9, 10, 12, 14, 16, 18, 20, 30 or 40), or more, D segments. The D segments may be derived from any vertebrate species but, most preferably, the D segments are human D segments (normally 27 functional D segments).). Preferably, the heavy chain locus comprises all 27 human D gene segments and all 6 human J gene segments. Alternatively, the heavy chain locus may comprise 21 human D gene segments and all 6 J gene segments. Where the heavy chain locus comprises 21 human D gene segments, the D gene segments may comprise in the following order 5' to 3', D 1-1, D2-2, D3-9, D3-10, D 4-11, D 5-12, D 6-13, D, 1-14, D 2-15, D 3-16, D 3-17, D 5-18, D 6-19, D 1-20, D 2-21, D 3-22, D 4-23, D 5-24, D 6-25, D 1-26, and D-7-27.

Preferably, the VH heavy chain locus comprises from two to twenty (2, 3, 4, 5, 6, 7, 8, 9, 10, 12, 14, 16, 18 or 20) or more J segments. The J segments may be derived from any vertebrate species but, most preferably, the J segments are human J segments (normally 6 J segments).

Preferably, the VH heavy chain locus comprises one or more VH3 genes, one or more human D segments and one or more human J segments.

The term 'VH gene' encompasses a naturally occurring VH coding sequence derived from human and VH genes from other vertebrates.

The VH gene must be capable of recombining with a D segment, a J segment and a constant heavy chain effector region (which may comprise several exons but excludes a CH1 exon) according to the present invention to generate a VH heavy chain only antibody, when the nucleic acid is expressed.

A VH gene according to the present invention also includes within its scope any gene sequence from other species encoding a homologue, derivative or protein fragment, which is capable of recombining with a D segment, a J segment and a constant heavy chain region (comprising one or more exons) according to the present invention to generate a heavy chain-only antibody as defined herein.

Thus VH coding sequences or homologues thereof may be derived from several naturally occurring sources using methods familiar to those skilled in the art.

A "VH domain" in the context of the present invention refers to an expression product of a VH gene when recombined with a D and a J segment as defined above. Preferably, the VH (or homologues thereof) domain is a VH3 domain and remains in solution and is active in a physiological medium without the need for any other factor to maintain solubility. Preferably, the ability of the soluble VH domain to bind antigen has been improved by VH, D and J recombination and somatic mutation. There is no dependency on the presence or otherwise of the enlarged CDR3 loop peculiar to the camelid species. The VH domain is able to bind antigen as a monomer, and, when combined with effector constant regions may be produced in mono-specific, bi-specific, multi-specific, bi-valent or multivalent forms, dependent on the choice and engineering of effector molecules used (eg IgG, IgA IgM etc) or alternative mechanisms of dimerisation and multimerisation. Any likelihood of binding with a VL domain when expressed as part of a soluble heavy chain-only antibody complex has been eliminated by removal of the CH1 exon (see Sitia et al. (1990) *Cell,* 60, 781-790; Janssens et al. 2006 Proc Natl Acad Sci USA. 103:15130-5). The VH domain alone can also be engineered with diverse protein domains to produce fusion proteins for targeted therapeutic and diagnostic purpose, for example with toxins, enzymes and imaging agents.

In the context of the present invention the terms 'a D segment' and 'a J segment' include naturally occurring sequences of D and J segments. Preferably, the D and J segments are derived from the same vertebrate from which the VH gene is derived. For example, if a VH3 gene is derived from a human and then solubilised or engineered, the D and J segments are preferably also derived from a human. Alternatively the VH3 homologous genes maybe derived, for example, from other primates or rodents and the D and J segments from human or visa versa.

The terms D segment and J segment also include within their scope derivatives, homologues and fragments thereof as long as the resultant segment can recombine with the remaining components of a heavy chain antibody locus as herein described to generate a heavy chain-only antibody as herein described. D and J segments may be derived from naturally occurring sources or they may be synthesised using methods familiar to those skilled in the art and described herein. The VH genes or homologues and the D and J segments are capable of recombination and preferably undergo somatic mutation.

The VH genes or homologues, the D segments and the J segments are preferably derived from a single vertebrate species. This may be any vertebrate species but is preferably a human.

In addition, a heterologous heavy chain locus according to the present invention comprises a region of DNA encoding a heavy chain constant polypeptide (a heavy chain constant region) providing effector functions in vivo (eg IgG, IgM, IgA, IgE, IgD or isotypes thereof).

The invention also provides a more efficient method to generate an antigen-specific heavy chain-only antibody by the methods of the present invention using, primarily, VH3 domains, D and J domains and constant regions. The latter would lack a CH1 region as described (U.S. Patent Publication 20090307787).

Mammals

The transgenic mammal used in the methods of the invention is not a human. The transgenic mammal is preferably a rodent such as a guinea pig, rat or mouse; rabbits are also included. Mice are especially preferred. Alternative mammals such as goats, sheep, cats, dogs or other animals may also be employed.

Transgenic animals are generated using established oocyte injection technology, ES cell technology, cloning or iPS (induced pluripotent stem cells) technology.

Figure 8:
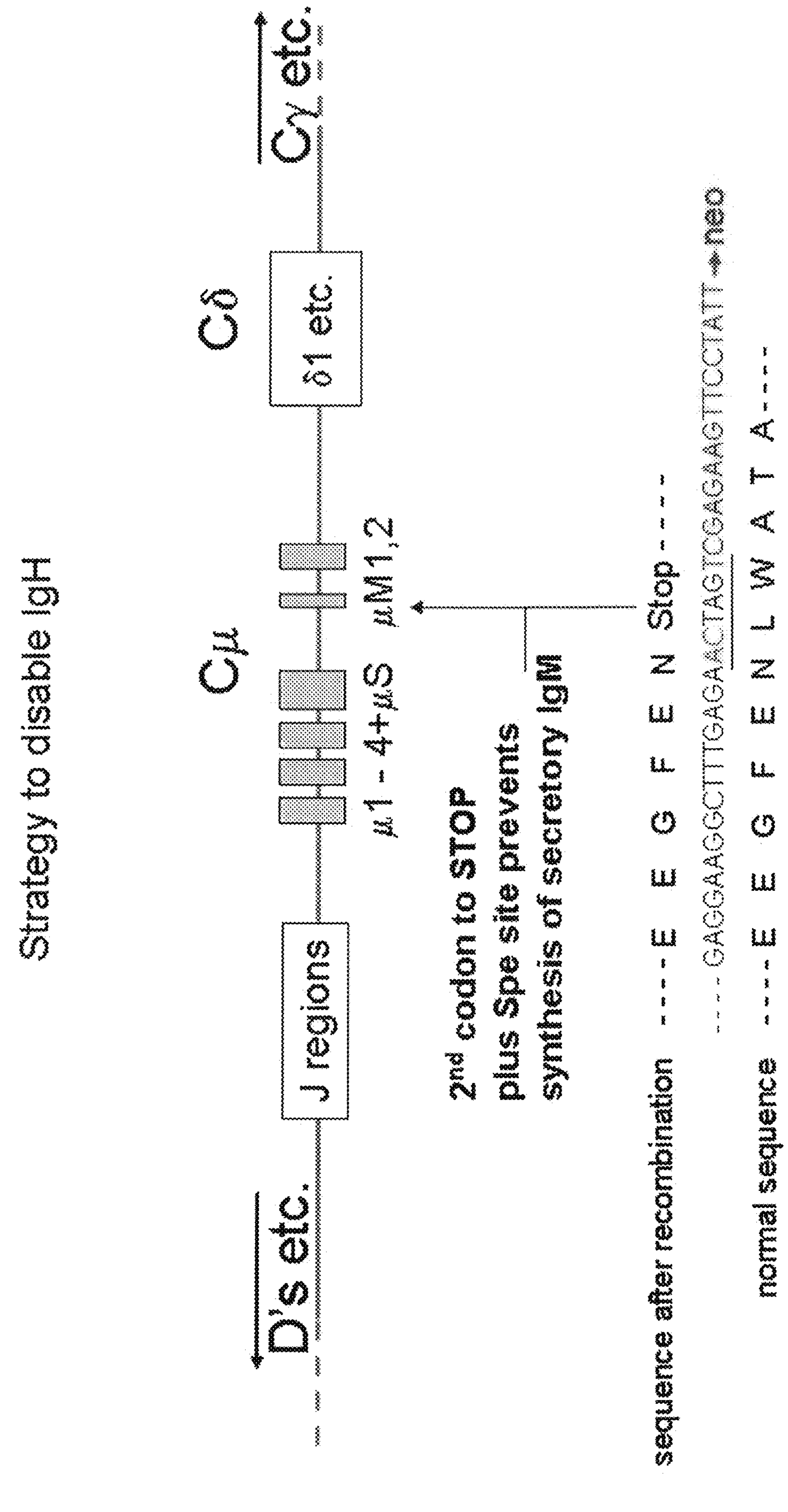
FIG. 8 depicts a strategy to disable mouse IgH.

Advantageously, heavy and optionally light chain loci endogenous to the mammal are deleted or silenced when a heavy chain-only antibody is expressed according to the methods of the invention or have an otherwise reduced capacity to produce endogenous immunoglobulin chains. For example, if mice are used, they can be μMTE mice as depicted in FIG. 8, obtained by homologous recombination of ES cells. The IgH locus can be inactivated by a strategy similar to that published by Kitamura and Rajewsky with the difference being that the stop codon is introduced into the $C_\mu$ regions at a position one amino acid before that described by Kitamura et al. (1991) Nature, 350, 423-426. Preferably, the mice are μMTE. Additionally, the mice can have the κ light chain locus inactivated as depicted in FIG. 9. Additionally the lambda light chin locus may be inactivated although it should be noted that the mouse lambda locus is used very infrequently.

Antibody-producing cells may be derived from transgenic animals according to the present invention and used, for example, in the preparation of hybridomas for the production of heavy chain-only antibodies as herein defined. In addition or alternatively, nucleic acid sequences may be isolated from transgenic mammals according to the present invention and used to produce VH domain heavy chain-only chain antibodies or bi-specific/bi-functional complexes thereof, using recombinant DNA techniques which are familiar to those skilled in the art.

Alternatively or in addition, antigen-specific heavy chain-only antibodies may be generated by immunisation of a transgenic animal according to the present invention.

Thus in a further aspect, the present invention provides a more efficient method for the production of heavy chain-only antibodies by immunising a transgenic mammal according to the present invention with an antigen.

In a preferred embodiment of this aspect of the invention, the mammal is a mouse.

Heavy Chain-Only Antibodies and Fragments Thereof.

In a further aspect, the present invention provides a heavy chain only antibody obtainable according to a method of the present invention and functional fragments and derivatives thereof.

A preferred functional fragment is an antigen-specific heavy chain binding domain i.e. a VH3 or homologous binding domain, as expressed by the VH, D, J locus as a result of recombination between single VH, D and J exons followed subsequently by somatic mutation. According to this aspect of the invention VH, D, J loci can be cloned from, e.g., mRNA isolated from an antibody-producing cell of an immunised transgenic animal as described above. Cloned sequences can then be displayed using a phage (Ward et al. *Nature* (1989) 341, 544-546) or similar display libraries, for example using yeast-based systems (Boder E T and Wittrup K D. (1997) *Nat. Biotechnol.* 15:553-7) and antigen-specific VH binding domains identified. Antigen-specific heavy chain binding domains can then be manufactured either alone or as fusion proteins in scalable bacterial, yeast or alternative expression systems. Sequences encoding VH binding domain can also be cloned from characterised hybridomas derived by classical procedures from immunised transgenic mice or by direct expression or cloning of the sequences from the B cells (and derivative cells) from immunised mice. These can then be used for the production of VH binding domains and derivatives thereof including the engineering of defined antibody classes (eg IgE or IgA) and variants thereof with differing effector functions.

Accordingly, the invention also provides a method of producing a VH (or homologous subclass) binding domain comprising the steps of:

a) isolating a cell or tissue expressing a soluble, antigen-specific heavy chain-only antibody of interest;

b) cloning the sequence encoding the VH binding domain from mRNA derived from the isolated cell or tissue;

c) displaying the encoded protein using a phage or similar library; or expressing the VH cDNA directly in mammalian cells or making hybridomas or directly obtaining the HCAb by DNA or protein sequencing d) identifying antigen-specific VH binding domains, and e) expressing the VH binding domains alone or as a fusion protein in bacterial, yeast, mammalian or alternative expression systems.

Where the VH binding domain is isolated from a characterised hybridoma or any B cell, the cloned VH binding domain sequence derived from mRNA can be directly cloned into an expression vector without recourse to additional selection steps using phage and other display systems.

Production systems for heavy chain only-antibody incorporating effector regions include mammalian cells in culture (eg CHO cells), plants (e.g. maize), transgenic goats, rabbits, cattle, sheep, chickens and insect larvae suited to mass rearing technology. Other production systems, including virus infection (e.g. baculovirus in insect larvae and cell-lines) are alternatives to cell culture and germline approaches. Other production methods will also be familiar to those skilled in the art. Where there is a requirement for heavy chain-only IgA or IgM assembly, the co-expression of a "J chain" is beneficial. Suitable methods for the production of camelid heavy chain-only antibody or VH binding domains alone are known in the art. For example camelid VH (VHH) binding domains have been produced in bacterial systems and camelid heavy chain-only homodimers have been produced in hybridomas and transfected mammalian cells (see Reichmann and Muyldermans (1999) *J. Immunol. Methods* 231, 25-38).

The present invention also provides a cultured host cell transformed with a heterologous heavy chain locus, or fragment thereof, according to the present invention.

The present invention also provides an effector molecule fusion protein comprising an antigen-specific VH binding domain according to the present invention having attached to an effector moiety (which provides additional effector activity). These effector molecules retain the physiological function conferred by the antigen-specific VH binding domain in combination with additional targeting or effector functions. Such combinations may provide functional monomers or, dependent on the design and interaction of effector domains, result in dimers, tetramers, pentamers, multimers or other complexes of molecules incorporating different VH binding domains, so imparting multi-valency and multi-specificity.

If the effector moiety comprises a binding domain, it may have a different specificity from the antigen-specific VH binding domain. The advantage of this arrangement is that the effector molecule can facilitate cross-linking of different targets. For example, a bispecific effector molecule may be utilised to enhance cell-cell interactions and cell/pathogen interactions. In this embodiment, the polypeptide complexes of the invention can be utilised, for example, to bridge polypeptide complexes between two cell types such as a pathogen and a macrophage (see Biburger, M et al. (2005) *J. Mol. Biol.* 346, 1299-1311)) or to capture both peptides of a toxin to improve efficacy (Laventie B J, Rademaker H J, et al Heavy chain-only antibodies and tetravalent bispecific antibody neutralizing Staphylococcus aureus leukotoxins. Proc Natl Acad Sci USA. 2011 Sep. 27; 108(39):16404-9). The use of VH binding domains is preferable to the use of scFV binding domains in such bi-specific designs. VH binding domains have high binding affinity and can be incorporated into such constructs with minimal vector construction and in the absence of design considerations necessary to maintain the specificity and affinity of scFVs relative to their tetrameric parental molecule.

The term 'effector moiety' as used herein includes any moiety that mediates a desired biological effect on a cell. The soluble effector moiety may be a peptide, polypeptide or protein or may be a non-peptidic structure. For example, the effector moiety may be an enzyme, hormone, cytokine, drug, pro-drug, toxin, in particular a protein toxin, a radionuclide in a chelating structure, a binding domain, a dimerising or interaction domain, an imaging agent, albumin, or an inhibitory agent.

Albumin may be utilised as an effector molecule to increase the stability, pharmacokinetic and/or pharmacodynamic properties of the antigen-specific VH binding domain (Sung C et al. (2003) *J. Interferon Cytokine Res;* 23(1):25-36). Alternatively, effector domains maybe chemically pegylated or naturally glycosylated so as to improve pharmacodynamic properties.

The effector moiety may be peptide bonded to the antigen-specific VH binding domain or it may be chemically bonded to the antigen specific heavy chain binding domain, for example by using a chemical linking structure such as a maleimide linker. Alternatively, the effector molecules of the invention may be expressed as fusion proteins. In the case of genetic fusions, the attachment of the various domains may be achieved using a recombinant DNA construct that encodes the amino acid sequence of the fusion protein, with the DNA encoding the various domains placed in the same reading frame. Such constructs are of value as diagnostics and therapeutics. As diagnostics the effector molecule can be a fluorescent protein (eg GFP) or enzyme (eg β-gal). Alternatively, the effector molecule can be a tag for enhanced binding to a substrate (eg poly histidine or a biotinylation site), an antigen to provide a site of attachment for secondary antibodies or a site for the attachment of fluorescent markers via a leucine zipper or similar binding motif.

Additionally, the effector molecule may comprise one or more of CH2, CH3 or CH4 antibody constant region domains and/or a J chain. In this embodiment of the invention, two or more effector molecules may associate to produce an effector molecule dimer or multimer. The effector molecules may be the same (enabling the production of an effector molecule homodimer or homomultimer) or different (enabling the production of an effector molecule heterodimer or heteromultimer). Preferably, the effector molecule dimer or multimer is bi-valent or multi-valent. Preferably, the constant regions for the two or more effector molecules are identical.

An exemplary effector molecule according to the invention is useful for cytochemical labelling, targeting methods or therapy. The effector molecule comprises an antigen-specific VH binding domain which targets a cancer cell surface marker and, as the soluble effector moiety, a pro-drug converting enzyme. The antigen-specific VH binding domain binds to the target and brings the effector domain into close proximity with the target such that it can exert a biological effect on the target in the presence of the pro-drug (e.g. nitroreductase with CB1954).

The present invention provides the use of a heavy chain-only antibody or a fragment thereof as herein described as an intracellular binding reagent, or an abzyme. Preferred heavy chain-only antibody fragments are soluble antigen-specific VH binding domains.

The present invention also provides, the use of an antigen-specific single chain antibody or VH binding domain according to the present invention as an enzyme inhibitor or receptor blocker. Preferred heavy chain-only antibody fragments are soluble antigen-specific VH binding domains.

The methods of the invention provide heavy chain-only antibodies, or fragments thereof, that are suitable for pharmaceutical use in humans, and so the invention provides a pharmaceutical composition comprising a heavy chain-only antibody, or a fragment thereof of the invention. These will typically be formulated before administration to patients.

For example, the antibodies, or fragments thereof, may be mixed with stabilisers, particularly if they are to be lyophilised. Addition of sugars (e.g. sucrose, trehalose) is typical to give stability during lyophilisation, and a preferred stabiliser is mannitol. Human serum albumin (preferably recombinant) can also be added as a stabiliser. Mixtures of sugars can also be used, e.g. sucrose and mannitol, trehalose and mannitol, etc.

Buffer may be added to the composition e.g. a Tris buffer, a histidine buffer, a glycine buffer or, preferably, a phosphate buffer (e.g. containing sodium dihydrogen phosphate and disodium hydrogen phosphate). Addition of buffer to give a pH between 7.2 and 7.8 is preferred, and in particular a pH of about 7.5.

For reconstitution after lyophilisation, sterile water for injection may be used. It is also possible to reconstitute a lyophilised cake with an aqueous composition comprising human serum albumin (preferably recombinant).

Generally, the antibodies of the invention, or fragments thereof, will be utilised in purified form together with pharmacologically appropriate carriers.

The invention thus provides a method for treating a patient, comprising administering a pharmaceutical composition of the invention to the patient. The patient is preferably a human, and may be a child (e.g. a toddler or infant), a teenager or an adult, but will generally be an adult.

The invention also provides heavy chain-only antibodies of the invention, or fragments thereof, for use as a medicament.

The invention also provides the use of the heavy chain-only antibodies of the invention, or fragments thereof of the invention in the manufacture of a medicament for treating a patient.

These uses, methods and medicaments are preferably for the treatment of one of the following diseases or disorders: wound healing, cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis, psoriasis and respiratory tract inflammation, asthma, immunodisorders and organ transplant rejection; cardiovascular and vascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection and parasitic infection, pathological conditions associated with the placenta and other pathological conditions.

In a further aspect still, the present invention provides the use of an antigen-specific heavy chain-only antibody or VH binding domain obtainable by the method of the present invention as a diagnostic, prognostic, or imaging agent.

EXAMPLES

Any suitable materials and/or methods known to those of skill can be utilized in carrying out the methods described herein.

General Techniques

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc. which are incorporated herein by reference) and chemical methods. In addition Harlow &

Lane., A Laboratory Manual Cold Spring Harbor, N.Y., is referred to for standard Immunological Techniques.

In the following examples, the transgenic mice can be modified to have no or very low expression of the endogenous mouse heavy chain genes and mouse light chain genes. For example, the mice can be μMTE mice as depicted in FIG. 8, obtained by homologous recombination of ES cells. The IgH locus can be inactivated by a strategy similar to that published by Kitamura and Rajewsky with the difference being that the stop codon is introduced into the $C_{\mu}$ regions at a position one amino acid before that described by Kitamura et al. (1991) Nature, 350, 423-426. Additionally, the mice can have the κ light chain locus inactivated as depicted in FIG. 9.

Methodology used for the generation and screening of transgenic mice following antigen challenge are essentially as previously described (Janssens et al. (2006) PNAS, 10, 103(41), 15130-5, WO2006/008548, WO2007/096779). General methods for deriving vertebrates, including mammals, other than mice, which express functional heterologous immunoglobulin loci and/or have engineered endogenous loci are as described in WO2006/047367. In the examples below, recombination in ES cells is used and the modified ES cells are used to generate mice with the desired properties. However, the same procedures could be carried out in induced pluripotent stem cells (iPS cells) which are then used to generate mice (e.g. Boland, Hazen, Nazor, Rodriguez, Gifford, Martin, Kupriyanov and Baldwin (2009), 461, 7260, 91-4 and references therein). Alternatively, the modifications are carried out in somatic cells or somatic stem cells which are subsequently reprogrammed into iPS cells to generate modified mice. Also, modified hematopoietic stem cells could be transplanted into recipient mice lacking B cells to generate human or human hybrid antibody Example 1

Figure 1:
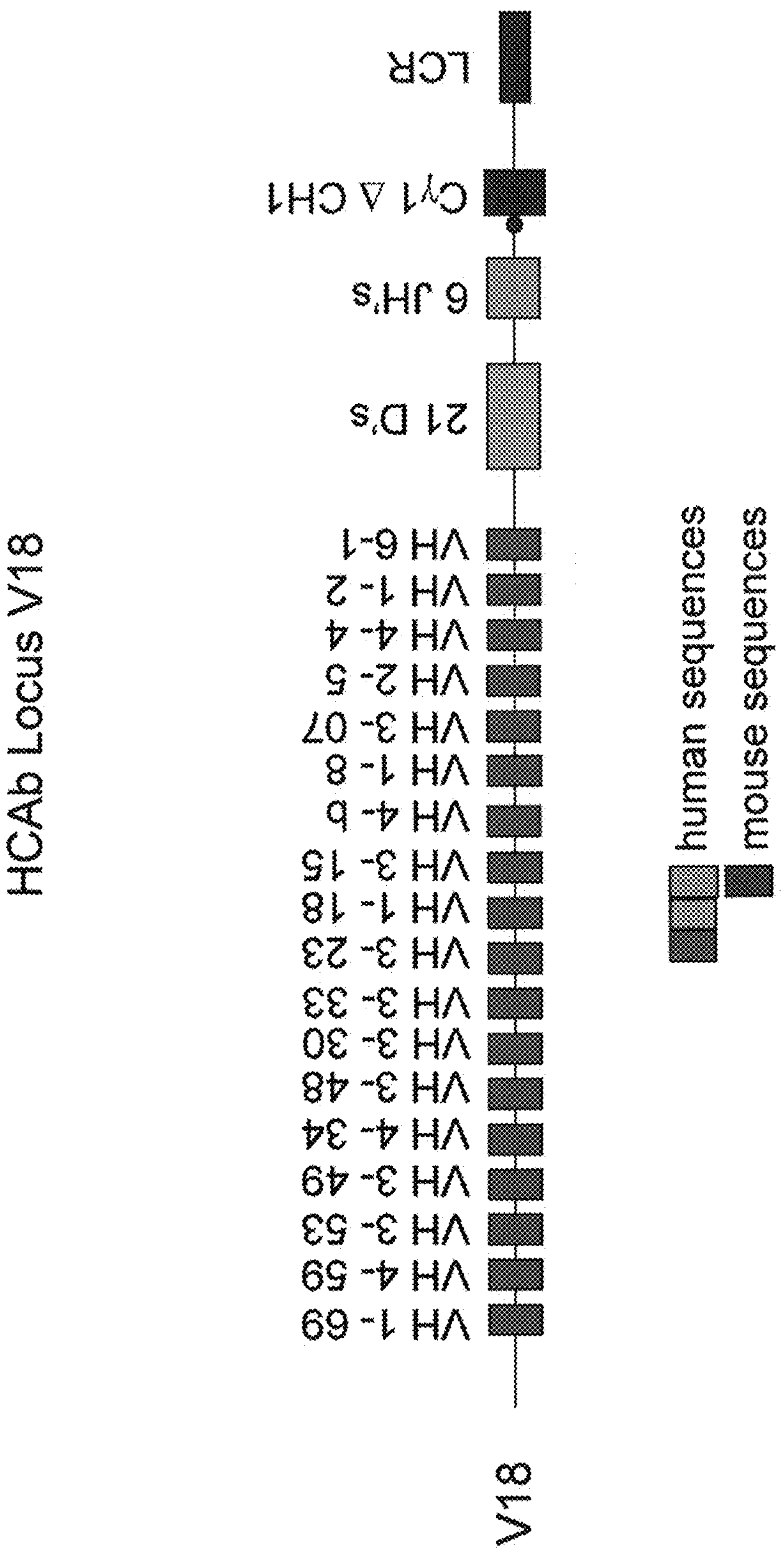
FIG. 1: depicts the structure of the V18 locus containing 18 human VH segments, 21 human D segments, all 6 human J segments and the murine Cγ1ΔCH1 constant region and murine LCR.

In previous experiments, transgenic mice were prepared to express a heavy chain locus wherein 18 human VH segments were linked to 21 human heavy chain diversity (D) and all 6 joining (J) segments, followed by the Cγ1 (minus CH1) murine constant region gene and murine heavy chain immunoglobulin 3' LCR (FIG. 1, designated “line 4”). The locus was also “repaired” by providing the additional D regions to obtain all 27 D regions in line sc27 (see example 2).

The transgene construct was introduced by breeding to mice where the heavy chain locus of the mouse was inactivated as discussed above, i.e., by the introduction of a stop codon in the mouse Cμ gene through homologous recombination and neomycin selection in ES cells. Similarly the mouse Ck locus was inactivated through the insertion of a short sequence that results causes out of frame reading containing novel stop codons. However this locus contains many VH segments that are intrinsically insoluble. Hence recombination with one of these segments does not lead to a soluble HCAb (even after antibody maturation through hypermutations) and as a result a loss of B cells. Thus, although these mice are capable to produce soluble HCAb, there are a low number of B cells producing a limited number of soluble high affinity HCAb.

Example 2

8V3 Constructs

To overcome this problem, a transgenic HCAb locus was generated containing intrinsically more soluble VH segments and reducing the number of insoluble VH segments. The most and second most soluble class of VH segments are the VH3 and VH4 class, while the other classes are much less soluble. A locus was generated by removing almost all of the VH segments in the V18 locus discussed above using a unique restriction I-Sce1 site just 5' of the VH6-1 (FIG. 1) leaving all of the D, J, C and LCR regions intact (BAC V18 decap). The V18 locus also lacked 6 of the DH regions which were not present on the original clone 1065 N8 containing human heavy chain D and J segments (BACPAC Recource Center, USA). The 6 missing DH segments were therefore isolated on one fragment using PCR amplification of human DNA and introduced into the BAC V18 decap at their normal position to restore the full complement of DH (27) segments in their normal order (V18decap-allD). This same procedure was carried out to generate the V18 line sc27 (above in example 1) to exclude any effect of the additional D segments.

Figure 2:
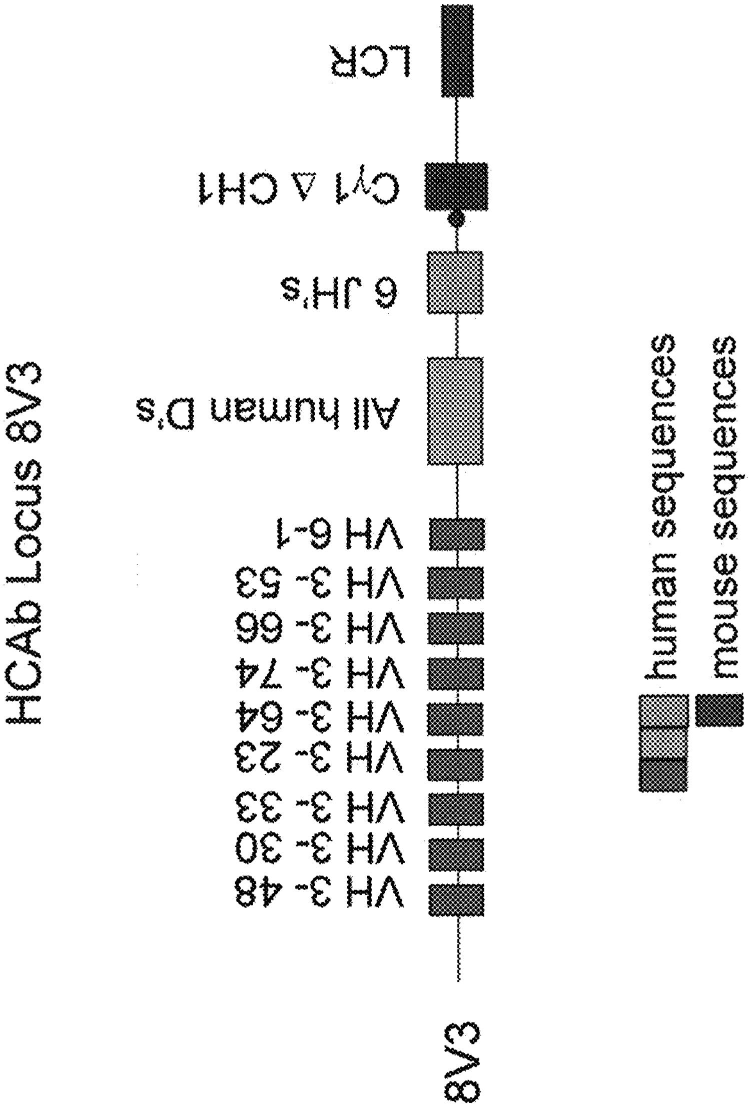
FIG. 2: depicts the structure of the 8V3 locus containing 8 human VH3 segments plus Vh6-1, all 27 human D and all 6 human J segments, the murine Cγ1ΔCH1 constant region and murine LCR.

Next, four new VH segments VH3-64, VH3-74, VH3-66, VH3-53 were isolated using PCR amplification and human DNA and each cloned as a SalI and XhoI restriction fragment. Ligation of such fragments is efficient (SalI and XhoI provide the same 5'-overhang), but destroys the ligated sites leaving a unique SalI and Xhoi at each end. This allows the continuous addition of fragments using a (unique) SalI cut of the receiving vector V18decap-allD containing the DJC and LCR segments. After introducing these 4 VH fragments the existing cluster of 4VH fragments (VH3-48:VH3-30:VH3-33:Vh3-23) used in V18 was ligated in to generate the locus designated 8V3 (FIG. 2). This locus contains, from 5' to 3,' VH3-48:VH3-30:VH3-33:Vh3-23:VH3-64:VH3-74:VH3-66; VH3-53, all of the human D and J regions including the regulatory sequences in their normal configuration in the genome, the murine Cγ1 (minus CH1) gene and the murine LCR with the sequence illustrated in FIG. 3. The founder mice were bred to mice with the same inactivated murine IgH and Ig□ background.

Example 3

Transgenic Mice, Breeding and Genotyping

The final BAC was introduced into transgenic mice by standard microinjection of fertilized eggs. Obviously, it could also be introduced via other technologies using ES cells or iPS cells. This could involve homologous recombination, TALE or ZnFinger technologies. These mice had an inactivated endogenous heavy chain locus and light chain □ locus (□MTE/□null) as described above. Similarly ES or iPS cells would have the endogenous Ig loci inactivated.

Transgenic loci were checked for integrity and number of copies by Southern blot and PCR analysis of tail DNA (Southern E M J. Mol. Biol. 1975 98: 503-517) using 5' and 3' end locus probes. Founders were bred as lines in the □MTE/□null background. Genotyping was done by standard PCR analysis using primers for each of the different regions of the locus.

Example 4

Flow Cytometric Analyses

Figure 4:
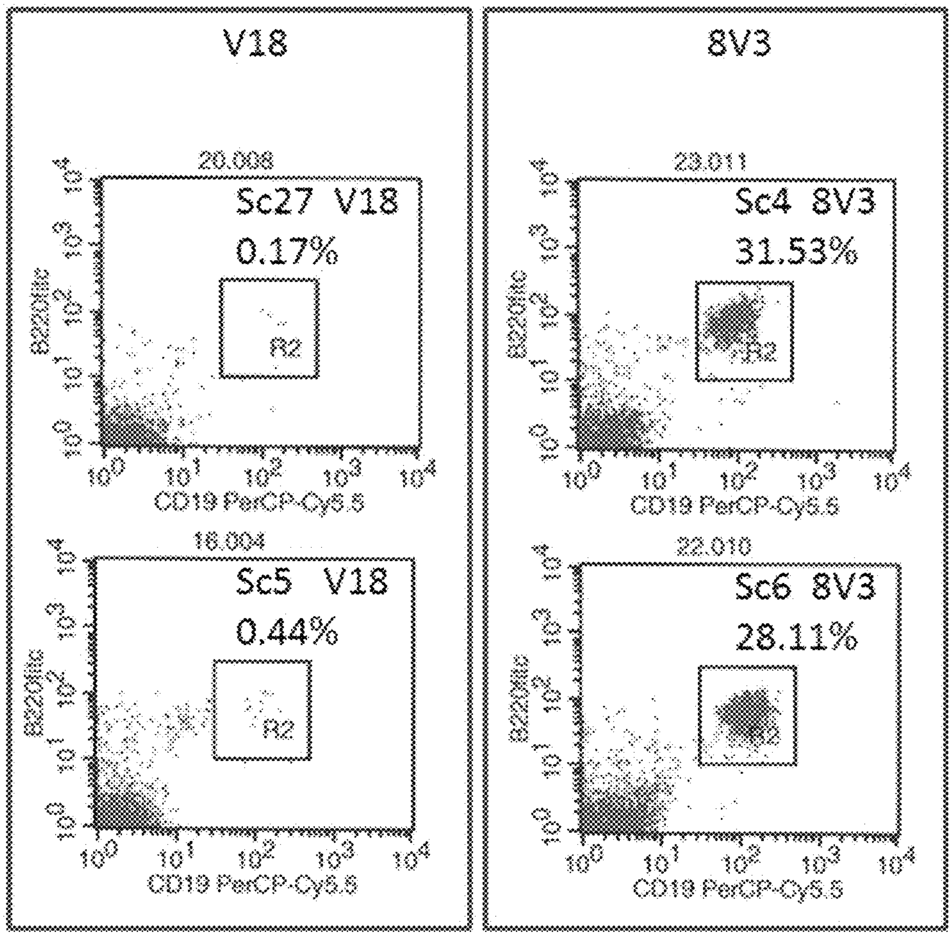
FIG. 4: depicts an example of B cell comparison between V18 and 8V3 mice. Spleen cells were sorted using CD19 (horizontal axis) and B220 (vertical axis). The number of B cells (center group of cells in each picture, boxed R2) is indicated as a percentage of the total number of cells.

Single cell suspensions were prepared from lymphoid organs in PBS, as described previously (Slieker W A, de Rijk-de Bruijn M F, Leenen P J, van Ewijk W. Int Immunol. 1993 September; 5(9):1093-8.). Approximately $1\times10^{6}$ cells were incubated with antibodies in PBS/0.5% bovine serum albumin (BSA) in 96 well plates for 30 min at 4° C. Cells were washed twice in PBS/0.5% BSA. For each sample, $3\times10^4$ events were scored using a FACScan analyzer (Becton Dickinson, Sunnyvale, Calif.). FACS data were analyzed using CellQuest version 1.0 computer software. Four-color analysis was performed on a Becton Dickinson FACS Calibur. The following mAbs were obtained from BD Pharmingen (San Diego, Calif.): FITC conjugated anti B220-RA3-6B2, PE conjugated anti CD19. FACS scan data of spleen cells, stained with anti-CD19 and anti-B220 are displayed in the bottom panel of FIG. 4.

Example 5

Western Blot Analyses

Figure 5:
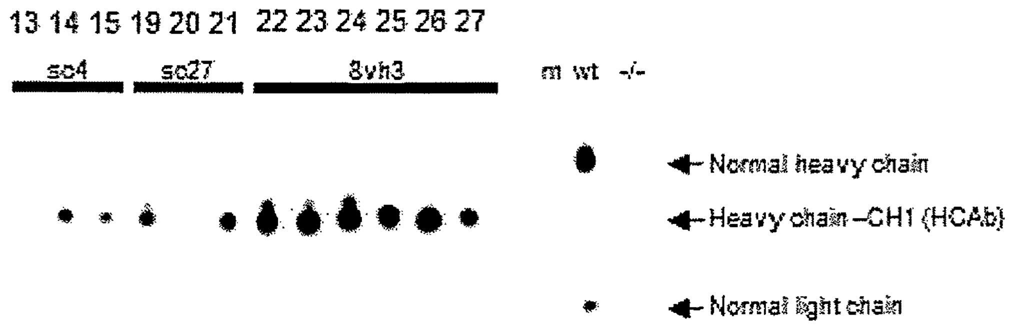
FIG. 5: depicts an example of Western blot analysis to determine the level of HCAb production, Sc4 and Sc27 are different V18 lines, 8V3 represents lines 4, 5 and 6. Wild type mice (wt) are shown on the right, −/− is a nontransgenic mice with inactivated heavy and kappa light chain loci, i.e the background mice of the transgenic lines. M is a marker lane.

FIG. 5 shows Western blots of sera of different transgenic mouse lines containing an HCAb locus V18 (line 4 and line 27, FIG. 1) or different 8V3 lines (lines 4, 5, 6) versus a non transgenic wt control mouse and the background heavy chain/kappa chain inactivated line (−/−). Sera were purified by prot A and gel fractionated under reducing conditions.

The signal shown in FIG. 5 was detected with an anti mouse IgG antibody by standard procedures.

Example 6

Immunization 8 week old mice were immunized with using Ribi as the adjuvant. 20 μg of CD34 antigen was injected respectively in the tail vein on days 0, 14, 28, 42 and i.p. on day 50. Blood was taken on day 0, 14 and 45. Spleen cells were fused with Sp2-O—Ag14 myeloma cells (gift from R. Haperen) on day 56 using a ClonalCell™-HY kit (StemCell Technologies, UK) according to the manufacturer's instructions.

Example 7

Serum Ig ELISA

Blood from 15-25 weeks old mice was collected in EDTA coated tubes, spun for 15' at room temperature (RT) and the supernatant diluted 1:5 in PBS. A 96 well plate was coated for 2 h with 5 mg/ml of a goat anti mouse IgG, washed with PBS, blocked for 1 h at RT with blocking solution (1.5% BSA/1.5% powder milk/0.1% tween 20/PBS) and washed three times with PBS. Dilution series of serum samples and standards were loaded and incubated for 2-4 h and the plates washed 6 times with PBS before addition of a secondary antibody (1:2000 diluted goat anti mouse IgG coupled to HRP (Sigma, Zwijndrecht, NL)). All dilutions were done in a blocking solution. After 1-2 h incubation at RT and washing in PBS, POD substrate (Roche) was added.

Figure 6:
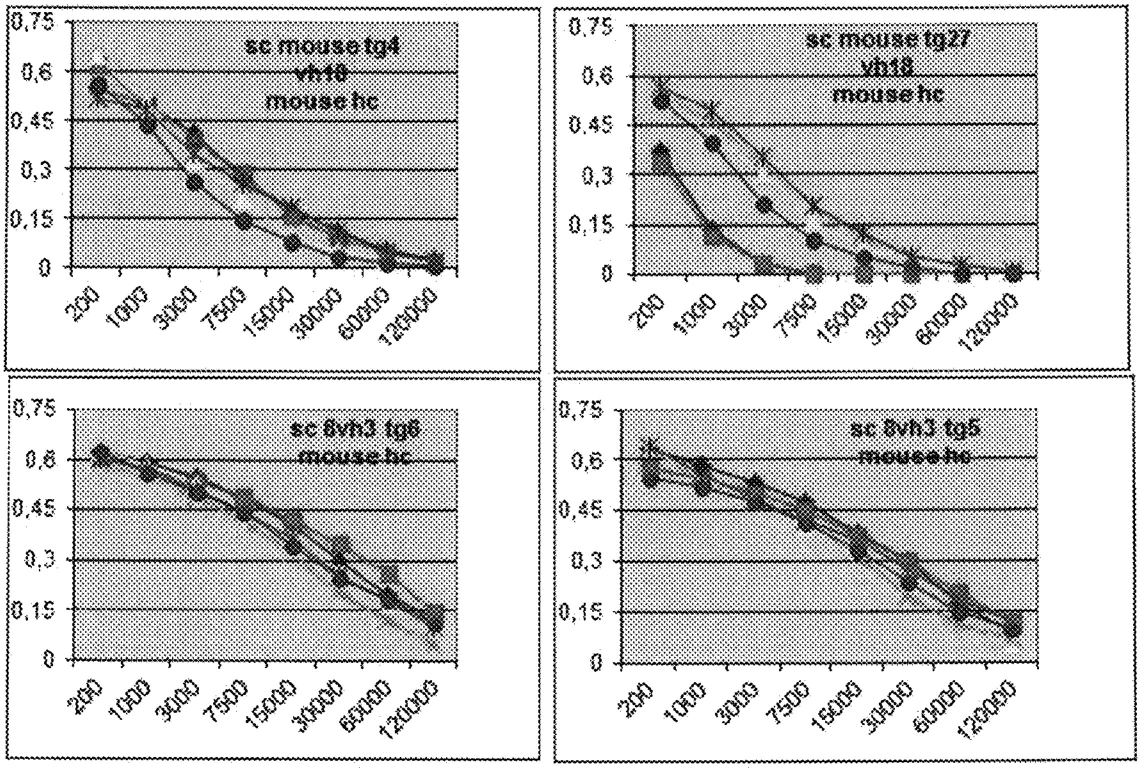
FIG. 6: depicts an example of results of ELISA analysis of CD34 immunized transgenic mice. The curves in each panel represent a separate mouse of a particular line (lines tg4 containing 21 D regions and tg27 containing all human D regions for V18; lines tg5 and tg6 for 8V3). Points on the line indicate the serum dilution shown at the bottom. The vertical axis is absorbance.

The ELISA for the detection of antigen specific soluble HCAb from the serum of the different mice is shown in FIG. 6.

This results show that the 8VH3 mice have a much more efficient response than the corresponding V18 mice containing all the different subclasses of VH segments. The immunised mice are subsequently used to isolate HCAb using previously described methods, such as standard hybridoma generation, the construction of phage display libraries or direct cloning and expression methods.

Example 8

8 week old mice were immunized as in the above example but with a peptide of human haemoglobin α (VLSPADKTNVKAAC, SEQ ID NO:4) and haemoglobin $\beta^S$ (VHLTPVEKSAVTALC, SEQ ID NO:3) with using Ribi as the adjuvant. The $\beta^S$ peptide is derived from the region where the normal β-globin protein differs from sickle cell β-globinx. 20 μg of peptide antigen was injected respectively in the tail vein on days 0, 14, 28, 42 and i.p. on day 50. Blood was taken on day 0, 14 and 45. Spleen cells will be fused with Sp2-O—Ag14 myeloma cells (gift from R. Haperen) on day 56 using a ClonalCell™-HY kit (StemCell Technologies, UK) according to the manufacturer's instructions.

Serum Ig ELISA

Blood was collected after the third immunisation in EDTA coated tubes, spun for 15' at room temperature (RT) and the supernatant diluted 1:5 in PBS. A 96 well plate was coated for 2 h with 5 mg/ml of a goat anti mouse IgG, washed with PBS, blocked for 1 h at RT with blocking solution (1.5% BSA/1.5% powder milk/0.1% tween 20/PBS) and washed three times with PBS. Dilution series of serum samples and standards were loaded and incubated for 2-4 h and the plates washed 6 times with PBS before addition of a secondary antibody (1:2000 diluted goat anti mouse IgG coupled to HRP (Sigma, Zwijndrecht, NL)). All dilutions were done in a blocking solution. After 1-2 h incubation at RT and washing in PBS, POD substrate (Roche) was added.

The ELISA for the detection of antigen specific soluble HCAb from the serum of four mice of the different V18 or 8V3 lines is shown in FIGS. 10 and 11.

These results show again that the 8VH3 mice have a much more efficient response than the corresponding V18 mice containing all the different subclasses of VH segments. The immunised mice are subsequently used to isolate HCAb using previously described methods, such as standard hybridoma generation, the construction of phage display libraries or direct cloning and expression methods.

The foregoing examples are meant to illustrate the invention and do not limit it in any way. Modifications within the spirit and scope of the invention are contemplated and included. All references cited herein are herein incorporated by reference in their entirety.

We claim:

1. A method for the production of a VH heavy chain-only antibody in a transgenic non-human mammal comprising the steps of a) expressing a transgene comprising a heterologous VH heavy chain locus in said mammal, wherein said locus comprises human VH gene segments and is incorporated into the genome of said mammal, wherein the VH heavy chain locus does not comprise all subclasses of human VH gene segments, and further wherein said heavy chain locus comprises three or more human VH3 gene segments, or three or more human VH3 and one or more human VH4 gene segments, one or more D gene segments, one or more J gene segments and a constant heavy chain region which does not encode a CH1 domain, and b) isolating VH heavy chain-only antibody, wherein said VH3 gene segments comprise at least one of VH3-66 or VH3-9, said mammal is a rat or mouse, and the endogenous heavy chain locus and one or both of the endogenous light chain loci of said rat or mouse has been silenced.

2. The method according to claim 1, wherein the D and J gene segments are human.

3. A method for the production of a VH heavy chain-only antibody in a transgenic non-human mammal comprising the steps of a) expressing a transgene comprising a heterologous VH heavy chain locus in said mammal, wherein said locus comprises human VH gene segments and is incorporated into the genome of said mammal, wherein the VH heavy chain locus does not comprise all subclasses of human VH gene segments, and further wherein said heavy chain locus comprises 8 VH3 gene segments, all of the human D gene segments, and all human of the J gene segments and a constant heavy chain region which does not encode a CH1 domain, and b) isolating VH heavy chain-only antibody, wherein said VH3 gene segments comprise at least one of VH3-66 or VH3-9, said mammal is a rat or mouse.

4. The method of claim 3, wherein the VH3 gene segments comprise VH3-48, VH3-30, VH3-33, VH3-23, VH3-64, VH3-74, VH3-66, and VH3-53.

5. The method of claim 1, wherein the heavy chain locus comprises all of the human VH3 segments.

6. The method of claim 1, wherein the heavy chain locus comprises all of the human VH4 segments.

7. The method of claim 1, wherein the constant heavy chain region of the heterologous heavy chain locus is of human origin.

8. A method of production and selection of heavy chain-only antibodies according to claim 7 further comprising the steps of:

c) injecting an antigen into the transgenic mammal;

d) isolating a cell or tissue expressing an antigen-specific heavy chain-only antibody of interest e) producing a hybridoma from the cell or tissue of step (b) and optionally cloning the heavy chain only antibody mRNA from said hybridoma for subsequent production in a heterologous expression system including a mammalian, plant, insect, microbial, or fungal system; and f) isolating VH heavy chain-only antibody.

9. The method of claim 7 further comprising the steps of:

c) injecting an antigen into the transgenic mammal;

d) isolating a cell or tissue expressing an antigen-specific heavy chain-only antibody of interest;

e) cloning the VH locus from mRNA derived from the isolated cell or tissue;

f) displaying the encoded protein using a phage or yeast library g) identifying antigen-specific VH domain(s)

h) expressing the VH domain(s) alone or as a fusion protein in bacterial or yeast expression systems; and i) isolating VH heavy chain-only antibody.

10. The method of claim 3, wherein the constant heavy chain region of the heterologous heavy chain locus is of human origin.

11. A method of production and selection of heavy chain-only antibodies according to claim 10 further comprising the steps of:

c) injecting an antigen into the transgenic mammal;

d) isolating a cell or tissue expressing an antigen-specific heavy chain-only antibody of interest e) producing a hybridoma from the cell or tissue of step (b) and optionally cloning the heavy chain only antibody mRNA from said hybridoma for subsequent production in a heterologous expression system including a mammalian, plant, insect, microbial, or fungal, system; and f) isolating VH heavy chain-only antibody.

12. The method of claim 10 further comprising the steps of:

c) injecting an antigen into the transgenic mammal;

d) isolating a cell or tissue expressing an antigen-specific heavy chain-only antibody of interest;

e) cloning the VH locus from mRNA derived from the isolated cell or tissue;

f) displaying the encoded protein using a phage or yeast library g) identifying antigen-specific VH domain(s)

h) expressing the VH domain(s) alone or as a fusion protein in bacterial or yeast expression systems; and i) isolating VH heavy chain-only antibody.

13. A method for the production of a VH heavy chain-only antibody in a transgenic non-human mammal comprising the steps of a) expressing a transgene comprising a heterologous VH heavy chain locus in said mammal, wherein said locus comprises human VH gene segments and is incorporated into the genome of said mammal, wherein the VH heavy chain locus does not comprise all subclasses of human VH gene segments, and further wherein said heavy chain locus comprises one or more human VH3 gene segments, one or more human VH4 gene segments, or both VH3 and VH4 gene segments, one or more D gene segments, one or more J gene segments and a constant heavy chain region which does not encode a CH1 domain, and b) isolating VH heavy chain-only antibody, wherein said VH3 gene segments comprise at least one of VH3-66 or VH3-9, said mammal is a rat or mouse, and the endogenous IgM heavy chain constant region of said rat or mouse cannot be expressed.

14. The method of claim 13, wherein the heavy chain locus comprises all of the human VH3 segments.

15. The method of claim 13, wherein the heavy chain locus comprises all of the human VH4 segments.

16. The method of claim 13, wherein the constant heavy chain region of the heterologous heavy chain locus is of human origin.

17. A method of production and selection of heavy chain-only antibodies according to claim 16 further comprising the steps of:

c) injecting an antigen into the transgenic mammal;

d) isolating a cell or tissue expressing an antigen-specific heavy chain-only antibody of interest e) producing a hybridoma from the cell or tissue of step (b) and optionally cloning the heavy chain only antibody mRNA from said hybridoma for subsequent production in a heterologous expression system including a mammalian, plant, insect, microbial, or fungal system; and f) isolating VH heavy chain-only antibody.

18. The method of claim 16 further comprising the steps of:

c) injecting an antigen into the transgenic mammal;

d) isolating a cell or tissue expressing an antigen-specific heavy chain-only antibody of interest;

e) cloning the VH locus from mRNA derived from the isolated cell or tissue;

f) displaying the encoded protein using a phage or yeast library g) identifying antigen-specific VH domain(s)

h) expressing the VH domain(s) alone or as a fusion protein in bacterial or yeast expression systems; and i) isolating VH heavy chain-only antibody.

* * * * *

SEQUENCE LISTING

```
<160> NUMBER OF SEQ ID NOS: 11

<210> SEQ ID NO 1
<211> LENGTH: 151549
<212> TYPE: DNA
<213> ORGANISM: Artificial Sequence
<220> FEATURE:
<223> OTHER INFORMATION: Hybrid immunoglobulin locus
<220> FEATURE:
<221> NAME/KEY: unsure
```

<222> LOCATION: 1379
<223> OTHER INFORMATION: "n" represents any nucleotide
<220> FEATURE:
<221> NAME/KEY: unsure
<222> LOCATION: 7413-7419
<223> OTHER INFORMATION: "n" represents any nucleotide

<400> SEQUENCE: 1
atccctagct gaagcttctg atggaattag aacttggcaa aacaatactg agaatgaagt 60
gtatgtggaa cagaggctgc tgatctcgtt cttcaggcta tgaaactgac acatttggaa 120
accacagtac ttagaaccac aaagtgggaa tcaagagaaa aacaatgatc ccacgagaga 180
tctatagatc tatagatcat gagtgggagg aatgagctgg cccttaattt ggttttgctt 240
gtttaaatta tgatatccaa ctatgaaaca ttatcataaa gcaatagtaa agagccttca 300
gtaaagagca ggcatttatc taatcccacc ccaccccac ccccgtagct ccaatccttc 360
cattcaaaat gtaggtactc tgttctcacc cttcttaaca aagtatgaca ggaaaaactt 420
ccattttagt ggacatcttt attgtttaat agatcatcaa tttctcgatt tctcgactat 480
tcctttgccc tcggacgagt gctggggcgt cggtttccac tatcggcgag tacttctaca 540
cagccatcgg tccagacggc cgcgcttctg cgggcgattt gtgtacgccc gacagtcccg 600
gctccggatc ggacgattgc gtcgcatcga ccctgcgccc aagctgcatc atcgaaattg 660
ccgtcaacca agctctgata gagttggtca agaccaatgc ggagcatata cgcccggagc 720
cgcggcgatc ctgcaagctc cggatgcctc cgctcgaagt agcgcgtctg ctgctccata 780
caagccaacc acggcctcca gaagaagatg ttggcgacct cgtattggga atccccgaac 840
atcgcctcgc tccagtcaat gaccgctgtt atgcggccat tgtccgtcag gacattgttg 900
gagccgaaat ccgcgtgcac gaggtgccgg acttcggggc agtcctcggc ccaaagcatc 960
agctcatcga gagcctgcgc gacggacgca ctgacggtgt cgtccatcac agtttgccag 1020
tgatacacat ggggatcagc aatcgcgcat atgaaatcac gccatgtagt gtattgaccg 1080
attccttgcg gtccgaatgg gccgaacccg ctcgtctggc taagatcggc cgcagcgatc 1140
gcatccatgg cctccgcgac cggctgcaga acagcgggca gttcggtttc aggcaggtct 1200
tgcaacgtga caccctgtgc acggcgggag atgcaatagg tcaggctctc gctgaattcc 1260
ccaatgtcaa gcacttccgg aatcgggagc gcggccgatg caaagtgccg ataaacataa 1320
cgatctttgt agaaaccatc ggcgcagcta tttacccgca ggacatatcc acgccctcnt 1380
acatcgaagc tgaaagcacg agattcttcg ccctccgaga gctgcatcag gtcggagacg 1440
ctgtcgaact tttcgatcag aaacttctcg acagacgtcg cggtgagttc aggctttttc 1500
atggtggcgg ctggatcggt cggtcgaaag gcccggagat gaggaagagg agaacagcgc 1560
ggcagacgtg cgcttttgaa gcgtgcagaa tgccgggcct ccggaggacc ttcgggcgcc 1620
cgccccgccc ctgagcccgc ccctgagccc gcccccggac ccaccccttc ccagcctctg 1680
agcccagaaa gcgaaggagc aaagctgcta ttggccgctg ccccaaaggc ctacccgctt 1740
ccattgctca gcggtgctgt ccatctgcac gagactagtg agacgtgcta cttccatttg 1800
tcacgtcctg cacgacgcga gctgcggggc ggggggaac ttcctgacta ggggaggagt 1860
agaaggtggc gcgaaggggc caccaaagaa cggagccggt tggcgcctac cggtggatgt 1920
ggaatgtgtg cgaggccaga ggccacttgt gtagcgccaa gtgcccagcg gggctgctaa 1980
agcgcatgct ccagactgcc ttgggaaaag cgcctcccct acccggtaga attcatcgct 2040
cgagcaattg gctagataac ttcgtataat gtatgctata cgaagttatc tagctctaga 2100

-continued

```
gtcgacgtct tgttacactt catcaagaat taacctctgc tgtttcctca aagtgtttaa   2160
ttggataatg aatttgtcta taaattgaag agttgaaata catcaaatat taatttgtaa   2220
taatctggca caaattatct aagcaaattc aataactaga tgtttttttca tttattttta   2280
tttaaaatca ggatctaagc actgacatgc tttaataaca tctgtgaccc tctcagcagt   2340
tttctcttct gagtatatga tctgctgtgg cagttttctt agcttcaatg ttacctcttt   2400
tggcaatgac taccgtcttt atatttgcca ggaatctggg ataagggagt gcttctaaga   2460
gttccctaac ttgcccattt tggtgggtgt tccagaacat atgagatgct ctgttgttaa   2520
caaagcatcc caaagccatg cactgcccta aaatgtgttt gtttcctagt ttgacaaatt   2580
ggaagttcta ataaatacaa tcacttctgc catctgggct gattttacat cagatagagg   2640
gctgtattcc aaagaaaagc ttacattagt aatagcaatt ctagtcagaa acctagagtt   2700
ttatcattga ggtgcaattc ataacaaata atattaggtc gaggttctca gtggcagtgt   2760
ctaaatctct taggtgtaca gggtcttccc tgttaacatg aagcatttat aagcacagtc   2820
atagtttcca gctatgcttc tccctgtctc attatcacca caaactatgg cctcacctgg   2880
aacttgggtt aatttccaaa taagtaattt tttagtgttt atgcctctag attattatgt   2940
gagaaagtta acattcagta gaaagttaaa aagaacattt gaactgacta aacaacacag   3000
acaatcaaga ataaaattca aagcctagat gtgagaggct ccaggcctgg ataatgcaat   3060
agttcatgta tgcaggcagt ttctttgccc agttctacac tgatacaccc agaatgtcag   3120
cttcatgcca gatttgactc ctattatgta gagacatggc aatacattct caagggtcac   3180
atgaaataat atgaaaattg gtgggaatag gggaggagac aactctgcaa ttctcatctg   3240
aaggaccagg aaagcctgga cagaccatct ccccagcctc cgtgactgca ccacgtgccc   3300
acatggacgc tcatccctga tagggtaaga agactccatt gatggggctg agcattttat   3360
gatagaaatt actagagact gacgtggagg tttcaacaac taatatttat aaccaaaatt   3420
taattacccc cacattgtta ccattttctt cagtgaaaaa ttgcttgcca tgattaagtt   3480
ttaagtagat ttccaatgtt cacaactgag cttccaagag agtcttgaga acaaaaacaa   3540
tgagggcaga gaaatctacc ttttctgcat tcaccactaa actcaagtgg actcagcact   3600
gcctttgatc actgctactt ctctgcagag ttcaggtttc tacttctcac aattctgaca   3660
cacattctac ctctcctcag atgtttggcc tctgcttctt gtaaggtcac cctctgttct   3720
taacttcttc tctgagtcat tttgtgaggt ggtcatgagc cattaaatgg atattttata   3780
ttttcccaac atgaatcaca tgagtggtca tgaattatac ttctgattat ggcagttgat   3840
ttttcttggc atgttcatga ctagtaatat ttgaagccat ttcattcaaa tcttcggggc   3900
ttcgtttttg ttgctatgac atttttctt ctattgagtc tttccactag tattataaca   3960
tgacctagta tccaggctca gttgtcatta ataataacca catatgtcaa aaatcatgca   4020
ttcttttcac agcagacata atttcctctt ttctgcagat gaagacacac tgctgagcta   4080
cccccactta caagaatata tgcacaatta tgatatcttc atttatttga ctaataagct   4140
atatcattct cccttcaaat tctttacccc ccagaagtcc tggacaaatt tctgcatctg   4200
ctcaaacgat aaactcagaa ctacatggtg agtaaaagtc acctggttct ggatattggg   4260
tccatctctt cccctccaat gtcccagagc acctcagcac acccgtccag gttctatcaa   4320
gaaagagtag ctcctgcaca ctgaaggaaa caattgagtt aagagaggac ctgcagatga   4380
tagacaatat tgaaaactgt taatatgaca aaggattact accaagcatg tgaaataagc   4440
tcaacgggtg cggtggttca tgtctgtagt accagcaatt tgggaggcaa gttgcgcaga   4500
```

-continued

```
tcacctgagg ttaggagctc gacaccagcc tgaccaacat aaagaacacc ctgtctctac   4560
taaaagtaca aaattagccg ggcatggtgg catgcgcctg taatcccagc tactcgggag   4620
gctgaggcag gagcatcact tgaacctggg aagtggaggt tgcggtgagc tgagatggca   4680
ccattgcact ccagcctggg caacaagagg gaaactccat ctcaaaaaaa aaattacaaa   4740
aaattagctg agcgtggtgg tgggcgcctg tatacccagc tgctagggag actgaggcag   4800
gagaatggct tgaacccagg aggtgaaggt tgcagtgagc tgagattgcg ccattgcact   4860
ccatcctggg caacaagagt gaaactccat ctcaaaaaaa aaaaaagaga cttgcaaagg   4920
gcaaatagat catagacaga cagatagata gatagaccta ttagtataca tacatacata   4980
tatatacact aatattcagg aaaatgcaaa ttcataatga gatgtctttt caccccttcat  5040
ctctgctaga aagtttgtta tctgaaaaac aaatacatac atacatactt attaaaagct   5100
ggccaggatg cctagaaagt aaaactcata gaccactggt ggaaatgtaa attagtgcag   5160
ccatcaaggg aaaaaaatag aactaccata tattccagca atccaactgc taagtatata   5220
tctatttaaa tatttaaaag aaaaaactaa tattgaagag atacctgtac acccatgttt   5280
attgcagcac taatcacaat ttctaggata tgaaatcaac atatgtgtcc atcaacagat   5340
gaatggatac ataaaatgtg atatatttac acaatggaat attattcagc cttaacaatg   5400
aaattctgcc gtttgaagca acatggatgg aatgggacac ctctatgttg agtgaaatga   5460
gtcagacaca gaaaaataaa taccgcattt ctcagcgtta cttctagaag taaatagtag   5520
agtagtggtg atgagatgcc aggaatgaga gaaggctgag ataagaagag gtttgttaac   5580
aaacacacaa ttacaggtag acaggaggga tgtgctctag tgttctacag cacagtaggg   5640
tgactacagt taacaatata ttgtacgttt tctgtttaca agaagccaga agagagaatt   5700
ttctatgcta ccaacacaaa taaatgttag tgtctgaact gacgaatttg ctcattgttc   5760
tgattttagt cataccaagt ggcacacatg tattcaaata tcacactgta ccccataaac   5820
ataagcagtt attatgtgcc aaatttgaaa aatcctttaa ttagaaggaa ttatattggc   5880
gtacattaca aatgattcaa cacagagaca ggaataaata ccatttttct ttgaaatagt   5940
taattaacta acaatgtagt tacattcatt tgcaccaaat cgtgtatttg ataatggtat   6000
gcatagacag atttatgcat aggataatat cttttaattt tagactacta cttaatacta   6060
taaatataaa taattttaaa acaactaagt aaaaagaata aagctgagaa aatgtgtgtg   6120
tggtgtgtga tgtgtgagct ttttcttgtg caccactgtg tccttggtgg atgtgtggtt   6180
catgtgtttg tttttattta ctctgtttgg ggttctcttt gcttctagga tctgtagttc   6240
agtttctttc acaaaattgg gaacattctt cgctattatc tttttcaaat agtttctgtg   6300
tatttataat ttctccttct cagatttaaa atatacacat actataattt tgatattaat   6360
gtttagtttc tttcttcact ctcttttcgt ttgcaattta ctttgtgaaa tttctaatga   6420
catactaatc acatggtttt attgaaaagc tgagccagct ctactgaggt gtgtgccaaa   6480
agattgctcg atgtttatac agcattgctt ttgatttctt atgcatttcc atttgattta   6540
ttcttagtat tttcatattt cagttcccta tctatgtcca cgatttcttt aagagattct   6600
tgcgtgtgaa ttatagttac tttacatatc ttgtttaatt agatatttat aacatctgtt   6660
tcatctacaa atctcatgct gatcatttgt ttattacaac tttggtactt ctcattaatg   6720
tatgtaataa ttgttgatag ccacagatac tgggatggac agtggatact ggccttatta   6780
tttcatttta tgcatttctg cctgtatttg accacacttt acctttgcca ggcctttact   6840
```

-continued

```
gtggaagtat ctgtgaatct tctcagaact atatttgaca ttcacttttg cagtggacat   6900
caaagttgaa gtctgttctt ctgtgtccac cagagacttc agttcctcca gtgatacctt   6960
gtttttcttt cctgcttggc tttgtctctt cacctgttcc ctcctccaga gaatcatgtt   7020
cagctccctc aggtggatta aaatgttatc taactgacaa ttgtgaaatt ggtggaaagc   7080
aatagaataa agggagattt tctgaccttt cttgggttca tattgtgaac atgagtctgg   7140
gtgtgacctt cccaatgttt ctgaacttcc tccagatgag atgttggtct gtgtgttctt   7200
gctcttttcc ctgctgtgga gtcctcttgt ttcccccagt tgttccctcc cgcagctcca   7260
atgttctctt tttgtgttat caccttacag atttgctgac tagaactgca gattagggct   7320
ctgattaaat aagaaggagg ggagatactt ctcaatggaa cttaggtgaa gacctctttt   7380
cccatctcag ttcttaaggg attgccccag tgnnnnnnna ctggttttgg tggcttgccc   7440
ctccaaaaaa tttctttgtt ctccagtggg gatatggaag gtgggtctga acacttttca   7500
gaagggtggg cactttttct ctcctagaca gacacaatgg gacagaacaa ttttggtgac   7560
tgtccccatt ttggggaaaa aggattcaat aggataggaa aactcttcag tctgtggtcc   7620
cttagaaatt caccctacaa cacatttacc acacttgact tcaagaaatc caatatatat   7680
gtgtgttttc atcttgtaat agcctacatt ttacatgcca tactctgcct cagttcagct   7740
cataccccag ctttgttact ctttacaaga acttgcctct ccctagattt cacatttgct   7800
gtttatctta aaacttcaag tatctaaagt attattttta aaaaatggcc agttgtggtg   7860
gctcacacct gtaatcccaa cgctttggga ggctgaggta tgtggatcac ctgaggtcag   7920
gagtttgaga ccaccctggc caacatggta aaacctgtct ctactaaaaa tacaaaaaaa   7980
aaaaaatagc ttggcatggt ggcaggcacc tgtaatccca gctactcggg aggctgatac   8040
tggagaatag cttgaaccca cgaggcagag tttgcaagtc gtaccattgc actccagcct   8100
gggcgacaga gtgagactct gtctcaaaaa aaaaaattcc aaaattccag ctcctctgtt   8160
tatctatttt tgttgatact gttgttgtaa aacataagta aaatatatta ttcatctatg   8220
tacatttcca agctgtgtag aagaattttt aataagaccc agagtaaaaa aagaatgcaa   8280
atatgtaggg gccagcccta cagggtctgt ggatctttct ccccatgtgc agagatgaga   8340
gatcatagaa ataaaggcac aagacaaaga gatagaagaa aaaacagccg ggcccagggg   8400
accactacca ccaagacaca gactagaagt ggccccaaat gcctggctct gctgttattt   8460
attggataca aggcaaaagg ggaagggtaa ggagtgtgag tcatctgcaa tgattgataa   8520
ggtcatgtgt gtcacgtgtc cgccagacag agggcacttc cctgtttggc agccgaggcg   8580
gagagagaga gaggacagct taggtcatta tttcttccat tctcttctca gaaagatcaa   8640
agactttaat actttcacta attctgctac tgctatctag agggcggagc aagtgtacag   8700
agtggaacat gagagtgaaa caggagtgtg accgctgaag cacagcatca cagagagacg   8760
tttaggcctc tggagggctg cgggcaggtt tgactgatgt caggccttcc acaagaggtg   8820
gtggagcaga gtcttctcta actcccccgg ggaaagggag actccctttc caggtcttct   8880
aagtaatggg tgccttccca ggcactggcg ctaccgctag actgaggagc cctctagtgg   8940
ccctgtccgg gcgtgacaga ggctcacact cctgtcttct ggtcacttct caccgtgtcc   9000
cttcagctcc tattgctgta tggcctggtt tttcctaggt tataattgta gagcaaggat   9060
tgttataatg ttggaataaa gagtaatgct acagactgat gattaatgat attcatatat   9120
aaacatatct ataacctatt actagtacaa ctattcttat tttacatatt ctcttcatta   9180
cactggaaca gcttgtgccc tcagtctctt gcctcagcac ctgggtggct tgccgcccag   9240
```

-continued

```
acaaatattg ttaagcttct taatagaaaa acaaattatg gtaaatgtgt tcactggaat   9300
actacccgtc atttataata aattaatgcc tgatacacag agcaacaagg taaaatatct   9360
aagtatttat gttgagtaaa ataagctaaa caaataagaa tatatactat gtaatttcat   9420
ttttataaat tctgataaat aaaaatgcat ctgaagtaaa ataatgaaga taagtagttg   9480
cctggggaaa tggtagaaga agggaggggg agaggaggag gaatacagca gaacaaaggg   9540
aaaatgttga gaagaattca cttgtccact ttcttgataa tgatagcagt tacatcattt   9600
ttattagttg tacattttaa atatgtgaag tttatcatct ttcaattaag cctcataaaa   9660
tgtcttacaa gcaaacaaat ggaaacttag acaaggaaag agtaatagaa agatagaaaa   9720
aataagttca atgtcagaag tacctgaaaa ttaatgtgcc tggatcctag ttctctccat   9780
attttcagaa gagtgctgga gggcagcaaa accacacatg ctcttattac ggaaagtggg   9840
ttctgataaa aacactagac acatccagct ttgtcctgga gttggtttag ggggatgtca   9900
gagacagtga tgaagagcac agggccagat accggggttc actcatccca gacatgagct   9960
cctagatgca tacagagccc ccccatgtgt gggtttactt ccacttctgt aaatggagaa  10020
aatattgtct cctacagaac atagtttaca tgaatactta aaatgaaata gggtgattag  10080
tgcaaagtgt ttatcacagc acaatttcat aataagacag catattttcc aaatgcaatc  10140
attgccagca aacttctaca gggcaccgtc gtcttatctg ggtacagcct actcctcaag  10200
ggtcccaccc tagagcttgc tatatagtag gagatatgca aatagggccc tccctctact  10260
gatgaaaacc aacccaaccc tgaccctgca gctctcagag aggtgcctta gccctggatt  10320
ccaaggcatt tccacttggt gatcagcact gaacacagag gactcaccat ggagttgggg  10380
ctgtgctggg ttttccttgt tgctatttta gaaggtgatt cacggaaaac tagagagatt  10440
tagtgtgtgt ggatatgagt gagagaaaca gtggatatgt gtggcagttt ctgaccttgg  10500
tgtctctttg tttgcaggtg tccagtgtga ggtgcagctg gtggagtctg gggggaggctt  10560
ggtacagcct gggggtccc tgagactctc ctgtgcagcc tctggattca ccttcagtag  10620
ctatagcatg aactgggtcc gccaggctcc agggaagggg ctggagtggg tttcatacat  10680
tagtagtagt agtagtacca tatattacgc agactctgtg aagggccgat tctccatctc  10740
cagagacaat gccaagaact cactgtatct gcaaatgaac agcctgagag acgaggacac  10800
ggctgtgtat tactgtgcga gagacacagt gaggggaggt cagtgtgagc ccagacacaa  10860
acctccctgc aggggtccgc aggaccacca gggggcgaca ggacactgag cacggggctg  10920
tctccagggc aggtgcaggt gctgctgagg gctggcttcc tgtcatggcc tggggcggcc  10980
tcattgtcaa gtttccccag ggaacttctc cagatttaca atcctgtact aatatttgat  11040
gtctctaaat gcaacctttt ttttcctttt tgtgtctgtt ttttttttt taaaaacagg  11100
aggacacatc ctcacctcca cagaagccac agtgtcactt tgggggcgga aataatcctt  11160
tcgtggtcaa cagggtgaga gttttgagga atcccaggga aacctgggga atgttttcca  11220
attagactca gggcagagac ctccatggga atccctgatt agaacaggct ttgagttctg  11280
atgggagcca aaagagaggc tcacccaggg tcagggttct taaaacctga tggttttcac  11340
agcaatcccc cttcatcttg tgaaactggg cacatctgac tcagactgat tcagttgacc  11400
ctctttctgc taatccattt tccttcccag tagacttgat tctcacagat ccctttcttc  11460
ttctctttcc tgaaaacaga ggatgtgttt tctgtagtcc tcgagccttg attgaagtgc  11520
tgagtaaatg gttgcaaaca taggtctaca tttttcaaat cattcaccat aaatttgaat  11580
```

-continued

```
tatttattaa ttacactcga ataaagcaat aaagaaactg atgagataat atttgactga  11640
attgcatcaa taaatagatc gatattaaca caaggaatat aactgatttc caaaaacata  11700
cacatgaacc gtggttcact ctgcgtattt agataaatta cagaaagttg tcataacaga  11760
tggggaatcc tgcagacttc actaggcatg ggccatgctg ccctggagtt gtctcagggg  11820
agctgcctcc tccagaggtt agagcacagg cccaggtaat aggactaaat ttttagatgt  11880
gttatcttag acacactgca caactgctgt gttctctatg taaattatct cctgtaaaat  11940
ataacattga agcctgcatt aaatatattg tgtaaatatg taagaataaa agaaagttat  12000
gagagctaag tgttaatcaa ggcacaagca tataagatat aactatattt tcctgaatga  12060
tggaattact accagtctcc cccaggacac ttcatctgcc ctgagcccag cctctcctca  12120
gatgtcccac ccagagcttg ctatatagtg ggggacatgc aaatagggcc ctccctctac  12180
tgatgaaaac cagcccagcc ctgaccctgc agctctggga gaggagccca gcactagaag  12240
tcggcggtgt ttccattcgg tgatcagcac tgaacacaga ggactcacca tggagtttgg  12300
gctgagctgg gttttcctcg ttgctctttt aagaggtgat tcatggagaa atagagagac  12360
tgagtgtgag tgaacatgag tgagaaaaac tggatttgtg tggcattttc tgataacggt  12420
gtccttctgt ttgcaggtgt ccagtgtcag gtgcagctgg tggagtctgg gggaggcgtg  12480
gtccagcctg ggaggtccct gagactctcc tgtgcagcgt ctggattcac cttcagtagc  12540
tatggcatgc actgggtccg ccaggctcca ggcaaggggc tggagtgggt ggcagttata  12600
tggtatgatg gaagtaataa atactatgca gactccgtga agggccgatt caccatctcc  12660
agagacaatt ccaagaacac gctgtatctg caaatgaaca gcctgagagc cgaggacacg  12720
gctgtgtatt actgtgcgag agacacagtg aggggaggtc attgtgcgcc cagacacaaa  12780
cctccctgca ggaacgctgg ggggaaatca gctgcagggg gcgctcagga gccactgatc  12840
agagtcagcc ctggaggcag gtgcagatgg aggctgtttc ctgtcaggat gtgggacttt  12900
gtcttcttct gacagttccc cagggaacct cttaaattta gaaaactgtg cctaacaatg  12960
tcttctctat gcatatgagg accttttctc cctggcacaa aatgcagatt gacgctgaca  13020
cggatggtcg acgctgctga cattcctaga taactgcagc tgtagttatg cctgctaagg  13080
tttgggcgca tggggcttgg cttttgtcag ctccctggga tttattttcc caaacaaaga  13140
aacctccagg ttaggggcac cctattcatt cccatcacct ggcatgattt aaaggataat  13200
tgcttagaat taaaatattg atccagattt tttatattcc ccatcgcttt ttgtttcttc  13260
tgggctgtag ccagagatca ttgattggcg ctcaggaata agcagagtta gtctaaaatg  13320
caggcaaata cttaaacaac tgaagagatt agaatttaaa gacaagtgta tgatatgttt  13380
tgaaatacaa tgtttctctt tccagttttg gtttttgtca gcagcaaata atgataagac  13440
tgagttgttt gcaaaataaa ctttagtctt aaacttggcc tgattatttg cataaagtgc  13500
agcaagaata ttaataataa ttctgtagga aaagcctgca agcaccagga gcttcacagt  13560
ctaacactat gagcacgtgc atcctcacgc aactcactga atatgtccaa gtcagcctgt  13620
tccgatctta aatgccatcc agtggcatct gccccaggta cactaataca tgggtcctgc  13680
ttctctctgc agccgcctct ctcctcagat ttcaggtttt gtgtattgtt tgttttctct  13740
ctgacatcaa cacagatatg ttgaaggttt tcttttttttt atttgtagtt gttcagcttt  13800
gttgttaatg aggtcagaat aagctcatag tttacacatt tttacattcc catgccgagt  13860
agctgctttt ctctatcaaa tccattaact gagagaacaa tcacatttcg ttacaggtga  13920
acagttaaat agtttggcat atatttctgt gctggaatct aatgcagctt gaaatcaagt  13980
```

-continued

```
catgcctcac tcattgaaaa aaacatggct aaattctcaa agaattgtgc tgagtgaaag  14040
aaactaagga atgaagagta aattttatat gatacatttg tagaaatttt agaagatgcc  14100
actattataa attaacatgg agaagattta agtgtttctg agaatatgct attgggagta  14160
atggggatgt gagttaaatt tcagaggaat aagagaaaga tttagggatt aatttttca   14220
aaccttgatt gaagtgctga gtaaatggtt gcaaacatag gtctacattt ttcaaatcat  14280
tcaccataaa tttgaattat ttattaatta cactcgaata aagcaataaa gaaactgatg  14340
agataatatt tgactgaatt gcatcaataa atagatcgat attaacacaa ggaatataac  14400
tgatttccaa aaacatacac atgaaccgtg gttcactctg cgtatttaga taaattacag  14460
aaagttgtca taacagatgg ggaatcctgc agacttcact aggcatgggc catgctgccc  14520
tggagttgtc tcaggggagc tgcctcctcc agaggttaga gcacaggccc aggtaatagg  14580
actaaatttt tagatgtgtt atcttagaca cactgcacaa ctgctgtgtt ctctatgtaa  14640
attatctcct gtaaaatata acattgaagc ctgcattaaa tatattgtgt aaatatgtaa  14700
gaataaaaga aagttatgag agctaagtgt taatcaaggc acaagcatat aagatataac  14760
tatattttcc tgaatgatgg aattactacc agtctccccc aggacacttc atctgccctg  14820
agcccagcct ctcctcagat gtcccaccca gagcttgcta tatagtgggg gacatgcaaa  14880
tagggccctc cctctactga tgaaaaccag cccagccctg accctgcagc tctgggagag  14940
gagcccagca ctagaagtcg gcggtgtttc cattcggtga tcagcactga acacagagga  15000
ctcaccatgg agtttgggct gagctgggtt ttcctcgttg ctcttttaag aggtgattca  15060
tggagaaata gagagactga gtgtgagtga acatgagtga gaaaaactgg atttgtgtgg  15120
cattttctga taacggtgtc cttctgtttg caggtgtcca gtgtcaggtg cagctggtgg  15180
agtctggggg aggcgtggtc cagcctggga ggtccctgag actctcctgt gcagcgtctg  15240
gattcacctt cagtagctat ggcatgcact gggtccgcca ggctccaggc aaggggctgg  15300
agtgggtggc agttatatgg tatgatggaa gtaataaata ctatgcagac tccgtgaagg  15360
gccgattcac catctccaga gacaattcca agaacacgct gtatctgcaa atgaacagcc  15420
tgagagccga ggacacggct gtgtattact gtgcgagaga cacagtgagg ggaggtcatt  15480
gtgcgcccag acacaaacct ccctgcagga acgctggggg gaaatcagct gcagggggcg  15540
ctcaggagcc actgatcaga gtcagccctg gaggcaggtg cagatggagg ctgtttcctg  15600
tcaggatgtg ggactttgtc ttcttctgac agttccccag ggaacctctt aaatttagaa  15660
aactgtgcct aacaatgtct tctctatgca tatgaggacc ttttctccct ggcacaaaat  15720
gcagattgac gctgacacgg atgaaaattc ctcaaccatg gtcacaagga tcagagtcct  15780
gagtaacctc agggcttcct ggtgattctt ctccaatcag acccaggaca gggacctccg  15840
tgagattccc tgactggaac agtctttatg gatcctggtc acagacaata gagaggctga  15900
accagggtca gcgtcatgta gaacgtcaca gatttcacgt ctgatccttc tcctgacacg  15960
aaagtatgca aatcagtatc agcaccgatc tgctcgacga tggaaagata gataccaaca  16020
tgagaaatgt atgacactca agaaaataaa actgtaggaa acttgctttt ctttatattt  16080
gttaggtaat caccacagtg tgtacacatc acaccatgtt cccattacag agaaaaggtt  16140
ctgcgaacct cacgagctgt gacccctgtg tgctgggctt ggttcaggga gaagtcaggt  16200
ccagtggtga gaagcacagg cccagatgcc caggctcact ctgaccaaaa gtgagcactg  16260
gggacattgt aaaacccacc tgtgcttttg ctgataattt ttcatcttta acatggaaat  16320
```

-continued

```
aatattgata ctatatacca tggtttctct gcgtatgtaa aaataaaaga tgattggtgc  16380
taactttaaa aatatgcagt ttatgtagat ctatggtacc tcaataaaac tgttttaaaa  16440
taaaaattac aaaattataa gatttttagg ttttaaggtt taagtttatc acaaaacaaa  16500
ctgacaatag gaaagcacaa tttcccaatg ctttcaatat cacagatctc cccgaggaca  16560
ttctgacatg ctctgagccc cactatctcc aaaggcctct caccccagag cttactatat  16620
agtaggagat atgcaaatag agccctccgt ctgctgatga aaaccagccc agccctgacc  16680
ctgcagctct gagagaggag cccagccctg ggattttcag gtgttttcat ttggtgatca  16740
ggactgaaca gagagaactc accatggagt ttgggctgag ctggcttttt cttgtggcta  16800
ttttaaaagg taattcatgg agaaatagaa aaattgagtg tgaatggata agagtgagag  16860
aaacagtgga tacgtgtggc agtttctgac cagggtttct ttttgtttgc aggtgtccag  16920
tgtgaggtgc agctgttgga gtctggggga ggcttggtac agcctggggg gtccctgaga  16980
ctctcctgtg cagcctctgg attcaccttt agcagctatg ccatgagctg ggtccgccag  17040
gctccaggga aggggctgga gtgggtctca gctattagtg gtagtggtgg tagcacatac  17100
tacgcagact ccgtgaaggg ccggttcacc atctccagag acaattccaa gaacacgctg  17160
tatctgcaaa tgaacagcct gagagccgag gacacggccg tatattactg tgcgaaagac  17220
acagtgaggg gaagtcattg tgagcccaga cacaaacctc cctgcaggaa cgatgggggg  17280
gaaatcagcg gcagggggcg ctcaggaccc gctgatcaga gtcatccgca gaggcaggtg  17340
cagatggagg ctgtttcctg tcagggtgtg ggacttcatc ttcttctgac agtttctcta  17400
gtgaacctct ctaacctcag aattctgtgc ttactaatgt catctctacg tatttttttaa  17460
aagatcattt taatatgagc acctattctc acacgcacca aatgcagatt gacgcttaca  17520
gagatgctcg acgaggaatg ctgaggggag ttgacttgtc accttcttaa aaatagagat  17580
tttatttttc aaagtttact attgtacaga ataaaatatgt gaattttctt atctgtcaat  17640
taaacctcat aaaatttatt acaaaaaaac tgaaatttta gacaaaaaga gggtgatagg  17700
aaggaacaaa taaatatgtt aaatgtcaaa tatacctaaa aatttatttg tctgacccct  17760
agttttctcc gtatttttag gtaaatgcag caaaatcaca caagttgtcg tggcaggaag  17820
tggattctgc aaaccacact aggcccgttt atctctgtcc tagagttggt taaaagagca  17880
actgaggcca gctgtgagga gcataggccc gggtactagg actcactcat gccagatata  17940
agcccttaga cacatacata gcccctccat gtgtgggttc acttttacat ctgtacatga  18000
agaaaccact gattcctaaa taacataatt tatacacata ggtaaaaata attaaaaatg  18060
tgatagttat taagtgttta tcacacaaca atttcacaat aaaacagcat tttcccaaat  18120
gtaatcattg tcatcgaaat ccccaaggac actctcatct gccctgggcc ctgccctctc  18180
ctcaggcatc tcaccccaga gcttgctata tagtaggaga catgcaaata ggtccctccc  18240
tctcctgatg aaaaccagcc cagccctgac tccgcagctc tgggagagga gcccccgccc  18300
tgggattccc aggtgttttc atttggtgat cagcactgaa cacagaagag tcatgatgga  18360
gtttgggctg agctgggttt tccttgttgc tatttttaaa ggtgattcat gaggaaatag  18420
agatattgag tgtgagtgga catgagtgag agaaacagtg gatttgtgtg gcagtttctg  18480
accttggtgt ctctgtgttt gcaggtgtcc agtgtgaggt gcagctggtg gagtctgggg  18540
aaggcttggt ccagcctggg gggtccctga gactctcctg tgcagcctct ggattcacct  18600
tcagtagcta tgctatgcac tgggtccgcc aggctccagg gaagggactg gaatatgttt  18660
cagctattag tagtaatggg ggtagcacat attatgcaga ctctgtgaag ggcagattca  18720
```

-continued

```
ccatctccag agacaattcc aagaacacgc tgtatcttca aatgggcagc ctgagagctg  18780
aggacatggc tgtgtattac tgtgcgagag acacagtgag gagaagttaa tgtgggacca  18840
tgcagaaacc tccctgcggg aacgctgggg aaagtcatct gcagggggcg ctcaggagcc  18900
actgatcaga gtcagcccca gcggcaggtg cagatgaagg ctgatttcct gtcacgatgt  18960
gggacttcat cttcttaaag tttctctact gaacctaagt tcggaattct gtgattacta  19020
gggtcatttc tactcgacga agttgaggga atttcacttg tccaccttcc ttataatggt  19080
aatagttatg ccatgattat cagttttaca ctttaaatat gtaaagttta taatctgtca  19140
atcaaatctt ataaaatgta ttatgaggaa acaagttgaa aattagacaa tgtaggagtg  19200
acagaaagat agatatgagt atgttgaatg tcagagatac ctgaaagttt atctacctga  19260
accctagttc tctccatagt ttaaggtaaa caggagagtg caggaaaatc atccatattc  19320
tgattaggca gtggcttctg caaaccacac taggcctggc cggctgtgtc ctggagttgg  19380
ctaagggagg agtcagggcc agtggtgaga agtgcaggcc cagataccag aactcactca  19440
tcccagacat gagctcttag atacacagag agcccatcca tgtgtggatt tatcttacat  19500
ctgtaagtag agaacattga ctcttacaga acataattta cacacatagg taaatctgaa  19560
ataaggtgat cagtgtgaag attttatcac agcacagttt cataataagc acaatttctc  19620
aaatcccatt gttgtcaccc atcttcctca ggacactttc atctgccctg ggtcctgctc  19680
tttcttcagg tgtctcaccc cagagcttga tatatagtag gagacatgca aatagggccc  19740
tcactctgct gaagaaaacc agccctgcag ctctgggaga ggagccccag ccctgggatt  19800
cccagctgtt tctgcttgct gatcaggact gcacacagag aactcaccat ggagtttggg  19860
ctgagctggg ttttccttgt tgctatttta aaaggtgatt catggagaac tggagatatg  19920
gagtgtgaat ggacatgagt gagataagca gtggatgtgt gtggcagttt ctgaccaggg  19980
tgtctctgtg tttgcaggtg tccagtgtga ggtgcagctg gtggagtccg gggaggctt  20040
agttcagcct ggggggtccc tgagactctc ctgtgcagcc tctggattca ccttcagtag  20100
ctactggatg cactgggtcc gccaagctcc agggaagggg ctggtgtggg tctcacgtat  20160
taatagtgat gggagtagca caagctacgc ggactccgtg aagggccgat tcaccatctc  20220
cagagacaac gccaagaaca cgctgtatct gcaaatgaac agtctgagag ccgaggacac  20280
ggctgtgtat tactgtgcaa gagacacagt gaggggaagt caatgtgagc ccagacacaa  20340
acctcgctgc aggggcatct gagaccacga gggggtgtcc tgggccctgt gaactgggct  20400
gctctccgtg gcagcggctg gtggtgctaa aggctgattt tctctcagca tctggggctg  20460
attcatcaag tttcctcaga gacctttcag attacaattc tgtacttacg tttaatgtct  20520
ctgaatgtga cactttcctt ccctggtgtg tctttgtttt tgtgacaaga ggacacattc  20580
tcacctccac agctcgacga agtgccgagt gaatggctgc aaacatagct ctacattttt  20640
caaatcattc cctataaatc tgaattaatt atttatttat tatacttgaa taaagcaata  20700
acgaagaaat aaatgaatat ttttgctaaa atggagcaat aaaaagactg atattgacag  20760
aagaaatatg actgacttct gaaaacacac atgaaccatg gttctctctg catatttagg  20820
tgaattacag aaagttgtca taacagatgg ggaatcctgc agacttcact aggcatggtc  20880
cacgctgccc tggagttgtc tcaggggagc tgcctcctcc ggtgattaga gcacaggccc  20940
agataatagg attacatttt tttagatgtg taaacttaga cgcactgcac agctgctgta  21000
ttctctatgt aaattatctt ctgtaaaata caacattaaa ggctgcatta aatatattgt  21060
```

-continued

```
gtaaatatgt aaaaataaaa tcagattatg agagctaaat gttaatcaag gcacaatcac  21120
ataatataaa attatatttt cctgaatgat ggaattacta ccaatctccc ccaggagact  21180
tcatctgcac tgggcccggc ctctcctcag atgtcccatc acagagcttg ctatataatg  21240
ggggacatgc aaatagggcc ctccctctgc tgatgaaaac cagcccagcc ctgaccctgc  21300
agctctggga gaggagccca gcactgggat tccgaggtgt ttccattcag tgatctgcac  21360
tgaacacaga ggactcgcca tggagtttgg gctgagctgg gttttccttg ttgctatttt  21420
aaaaggtgat tcatggagaa ctagagatat tgagtgtgag tgaacacgag tgagagaaac  21480
agtggatatg tgtggcagtt tctaaccaat gtctctgtgt ttgcaggtgt ccagtgtgag  21540
gtgcagctgg tggagtctgg aggaggcttg atccagcctg gggggtccct gagactctcc  21600
tgtgcagcct ctgggttcac cgtcagtagc aactacatga gctgggtccg ccaggctcca  21660
gggaaggggc tggagtgggt ctcagttatt tatagctgtg gtagcacata ctacgcagac  21720
tccgtgaagg gccgattcac catctccaga gacaattcca agaacacgct gtatcttcaa  21780
atgaacagcc tgagagctga ggacacggct gtgtattact gtgcgagaga cacagtgagg  21840
ggaggccatt gtgcgcccag acacaaacct ccctgcagga acgttggggg aatcagcggc  21900
agggggcgct caggagccac tgatcagagt cagccccgga ggcaggtgca ggtggaggct  21960
gtttcctgtc aggatgtggg acttcatctt cttccaacag tttctctaat gaacctctct  22020
aattttagaa ttctgtggtt cctaatgtca tctctacctc gacgtcgagg atgcggatgt  22080
gatttaagtt tcagaggaat aagaaaaaag atttagggat taatttaatt attcaaaact  22140
tgattgaagt gccgagtgaa tggctccaaa catagtctac atttttcaaa tcattcccta  22200
taaatttgaa ttaattattt atttttatac ttgaataaag caataacaaa gaaataaatg  22260
aatattttttg ctaaaatgga gcaataaaaa gactgatatt gacagaagaa atatgactga  22320
cttctgaaaa tacacacaca tgagccgtgg ttctctctac atatttagat aaattacaga  22380
aagttgtcat aactgatggg gaatcctgca gacttcacta ggcatagtcc acactgccct  22440
ggagttgtct caggggagct gcctcctcca gtggttagag cacaggccca ggtaatagga  22500
ctcatttttt tagatgtgta attttagaca cactgcacaa ctgctgtgtt ctctgtgcaa  22560
attatctcct gtaaaatgta acattgaaac ctgccttaaa tatattgtgt aaatatgtaa  22620
aaataaaatc agattgtgag agctaaatgc taatcaaggc gcaatcacgt aatatacaat  22680
tatattttcc tgaatgatgg aattaatacc aatctccccc aggacacttc atctgcacgg  22740
agcccggcct ctcctcagat gtcccacccc agagcttgct atatagtcgg ggacatccaa  22800
atagggccct ccctctgctg atgaaaacca gcccagctga ccctgcagct ctgggagagg  22860
agcccagcac tgggattccg aggtgtttcc attcggtgat cagcactgaa cacagaggac  22920
tcaccatgga gttttggctg agctgggttt tccttgttgc tattttaaaa ggtgattcat  22980
ggagaactag agatattgag tgtgagtgaa cacgagtgag agaaacagtg gatatgtgtg  23040
gcagtttcta accaatgtct ctgtgtttgc aggtgtccag tgtgaggtgc agctggtgga  23100
gtctggagga ggcttgatcc agcctggggg gtccctgaga ctctcctgtg cagcctctgg  23160
gttcaccgtc agtagcaact acatgagctg ggtccgccag gctccaggga aggggctgga  23220
gtgggtctca gttatttata gcggtggtag cacatactac gcagactccg tgaagggccg  23280
attcaccatc tccagagaca attccaagaa cacgctgtat cttcaaatga acagcctgag  23340
agccgaggac acggccgtgt attactgtgc gagagacaca gtgaggggaa gtcattgtgc  23400
gcccagacac aaacctccct gcaggaacgc tgggggaaa tcagcggcag gggcgctca  23460
```

ggagccactg atcagagtca gccccggagg caggtgcaga tggaggctga tttcctgtca 23520
ggatgtggga ctttgtcttc ttctgacggt tccccaggga acctctctaa gtttagcatt 23580
ctgtgcctat gaacgtcttc tctaagtatt tgaaagagat tattttaata tgaagagcag 23640
ttctcactcg ccctcgacga gcatgtgcac atttcattaa acccactgtg tatgcagccc 23700
ctcccaagtg ctggcaggcc actgtacatg tgggcagccc actccaaggg aagaatcaag 23760
ggagaagaaa tacaaacccc agaaccatgt caatgtataa aaccccaagt caagggccgg 23820
acagagcact tagatctctc aagtcgccca cttagccctc ttccaagtgt actttacttc 23880
ctttagttcc cactttaaaa ctttaataaa catttactcc tgctctaaaa cttgcttggg 23940
tctctcactc ttctgtatgc cccttggcca aattctttcc tccaaggagg cgagaatcaa 24000
gttgctgcag acctgtatgg attcgctcct gctaacagat agctggatgg gtggacagat 24060
gcatgaatta gtggatggac gtttggatgt gtgggtgggt gggtggattg tgggatggct 24120
ggatgaatgc atggctggat gggtggacag atgcatgaat tagtggatgg atgtttggat 24180
gtgtgagtgg gtgggtggat tgtgggatgg ctggatgaat gcatggctgg atgggtggac 24240
agatgcatga attcgtggat ggacgtttgg atgtgtgggt gggtgggtgg attgtgggat 24300
ggctggatga atgcatggct ggatgggtgg acagatgcat gaattcgtgg atggacgttt 24360
ggatgtgtgg gtgggtgggt ggattgtggg atggctggat gaatgcatgg ctggatgggt 24420
ggacagatgc atgaattcgt ggatggacgt ttggatgtgt gggtgggtgg gtggattgtg 24480
ggatggctgg atgaatgcat ggctgggtgg gtggatggat gcatggataa gtggtggacg 24540
gatggacggg tgagtggatg ggtggatgtg tgtgtggatg ggtggatagg aaagccctct 24600
aattgattac agggctcagt gtgtgcttca acatcatgat ggcatcatca cattggtccc 24660
tgtatgaagc agtgggggag gagagtgtac caggggagca ggaatgactc ttctccagaa 24720
tcgacctctc ccaccctgca gcctgggctg tgcaggccac attggagaag gtgcggtcga 24780
ctactcctaa atgttgttgt gtccaatggc tttttgacgt tgatgtagga atgagcctac 24840
atctccacca tagatggaac tgtttgggtc cccaaagcag aaagcctctt ctgttgcagg 24900
tgctgaagtt tccatcttct tctgcttata cggaagctca cgcatccctt ggatggcagg 24960
cgtcaggttc ctgtgcgcac tgagttcccc ccttacatgc tttggacaga agtgtgagac 25020
acacaagatt gctgcaggaa gtccacctgt ggggatgctg cgacttctcc agcaagaaca 25080
cgagtctgct cattgaccat caccacacat aacaaattaa gtgtcccttt tttgataaca 25140
cgtcattgtt tcacagagta ttcttttaaa gtgtataagt tgactgcagt tattattttt 25200
tacttctgtt actaatttac tcataattag gcacaattta cacttaagaa atttcttaat 25260 agtttttttcc tccttaaggt gaactacagt cagataacat acttatcaat tgtctctagc 25320
tcttgtcaga aaagcatata gatgtgtgtg tgcgtgtgtc ttggcctttc caatgatgaa 25380
ttaagatgtg cattgagaag gcattcactt tatttgacgt taaggaagta ccaagaagac 25440
gctctccaca gaccctggga aagccagcag ctgcaccccg aggctgtgcc aggcagggaa 25500
caaggaggca gcaccacctg ctgggcaggg aaaatgtcct cccagtccct gccgcttctc 25560
tgcagaggca caaagagctg ccccttctcc tgggccttct cctgggctga tgagattgct 25620
ccccgatatg ccaaatcagg gttgtgcatc tgaggctctg tctagactct cagctccttc 25680
ctactcctgc aaagtgaaga aaacaatgcc aaggggtcct ggaggcgtct ctacccctgg 25740
agagttttga ctctcttcaa tagtctccac taccctgccc tcactccatg tcctccgttt 25800

-continued

```
ctccctaaag cggtgcccag tctgattgca ctgtggcagg gataacgagg ggccaggaca  25860
tcaggggaga gaagtttcta cctgagtcac agcagcggct gccctgcaga ctcctgaaga  25920
cacaagacac atttccatcc cagagaccca gcgaaatgca acctcaggct agagacagcc  25980
agttattttt tcttgttctg tcctggagag gccactgaga aagtcgagcc ccttgttgag  26040
gaaaacatga gatctctgtg tgtcgtcctc tgcctgatgg ctgtacctcc atgtgagtgt  26100
ctcagagatt tcagaacggg ggctgtgggc tgtggtgtcc gcttgtgact catctctttg  26160
cttcttgtcc ctgagtgtcc tgcatcagat gcagctactg gagtcatgcc cagggctggt  26220
gaggtcctca cagacctctg ggcctggacc cagcagccct ctgggaaggc gctggggcac  26280
ctcagctcca ggggcagcac acacttcagc ccagcctttc tgggccaact ctccatctgt  26340
agagacacat ccaaggccca gttatccctg cagctgagct ccgtgatggc caagggcagg  26400
gccgcacatt cccgtgggag acagaatggg gacctcagcg tgagcccaga cacaaacctc  26460
cctgcaggga agcacaagac caccaggcgg cgctccagac cacacagcgg ccccagaagc  26520
aggttttagg gggcggggca gacgtgtccg cgttgagtca ggtcactggt tttactttcc  26580
ctgaacaaac ggcctctgcc aaggactcac tgcacctctc accttcacag ttgttttttt  26640
ttttttttta atcaccctgt agggttttgc tagctaattt agatattgag gagtgcttca  26700
tacttccttg ggcctctgct tgcagaaaca tagcaattgt aaggaggcac gtgggaaagc  26760
cccggctcgg tgacccgggg gatgctgctg tagccctggc aagagggcgt cgggccgcag  26820
taacaaaggt gcagacggct ctcagcctgc gcccgcggag tacaacacat aagggctgta  26880
acctaacgaa aaaagaatcg cagtgcaact gtcctgcatt tgagtttgtg atcagttttg  26940
ccctttgtct ttaacaggtt ctaacataaa attttgaatg ctggttcaag ccctgtgggt  27000
aaaatgcact tacccacatt ccttaaacaa atagaacact gaggtggaaa tgttttgaaa  27060
aagtagtttt cagacatttg gaaacaagca tcacaggatc ataacccctg agaaaagaaa  27120
aacaaatgaa cgaatcctgc tattgcctga aagcagctgc caggacacac ggaaaggctt  27180
agtgagctga gcggacagag agcagagttc aaggcagcag cagcccgagg ggaggagcac  27240
cggggagcag gctgctgtgc agccaggatg ggccggggtg gggcgggggg agaacagctg  27300
gagacttgcc gcagggaggg ggatccctca ggtttggggc tgagaactga cttatgcctg  27360
acttatgcct gcatgaaaag aaactactcg atatcagggg gaaatcacca gaaacctgtg  27420
gacccaaaac tacacagagc ctacacaagg aaagcattgt ttgtgttctc ccagccaggg  27480
tggaaagacc ttgagatatg taaagcttca agcaatcttc cgaagtaatc tcgtgagtag  27540
tggtgccaca ttaattcagg actaaagact gctctgaact gaacctaaga aatgcttcaa  27600
gtgtagcctg gagcccgggt gcagtggctc acacctgtaa tcccagcact gtgggaggcc  27660
gaggcaggcg gatcacttga ggtcaggact ttgagaccag cctggccaac atggcaaaac  27720
ctgtctctac taaaaacaca aaaattagct gggcatggtg gcagatgcct gtaatcacct  27780
cccacctgga cccttccttg atacatcaga attacaacta gagatgagat tggggtgggg  27840
acacagagcc agaccgtatc acataggaac ctaaaaggat aataaagtag gaaaacttcc  27900
cacatcagta accctttatc cgatagtaat cccaatctgc aaagtaaaac tgtgtgattt  27960
tactaagata acggaatctt ctctacagaa ggactttcca gtgcaaaagc tccccaccct  28020
caccatgaaa tgcacgtgac catttccaat ttgtgtaaag tcctcagtta gtactgagac  28080
ttcggaaggt tagaaatccc tttgctcatg ctgcatggtc cggatgagat gtaagaatca  28140
ttagctaata gacatgcaac agcttttgtg cgaaagatgt tatgagacat ttaaggtatt  28200
```

-continued

```
tgcttgtgct tactaagcat tcattgtatc attggagcac atgtgctttt ataccctgga  28260
gaaattccag taattgaatt gctgggttga atgggatttt gatttggatt aaatttaaac  28320
tatagatttt atttagggaa aactggcatc ttaattatgt tattgggggg cccttgctcc  28380
cagagctccc aagatggtgg caggccgctt ccaaaatgac cgcaggccac ttccaagatg  28440
gtggcaagcc tcatgttctc tgacctgggg ttcttggcct cacggattcc aaggaatgga  28500
agcttgggcc atgcagtgag tgttatagct ctattagaag ccgtgggtca cggaagagaa  28560
ccgtggaacc cagtgactag tgttcagctc gattaggacg aacccaggca cttagccgtg  28620
caggaacaat ggcgagcatt tggcccgatc gagagtggca atgggcgcct cgccggatca  28680
ggagcacagc ggataccctg atggatccgg agggatggaa gccagcggtg ggtctcccac  28740
gggggcaaac agcagtggtg gacggtgagc gaaagcgaag ctcgagccgt aacaaacatg  28800
gaccagaaga gtgcagttgc aagatttagt agagtgaaga cagagctccc atacaaaggg  28860
aggggaccca aagagggtag ctgttaccgg ctcgaatgcc tgggtttata tcccgatcat  28920
tgtccctccc gctgtgctct caggtgatag atgattggct atttctttac ctcctgcttt  28980
tgcctaatta gcattttagt gaactctctt tactatctga ttggtcgggt gtgagctgag  29040
ttgcaagccc cgtgtttaaa ggtggaagtg gtcaccttcc cagctgggct tagggattct  29100
tagtcggcct aggaaatcca gctagtcctg tctctcaatt acactgagtt ttccaatcca  29160
tgcatccaat atgtggtgta tctcttcata tgttcatagc ctctgagcaa tgttttacaa  29220
ttttctgtgt aaagaactcc acatcgtttt atgtttcttc taaggtatat cctgattgct  29280
ttttatgtct tcacaagttt ttccctttca aaattaattt tccaattgtt tggtgctaat  29340
atgctcaaat gtccttgatt ttcttagttt gaacagtccg ttttcgtttt ggggatttat  29400
tttttttca gattctttaa gattttctat gtctataacc atataatctc tgaacagaga  29460
cagttttgct tttccctttc aacttgaggt aggttttctg ggtagttcag gacgcgcagg  29520
cactgggtgg gtggtgttag cagctgcacg atgccttgga gaggacactc tcgggggact  29580
gtggccgctg ctcagctgtg actgttctta tagcaccagc agctgcggcc accattctta  29640
tccaatttcc aaagccacac cacaggccct ctcaagaacg aggcgtggag gctatgccct  29700
ctcctggaca catcatcatt cccaagcccc acgatgtggg ccccatggga cgcacacctt  29760
tgtctgtcca gacctcagcc ccacctcctc atcctgcacc agaactcttc agagcccagt  29820
gcatgaaatg ggctaccaag gaaatgaggg taggttcctg agaggaaact ggccctgcat  29880
ttgggagcta agagtctgct aattcgcctg gcagccctgt gcagccctcc gtggctacag  29940
tccaccccgt gcccatcagt gcctccttcc tgtgcaagcc tggacctcgc cctgggctca  30000
ggatgggctg tagaccgaga atgcaggcgg gaaagtcgtt gtctatcggg gccatagtca  30060
ggttctacag tgagtcaggg aaagacctgt ggaggtgtgg atgaggacaa tgggtccacc  30120
atcaacagga ggacacgggt tcgacccctt gcagaggcac agtcccacat cactgggagg  30180
cagccacact cactgcctcg ccctctcctc acacagtgca gtttccacgt tcacagcccc  30240
agccagtcac caggaatgcc ctgggggcgg cctttcccca gtgcaccccg agccctccct  30300
tggctgtgcg gtgagctcca tgcccaggag atatccaccc atagtcctcc ggaaagcagc  30360
tgacctgcca tgccctggaa ccacaaatcc ccacagatca gccagcctgc agtgggcctt  30420
ggatgtggtg aggagtggtg gcaccccgt tcccacccca cagatgcaac gcctgtgggt  30480
gacgcatgtg agtactgagg agtagagggt agaactgtag gccccgagaa ccacagaaac  30540
```

-continued

```
tcgggtgtta cactctgggg ccatgtaagg agaaagtgtc actggacaga aacaggcccc  30600
tcctagacac tgtgtgcgcc atagtcacct gtcattagct ctcactcttg cagattcatg  30660
attgaggtgg ttaaaaaaaa aaaagctcct actcacccat ccaaccccat cctggggtgt  30720
ttccaccacc cttggggttt gggatgagct gcccttgccc actgtgctct gtggacctcc  30780
ctttagaagc tcacagctcc ctgcactcgg ctccatcctg ccccaccaca cagaagcaaa  30840
acccctctcc tttccactgc aggcttttcc tggaccagaa tgctgacctg ctgcccttca  30900
ctcccgaagt ggtgggactg cctggggtgg tgtgggtgtt gagccttctt actctaggga  30960
cctggcacct ggccccaggg gcacagggat ggtgcatctg cctagggatg cctcctcatg  31020
ccagggggtg ggggttagta ccatcggccc tcaggatttg ttgcatgaat gagtgaatgg  31080
gtgaataaat gaaggggatc tgatctatga ataagggtat atggactttg gttgatgtag  31140
gacgccaaat gctggaattt cggagtcatc acacccaggg gccctgcctc tgagctcctc  31200
tttgcatcca atctgctgaa gaacatggct ctagggaaac ccagttgtag acctgagggc  31260
cccggctctt caatgagcca tctccgtccc ggggccttat atcagcaagt gacgcacaca  31320
ggcaaatgcc agggtgtggt ttcctgttta aatgtagcct cccccgctgc agagctgcag  31380
agcctgctga attctggctg accagggcag tcacccgagc tccagacaat gtctgtctcc  31440
ttcctcatct tcctgcccgt gctgggcctc ccatggggtc agtgtcaggg agatgccgta  31500
ttcacagcag cattcacaga ctgaggggtg tttcactttg ctgtttcctt ttgtctccag  31560
gtgtcctgtc acaggtacag ctgcagcagt caggtccagg actggtgaag ccctcgcaga  31620
ccctctcact cacctgtgcc atctccgggg acagtgtctc tagcaacagt gctgcttgga  31680
actggatcag gcagtcccca tcgagaggcc ttgagtggct gggaaggaca tactacaggt  31740
ccaagtggta taatgattat gcagtatctg tgaaaagtcg aataaccatc aacccagaca  31800
catccaagaa ccagttctcc ctgcagctga accctgtgac tcccgaggac acggctgtgt  31860
attactgtgc aagagacaca gtgaggggaa gtcagtgtga gcccagacac aaacctccct  31920
gcagggatgc tcaggacccc agaaggcacc cagcactacc agcgcagggc ccagaccagg  31980
agcaggtgtg gagttaagca aaaatggaac ttcttgctgt gtcttaaact gttgttgttt  32040
tttttttttt tttggctcag caacagagat catagaaaac ccttttttcat atttttgaaa  32100
tctgttctta gtctaatgga gattctctga tatgtgacaa tgtttttctc ttgctgtttt  32160
tggaattctt tgtctttgac ttttgacaac ttgacttttg acagtgtgcc tcaaagaagt  32220
tctattttgg gttctgtgaa cctcctggat ctgggaagtt ttcagctatg atttcattaa  32280
acgtgttttc tacaccattt ccctactctt ttggaatacc cataatgcaa atatttgttc  32340
acttaattgt gtcccataaa tgctggggat tttcttcatt ccttttttact cttttttttct  32400
ttttattcat ctgcctgaat tatttcaaaa gatctgtctt caacttcaga aactcttttg  32460
cttggcctag tctaatcttg aaggtctcaa ttgtactttt aatttcattc attgaattct  32520
tcaactctgg aatttctgtt ggttcttttt tatgatactt atctctttgt tgaattcctc  32580
attcaaatga taaattgttt tcctgatttc actgaatttt ctatctgtac actattgtat  32640
ctccctgagt ttcttagaga ttatcctttt gaattatttt tctgacattc tgtatatttc  32700
cttatgattg ggtctgctta ctggagaatg actgttgtct ttttcaggtg ccgtgtttcc  32760
tggccttttc atgttttatg tgttcctacg ttgatttcta cacatctggc ggaccagtca  32820
tcccttgcaa tttaatggag taggttttgc aggaaaagac ttcctagtac agacgggtct  32880
cagggtgtca gtgtggcggg gcgtgctggc tttagttcta ggttgacgca gtagcgtagt  32940
```

-continued

```
ctccatgtcg tttcttcagc tgccgtccac attggtgacg tttgcgagtg tctcagtggc  33000
ctgggctgag aggtttgtgg cagtggaagt gcaacgttgc tagaggtgga ctcaccaggc  33060
tgtttctgag gtcgaggcac atgcatgcac atggtggatt gaccaacttg gtgccaggct  33120
cactagggtt ggggacatgg ggctgtttct caggcccagg atgcaaacac aagtctcttt  33180
ggctggcctg gggtgtggc ttctgagggc aatccacagg gctgtttctc aggttcagga  33240
cacaagtgca tggccgctca actggcctgg gcatgtgtct cccagggcca ccccatgggc  33300
tctctctcag acccaggaca tggccacatg gcttcctcag ctggcctggg tgtgtgtctg  33360
cttggggcct gcaggggcac agggttattt ctcaggccgg ggtcatgggc gcacagctgc  33420
ttgctggctt ataggagtgc ctgccagggg tggcccatga tgctgtttct caggcccgcg  33480
cgactgaata cataaacagg acacagcatt ttgctgcata aagcaaacac agcgttactt  33540
tttttttct aaatgacatt ttttattaga tattgtcttt attgacattt caaatgttat  33600
cccctttcct ggtttaccct ctgaaatccc ctatctcctc cccctccccc tgctcaccaa  33660
tccacccact cccacttcca ggccctggca atcccctata tttgggcata gagccttcac  33720
aggaccaagg tactctcctt gcattgatga ccaactagtc cattctctgc tacaaatgca  33780
gctagatcta tgagtcccac catgttttct tttgttggtg gtttcatgcc agggagctct  33840
tggagtactg attggttcat attgttgttc tccctatggg gttacaaaac ccttcaactt  33900
cttgggtcct ttctctggct gcctcattgg ggaccttgtg cgaagtccaa tggatgactg  33960
tgagcatcca cttctgtatt tgccaggcac tggcagagcc tctcagaaga cagctatatc  34020
aagatcctgg cagcaagctc ttgttggtat ccacaaaagt gtctggtggt tgtctatggg  34080
atggatcccc aaaggggcag tctctggatg gtcattcctt cagtctctgt tccacacttt  34140
gtctctttaa ctccttccat gactatttta ttcctccctc taagaaggac cgaagtattc  34200
atactttggt cttccttctt gaaattcatg tgttttgtga attgtatctt tgatattccg  34260
aacttctggg ctaatatcca cttatcagtg agtgaatatc atgtgtgttc ttatgtgatt  34320
gagttacctc actcaggatg atatcctcca gaaccatcca tttgtctaag aatttaatga  34380
attcattgtt tttaatagct gaggagtact ccattgtgta aatgtaccac attttctgta  34440
cccattgttc tcttgaggga catctgggtt ctttaaagct tctggacatt aaatataagg  34500
ctgctatgga aatagtggag aatgtgtcct tattacatgt tggagcatct tctgggtata  34560
tgcccaggag tgctattgct ggatcctctg atagtactat gtccaatttt ctgaggaact  34620
gccaaactgg tttacagagt ggttgtgcca gcttgcaatt ccaccagcaa tggagaaatg  34680
ttccccttcc tccacatcct caccaacatc tgctgtcacc tcaatttgtt cttagtgatt  34740
cagacaggtg tgaggtggaa tatcagggtt gtttggcatt tccctgatga ctagtgatat  34800
tgaaaaaaat tttaagtgtt tctcagccat tcagtattct tcagttgaga attcactgtt  34860
tagctctgta ctcaggtttt tttaataggg ttatttggtt ttctggagtc taacgtcttg  34920
aattctttct atatattgga tattagccct ctgtcatatt taggattggt aaagatcttt  34980
cccaatatgt tggctgcctt tttgtgtcct ttgccttaca gaaccttttt aattttatga  35040
ggtcccattt gctaattctt cattttacag caaaagccat tggtgttctg ttcaaaaatc  35100
tttccccctg aaccctatct tcgaggatct tccccacttt ctcctctata agtttcagtg  35160
tctctattat tgtgctgagg tccttgatcc acttgaactt gagcattgtt caaggagata  35220
agaatggatc aattcgaatt cttctacatg ataacagcca gttgagccag caccatttgt  35280
```

-continued

```
tgaaaattct cttttttgca ctggatagtt ttagcacttt tgtcaaagat caagtgacta  35340
tggctcttca actatggctc attccattga tcaacttgtc tgtcactgta caagcaccat  35400
gcaattttta ttgcaattgc ttagtattac accttgaggt caaggatggt cattccacca  35460
gaggttcttc tatggttgag aagagttttt gctatcctag gtttttgtta ttccagatga  35520
atttgcaaat ggccctttct aactcagtga agaattgagg tggaattttg atgggaattt  35580
tattgaatct gtagattgca ttcaacaaga tagccattta taatacatta atcctgccag  35640
tccatgagca tgggagatct ttccatcttc cgagatcttc ttcgatttct ttcttcagag  35700
acttgaagtt tttatcatac agatctttca cttccttagt tagagtcaca ccaaggtatt  35760
ttatattatt tgtgactact gtgaaggttg ttgtttccct gatttcttcc tcagcctgtt  35820
catcctttgt gtagagaaag gccactgatt tatttgagtt aatattgtat ccagctaatt  35880
cactgaagtt gtttatcagg tttaggagtt ctcttgtgga atttttggaa tcacatgtgt  35940
atactattat atcatctgca attagtgata ttttgacttc ttctttccca aattgtatcc  36000
ctttgatctc cttttgttgt ctaattgccc acactaggac tcgggcagcc ttagtgccta  36060
gtccctgatt ttagtgtgat ttgttcaagt ttctctccac ttagtcggat gttggctact  36120
gatttgctgt atattgcttt tattatgttt aggtatgggc cttgaattcc tgatctttcc  36180
aatactttta tcatgaatgg gtgttgaatt ttgtcaaatg ctttctcaac acctacaaag  36240
atgatcatgt agattttgtc tttcagtttg attatatagt gtattatgtt gatggatttc  36300
catatattaa accatccctg catccctggg atgaagccta cttggtcatg atagacgatt  36360
gttttgatgt gttcttggat tcagttagtg agaaatatat tgagtatttt tacatcgata  36420
ttcataaggg aaattggtct gaagttctct ttctttgttg ggtctttatg tggtttagtt  36480
atcagagtca tcgtagcttc atagaacaaa ttgagtagag taccttctgt ctctattttg  36540
tggtatagtt tgaggagatt tggaaatatg tcttcttggg acgtctgaga gaattctgca  36600
ctaaacccat ctgatcctgg gcttctttgg gggggggga ctattaatga ctgcttctat  36660
ttctttaggg gaaatgggac tgtttagatt gttaatatga tcctgaatag aaatctgatc  36720
tgatctagaa aattgtccat tttattcagg ttttccagtt ttgttgagta ttgccttttg  36780
tggtagggtc tgatgatgtt ttggatttcc ttaggttctg ttgttatgtc ttcttttcca  36840
tttctcattt tgttaattag gatactgtcc ctgtgtcctc tagttactct ggctaagcgt  36900
ttatctatct tattgatttt ctcaaagaac cagctcctgg tttggttgat tctttgtata  36960
gttctttttg tttccacttg attgatttct gccctaagtt tgattgtttc ctgctgtcta  37020
ctcctcttgg gtgaatttgc ttccttttgt tctagagctt ttaggtgtgc tgtcaagctg  37080
atagggtatg ctctctctag tttctttttg gcggcactca tagctaggag ttttcctctt  37140
agcagtgctt tcattacgtc ctgtaagttt gggtatgttg tggcttcatt tgcattaaat  37200
tctaataagt ctttaatctc tttccttctt tcttccttga ccgagttatc attgactaga  37260
gtgttcatca gcttccacat caatgttggc ttttaattat ttatgttttt attgaggatc  37320
agcctttgtc ggtggtgatc ttctaggatg cacgggaaat tttcaatatt tttgtatcta  37380
ttgaggcctg ttttgtgacc aattatacgg tcaattttgg agaaagtacc gtgaggtact  37440
gagaagatgg tatatctttt tgttttagga taaaatgttc tgtagatatc tgttaaatcc  37500
atttgtttca taacttctgt tagtttcact gtgtctctgc ttagtttctg attccagaat  37560
ctgtccaatg ataagagtag ggtattaaat tctcccacta ctattgtgtg aggtacaatg  37620
tgtggtttga gctttaaaag agtttcctta atgaatgtgg atggccttgc atttggagca  37680
```

tagttattca gaattgagag ttcctcttgg aagattttac ctttgatgag tataaaatgc 37740
ccctccttgt cttttttgat acctttgggt tagaagtgga ttttattcga tattagaatg 37800
gctaatccat cttgtttctt tgagatgttt gcttggaaaa ttattttcct gccctttact 37860
cggtggtagt gtctgtctta gtccctgagg tgggtttcct gtatacagca aaatgttggg 37920
tcctggttat gtagccagtc tgttagtctg tctttttatc aggtaattga gtccattgat 37980
attaagagct attaaggaaa agtaattggt gcttcctgtt atttttgttg ttagacttgg 38040
gattctgttc ttgtggctat cttcttttag gtttgttgaa ggattacttt cttgcttttt 38100
ttagggtgta atttccctct ttgtgttgga gttttctctt tattatcctt tgaagggctg 38160
gattcatgga aagatgttgg gtgaatttgg ttttgtcatg gaattctttg gtttctccat 38220
ctataattga gagttttgct gggtatagta gcctaagctg gcatttgtgc tctcttagtg 38280
tctataacat ctgtccagga tcttctggct ttcataatct ctggtgagaa gtctggtgta 38340
attctgatag gcctgccttt atatgttact tgaccttttt cccttactgc tttaaatatt 38400
ctatcttcat ttagtgcatt ttttttctga ttttttatgt gtcaggagga atttcttttc 38460
tgctccagtc tattcggatt ctgtaggcta cttctatgtt catgggcatc tccttcttta 38520
ggttacggac gttttcttct ataattttgt tgaagatatt tactggccct ttaagttgaa 38580
aatctccatt ctcatctata cctattatct ttaggtttgg tcttctcatt gtgtcctgga 38640
tttcctggat gttttgagtt aggatctttt ttgcattttg cattttttttt tattgttgtg 38700
cccatgtttt ctacggaatc ttatgcacct gagactctct cttctacctc ttgtattcta 38760
ttggctgatg cttccaccta tgtttctcga tttctttcct aggatttcta tccccagagt 38820
tgtctccctt tgtgatttct ttattgtttc tacttccatt tttagatttt gaatggttct 38880
gttcgattcc atcgcctgtt gggttgtgtt tttctgtatt tctttgaggg atttttgtgc 38940
ttcatcttta aggtcttcta cctgtttagg agtgttttcc tataattctt tgagggattt 39000
ttgtgttttc tctttaaggg cttctagcaa tttagcagtg ttctcctgta tttctttaag 39060
tgagttatta atgcccttct taaaatcctc taccaacatc attagatatg attttaaatc 39120
cgaatcttgc ttttcaggtg tgttggggta tccaggactc actgtggggg gagtactggg 39180
ttctgatgat gaaaactggt cttggttttt attagtaaga ttcctacttt tgccttccac 39240
catctgataa tatctgttgt tagatattct agctgtctct ggctggagct tgttcctcct 39300
gtgattctgt cagcctctgt cagcactcct gggagtacaa ctcttttctg agtcccaatg 39360
ttcagagcat tctctgcagg caagctctcc tctggcaggt aaggtgccca gagctcttga 39420
gctcagctcc acctcctgac tgcagatgaa gacccaaagg gaccctgtcc aataagctct 39480
gttgcttctg ccacccacat gctctcctgt gcgaactggt ctctgagaga cccgggatac 39540
aagatggtac tctcacctga atcccagggt caaagccctc cctggaggct gactctcctc 39600
ttgtgggaag gtgcacagag gtctggagct cagctctgcc tcctggctga agatgaaggc 39660
ccgaagggac cctgtccaag aagctttgtt gcttctggga cccacatgct ctcctacatg 39720
gactggtctc tgagagacca gggattcaag atggtgctct cacctgagtc ccagggtcag 39780
agccctctct ggaggccaac tctcctcagt gatcctaaga tcctgggtat gctagggtgc 39840
ctatggcatg gagagtcctc tgaggaatgt gggactgtct gctgagtttc cacccaaggt 39900
ggtgctgggc tggctccagt cagaatgaac ccagactctg gttgggcagg tttccagtcc 39960
tgttggccca agcccctctg ggttgtttta gaacagatgt tgctttccac tcaccagtga 40020

-continued

```
tcccaagatc ctgggcgtgc tagggtgcct gctatgtgga gagtccactg gggaccttag  40080
gagcatacat caagttcaca cccatggtgg caaggagctg gtgcctacca gaacaaaccc  40140
cgggcacttt tactgaccct ttaagttgaa aatcttcatt ctcatctata cctattatcc  40200
ttaggtttgg tcttctcatt gtgtcctgga tttcctggat gttttgactt aagatctttt  40260
tgcattttgc attttttga ttgttgtgtc catgttctct ctggaatctt ctacacctga  40320
gattctctcc tctgtatctt gtattctgtt ggtgatgctt gcatctattg ctcctgatct  40380
ctttcctagg gtttctatct ccagagtttt ctccctttgt gatttcttta ttatttctac  40440
ttccattttt agatcctaga tgattttgtt aaattccttc acctgtttgg ttgtgtgttc  40500
ctgtaattct ttaagggatt tttgtatttc ctctttaagg gcttctacct gtttagctgt  40560
gttctactgt atttctttaa aggacttatg aatgtccttc ttaaaaacct ctaccagcat  40620
catgagatgt gatcttaaat gtcaatcttc cctttctggt gtgttggggt atccaggact  40680
tgctgtggtt ggagttctgg gttctggtaa acctgcctta gagggtcacc acagagtaat  40740
gatagcacta cttttaaaca ggggaagatg atgaaataat tgctgtggga aaatgcaagg  40800
aaggctccaa cacatgtagg catctatgaa ggtctcaaat cttcaaaatc caaaaccacc  40860
aagaaagaaa gaaagaaaga aagaaagaaa gaaagaaaga aagaaagaaa gaaagaaaga  40920
aagaaagaaa gaaaggaagg aaggaaggaa ggaaggaagg aaggaaggaa ggaaggaagg  40980
aaggaaggaa ggaaggaagg aaggaagatt ctaaaagtag tcacctgcac caggtgcctg  41040
gggagtcact cagcagccct agactgagaa agcttgaaga aagtagaaat agagaaagtg  41100
tacagccagt atcctctagc tactcacatc caaacagggc ctcctgactg ctctgagcct  41160
gtcctaagaa cagcaatgat gccacagaaa tttttagagt gaaccctgaa ggaacttgag  41220
gccgatatga gaaagccagt cccagaggaa aggaaaaccc gtagagagaa aacaggtgag  41280
ttagtgcatt aaaggggctg agcaggcaac gcgccgtcga ccggaggagt ttcttccctg  41340
tgcggagtcc acgggcctcc tgtgagtgtg tgcatgggca caagtgtgtg tgtggctctg  41400
ctgtgtgtct gtacacacat atgttttggg tttttttgtg tctcagacca cagagtctgc  41460
ccctcccacc aaagcccagg cagaaggatg aacccacgcc cctggggccc aggcctcagc  41520
agcctctgcg ggatcattgt tcccagttgt cacttgcctt tgccacagcc ctatttctcc  41580
acaattcctt aaagtcctca acatgcattt aaggcacaaa ggtgaaactg cccagaaaca  41640
tctgactccg ccgtggaacc caggagcaag ctgggttagc taaggagcgg ggccgttggc  41700
agaggctggg gatccaggct gaactttgga ggaggcatgt cccagcatgg gctcctgact  41760
atgtcctcct gggacaaacc caaacccact ctttgaatat gggagggact ttgctggccc  41820
cggccctgac cgcagcactt ggaaactgag gagtggtcgc ctcctccgtg tcacagctgc  41880
ccgttcacca tcatagaagc aactctgtca cctccatggg cccctctgtg gctgctgcct  41940
gggtccaagc tgagcccagc tgcccaggcc cagaaggaaa gcccaggcca ggtgcccagc  42000
acagaggcag tcacataccc cggggagagc cacagcaagc agccaatatt gcccaggaga  42060
ggagtagctg acaaggcaga acgtgagctg ccatcggctc gagaggcttt gctggtcctc  42120
ctggggctct ggacatgacc aggaggagcg agggaagaag tcgcatggtg gtcccatcct  42180
gggtggggcc tgatggcagc tggccacccg tcccagagtg gcagccagat gccagcgcca  42240
ttcccacagt cacatcattg gtcacagaat gcaggacata gagtgtcttc tttccatcac  42300
agtgctgtcc agacccatag cctagggtag acctggaaga ttcaatgtcc acacccgggg  42360
ctggagcgta gccatgagcc acgccccctg cccgtgcatg gaaagccagc ccaagctctg  42420
```

-continued

```
ctccatccct agccaaagtc agtgtccttt ccccttctcc caagtgagct ctagccacct  42480
gcctaccctg ccatctgagg atgacagcct tcattccatt ggaacctggc tctgccacca  42540
gcaggcttgc agtcctgggc agactccgtc acctctctat gcctcagcct ttccatctgc  42600
acaggaggaa gatgatgatg gtggtgatga tgatggcgat ggtttccttt tgcatctgag  42660
gcaaggacta attgagatga tacacatcag gcactgggta tggtgctggt ccttcctgag  42720
cactcaatct atgtgagctg tccttgtgaa atgggtgtca ccacatttcc ccacgcagaa  42780
catcctttgt ctgccatact tgaaacgtct gccccaatac taacagctcc tcatggaaga  42840
tgtgcccacc cacccaccct catactccca aaggtgcccg tgctttatca agccaaagtc  42900
cagccaggaa ctttacagca gcatcccttt ccctctccaa gcaccaagga gcaaggcaaa  42960
gcactacatc ttccatctgg aggcaatgcc accctcttct cccattttca ctgccatccc  43020
taagaggcag tgcttcccca aaaggttcca tagcagcctg cctacagcaa ctctgttcac  43080
acgagtttca gcatccttgc agtggctccc ctgccatgct gtggctcttc attcaccctc  43140
ttctcctgct ccccgtgaca ggcatagatt ctgagtgatc tggatacatt gctttgttta  43200
ataacattac agcttctgtg ctgaaaaaga tacagcagat agagaaggca attgttgaac  43260
acaaaatagt gacagcagag atgacggcaa gttggcattt ttcttttcta gcaataaaac  43320
ttaaagctga ctcaaggaga aatggaaatc ataattggaa cagtaatcct caagaaagca  43380
ttaagattat taaataattg ccctcacaga tgacttcagg ccaagatggc tttatgggtg  43440
aagtttagac tttcacaaaa ctaatcagtt cccataagaa ctgctccagg atttggagga  43500
acatgggaaa gtctattaaa gggatcacaa ttcacagtcc ccagagtaaa acatgggcta  43560
acttgcattt tggcaaagag ccaaatgtta taaatgacat cctagaaggc caaattctgt  43620
ccatctcgtt gaacaaggac ttacaccagg aatttagaac tatttatagc tcatccccacc  43680
actcaggcca atgatgaccc atgatcatct caccagaaat ggaaagactc agatgattaa  43740
tagagtctca atttctctga gacatctaag agcccagccc aagcccagac ccaggagggc  43800
acccaggcct ggacagagaa cactgatatc acaccagccc tccagaggga agcagagact  43860
ccttcaagct ctggaaacac aggcccagac agctgcccaa agttgggcag gcttcactgc  43920
aaacccaaat catgaagcta ggtaacacct ttacagattc tttacattta aaaatcatca  43980
aaacaagagt aaataataaa ctcaaataat attaatctaa tatgtaaagg tcttgtacca  44040
ttattatgca aacaacatac ataagctaat aagaaaaaga acaaatccct taagaaatca  44100
gcaaaaagga tataacacaa tttctaaaag aaaacaaatg gctagcacac ataaggaaaa  44160
cactttgtga acagacattc ttcagaacat tatttataat tataaaatag ttgaaagcaa  44220
gatagtgcct gaagaaatta tggtgcatac attagtggga ctattctgca aacattccca  44280
attatacttg tcacatatct gtgataacgt gacagccagc attcatgggg tgacctcatt  44340
tggtaaaagg gtgcaaagct caacacgcat tgtgagatga ctgtggtgta aaattagtgg  44400
gattattccg caaacattcc caattatact taccgcatat ctgtgataac atgacagcat  44460
tcatggggtg acctcatttg gtaaaagggt gcaaagctca acacgcattg tgagatgact  44520
ggtgtaaata caaagaccaa actgtgaaaa ggagtccatc aattaatcga tgcttacctt  44580
cagttttggg ctaattttta aagtatgcta taagcatatg ctcctgttat aacagaatgg  44640
agggattatg agagatgatg caggtgtgtc ctgggcctcc cctggcccac tgggccctag  44700
agatgccttc ccaggcatcg ctgtcagggc ttccctcaga gggagtcctg tattgacctc  44760
```

-continued

```
accaccaagg tctggagcag gggatcctta gatattggtt ggggttatct caccttaggt  44820
ctgaatatgg ggttgtctta gactgttttg tgctgttaga atagaatacc caagactggg  44880
aaatttatac tgaacggaaa tttatttctc acagttctag aggctgtgaa gtccaagagc  44940
acaggtgcca gagcaagtcc aagagcaagg gaaagtccaa agcaagtcca ggagcatctg  45000
gcgaggacct tcttgctgtg tcatcacatg gcggaaggca agaaagagag caagaggggg  45060
ccgaactcac ccttttataa cagcaccaat cccacccatg aggtggggac cttatgacct  45120
aatcactctt catactgtta caatggcaat gaaatttcaa catgagtttt ggaggagaga  45180
agcattcaaa ccacagcaag ggtgctccta cctcctctct cagggcatct gcagaaagag  45240
ctgcaactgc acgtccttcc tccgtccatc ctccatccct tcccaatgtc cgtgcatatc  45300
ctgtgaccca ggaggtctgg catagggggt gctcctgcct taggtctgag gccctgtctg  45360
aagaggggta ggtgaggagg ccatctgatg gtctgggcca agacagtcac aggacgcatc  45420
atttatcatc aaggaggctg agggttgagt ctccaggtcc agggaactcc ccacaaagtg  45480
ggaaccctgc ccagctccac acagcctctg ctgggggacc ctgctctggt gcagagcctg  45540
gggacaggtc ttgagctcag ccagagtctg cctccctgtc atttaggaac taaaccaagc  45600
ggcaggatgc tggagcccag cccccatctg accttacagg gccaaggctg gggccctggg  45660
ttcccctcaa ggcacagcag gactggagcc ccaggcagtg caggagtggc caaagctggg  45720
gcttcctcca gagcccccaa gcatcatggc accaagaagg gtaggaccct ggcctgagga  45780
attggcacca aagccccaga aactaccctg gacaccatgg agagaggctt ggaggggaag  45840
caccaggcac tgcctcccct tctgatccca cctgaggtgg ctgccaagcc cagagagccg  45900
ctctgatgtc ccccagccct gcagcccagg gatacctgta ctgtgcccct gggggacccc  45960
tggccagtct gtgcaaagaa gtcaccaccc tacactcaga gacagtgggg gtcctcgtcc  46020
cacatcctca gagcatggcc cggctgctgc agggatggtc tccttgtcct cagagcatgg  46080
cccggctgct gcagggatgg tctccttgtc ctcagagcat ggcccagctg ctgcagggat  46140
ggtctcctgg aggcccccca gtgctctatt gtcagggctc cctccacccc cccgcaccaa  46200
gagagagcca gaccccagca aggcttccag tggcttcagg tcacacccct aggctgaccc  46260
cagccccatt aacacctgcc tgagaaagct ccacgcacca gaactgaccg tctgctccaa  46320
ctcttgacct cccgttctca gggcgtctgc tgaaaaggct gcaactgcac atccttcctc  46380
cgtccgttcc cgatgtccgt gtgtctcctg tggccaggaa ggtctttctc gggacctgag  46440
agccgctccc tgaagtgtcc ccattgggaa ggatggggcc tgtgtctcca ggctctggga  46500
ggacagaatc ctgacctcaa cagtggccgg cacggacaca actggcccca tcccggggac  46560
gctgaccagc gctgggcaac ttttcccttc cccgacgact gagccccgag caccctccct  46620
gctcccctac cacctccctt tacaaggctg tggcctctgc acagatgata atggagcttg  46680
gctcattccc ctagagtcgg tagggagtta aggacaaaac tcagtttcct ccacctgaac  46740
tcaagtctgc ctatgtttac ctaatcacac ctggtggaca gtttggacaa acttgcacac  46800
tcagagacac agacacttct agaaatcatt atctccctgc cccggggacc ccactccagc  46860
agaagtctgc taggcactgg cctgggccct cctgctgtcc taggaggctg ctgacctcct  46920
gcctggctcc tgtccccagg tccagagtca gagcagactc cagggacgct gcaggctagg  46980
aagccgcccc ctccaggcca gggtctagtg caggtgccca ggacaagaaa gattgtgaat  47040
gcaggaatga ctgggccaca cccctcccgt gcacgccccc tcctgccctg caccccacag  47100
cccagccccc cgtgctggat gcccccccac agcagaggtg ctgttctgtg atcccctggg  47160
```

```
aaagacgccc tcaacctcca ccctgtccca cggcccaagg aagacaagac acaggccctc  47220
tcctcacagt ctccccacct ggctcctgct gggaccctca aggtgtgaac agggaggatg  47280
gttgtctggg tggcccctag gagcccagat cttcactcca cagaccccaa cccaagcacc  47340
cccttctgca gggcccagct catccccctc ctcctccctc tgctctcctc tcgtcgcctc  47400
tacgggaaat ccgggactca gcagtaaccc tcaggaagca gggcccaggc gccgtttaat  47460
aggaggcttc ctcacaatga aacttttaga aagccttgac tacaatgatg accttggtgt  47520
ggctgtgaac actgtcagct cccacagctg ctgcagcaaa aaatgtccat agacagggtg  47580
ggggcccggg gtcgtctgct gtcctgctca gcccacagca cgcatggagg atctgaggtg  47640
ccacacctga cgcccaggcc agaacatgcc tccctccagg gtgacctgcc atgtcctgca  47700
ttgctggagg gacaggggca gcctatgagg atctggggcc aggagatgaa tcctattaac  47760
ccagaggaaa actaacagga cccaagcacc ctccccgttg aagctgacct gcccagaggg  47820
gcctgggccc accccacaca ccggggcgga atgtgtacag gccccggtct ctgtgggtgt  47880
tccgctaact ggggctccca gtgctcaccc cacaactaaa gcgagcccca gcctccagag  47940
cccccgaagg agatgccgcc cacaagccca gcccccatcc aggaggcccc agagctcagg  48000
gcgccggggc agattctgaa cagccccgag tcacggtggg tacaactgga acgaccaccg  48060
tgagaaaaac tgtgtccaaa actgtctcct ggcccctgct ggaggccgcg ccagagaggg  48120
gagcagccgc cccgaaccta ggtcctgctc agctcacacg acccccagca cccagagcac  48180
agtggagtcc ccactgaatg gtgaggatgg ggaccagggc tccagggggt catggaaggg  48240
gctggacccc atcctactgc tatggtccca gtgctcctgg ccagaaacga ccctaccacc  48300
gacaagagtc cctcagggaa acgggggtca ctggcacctc ccagcatcaa ccccaggcag  48360
cacaggcata aaccccacat ccagagccga ctccaggagc agagacaccc cagtaccctg  48420
ggggacaccg accctgatga ctccccactg gaatccaccc cagagtccac caggaccaaa  48480
gaccccgccc ctgtctctgt ccctcactca ggacctgctg cggggcgggc catgagacca  48540
gactcgggct tagggaacac cactgtggcc ccaacctcga ccaggccaca ggcccttcct  48600
tcctgccctg cggcagcaca gactttgggg tctgtgcaga gaggaatcac agaggcccca  48660
ggctgaggtg gtgggggtgg aaggccccca ggaggtggcc cacttccctt cctcccagct  48720
ggaacccacc atgaccttct taagataggg gtgtcatccg aggcaggtcc tccatggagc  48780
tcccttcagg ctcctccctg gtcctcacta ggcctcagtc ccggctgtgg gaatgcagcc  48840
accacaggca caccaggcag cccagaccca gccagcctgc agtgcccaag cccacattct  48900
ggagcagagc aggctgtgtc tgggagagtc tgggctcccc accgcccccc cgcacacccc  48960
acccacccct gtccaggccc tatgcaggag ggtcagagcc ccccatgggg tatggactta  49020
gggtctcact cacgcggctc ccctcctggg tgaaggggtc tcatgcccag atccccacag  49080
cagagctggt caaaggtgga ggcagtggcc ccagggccac cctgacctgg accctcaggc  49140
tcctctagcc ctggctgccc tgctgtccct gggaggcctg gactccacca gaccacaggt  49200
ccagggcacc gcccataggt gctgcccaca ctcagttcac aggaagaaga taagctccag  49260
acccccaaga ctgggacctg ccttcctgcc accgcttgta gctccagacc tccgtgcctc  49320
ccccgaccac ttacacacgg gccagggagc tgttccacaa agatcaaccc caaaccggga  49380
ccgcctggca ctcgggccgc tgccacttcc ctctccattt gctcccagca cctctgtgct  49440
ccctccctcc tccctccttc aggggaacag cctgtgcagc ccctccctgc accccacacc  49500
```

-continued

```
ctggggaggc ccaaccctgc ctccagccct ttctcccccg ctgctcttcc tgcccatcca  49560
gacaaccctg gggtcccatc cctgcagcct acaccctggt ctccacccag acccctgtct  49620
ctccctccag atacccctcc caggccaacc ctgcacatgc aggccctccc cttttctgct  49680
gccagagcct cagtttctac cctctgtgcc taccccctgc ctcctcctgc ccacaactcg  49740
agctcttcct ctcctggggc ccctgagcca tggcactgac cgtgcactcc cacccccaca  49800
ctgcccatgc cctcaccttc ctcctggaca ctctgacccc gctcccctct tggacccagc  49860
cctggtattt ccaggacaaa ggctcaccca agtcttcccc atgcaggccc ttgccctcac  49920
tgcccggtta cacggcagcc tcctgtgcac agaagcaggg agctcagccc ttccacaggc  49980
agaaggcact gaaagaaatc ggcctccagc accctgatgc acgtccgcct gtgtctctca  50040
ctgcccgcac ctgcagggag gctcggcact ccctgtaaag acgagggatc caggcagcaa  50100
catcatggga gaatgcaggg ctcccagaca gcccagccct ctcgcaggcc tctcctggga  50160
agagacctgc agccaccact gaacagccac ggagcccgct ggatagtaac tgagtcagtg  50220
accgacctgg agggcagggg agcagtgaac cggagcccag accataggga cagagaccag  50280
ccgctgacat cccgagcccc tcactggcgg ccccagaaca ccgcgtggaa acagaacaga  50340
cccacattcc cacctggaac agggcagaca ctgctgagcc cccagcacca gccctgagaa  50400
acaccaggca acggcatcag agggggctcc tgagaaagaa aggaggggag gtctccttca  50460
ccagcaagta cttcccttga ccaaaaacag ggtccacgca actcccccag gacaaaggag  50520
gagccccctg tacagcactg ggctcagagt cctctccaac acaccctgag tttcagacaa  50580
aaaccccctg gaaatcatag tatcagcagg agaactagcc agagacagca agaggggact  50640
cagtgactcc cgcggggaca ggaggatttt gtgggggctc gtgtcactgt gaggatattg  50700
tagtagtacc agctgctatg cccacagtga cacagcccca ttcccaaagc cctgctgtaa  50760
acgcttccac ttctggagct gaggggctgg ggggagcgtc tgggaagtag ggcctagggg  50820
tggccatcaa tgcccaaaac gcaccagact cccccccaga catcacccca ctggccagtg  50880
agcagagtaa acagaaaatg agaagcagct gggaagcttg cacaggcccc aaggaaagag  50940
ctttggcggg tgtgcaagag gggatgcggg cagagcctga gcagggcctt ttgctgtttc  51000
tgctttcctg tgcagatagt tccataaact ggtgttcaag atcgatggct gggagtgagc  51060
ccaggaggac agtgtgggaa gggcacaggg aaggagaagc agccgctatc ctacactgtc  51120
atctttcaag agtttgccct gtgcccacaa tgctgcatca tgggatgctt aacagctgat  51180
gtagacacag ctaaagagag aatcagtgaa atggatttgc agcacagatc tgaataaatt  51240
ctccagaatg tggagccaca cagaagcaag cacaaggaaa gtgcctgatg caagggcaaa  51300
gtacagtgtg taccttcagg ctgggcacag acactctgaa aagccttggc aggaactccc  51360
tgcaacaaag cagagccctg caggcaatgc cagctccaga gccctccctg agagcctcat  51420
gggcaaagat gtgcagaaca tatgtttgtc atagccccaa actgagaatg aagcaaacag  51480
ccatctgaag gaaaacaggc aaataaacga tggcaggttc atgaaatgca aacccagaca  51540
gccagaagga caacagtgag ggttacaggt gactctgtgg ttgagttcat gacaatgctg  51600
agtaattgga gtaacaaagg aaagtccaaa aaatactttc aatgtgattt cttctaaata  51660
aaatttacag ccggcaaaat gaactatctt cttaagggat aaactttcca ctaggaaaac  51720
tataaggaaa atcaagaaaa ggatgatcac ataaacacag tggtcgttac ttctactggg  51780
gaaggaagag ggtatgaact gagacacaca gggttggcaa gtctcctaac aagaagagaa  51840
caaatacatt acagtacctt gaaaacagca gttaaaattc taaattgcaa gaagaggaaa  51900
```

atgcacacag ctgtgtttag aaaattctca gtccagcact gttcataata gcaaagacat 51960
taacccaggt tggataaata aacgatgaca caggcaattg cacaatgata cagacataca 52020
ttcagtatat gagacattga tgatgtatcc ccaaagaaat gactttaaag agaaaaggcc 52080
tgatatgtgg tggcactcac ctccctgggc atccccggac aggctgcagg cacactgtgt 52140
ggcagggcag gctggtacct gctggcagct cctggggcct gatgtggagc aggcacagag 52200
ccgtatcccc ccgaggacat atacccccaa ggacggcaca gttggtacat tccggagaca 52260
agcaactcag ccacactccc aggccagagc ccgagaggga cgcccatgca cagggaggca 52320
gagcccagct cctccacagc cagcagcacc tgtgcagggg ccgccatctg gcaggcacag 52380
agcatgggct gggaggaggg gcagggacac caggcagggt tggcaccaac tgaaaattac 52440
agaagtctca tacatctacc tcagccttgc ctgacctggg cctcacctga cctggacctc 52500
acctggcctg gacctcacct ggcctagacc tcacctctgg gcttcacctg agctcggcct 52560
cacctgactt ggaccttgcc tgtcctgagc tcacatgatc tgggcctcac ctgacctggg 52620
tttcacctga cctgggcttc acctgacctg ggcctcatct gacctgggcc tcactggcct 52680
ggacctcacc tggcctgggc ttcacctggc ctcaggcctc atctgcacct gctccaggtc 52740
ttgctggaac ctcagtagca ctgaggctgc aggggctcat ccagggttgc agaatgactc 52800
tagaacctcc cacatctcag ctttctgggt ggaggcacct ggtggcccag ggaatataaa 52860
aagcctgaat gatgcctgcg tgatttgggg gcaatttata aacccaaaag gacatggcca 52920
tgcagcgggt agggacaata cagacagata tcagcctgaa atggagcctc agggcacagg 52980
tgggcacgga cactgtccac ctaagccagg ggcagacccg agtgtccccg cagtagacct 53040
gagagcgctg ggcccacagc ctcccctcgg tgccctgcta cctcctcagg tcagccctgg 53100
acatcccggg tttccccagg cctggcggta ggtttggggt gaggtctgtg tcactgtggt 53160
attacgattt ttggagtggt tattataccc acagtgtcac agagtccatc aaaaacccat 53220
ccctgggaac ctgctgccac agccctccct gtggggcacc gccgcgtgcc atgttaggat 53280
tttgactgag gacacagcac catgggtatg gtggctaccg cagcagtgca gcctgtgacc 53340
caaacacaca gggcagcagg cacaacagac aagcccacaa gtgaccaccc tgagctcctg 53400
cctgccagcc ctggagacca tgaaacagat ggccaggatt atcccatagg tcagccagac 53460
ctcagtccaa caggtctgca tcgctgctgc cctccaatac cagtccggat ggggacaggg 53520
ccggcccaca ttaccatttg ctgccatccg gccaacagtc ccagaagccc ctccctcaag 53580
gctgggccac atgtgtggac cctgagagcc ccccatgtct gagtaggggc accaggaagg 53640
tggggctggc cctgtgcact gtcactgccc ctgtggtccc tggcctgcct ggccctgaca 53700
cctgggcctc tcctgggtca tttccaagac agaagacatt cccaggacag ctggagctgg 53760
gagtccatca tcctgcctgg ccatcctgag tcctgcgcct ttccaaacct cacccgggaa 53820
gccaacagag gaatcacctc ccacaggcag agacaaagac cttccagaaa tctctgtctc 53880
tctccccagt gggcaccctc ttccagggca gtcctcagtg atatcacagt gggaacccac 53940
atctggatcg ggactgcccc cagaacacaa gatggcccac agggacagcc ccacagccca 54000
gcccttccca gacccctaaa aggcgtccca ccccctgcat ctgccccagg gctcaaactc 54060
caggaggact gactcctgca caccctcctg ccagacatca cctcagcccc tcctggaagg 54120
gacaggagcg cgcaagggtg agtcagaccc tcctgccctc gatggcaggc ggagaagatt 54180
cagaaaggtc tgagatcccc aggacgcagc accactgtca atgggggccc cagacgcctg 54240

-continued gaccagggcc tgcgtgggaa aggcctctgg gcacactcag gggctttttg tgaagggtcc 54300
tcctactgtg tgactacagt aactaccaca gtgatgaacc cagcagcaaa aactgaccgg 54360
actcccaagg tttatgcaca cttctccgct cagagctctc caggatcaga agagccgggc 54420
ccaagggttt ctgcccagac cctcggcctc tagggacatc ttggccatga cagcccatgg 54480
gctggtgccc cacacatcgt ctgccttcaa acaagggctt cagagggctc tgaggtgacc 54540
tcactgatga ccacaggtgc cctggcccct tccccgccag ctgcaccaga ccccgtcctg 54600
acagatgccc cgattccaac agccaattcc tggggccagg aatcgctgta gacaccagcc 54660
tccttccaac acctcttgcc aattgcctgg attcccatcc cggttggaat caagaggaca 54720
gcatccccca ggctcccaac aggcaggact cccacaccct cctctgagag gccgctgtgt 54780
tccgtagggc caggctgcag acagtccccc tcacctgcca ctagacaaat gcctgctgta 54840
gatgtcccca cctggaaaag accactcatg gagcccccag ccccaggtac agccatagag 54900
agagtctctg aggcccctaa gaagtagcca tgcccagttc tgccgggacc ctcggccagg 54960
ctgacaggag tggacgctgg agctgggccc acactgggcc acataggagc tcaccagtga 55020
gggcaggaga gcacatgccg gggagcaccc agcctcctgc tgaccagagg cccgtcccag 55080
agcccaggag gctgcagagg cctctccagg gggacactgt gcatgtctgg tccctgagca 55140
gcccccccatg tccccagtcc tgggggcccc tggcacagct gtctggaccc tctctattcc 55200
ctgggaagct cctcctgaca gccccgcctc cagttccagg tgtggttatt gtcagggggt 55260
gtcagactgt ggtggataca gctatggtta ccacagtggt gctgcccata gcagcaacca 55320
ggccaagtag acaggcccct gctgtgcagc cccaggcctc cagctcacct gcttctcctg 55380
gggctctcaa ggctgctgtt ttctgcactc tcccctctgt ggggagggtt ccctcagtgg 55440
gagatctgtt ctcaacatcc cagggcctca ttcctgcaag gaaggccaat ggatgggcaa 55500
cctcacatgc cgcggctaag atagggtggg cagcctggcg gggacaggac atcctgctgg 55560
ggtatctgtc actgtgccta gtggggcact ggctcccaaa caacgcagtc ctcgccaaaa 55620
tccccacggc ctccccccgct aggggctggc ctgatctcct gcagtcctag gaggctgctg 55680
acctccagaa tggctccgtc cccagttcca gggcgagagc agatcccagg ccggctgcag 55740
actgggaggc cacccctcc ttcccagggt tcactgcagg tgaccagggc aggaaatggc 55800
ctgaacacag ggataaccgg gccatccccc aacagagtcc acccccctcct gctctgtacc 55860
ccgcaccccc aaggccagcc catgacatcc gacaacccca caccagagtc actgcccggt 55920
gctgccctag ggaggacccc tcagccccca ccctgtctag aggactgggg aggacaggac 55980
acgccctctc cttatggttc ccccacctgg ctctggctgg gacccttggg gtgtggacag 56040
aaaggacgct tgcctgattg gcccccagga gcccagaact tctctccagg gaccccagcc 56100
cgagcacccc cttacccagg acccagccct gcccctcctc ccatctgctc tcctctcatc 56160
accccatggg aatccagaat ccccaggaag ccatcaggaa gggctgaggg aggaagtggg 56220
gccactgcac caccaggcag gaggctccgt ctttgtgaac ccagggaggt gccagcctcc 56280
tagagggtat ggtccaccct gcctatggct cccacagtgg caggctgcag ggaaggacca 56340
gggacggtgt gggggagggc tcagggcccc gcgggtgctc catcttggat gagcccatct 56400
ctctcaccca cggactcacc cacctcctct ccaccctggc cacacgtcgt ccacaccatc 56460
ctaagtccca cctacaccag agccggcaca gccagtgcag acagaggctg gggtgcaggg 56520
gggccgccag ggcagctttg gggagggaag gatggaggaa ggggagttca gtgaagaggc 56580
ccccctcccc tgggtccagg atcctcctct gggacccccg gatcccatcc cctccaggct 56640
ctgggaggag aagcaggatg ggagaatctg tgcgggaccc tctcacagtg gaatacctcc 56700
acagcggctc aggcaagacc caaaagcccc tcagtgagcc ctccactgca gtcctgggcc 56760
tgggtagcag cccctcccac agaggatgaa cccagcaccc cgaggatgtc ctgccagggg 56820
gagctcagag ccatgaagga gcaggatatg ggacccccga tacaggcaca gacctcagct 56880
ccattcagga ctgccacgtc ctgccctggg aggaacccct ttctctagtc cctgcaggcc 56940
aggaggcagc tgactcctga cttggacgcc tattccagac accagacaga ggggcaggcc 57000
ccccagaacc agggatgagg acgccccgtc aaggccagaa aagaccaagt tgtgctgagc 57060
ccagcaaggg aaggtcccca aacaaaccag gaagtttctg aaggtgtctg tgtcacagtg 57120
gagtatagca gctcgtccca cagtgacact cgccaggcca gaaaccccat cccaagtcag 57180
cggaatgcag agagagcagg gaggacatgt ttaggatctg aggccgcacc tgacacccag 57240
gccagcagac gtctcctgtc catggcaccc tgccatgtcc tgcatttctg gaagaacaag 57300
ggcaggctga agggggtcca ggaccaggag atgggtcccc tctacccaga gaaggagcca 57360
ggcaggacac aagcccccctc cccattgagg ctgacctgcc cagagggtcc tgggcccacc 57420
ccacacaccg gggcggaatg tgtgcaggcc tcggtctctg tgggtgttcc gctagctggg 57480
gctcacagtg ctcaccccac acctaaaacg agccacagcc tcagagcccc tgaaggagac 57540
cccgcccaca agcccagccc ccacccagga ggccccagag cacagggcgc cccgtcggat 57600
tctgaacagc cccgagtcac agtgggtata actggaacta ccactgtgag aaaagcttcg 57660
tccaaaacgg tctcctggcc acagtcggag gccccgccag agaggggagc agccacccca 57720
aacccatgtt ctgccggctc ccatgacccc gtgcacctgg agccccacag tgtccccact 57780
ggatgggagg acaagggccg ggggctccgg cgggtcgggg caggggcttg atggcttcct 57840
tctgccgtgg ctccagtgcc cctggctgga gttgaccctt ctgacaagtg tcctcagaga 57900
gtcagggatc agtggcacct ccctaacatc aaccccacgc agcgcaggca caaaccccac 57960
atccagggcc aactccagga acagagacac cccaataccc tgggggaccc caaccctgat 58020
gactcccgtc ccatctctgt ccctcacttg gggcctgctg cggggcgagc acctgggagc 58080
aaactcagga ttaggggaca ccactgtggg cctgacctcg agcaggccac agacccttcc 58140
ctcctgccct ggtgcagcac agactttggg gtctgggcag ggaggaactt ctggcaggtc 58200
accaagcaca gagcccccag gctgaggtgg ccccaggggg aaccccagca ggtggcccac 58260
taccccttcct cccagctgga ccccatgtct tccccaagat aggggtgcca tccaaggcag 58320
gtcctccatg gagcccccctt caggctcctc tccagaccc actgggcctc agtccccact 58380
ctaggaatgc agccaccacg ggcacaccag gcagcccagg cccagccacc ctgcagtgcc 58440
caagcccaca ccctggagga gagcagggtg cgtctgggag gggctgggct ccccaccccc 58500
acccccacct gcacacccca cccacccttg cccgggcccc ctgcaggagg gtcagagccc 58560
ccatgggata tggacttagg gtctcactca cgcacctccc ctcctgggag aaggggtctc 58620
atgcccagat ccccccagca gcgctggtca caggtagagg cagtggcccc agggccaccc 58680
tgacctggcc cctcaggctc ctctagccct ggctgccctg ctgtccctgg gaggcctggg 58740
ctccaccaga ccacaggtct agggcaccgc ccacactggg gccgcccaca cacagctcac 58800
aggaagaaga taagctccag acccccaggc ccgggacctg ccttgctgct acgacttcct 58860
gccccagacc tcgttgccct cccccgtcca cttacacaca ggccaggaag ctgttcccac 58920
acagaccaac cccagacggg gaccacctgg cactcaggtc actgccattt ccttctccat 58980

-continued

```
tcacttccaa tgcctctgtg cttcctccct cctccttcct tcgggggagc accctgtgca  59040
gctcctccct gcagtccaca ccctggggag acccgaccct gcagcccaca ccctggggag  59100
acctgaccct cctccagccc tttctccccc gctgctcttg ccacccacca agacagccct  59160
ggggtcctgt ccctacagcc cccacccagt tctctaccta gacccgtctt cctccctcta  59220
aacacctctc ccaggccaac cctacacctg caggccctcc cctccactgc caaagaccct  59280
cagtttctcc tgcctgtgcc cacccccgtg ctcctcctgc ccacagctcg agctcttcct  59340
ctcctagggc ccctgaggga tggcattgac cgtgccctcg cacccacaca ctgcccatgc  59400
cctcacattc ctcctggcca ctccagcccc actcccctct caggcctggc tctggtattt  59460
ctgggacaaa gccttaccca agtctttccc atgcaggcct gggcccttac cctcactgcc  59520
cggttacagg gcagcctcct gtgcacagaa gcagggagct cagcccttcc acaggcagaa  59580
ggcactgaaa gaaatcggcc tccagcgcct tgacacacgt ctgcctgtgt ctctcactgc  59640
ccgcacctgc agggaggctc ggcactccct ctaaagacga gggatccagg cagcagcatc  59700
acaggagaat gcagggctac cagacatccc agtcctctca caggcctctc ctgggaagag  59760
acctgaagac gcccagtcaa cggagtctaa caccaaacct ccctggaggc cgatgggtag  59820
taacggagtc attgccagac ctggaggcag gggagcagtg agcccgagcc cacaccatag  59880
ggccagagga cagccactga catcccaagc cactcactgg tggtcccaca acaccccatg  59940
gaaagaggac agacccacag tcccacctgg accagggcag agactgctga gacccagcac  60000
cagaaccaac caagaaacac caggcaacag catcagaggg ggctctggca gaacagagga  60060
ggggaggtct ccttcaccag caggcgcttc ccttgaccga agacaggatc catgcaactc  60120
ccccaggaca aaggaggagc cccttgttca gcactgggct cagagtcctc tccaagacac  60180
ccagagtttc agacaaaaac cccctggaat gcacagtctc agcaggagag ccagccagag  60240
ccagcaagat ggggctcagt gacacccgca gggacaggag gattttgtgg gggctcgtgt  60300
cactgtgagg atattgtact aatggtgtat gctataccca cagtgacaca gccccattcc  60360
caaagcccta ctgcaaacgc attccacttc tggggctgag gggctggggg agcgtctggg  60420
aaatagggct caggggtgtc catcaatgcc caaaacgcac cagactcccc tccatacatc  60480
acacccacca gccagcgagc agagtaaaca gaaaatgaga agcaagctgg ggaagcttgc  60540
acaggcccca aggaaagagc tttggcgggt gtgtaagagg ggatgcgggc agagcctgag  60600
cagggccttt tgctgtttct gctttcctgt gcagagagtt ccataaactg gtgttcgaga  60660
tcaatggctg ggagtgagcc caggaggaca gcgtgggaag agcacaggga aggaggacca  60720
gccgctatcc tacactgtca tctttcgaaa gtttgccttg tgcccacact gctgcatcat  60780
gggatgctta acagctgatg tagacacagc taaagagaga atcagtgaga tggatttgca  60840
gcacagatct gaataaattc tccagaatgt ggagcagcac agaagcaagc acacagaaag  60900
tgcctgatgc aaggacaaag ttcagtgggc accttcaggc attgctgctg ggcacagaca  60960
ctctgaaaag ccctggcagg aactccctgt gacaaagcag aaccctcagg caatgccagc  61020
cccagagccc tccctgagag cctcatgggc aaagatgtgc acaacaggtg tttctcatag  61080
ccccaaactg agagcaaagc aaacgtccat ctgaaggaga acaggcaaat aaacgatggc  61140
aggttcatga aatgcaaacc cagacagcca caagcacaaa agtacagggt tataagcgac  61200
tctggttgag ttcatgacaa tgctgagtaa ttggagtaac aaagtaaact ccaaaaaata  61260
ctttcaatgt gatttcttct aaataaaatt tacaccctgc aaaatgaact gtcttcttaa  61320
gggatacatt tcccagttag aaaaccataa agaaaaccaa gaaaaggatg atcacataaa  61380
```

cacagtggtg gttacttctg ctggggaagg aagagggtat gaactgagat acacagggtg 61440
ggcaagtctc ctaacaagaa cagaacgaat acattacagt accttgaaaa cagcagttaa 61500
acttctaaat tgcaagaaga ggaaaatgca cacagttgtg tttagaaaat tctcagtcca 61560
gcactgttca taatagcaaa gacattaacc caggtcggat aaataagcga tgacacaggc 61620
aattgcacaa tgatacagac atatatttag tatatgagac atcgatgatg tatccccaaa 61680
taaacgactt taaagagata aagggctgat gtgtggtggc attcacctcc ctgggatccc 61740
cggacaggtt gcaggctcac tgtgcagcag ggcaggcggg tacctgctgg cagttcctgg 61800
ggcctgatgt ggagcaagcg cagggccata tatcccggag gacggcacag tcagtgaatt 61860
ccagagagaa gcaactcagc cacactcccc aggcagagcc cgagagggac gcccacgcac 61920
agggaggcag agcccagcac ctccgcagcc agcaccacct gtgcacgggc caccaccttg 61980
caggcacaga gtgggtgctg agaggagggg cagggacacc aggcagggtg agcacccaga 62040
gaaaactgca gacgcctcac acatccacct cagcctcccc tgacctggac ctcactggcc 62100
tgggcctcac ttaacctggg cttcacctga ccttggcctc acctgacttg gacctcgcct 62160
gtcccaagct ttacctgacc tggcctcaa ctcacctgaa cgtctcctga cctgggttta 62220
acctgtcctg gaactcacct ggccttggct tcccctgacc tggacctcat ctggcctggg 62280
cttcacctgg cctgggcctc acctgacctg gacctcatct ggcctggacc tcacctggcc 62340
tggacttcac ctggcctggg cttcacctga cctggacctc acctggcctc aggcctcacc 62400
tgcacctgct ccaggtcttg ctggagcctg agtagcactg agggtgcaga agctcatcca 62460
gggttgggga atgactctag aagtctccca catctgacct ttctgggtgg aggcagctgg 62520
tggccctggg aatataaaaa tctccagaat gatgactctg tgatttgtgg gcaacttatg 62580
aacccgaaag gacatggcca tggggtgggt agggacatag ggacagatgc cagcctgagg 62640
tggagcctca ggacacaggt gggcacggac actatccaca taagcgaggg atagacccga 62700
gtgtccccac agcagacctg agagcgctgg gcccacagcc tcccctcaga gccctgctgc 62760
ctcctccggt cagccctgga catcccaggt ttccccaggc ctggcggtag gtttagaatg 62820
aggtctgtgt cactgtggta ttacgatatt ttgactggtt attataacca cagtgtcaca 62880
gagtccatca aaaacccatg cctggaagct tcccgccaca gccctcccca tggggccctg 62940
ctgcctcctc aggtcagccc cggacatcct gggtttcccc aggctgggcg gtaggtttgg 63000
ggtgaggtct gtgtcactgt ggtattacta tggttcgggg agttattata accacagtgt 63060
cacagagtcc atcaaaaacc catccctggg agcctcccgc cacagccctc cctgcagggg 63120
accggtacgt gccatgttag gattttgatc gaggagacag caccatgggt atggtggcta 63180
ccacagcagt gcagcctgtg acccaaaccc gcagggcagc aggcacgatg gacaggcccg 63240
tgactgacca cgctgggctc cagcctgcca gccctggaga tcatgaaaca gatggccaag 63300
gtcaccctac aggtcatcca gatctggctc cgaggggtct gcatcgctgc tgccctccca 63360
acgccagtcc aaatgggaca gggacggcct cacagcacca tctgctgcca tcaggccagc 63420
gatcccagaa gcccctccct caaggctggc cacatgtgtg gacactgaga gccctcatat 63480
ctgagtaggg gcaccaggag ggaggggctg gccctgtgca ctgtccctgc tcctgtggtc 63540
tctggcctgc ctggccctga cacctgagcc tctcctgggt catttccaag acagaagaca 63600
ttcctgggga cagccggagc tgggcgtcgc tcatcctgcc cggccgtcct gagtcctgct 63660
catttccaga cctcaccggg gaagccaaca gaggactcgc ctcccacatt cagagacaaa 63720
gaaccttcca gaaatccctg cctctctccc cagtggacac cctcttccag gacagtcctc 63780
agtggcatca cagcggcctg agatccccag gacgcagcac cgctgtcaat aggggcccca 63840
aatgcctgga ccagggcctg cgtgggaaag gcctctggcc acactcgggc tttttgtgaa 63900
gggccctcct gctgtgtgac tacagtaact accatagtga tgaacccagt ggcaaaaact 63960
ggctggaaac ccaggggctg tgtgcacgcc tcagcttgga gctctccagg agcacaagag 64020
ccgggcccaa ggatttgtgc ccagaccctc agcctctagg gacacctggg ccatctcagc 64080
ctgggctggt gccctgcaca ccatcttcct ccaaataggg gcttcagagg gctctgaggt 64140
gacctcactc atgaccacag gtgacctggc ccttccctgc cagctatacc agaccctgtc 64200
ttgacagatg ccccgattcc aacagccaat tcctgggacc ctgaatagct gtagacacca 64260
gcctcattcc agtacctcct gccaattgcc tggattccca tcctggctgg aatcaagaag 64320
gcagcatccg ccaggctccc aacaggcagg actcccgcac accctcctct gagaggccgc 64380
tgtgttccgc agggccaggc cctggacagt tcccctcacc tgccactaga gaaacacctg 64440
ccattgtcgt ccccacctgg aaaagaccac tcgtggagcc cccagcccca ggtacagctg 64500
tagagacagt cctcgaggcc cctaagaagg agccatgccc agttctgccg ggaccctcgg 64560
ccaggccgac aggagtggac gctggagctg ggcccacact gggccacata ggagctcacc 64620
agtgagggca ggagagcaca tgccggggag cacccagcct cctgctgacc agaggcctgc 64680
cccagagccc aggaggctgc agaggcctct ccagggagac actgtgcatg tctggtacct 64740
aagcagcccc ccacgtcccc agtcctgggg gcccctggct cagctgtctg ggccctccct 64800
gctccctggg aagctcctcc tgacagcccc gcctccagtt ccaggtgtgg ttattgtcag 64860
gcgatgtcag actgtggtgg atatagtggc tacgattacc acagtggtgc cgcccatagc 64920
agcaaccagg ccaagtagac aggcccctgc tgcgcagccc caggcatcca cttcacctgc 64980
ttctcctggg gctctcaagg ctgctgtctg tcctctggcc ctctgtgggg agggttccct 65040
cagtgggagg tctgtgctcc agggcaggga tgattgagat agaaatcaaa ggctggcagg 65100
gaaaggcagc ttcccgccct gagaggtgca ggcagcacca cggagccacg gagtcacaga 65160
gccacggagc ccccattgtg ggcatttgag agtgctgtgc ccccggcagg cccagccctg 65220
atggggaagc ctgtcccatc ccacagcccg ggtcccacgg gcagcgggca cagaagctgc 65280
caggttgtcc tctatgatcc tcatccctcc agcagcatcc cctccacagt ggggaaactg 65340
aggcttggag caccacccgg ccccctggaa atgaggctgt gagcccagac agtgggccca 65400
gagcactgtg agtaccccgg cagtacctgg ctgcagggat cagccagaga tgccaaaccc 65460
tgagtgacca gcctacagga ggatccggcc ccacccaggc cactcgatta atgctcaacc 65520
ccctgccctg gagacctctt ccagtaccac cagcagctca gcttctcagg gcctcatccc 65580
tgcaaggaag gtcaagggct gggcctgcca gaaacacagc accctcccta gccctggcta 65640
agacagggtg ggcagacggc tgtggacggg acatattgct ggggcatttc tcactgtcac 65700
ttctgggtgg tagctctgac aaaaacgcag accctgccaa aatccccact gcctcccgct 65760
aggggctggc ctggaatcct gctgtcctag gaggctgctg acctccagga tggctccgtc 65820
cccagttcca gggcgagagc agatcccagg caggctgtag gctgggaggc cacccctgcc 65880
cttgccgggg ttgaatgcag gtgcccaagg caggaaatgg catgagcaca gggatgaccg 65940
ggacatgccc caccagagtg cgccccttcc tgctctgcac cctgcacccc ccaggccagc 66000
ccacgacgtc caacaactgg gcctgggtgg cagccccacc cagacaggac agacccagca 66060
ccctgaggag gtcctgccag ggggagctaa gagccatgaa ggagcaagat atggggcccc 66120

```
cgatacaggc acagatgtca gctccatcca ggaccaccca gcccacaccc tgagaggaac  66180
gtctgtctcc agcctctgca ggtcgggagg cagctgaccc ctgacttgga cccctattcc  66240
agacaccaga cagaggcgca ggccccccag aaccagggtt gagggacgcc ccgtcaaagc  66300
cagacaaaac caaggggtgt tgagcccagc aagggaaggc ccccaaacag accaggaggt  66360
ttctgaaggt gtctgtgtca cagtggggta tagcagcagc tggtaccaca gtgacactca  66420
cccagccaga aaccccattc caagtcagcg gaagcagaga gagcagggag gacacgttta  66480
ggatctgaga ctgcacctga cacccaggcc agcagacgtc tcccctccag ggcaccccac  66540
cctgtcctgc atttctgcaa gatcaggggc ggcctgaggg gggtctagg gtgaggagat  66600
gggtcccctg tacaccaagg aggagttagg caggtcccga gcactctccc cattgaggct  66660
gacctgccca gagagtcctg ggcccacccc acacaccggg gcggaatgtg tgcaggcctc  66720
ggtctctgtg ggtgttccgc tagctggggc tcacagtgct caccccacac ctaaaatgag  66780
ccacagcctc cggagccccc gcaggagacc ccgcccacaa gcccagcccc cacccaggag  66840
gccccagagc tcagggcgcc ccgtcggatt ccgaacagcc ccgagtcaca gcgggtataa  66900
ccggaaccac cactgtcaga atagctacgt caaaaactgt ccagtggcca ctgccggagg  66960
ccccgccaga gagggcagca gccactctga tcccatgtcc tgccggctcc catgaccccc  67020
agcacgcgga gccccacagt gtccccactg gatgggagga caagagctgg ggattccggc  67080
gggtcggggc aggggcttga tcgcatcctt ctgccgtggc tccagtgccc ctggctggag  67140
ttgacccttc tgacaagtgt cctcagagag acaggcatca ccggcgcctc ccaacatcaa  67200
ccccaggcag cacaggcaca aaccccacat ccagagccaa ctccaggagc agagacaccc  67260
caataccctg gggggacccg accctgatga cttcccactg gaattcgccg tagagtccac  67320
caggaccaaa gaccctgcct ctgcctctgt ccctcactca ggacctgctg ccgggcgagg  67380
ccttgggagc agacttgggc ttaggggaca ccagtgtgac cccgaccttg accaggacgc  67440
agacctttcc ttcctttcct ggggcagcac agactttggg gtctgggcca ggaggaactt  67500
ctggcaggtc gccaagcaca gaggccacag gctgaggtgg ccctggaaag acctccagga  67560
ggtggccact ccccttcctc ccagctggac cccatgtcct ccccaagata agggtgccat  67620
ccaaggcagg tgctccttgg agccccattc agactcctcc ctggacccca ctgggcctca  67680
gtcccagctc tggggatgaa gccaccacaa gcacaccagg cagcccaggc ccagccaccc  67740
tgcagtgccc aagcacacac tctggagcag agcagggtgc ctctgggagg ggctgagctc  67800
cccaccccac ccccacctgc acaccccacc cacccctgcc cagcggctct gcaggagggt  67860
cagagcccca catggggtat ggacttaggg tctcactcac gtggctccca tcatgagtga  67920
aggggcctca agcccaggtt cccacagcag cgcctgtcgc aagtggaggc agaggcccga  67980
gggccaccct gacctggtcc ctgaggttcc tgcagcccag gctgccctgc tgtccctggg  68040
aggcctgggc tccaccagac cacaggtcca gggcaccggg tgcaggagcc acccacacac  68100
agctcacagg aagaagataa gctccagacc cccagggcca gaacctgcct tcctgctact  68160
gcttcctgcc ccagacctgg gcgccctccc ccgtccactt acacacaggc caggaagctg  68220
ttcccacaca gaacaacccc aaaccaggac cgcctggcac tcaggtggct gccatttcct  68280
tctccatttg ctcccagcgc ctctgtcctc cctggttcct ccttcggggg aacagcctgt  68340
gcagccagtc cctgcagccc acaccctggg gagacccaac cctgcctggg gcccttccaa  68400
ccctgctgct cttactgccc acccagaaaa ctctggggtc ctgtccctgc agtccctacc  68460
```

-continued

```
ctggtctcca cccagacccc tgtgtatcac tccagacacc cctcccaggc aaaccctgca  68520
cctgcaggcc ctgtcctctt ctgtcgctag agcctcagtt tctcccccct gtgcccacac  68580
cctacctcct cctgcccaca actctaactc ttcttctcct ggagcccctg agccatggca  68640
ttgaccctgc cctcccacca cccacagccc atgccctcac cttcctcctg gccactccga  68700
ccccgccccc tctcaggcca agccctggta tttccaggac aaaggctcac ccaagtcttt  68760
cccaggcagg cctgggctct tgccctcact tcccggttac acgggagcct cctgtgcaca  68820
gaagcaggga gctcagccct tccacaggca gaaggcactg aaagaaatcg gcctccagca  68880
ccttgacaca cgtccgcccg tgtctctcac tgcccgcacc tgcagggagg ctccgcactc  68940
cctctaaaga caagggatcc aggcagcagc atcacgggag aatgcagggc tcccagacat  69000
cccagtcctc tcacaggcct ctcctgggaa gagacctgca gccaccacca aacagccaca  69060
gaggctgctg gatagtaact gagtcaatga ccgacctgga gggcagggga gcagtgagcc  69120
ggagcccata ccatagggac agagaccagc cgctgacatc ccgagctcct caatggtggc  69180
cccataacac acctaggaaa cataacacac ccacagcccc acctggaaca gggcagagac  69240
tgctgagccc ccagcaccag ccccaagaaa caccaggcaa cagtatcaga gggggctccc  69300
gagaaagaga ggaggggaga tctccttcac catcaaatgc ttcccttgac caaaaacagg  69360
gtccacgcaa ctcccccagg acaaaggagg agccccctat acagcactgg gctcagagtc  69420
ctctctgaga caccctgagt ttcagacaac aacccgctgg aatgcacagt ctcagcagga  69480
gaacagacca aagccagcaa aagggacctc ggtgacacca gtagggacag gaggattttg  69540
tgggggctcg tgtcactgtg aggatattgt agtggtggta gctgctactc ccacagtgac  69600
acagacccat tcccaaagcc ctactgcaaa cacacccact cctggggctg aggggctggg  69660
ggagcatctg ggaagtaggg tccaggggtg tctatcaatg tccaaaatgc accagactcc  69720
ccgccaaaca ccaccccacc agccagcgag cagggtaaac agaaaatgag aggctctggg  69780
aagcttgcac aggccccaag gaaagagctt tggcaggtgt gcaagagggg atgcaggcag  69840
agcctgagca gggccttttg ctgtttctgc tttcctgtgc agagagttcc ataaactggt  69900
gttcaagatc agtggctggg aatgagccca ggagggcagt ctgtgggaag agcacaggga  69960
aggaggacca gccgctatcc tacactgtca tctttcaaaa gtttgccttg tgaccacact  70020
attgcatcat gggatgctta agagctgatg tagacacagc taaagagaga atcagtgaga  70080
tgaatttgca gcatagatct gaataaactc tccagaatgt ggagcagtac agaagcaaac  70140
acacagaaag tgcctgatgc aaggacaaag ttcagtgggc accttcaggc attgctgctg  70200
ggcacagaca ctctgaaaag ccctggcagg atctccctgc gacaaagcag aaccctcagg  70260
caatgccagc cccagagccc tccctgagag cgtcatgggg aaagatgtgc agaacagctg  70320
attatcatag actcaaactg agaacagagc aaacgtccat ctgaagaaca gtcaaataag  70380
caatggtagg ttcatgcaat gcaaacccag acagccaggg gacaacagta gagggctaca  70440
ggcggctttg cggttgagtt catgacaatg ctgagtaatt ggagtaacag aggaaagccc  70500
aaaaaatact tttaatgtga tttcttctaa ataaaattta caccaggcaa aatgaactgt  70560
cttcttaagg gataaacttt cccctggaaa aactacaagg aaaattaaga aaacgatgat  70620
cacataaaca cagttgtggt tacttctact ggggaaggaa gagggtatga gctgagacac  70680
acagagtcgg caagtctcca agcaagcaca gaacgaatac attacagtac cttgaataca  70740
gcagttaaac ttctaaatcg caagaagagg aaaatgcaca cagctgtgtt tagaaaattc  70800
tcagtccagc actattcata atagcaaaga cattaaccca ggttggataa ataaatgatg  70860
```

-continued acacaggcaa ttgcacaatg atacagacat acatttagta catgagacat cgatgatgta 70920
tccccaaaga aatgacttta aagagaaaag gcctgatgtg tggtggcact cacctccctg 70980
ggatccccgg acaggttgca ggcacactgt gtggcagggc aggctggtac atgctggcag 71040
ctcctggggc ctgatgtgga gcaagcgcag ggctgtatac cccaaggat ggcacagtca 71100
gtgaattcca aagagaagca gctcagccac actgcccagg cagagcccga gagggacgcc 71160
cacgcacagg gaggcagagc ccagctcctc cacagccacc accacctgtg cacgggccac 71220
caccttgcag gcacagagtg ggtgctgaga ggaggggcag ggacaccagg cagggtgagc 71280
acccagagaa aactgcagaa gcctcacaca tccacctcag cctcccctga cctggacctc 71340
acctggtctg gacctcacct ggcctgggcc tcacctgacc tggacctcac ctggcctggg 71400
cttcacctga cctggacctc acctggcctc cggcctcacc tgcacctgct ccaggtcttg 71460
ctggaacctg agtagcactg aggctgcaga agctcatcca gggttgggga atgactctgg 71520
aactctccca catctgacct ttctgggtgg aggcatctgg tggccctggg aatataaaaa 71580
gccccagaat ggtgcctgcg tgatttgggg gcaatttatg aacccgaaag gacatggcca 71640
tggggtgggt agggacatag ggacagatgc cagcctgagg tggagcctca ggacacagtt 71700
ggacgcggac actatccaca taagcgaggg acagacccga gtgttcctgc agtagacctg 71760
agagcgctgg gcccacagcc tcccctcggt gccctgctgc ctcctcaggt cagccctgga 71820
catcccgggt ttccccaggc cagatggtag gtttgaagtg aggtctgtgt cactgtggta 71880
ttatgattac gtttggggga gttatcgtta tacccacagc atcacacggt ccatcagaaa 71940
cccatgccac agccctcccc gcaggggacc gccgcgtgcc atgttacgat tttgatcgag 72000
gacacagcgc catgggtatg gtggctacca cagcagtgca gcccatgacc caaacacaca 72060
gggcagcagg cacaatggac aggcctgtga gtgaccatgc tgggctccag cccgccagcc 72120
ccggagacca tgaaacagat ggccaaggtc accccacagt tcagccagac atggctccgt 72180
ggggtctgca tcgctgctgc cctctaacac cagcccagat ggggacaagg ccaaccccac 72240
attaccatct cctgctgtcc acccagtggt cccagaagcc cctccctcat ggctgagcca 72300
catgtgtgaa ccctgagagc accccatgtc agagtagggg cagcagaagg gcggggctgg 72360
ccctgtgcac tgtccctgca cccatggtcc ctcgcctgcc tggccctgac acctgagcct 72420
cttctgagtc atttctaaga tagaagacat tcccggggac agccggagct gggcgtcgct 72480
catcctgccc ggccgtcctg agtcctgctt gtttccagac ctcaccaggg aagccaacag 72540
aggactcacc tcacacagtc agagacaaag aaccttccag aaatccctgt ctcactcccc 72600
agtgggcacc ttcttccagg acattcctcg gtcgcatcac agcaggcacc cacatctgga 72660
tcaggacggc ccccagaaca caagatggcc catggggaca gccccacaac ccaggccttc 72720
ccagacccct aaaaggcgtc ccaccccctg cacctgcccc agggctaaaa atccaggagg 72780
cttgactccc gcataccctc cagccagaca tcacctcagc cccctcctgg aggggacagg 72840
agcccgggag ggtgagtcag acccacctgc cctcgatggc aggcggggaa gattcagaaa 72900
ggcctgagat ccccaggacg cagcaccact gtcaatgggg gccccagacg cctggaccag 72960
ggcctgcgtg ggaaaggccg ctgggcacac tcaggggctt tttgtgaagg cccctcctac 73020
tgtgtgacta cggtgactac cacagtgatg aaactagcag caaaaactgg ccggacaccc 73080
agggaccatg cacacttctc agcttggagc tctccaggac cagaagagtc aggtctgagg 73140
gtttgtagcc agaccctcgg cctctaggga caccctggcc atcacagcgg atgggctggt 73200

-continued

```
gccccacatg ccatctgctc caaacagggg cttcagaggg ctctgaggtg acttcactca  73260
tgaccacagg tgccctggcc ccttccccgc cagctacacc gaaccctgtc ccaacagctg  73320
ccccagttcc aacagccaat tcctggggcc cagaattgct gtagacacca gcctcgttcc  73380
agcacctcct gccaattgcc tggattcaca tcctggctgg aatcaagagg gcagcatccg  73440
ccaggctccc aacaggcagg actcccgcac accctcctct gagaggccgc tgtgttccgc  73500
agggccaggc cctggacagt tcccctcacc tgccactaga gaaacacctg ccattgtcgt  73560
ccccacctgg aaaagaccac tcgtggagcc cccagcccca ggtacagctg tagagagact  73620
ccccgaggga tctaagaagg agccatgcgc agttctgccg ggaccctcgg ccaggccgac  73680
aggagtggac actggagctg ggcccacact gggccacata ggagctcacc agtgagggca  73740
ggagagcaca tgccggggag cacccagcct cctgctgacc agaggcctgc cccagagccc  73800
aggaggctgc agaggcctct ccagggggac actgtgcatg tctggtccct gagcagcccc  73860
ccacgtcccc agtcctgggg gcccctagca cagctgtctg gaccctccct gttccctggg  73920
aagctcctcc tgacagcccc gcctccagtt ccaggtgtgg ttattgtcag gggtgtcag   73980
actgtggtgg atacagctat ggttaccaca gtggtgctgc ccatagcagc aaccaggcca  74040
agtagacagg cccctgctgt gcagccccag gcctccagct cacctgcttc tcctggggct  74100
ctcaaggtca ctgttgtctg tactctgccc tctgtgggga gggttctctc agtgggaggt  74160
ctgttctcaa catcccaggg cctcatgtct gcacggaagg ccaatggatg ggcaacctca  74220
catgccgcgg ctaagatagg gtgggcagcc tggcggggga cagtacatac tgctggggtg  74280
tctgtcactg tgcctagtgg ggcactggct cccaaacaac gcagtcctca ccaaaatccc  74340
cacagcctcc cctgctaggg gctggcctga tctcctgcag tcctaggagg ctgctgacct  74400
ccagaatgtc tccgtcccca gttccagggc gagagcagat cccaggccgg ctgcagactg  74460
ggaggccacc ccctccttcc cagggttcac tggaggtgac caaggtagga aatggcctta  74520
acacagggat gactgcgcca tcccccaaca gagtcagccc cctcctgctc tgtaccccgc  74580
accccccagg ccagtccacg aaaaccaggg ccccacatca gagtcactgc ctggcccggc  74640
cctggggcgg acccctcagc ccccaccctg tctagaggac ttggggggac aggacacagg  74700
ccctctcctt atggttcccc cacctgcctc cggccgggac ccttggggtg tggacagaaa  74760
ggacacctgc ctaattggcc cccaggaaca cagaacttct ctccagggac cccagcccga  74820
gcaccccctt acccaggacc cagccctgcc cctcctcccc tctgctctcc tctcatcacc  74880
ccatgggaat ccggtatccc caggaagcca tcaggaaggg ctgaaggagg aagcggggcc  74940
gtgcaccacc gggcaggagg ctccgtcttc gtgaacccag ggaagtgcca gcctcctaga  75000
gggtatggtc caccctgcct ggggctccca ccgtggcagg ctgcggggaa ggaccaggga  75060
cggtgtgggg gagggctcag ggccctgcgg gtgctcctcc atcttcggtg agcctccccc  75120
ttcacccacc gtcccgccca cctcctctcc accctggctg cacgtcttcc acaccatcct  75180
gagtcctacc tacaccagag ccagcaaagc cagtgcagac aaaggctggg gtgcaggggg  75240
gctgccaggg cagcttcggg gagggaagga tggagggagg ggaggtcagt gaagaggccc  75300
ccttcccctg ggtccaggat cctcctctgg gacccccggc tcccatcccc tcctggctct  75360
gggaggagaa gcaggatggg agaatctgtg cgggaccctc tcacagtgga atatccccac  75420
agcggctcag gccagaccca aaagcccctc agtgagccct ccactgcagt cctgggcctg  75480
ggtagcagcc cctcccacag aggacagacc cagcaccccg aagaagtcct gccaggggga  75540
gctcagagcc atgaaagagc aggatatggg gtccccgata caggcacaga cctcagctcc  75600
```

-continued atccaggccc accgggaccc accatgggag gaacacctgt ctccgggttg tgaggtggct 75660
ggcctctgtc tcggacccca ctccagacac cagacagagg ggcaggcccc ccaaaaccag 75720
ggttgaggga tgatccgtca aggcagacaa gaccaagggg cactgacccc agcaagggaa 75780
ggctcccaaa cagacgagga ggtttctgaa gctgtctgta tcacagtggg gtatagcagt 75840
ggctggtacc acagtgacac tcgccaggcc agaaaccccg tcccaagtca gcggaagcag 75900
agagagcagg gaggacacgt ttaggatctg aggccgcacc tgacacccag ggcagcagac 75960
gtctcccctc cagggcaccc tccaccgtcc tgcgtttctt caagaatagg ggcggcctga 76020
gggggtccag ggccaggcga taggtcccct ctaccccaag gaggagccag gcaggacccg 76080
agcaccgtcc ccattgaggc tgacctgccc agacgggcct gggcccaccc cacacaccgg 76140
ggcggaatgt gtgcaggccc cagtctctgt gggtgttccg ctagctgggg cccccagtgc 76200
tcaccccaca cctaaagcga gccccagcct ccagagcccc ctaagcattc cccgcccagc 76260
agcccagccc ctgcccccac ccaggaggcc ccagagctca gggcgcctgg tcggattctg 76320
aacagccccg agtcacagtg ggtataactg gaacgaccac cgtgagaaaa actgtgtcca 76380
aaactgactc ctggcagcag tcggaggccc cgccagagag gggagcagcc gccctgaacc 76440
catgtcctgc cggttcccat gacccccagc acccagagcc ccacggtgtc cccgttggat 76500
aatgaggaca agggctgggg gctccggtgg tttgcggcag ggacttgatc acatccttct 76560
gctgtggccc cattgcctct ggctggagtt gacccttctg acaagtgtcc tcagaaagac 76620
agggatcacc ggcacctccc aatatcaacc ccaggcagca cagacacaaa ccccacatcc 76680
agagccaact ccaggagcag agacacccca acactctggg ggaccccaac cgtgataact 76740
ccccactgga atccgcccca gagtctacca ggaccaaagg ccctgccctg tctctgtccc 76800
tcactcaggg cctcctgcag ggcgagcgct tgggagcaga ctcggtctta ggggacacca 76860
ctgtgggccc caactttgat gaggccactg acccttcctt cctttcctgg ggcagcacag 76920
actttggggt ctgggcaggg aagaactact ggctggtggc caatcacaga gcccccaggc 76980
cgaggtggcc ccaagaaggc cctcaggagg tggccactcc acttcctccc agctggaccc 77040
caggtcctcc ccaagatagg ggtgccatcc aaggcaggtc ctccatggag ccccccttcag 77100
actcctcccg ggaccccact ggacctcagt ccctgctctg ggaatgcagc caccacaagc 77160
acaccaggaa gcccaggccc agccaccctg cagtgggcaa gcccacactc tggagcagag 77220
cagggtgcgt ctgggagggg ctaacctccc caccccccac cccccatctg cacacagcca 77280
cctaccactg cccagaccct ctgcaggagg gccaagccac catggggtat ggacttaggg 77340
tctcactcac gtgcctcccc tcctgggaga aggggcctca tgccgagatc cctgcagcac 77400
tagacacagc tggaggcagt ggccccaggg ccaccctgac ctggcatcta aggctgctcc 77460
agcccagaca gcactgccgt tcctgggaag cctgggctcc accagaccac aggtccaggg 77520
cacagcccac aggagccacc cacacacagc tcacaggaag aagataagct ccagacccca 77580
gggcgggacc tgccttcctg ccaccactta cacacaggcc agggagctgt tcccacacag 77640
atcaacccca aaccgggact gcctggcact agggtcactg ccatttccct ctccattccc 77700
tcccagtgcc tctgtgctcc ctccttctgg ggaacaccct gtgcagcccc tccctgcagc 77760
ccacacgctg gggagacccc accctgcctc gggccttttc tacctgctgc acttgccgcc 77820
cacccaaaca accctgggta cgtgaccctg cagtcctcac cctgatctgc aaccagaccc 77880
ctgtccctcc ctctaaacac ccctcccagg ccaactctgc acctgcaggc cctccgctct 77940

-continued

```
tctgccacaa gagcctcagg ttttcctacc tgtgcccacc ccctaacccc tcctgcccac  78000
aacttgagtt cttcctctcc tggagccctt gagccatggc actgacccta cactcccacc  78060
cacacactgc ccatgccatc accttcctcc tggacactct gaccacgctc ccctccctct  78120
cagacccggc cctggtattt ccaggacaaa ggctcaccca agtcttcccc atgcaggccc  78180
ttgccctcac tgcctggtta cacgggagcc tcctgtgcgc agaagcaggg agctcagctc  78240
ttccacaggc agaaggcact gaaagaaatc ggcctccagt gccttgacac acgtccgcct  78300
gtgtctctca ctgcctgcac ctgcagggag gctccgcact ccctctaaag atgagggatc  78360
caggcagcaa catcacggga gaatgcaggg ctcccagaca gcccagccct ctcgcaggcc  78420
tctcctggga agagacctgc agccaccact gaacagccac ggaggtcgct ggatagtaac  78480
cgagtcagtg accgacctgg agggcagggg agcagtgaac cggagcccat accataggga  78540
cagacaccag ccgctaacat cccgagcccc tcactggcgg ccccagaaca ccccgtggaa  78600
acagaacaga cccacagtcc cacctggaac agggcagaca ctgctgagcc cccagcacca  78660
gccccaagaa acactaggca acagcatcag agggggctcc tgagaaagag aggaggggag  78720
gtctccttca ccatcaaatg cttcccttga ccaaaaacag ggtccacgca actcccccag  78780
gacaaaggag gagccccctg tacagcactg ggctcagagt cctctctgag acaggctcag  78840
tttcagacaa caacccgctg gaatgcacag tctcagcagg agagccaggc cagagccagc  78900
aagaggagac tcggtgacac cagtctcctg tagggacagg aggattttgt gggggttcgt  78960
gtcactgtga gcatattgtg gtggtgactg ctattcccac agtgacacaa ccccattcct  79020
aaagccctac tgcaaacgca cccactcctg gggctgaggg gctgggggag catctgggaa  79080
gtatggccta ggggtgtcca tcaatgccca aaatgcacca gactctcccc aagacatcac  79140
cccaccagcc agtgagcaga gtaaacagaa aatgagaagc agctgggaag cttgcacagg  79200
ccccaaggaa agagctttgg caggtgtgca agaggggatg tgggcagagc ctgagcaggg  79260
ccttttgctg tttctgcttt cctgtgcaga gagttccata aactggtatt caggatcaat  79320
ggctgggagt gagcccagga ggacagtgtg ggaagagcac agggaaggag gaccagccgc  79380
tatcctacac tgtcatcttt tgaaagtttg ccctgtgccc acaatgctgc atcatgggat  79440
gcttaacagc tgatgtagac acagctaaag agagaatcag tgaaatgcat ttgcagcaca  79500
gatctgaata aatcctccag aatgtggagc agcacagaag caagcacaca gaaagtgcct  79560
gatgccaagg caaagttcag tgggcacctt caggcattgc tgctgggcac agacactctg  79620
aaaagcactg gcaggaactg cctgtgacaa agcagaaccc tcaggcaatg ccagccctag  79680
agcccttcct gagaacctca tgggcaaaga tgtgcagaac agctgtttgt catagcccca  79740
aactatgggg ctggacaaag caaacgtcca tctgaaggac aacagacaaa taaacgatgg  79800
caggttcatg aaatgcaaac taggacagcc agaggacaac agtagagagc tacaggcggc  79860
tttgcggttg agttcatgac aatgctgagt aattggagta acagaggaaa gcccaaaaaa  79920
tacttttaat gtgatttctt ctaaataaaa tttacacccg gcaaaatgaa ctatcttctt  79980
aagggataaa ctttcccctg gaaaaactat aaggaaaatc aagaaaacga tgatcacata  80040
aacacagtgg tggttacttc tactggggaa ggaagagggt atgagctgag acacacagag  80100
tcggcaagtc tcctaacaag aacagaacaa atacattaca gtaccttgaa aacagcagtt  80160
aaacttctaa atcgcaagaa gaggaaaatg cacacacctg tgtttagaaa attctcagtc  80220
cagcactgtt cataatagca aagacattaa cccaggttgg ataaataagc gatgacacag  80280
gcaattgcac aatgatacag acatacattc agtatatgag acatcgatga tgtatcccca  80340
```

aagaaatgac tttaaagaga aaaggcctga tgtgtggtgg caatcacctc cctgggcatc 80400
cccggacagg ctgcaggctc actgtgtggc agggcaggca ggcacctgct ggcagctcct 80460
ggggcctgat gtggagcagg cacagagctg tatatcccca aggaaggtac agtcagtgca 80520
ttccagagag aagcaactca gccacactcc ctggccagaa cccaagatgc acacccatgc 80580
acagggaggc agagcccagc acctccgcag ccaccaccac ctgcgcacgg gccaccacct 80640
tgcaggcaca gagtgggtgc tgagaggagg ggcagggaca ccaggcaggg tgagcaccca 80700
gagaaaactg cagaagcctc acacatccac ctcagcctcc cctgacctgg acctcacctg 80760
gcctgggcct cacctgacct ggacctcacc tggcctgggc ttcacctggc ctgggcttca 80820
cctgacctgg acctcacctg gcctcgggcc tcacctggcc tgggcttcac ctggcctggg 80880
cttcacctga cctggacctc acctggcctg ggcctcacct gacctggacc tcacctggcc 80940
tgggcttcac ctggcctggg cttcacctgg cctgggcttc acctgacctg gacctcacct 81000
ggcctgggct tcacctgacc tggacctcac ctggcctcag gcctcacctg cacctgctcc 81060
aggtcttgct ggagcctgag tagcactgag gctgtaggga ctcatccagg gttggggaat 81120
gactctgcaa ctctcccaca tctgaccttt ctgggtggag gcacctggtg gcccagggaa 81180
tataaaaagc cccagaatga tgcctgtgtg atttgggggc aatttatgaa cccgaaagga 81240
catggccatg gggtgggtag ggacagtagg gacagatgtc agcctgaggt gaagcctcag 81300
gacacaggtg ggcatggaca gtgtccacct aagcgaggga cagacccgag tgtccctgca 81360
gtagacctga gagcgctggg cccacagcct cccctcgggg ccctgctgcc tcctcaggtc 81420
agccctggac atcccgggtt tccccaggcc tggcggtagg tttgaagtga ggtctgtgtc 81480
actgtggtat tactatgata gtagtggtta ttactaccac agtgtcacag agtccatcaa 81540
aaactcatgc ctgggagcct cccaccacag ccctccctgc gggggaccgc tgcatgccgt 81600
gttaggattt tgatcgagga cacggcgcca tgggtatggt ggctaccaca gcagtgcagc 81660
ccatgaccca aacacacggg gcagcagaaa caatggacag gcccacaagt gaccatgatg 81720
ggctccagcc caccagcccc agagaccatg aaacagatgg ccaaggtcac cctacaggtc 81780
atccagatct ggctccaagg ggtctgcatc gctgctgccc tcccaacgcc aaaccagatg 81840
gagacagggc cggccccata gcaccatctg ctgccgtcca cccagcagtc ccggaagccc 81900
ctccctgaac gctgggccac gtgtgtgaac cctgcgagcc ccccatgtca gagtaggggc 81960
agcaggaggg cggggctggc cctgtgcact gtcactgccc ctgtggtccc tggcctgcct 82020
ggccctgaca cctgagcctc tcctgggtca tttccaagac attcccaggg acagccggag 82080
ctgggagtcg ctcatcctgc ctggctgtcc tgagtcctgc tcatttccag acctcaccag 82140
ggaagccaac agaggactca cctcacacag tcagagacaa cgaaccttcc agaaatccct 82200
gtttctctcc ccagtgagag aaaccctctt ccagggtttc tcttctctcc caccctcttc 82260
caggacagtc ctcagcagca tcacagcggg aacgcacatc tggatcagga cggcccccag 82320
aacacgcgat ggcccatggg gacagcccag cccttcccag acccctaaaa ggtatcccca 82380
ccttgcacct gccccagggc tcaaactcca ggaggcctga ctcctgcaca ccctcctgcc 82440
agatatcacc tcagccccct cctggagggg acaggagccc gggagggtga gtcagaccca 82500
cctgccctca atggcaggcg gggaagattc agaaaggcct gagatcccca ggacgcagca 82560
ccactgtcaa tgggggcccc agacgcctgg accagggcct gtgtgggaaa ggcctctggc 82620
cacactcagg ggctttttgt gaagggccct cctgctgtgt gactacggtg gtaactccca 82680

-continued

```
cagtgatgaa accagcagca aaaactgact ggactcgcag ggtttatgca cacttctcgg  82740
ctcggagctc tccaggagca caagagccag gcccgagggt ttctgcccag accctcggcc  82800
tctagggaca cccgggccat cttagccgat gggctggtgc cctgcacacc gtgtgctgcc  82860
aaacaggggc ttcagagggc tctgaggtga cttcactcat gaccacaggt gccctggtcc  82920
cttcactgcc agctgcacca gaccctgttc cgagagatgc cccagttcca aaagccaatt  82980
cctggggccg ggaattactg tagacaccag cctcattcca gtacctcctg ccaattgcct  83040
ggattcccat cctggctgga atcaagaggg cagcatccgc caggctccca acaggcagga  83100
ctcccacaca ccctcctctg agaggccgct gtgttccgca gggccaggcc gcagacagtt  83160
cccctcacct gcccatgtag aaacacctgc cattgtcgtc cccacctgga aaagaccact  83220
tgtggagccc ccagccccag gtacagctgt agagagagtc ctcgaggccc ctaagaagga  83280
gccatgccca gttctgccgg gaccctcggc caggccgaca ggagtggacg ctggagctgg  83340
gcccacactg ggccacatag gagctcacca gtgagggcag gagagcacat gccggggagc  83400
acccagcctc ctgctgacca gagacccgtc ccagagccca ggaggctgca gaggcctctc  83460
caggggggaca cagtgcatgt ctggtccctg agcagccccc aggctctcta gcactggggg  83520
cccctagcac agctgtctgg accctccctg ttccctggga agctcctcct gacagccccg  83580
cctccagttc caggtgtggt tattgtcagg gggtgccagg ccgtggtaga gatggctaca  83640
attaccacag tggtgccgcc catagcagca accaggccaa gtagacagac ccctgccacg  83700
cagccccagg cctccagctc acctgcttct cctggggctc tcaaggctgc tgtctgccct  83760
ctggccctct gtggggaggg ttccctcagt gggaggtctg tgctccaggg cagggatgac  83820
tgagatagaa atcaaaggct ggcagggaaa ggcagcttcc cgccctgaga ggtgcaggca  83880
gcaccacaga gccatggagt cacagagcca cggagccccc agtgtgggcg tgtgagggtg  83940
ctgggctccc ggcaggccca gccctgatgg ggaagcctgc cccgtcccac agcccaggtc  84000
cccaggggca gcaggcacag aagctgccaa gctgtgctct acgatcctca tccctccagc  84060
agcatccact ccacagtggg gaaactgagc cttggagaac cacccagccc cctggaaaca  84120
aggcggggag cccagacagt gggcccagag cactgtgtgt atcctggcac taggtgcagg  84180
gaccacccgg agatccccat cactgagtgg ccagcctgca gaaggaccca accccaacca  84240
ggccgcttga ttaagctcca tccccctgtc ctgggaacct cttcccagcg ccaccaacag  84300
ctcggcttcc caggccctca tccctccaag gaaggccaaa ggctgggcct gccaggggca  84360
cagtaccctc ccttgccctg gctaagacag ggtgggcaga cggctgcaga taggacatat  84420
tgctggggca tcttgctctg tgactactgg gtactggctc tcaacgcaga ccctaccaaa  84480
atccccactg cctcccctgc taggggctgg cctggtctcc tcctgctgtc ctaggaggct  84540
gctgacctcc aggatggctt ctgtccccag ttctagggcc agagcagatc ccaggcaggc  84600
tgtaggctgg gaggccaccc ctgtccttgc cgaggttcag tgcaggcacc caggacagga  84660
aatggcctga acacagggat gactgtgcca tgccctacct aagtccgccc ctttctactc  84720
tgcaaccccc actccccagg tcagcccatg acgaccaaca acccaacacc agagtcactg  84780
cctggccctg ccctggggag gacccctcag cccccaccct gtctagagga cttgggggga  84840
caggacacag gccctctcct tatggttccc ccacctggct cctgccggga cccttggggt  84900
gtggacagaa aggacgcctg cctaattggc ccccaggaac acagaacttc tctccaggga  84960
ccccagcccg agcacccccct tacccaggac ccagccctgc ccctcctccc ctctgctctc  85020
ctctcatcac tccatgggaa tccagaatcc ccaggaagcc atcaggaagg gctgaaggag  85080
```

gaagcggggc cgctgcacca ccgggcagga ggctccgtct tcgtgaaccc agggaagtgc 85140
cagcctccta gagggtatgg tccaccctgc ctggggctcc caccgtggca ggctgcgggg 85200
aaggaccagg gacggtgtgg gggagggctc agggccctgc aggtgctcca tcttggatga 85260
gcccatccct ctcacccacc gacccgccca cctcctctcc accctggcca cacgtcgtcc 85320
acaccatcct gagtcccacc tacaccagag ccagcagagc cagtgcagac agaggctggg 85380
gtgcaggggg gccgccaggg cagctttggg gagggaggaa tggaggaagg ggaggtcagt 85440
gaagaggccc ccctcccctg ggtctaggat ccacctttgg gacccccgga tcccatcccc 85500
tccaggctct gggaggagaa gcaggatggg agattctgtg caggaccctc tcacagtgga 85560
atacctccac agcggctcag gccagataca aaagcccctc agtgagccct ccactgcagt 85620
gctgggcctg ggggcagccc ctcccacaga ggacagaccc agcaccccga agaagtcctg 85680
ccagggggag ctcagagcca tgaaggagca agatatgggg accccaatac tggcacagac 85740
ctcagctcca tccaggccca ccaggaccca ccatgggtgg aacacctgtc tccggcccct 85800
gctggctgtg aggcagctgg cctctgtctc ggaccccccat tccagacacc agacagaggg 85860
acaggccccc cagaaccagt gttgagggac accccctgtcc agggcagcca agtccaagag 85920
gcgcgctgag cccagcaagg gaaggccccc aaacaaacca ggaggtttct gaagctgtct 85980
gtgtcacagt cgggtatagc agcggctacc acaatgacac tgggcaggac agaaacccca 86040
tcccaagtca gccgaaggca gagagagcag gcaggacaca tttaggatct gaggccacac 86100
ctgacactca agccaacaga tgtctcccct ccagggcgcc ctgccctgtt cagtgttcct 86160
gagaaaacag gggcagcctg aggggatcca gggccaggag atgggtcccc tctaccccga 86220
ggaggagcca ggcgggaatc ccagccccct ccccattgag gccatcctgc ccagaggggc 86280
ccggacccac cccacacacc caggcagaat gtgtgcaggc ctcaggctct gtgggtgccg 86340
ctagctgggg ctgccagtcc tcaccccaca cctaaggtga gccacagccg ccagagcctc 86400
cacaggagac cccacccagc agcccagccc ctacccagga ggccccagag ctcagggcgc 86460
ctgggtggat tctgaacagc cccgagtcac ggtgggtata gtgggagcta ctaccactgt 86520
gagaaaagct atgtccaaaa ctgtctcccg gccactgctg gaggcccagc cagagaaggg 86580
accagccgcc cgaacatacg accttcccag ccctcatgac ccccagcact tggagctcca 86640
cagtgtcccc attggatggt gaggatgggg gccggggcca tctgcacctc ccaacatcac 86700
ccccaggcag cacaggcaca aaccccaaat ccagagccga caccaggaac acagacaccc 86760
caataccctg gggaccctg gccctggtga cttcccactg ggatccaccc ccgtgtccac 86820
ctggatcaaa gaccccaccg ctgtctctgt ccctcactca gggcctgctg aggggcgggt 86880
gctttggagc agactcaggt ttaggggcca ccattgtggg gcccaacctc gaccaggaca 86940
cagatttttc tttcctgccc tggggcaaca cagactttgg ggtctgggca gggaggacct 87000
tctggaaagt caccaagcac agagccctga ctgaggtggt ctcaggaaga cccccaggag 87060
ggggcttgtg ccccttcctc tcatgtggac cccatgcccc ccaagatagg ggcatcatgc 87120
agggcaggtc ctccatgcag ccaccactag gcaactccct ggcgccggtc cccactgcgc 87180
ctccatcccg gctctgggga tgcagccacc atggccacac caggcagccc gggtccagca 87240
accctgcagt gcccaagccc ttggcaggat tcccagaggc tggagcccac ccctcctcat 87300
ccccccacac ctgcacacac acacctaccc cctgcccagt ccccctccag gagggttgga 87360
gccacccata gggtgggcgc tccaggtctc actcactcgc ttcccttcct gggcaaagga 87420

-continued gcctcgtgcc ccggtccccc ctgacggcgc tgggcacagg tgtgggtact gggccccagg 87480
gctcctccag ccccagctgc cctgctctcc ctgggaggcc tgggcaccac cagaccacca 87540
gtccagggca cagccccagg gagccgccca ctgccagctc acaggaagaa gataagcttc 87600
agaccctcag ggccgggagc tgccttcctg ccaccccttc ctgccccaga cctccatgcc 87660
ctcccccaac cacttacaca caagccaggg agctgtttcc acacagttca accccaaacc 87720
aggacggcct ggcactcggg tcactgccat ttctgtctgc attcgctccc agcgcccctg 87780
tgttccctcc ctcctccctc cttcctttct tcctgcattg ggttcatgcc gcagagtgcc 87840
aggtgcaggt cagccctgag cttggggtca cctcctcact gaaggcagcc tcagggtgcc 87900
caggggcagg cagggtgggg gtgaggcttc cagctccaac cgctccacta gccgagacta 87960
aggaagtgag aggcagccag aaatccagac cattccatag caaatggatt tcattaaagt 88020
taccagactt cagtgtaagt aacatgagcc ccatgcacaa caatccctta tgaaggggaa 88080
gtcagtgtcg cctcggattt cttgaaaaac acaaaaactt atcaatgcct gtaaaagtct 88140
gttggaaaga aaatatgatt caagaatgtt atgcccaaca aagctggcat attttctacc 88200
cggacacact cagggaatgt ggtcccttga gtgcttctct cactgcgtaa atcctacgtg 88260
gtgtttaagc atattcataa atgtgtatgt ctatttttat gtgtaagatg gttcattttt 88320
attttattta ttcaatatgt acaataaaga atattgacaa ataggctgga catggtggct 88380
cccacctgta atcccagccc tttgggaggc cgaggcgggc agatcacctg aggtctggag 88440
ttcgagacca gcctggccaa catgatgaaa acccatctct actaaaaata caaagattag 88500
ccaggcatgg tggtgcatgc ctgtaatccc agccactcag gaggctgaga caggagaaat 88560
gcgtgaaccc ggaaggcgga ggttgcagtg agccgagatc acaccactgc actccagcct 88620
ggcgacagag caagattcca tctcaaaaaa aaaaaaagac aaagaaattt gttttttga 88680 ataaagacaa atttcatcac acgaagataa agatgcaaag ctccagacag gaaggcacgg 88740
acagcacagt gaagcccgga gcgggcgctg gggggccagg ggcatggcgg gggtgccagc 88800
gtctctcggt gcctaccatg gccactccag cctgtgttct cacgaggatg gctgtgcaat 88860
gctaggagcg tgttcgaagc tctagggcaa ccactggaag tgaggctgag gagcagagcc 88920
cagaggcccg tggagctgat gaaaagaaag ctggagaaag tgtttgctgc ctcccaacat 88980
ggtaagaaaa gatagaaaga gagagcacac ggcaaaggga gcttgctgag ggactcttta 89040
caatggcttg cacagagctc agggggtctg ggaggctagg gccctgcgca gggcagtcac 89100
cccagcctgc tgaccaaggt ttgctgcagg cagctctggg ggtggttgag gcgcggtccc 89160
tggagccacc cctcaaggga acgaggcagc agagtgggcc aaggcccagg tcggctgcaa 89220
ggctgcccag gacttggggt ccttacatca gcagccactg atgcagctgg cccagagaga 89280
ggcgccgagc aggttgcctc caggggacaa accaggtcgg agagggtgag gcagtggatg 89340
gagccacaac aaccccgggc acgggtgaca cgcacgttca tgcacatctg acccttcctc 89400
cctcaccaaa caggtccccc tgccttcccc atggttgcga aaaagcaaaa tgtagacgtt 89460
ttttcttttt taattcatgt tttaattgac aaatgaagcc gtatatattt attgtgtaca 89520
acatgatgct ttaaaatatg tatacatcgt ggaacagcaa cgttgagcta atttaacacg 89580
cattacttca catacttgtc atctttttgtg gcgagaatgc ttaaaatcca ctctcttagt 89640
attttttaag aatgcaatac attgttgtca actgtggtca ccgtcatgca tagccaagct 89700
cccgacctca ccctcctgcc agctcaggct gtgcatcctt tcaccagcat cccccacccc 89760
ggcccctggc cctggtaact accactctat actctacgta tgagttcagc tttttaagat 89820

-continued

```
tccacagatg aatgagatca tacagtattt gctttctatg cctggcttat tttagttaac  89880
acactgtcct ccagatccat ccgttgttgc aaatgacagg gtttcattct ttttaaagtc  89940
taaagagtat tccattgtgt caatggacct catttgcttt atccatgcat caactatgga  90000
catttaggtt gattccattt cttagctgtt gtggatggtg ctgcagtaaa catggggctg  90060
cagatgtctc ttcaacatac tgacatcatg tcctttggat aaatacccag tagtgggatc  90120
gctggatcac aatgtacagt ttgtttttta atggaaactt tcattttttg gtgaaattag  90180
gaaaacagat aaaacccaca gaatccaaaa tatatgtgaa gatgccaaaa acagttgaca  90240
ttgggcagag gtcacatgga aggaagtgaa tacatgacgg ggtgtgaggg cccagaggca  90300
gctgaaatac gctttctaaa cacaaggacc tcttctgaga gggcagaagt tttatcctgc  90360
acatgcaatg accagcacag ctaaaataca ctttctaaac atgaggacct cttctgagag  90420
ggcagcttta tcctgcaaat gcaatgacca gcacaggacc cagaataaag agagttgcca  90480
gcggacgcct ggtgtccatg tgtccaggtg agttcgagat gcggacggcg ctggccagcc  90540
agtcacaccc taagtcaatc tgctgcatgc atttgtcctt gccacagcag aaaacgagaa  90600
agcctttggg ctgcaaagct tcacaggctc ctcttctccc gactccatgg aaacagctac  90660
aaagagcagg cccagtagag cttaattcat gaaaatgagt aataaacttg aactggaaca  90720
gtatcgactt tttagaaacg gcagcaaagt gtataaaaaa tattcaccag aacaatattt  90780
ccaaacgatg agatgagaat ttcagccaag taatcctcca tggatagaaa ataatgaagg  90840
gattggattt atgaaggaaa atcatggagc tcaaatacaa gagaagagaa tcaaaaatga  90900
acaggaggag ataaaatatg gtttggccaa agttacaaaa taaatttttt aaaaaccctt  90960
catcatggca agtagaaaga gcgagaggaa aaacagatcc cgtggaagac acaaatagga  91020
catggggaga aaaatgaatg agatgaaaca gagcagaaat aaaattttac ggaactaaag  91080
acaagtgatc tgaacctgcc tggggcctgg gggacctcgc caccctgaag ggaaagaaca  91140
tgcctggctg gctttgccac ctgctcattg cagagcccca cagcttgcaa caaacatagg  91200
cggtagccag ggagtggtta cagcaggcct tgagcaagac ccagtgttgt gctgacttca  91260
ggtctgaccc agcactgtca tagtggtggt gtccatagtg gtagtggggg tgcttgtgtc  91320
actccacccc catctccagg aggctcagaa cagacagaga gagactccat ttgtttggga  91380
gaaagtaagg gatgagaaca agagtctctg cctggtaatc cagagaatta ttctagatct  91440
tggccaagat tatcaaagca gtacctctat gagtcttttg ggcttggagt cccccctaaag  91500
cagatatagc taagatcaca acacccaagt ccttttgaat atgtgggaag acttcccaag  91560
gacaggagca aacaaacaag cccagactgc aaaaaaacaa gcccagactg caataaacac  91620
ctcactcttc aatgcccagg cactgaagaa catctcctag cagcaacacc atccaggaaa  91680
acatggcctc aaccagtgaa ctaaataagg caccagggac cagtctcgga gaaatagagg  91740
tatgttatct ttcagagaat tcaaagtagc tttgttgagg aaactcaaag aaattcaaga  91800
taacacagtg aaggaattca gaatcctatc cgataaattt aacagagatt gaagcaatta  91860
aaaagaatta agcagaaatt atggagctga aaaatgcaat tggcatactg aaaaatgcat  91920
cagagtattt tcatagcctc ttatatcaag tagaagaaag aattagtgag cttgaaaaca  91980
ggctatttgg aaaagcacga taaaaggaga caaaagagaa aagaataaat aacaatgaag  92040
catatctaca ggatctagaa aatagcctca aaaggccaaa tctaagaatt attagcctta  92100
aagaggaggt agagaaagag ggatggagag tttattcaaa gggataataa cagaaaactt  92160
```

-continued

```
cccaaaccta gagaaagata tcaatatcca aatgcaagaa ggatgtagta caccaaggag  92220
atttaatgca aagaagacta cctcaaggca ttcaatactc aaactcccat atgacaagga  92280
ctttaaaaag atcctaaaag cagcaaaaga aaagaaatga ataaaatact atggagctcc  92340
aatatgtctg gcagcagact tttcagtgaa gactttatat gccaggagag agtgtcataa  92400
tggatttaaa gtgctgaagg aaaaaacttt taccctcgaa cagtatagct ggtgaaatta  92460
tccttcaaac atgaaggaga aataatttgt ttccagacaa atgttgaggg atttcatgaa  92520
caccagacct gtcttttaag aaatgctaaa gggagtactt caatcagaaa gaaacacgtt  92580
agtgaacaat aagaaatcat ctgaaggcac aaaactcacc ggtaatagta agtacacaga  92640
aaaacacaga atattataac actgtaactg tggtgtgtaa actccttttg tttgtttgtt  92700
tgtttgtttg tttgttttttg tttttagacg gagttttgct ccagcccagg ctggagtgca  92760
atggcacaat ctcagctcac tgcaacttcc acctcccggg ttcaagcaat tctcctgcct  92820
cagcctccca agtagctggg attacaggca tgtgctacca tgtccagcta attttgtatt  92880
ttagtagaga cggtgtttca ccatgttggt caggctagcc ttatcttgag tagaaaaact  92940
aaatgatgaa gcaatgaaaa ataataacta caacttttca agacatagta caataagata  93000
taaatcataa caaaaagtta aaaggtggag ggatgaagtt aaggcaaaga gtctttatta  93060
gttttctttt tacttgtctg tttatgcaaa cagtgttaag ttgtcatcag tttaaaataa  93120
tgggtcataa gatactattt gcaagcctca tggtaacgtc aaaccaaaag caatacaaca  93180
gatacacaaa aaacaaaaag caagaagcta aattacgtca tcagagaaaa tcaccttcac  93240
taaaaggaag acggagaaaa gaatgaagag agagaagacc aaaagcaaat agcaatatgg  93300
caggagtaag tccttactta tcaataatac cattgaatgt aaatggacta aactctccaa  93360
tcaaaagaca tagagtggct gaatcaatta aagaaaaaac aagacccatt gatctgttgt  93420
ccacaagaaa cacactttat ctataaagac acacatagac tgaaaacaaa gggatggaaa  93480
aagatactcc acgccaatgg aaaccaaaga aagagcagga gtagctacac ttatatcagg  93540
caaaatagat ttcaagacaa aaactataag aagagacaag gtcactaatg ataaacaggt  93600
caattcagca agaggatata acaattgtaa atatatatgc acccaatgct ggagcaccca  93660
gatatataaa gcaagtattt actagagcta aagagagaaa tagactccaa tgcaataata  93720
gctggagatt tcaacatccc actttcaaca ttgaacagat cctccagata gaaaatcaac  93780
aaagaaatat tggacttaat ctgcactatc gaccaaatgg atctaacaga tatttacaga  93840
acatttcatc caacagctgc agaacacaca ttcttttcct cagcacatag atcattctca  93900
aggatagacc atatgttggg tcacaaaaca agttttaaaa tattcaaata cattgaaata  93960
atatcaagca tcttctgtga ccacaatgga ctaaaactag aaatcaataa caagaggaat  94020
tttggaaact atataaatat atggaaatta atgaatgctg agtgggtcaa tgaagcaatt  94080
aagaaggaaa ctgaaatttt tcttggaacg aatgatcatg gaaacagaaa ataccaaaac  94140
ctatgggata cagcaaaagc agtactaaga gggaagttta cagctacaaa tgcttacatt  94200
aaaaaagaag aaaaacttca ataaaaaaac ctaacaatgc atcttaaaga actagaaaag  94260
caagaggaaa tcaaatccaa aattagtaga agaaaacagt aaaggtcaga gcagaaataa  94320
gtaaaattga aatgaagaaa acaatacaaa agatcaataa aacaacaggt tgttttcttg  94380
aaaagttaaa caaaattgac aaacctttag ccagactaag aaaaaaagac agaagatcca  94440
aataaataaa atcagagatg aaaaaggtga cattacaact tacaccacag aaattcaaag  94500
gatcattagt ggctactata agcaactata tgccaataaa ttggaaaatc tagaagaaat  94560
```

gcagaaattc ctagacacat acaacctccc aagattaaac caagaagaaa ttcaaaacct 94620
gaacagactg ataacaagta atgagatcaa agccgtaata aaaagcctcc cagtaaagag 94680
aagcccagga cccgacggct tcactgctga attctaccaa acatttaaag tagaactaat 94740
accaatccta ctcaaactat tccaaaaaat agaggtggaa ggaatacttc aaaactcatt 94800
atacgaggcc agtattaacc tgacaccaaa actagacaaa gacacatgaa aaaaagaaaa 94860
ctacaggcca atatgtctga tgaatattga cacaaaaatc ctcaacaaaa tactagcaaa 94920
ccaaattcaa ctacacatta gaaagttcac tcatcatgac caagtggaat ttatctaact 94980
tgggatgcaa agatggttca acatatgcaa atcaatcaat gtgatacatc atatcaacag 95040
aatgaacaac aaaaaccatt tgatcattta attgatactg aaaaagcatt tgataaaatt 95100
caacattcct tcataataaa aattctcttc tatactaggt acaaaagaaa cttacctcaa 95160
cataataaag ccatatatga cagtcccaca gtatgatact aaatgaggaa aaactgagag 95220
cctttcctct acgatctgga acatgacaaa gatgcccact ttcatcactg ttattcaaca 95280
tagtactgga agtcctagct ggagcgatca gacaagagaa agatataaaa gacatccaaa 95340
ttggaaagga ataagtcaaa ttatcctcat ttgcatatgg tatgatcttc tatttagagc 95400
taactaaaga ctccaccaaa aaaagttatt agaactgacg aacaaattca gtaaagctgc 95460
aggatacaaa atcaacatac aaaaatcagt agcatttcta tatgccaaca atgaccaatg 95520
tgaaaaagaa attaaaaagt aaccctattt acaataacca caaataaaca cctaggaatt 95580
aaccaaagag gtaaaagatt tctgtaatga aaactataaa aaactgatga aagaaattga 95640
agagtacacc aaaaaatgga aagcaattgc atgttcatgg attagaagaa tcagtgttgt 95700
tataatgtcc atactatcca aagcaatcta cagattcaat gcaatcctta tcaaaatacc 95760
aatgacatca ttcacagaaa tagaaaaaaa aaatcctaaa atttacgtgg aaccacaaag 95820
acccagaata gccaaagctc tcctaagcaa aaagaacgaa actgtaggaa tgacattgcc 95880
tgtcttcaaa ttctactaca gagctataga tagtaaccaa aacagcgtgg tactagcata 95940
aaaacagaca cagagacaaa cagaacaaaa tttaaaaacc cagaaataaa tccacacacc 96000
tacagcaaat tcatttttga caaagttgcc aagaacatac tctggggaat agataatgat 96060
atctcttcaa taaataatgt ggggaaaact ggatatccat atacataaca gtgaaactag 96120
acccctctct ctctcactat atacaaaaat caaatcaaaa ttgtttaagg acttaaatct 96180
aagacctcat actatgaaac cactgcaaga caaccttggc ggaaactctc caagacatca 96240
gtccaggcaa agatttcttg agtaatatcc cacaagcaca gacaaccaaa gcaaaaatgg 96300
acaaatggga tcacatcaag ttaaaaagct tctgcacagt aagggaaaca accaacaaaa 96360
tgaagagaca acccacagaa tgggagaaaa tatttgaaaa atacccatct ggcaagggat 96420
taaaaaccag aatatatgca gaatatataa ggagctcaaa cagtgctata gaaaaaaaaa 96480
tctaataatc tgatttaaaa atgggaaaaa tgttagaata gacatttctt aaaataagac 96540
atacagatgg caaaccgaca tggaacggtg ctcaacatca tggattatca cagaaacaca 96600
atcaatcaaa actaaaacta aaatgtgcta tcatctcacc ccagttaaaa tggctgatat 96660
ccagaagaca ggcaataaca aatgctggca aggatgtggg gaaaagggag cccccataca 96720
ctgttgctgg gattgtaaat tagtacaacc actgtggaga gcagcatgaa agttcctcaa 96780
aaaactgaaa gaaagctacc ataggatcca gcaatcccac tgctgtgtat atactacaaa 96840
agaaaggaag tcagtatatg aagaggtatc tgcactccca tgtttgttgc agccctgttc 96900

-continued acaacagcca agatttggaa gcaacctaag tgtccatcag cagttgaatg tataaagaaa 96960
atgtggtgca tatacacaat ggagtattat tcaataataa aaaggaatga gattgagtca 97020
tttgcaacaa catggatgga actggagatc attatgtgaa gtgaaataag ccaggcacag 97080
aaagacaaac attacaatgt tcttacttat taatgagatc taaaaatcaa aacaattgca 97140
cccatgttca taaagagtaa aaggatggtt accagatgct gagaacggtg gtggggggat 97200
agggaaaggt ggcagtggtt aacgggtaca aaaaaataga aagaatgaat aagacttact 97260
acttgatagc acagcaaggt ggctatagtc agtaatttag ttgtatattt ttaataatga 97320
aaggtgtata attggattgt ttctaacaca aaggataatg cttaagagga tggatacccc 97380
attttccatg atgtgattat ttcacattgc acgcctagat caaaacatcc aatgtacccc 97440
ataaatatat acatcttcta tgtacccata aaaattctgt aaaataaaat atataaaaag 97500
aggtgacaga tatggaagac aggcaaagaa gagacgacat ccacataatc cgagtaccta 97560
agaaagaatg gagtccagtg catctcagga gccaccattc taagccaatt ttctctggtt 97620
ctctcagtca ccctaccaat acgtgggcaa tcttgtttta tttcaggata gagtttttga 97680
aattatagat ttaagtatgc tttctgttct attacttttg gtaattaatt ttagaaagaa 97740
ctaatttggg cacaaatttg aaaaaattct aaatccaaaa aaaaaaagaa aaaaacacac 97800
acacaatcat ctataagggg gatgatgacc agtcctagat ttctcaccag ccacattcaa 97860
gatcagtaaa tggtaggaca aaacctgtag ggtccttaag ggggaaagaa gtagtggata 97920
gtccagagtc tatatacagc caactgttct tgaagaaaaa aggctgctga aaaggagttc 97980
caaacattct ataatccata atctcatgat gaaactacta gaggaagacc accagccatc 98040
aaaaggtgct tggagaaccc agggccaaga accaaaagta aatattaagt gtccttaact 98100
gcgagactaa gatagaaatg actgtggggg accatgtggc ctcaacagag gtgaaatggt 98160
gtctgcctga caaagtggac attttacaat gatcaaaaca cagaatatga gatagagagc 98220
acttctgaat tactgcctca ctccaaataa ctctcagcca aaggacttca gtaaaaccaa 98280
attgggcata ttagacagta caaacaaatt ctaagaaaat aatattactg attacaatca 98340
catgatgcta gagatggagg ggaaaaggaa gaggaaacca ggtaatttca tactcgtata 98400
tagtaaagaa ctaaagtaca ttgtccaaag aagaacaaag aatattttgg aaagttataa 98460
aggtagccac tacacataga agatagcaaa gaacaagaaa acttaagatg gaaaactttt 98520
tggaagcata aaaatagaaa atataaacta ctaagataag attgaagcca aacagatcta 98580
tgaaaacaac aaacatcaat ggccttaact tgcctattaa aaggaagaga ctttcaaatt 98640
ggaccacaag ataaaaccca actctatata gcatatgagt attacacaca aaatgggaaa 98700
agctgaaaaa acttgggcaa aattcacccc aagcaaattc cactgtttcc tttgggacaa 98760
aatgccaagc tccatgccag ggaagatgat tctcctcaga ccttctcctc actctcccag 98820
tcctcttagg gaaggaattg ggtgttagag gagggagact ctgtcgatta tcagctgaag 98880
cagtggtgtg ctcctgcgtt gcttctgacc tgggaaatga agcagcaaga ctctttctgc 98940
tgtgtctttg cccagaaggg ccatcccccc agagcagagt acccaggccg gcaggagcag 99000
tggtggaagc gtggaaacca cgtctcctac agcagagacc atcagaagcg gagcctcggg 99060
tataagggaa acaacgcgtt ctccctaacc tgggagtgac agacagcgtc attcctcaca 99120
gtgataccct gtgttctagc catctggccc atgacagagc cagcccagag ccagcccaga 99180
gccagcccct gaccatcctg gagcctggcc agctcgccaa gctgcaccat aggcctggaa 99240
ggcgtggaga cctgcggcag tgccctgtcc tcccgtgagg cctgccatcc ctgccagggg 99300

-continued

```
tcgcctctgg cttctccttc tccaggaccg cacggtccag aggctcagtg cctggagtag  99360
gtgttgcctc cctgcttcta ggcccagacc ctcccttgtt cctgaccccg ggcctttccc  99420
tctggcttgg acatccaggg ccctgtctca gctggggagc tgctcctgct caaggactgt  99480
cttccgcggg atcgaaaggc cgcgtcctga acaatgcgtg ggccacgtga gcggagcagg  99540
ctctaaaggc cgcgtcctaa acagtgcgtg ggccacgtga gcggagcagg ctctaaaggc  99600
cgcgtcctaa acagtgcgtg ggccacgtga gcggagcagg ctctaaaggc cgcgtcctaa  99660
acagtgcgtg ggccacgtga gcggagcagg ctctaaaggc cgcgtcctaa acagtgcgtg  99720
ggccacgtga gcggagcagg ctctaaaggc cgcgtcctaa acagtgcgtg ggccacgtga  99780
gcggagcagg ctctaaaggc cgcgtcctaa acagtgcgtg ggccacgtga gcggagcagg  99840
ctctaaaggc cgcgtcctaa acagtgcgtg ggccacgtga gcggagcagg ctctaaaggc  99900
cgcgtcctaa acagtgcgtg ggccacgtga gcggagcagg ctctaaaggc cgcgtcctaa  99960
acagtgcgtg ggccacggga gcggagcaga ctctaaaggc cgcgtcctaa acagtgtgtg 100020
ggccacgtga gcgaagcgcc ctctccactg ccctcggggc cgcagctccc agctcagctc 100080
ccagccctgc tcagggcagc caggccagga ggtaccatcc aggctaagtg accctcaggg 100140
gggacaggtg ccccaggaga tgccagctgt tgggagaggc tgggggacca actcgacctg 100200
gcctgtgggc cctgccctgg ccacccattg taggatccag ccgccacgcc tgtgacactc 100260
gtgtgctttc cctggtgtgt gcttgtggca ggtgggggca gagggtcctc aggccagaga 100320
gccactcccc cagcgccaga ccaccctctt cctcactccc ccacctcacc ccctcacagg 100380
tgcctcccag gccatcaggg cccaaccacc cctaaacaaa tgggttctcg gcccctcgtg 100440
gctggaggtg ggttctctca ccattcccag cctaagactc catccccatg ctggcagctg 100500
ttcaaccatg tctagagaga tccactgtcc cagacagcac ctcagggtcc cccgtcctgc 100560
ctggaaccct gtaggaaact ccacaaaccg ccgccattct gtccacaccc ctacaggagc 100620
cccaaccctc tccccacatc caggcttccc tcccagaccc ctcatccctg cccgcacggt 100680
gcctgagggg gccttcttgg gcagcgccta agcaagcccc cagcaccctt cggcccccttc 100740
aaggcacaca ggccccccttt ccacccagcc tcaggaaacc acctgtgtcc tccaacgaca 100800
ggtcccagcc tcccagcctt tgccttgcct gttcctctcc ctggaactct gccccgacac 100860
agaccctccc cagcaagccc gcaggggcac ctcccctgcc cccagacacc ctgtgcccgt 100920
cagttcatcc ccagcagagg ccctcaccag gcacaccccc atgctcacac ctggccccag 100980
gcctcagcct ccctgagggc cccacccagc ccgcgtctgg ccagtggtgc gtgcaaagcc 101040
cctcacccag actcggcgga aggcagccag tgcaggcctg gggaggggct ctccttagac 101100
caccttgcac cttccctggc acccaccatg ggaagagctg agactcactg aggaccagct 101160
gaggctcaga gaagggaccc agcactggtg gacacgcagg gagcccacgc cagggcgccg 101220
tggtgagtga ggcccagtgc cacccactga ggcctcccgt tcagtgggac gacggtgaac 101280
aggtggaacc aaccaggcaa cccccgccgg gccccacaga cgggatcaga gcaggaaagg 101340
cttcctgccc ctgcaggcca gcgaggagcc ctggcggggg ccgtggccct ccaggcgagg 101400
aggctcccct ggccaccgcc acccgggcct ctctgctgct gggaaaacaa gtcagaaagc 101460
aagtggatga gaggtggcgt gacagaccca gcttcagatc tgctctaatt tacaaaagaa 101520
aaggaaaaac acacttggca gccttcagca ctctaatgat tcttaacagc agcaaattat 101580
tggcacaaga ctccagagtg actggcaggg ttgagggctg ggtctcccca cgtgttttgg 101640
```

-continued ggctaacagc ggaagggaga gcactggcaa aggtgctggg ggcccctgga cccgacccgc 101700
cctggagacc gcagccacat cagcccccag ccccacaggc cccctaccag ccgcagggtt 101760
ttggctgagc tgagaaccac tgtgctaact ggggacacag tgattggcag ctctacaaaa 101820
accatgctcc cccgggaccc cgggctgtgg gtttctgtag cccctggctc agggctgact 101880
caccgtggct gaatacttcc agcactgggg ccagggcacc ctggtcaccg tctcctcagg 101940
tgagtctgct gtctggggat agcggggagc caggtgtact gggccaggca agggctttgg 102000
cttcagactt ggggacaggt gctcagcaaa ggaggtcggc aggagggcgg agggtgtgtt 102060
tttgtatggg agaagcagga gggcagaggc tgtgctactg gtacttcgat ctctggggcc 102120
gtggcaccct ggtcactgtc tcctcaggtg agtcccactg cagccccctc ccagtcttct 102180
ctgtccaggc accaggccag gtatctgggg tctgcagccg gcctgggtct ggcctgaggc 102240
cacaccagct gccatccctg ggtctccgc catgggctgc atgccagagc cctgctgtca 102300
cttagccctg gggccagctg gagcccccaa ggacaggcag ggaccccgct gggcttcagc 102360
cccgtcaggg accctccaca ggtagcaagc aggccgaggg cagggacggg aaggagaagt 102420
tgtgggcaga gcctgggctg gggctgggcg ctggctgttc atgtgccggg gaccaggcct 102480
gcgctttagt gtggctacaa gtgcttggag cactggggcc agggcagccc ggccaccgtc 102540
tccctgggaa cgtcacccct ccctgcctgg gtctcagccc gggggtctgt gtggctgggg 102600
acagggacgc cggctgcctc tgctctgtgc ttgggccatg tgacccattc gagtgtcctg 102660
cacgggcaca ggtttgtgtc tgggcaggaa cagggactgt gtccctgtgt gatgcttttg 102720
atatctgggg ccaagggaca atggtcaccg tctcttcagg taagatggct ttccttctgc 102780
ctcctttctc tgggcccagc gtcctctgtc ctggagctgg gagataatgt ccgggggctc 102840
cttggtctgc gctgggccat gtggggccct ccggggctcc ttctccggct gtttgggacc 102900
acgttcagca gaaggccttt ctttgggaac tgggactctg ctgctggggc aaagggtggg 102960
cagagtcatg cttgtgctgg ggacaaaatg accttgggac acggggctgg ctgccacggc 103020
cggcccggga cagtcggaga gtcaggtttt tgtgcacccc ttaatggggc ctcccacaat 103080
gtgactactt tgactactgg ggccagggaa ccctggtcac cgtctcctca ggtgagtcct 103140
cacaacctct ctcctgcttt aactctgaag ggttttgctg catttttggg gggaaataag 103200
ggtgctgggt ctcctgccaa gagagccccg gagcagcctg gggggctcag gaggatgccc 103260
tgaggcaaca gcggccacac agacgagggg caagggctcc agatgctcct tcctcctgag 103320
cccagcagca cgggtctctc tgtggccagg gccaccctag gcctctgggg tccaatgccc 103380
aacaaccccc gggccctccc cgggctcagt ctgagagggt cccagggacg tagcggggcg 103440
ccagttcttg cctggggtcc tggcattgtt gtcacaatgt gacaactggt tcgacccctg 103500
gggccaggga accctggtca ccgtctcctc aggtgagtcc tcaccacccc ctctctgagt 103560
ccacttaggg agactcagct tgccagggtc tcagggtcag agtcttggag gcattttgga 103620
ggtcaggaaa gaaagccggg gagagggacc cttcgaatgg gaacccagcc tgtcctcccc 103680
aagtccggcc acagatgtcg gcagctgggg ggctccttcg gctggtctgg ggtgacctct 103740
ctccgcttca cctggagcat tctcaggggc tgtcgtgatg attgcgtggt gggactctgt 103800
cccgctccaa ggcacccgct ctctgggacg ggtgcccccc ggggtttttg gactcctggg 103860
ggtgacttag cagccgtctg cttgcagttg gacttcccag gccgacagtg gtctggcttc 103920
tgaggggtca ggccagaatg tggggtacgt gggaggccag cagagggttc catgagaagg 103980
gcaggacagg gccacggaca gtcagcttcc atgtgacgcc cggagacaga aggtctctgg 104040

-continued gtggctgggt ttttgtgggg tgaggatgga cattctgcca ttgtgattac tactactact 104100
acggtatgga cgtctggggc caagggacca cggtcaccgt cggtcaccgt ctcctcaggt 104160
aagaatggcc actctagggc ctttgttttc tgctactgcc tgtggggttt cctgagcatt 104220
gcaggttggt cctcggggca tgttccgagg ggacctgggc ggactggcca ggaggggacg 104280
ggcactgggg tgccttgagg atctgggagc ctctgtggat tttccgatgc ctttggaaaa 104340
tgggactcag gttgggtgcg tctgatggag taactgagcc tgggggcttg gggagccaca 104400
tttggacgag atgcctgaac aaaccagggg tcttagtgat ggctgaggaa tgtgtctcag 104460
gagcggtgtc tgtaggactg caagatcgct gcacagcagc gaatcgtgaa atattttctt 104520
tagaattatg aggtgcgctg tgtgtcaacc tgcatcttaa attctttatt ggctggaaag 104580
agaactgtcg gagtgggtga atccagccag gagggacgcg tagccccggt cttgatgaga 104640
gcagggttgg gggcaggggt agcccagaaa cggtggctgc cgtcctgaca ggggcttagg 104700
gaggctccag gacctcagtg ccttgaagct ggtttccatg agaaaaggat tgtttatctt 104760
aggaggcatg cttactgtta aaagacagga tatgtttgaa gtggcttctg agaaaaatgg 104820
ttaagaaaat tatgacttaa aaatgtgaga gattttcaag tatattaatt tttttaactg 104880
tccaagtatt tgaaattctt atcatttgat taacacccat gagtgatatg tgtctggaat 104940
tgaggccaaa gcaagctcag ctaagaaata ctagcacagt gctgtcggcc ccgatgcggg 105000
actgcgtttt gaccatcata aatcaagttt attttttaa ttaattggcg cgcgccctct 105060
gtgacagcat ttatacagta tccgatgcat agggacaaag agtggagtgg ggcactttct 105120
ttagatttgt gaggaatgtt ccgcactaga ttgtttaaaa cttcatttgt tggaaggaga 105180
gctgtcttag tgattgagtc aagggagaaa ggcatctagc ctcggtctca aaagggtagt 105240
tgctgtctag agaggtctgg tggagcctgc aaaagtccag ctttcaaagg aacacagaag 105300
tatgtgtatg gaatattaga agatgttgct tttactctta agttggttcc taggaaaaat 105360
agttaaatac tgtgacttta aaatgtgaga gggttttcaa gtactcattt ttttaaatgt 105420
ccaaaattct tgtcaatcag tttgaggtct tgtttgtgta gaactgatat tacttaaagt 105480
ttaaccgagg aatgggagtg aggctctctc ataacctatt cagaactgac ttttaacaat 105540
aataaattaa gtttcaaata tttttaaatg aattgagcaa tgttgagttg gagtcaagat 105600
ggccgatcag aaccagaaca cctgcagcag ctggcaggaa gcaggtcatg tggcaaggct 105660
atttggggaa gggaaaataa aaccactagg taaacttgta gctgtggttt gaagaagtgg 105720
ttttgaaaca ctctgtccag ccccaccaaa ccgaaagtcc aggctgagca aaacaccacc 105780
tgggtaattt gcatttctaa aataagttga ggattcagcc gaaactggag aggtcctctt 105840
ttaacttatt gagttcaacc ttttaatttt agcttgagta gttctagttt ccccaaactt 105900
aagtttatcg acttctaaaa tgtatttaga attcattttc aaaattaggt tatgtaagaa 105960
attgaaggac tttagtgtct ttaatttcta atatatttag aaaacttctt aaaattactc 106020
tattattctt ccctctgatt attggtctcc attcaattct tttccaatac ccgaagcatt 106080
tacagtgact ttgttcatga tcttttttag ttgtttgttt tgccttacta ttaagacttt 106140
gacattctgg tcaaaacggc ttcacaaatc tttttcaaga ccactttctg agtattcatt 106200
ttaggagaaa gacttttttt ttaaatgaat gcaattatct agacttattt cagttgaaca 106260
tgctggttgg tggttgagag gacactcagt cagtcagtga cgtgaagggc ttctaagcca 106320
gtccacatgc tctgtgtgaa ctccctctgg ccctgcttat tgttgaatgg gccaaaggtc 106380

-continued tgagaccagg ctgctgctgg gtaggcctgg actttgggtc tcccacccag acctgggaat 106440
gtatggttgt ggcttctgcc acccatccac ctggctgctc atggaccagc cagcctcggt 106500
ggctttgaag gaacaattcc acacaaagac tctggacctc tccgaaacca ggcaccgcaa 106560
atggtaagcc agaggcagcc acagctgtgg ctgctgctct taaagcttgt aaactgtttc 106620
tgcttaagag ggactgagtc ttcagtcatt gctttagggg gagaaagaga catttgtgtg 106680
tcttttgagt accgttgtct gggtcactca catttaactt tccttgaaaa actagtaaaa 106740
gaaaaatgtt gcctgttaac caataatcat agagctcatg gtactttgag gaaatcttag 106800
aaagcgtgta tacaattgtc tggaattatt tcagttaagt gtattagttg aggtactgat 106860
gctgtctcta cttcagttat acatgtgggt ttgaattttg aatctattct ggctcttctt 106920
aagcagaaaa tttagataaa atggatacct cagtggtttt taatggtggg tttaatatag 106980
aaggaattta aattggaagc taatttagaa tcagtaagga gggacccagg ctaagaaggc 107040
aatcctggga ttctggaaga aaagatgttt ttagttttta tagaaaacac tactacattc 107100
ttgatctaca actcaatgtg gtttaatgaa tttgaagttg ccagtaaatg tacttcctgg 107160
ttgttaaaga atggtatcaa aggacagtgc ttagatccga ggtgagtgtg agaggacagg 107220
ggctggggta tggatacgca gaaggaaggc cacagctgta cagaattgag aaagaataga 107280
gacctgcagt tgaggccagc aggtcggctg gactaactct ccagccacag taatgaccca 107340
gacagagaaa gccagactca taaagcttgc tgagcaaaat taagggaaca aggttgagag 107400
ccctagtaag cgaggctcta aaaagcacag ctgagctgag atgggtgggc ttctctgagt 107460
gcttctaaaa tgcgctaaac tgaggtgatt actctgaggt aagcaaagct gggcttgagc 107520
caaaatgaag tagactgtaa tgaactggaa tgagctgggc cgctaagcta aactaggctg 107580
gcttaaccga gatgagccaa actggaatga acttcattaa tctaggttga atagagctaa 107640
actctactgc ctacactgga ctgttctgag ctgagatgag ctggggtgag ctcagctatg 107700
ctacgctgtg ttggggtgag ctgatctgaa atgagatact ctggagtagc tgagatgggg 107760
tgagatgggg tgagctgagc tgggctgagc tagactgagc tgagctaggg tgagctgagc 107820
tgggtgagct gagctaagct ggggtgagct gagctgagct tggctgagct agggtgagct 107880
gggctgagct ggggtgagct gagctgagct ggggtaagct gggatgagct ggggtgagct 107940
gagctgagct ggagtgagct gagctgggct gagctggggt gagctgggct gagctgggct 108000
gagctgggct gagctggggt gagctgagct ggggtgagct gagctgagct ggggtgagct 108060
gagctgagct ggggtgagct ggggtgagct gagctggggt gagctgagct gagctggggt 108120
gagctgagct ggggtgagct gagctgagct ggggtgagct gagctgagct gagctgagct 108180
gagctggggt gagctgagct gagctgagct ggggtgagct ggggtgagct gagctgagct 108240
ggagtgagct gagctgggct gagctggggt gagctgggct gagctggggt gagctgagct 108300
gagctgagct gagctggggt gagctgagct gagctggggt gagctgagct ggggtgagct 108360
gggctgagct gagctgagct gagctgagct gagctgagct gagctgagct gagctgagct 108420
gagctgagct gagctgagct gagctgagct ggggtgagct gagctgagct gggctgagct 108480
ggggtgagct gggctgagct gggctgagct gggctgagct ggggtgagct gagctggggt 108540
gagctgagct gagctgggct gagctgagct gagctggggt gagctgagct gagctggggt 108600
gagctgagct gagctgagct ggggtgagct gagctgggct gagcagggct gagctggggt 108660
gagctgagct gagctggggt gagctgggct gagctgggct gagctgagct gagctgggct 108720
gagctgggct gagctgggct gagctgggct gagctgggct gagctggggt gagctgagct 108780

-continued gagctggggt gagctggggt gagctgagct ggggtgagct gagctggggt gagctgagct 108840
gagctggggt gagctgagct ggggtgagct gagctgagct ggggtgagct gagctgagct 108900
ggggtgagct gagctagggt gaactgggct gggtgagctg gagtgagctg agctgaggtg 108960
aactggggtg agccgggatg ttttgagttg agctggggta agatgagctg aactggggta 109020
aactgggatg agctgtggtg agcggagctg gattgaactg agctgtgtga gctgagctgg 109080
ggtcagctga gcaagagtga gtagagctgg ctggccagaa ccagaatcaa ttaggctaag 109140
tgagccagat tgtgctggga tcagctgtac tcagatgagc tgggatgagg taggctggga 109200
tgagctgggc tagctgacat ggattatgtg aggctgagct agcatgggct ggcctagctg 109260
atgagctaag cttgaatgag cggggctgag ctggactcag atgtgctaga ctgagctgta 109320
ctggatgatc tggtgtaggg tgatctggac tcaactgggc tggctgatgg gatgcgccag 109380
gttgaactag gctcagataa gttaggctga gtagggcctg gttgagatgg ttcgggatga 109440
gctgggaaaa gatggactcg gaccatgaac tgggctgagc tgggttggga gaccatgaat 109500
tgagctgaac tgagtgcagc tgggataaac tgggttgagc taagaataga ctacctgaat 109560
tgtgccaaac tcggctggga tcaattggaa attatcagga tttagatgag ccggactaaa 109620
ctatgctgag ctggactggt tggatgtgtt gaactggcct gctgctgggc tggcatagct 109680
gagttgaact taaatgagga aggctgagca aggctagcct gcttgcatag agctgaactt 109740
tagcctagcc tgagctggac cagcctgagc tgagtaggtc taaactgagt taaaaatcaa 109800
cagggataat ttaacagcta atttaacaag cctgaggtct gagattgaat gagcagagct 109860
gggatgaact gaatgagttt caccaggcct ggaccagtta ggctaggacc tcgttctata 109920
gaggcagact gtgtgctaca gtggagtttc aagatgattc catgagtcct ccccgccccc 109980
aacataaccc accttcctcc taccctacac gcctgtctgg tgtgtaaatc ccagctttgt 110040
gtgctgatac agaagcctga gcccctcccc cacctccacc tacctattac tttgggatga 110100
gaatagttct cccagccagt gtctcagagg gaagccaagc aggacaggcc caaggctact 110160
tgagaagcca ggatctaggc ctctccctga gaacgggtgt tcatgcccct agagttggct 110220
gaagggccag atccacctac tctagaggca tctctccctg tctgtgaagg cttccaaagt 110280
cacgttcctg tggctagaag gcagctccat agccctgctg cagtttcgtc ctgtatacca 110340
ggttcaccta ctaccatatc tagccctgcc tgccttaaga gtagcaacaa ggcgcgtcaa 110400
acttacccta cctttatcct ggtggcttct catctccaga ccccagtaac acatagcttt 110460
ctctccacag tgcccaggga ttgtggttgt aagccttgca tatgtacagg taagtcagta 110520
ggcctttcac cctgacccca gatgcaacaa gtggccatgt tagagggtgg cccaggtatt 110580
gacctatttc cacctttctt cttcatcctt agtcccagaa gtatcatctg tcttcatctt 110640
ccccccaaag cccaaggatg tgctcaccat tactctgact cctaaggtca cgtgtgttgt 110700
ggtagacatc agcaaggatg atcccgaggt ccagttcagc tggtttgtag atgatgtgga 110760
ggtgcacaca gctcagacga aaccccggga ggagcagatc aacagcactt tccgttcagt 110820
cagtgaactt cccatcatgc accaggactg gctcaatggc aaggagttca aatgcagggt 110880
caacagtgca gctttccctg cccccatcga gaaaaccatc tccaaaacca aaggtgagag 110940
ctgcagtgtg tgacatagaa gctgcaatag tcagtccata gacagagctt ggcataacag 111000
acccctgcct tgtccatgac ctctgtgcta accaatctct ttacccaccc acaggcagac 111060
cgaaggctcc acaggtgtac accattccac ctcccaagga gcagatggcc aaggataaag 111120

-continued

```
tcagtctgac ctgcatgata acaaacttct tccctgaaga cattactgtg gagtggcagt 111180
ggaatgggca gccagcggag aactacaaga acactcagcc catcatggac acagatggct 111240
cttacttcgt ctacagcaag ctcaatgtgc agaagagcaa ctgggaggca ggaaatactt 111300
tcacctgctc tgtgttacat gagggcctgc acaaccacca tactgagaag agcctctccc 111360
actctcctgg taaatgatcc cagtgtcctt ggagccctct ggtcctacag gactctgaca 111420
cctacctcca cccctccctg tgtaaataaa gcacccagca ctgccttggg accctgcaat 111480
aatgtcctgg tgatttctga gatgtagagt ctagctaggt catggaatga ggggtctcca 111540
tggtttgagg cctgagttgt gactaaggaa aaacccatag gcctacactg ccacacccag 111600
cacttttgaa tttgcctgac atgaaaagaa tttacctctc cctggaaagt ggagccttat 111660
ccctaggcag ttcccttacc agaccttcct ctagcttgca ctttgttctg ggcacagaat 111720
gtgtctaacc ccccaaagca aggaagacac aacctctacc tccctcactc tgtccttacc 111780
ccttttcctg gctaagcatc tcactgagtg cgctgaatag atgcatgtgg ccacagtctt 111840
gcagacagac ccttgccatc tctccactca gctttccaga ggctaagtct agcccgtatg 111900
gtgataatgc agggagctct atgctatctc agtgctatca gactcccaag tggaggatga 111960
acatggaccc attaaaacca acctgcgcag caacaccctg ccaataaggc ccgtatgtga 112020
aaatgtgcac acatctacac atgcacaggc acacacacac acacatgcat gggcacacac 112080
acatacagag agagagaatc acagaaactc ccatgagcat cctatacagt actcaaagat 112140
aaaaaggtac caggtctacc cacatgatca tcctcggcat ttacaagtgg gccaactgat 112200
acagataaaa cttttctatg ccaaggacgc caacatatac acaagtccgc tcatgacaaa 112260
tctgtccctg aacctcagac tggcgcccgt gactcataca gtggacactc ctccaaagct 112320
gtatagcttc ctttacttcc ctgtgtgtac tttctctgaa gtacactcat cacacagaag 112380
aggccctgtg attactctgg ccctctgttc ttggtcatca gagaatagac agaagatcag 112440
gcaaactaca cagacacttc ccacaatcat cacaggccct gactctgctc tccagtctca 112500
aaactgaagg ctggagcaca cagaataagc tcctgcacag gccaggccag tatcgggtcc 112560
agtgtgtctg actgagccca gggacaaaat ggcagcactt tggggaactg aggtttctgg 112620
tccaagaagg agagatggag gcccagggag ggtctgctga cccagcccag cccagcccag 112680
ctgcagcttt ctcctgggcc tccatacagc ctcctgccac acagggaatg gccctagccc 112740
caccttattg ggacaaacac tgaccgccct ctctgtccag ggctgcaact ggacgagacc 112800
tgtgctgagg cccaggacgg ggagctggac gggctctgga cgaccatcac catcttcatc 112860
agcctcttcc tgctcagtgt gtgctacagc gctgctgtca cactcttcaa ggtcagccat 112920
actgtcccca cagtgtctac aatgtcctca tactcttccc catactgtcc ctgtggtgac 112980
ctataccccca cactgtccca tgctaatgac cacagtctta catgctatgt aatgctgtct 113040
acccttctgt atgcacagtc tcacaatgtc ccatgcagtc tccacgatgc tccatactgt 113100
ccccattcca acccatgctg ccccttgttc cccgctatgc tgtcccatgc tattgtctgt 113160
attttcatgc tcttttcaca ctgtccctag tgtcacattc tgcccatgtt gtccaccaca 113220
ttgtccccac tctgtacaca gcctcacact gtaccctgct acccgataat gttccctgtt 113280
gtccccaact ctctccctgc accatttgtc aactgtcccc tgaattccca tgttgttccc 113340
acactgttag tgtgtaatgt gctctgtccc aggtgtacct tgttccgtgc tgtctcactt 113400
catcgcccat tctgtccttg tactaacccc actctatcac cacactgtcc ctatgcactg 113460
cccacattgt cctcatactg tcccattttg tatcttcatc ctgtccccat agtgtccaat 113520
```

```
gatctacccc acactattcc cacttcatgc ccctacaatt tccctattcc attcctctct 113580
ggtcaccatg ccatccttcc cactcctgca cagctggaga gggactcccg ggatgagtcc 113640
ttgcccagat gagctaccta tctagaggag tcttcaggtg ggaagggaat gcagtcttga 113700
tcttggtctt attcaccctg tctcacaggt aaagtggatc ttctcctcgg tggtggagct 113760
gaagcagaca ctggttcctg aatacaagaa catgattggg caagcaccct aggccacctc 113820
ctgtaatggc atttcccagg ccccgaagga ccctgtccaa tatgccaagc agcacaactg 113880
agatcacact gtctgctcat ctcgctttcc tccgaccccg agactcagct actctcaaat 113940
tttccctctc tgaaggacca tgtggacatt acattgctcc aggccacagc caccaggacc 114000
taaaacacca tcacagcagc accaaagaca ctggatagac ccacaagggc aatagtttcc 114060
tcaacagtat atccaaactg ttgggacaaa cgagcaatca ctgaagaagt gacaagttcc 114120
cacaatgtca gtgtccagct gagaagggac aaaaagtggt accagccctg tccacaccac 114180
cttctaattc acaggaatac gtgatagaag aggcaggttg tagatccgaa agatgagaca 114240
gattttatca actccagaaa gagctgggtc caactgaatt attctagcga ccttggcatt 114300
gtcatgacct gccatgacct tcctccttaa cacttcgata aaccctggga tatggaaaat 114360
gcctgtgttt ctcagggttt gggaaagaac catccatgtt gggattcttg tgtagatcct 114420
ccttctggtc acagatgcaa tacactggat tttcaggcaa aggagcaaat tcacagacaa 114480
ctctggccct acagccctaa gacctagaca ccaccatctc cttggaatta tcaaatttaa 114540
cacccggcac acaacaaaga aggactggga ctttgaggcc tttgtgtagc cctagagggg 114600
gcagaggcca ctgagcaggg attgggtgat cacaaggacc tcctggagag ggacctgagg 114660
agcaggttcc aattgggcca aagaaagaag aacaacaata gagatgaagg atgctggaaa 114720
gagccatggt acagcagtct tgtccttcag acatgactct tacagcccag gactcttaca 114780
gtagctagct ggagcagaag tccaagggat taccatgccc tagggccaca ggctactgga 114840
gggtggagtg agtctactac acaggtccaa tgcctgtttc tccattgctt ctcagccaat 114900
gagaaatcag agtctccacc tccaagaaaa aggaaggtgg aaatgaaagg tgagcacctg 114960
ccttcccgtg actggcagaa agatctccac ggactcaagg ctttgacttc aaacggcgcg 115020
ccaatcttcc agaagccagg ctgggacctc agcaaaaggg aagacataac ccaactccag 115080
gatgccctgt ggctgatcac tcttgtcttg gcggggatga aggttggaga aaggcctcca 115140
cgtttcagag ctaagaccga cgtgacaact tcccagccca ctcacagact ttcctgagca 115200
ataaattgat gcaaaaccac aaattcctac tctcaaaaac aaacattaac aaaggattgg 115260
gggagggggt caggggtagt atggtggcgt tgggcagggt aaactcaggg tacccattgt 115320
ctaatgtctg agacataact tgaacatatg tgtagctgca gccaaagatg aacaagtgat 115380
ggtatttgtg tcctcttcag acccgatacc aggtcattaa gcttgagatc tggacctgat 115440
ttctaaacat ttggcctctg tgagcaccct tggcaaatac tgaacagcaa accctggtcc 115500
tggctgtgaa ccttggtcct gatcactgag ccctatattg gtaactgaac cgtgatcctg 115560
atctctgacc tcagtcatgg tcatgaggcc ctggtcctgg ccactcattc taataactgg 115620
tccctagtcc tgagccctga accttggtcc aggtcactga atcctagtca tgatcactgg 115680
gtttgatcct cattactgag cctagtcttg atcaccgatg actggttttg atcatagcaa 115740
ttaacctgat cactagtccc cgttcctcat cactgggcca tgatactggt cactgggtcc 115800
tgatcctgat cactaaatcc tgtttctaaa caatgtgtag tggaatgtat agtgaagcct 115860
```

-continued ttgtgtctgg ctctgggtga aatgtctcag cagagccttt gctaggtttg ggttaatcag 115920
ttggggctga gaaatgtttt tgaggctgtt tgaacttcaa aagaagaaat gtctccctgg 115980
acaatctgca catttgcagc tgcgcaaacc ttcatcctaa aacttaactc ctggcaaact 116040
tagaattctt acttttaata atggctagcc atggttgaaa gggactgaga tgtctgtggg 116100
tgggtggaac ctttcccagc tccaagtaac tctgtatact gtttgaataa agtaactgaa 116160
gtgagctagc tggggtcaat cttctttcca aggagaataa agccctccgc tcctccagaa 116220
aatgaaggct tagctccttg gttagcttct ctctctactg cggcacctac aaccaactca 116280
gcagtcctag gttcctgtca ccagatccag tcctgatagc taagtgtcaa tcctcgtcac 116340
taaggcctga tccttagcaa tatgcctggg gtctgataat cagactgaca ttctgataac 116400
tggacccaga ttcttatcac tgggtctttg tcctggtcat gggcatttga ccctagtcta 116460
cagcactgag ttctgggcat ggaccctggg tcccagttct agatactgag ttctggttct 116520
aataactggc tcctgtactg atcgatgggt cctgacctag tcattgggcc ctgatcctca 116580
acattgactt caaaacctga actctagccc catgcctcat tcacattagg aggatcccta 116640
caggggattc ctgcagaaga ttccagaatc cccacaacac tgttcacaca ctgggctgca 116700
actgggacag tgacccettt gctcatagga cttgcccagg ctcagatgca ctgaatggag 116760
acaaagcaag cccaggccct gggagatgga gcctctggcc tggggtctac agatgtgggg 116820
tcagcatcat agggaggttt gcagggcagg tgtggggcag ggcagaagtg gtcatgcttg 116880
tagatactat ttttctctcc tctggagcct cctttgtcta tcacctgctg tcctgggatc 116940
tctatctggg gtcaacaatg tttgcagtac aggtgtgggg gtagggcagg gatgttcaca 117000
ttagcaactt gtttttctct cttctgaagt ctctgttgtc tatcacctgc tgaaacattc 117060
aaagcagctc tgagctgagg gcagctgagt catcctgagc ctgtctcagc acaggtgccc 117120
caaaccagag ctactgttct gagaatcaca ccacactgga ccaggccagg tgggcctggg 117180
gcctggatga ggggtgggag ccaggggagc cctgccaggg gctgaggagg ccccaacccc 117240
catcacccaa ggccatccac actcgtgcct taatgaggcc atgttctgtc ccaatgagaa 117300
caagtccaat taagattaag tatggtcttc ccaggatcat ccagagtcaa ggggtgtcag 117360
ccagggacaa cccagaccag cctgaggtca gccagcatca cccaaggcca cacagctatt 117420
ctggcagagg actagaatag tcagctcatc gaggccctgg agatgcagaa tggagagttt 117480
atccctgcca gacagggttc ctcagatagg caggtccctc accacacatg acctccctga 117540
atatttccca gagtccagtt ggttctagac tatcacaata gtcttctgta ttcctgataa 117600
gcatgcagaa agctaacagg atgacaagaa attttatgca gaaaacagaa gcatctacag 117660
gatagaacag aggagaatag atactggaag tctgctggag accccagtgg agtctctttg 117720
tagagtcaag ctgtaagatc aaacctgcac tgagcctcaa gattgagtca agtacagagg 117780
caaccttcag gaccctaaag accttacagg caatggacag gatggagtcc aggcagacaa 117840
gtaaacgggc agtcatatgt aacataatga accatgtcaa cagagggtac tgagccaagg 117900
aaggctctgg gacacttgtg gataatctgc cactggatct cttgatgtat ataccaggtg 117960
atcagatgac agtttagtgg cgccatcgcc gttacagtgt taggtgttgt cctcgtcatg 118020
ggttcacgtg agaatgtgac accttttttag ttggatgtgt acagtaagct ctcaggcctg 118080
gtgttcctgg tatgatttta atgatccatg tgttcctata tctttaataa gtttataggg 118140
tgacattaag cttggggata agttgtttat caggctgtgc ctttagaagt tgatgtgcag 118200
ggattgttgt ttacaccaag atgcccagtc ttcctccagc ttccaaacgg agtcaaaggc 118260
catttgaaaa tgtgaaacct ctcagggcaa ggtacaatct ttttttttt taaagccact 118320 acctcacaca acatggagta atttaaagca gggtacagct tgatcgaaac acacacacac 118380
acacacgcat acacacaatg taagataccg agaaggggat caagggacac agaagtagag 118440
agagaatgag acagttcagg gatgtagaga tgagaggtaa ctagaggaaa ggagaaacac 118500
aaggactgga gggtaaagag ccagggacag aaagatccat gcaagcaaga cagacagaca 118560
caaggaaggg aaaggtggga agagacagac agacaaggtg cagcaatgta gcccacctga 118620
gactcccatg aaagtctggc acccactctc agatgaaagc caagtaccta cagacacgta 118680
cccacagcac ccacacagag cacctgcctg cctaactcaa gcccacctac ccatcgcctc 118740
tcctccaggc ctctgtcctc aggaagcaca ctgagggtaa ctcagtctgg acacttctaa 118800
ctatggctta gtgaacagcc tgagaggctc tggatccaca ggtcactacc acttgctggc 118860
cctgtgctcc atgccatgct tcaggggggg attcactgaa tgcatgaacc atagtctggg 118920
gtcaacatgt actaagggat aggatcctat caggatttgt ccaaataagg tccaaacaaa 118980
gtgaagaagg tgataggcga gaacagctgg cagctgagag aacgctggcc agttcttagg 119040
ccagagctta gggacaattt ccagacctag cctttcatct caactctagg tcatgggtaa 119100
cttcccagat ctctattttg ttcctggtaa ctatgcatgc tggtacaagt ctaagaacct 119160
cggtgagaca cagaaccagt aagatgaaag catccgtgga taaggaagaa aggagaagag 119220
tagaagggac aggaccctgg acacatgaga ttcccacacc caggaactgc tcatccagcc 119280
cgagaaacgg tataccccta gcacacagaa agaaaacagt accacaggtc taaaagagta 119340
gagtcagtgg gaaggggtac tactagggcg cctcctgcct ggtccaggag cagaggctgg 119400
gaaggggcac taaacagggg gaagcatgga gacagggaga tgaaggagcc tttgggactg 119460
catggtggga actagactgt tctctgaatg agcctgtgtg tgtggcagct gcctgagagg 119520
gaagacaccc agaggccagg cagaggaaaa gagtaatcag ggctgagggg actggggtgg 119580
gggtctgagg aagtcaaggt agctatcgcc catttatcag ggccatgaca tgcacttcat 119640
gggcacatat ctaaaaccag acctggccct cacctacact cagacaatgt cccttttgtg 119700
gatttaggga tttcagtact tcatcccatg gcctctcaaa ctggaagatc catctaaaag 119760
gctgatgttg tggtatcagg gcccaggact agagaatggg acactgagtg gcagaggtgc 119820
agaggacaca tacactcact cagatgaaag caatgcacaa gaagacagag ccatgtatga 119880
acactcctca gactcagacc cacagcactc acacccagct ccccacagac acacacagcc 119940
cctgcctgcc tgttccaaaa atcaaaccca tctacccact ccctctcctg caggcctttg 120000
tcctcagagt ggcacactga aggtagctca gcctgaacac ttcccatggg acctggtgaa 120060
cagcaggagc ctctggtcca cactccccac ctcttgttag ccctgtagtc tatgtgatgc 120120
tgttgagaac agggtacatg gcctctgcct ggtacagtct ggggtgcagg cttcaggtga 120180
ggcccaagtg tgaagagtgc agaagacagt gggcagagct gagagactgc tagccagttt 120240
tgttcaaagg actgtgatgg ctgctccagg ctactgaaca ttccaggact gcttcctacc 120300
ctcctcaaag atgctggaac acaaccaatc ctcaacacaa tccaatgtag ttgcctgtag 120360
cagggcatgc ctctgtacag cagggagtca cacagagcca catgagactc tagacctggg 120420
gactgcagag gggaaggcat gtccaagacg gcctcctcct tgttacccta ggttttcagg 120480
cctcaggata accactgaac aacatatgct gagtcctgtt ccccaggatg ctgatggaca 120540
ccaggtcaca gggctagagg ccaggagggc tagagcctgt gggcaggggg gctatattca 120600
ttcttcctgt gcttgcccag gagcaggtgc tgggcagggg cacaggacag ggtgaggcag 120660
ggagacaggg gcatgaaggg gcctctggga ccacaaggtg ggaactaggc tgtgcctgac 120720
tgagcctgtg tgtgtgacag ctgattcatg gggaagacac ccagagacca ggcagaggaa 120780
aagagtaatc agggctgagg tgactggggg ttgggaggtc tgaggaggta gaggcagcta 120840
tgtcccattt gtcagggtat ggggacatgt acttcataga cacagatcta agaaccaggc 120900
gtggttccca cctaccccca gacagtgtcc ctcatatggg cttagggatt tcagtacttc 120960
atcccacggc ctcacacctt ggaagatcca cctcaaaggc tgatgttgtg gtgtgggggt 121020
ccaggactgg ggccagggac actggttggc agaggtgccc aggacataga gtgctcagag 121080
tgtagttggg gacatgctga gcactgttcc tctgtgaggg gacaggctga gacagggact 121140
gaagtccatc cataggctca gcacatacca ggctctggat gggaacactg agctctgcca 121200
ccctccaaca tctggcacag cagcctcctg tgccagggaa gctagtcagc agggacagag 121260
ttcctgtccg ggctggatgg agtcttctct gctagcatcc aaaataagtg catcttcagc 121320
aataaggtcc agtcatggtg gacggccagg aacaaaggca gtaaacagcc tggtttgtgt 121380
ttggttatct acagtctctc tcactaaagc atcaagactt cttttaataa atttagaagt 121440
tgttttcttt tgaaacacgg tctctctatg tagtcctggg ggtcctggaa ctccctgtgt 121500
agaagaccag actgtcttca aacttaagga gatcctcctg tctctgcttc ctgaatgctg 121560
ggattaaaag catgtgccac cacacccaac ctaacccttt cttctgagag caacatgcat 121620
acaatttccc ctcttatttc cccagatttt caatcctttt atccacactt aaatctttaa 121680
tgctaaaatc tccctccctc catttccaag ctgcatgtgt tctactattc cctcaaatta 121740
tttttccttg tgtgcaggtt ttagatttga atgcaggaag ccttcactct ggcaaagcct 121800
cccccaaccc agcctttccc atttccacac ctcctaacac gtgatttagc ccacatcccc 121860
tcatgtgtat ggtgtttccc ttcagtctga ggtattaccc ccagtgtccc cttacagctg 121920
cctatggtca caaatacctt tcatctgttt ttgctgtgga aagcgtttat ttccccttga 121980
attttaatag ctttctgggt atactaccct gggttgagag tttagatttt tcagatcttg 122040
gaatatgtct ttctagacat ctagccttaa atgtttctac tgggggctac agaaatggct 122100
tggtggttga caacacatga tgttcttgca gaggagtggg ttttgattcc tagtacccca 122160
tatcagctaa gagctatgga agacacaaat ggaagagggg actctgagat tctgagaaaa 122220
gcctcatggt taagggtaca ctgagatact gagagagaaa gacagagaca ctgagaaaga 122280
cagaagcaca gaccactaaa agagacaggg aaacagagag agacagtgat gagatgcagg 122340
gacagagcaa cccagagaga cagacagaga catagacact gatagagaca caaagaagag 122400
aggggtcgtg gaagttttga gagaaactgg taggaggtga gagagacaca gagccaatac 122460
agacacagaa agacagagac tccagagaga cagagactga gagagacaga gactgggaga 122520
gacaaagata ctgagacagt cagagacacc aatgggtgct tttccagggg atccagattc 122580
aattcccagc acccacatgg cagctctcta ctgtaatccc agttccaggg tgccctgaaa 122640
aatccttcat gcatgtgaag cttagaagct cacacacaaa cacacagaca gacagacaga 122700
cagacagaca gacagacaca cacacacaca cacactcaaa tgaagagtgt ggttctcttt 122760
ctctctctct gatgaaagcc atgcaccaga agacagagcc atgtgtgaac actcctcaga 122820
ctcagaccca cagcactcac acccagctcc ccacagacac acacagccct gcctgcctgc 122880
ctgttccaaa actcaaaccc atctacccac tccctctcct gcaggccttt gtcctcagag 122940
tggcacactg aaggtagctc agcctggaca cttcccatgg gacctggtga acagcaggag 123000
cctctggtcc acactcccca cctcttgtta gccctgtagt ctatgtgatg ctgttgagaa 123060
cagggtacat ggcctctgcc tggtacagtc tggggtgcag gcttcagggg aggcccaagt 123120
gtgaagagtt cagaagacag taggcagatc tgagagactg ctaaccaatt ttgttcaaag 123180
gacagtgatg gctgctccag gctactgaac atcccaggtc tgcttcctac cctcctccaa 123240
gctgttggag cacaaccaac catctttgta attgcccagt tgtttgttat tgcctatagc 123300
agggcatgcc tctgcacacc agggagtcac acagagccac atgagactct agacctgggg 123360
actgcagagg gaaaggcatg tccaagaggg cctcctcctt gggacactgg gattccaggt 123420
ctcaggataa ccactgaaca acatctgctg agtcctgttc cccaggatcc tgatggaccc 123480
caggaggtca cagagctaga ggccaggagg gctagagcct ttgggaaggg ggaatgttag 123540
ggtttctccc atcctggtcc aggagctgct cacctgacag tgatacagga cagggtaagg 123600
cagagacagg gggatgaagg aaactttggg agcacatggt gggagtgtag gttgtgcttt 123660
tgcttagcct gtgtatatag cagctgcatc attgggaaga cactcagagg cccgacagag 123720
gaagagtaat caaggctgag gggacagcag tgtctaagga agtggaggca gctatggtcc 123780
atttgtcata gtattgggac atgtacttca tgaacactga tctatggacc aagcctggtt 123840
gtcatctgcc ctcagtcagt gtccctcatg tgggtttagg aatttcagta cttcatccca 123900
caagccagtc acattggaac ataaatgaaa tgctgatgct gtggtgctgg ggcccaggag 123960
tgcggggtta gtatactggg tgacagaggg tgtccagtaa atagattgct tagagtgtag 124020
gtggggacaa gctgtgcagt gttcctccat gaggggaaag actggtacag gttttgacat 124080
ctctttcgta tccataggcc ctgccatact gcccttgtcc atggtccctg tggggtcaca 124140
tacttagtgt caagtaaacc ataccacaaa ctggaagggt ctacactatc cttgtaggtt 124200
ctacactctc catgacttct cccaactcac acagactgtt ccaatacact actctcttca 124260
gtgggcaatc atgccatgaa cagagagtgg agggttatgg ttgccctata ttctgacaca 124320
tccaacagtc ttgtgcattt gactctcatg tgtacaagcg tgctcaggcc tgctgtagtc 124380
ccctcgagac agtgatgcct tccttgagag ccgattctca ctgtcagcat ctcctcagac 124440
caaagcccta tagatccagc ctctttgagg agctaatgta gtcagtcaca gggcttgatg 124500
ttggtggcta tagctgctgt ccccatggct gccagagatg cttgaccacc ataatcccag 124560
acttgagcat aggaataacc tggaatcaac agcatccaga cactgtaggg actggccaga 124620
gatgtgcata gaccctatgt catgtgacca agacctcttt ttctagtatc ttatttcatg 124680
aaagtctaca aaatacgatc ttctattcct tttattcctc tttgcctgct aacatggaac 124740
cttctagaaa gagggtcccc tctctgtcta ctgactgtga agatagatcc tgtaggtgtg 124800
atcacagagt aatgtttcat ttcttggcca gtctcaagcc aggggactca gggagagaga 124860
caggagaagg agagatgggg agagagacag aaagacagaa aaacaaagca agggagagac 124920
agaagcaggc agacctggag actgggtgct taggaaagag ataaatgtgg atacagggag 124980
tgaaagatag ggaattgaag acagaggtgg agataaagac cagaatatgg gagtcagaga 125040
cagacaagag atatagagat caatataggc aaacagagac tgagaaagac agtgatgaga 125100
cagagagaca tggagacaga caaggagaca gacatggaga cagacaagga gacagagata 125160
gaaataggga gagaaaataa tacataatta gtggttgatt aaggaagaga taatgaatgg 125220
caagaagaga cagaggcagg gagagacata tacaggtaga gaaaaagatg aagacagaca 125280
gagagagact gaaagaggga gaaagataca gagagaagag agactatgaa acaggcagag 125340

-continued

```
atataaagac agtgagagaa aaacagagag acagagatgg aagagagaca gagagacagg 125400
gagatagaga aatgggaaga caggaggacc aagagaagag acacacggcg aggcaagatg 125460
tagtagagag acctctgatg gaatcggcat aggtggaggc aaacatagat agactctctc 125520
caactgcagt tgacagactg agcagagaga ataccattca gagagaaaca gaggctaagg 125580
ctaggaaagg caagagtagc cagaggagac agagttgagc ctgtgggaca ggaccagacg 125640
ccatcttgga agaggcagtg acaagccagg gaggtgacag gctggtacag tttctatccc 125700
acagtccaca ggctggtgtc acaggcctgt ctcctcgtgg ccacagtcta tccctgcctg 125760
ccaagcctgt ctgtggaggg atgggggggg ggggggctgg gctgaggcag gccaggactt 125820
ttccagtgga gtggccaggc actgggctga gggcatgatc cctgcccacc atcccagtgg 125880
gtctgggtaa tggatggcct tgattatttt ccttcgtgtt tagggtggaa cctgcttaga 125940
ggcagctagg gctctccatg atggcctagc ctgtggtgag ttaatgaacc cctaagggta 126000
gttcttccac atgggctagg gttacaatct gggggttggg ggctcagata tcagtaccag 126060
aaacaaggct tactcccaac atgtcacact cgcacacaca cagctgccga gttactcatt 126120
ctgtgcagag ttggctcaca agggcacatg caaatggatg tttgtttcat acagaaaaac 126180
atgtttctca ctttctgagg ttgtttccag aaatagcatc agtgactccc ccacctgcag 126240
ctgcaggttc accccaacct ggccaggctg accagccttg gggatggggg actcccagca 126300
taggccactg ggactggggg tccatgaccc ctattgatga tgttgaattc agtgtttccc 126360
agttatcacc actgctggaa tctgacccac caagaggaca tgacaggaga tgggcaagga 126420
tgggtggctc aacaccccag ggaagtgaga gaggcaggaa ggctgtaggt gtgctccaga 126480
tcctgggtct acccagaacc atgggaatgg tgggcagtga tcatgccctc agcccagtcc 126540
ctggccactc cactggaaaa gtcttggcct gcctcagccc agacccccctc ccccacccct 126600
tctcagacag acttggcaga cagggagcta gcctgtggcc acatggagac aggcctgtga 126660
ctccaacctg tggactgtgg gatagaaact gtaccagcct gtcacctccc tgcttgtcac 126720
tggctctttc aagatggtgt ctgaccctgg ctccatctct ggccaaccct gcctttccca 126780
gccttagcct ctgcctcttt ctctctctct cagtgtgatt cttgctcagt ctgtccctca 126840
gttactgtct ctccatctct aacaaaacat aagagctgtc tctattaaca ccttgtctct 126900
cctctttctt cttctccttc tccttctcct tctccttcct ctctctctct ctctctctct 126960
ctctctctct ctctctctct ctctctctct ctctctctct ctctcatctc tgcttgtgcc 127020
ccctttctct aggtgcacat ctcctacctc tgtctgtcta tctgtgtctc ttccttctgt 127080
catctcctct ctatcattct ttcagtcctt ctctatgtct cttttctgtt gatgtctgtc 127140
tttgtgtgtc tctctctcca tcccattcct tttatgactc tggctcccct tatctctctg 127200
tctgtatttc tgccccactt ctctgtcttc ctatcttttt gtcttttctc tgtttctgat 127260
ttttctctcc atgtctttct ctccactttt ctctctccct ttctgagtct tcctgcatct 127320
gtctcattgc ttctccatct cgctctctct ttctctgttt tctgtctctg ttcttgtatc 127380
tctgtgtgcc tctccatgtc tctctgctgt ctctttttct ccatacagca atttactaaa 127440
agaacaaaca tcaaggcagg aaagtatata tatttcaaat aaaagttctt caaattgcta 127500
tgtcctatac tccaagaagc atttccaaag tatagattaa tttaaccctt ttaaatgaaa 127560
agatacattt ttaacttcta aagtgtctcc acaaagaaat gaatgttttt aattaagaaa 127620
tgttgtaatt tagtgttggg ctcctgtctt ataatgtaca cttccttata aatctagcca 127680
tgtggcttat atccatttgg tatgctcgga gctttatgta ataaacgtct tcccgatagg 127740
```

-continued tgcaaggatt ggtgttttgt actgcttact acatacatgc ttttaatcat tccaggacat 127800
accgtccctc tgctgctgct tctcaccgtc tttgcctttc tctcaccctg tccatctttc 127860
tctctcccca tctctctgtt tctgtccctt cctgtttcag tctctctcca atctccctgt 127920
gtttctctct ctctctctct cctgatgtct ctttctctgt gggcttgtct ccccatctgt 127980
cctcttcatt tctgtatttc tccttatctt tctatctctg tccatgactc tgtctctttc 128040
tgcctcgttc atcccctgcc cccctgaagg cacaatgaca cttttatcag ggtttaatag 128100
gaaagtttca gggcaggaaa gttgtaagac tcaagcagct gccccgagga ggccagtggg 128160
ggagattggt aaaaagccat gacatctaat ctgacatgga ggtcaggcac atgtcccaca 128220
agcagccaca tggcgagaag gggggcagtta gagaacaagt aagaaagccc agcatgttgg 128280
ggaggaagcc aaggtgttaa ggaaaacttg ctcagaggga gacagaaaga aggaagctac 128340
aattctgtga attcagaaag gaagctgact tacagcccca catggctata gcccctaagc 128400
ttctggccct tcctcttctg tctcttcctg ttctctgtca cccctgtttc tccctattct 128460
ctgtcacacc tgtctctgtg ctcccattaa tctctctctg tctctacaca tctccacctc 128520
tgcctccttc atctctgtct tttccggaac cctgtctgtc tctgtcaggc ttctccttgt 128580
ctccccctgc agacttgcag tttctccctt tgtcttcctc tgtcttacct ttattatgtc 128640
tccccgtctt tcctaccttc ctgactttct gtctcttacc ctgagtcccc tggcctgaaa 128700
ctggccaaga aggaaaacat cagtctgtga tcactcctac agggtctgtc tccatagcca 128760
gcagagaggg gaccctcttt ctagaaggtt ccctgttcgc aggcaatgaa gaataaaagg 128820
aatagaagat cccgttgcat taaggtttca tgagataaca tactaggaaa agagaccttg 128880
gtctacgtag aagtctggtc agtccctgaa gtgtctagac gcacttgatc cctaggccat 128940
cactatgtct gaggtcatgg tggtcaagca tctctggcag tcacagtgaa agcagctgtg 129000
gtcaccaaca tcaagccctg tgactacaat agctcctcaa agaggctggg tctgtggggt 129060
tttgttttga gggtcagcta gaaatgggag tgagtccaag gaagacccac tgcccccgcc 129120
cccgagagat aggggaatga gcatgcttgc acacgtggac atgaaaggca caagagtgtt 129180
gtatgtgaca gtttgaggtg accacattct gccctctctg tgcctgtcat ggttacaact 129240
gaggacagtg gtggatttgg gcagagtctg tgtgagctgg gagaagctgt ggagagttgc 129300
aagcatggca tgtagatatc agaagccctg gtcttccagc agtcctcatg gtgatggttc 129360
agtaggacac tggatgtgtg gcccatgcta gggtcatggg caaggctggt atgggttgac 129420
tctatggctg gacaaagagc tttaacctcg tcagcttccg caatatggag gaacactgca 129480
cagcttgccc ccacctgcac tctgagcact ctgtacactg gacatgctct actacccagt 129540
gtctcagact ccagtcctgg gccccagccc catagcacaa ccatgtttat aatccctcca 129600
gtgtgagagg ccatgaaatg ttgtggagct cagtctgaag gcaggtggga gacaggcatg 129660
cttttggatc catgtccatg aagtatatgt ccacattcca tgacaaagga gccgaagcca 129720
cctctatttt ctcaaggacc ccctcagtcc tcattactct tcctctgcct ggcctctgga 129780
tgtcttcccc atgaatcagc tgtcacaaac acaggctcag tcagagcaca gtctagttcc 129840
caccttgtgg tcccaaaggc tctttcacgc cagtgtctcc ctgccttacc ctgtcatgca 129900
cctctggcca gccagctgct cctgggcaag gacgagaaga agccaagtag ttcctcttct 129960
cacagactct agtcctgctg gcctctaact ctgtaacctt ctggtgtcca tcaggatcct 130020
ggggccacat cactctgagt gtgtttatca ccggcaatcc tgagggctaa gatttcagat 130080

-continued tctaaaggag gaggcccccg tggacatgcc ttcccctctg cagtccccag gtctagagtc 130140
tcatgtggct ctgtgtgact ccctgatgta cagaggcatg ccctgctaca ggcaattaca 130200
atggattggg tagagggttg gttgtgctcc aacatctttg aggagggtag gaagcagacc 130260
tgggatgttc agtagcctgg agcagccatc actgtccttt gaacaaaact ggccagcact 130320
ctctcagctc tgcccactgt cttctgtact cttcacactt gggcctcacc tgaagcctgc 130380
accccagact gtaccaggca gaggccatgt accctgctct cagatgatgt ttcatacaga 130440
ttacagagct aacaagaggt gtggtgtgtg gaccagaggc tcatgctgtg tagtcaccca 130500
tggtcctgct gaaaagcagg ctggggctaa aaagagaata gagtatgaga cacaccaaga 130560
caaatgctga tcaaagccca atgtttacta aaaatctgtg cttatataaa aggaaagccc 130620
ttctcctgca gatccacttt tgatgtctgt tgccagcctg taagcaattt gtctgacagc 130680
actagtttga caagaaggtg tcaatcactg ctgtctttgg aatctctcag cctctcagca 130740
ggtatcagtg tcttggagaa gaagagcaat ggtgacagaa caatagaatc atctaggtgg 130800
gaaggctcta ccccaggtgg tctcattctc agtggcagca aggtctgagc cagcctgctc 130860
aaggctgggg gaggctacaa tgttattcaa caggtcccat gggaagtgtc caggctgagc 130920
tactcagtgt gccactctga ggacaaaggc ctgcaggaga gggaatgggt agatgggttt 130980
gaggtttgga acaggcaggc aggggctgtg tgtgtctgtg gggagctggg tgtgagtgct 131040
gtgggtctga gtctgagggg tgttcacaca tggctctgtc ttctggtgca tggctttcat 131100
ctgagagaga gaaagagaac cacactcttc attagagtgt gtgtgtgtgt gtgtgtgtgt 131160
gtgtgtgtgt gtgtgtgtgt gtgtgtttgt atgtgagtct gtctgctgtc tgtgtgtaaa 131220
tgtgagcttc tatgcttcac atgcatgaag gatccttcag ggcaccctgg aactgggatt 131280
acagtagaga gctgccatgt gggtgctggg aattgaatct ggatcccctg gaaaagcagc 131340
cagtgctctt aatccttttg gtgtctctgc ctgtctcagt atctctgtct ctctcagtct 131400
ctgtctctct ggagtctctg tctttctgtg tctgtactgc ctctgtgtct cccacacctc 131460
ctaccagttg ctctcaaaac ttccacgtcc cccctcttct tcatgtctct atcagtgtct 131520
gtgtctctgt ctgtctctct gtgtctctct gtccctgcag ctcatgactg tttctctcta 131580
agtgtttccc tgtctctttc agtggtctgt gcttctgtct ttctcagtgt ctctgtcttt 131640
ctacttcaga atctcagagt cccctcttcc atttgtgtcc cttcttgggc tcattcactc 131700
tgcctccagt gtcatcactt gtgagaccag aacctactat gagtccagag gactgtcctt 131760
catggtctgt gaccagctgt gatctgggga acactgggga aggcatgaac agggagggac 131820
ctgcctgtct gtggagccct gcctgtcagc atgaactccc cattctgcac caccagagcc 131880
ctgctgagct gactattcca caccacctcc agaaaagggc attgaatcct gtggaaccga 131940
tggctcttag ctgatacggg gtactaggaa tcaaaaccca ctcctctgca agaacatcat 132000
gtgttgtcaa ccaccaagcc atttctgtag ccccacagta gaaacattta aggctagatg 132060
tctagaaaga catattccaa gatctgaaaa atctaaactc tcaacccagg gtagtatacc 132120
cagaaagcta ttaaatttca ggagaaaata aaaaagcttt ccacagcaaa aacagatgaa 132180
aggtatttgt gaccatagac agctgtaagg ggacactggg ggtaatacct cagactgaag 132240
ggaaacacca tacacatgag gggacgtggg ctaaatcacg tgttaggagg tgtggagatg 132300
ggaaaggctg ggtgggggga ggctttgcca gagtgaaggc ttcctgcact caaatctaaa 132360
acctgcacac aaggaaaaat aatttgaggg aatagtagaa cacatgcagc ttggaaatgg 132420
agggagggag attttagcat taaagtttta agtgtggata aaaggattgg aaatctgggg 132480
aaataagagg ggaaattgta tgcatgttgt tctcagaaga aagggttagg ttgggtgtgg 132540
tggcacatgc ttttaatccc agcattcagg aagcagagac aggaggatct ccttaagttt 132600
gaagacagcc tggtcttcta cacagggagt tccaggacac ccaggactac atagagagac 132660
cgtgtttcaa aagaaaacag tttctaaatt tattaaaaga agtcttgatg ctttagtgag 132720
ggagactgta gataaccaaa cacaaaccag gctgtttact gcctttgatc ctggccctcc 132780
accatgactg gaccttattg ctgaagatgc acttattttg gatgcagagc aaagaagact 132840
ccatccagcc tggacaggaa ctctgtccct gctgactagc ttccctggca cgggaggctg 132900
ctgtgccagc tgttggaggg tggcagagct tagtgttccc atccagagcc tggtatgtgc 132960
tgagcctatg aatggacttc agtccctgtc tcagcctgtc ccctcacaga ggaacagtgc 133020
tcagcatgtc cccaactaca ctctgagcac tctatgtcct gggtacctct gccaaccagt 133080
gtccctgacc ccagtcctgg acccccacac cacaacatca gcctttgagg tggatcttcc 133140
aaagtgtgag gccgtgggat gaagtactga aatccctaag cccatatgag ggacactgtt 133200
tgggggtagg tgggaaccac gcctggttct tagatctgtg tctatgaagt acatgtccca 133260
ataccctaac aaatgggaca tagctgcctc tacctcctca gaccccccaa accgcagtcc 133320
cctcagccct gattactctt ttcctctgcc tggtctctgg gtgtcttccc catgaatcag 133380
ctgtcacaca cacacaggct cagtcaggca cagcctagtc cccaccttgt ggtcccaaag 133440
gccccttcat gcccctgtct ccctgcctca ccctgtcctg tgcccctgcc cagcacctgc 133500
tcctgggcaa gcacaggaag aatgaatata gtccccctgc ccacaggctc tagccttcct 133560
ggcctctagc cctgtgacct ggtgtccatc agcatcctgc acaacaggac tcagcatatg 133620
ttgttcagtg gttatcctga ggcctgaaaa cctagggtaa caaggaggag gccctcttgg 133680
acatgccttc ccctctgcag tccccaggtc tagagtctca tgtggctctg tgtgactccc 133740
tgctgtacag aggcatgccc tgctataggc aactacaatg gattgtgttg agggttggtt 133800
gtgtttcagc agcttggagg agggtaggaa gcagacctgg gatgttcagt agcctggagc 133860
agccatcact gtcctttgaa caaaactggc cagcactctc tcagctctgc ccactgtctt 133920
ctgcactctt cacacttggg catcccctga agcctgcacc ccagactgta ccaggcagag 133980
gccatgtacc ctgctctcaa cagcatcaca tagactacag ggctaacaag aggtggggag 134040
tgtggaccag aggctcctgc tgttcaccag gtcccatggg aagtgtccag gctgagctac 134100
cttcagtgtg ccactctgag gacaaaggcc tgcaggagag ggagtgggca gatgggtttg 134160
aggtttggaa caggcaggca ggcaggcagg ggctgtgtgt gtctgtgggg agctgggtgt 134220
gagtactgtg ggtctgagtc tgaggagtgt tcacacatgg ctctgtcttc tggtgcatgg 134280
cttccatctg agggggtgtg tgtgtgtgtg tgtgtgtgtg tgtgtgtgtg tgtgtgtgtg 134340
agcttctaag cttcgcatgc atgaatgatc cttcagagca ccctggaact gggattacag 134400
aggtgagctg ccatgtgggt gctgggaatt gaatctggat cccctggaaa tcagccagtg 134460
ctcttaatcc tttttgtgtc tctgcctgtc tcagtatctc tgtctctctc agtctctgtc 134520
tctctggagt ctctgtcttt ctatgtctgt actgcctctg tgtctccctc acctcctacc 134580
agttgctctc aaaacttcca tgtccccccc ttctctgagt ttctatcagt gtctgtgtct 134640
ccgtctgtct ctctgtgtct ctctgtccct gcagcccatg actgtttctc tctaagtgtt 134700
tccctgtctc tttcagtggt ctgtgcttct gtctttctca gtgtctctgt ctttctctct 134760
cagaatctca gtgtcccctc ttccatttgt gtcccttctt gggctcattc actctgcctt 134820
cagtgtcatc acttgtgaga ccagaaccta ctatgagtcc agaggactgt ccttcatggt 134880
ctgtgaccag ctgtgatctg gggaacactg gggaaggcat gagcagggag ggacctgcct 134940
gtctgtggag ccctgcctgt ccgcatgaac tccccattct gcaccaccag agccctgctg 135000
agctgactat tccacaccac ctccagaaag gggcattgaa tcacgtggaa cctaagaaca 135060
ccgtgttgtc aaccaccaag ccatttctgt agccccacag tagaaacatt taaggctaga 135120
tgtctagaaa gacatattcc aagatctgaa aaaaatctaa actctcaacc cagggtagta 135180
tacccagaaa gctattaaat ttcaggagaa aataaaaaag ctttccacag caaaaacaga 135240
tgaaaggtat ttgtgaccat agacagctgt aaggggacac tgggggtaat acctcagact 135300
gaagggaaac accatacaca tgaggggacg tgggctaaat cacgtgttag gaggtgtgga 135360
gatgggaaag gctgggtggg gggaggcttt gccagagtga aggcttcctg cactcaaatc 135420
taaaacctgc acacaaggaa aaataatttg agggaatagt agaacacatg cagcttggaa 135480
atggagggag ggagatttta gcattaaagt tttaagtgtg gataaaagga ttggaaatct 135540
ggggaaataa gaggggaaat tgtatgcatg ttgttctcag aagaaagggt taggttgggt 135600
gtggtggcac atgcttttaa tcccagcatt caggaagcag agacaggagg atctccttaa 135660
gtttgaagac agcttggtct tctacacagg gagttccagg acacccagga ctacatagag 135720
agaccgtgtt ttaaaagaaa acagtttcta aatttattaa aagaagtctt gatgctttag 135780
tgagggagac tgtagataac caaacacaaa ccaggctgtt tactgccttt gatcctggcc 135840
ctccaccatg actggacctt attgctgaag atgcacttat tttggatgca gagcagagaa 135900
gactccatcc agcctggaca ggaactctgt ccctgctgac tagcttccct ggcacgggag 135960
gctgctgtgc cagctgttgg agggtggcag agctcagtgt tcccatccag agcctggtat 136020
gtgctgagcc tatggatgga cttcagtccc tgtctcagcc tgtcccctca cagaggaaca 136080
gtgctcagca tgtccccaac tgcactctga gcactctatg tcctgggtac ctctgccaac 136140
cagtgtccct gaccccagtc ctagaccccc acaccacaac atcagccttt gaggtggatc 136200
ttccaaagtg tgaggccgtg ggatgaagta ctgaaatccc taagcccata tgagggacac 136260
tgtctggggg taggtgggaa ccacgcctgg ttcttagatc tgtgtctatg aagtacatgt 136320
ccccataccc tgacaaatgg gacatagctg cctctacctc ctcagacctc cccaaccccc 136380
agtcccctca gccctgatta ctcttttcct ctgcctggtc tctgggtgtc ttccccatga 136440
atcagctgtc acacacacac aggctcagtc aggcacagcc tagttcccac cttgtggtcc 136500
cagaggcccc ttcatgcccc tgtctccctg cctcaccctg tcctgtgccc ctgcccagca 136560
cctgctcctg ggcaagcaca ggaagaatga atatagtccc cctgcccaca ggctctagcc 136620
ctcctggcct ctagccctgt gacctggtgt ccatcagcat cctggggaac aggactcagc 136680
atatgttgtt cagtggttat cctgaggcct gaaaacctag ggtaacaagg aggaggccct 136740
cttggacatg ccttcccctc tgcagtcccc aggtctagag tctcatgtgg ctctgtgtga 136800
ctccctgatg tacagaggca tgccctgcta taggcaacta caatggatta tgttgagggt 136860
tggttgtgtt tcagcagctt tgaggagggt aggaagcagt cctggaatgt tcagtagcct 136920
ggagcagcca tcactgtcct ttgaacaaaa ctggccagca ctctctcagc tctgcccact 136980
gtcttctgca ctcttcacac ttgggcatcc cctgaagcct gcaccccaga ctgtaccagg 137040
cagaggccat gtaccctgct ctcaacagca tcacatagac tacagggcta gcaaagaggt 137100
ggggagtgtg gaccagaggc tcctactgtt caccaggtcc catgggaagt gtccaggctg 137160
agctaccttc agtgtgccac tctgaggaca aaggcctgca ggagagggaa tgggtagatg 137220
ggtttgatgt ttggaacagg caggcagggg ctgtgtgtgt ctgtggggag ctgggtgtga 137280
gtgctatggg tctgagtctg aggggtgttc acacatggct ctggtgcatg gctctcatct 137340
gtgtgtgtgt gtgccacagg ctccatttga gtgctcggtt ggctccattg ctgtacctct 137400
gtctcccttg ttttctatct gtctgtcctc cctgtctgtc tgtctctcct ttcctatgcc 137460
tcctcctcat atccatgtct gcatctcttt ctatcagtct ctatccctgt gacccctggt 137520
ttccatttct gtctttctgc atatctttcc atctttctct ctgtgtgtct gtcctcatct 137580
cttccagtgt ccgtgtttct gtttccctct gttcccatgc ggaggtatgt tctcacaatc 137640
cttaagttcc ctggtcccct gtcccccatt tcttgtcata ttatcccatc agtgtctctg 137700
tgcctctctg tctgtgtctc tgtgttgtct ctgtgtgtgt ctctcagtat ctctctctct 137760
ctctctctct ctctctctct cagtatctgt atttctttta gtaactttgc tatcttttta 137820
agtatctctg tctttcttca tctctgtctc tcttgaggtc tctgtctttc tgcatgtcta 137880
atgtttctgt atctctctca cctcatctct gcctctctca atattcagta gatccatgcc 137940
cctttattct ttgtgcctct gtctctgttt gtctctttct ctgtctctct gtctttctct 138000
ctctcagaat ctgtgtccct catgttattt ctcaaaatgc ctccctaact ctttcaataa 138060
cagtttctgc ctcttctttc tgggcctggc tcaatcttcc ttcttggacc tcagtttcat 138120
tggttgtgag accataccct gctatgagtc cagaggactg tcctccatag tctagaacca 138180
catgctatct aagggatatt ggggcaatac atgtgtagtg agatacctgc ctttctgatg 138240
agccctgtct ggcagggata aattctccat tctgcatctc cagggccttg ctgagctgac 138300
tattctagtc ctctgccaga atagctgtgt ggccttgggt gatgctggct gacctcaggc 138360
tggtctgggt tgtctctggc tgacacccct tgactctgga tgaccctggg aagaccatac 138420
ttaatcttaa ttggacttgt tctcattggg acagaacatg gcctcactaa ggcacgagtg 138480
tggatggcct tgggtgatgg gggttggggc ctcctcagcc cctggcaggg ctcccctggc 138540
tcccacccct catccaggtc ccaggcccac ctggcctggt ccagtgtggt gtgattctca 138600
gaacagtagc tctggtttgg ggcacctgtg ctgagaaagg ctcaggatga ctcagctgcc 138660
ctcagctcag agctgctttg aatgtttcag caggtgatag acaacagaga cttcagaaga 138720
gagaaaaaca agttgctaat gtgaacatcc ctgccctacc cccacacctg tactgcaaac 138780
attgttgacc ccagatagag atcccaggac agcaagtgat agacaaagga ggctccagag 138840
gagagaaaaa tagtatctac aagcatgacc acttctgccc tgccccacac ctgccctgca 138900
aagctcccca ggatgctgac cccacatctg tagaccccag gccagaggct ccatctccca 138960
gggcctgggc ttgctttgtc tccattctgt gcctctgagc ctgggcaagg ccaatgagca 139020
aaggggtcac tgtcccagtt gcagcccagt gtgtgaacag tgttgtgggg attctggaat 139080
cttctgcagg aatcccctgt agggatcctc ctaatgtgaa tgaggcttgg aatagcaaag 139140
ggacgtcttg taaaatacca ctgattcctt gggcctcaga caatggattt gagatgagga 139200
ccaaggtcca gggccagtgt tggtaagcag aatttggggc tagagttcag gcttagaagt 139260
caatgatgag ggccagggcc cagtgactag gtcagggccc attgatcagt acaggaccca 139320
gttgttagag ccggagctca atgatctgga ccaagtcaca aggccaaatg atcaggatca 139380
gtagccagtt accaggaccg agatccaggt ttcacagcca aagccaggtt accccaacca 139440
gagaccattc atcggaatct gggtctgttg atcggagccc aagcacgctg ctgtaaacca 139500
gagctgctct aaagcagaac tcagtgctga gcaccagaga taagtgatga gaccaggatt 139560

-continued cagtgattaa ggaaacaaaa ccaaaggtca ataggatatt atgtggagag aggggagaga 139620
gagagagaga gaggacagag agagaaagag cggtaggttc aggactaagt ctcagtgagg 139680
agggtcagga gtcagtggtt tgaacccaga cacactgctc aggtccacag ttcaacggtg 139740
agagccaggg gtcagctatc agaaccaggt ccagtaacta caaccaaaaa ccagtggccc 139800
caaccaaaaa ccagttacta aaacccgaat agaatagaaa ctagccaggc agtgatagct 139860
ttaatcccaa tactcaggag tcagaggcag gtggatctct gagttcaagg tcagcctggt 139920
ctacacaatg agttctaaga cagccagggc tacacagaga aaccctgtct ggaaaacaag 139980
caaaagccta gaaaccgtgg actcagtggt cagtggcagt tcttggtgac taagaccatg 140040
gtcaagaggt caagcaggac tcagcggtta gaatcagggc atgggtgatg acagcctgtt 140100
ccagggatca gaaccaggtc taagggcaaa ggccatgact gagtcatcaa acagtgtctc 140160
ttcataagtc ctagccaggc ccaaccaggc ctagggtgtc agatcaggca agactgatgc 140220
ggtatgtgtg aggtggtatg acaatacatc tcagtatctc tgggacccca ccaccatctt 140280
ccctgcctcg gtccactcac aaatctctgg ctctctcact gtctttgtct cattcttgtc 140340
tagctttcta ccgtgtcccc tctccccaca tttgtctctc ccagtatctg tctctctgaa 140400
agtctctgtg tcccctctga ctttctcagt gcttatgttc cctgcccctt gatcatttga 140460
gagggggatg gtaagtagag aattatggaa cagtgagtgt gtgtctctat atgtgtgtgt 140520
gtgtctgtgg ggctggcagt gggtatgtgt gagtatgtgt gtgtctgtgt gagtgtgtgt 140580
ctgtggggtg acagtatgta tgagtgtcag tgtgtgtgtg tgtgtgtgtg tgtgtgtgtg 140640
tgtgtgtgtg tgtgtgtctg tgtgtctgtg tgtctgtgtg tctgtgtgtc tgtgtgtctg 140700
tggggtggca gtgtacatgt gtgagtgtgt gaatcaaaat gtgtgagcat gtgtgtgtgg 140760
aggtggtaat gtatgtatgt atgtctgtgt gtatgagtgt gtgtctatgg gagtggcagt 140820
gtatatgtgt gagtatattg tgtattgtgg gtacgggtgt gtgtctgtgt gagtgtgtgt 140880
ttctatgtgt ctgtggaggt aacagtgtgt atgtgtgagt gtgtgtctat atgagtgtct 140940
gtatgtgtgt gtgtatgaga gagagagaga gagaaagaga gagtgtgtgc agggtgatag 141000
tgtatatatg tgagtttgtg tgtatgtgag tgtgtgtttg tgtgtatgaa tgtgtgtgtt 141060
tatggggtga cagtatgtat gtatgagtgc atgtgtctgt ggggtagcag tgtgtatgtg 141120
tgagtgtgtg tgtgtgtgtg tgtgtgtgtg tggtatgtgt gtgtgtgaga gagagagtgc 141180
agggtgatag tgtatatatg tgagtgtgtg tgtctgtttg tgagagtgtg tgtttgtgtg 141240
tatgagtgtg tgtgtctatg gagtgacact atgtatgcat gagtgcatgt gtctgtggga 141300
tagcagtgta tatgtgggag tgtgtgtgtg tgtgtatgtg cagggtggta gtgtatatat 141360
gtgagagtgt gtgtttgtgt gtatgagtgt gtatgtctat ggggtgacag tatggatgga 141420
tgtatgagtg cctgtggggc agcagtgtgt atatgtgagt gtgtgtgtgt gtgtgtgtgt 141480
gtgtgtgtgt gtgtgtgcag tgtgagagtg tatatatgtg agtgtgtgtg tctgtgtgtg 141540
tgagtgtgtg tgtttgtgtg tatgagtgtg tgtgtctatg ggatgacagt atgtatgtat 141600
gagtgcatgt gtctgtgggg cagcagtgtg tatggtgagt gtgtgtgtga gtgtgtgtgt 141660
ctgtgtgtgt gtgtgtgtgt gtgtgtgtgt gtgtgtgtgt gtgtgtgcca cttccctaat 141720
atgttctctt ccagctatgg cttctgcttc atccttcact caaggccaga cctcactggc 141780
cagtccacag cataatacca gccatgcctc tacccaataa ttgtatgtgt cagggagcca 141840
agaggatgga cagggatctt gttcttgggg tgagaatgtg agaacttttg gggagccctt 141900
ccacacaccc atgcagtagt agacacctct gcaaagctat gcacatcctc acactagcac 141960
actgcacaac catgcactct ctgcagactc actgttcacc atgaacccag ctagtcagat 142020
tcatatgtga aactcatatc agcctctgca cacacataca cacatattac acccatgcac 142080
acacatgtac acatacatac acatgtacac atacatgtgt acacacacat atagagaagg 142140
cattggtggg gaaaacatta ggccatggct acagtacagg gcacaaggat ggtggtacag 142200
aatgaggtca ggctgggtca gcataacaag aacacttgga caaagtgagg gtagtgtgtg 142260
tgtgtgtgtg tgtgtgtgtg tgtgtgtgtg tatgtgtgtg tgtgtgtaca cgttgaaagt 142320
cttcagtaga ctggtatcac tagccctgat atgggcaaca cagcaagcct gggtcacact 142380
caagctgagt atcagggtaa ccagggcctt ctaaccaagg gtagatgcag cctgtgttcc 142440
gtttactgac cagtgagaag ccatgagctg aaccagacca gaagaccctt actgttccca 142500
cccaaccccc acccagttta gtctcagcaa gaccctgtac tgtgggccac agctctcccc 142560
cacaccccac ctgtagcaca aacactattt gcaaacattt ctaaaaatga tgagaacagg 142620
aaccacagag cagagggggg gactggcgtg gaaagcccca ttcacccatg ggactgaaac 142680
tcggggaacc agaaccgtaa ggagatttgc atggtgctgg gggaggttgg ccctggatca 142740
gtgagcccag agagttactg gtttctcact tccatcaggt caacctcctc aacccccaaa 142800
aatggccagg cctaggctat ggatgagttt caatgaccag gccctaagga cgagtcacag 142860
aggacttcct ggtgggctca ggcagcagac ctgcccagat ggattgcaga accaggggga 142920
gccatggcca ggaaggccag acgccttagg ggtgtgctgt ctctgcatcc tttgccctct 142980
ctgctcctca cagtccatct gccatctcac aatccctcct gtcgctctgg ggcccagacc 143040
tggccagtct gggtacctgt ggaatacacc caaagaagca atccccagcc tcaggaccca 143100
caactacttc ccctacagac atgagtgatc tcagcccaca tgtctggggg ccacagaagc 143160
ccctaagacc ctactctgct aataggccct cctcccacca gccaagacaa tacacaggca 143220
aggtgatgtg gatgagtcac cccatgggta cctgtgtctg agatacaccc tgtgggtatc 143280
ctggccagaa tctggtgacc aacccaacct gtgtccctag aggagaactc tgtgcctgca 143340
ctcacctacc cacctaactc caagcttggt atgatgcaga gcccctgtgt agacctaaaa 143400
gtcagccata ggacagggtc aagaatgact cttcctacac ataaagtctt ctactaagac 143460
agtaaggtag acacacaaac atacccggat gcagagacac acaggcatgc agagaaggca 143520
tgtagacaca aacgcatgca taaacgcaca aacatacaga tatatgctga caaatataca 143580
cagcaactta caagtacaca gacacacaaa cagacaaaca tgcacagaca gaaacacaca 143640
gagctcaaaa tcaagtatac acagacaaat ttacacagag acttacagat acacagatat 143700
atgagacaca cccaaacaga cacacacatg ggggcacaga aaaacataca agcagacaca 143760
tgcagactta aagacccaca agacatggag agatacaaaa acacacaaca cagacacaga 143820
gatatagaga cacacagacc cacaaatatg aacagacaca gagacaccca gaaacaaaaa 143880
cacactcagg cattccactc ccaatgggcg tacacatggg catacacagc ccagtcacac 143940
agacaaacat aacacataca gaagtgcagg catacatatc acacaataca cgctggtatt 144000
cacacacagg tgtgctcaca aaccccacac actcacacat aaaagttgac actggcactc 144060
ccactccgag gcacatgctt agccacagcc ggctgacact gcacacccca cacacgttcc 144120
agagactccc acagaactgg aagctcaccc aggcccaccc aggctctcag gccacacaca 144180
tgggacatct cagagacatg tgggatacag ttgctcacag gtttcatgag gactcacagg 144240
cctgtccttg aacattcccc tgagcagggg ctcccttctt aaagcacagg gatcccattc 144300

-continued

```
tttacagata agcacccaga cagaggcact accaggccca gaccacacta gacacacaca 144360
gctctgcatt gtcccacact caaacacagc tctgtcgcct gagctcatgc cagtcacaca 144420
gaacacagac atgggctcgt gtgctagaga gacataagca atggtagcca aggtgctcac 144480
atcatgccca tacacacaca cacacacaca cacacacaca cacacacaca cacacacaca 144540
caccctgtga acaggcctgc agtcctgact gaagccctgc tctacccaat ttagtgagtc 144600
ctgcacctga accctcttac cctcacagcc cctgacctct ccctgtgtgc tgctcagcta 144660
tggccccttc ccattcctaa cgtgccaccc taagatgtcg gttccgtgca tcaccgcaca 144720
catgctcttg ggataaggcc ttagaaggct ctgtaccatc tgcagctcat gccactgcct 144780
tccctggtaa ccctctcctg catacaaggg ctgcaagggt caatgatatg aatccatcca 144840
tgctctgacc ccagcttggc ccagggcagc catgatggga ggacaacccc tgaccccagc 144900
ctaagatagt tgttgcacag agcagtccct taacgcagga taactgttgg aggtaggcag 144960
cacttgaccc ctgcccaagc tagatgatgg gagaggatag gtccagccat tgacagctgc 145020
tgtagcaagg caggccctgg tcccaggtta actcaaggct gctgcttagg caacccctga 145080
ctccagctcc agaagtctgc tgggggtgta tcctctggct acaggagctg aacaaatggc 145140
gcgccgcggc cgctcgacca attctcatgt ttgacagctt atcatcgaat ttctgccatt 145200
catccgctta ttatcactta ttcaggcgta gcaaccaggc gtttaagggc accaataact 145260
gccttaaaaa aattacgccc cgccctgcca ctcatcgcag tactgttgta attcattaag 145320
cattctgccg acatggaagc catcacaaac ggcatgatga acctgaatcg ccagcggcat 145380
cagcaccttg tcgccttgcg tataatattt gcccatggtg aaaacggggg cgaagaagtt 145440
gtccatattg gccacgttta aatcaaaact ggtgaaactc acccagggat tggctgagac 145500
gaaaaacata ttctcaataa accctttagg gaaataggcc aggttttcac cgtaacacgc 145560
cacatcttgc gaatatatgt gtagaaactg ccggaaatcg tcgtggtatt cactccagag 145620
cgatgaaaac gtttcagttt gctcatggaa aacggtgtaa caagggtgaa cactatccca 145680
tatcaccagc tcaccgtctt tcattgccat acggaactcc ggatgagcat tcatcaggcg 145740
ggcaagaatg tgaataaagg ccggataaaa cttgtgctta tttttcttta cggtctttaa 145800
aaaggccgta atatccagct gaacggtctg gttataggta cattgagcaa ctgactgaaa 145860
tgcctcaaaa tgttctttac gatgccattg ggatatatca acggtggtat atccagtgat 145920
tttttctcc attttagctt ccttagctcc tgaaaatctc gataactcaa aaaatacgcc 145980
cggtagtgat cttatttcat tatggtgaaa gttggaacct cttacgtgcc gatcaacgtc 146040
tcattttcgc caaaagttgg cccagggctt cccggtatca acagggacac caggatttat 146100
ttattctgcg aagtgatctt ccgtcacagg tatttattcg cgataagctc atggagcggc 146160
gtaaccgtcg cacaggaagg acagagaaag cgcggatctg ggaagtgacg gacagaacgg 146220
tcaggacctg gattggggag gcggttgccg ccgctgctgc tgacggtgtg acgttctctg 146280
ttccggtcac accacatacg ttccgccatt cctatgcgat gcacatgctg tatgccggta 146340
taccgctgaa agttctgcaa agcctgatgg gacataagtc catcagttca acggaagtct 146400
acacgaaggt tttgcgctg gatgtggctg cccggcaccg ggtgcagttt gcgatgccgg 146460
agtctgatgc ggttgcgatg ctgaaacaat tatcctgaga ataaatgcct tggcctttat 146520
atggaaatgt ggaactgagt ggatatgctg tttttgtctg ttaaacagag aagctggctg 146580
ttatccactg agaagcgaac gaaacagtcg ggaaaatctc ccattatcgt agagatccgc 146640
attattaatc tcaggagcct gtgtagcgtt tataggaagt agtgttctgt catgatgcct 146700
```

gcaagcggta acgaaaacga tttgaatatg ccttcaggaa caatagaaat cttcgtgcgg 146760
tgttacgttg aagtggagcg gattatgtca gcaatggaca gaacaaccta atgaacacag 146820
aaccatgatg tggtctgtcc ttttacagcc agtagtgctc gccgcagttg agcgacaggg 146880
cgaagccctc gagtgagcga ggaagcacca gggaacagca cttatatatt ctgcttacac 146940
acgatgcctg aaaaaacttc ccttggggtt atccacttat ccacggggat atttttataa 147000
ttattttttt tatagttttt agatcttctt ttttagagcg ccttgtaggc ctttatccat 147060
gctggttcta gagaaggtgt tgtgacaaat tgccctttca gtgtgacaaa tcaccctcaa 147120
atgacagtcc tgtctgtgac aaattgccct taaccctgtg acaaattgcc ctcagaagaa 147180
gctgtttttt cacaaagtta tccctgctta ttgactcttt tttatttagt gtgacaatct 147240
aaaaacttgt cacacttcac atggatctgt catggcggaa acagcggtta tcaatcacaa 147300
gaaacgtaaa aatagcccgc gaatcgtcca gtcaaacgac ctcactgagg cggcatatag 147360
tctctcccgg gatcaaaaac gtatgctgta tctgttcgtt gaccagatca gaaaatctga 147420
tggcacccta caggaacatg acggtatctg cgagatccat gttgctaaat atgctgaaat 147480
attcggattg acctctgcgg aagccagtaa ggatatacgg caggcattga agagtttcgc 147540
ggggaaggaa gtggtttttt atcgccctga agaggatgcc ggcgatgaaa aaggctatga 147600
atcttttcct tggtttatca aacgtgcgca cagtccatcc agagggcttt acagtgtaca 147660
tatcaaccca tatctcattc ccttctttat cgggttacag aaccggttta cgcagtttcg 147720
gcttagtgaa acaaaagaaa tcaccaatcc gtatgccatg cgtttatacg aatccctgtg 147780
tcagtatcgt aagccggatg gctcaggcat cgtctctctg aaaatcgact ggatcataga 147840
gcgttaccag ctgcctcaaa gttaccagcg tatgcctgac ttccgccgcc gcttcctgca 147900
ggtctgtgtt aatgagatca acagcagaac tccaatgcgc ctctcataca ttgagaaaaa 147960
gaaaggccgc cagacgactc atatcgtatt ttccttccgc gatatcactt ccatgacgac 148020
aggatagtct gagggttatc tgtcacagat ttgagggtgg ttcgtcacat ttgttctgac 148080
ctactgaggg taatttgtca cagttttgct gtttccttca gcctgcatgg attttctcat 148140
actttttgaa ctgtaatttt taaggaagcc aaatttgagg gcagtttgtc acagttgatt 148200
tccttctctt tcccttcgtc atgtgacctg atatcggggg ttagttcgtc atcattgatg 148260
agggttgatt atcacagttt attactctga attggctatc cgcgtgtgta cctctacctg 148320
gagtttttcc cacggtggat atttcttctt gcgctgagcg taagagctat ctgacagaac 148380
agttcttctt tgcttcctcg ccagttcgct cgctatgctc ggttacacgg ctgcggcgag 148440
cgctagtgat aataagtgac tgaggtatgt gctcttctta tctccttttg tagtgttgct 148500
cttattttaa acaactttgc ggtttttttga tgactttgcg attttgttgt tgctttgcag 148560
taaattgcaa gatttaataa aaaaacgcaa agcaatgatt aaaggatgtt cagaatgaaa 148620
ctcatggaaa cacttaacca gtgcataaac gctggtcatg aaatgacgaa ggctatcgcc 148680
attgcacagt ttaatgatga cagcccggaa gcgaggaaaa taacccggcg ctggagaata 148740
ggtgaagcag cggatttagt tggggtttct tctcaggcta tcagagatgc cgagaaagca 148800
gggcgactac cgcacccgga tatggaaatt cgaggacggg ttgagcaacg tgttggttat 148860
acaattgaac aaattaatca tatgcgtgat gtgtttggta cgcgattgcg acgtgctgaa 148920
gacgtatttc caccggtgat cggggttgct gcccataaag gtggcgttta caaaacctca 148980
gtttctgttc atcttgctca ggatctggct ctgaaggggc tacgtgtttt gctcgtggaa 149040

-continued ggtaacgacc cccagggaac agcctcaatg tatcacggat gggtaccaga tcttcatatt 149100
catgcagaag acactctcct gcctttctat cttggggaaa aggacgatgt cacttatgca 149160
ataaagccca cttgctggcc ggggcttgac attattcctt cctgtctggc tctgcaccgt 149220
attgaaactg agttaatggg caaatttgat gaaggtaaac tgcccaccga tccacacctg 149280
atgctccgac tggccattga aactgttgct catgactatg atgtcatagt tattgacagc 149340
gcgcctaacc tgggtatcgg cacgattaat gtcgtatgtg ctgctgatgt gctgattgtt 149400
cccacgcctg ctgagttgtt tgactacacc tccgcactgc agtttttcga tatgcttcgt 149460
gatctgctca agaacgttga tcttaaaggg ttcgagcctg atgtacgtat tttgcttacc 149520
aaatacagca atagtaatgg ctctcagtcc ccgtggatgg aggagcaaat tcgggatgcc 149580
tggggaagca tggttctaaa aaatgttgta cgtgaaacgg atgaagttgg taaaggtcag 149640
atccggatga gaactgtttt tgaacaggcc attgatcaac gctcttcaac tggtgcctgg 149700
agaaatgctc tttctatttg ggaacctgtc tgcaatgaaa ttttcgatcg tctgattaaa 149760
ccacgctggg agattagata atgaagcgtg cgcctgttat tccaaaacat acgctcaata 149820
ctcaaccggt tgaagatact tcgttatcga caccagctgc cccgatggtg gattcgttaa 149880
ttgcgcgcgt aggagtaatg gctcgcggta atgccattac tttgcctgta tgtggtcggg 149940
atgtgaagtt tactcttgaa gtgctccggg gtgatagtgt tgagaagacc tctcgggtat 150000
ggtcaggtaa tgaacgtgac caggagctgc ttactgagga cgcactggat gatctcatcc 150060
cttcttttct actgactggt caacagacac cggcgttcgg tcgaagagta tctggtgtca 150120
tagaaattgc cgatgggagt cgccgtcgta aagctgctgc acttaccgaa agtgattatc 150180
gtgttctggt tggcgagctg gatgatgagc agatggctgc attatccaga ttgggtaacg 150240
attatcgccc aacaagtgct tatgaacgtg gtcagcgtta tgcaagccga ttgcagaatg 150300
aatttgctgg aaatatttct gcgctggctg atgcggaaaa tatttcacgt aagattatta 150360
cccgctgtat caacaccgcc aaattgccta aatcagttgt tgctcttttt tctcaccccg 150420
gtgaactatc tgcccggtca ggtgatgcac ttcaaaaagc ctttacagat aaagaggaat 150480
tacttaagca gcaggcatct aaccttcatg agcagaaaaa agctggggtg atatttgaag 150540
ctgaagaagt tatcactctt ttaacttctg tgcttaaaac gtcatctgca tcaagaacta 150600
gtttaagctc acgacatcag tttgctcctg gagcgacagt attgtataag ggcgataaaa 150660
tggtgcttaa cctggacagg tctcgtgttc caactgagtg tatagagaaa attgaggcca 150720
ttcttaagga acttgaaaag ccagcaccct gatgcgacca cgttttagtc tacgtttatc 150780
tgtctttact taatgtcctt tgttacaggc cagaaagcat aactggcctg aatattctct 150840
ctgggcccac tgttccactt gtatcgtcgg tctgataatc agactgggac cacggtccca 150900
ctcgtatcgt cggtctgatt attagtctgg gaccacggtc ccactcgtat cgtcggtctg 150960
attattagtc tgggaccacg gtcccactcg tatcgtcggt ctgataatca gactgggacc 151020
acggtcccac tcgtatcgtc ggtctgatta ttagtctggg accatggtcc cactcgtatc 151080
gtcggtctga ttattagtct gggaccacgg tcccactcgt atcgtcggtc tgattattag 151140
tctggaacca cggtcccact cgtatcgtcg gtctgattat tagtctggga ccacggtccc 151200
actcgtatcg tcggtctgat tattagtctg ggaccacgat cccactcgtg ttgtcggtct 151260
gattatcggt ctgggaccac ggtcccactt gtattgtcga tcagactatc agcgtgagac 151320
tacgattcca tcaatgcctg tcaagggcaa gtattgacat gtcgtcgtaa cctgtagaac 151380
ggagtaacct cggtgtgcgg ttgtatgcct gctgtggatt gctgctgtgt cctgcttatc 151440
cacaacattt tgcgcacggt tatgtggaca aaatacctgg ttacccaggc cgtgccggca 151500
cgttaaccgg gctgcatccg atgcaagtgt gtcgctgtcg agcggccgc 151549

<210> SEQ ID NO 2
<211> LENGTH: 162877
<212> TYPE: DNA
<213> ORGANISM: Artificial Sequence
<220> FEATURE:
<223> OTHER INFORMATION: Hybrid immunoglobulin locus
<220> FEATURE:
<221> NAME/KEY: unsure
<222> LOCATION: 1379
<223> OTHER INFORMATION: "n" represents any nucleotide
<220> FEATURE:
<221> NAME/KEY: unsure
<222> LOCATION: 16903-16909
<223> OTHER INFORMATION: "n" represents any nucleotide
<220> FEATURE:
<221> NAME/KEY: unsure
<222> LOCATION: 35206-35211
<223> OTHER INFORMATION: "n" represents any nucleotide

<400> SEQUENCE: 2
atccctagct gaagcttctg atggaattag aacttggcaa aacaatactg agaatgaagt 60
gtatgtggaa cagaggctgc tgatctcgtt cttcaggcta tgaaactgac acatttggaa 120
accacagtac ttagaaccac aaagtgggaa tcaagagaaa aacaatgatc ccacgagaga 180
tctatagatc tatagatcat gagtgggagg aatgagctgg cccttaattt ggttttgctt 240
gtttaaatta tgatatccaa ctatgaaaca ttatcataaa gcaatagtaa agagccttca 300
gtaaagagca ggcatttatc taatcccacc ccacccccac ccccgtagct ccaatccttc 360
cattcaaaat gtaggtactc tgttctcacc cttcttaaca aagtatgaca ggaaaaactt 420
ccattttagt ggacatcttt attgtttaat agatcatcaa tttctcgatt tctcgactat 480
tcctttgccc tcggacgagt gctggggcgt cggtttccac tatcggcgag tacttctaca 540
cagccatcgg tccagacggc cgcgcttctg cgggcgattt gtgtacgccc gacagtcccg 600
gctccggatc ggacgattgc gtcgcatcga ccctgcgccc aagctgcatc atcgaaattg 660
ccgtcaacca agctctgata gagttggtca agaccaatgc ggagcatata cgcccggagc 720
cgcggcgatc ctgcaagctc cggatgcctc cgctcgaagt agcgcgtctg ctgctccata 780
caagccaacc acggcctcca gaagaagatg ttggcgacct cgtattggga atccccgaac 840
atcgcctcgc tccagtcaat gaccgctgtt atgcggccat tgtccgtcag gacattgttg 900
gagccgaaat ccgcgtgcac gaggtgccgg acttcggggc agtcctcggc ccaaagcatc 960
agctcatcga gagcctgcgc gacggacgca ctgacggtgt cgtccatcac agtttgccag 1020
tgatacacat ggggatcagc aatcgcgcat atgaaatcac gccatgtagt gtattgaccg 1080
attccttgcg gtccgaatgg gccgaacccg ctcgtctggc taagatcggc cgcagcgatc 1140
gcatccatgg cctccgcgac cggctgcaga acagcgggca gttcggtttc aggcaggtct 1200
tgcaacgtga caccctgtgc acggcgggag atgcaatagg tcaggctctc gctgaattcc 1260
ccaatgtcaa gcacttccgg aatcgggagc gcggccgatg caaagtgccg ataaacataa 1320
cgatctttgt agaaaccatc ggcgcagcta tttacccgca ggacatatcc acgccctcnt 1380
acatcgaagc tgaaagcacg agattcttcg ccctccgaga gctgcatcag gtcggagacg 1440
ctgtcgaact tttcgatcag aaacttctcg acagacgtcg cggtgagttc aggctttttc 1500
atggtggcgg ctggatcggt cggtcgaaag gcccggagat gaggaagagg agaacagcgc 1560

-continued

```
ggcagacgtg cgcttttgaa gcgtgcagaa tgccgggcct ccggaggacc ttcgggcgcc   1620
cgccccgccc ctgagcccgc ccctgagccc gcccccggac ccaccccttc ccagcctctg   1680
agcccagaaa gcgaaggagc aaagctgcta ttggccgctg ccccaaaggc ctacccgctt   1740
ccattgctca gcggtgctgt ccatctgcac gagactagtg agacgtgcta cttccatttg   1800
tcacgtcctg cacgacgcga gctgcggggc ggggggggaac ttcctgacta ggggaggagt   1860
agaaggtggc gcgaaggggc caccaaagaa cggagccggt tggcgcctac cggtggatgt   1920
ggaatgtgtg cgaggccaga ggccacttgt gtagcgccaa gtgcccagcg gggctgctaa   1980
agcgcatgct ccagactgcc ttgggaaaag cgcctcccct acccggtaga attcatcgct   2040
cgagcaattg gctagataac ttcgtataat gtatgctata cgaagttatc tagctctaga   2100
gtcgacgatt gaagagtgtg ataagtgccc agaccaagca gaacagaaat cagcatgtaa   2160
agatgatgat ctatggatat gatctaaaac catgtaaata cttcaaataa ttctatttaa   2220
tgcagtttga aataaaacac aaacttattc aaaatacaaa ttacttggta attattttgg   2280
gagctatgag ttcaccaaga aactcaaatt cctatttcta tttcaacccc tgattcctac   2340
tgtcaatggg agggaagtct cagaaccaat cacacatcag acggcaaatc tgtcaaccaa   2400
gagtctttcc actgaaggac ctgggaggtc aggaccctca ggaaagtgct ggggaccctg   2460
tcttgggagt gcccagcaga tctcagaact ctccatgggt cctgctggac actcatgtag   2520
ggtaacgagt ggccaccttt tcagtgttac cagtgagctc tgagtgttcc taacgggacc   2580
aggatgggtc taggtgcctg ctcaatgtca gagacagcaa tggtcccaca aaaaacccag   2640
gtaatcttta ggccaataaa atgtgggttc acagtgagga gtgcatcctg gggttggggt   2700
ttgttctgca gcgggaagag cgctgtgcac agaaagctta gaaatggggc aagagatgct   2760
tttcctcagg caggatttag ggcttggtct ctcagcatcc cacacttgta cagctgatgt   2820
ggcatctgtg ttttctttct catcctagat caggctttga gctgtgaaat accctgcctc   2880
atgcatatgc aaataacctg aggtcttctg agataaatat agatatattg gtgccctgag   2940
agcatcacat aacaaccaca ttcctcctct gaagaagccc ctgggagcac agctcatcac   3000
catggactgg acctggaggt tcctctttgt ggtggcagca gctacaggta aggggcttcc   3060
tagtcctaag gctgaggaag ggatcctggt ttagttaaag aggattttat tcacccctgt   3120
gtcctctcca caggtgtcca gtcccaggtg cagctggtgc agtctggggc tgaggtgaag   3180
aagcctgggt cctcggtgaa ggtctcctgc aaggcttctg gaggcacctt cagcagctat   3240
gctatcagct gggtgcgaca ggcccctgga caagggcttg agtggatggg agggatcatc   3300
cctatctttg gtacagcaaa ctacgcacag aagttccagg gcagagtcac gattaccgcg   3360
gacaaatcca cgagcacagc ctacatggag ctgagcagcc tgagatctga ggacacggcc   3420
gtgtattact gtgcgagaga cacagtgtga aaacccacat cctgagagtg tcagaaaccc   3480
tgagggagaa ggcagctgtg ccgggctgag gagatgacag ggttattag gtttaaggct   3540
gtttacaaaa tgggttatat atttgagaaa aaaagaacag tagaaacaag tacatactct   3600
aattttaaga taaatattcc attcaagagt cgtaatataa gccaaattca cagagtggaa   3660
aaggccacac tctataacgt tgatacaaac attccatgaa ggtgctactg tgaacaagtt   3720
ttcaaattgg atgaatacat gatttggagc aaggttattt gatcatgtgg tgagactaag   3780
aatgctcgac tctggacttg agtgtcattg tccagccatg ttgcacaagt gtgtcctgtc   3840
agggaaggat cagagttcct tgtgctctca gagggaaggg gtcacagagt tcctctctgg   3900
ttcccaggaa aggtaatcgc actaatcttc atgatcttca tgagactatc ctccagtgct   3960
```

-continued

```
gacctgttat agagtttttg tctgaagttc tcactgcaat ccccaatcta catattttca   4020
atcagaagtg tttagaggcc aggacacatc ttcaaggtca cacattgaga aggatgtaga   4080
tatgtcccac taccttctcc tgagatctca gacagaatcc cagatttcaa aaggacacag   4140
aaggacagct ctcaggtgct tttaaaaaat gacccacttc cagggacagg gagcttccct   4200
ataaccatgg tggatgttct gaactacaat aaacattgga tggatccagg attgtttgaa   4260
gtcactgtca ttattacatt cagctgctgt ttcaatgtgt ctgaagtagt aaatgacaat   4320
ttagatgaca atttatatga atcttcaagg gtagaacaat attgaccata ttccaaaatc   4380
tgtccttgat ccatgatcac actcatctcc cagaccaggt ccttcagcac gtctctttac   4440
ctgaaagaag aggactctgg gcttggagag gggagacccc aagaagacaa ctgagttctc   4500
aaagggcaca gccagcatcc tactcccagg gcgagcccaa aagactgggg cctccctcct   4560
cctttttcac ctctccatac aaaggcacca cccacatgca aatcctcact taagcaccca   4620
caggaaacca ccacacattt ccttaaattc aggttccagc tcacatggga aatactttct   4680
gagagtcctg gacctcctgt gcaagaacat gaaacatctg tggttcttcc ttctcctggt   4740
ggcagctccc agatgtgagt atctcaggga tccagacatg gggatatggg aggtgcctct   4800
gatcccaggg ctcactgtgg gtctctctgt tcacaggggt cctgtcccag gtgcagctgc   4860
aggagtcggg cccaggactg gtgaagcctt cggagaccct gtccctcacc tgcactgtct   4920
ctggtggctc catcagtagt tactactgga gctggatccg gcagccccca gggaagggac   4980
tggagtggat tgggtatatc tattacagtg ggagcaccaa ctacaacccc tccctcaaga   5040
gtcgagtcac catatcagta gacaagtcca agaaccagtt ctccctgaag ctgagctctg   5100
tgaccgctgc ggacacggcc gtgtattact gtgcgagaga cacagtgagg ggaggtgagt   5160
gtgagcccag acaaaaacct ccgtgcaggg aggcggaggg gaccggcgca ggtgctgctc   5220
agagccagca gggggcgcgc ggggcccaca gagcaggagg cccggtcagg agcaggtgca   5280
gggagggcgg ggcttcctca tctgctcagt ggtctccctc ctcgccagca cctcagctgt   5340
ccccaggggt cctctttctt tattatctgt ggttctgctt cctcacattc ttgtgccaag   5400
aaagaaatga ggaagacaaa ttttcgtctg tagttgaagt ttcaccaatc tcgagacgat   5460
gcggatgtga tttaagtttc agaggaataa aaaaaaagat ttagggatta atttaattat   5520
tcaaaagttg attgaagtgc cgagtgaatg gctgcaaaca tagtctacat ttttcaaatc   5580
attccctata aatttgaatt aattatttat ttttatactt gaataaagca ataacaaaga   5640
aataaatgaa tatttttgct aaaatggagc aataaaaaga ctgatattga cagaagaaat   5700
atgactgact tctgaaaata cacacacatg agccgtggtt ctctctacat atttagataa   5760
attacagaaa gttgtcataa ctgatgggga atcctgcaga cttcactagg catagtccac   5820
actgccctgg agttgtctca ggggagctgc ctcctccagt ggttagagca caggcccagg   5880
taataggact cattttttta gatgtgtaat tttagacaca ctgcacaact gctgtgttct   5940
ctgcgcaaat tatctcctgt aaaatgcaac attgaaacct gccttaaata tattgtgtaa   6000
atatgtaaaa ataaaatcag attgtgagag ctaaatgcta atcaaggcgc aatcacgtaa   6060
tatacaatta tattttcctg aatgatggaa ttaataccaa tctcccccag gacacttcat   6120
ctgcacggag cccggcctct cctcagatgt cccaccccag agcttgctat atagtcgggg   6180
acatgcaaat agggccctcc ctctgctgat gaaaaccagc ccagctgacc ctgcagctct   6240
gggagaggag cccagcactg ggattccgag gtgtttccat tcggtgatca gcactgaaca   6300
```

cagaggactc accatggagt tttggctgag ctgggttttc cttgttgcta tttcaaaagg 6360
tgattcatgg agaactagag atatcgagtg tgagtgaaca cgagtgagag aaacagtgga 6420
tatgtgtggc agtttctaac caatgtctct gtgtttgcag gtgtccagtg tgaggtgcag 6480
ctggtggaga ctggaggagg cttgatccag cctggggggt ccctgagact ctcctgtgca 6540
gcctctgggt tcaccgtcag tagcaactac atgagctggg tccgccaggc tccagggaag 6600
gggctggagt gggtctcagt tatttatagc ggtggtagca catactacgc agactccgtg 6660
aagggccgat tcaccatctc cagagacaat tccaagaaca cgctgtatct tcaaatgaac 6720
agcctgagag ccgaggacac ggccgtgtat tactgtgcga gagacacagt gaggggaagt 6780
cattgtgcgc ccagacacaa acctccctgc aggaacgctg gggggaaatc agctgcaggg 6840
ggcgctcagg agccactgat cagagtcagc cccggaggca ggtgcagatg gaggctgatt 6900
tcctgtcagg atgtgggact ctgtcttctt ctgacggttc cccagggaac ctctctaagt 6960
ttagcattct gtgcctatga acgtcttctc taagtatttg aaagagatta ttttaatatg 7020
aagagcagtt ctcactcgtc gacctcttct gaaggaccat gaatgcctca accaaccatc 7080
tcccctgcct ccatgaccag aaatgcacca cgtgcccaca cggatattca tccctcatgg 7140
ggataagact ccattgatga ggctgactat tttatcatat aaaattacta aagactgatt 7200
taagggtttc aaaaactaat tgaactctgt tgttctatgt ccaccagaga ttacaaatct 7260
tccaatgatg ccttctttgt tttttgtctg cttgactttg tctcttcaac ttgttctgta 7320
ccccagagaa tctctttcag ctccctcagg tgcattcaat tgttttattt aactgacaat 7380
ttctaaatca gttaaagaca ttacgctaaa gactccatat tcctaggtcc atattccttt 7440
ttccatattc ctaggaaggc attgtgaccc agagtctggg catgaccttg tgagtgttcc 7500
tgaccctcct ccatatgaga tgctggtctg ggtgttcttg ccccttttccc tggggtagag 7560
tcctcctgtt ttccccaggt gctccctccc acagctctag tgttctcaat cagtgtcatc 7620
accttccaga tcttctgccc tgccctgcag actaaggctc tgattccata agcaagatag 7680
gggagctgct cctcaataga tctttggtga ggatctctgt tcccatctca attcctgtag 7740
ggtggaacca gtgttcctag gattctggtt tcagtagctt gtccctgcag agtaaattct 7800
tagttctgta gggggattaa gggagttggg tctgaataca ttttagatgt cgaggatctt 7860
gttctctccc agaaagacac ttcgggaaag taagactttg gtaactgtcc cctttcttgg 7920
ggaaagggat tcaagaggat aggttgcttt tgggcatgtg gtcccttaaa atttcacact 7980
aaaaagcgtt tcccacactc aatttcaagc agcccaatat atatttgtat tttttcttgg 8040
aacagacaat attttatatt ccagactctg ccttaggtaa tttcaaaccc cggctttgtt 8100
actctctaca agaaattgct tctccataag cttcagattt gttgtgtgtt ttgaaatttt 8160
atcagaaata ttaaagaaaa ttggcaaaat tccatcctcc atgtttatct gttattgttg 8220
atgcagttgt aaaaaataag aaaaatatat tccttttttc tgtacatttc caagcttagt 8280
agcaaatttt tagtaacacc cagaataata aaaaattcaa atattgttta gctgcttaat 8340
aggaaaacaa attatagtaa atttgtttgc tagaatgcta cccagcattt ataataagta 8400
aacatttgat atacccaact acaaggtaaa atatccattt atgctaacta aaataagcca 8460
aacaaatgag aatatatact gttatttcat ttttataaat tctgaaaaat taaaatgaat 8520
ttgcagcaat gtaaagatca gtagttgcca gggaaatggt agaagaaaga aaggaaaagg 8580
agaaagaata cagaaaaaca aaaggaaatg ttaagaattc tcttgtccaa cttgataagg 8640
atgacggtta catcattttt atcaactgta atctttaaat atgtgaaagt ttattatccg 8700

-continued

```
taaactaaac gttataaact ttattacaag caaaaattga aagttagaca acaaggagtg   8760
atagaaagag aaaatgtata ttaaatttca gaaatattta agaatgtatc tgcctgaacc   8820
ctagttctca ccatatcttt aggtgaatgc taaaatgcag caaaatcacg catgttctca   8880
ctacagaaag tgggttctac aaaccacact cggcacattt agctttgtcc tggagttggt   8940
gcagggagtt attggggcca gtgatgagga gcacaggcca agataccagc gattacttat   9000
cccaaacatg agctctaaca tacacactta gtcccttttc cgtgtgtggt ttacttccac   9060
atctgtacat ggagagacca ctgactgaca aaatataatt tatacaaata tgtaaaatta   9120
aatagggtga tcagttcaag gtgtttatca cagcataatt ttacaataag acagcatatt   9180
tcccaaatac catcattgtc accaaactcc ttcaaggcac agtcatctta tctgggcccc   9240
gtcctctcct caggtgtccc accccagagc ttggtatata gtaggagaca tgcaaataag   9300
gccctccctc tgctgatgaa aatgagccca gccctgaccc tgcagctctg ggagaggagc   9360
cccagccgtg agattcccag gagtttccac ttggtgatca gcactgaaca cagaccacca   9420
accatggagt ttgggcttag ctgggttttc cttgttgcta ttttaaaagg taattcatgg   9480
tgtactagag atactgagtg tgaggggaca tgagtggtag aaacagtgga tatgtgtggc   9540
agtttctgac cttggtgttt ctgtgtttgc aggtgtccaa tgtgaggtgc agctggtgga   9600
gtctggggga ggcttggtac agccagggcg gtccctgaga ctctcctgta cagcttctgg   9660
attcaccttt ggtgattatg ctatgagctg gttccgccag gctccaggga aggggctgga   9720
gtgggtaggt ttcattagaa gcaaagctta tggtgggaca acagaatacg ccgcgtctgt   9780
gaaaggcaga ttcaccatct caagagatga ttccaaaagc atcgcctatc tgcaaatgaa   9840
cagcctgaaa accgaggaca cagccgtgta ttactgtact agagacacag tgaggggagg   9900
tcaatgtgag cccagacaca aacctccctg caggggcgca cagagccacc agggggcgct   9960
agggaccgac tgagtacggg acaggtccca ggagcaggtg caggggggagg tttccttttt  10020
ccttggctgg aaaagtcacc tttatcttcc caggactcga cgatgagact atcctccagt  10080
gctgatgtac tatagagttt tcatctgaag ctgtcactgc tatccccaat gtacatcttt  10140
tcacacagaa atgtttagag gtcaggccat attctcaggg ttacacattg agaaggatgg  10200
agatatattc tactaccttc tcctgagatc tcacacacaa tctcaaattt caaaaggtct  10260
cagaagggca gctctcaggt actatttaaa aataacccac ttcctgggac aggtagcatc  10320
cttctaacca tgatggatgt tctgaactac agtacacatt gcatggatcc gggtttgtct  10380
caattcactg tgattattac actcagcagc tgtttcaata tgtctgaagg ggtaaatgac  10440
aatttaggtg acctgggtgt atggttggtg ttatatgaat ctttaaatgt agaacagtat  10500
taactgtatt ccaaaatctg tctttgatcc atgatcacac ttgtctccca gaccagctcc  10560
ttcagcacat ttcctacctg gaagaagagg actctgggtt tggtgagggg aggccacagg  10620
aagagaactg agttctcaga gggcacagcc agcatacacc tcccagggtg agcccaaaag  10680
actggggcct ccctcatccc tttttaccta tccatacaaa ggcaccaccc acatgcaaat  10740
cctcacttag gcacccacag gaaatgacta cacatttcct taaattcagg gtccagctca  10800
catgggaagt gctttctgag agtcatggac ctcctgcaca agaacatgaa acacctgtgg  10860
ttcttcctcc tcctggtggc agctcccaga tgtgagtgtc tcaggaatgc ggatatgaag  10920
atatgagatg ctgcctctga tcccagggct cactgtgggt ttctctgttc acaggggtcc  10980
tgtcccaggt gcagctacag cagtggggcg caggactgtt gaagccttcg gagaccctgt  11040
```

-continued

```
ccctcacctg cgctgtctat ggtgggtcct tcagtggtta ctactggagc tggatccgcc  11100
agcccccagg gaaggggctg gagtggattg gggaaatcaa tcatagtgga agcaccaact  11160
acaacccgtc cctcaagagt cgagtcacca tatcagtaga caagtccaag aaccagttct  11220
ccctgaagct gagctctgtg accgccgcgg acacggctgt gtattactgt gcgagaggca  11280
cagtgagggg aggtgagtgt gagcccagac aaaaacccc ctgcaggtag gcagaggggg  11340
cgggcgcagg tactgctcaa gaccagcagg tggcgcgcgg cgcccacaga tcccgaggcc  11400
gggtccggag caggtgcaag gagggcgggg cttcctcaac agctcagtgg tctgtctcct  11460
cgccagcacc tcagatgtcc ccaggactct ctttctttat tatctgtggt tctgcttcct  11520
cacatccttg tggcagggaa gaaaggagga agacaatttt tctgtttact gttgaggttt  11580
caccaattac ctcgacgtct tgttacactt catcaagaat taacctctgc tgtttcctca  11640
aagtgtttaa ttggataatg aatttgtcta taaattgaag agttgaaata catcaaatat  11700
taatttgtaa taatctggca caaattatct aagcaaattc aataactaga tgtttttttca  11760
tttattttta tttaaaatca ggatctaagc actgacatgc tttaataaca tctgtgaccc  11820
tctcagcagt tttctcttct gagtatatga tctgctgtgg cagttttctt agcttcaatg  11880
ttacctcttt tggcaatgac taccgtcttt atatttgcca ggaatctggg ataagggagt  11940
gcttctaaga gttccctaac ttgcccattt tggtgggtgt tccagaacat atgagatgct  12000
ctgttgttaa caaagcatcc caaagccatg cactgcccta aaatgtgttt gtttcctagt  12060
ttgacaaatt ggaagttcta ataaatacaa tcacttctgc catctgggct gattttacat  12120
cagatagagg gctgtattcc aaagaaaagc ttacattagt aatagcaatt ctagtcagaa  12180
acctagagtt ttatcattga ggtgcaattc ataacaaata atattaggtc gaggttctca  12240
gtggcagtgt ctaaatctct taggtgtaca gggtcttccc tgttaacatg aagcatttat  12300
aagcacagtc atagtttcca gctatgcttc tccctgtctc attatcacca caaactatgg  12360
cctcacctgg aacttgggtt aatttccaaa taagtaattt tttagtgttt atgcctctag  12420
attattatgt gagaaagtta acattcagta gaaagttaaa aagaacattt gaactgacta  12480
aacaacacag acaatcaaga ataaaattca aagcctagat gtgagaggct ccaggcctgg  12540
ataatgcaat agttcatgta tgcaggcagt ttctttgccc agttctacac tgatacaccc  12600
agaatgtcag cttcatgcca gatttgactc ctattatgta gagacatggc aatacattct  12660
caagggtcac atgaaataat atgaaaattg gtgggaatag gggaggagac aactctgcaa  12720
ttctcatctg aaggaccagg aaagcctgga cagaccatct ccccagcctc cgtgactgca  12780
ccacgtgccc acatggacgc tcatccctga tagggtaaga agactccatt gatggggctg  12840
agcattttat gatagaaatt actagagact gacgtggagg tttcaacaac taatatttat  12900
aaccaaaatt taattacccc cacattgtta ccattttctt cagtgaaaaa ttgcttgcca  12960
tgattaagtt ttaagtagat ttccaatgtt cacaactgag cttccaagag agtcttgaga  13020
acaaaaacaa tgagggcaga gaaatctacc ttttctgcat tcaccactaa actcaagtgg  13080
actcagcact gcctttgatc actgctactt ctctgcagag ttcaggtttc tacttctcac  13140
aattctgaca cacattctac ctctcctcag atgtttggcc tctgcttctt gtaaggtcac  13200
cctctgttct taacttcttc tctgagtcat tttgtgaggt ggtcatgagc cattaaatgg  13260
atattttata ttttcccaac atgaatcaca tgagtggtca tgaattatac ttctgattat  13320
ggcagttgat ttttcttggc atgttcatga ctagtaatat ttgaagccat ttcattcaaa  13380
tcttcggggc ttcgtttttg ttgctatgac attttttctt ctattgagtc tttccactag  13440
```

```
tattataaca tgacctagta tccaggctca gttgtcatta ataataacca catatgtcaa  13500
aaatcatgca ttcttttcac agcagacata atttcctctt ttctgcagat gaagacacac  13560
tgctgagcta cccccactta caagaatata tgcacaatta tgatatcttc atttatttga  13620
ctaataagct atatcattct cccttcaaat tctttacccc ccagaagtcc tggacaaatt  13680
tctgcatctg ctcaaacgat aaactcagaa ctacatggtg agtaaaagtc acctggttct  13740
ggatattggg tccatctctt cccctccaat gtcccagagc acctcagcac acccgtccag  13800
gttctatcaa gaaagagtag ctcctgcaca ctgaaggaaa caattgagtt aagagaggac  13860
ctgcagatga tagacaatat tgaaaactgt taatatgaca aaggattact accaagcatg  13920
tgaaataagc tcaacgggtg cggtggttca tgtctgtagt accagcaatt tgggaggcaa  13980
gttgcgcaga tcacctgagg ttaggagctc gacaccagcc tgaccaacat aaagaacacc  14040
ctgtctctac taaaagtaca aaattagccg ggcatggtgg catgcgcctg taatcccagc  14100
tactcgggag gctgaggcag gagcatcact tgaacctggg aagtggaggt tgcggtgagc  14160
tgagatggca ccattgcact ccagcctggg caacaagagg gaaactccat ctcaaaaaaa  14220
aaattacaaa aaattagctg agcgtggtgg tgggcgcctg tatacccagc tgctagggag  14280
actgaggcag gagaatggct tgaacccagg aggtgaaggt tgcagtgagc tgagattgcg  14340
ccattgcact ccatcctggg caacaagagt gaaactccat ctcaaaaaaa aaaaaagaga  14400
cttgcaaagg gcaaatagat catagacaga cagatagata gatagaccta ttagtataca  14460
tacatacata tatatacact aatattcagg aaaatgcaaa ttcataatga gatgtctttt  14520
caccccttcat ctctgctaga aagtttgtta tctgaaaaac aaatacatac atacatactt  14580
attaaaagct ggccaggatg cctagaaagt aaaactcata gaccactggt ggaaatgtaa  14640
attagtgcag ccatcaaggg aaaaaaatag aactaccata tattccagca atccaactgc  14700
taagtatata tctatttaaa tatttaaaag aaaaaactaa tattgaagag atacctgtac  14760
acccatgttt attgcagcac taatcacaat ttctaggata tgaaatcaac atatgtgtcc  14820
atcaacagat gaatggatac ataaaatgtg atatatttac acaatggaat attattcagc  14880
cttaacaatg aaattctgcc gtttgaagca acatggatgg aatgggacac ctctatgttg  14940
agtgaaatga gtcagacaca gaaaaataaa taccgcattt ctcagcgtta cttctagaag  15000
taaatagtag agtagtggtg atgagatgcc aggaatgaga gaaggctgag ataagaagag  15060
gtttgttaac aaacacacaa ttacaggtag acaggaggga tgtgctctag tgttctacag  15120
cacagtaggg tgactacagt taacaatata ttgtacgttt tctgtttaca agaagccaga  15180
agagagaatt ttctatgcta ccaacacaaa taaatgttag tgtctgaact gacgaatttg  15240
ctcattgttc tgattttagt cataccaagt ggcacacatg tattcaaata tcacactgta  15300
ccccataaac ataagcagtt attatgtgcc aaatttgaaa aatcctttaa ttagaaggaa  15360
ttatattggc gtacattaca aatgattcaa cacagagaca ggaataaata ccatttttct  15420
ttgaaatagt taattaacta acaatgtagt tacattcatt tgcaccaaat cgtgtatttg  15480
ataatggtat gcatagacag atttatgcat aggataatat cttttaattt tagactacta  15540
cttaatacta taaatataaa taattttaaa acaactaagt aaaaagaata aagctgagaa  15600
aatgtgtgtg tggtgtgtga tgtgtgagct ttttcttgtg caccactgtg tccttggtgg  15660
atgtgtggtt catgtgtttg tttttattta ctctgtttgg ggttctcttt gcttctagga  15720
tctgtagttc agtttctttc acaaaattgg gaacattctt cgctattatc tttttcaaat  15780
```

-continued agtttctgtg tatttataat ttctccttct cagatttaaa atatacacat actataattt 15840
tgatattaat gtttagtttc tttcttcact ctcttttcgt ttgcaattta ctttgtgaaa 15900
tttctaatga catactaatc acatggtttt attgaaaagc tgagccagct ctactgaggt 15960
gtgtgccaaa agattgctcg atgtttatac agcattgctt ttgatttctt atgcatttcc 16020
atttgattta ttcttagtat tttcatattt cagttcccta tctatgtcca cgatttcttt 16080
aagagattct tgcgtgtgaa ttatagttac tttacatatc ttgtttaatt agatatttat 16140
aacatctgtt tcatctacaa atctcatgct gatcatttgt ttattacaac tttggtactt 16200
ctcattaatg tatgtaataa ttgttgatag ccacagatac tgggatggac agtggatact 16260
ggccttatta tttcatttta tgcatttctg cctgtatttg accacacttt acctttgcca 16320
ggcctttact gtggaagtat ctgtgaatct tctcagaact atatttgaca ttcacttttg 16380
cagtggacat caaagttgaa gtctgttctt ctgtgtccac cagagacttc agttcctcca 16440
gtgatacctt gtttttcttt cctgcttggc tttgtctctt cacctgttcc ctcctccaga 16500
gaatcatgtt cagctccctc aggtggatta aaatgttatc taactgacaa ttgtgaaatt 16560
ggtggaaagc aatagaataa agggagattt tctgaccttt cttgggttca tattgtgaac 16620
atgagtctgg gtgtgacctt cccaatgttt ctgaacttcc tccagatgag atgttggtct 16680
gtgtgttctt gctcttttcc ctgctgtgga gtcctcttgt ttccccccagt tgttccctcc 16740
cgcagctcca atgttctctt tttgtgttat caccttacag atttgctgac tagaactgca 16800
gattagggct ctgattaaat aagaaggagg ggagatactt ctcaatggaa cttaggtgaa 16860
gacctctttt cccatctcag ttcttaaggg attgccccag tgnnnnnnna ctggttttgg 16920
tggcttgccc ctccaaaaaa tttctttgtt ctccagtggg gatatggaag gtgggtctga 16980
acacttttca gaagggtggg cactttttct ctcctagaca gacacaatgg gacagaacaa 17040
ttttggtgac tgtccccatt ttggggaaaa aggattcaat aggataggaa aactcttcag 17100
tctgtggtcc cttagaaatt caccctacaa cacatttacc acacttgact tcaagaaatc 17160
caatatatat gtgtgttttc atcttgtaat agcctacatt ttacatgcca tactctgcct 17220
cagttcagct catacccag ctttgttact ctttacaaga acttgcctct ccctagattt 17280
cacatttgct gtttatctta aaacttcaag tatctaaagt attattttta aaaaatggcc 17340
agttgtggtg gctcacacct gtaatcccaa cgctttggga ggctgaggta tgtggatcac 17400
ctgaggtcag gagtttgaga ccaccctggc caacatggta aaacctgtct ctactaaaaa 17460
tacaaaaaaa aaaaaatagc ttggcatggt ggcaggcacc tgtaatccca gctactcggg 17520
aggctgatac tggagaatag cttgaaccca cgaggcagag tttgcaagtc gtaccattgc 17580
actccagcct gggcgacaga gtgagactct gtctcaaaaa aaaaaattcc aaaattccag 17640
ctcctctgtt tatctatttt tgttgatact gttgttgtaa aacataagta aaatatatta 17700
ttcatctatg tacatttcca agctgtgtag aagaattttt aataagaccc agagtaaaaa 17760
aagaatgcaa atatgtaggg gccagcccta cagggtctgt ggatctttct ccccatgtgc 17820
agagatgaga gatcatagaa ataaaggcac aagacaaaga gatagaagaa aaaacagccg 17880
ggcccagggg accactacca ccaagacaca gactagaagt ggccccaaat gcctggctct 17940
gctgttattt attggataca aggcaaaagg ggaagggtaa ggagtgtgag tcatctgcaa 18000
tgattgataa ggtcatgtgt gtcacgtgtc cgccagacag agggcacttc cctgtttggc 18060
agccgaggcg gagagagaga gaggacagct taggtcatta tttcttccat tctcttctca 18120
gaaagatcaa agactttaat actttcacta attctgctac tgctatctag agggcggagc 18180
aagtgtacag agtggaacat gagagtgaaa caggagtgtg accgctgaag cacagcatca 18240
cagagagacg tttaggcctc tggagggctg cgggcaggtt tgactgatgt caggccttcc 18300
acaagaggtg gtggagcaga gtcttctcta actcccccgg ggaaagggag actccctttc 18360
caggtcttct aagtaatggg tgccttccca ggcactggcg ctaccgctag actgaggagc 18420
cctctagtgg ccctgtccgg gcgtgacaga ggctcacact cctgtcttct ggtcacttct 18480
caccgtgtcc cttcagctcc tattgctgta tggcctggtt tttcctaggt tataattgta 18540
gagcaaggat tgttataatg ttggaataaa gagtaatgct acagactgat gattaatgat 18600
attcatatat aaacatatct ataacctatt actagtacaa ctattcttat tttacatatt 18660
ctcttcatta cactggaaca gcttgtgccc tcagtctctt gcctcagcac ctgggtggct 18720
tgccgcccag acaaatattg ttaagcttct taatagaaaa acaaattatg gtaaatgtgt 18780
tcactggaat actacccgtc atttataata aattaatgcc tgatacacag agcaacaagg 18840
taaaatatct aagtatttat gttgagtaaa ataagctaaa caaataagaa tatatactat 18900
gtaatttcat ttttataaat tctgataaat aaaaatgcat ctgaagtaaa ataatgaaga 18960
taagtagttg cctggggaaa tggtagaaga agggaggggg agaggaggag gaatacagca 19020
gaacaaaggg aaaatgttga gaagaattca cttgtccact ttcttgataa tgatagcagt 19080
tacatcattt ttattagttg tacattttaa atatgtgaag tttatcatct ttcaattaag 19140
cctcataaaa tgtcttacaa gcaaacaaat ggaaacttag acaaggaaag agtaatagaa 19200
agatagaaaa aataagttca atgtcagaag tacctgaaaa ttaatgtgcc tggatcctag 19260
ttctctccat attttcagaa gagtgctgga gggcagcaaa accacacatg ctcttattac 19320
ggaaagtggg ttctgataaa aacactagac acatccagct ttgtcctgga gttggtttag 19380
ggggatgtca gagacagtga tgaagagcac agggccagat accggggttc actcatccca 19440
gacatgagct cctagatgca tacagagccc ccccatgtgt gggtttactt ccacttctgt 19500
aaatggagaa aatattgtct cctacagaac atagtttaca tgaatactta aaatgaaata 19560
gggtgattag tgcaaagtgt ttatcacagc acaatttcat aataagacag catattttcc 19620
aaatgcaatc attgccagca aacttctaca gggcaccgtc gtcttatctg ggtacagcct 19680
actcctcaag ggtcccaccc tagagcttgc tatatagtag gagatatgca aatagggccc 19740
tccctctact gatgaaaacc aacccaaccc tgaccctgca gctctcagag aggtgcctta 19800
gccctggatt ccaaggcatt tccacttggt gatcagcact gaacacagag gactcaccat 19860
ggagttgggg ctgtgctggg ttttccttgt tgctatttta gaaggtgatt cacggaaaac 19920
tagagagatt tagtgtgtgt ggatatgagt gagagaaaca gtggatatgt gtggcagttt 19980
ctgaccttgg tgtctctttg tttgcaggtg tccagtgtga ggtgcagctg gtggagtctg 20040
ggggaggctt ggtacagcct ggggggtccc tgagactctc ctgtgcagcc tctggattca 20100
ccttcagtag ctatagcatg aactgggtcc gccaggctcc agggaagggg ctggagtggg 20160
tttcatacat tagtagtagt agtagtacca tatattacgc agactctgtg aagggccgat 20220
tctccatctc cagagacaat gccaagaact cactgtatct gcaaatgaac agcctgagag 20280
acgaggacac ggctgtgtat tactgtgcga gagacacagt gaggggaggt cagtgtgagc 20340
ccagacacaa acctccctgc aggggtccgc aggaccacca gggggcgaca ggacactgag 20400
cacggggctg tctccagggc aggtgcaggt gctgctgagg gctggcttcc tgtcatggcc 20460
tggggcggcc tcattgtcaa gtttccccag ggaacttctc cagatttaca atcctgtact 20520

-continued

```
aatatttgat gtctctaaat gcaacctttt ttttcctttt tgtgtctgtt tttttttttt  20580
taaaaacagg aggacacatc ctcacctcca cagaagccac agtgtcactt tgggggcgga  20640
aataatcctt tcgtggtcaa cagggtgaga gttttgagga atcccaggga aacctgggga  20700
atgttttcca attagactca gggcagagac ctccatggga atccctgatt agaacaggct  20760
ttgagttctg atgggagcca aaagagaggc tcacccaggg tcagggttct taaaacctga  20820
tggttttcac agcaatcccc cttcatcttg tgaaactggg cacatctgac tcagactgat  20880
tcagttgacc ctctttctgc taatccattt tccttcccag tagacttgat tctcacagat  20940
ccctttcttc ttctctttcc tgaaaacaga ggatgtgttt tctgtagtcc tcgagccttg  21000
attgaagtgc tgagtaaatg gttgcaaaca taggtctaca tttttcaaat cattcaccat  21060
aaatttgaat tatttattaa ttacactcga ataaagcaat aaagaaactg atgagataat  21120
atttgactga attgcatcaa taaatagatc gatattaaca caaggaatat aactgatttc  21180
caaaaacata cacatgaacc gtggttcact ctgcgtattt agataaatta cagaaagttg  21240
tcataacaga tggggaatcc tgcagacttc actaggcatg ggccatgctg ccctggagtt  21300
gtctcagggg agctgcctcc tccagaggtt agagcacagg cccaggtaat aggactaaat  21360
ttttagatgt gttatcttag acacactgca caactgctgt gttctctatg taaattatct  21420
cctgtaaaat ataacattga agcctgcatt aaatatattg tgtaaatatg taagaataaa  21480
agaaagttat gagagctaag tgttaatcaa ggcacaagca tataagatat aactatattt  21540
tcctgaatga tggaattact accagtctcc cccaggacac ttcatctgcc ctgagcccag  21600
cctctcctca gatgtcccac ccagagcttg ctatatagtg ggggacatgc aaatagggcc  21660
ctccctctac tgatgaaaac cagcccagcc ctgaccctgc agctctggga gaggagccca  21720
gcactagaag tcggcggtgt ttccattcgg tgatcagcac tgaacacaga ggactcacca  21780
tggagtttgg gctgagctgg gttttcctcg ttgctctttt aagaggtgat tcatggagaa  21840
atagagagac tgagtgtgag tgaacatgag tgagaaaaac tggatttgtg tggcattttc  21900
tgataacggt gtccttctgt ttgcaggtgt ccagtgtcag gtgcagctgg tggagtctgg  21960
gggaggcgtg gtccagcctg ggaggtccct gagactctcc tgtgcagcgt ctggattcac  22020
cttcagtagc tatggcatgc actgggtccg ccaggctcca ggcaaggggc tggagtgggt  22080
ggcagttata tggtatgatg gaagtaataa atactatgca gactccgtga agggccgatt  22140
caccatctcc agagacaatt ccaagaacac gctgtatctg caaatgaaca gcctgagagc  22200
cgaggacacg gctgtgtatt actgtgcgag agacacagtg aggggaggtc attgtgcgcc  22260
cagacacaaa cctccctgca ggaacgctgg ggggaaatca gctgcagggg gcgctcagga  22320
gccactgatc agagtcagcc ctggaggcag gtgcagatgg aggctgtttc ctgtcaggat  22380
gtgggacttt gtcttcttct gacagttccc cagggaacct cttaaattta gaaaactgtg  22440
cctaacaatg tcttctctat gcatatgagg accttttctc cctggcacaa aatgcagatt  22500
gacgctgaca cggatggtcg acgctgctga cattcctaga taactgcagc tgtagttatg  22560
cctgctaagg tttgggcgca tggggcttgg cttttgtcag ctccctggga tttattttcc  22620
caaacaaaga aacctccagg ttaggggcac cctattcatt cccatcacct ggcatgattt  22680
aaaggataat tgcttagaat taaaatattg atccagattt tttatattcc ccatcgcttt  22740
ttgtttcttc tgggctgtag ccagagatca ttgattggcg ctcaggaata agcagagtta  22800
gtctaaaatg caggcaaata cttaaacaac tgaagagatt agaatttaaa gacaagtgta  22860
tgatatgttt tgaaatacaa tgtttctctt tccagttttg gtttttgtca gcagcaaata  22920
```

atgataagac tgagttgttt gcaaaataaa ctttagtctt aaacttggcc tgattatttg 22980
cataaagtgc agcaagaata ttaataataa ttctgtagga aaagcctgca agcaccagga 23040
gcttcacagt ctaacactat gagcacgtgc atcctcacgc aactcactga atatgtccaa 23100
gtcagcctgt tccgatctta aatgccatcc agtggcatct gccccaggta cactaataca 23160
tgggtcctgc ttctctctgc agccgcctct ctcctcagat ttcaggtttt gtgtattgtt 23220
tgttttctct ctgacatcaa cacagatatg ttgaaggttt tctttttttt atttgtagtt 23280
gttcagcttt gttgttaatg aggtcagaat aagctcatag tttacacatt tttacattcc 23340
catgccgagt agctgctttt ctctatcaaa tccattaact gagagaacaa tcacatttcg 23400
ttacaggtga acagttaaat agtttggcat atatttctgt gctggaatct aatgcagctt 23460
gaaatcaagt catgcctcac tcattgaaaa aaacatggct aaattctcaa agaattgtgc 23520
tgagtgaaag aaactaagga atgaagagta aattttatat gatacatttg tagaaatttt 23580
agaagatgcc actattataa attaacatgg agaagattta agtgtttctg agaatatgct 23640
attgggagta atggggatgt gagttaaatt tcagaggaat aagagaaaga tttagggatt 23700
aattttttca aaccttgatt gaagtgctga gtaaatggtt gcaaacatag gtctacattt 23760
ttcaaatcat tcaccataaa tttgaattat ttattaatta cactcgaata aagcaataaa 23820
gaaactgatg agataatatt tgactgaatt gcatcaataa atagatcgat attaacacaa 23880
ggaatataac tgatttccaa aaacatacac atgaaccgtg gttcactctg cgtatttaga 23940
taaattacag aaagttgtca taacagatgg ggaatcctgc agacttcact aggcatgggc 24000
catgctgccc tggagttgtc tcaggggagc tgcctcctcc agaggttaga gcacaggccc 24060
aggtaatagg actaaatttt tagatgtgtt atcttagaca cactgcacaa ctgctgtgtt 24120
ctctatgtaa attatctcct gtaaaatata acattgaagc ctgcattaaa tatattgtgt 24180
aaatatgtaa gaataaaaga aagttatgag agctaagtgt taatcaaggc acaagcatat 24240
aagatataac tatattttcc tgaatgatgg aattactacc agtctccccc aggacacttc 24300
atctgccctg agcccagcct ctcctcagat gtcccaccca gagcttgcta tatagtgggg 24360
gacatgcaaa tagggccctc cctctactga tgaaaaccag cccagccctg accctgcagc 24420
tctgggagag gagcccagca ctagaagtcg gcggtgtttc cattcggtga tcagcactga 24480
acacagagga ctcaccatgg agtttgggct gagctgggtt ttcctcgttg ctcttttaag 24540
aggtgattca tggagaaata gagagactga gtgtgagtga acatgagtga gaaaaactgg 24600
atttgtgtgg cattttctga taacggtgtc cttctgtttg caggtgtcca gtgtcaggtg 24660
cagctggtgg agtctggggg aggcgtggtc cagcctggga ggtccctgag actctcctgt 24720
gcagcgtctg gattcacctt cagtagctat ggcatgcact gggtccgcca ggctccaggc 24780
aaggggctgg agtgggtggc agttatatgg tatgatggaa gtaataaata ctatgcagac 24840
tccgtgaagg gccgattcac catctccaga gacaattcca agaacacgct gtatctgcaa 24900
atgaacagcc tgagagccga ggacacggct gtgtattact gtgcgagaga cacagtgagg 24960
ggaggtcatt gtgcgcccag acacaaacct ccctgcagga acgctggggg gaaatcagct 25020
gcagggggcg ctcaggagcc actgatcaga gtcagccctg gaggcaggtg cagatggagg 25080
ctgtttcctg tcaggatgtg ggactttgtc ttcttctgac agttccccag ggaacctctt 25140
aaatttagaa aactgtgcct aacaatgtct tctctatgca tatgaggacc ttttctccct 25200
ggcacaaaat gcagattgac gctgacacgg atgaaaattc ctcaaccatg gtcacaagga 25260

-continued

```
tcagagtcct gagtaacctc agggcttcct ggtgattctt ctccaatcag acccaggaca  25320
gggacctccg tgagattccc tgactggaac agtctttatg gatcctggtc acagacaata  25380
gagaggctga accagggtca gcgtcatgta gaacgtcaca gatttcacgt ctgatccttc  25440
tcctgacacg aaagtatgca aatcagtatc agcaccgatc tgctcgacga tggaaagata  25500
gataccaaca tgagaaatgt atgacactca agaaaataaa actgtaggaa acttgctttt  25560
ctttatattt gttaggtaat caccacagtg tgtacacatc acaccatgtt cccattacag  25620
agaaaaggtt ctgcgaacct cacgagctgt gacccctgtg tgctgggctt ggttcaggga  25680
gaagtcaggt ccagtggtga gaagcacagg cccagatgcc caggctcact ctgaccaaaa  25740
gtgagcactg gggacattgt aaaacccacc tgtgcttttg ctgataattt ttcatcttta  25800
acatggaaat aatattgata ctatatacca tggtttctct gcgtatgtaa aaataaaaga  25860
tgattggtgc taactttaaa aatatgcagt ttatgtagat ctatggtacc tcaataaaac  25920
tgttttaaaa taaaaattac aaaattataa gatttttagg ttttaaggtt taagtttatc  25980
acaaaacaaa ctgacaatag gaaagcacaa tttcccaatg ctttcaatat cacagatctc  26040
cccgaggaca ttctgacatg ctctgagccc cactatctcc aaaggcctct caccccagag  26100
cttactatat agtaggagat atgcaaatag agccctccgt ctgctgatga aaaccagccc  26160
agccctgacc ctgcagctct gagagaggag cccagccctg ggattttcag gtgttttcat  26220
ttggtgatca ggactgaaca gagagaactc accatggagt ttgggctgag ctggcttttt  26280
cttgtggcta ttttaaaagg taattcatgg agaaatagaa aaattgagtg tgaatggata  26340
agagtgagag aaacagtgga tacgtgtggc agtttctgac cagggtttct ttttgtttgc  26400
aggtgtccag tgtgaggtgc agctgttgga gtctggggga ggcttggtac agcctggggg  26460
gtccctgaga ctctcctgtg cagcctctgg attcaccttt agcagctatg ccatgagctg  26520
ggtccgccag gctccaggga aggggctgga gtgggtctca gctattagtg gtagtggtgg  26580
tagcacatac tacgcagact ccgtgaaggg ccggttcacc atctccagag acaattccaa  26640
gaacacgctg tatctgcaaa tgaacagcct gagagccgag gacacggccg tatattactg  26700
tgcgaaagac acagtgaggg gaagtcattg tgagcccaga cacaaacctc cctgcaggaa  26760
cgatgggggg gaaatcagcg gcagggggcg ctcaggaccc gctgatcaga gtcatccgca  26820
gaggcaggtg cagatggagg ctgtttcctg tcagggtgtg ggacttcatc ttcttctgac  26880
agtttctcta gtgaacctct ctaacctcag aattctgtgc ttactaatgt catctctacg  26940
tattttttaa aagatcattt taatatgagc acctattctc acacgcacca aatgcagatt  27000
gacgcttaca gagatgctcg accactggga ttcctaaggc caattcagta tttcaaaaga  27060
tggtgtgaga agcacaggct gtcactaaag gagaattctg agccagggca cagccacttt  27120
atacttggct ggggacactg gtaggaatat actctgtgag atcagacagg aacctccttg  27180
caggggcagg gcagggctgc agggggcgct caggacacac agagcacagg cttccgcccc  27240
agagcaggtg aaggaggctg gggaggggtt cctctcaggg cctgggactt cctttaaaaa  27300
atctaaaata agtatttcac aaggactgcc gatgtttata taaatatcct attcaattgt  27360
gagcatttat gaaactcgat gttgtaatga gaaccacttt tacaatggga atttcaaact  27420
tccctagaca tcttaatagt aagcagctgg aggtcaggag gagatccttt cttataaata  27480
agtgcaattt ttggagaaac acactcattc ccaaaatagc acattcacat attaaggtct  27540
agaaatgatt cgagttgccc ctgagacagt caaatgtggg ttctaagtga ggtgcgtgtc  27600
ctgggggagc ttgttctcca gtgggggaag ctctgtcaac acagagttca gggatggata  27660
```

```
ggggatgcgt ggcctctaac aggattacgg ctttaaccct cagcttctac aattgtgtcg  27720
tccatgtgtc atgtatttgc tctttctcat cctgggtcag gaattgggct attaaatagc  27780
atccttcatg aatatgcaaa taactgaggt gaatatagat atctgtgtgc cctgagagca  27840
tcacccaaaa accacacccc tccttgggag aatcccctag atcacagctc ctcaccatgg  27900
actggacctg gagcatcctt ttcttggtgg cagcagcaac aggtaacgga ctccccagtc  27960
ccagggctga gagagaaacc aggccagtca tgtgagactt cacccactcc tgtgtcctct  28020
ccacaggtgc ccactcccag gtgcagctgg tgcagtctgg agctgaggtg aagaagccta  28080
gagcctcagt gaaggtctcc tgcaaggctt ctggttacac ctttaccagc tactatatca  28140
gctgggtgtg acaggcccct gaacaagggc ttgagtggat gggatggatc aacacttaca  28200
atggtaacac aaactaccca cagaagctcc agggcagagt caccatgacc agagacacat  28260
ccacgagcac agcctacatg gagctgagca gcctgagatc tgacgacatg gccgtgtatt  28320
actgtgcgag agacacagtg tgaaaaccca catcctgagg gtgtcagaaa ccccagggag  28380
gaggcagctg cagtgaattt gaggagatta cagggcttac aatgtttaaa gttgtttaga  28440
aaatgagctg agcaactgag gaatgtaagt aatagaaaca tggatgcact ctatatagga  28500
aatgtttctt tcagctgtca ccctatatgc aaaattcaga gtggtaaaga cagcaatcag  28560
tgaggctgat gcaaagaatc ccatggaggc cttgtgcaga catataggtt ttaaaatcag  28620
atagataaat aatttggaac aagattgctg gtaacgtggc taagactact cgaccacctt  28680
ggtaactagg atggttacat caggtttatc aattgtacac tttaaatatg tgaagtttat  28740
tatcagtaaa ctgaaattta taaaatttat taccagcaaa caaatgaaaa cttgcacaag  28800
aaataagtga cataaagata gaaaaaatat taaatttcag aaacacctaa taatttatct  28860
tcgtgaaccc tagttctcac catattttta ggtgaatgct agaatgcagc aaaattacac  28920
atgctctcaa tacagaaagt gggtttcaca aaccacacta ggcatgctca gctctgtcct  28980
ggagttgggt tagggagtaa tatagggcca gtggatgagg agcacaggcc tagatactgg  29040
ggctcactaa cctcaggtat gagctcttag atacatacaa agcccctcca cgcatgggtt  29100
tacttcccca tctgtaaatt gagaaaccat tgacccctaa aaatatgatt tacacaaata  29160
tgtaaaaatg taagagagtg attagtgcaa agtgtttatc acagcacaat ttcataacaa  29220
gacagcaagt tttccaaaca gcatcattgt cattagattc ctgcagggca tcattacctt  29280
atctgggccc tgccctctgt tcaggcatcc caccccagag cttgctatat agtaggtgac  29340
atgcaaatag ggccctccct ctcctgatga aaaccagccc agtcctgacc ctgcagctct  29400
gggagaggag ccccagcctt gggattccca agtgttttca ttcagtgatc aggactgaac  29460
acagaggact caccatggag tttgggctga gctggatttt ccttgctgct attttaaaag  29520
gtgatttatg gagaactaga gagattaagt gtgagtggac gtgagtgaga gaaacagtgg  29580
atatgtgtgg cagtttctga tcttagtgtc tctgtgtttg caggtgtcca gtgtgaggtg  29640
cagctggtgg agtctggggg aggcttggta aagcctgggg ggtcccttag actctcctgt  29700
gcagcctctg gattcacttt cagtaacgcc tggatgagct gggtccgcca ggctccaggg  29760
aaggggctgg agtgggttgg ccgtattaaa agcaaaactg atggtgggac aacagactac  29820
gctgcacccg tgaaaggcag attcaccatc tcaagagatg attcaaaaaa cacgctgtat  29880
ctgcaaatga acagcctgaa aaccgaggac acagccgtgt attactgtac cacagacaca  29940
gtgaggggag gtcagtgtga gcccggacac aaacctccct gcaggggcgc gcggggccac  30000
```

-continued

```
caggggggcgc tcgtgaccca ctgagggcgg gacaggtccc aggagcaggt gccgggagag  30060
gtttcctttc tcctcagctg gaaaagtcag gtttatcttc gcaggactct ggagtcttct  30120
aggctgtgct cgacagtgca atgatatagt ttagatgttt tcccttccaa atgtcatggt  30180
gaaatgtgat tctcaatgtt ggaggtggga ccgactggga ggttttgggt catggggaaa  30240
gatccttcag gaatggcttg ggaaccaccc catggcactt agtgaattct tgctgtgtta  30300
gctactatga gatctgattg ttaaaaagag tctggcaacc cttcttgcca ctcatgtccc  30360
agctctcacc atgtgacata gcctgttccc cctttgcctt ccatcatgat tgtaaagcag  30420
atcctggtgc catgcttctc acacagcctt cagaactgta agccaaatgt gcctcctttc  30480
tttgtaaatc acttggcctc aggtattaat ttataggaat gcaaaagaga ctaacacacc  30540
gtccaaagca ttacacagat tcaacactat ttttatcaaa tgaccaatat aattgattac  30600
atatttagaa aaaaaatact aaaattccta cagaatcaaa aaagagtctg aatagcaaaa  30660
gcaatcctaa gcaaaaagac cgaagctgga agcaccacat tctctgacct caaattatac  30720
tacatgaata taataagaaa gacagcatgc tactagtaga aaaaaacagc ccagaaagaa  30780
agccaaatat ctaaaaccaa ctgttgtttg acaaaactga caaaaatata cactggagaa  30840
acaaccctct attcaataag tggtgcaggg aaaattaggt ggcttatgtg gaagaataga  30900
acgagacttc catatcaccg tagacacaaa ttaactgaat atggattcag tgtttaaatt  30960
tataaactaa aactataaaa atacttgaat aaaatctaaa aagagtcctc tggacattgg  31020
tctaagcaaa caatatacga ctaagacttc aaaagcaaat gcaataaaaa cagaagtaga  31080
caaacaggat ttagttgaac taaaggtctt ctgcacagca aaagaaataa ccaacatggt  31140
gaccagacaa tctgcaaatg gaaaaaatat ctggaatcta ttcatcttgc aaagggctaa  31200
tatatagaat ctacaagtaa ctcaaataag tcaactaaaa attacaaata acttcattaa  31260
agaatagaca taaacagaca tttatcaaaa gaatacacag aagtggccaa cacaaataag  31320
aaaatatact cagcatcacc aatcatctga taaatgtaaa ttagaaacaa cgtgatacgg  31380
catcttccac cagtcagaat ggctgttatt acaaataaaa acagcaggtt tttgcagaca  31440
aacataggaa aaataatgat ttatatatgc ttggtgagaa tgtaaattag tacaacctcc  31500
atgaaaaaca acatagaaat ttctcaaaga actaaaatta gaattaccat ttcttccagt  31560
gagctgtccc agtaggcatg ttcctcccaa actttttatat cagagaatgt tgcctgcact  31620
catatgttta tttcaacacc attttcaata gaaaagtcaa ataatctaag tgtcaatcag  31680
tggatgatta gataaaatat gatatatgta aatcatggaa tactatgcag ccagtatggt  31740
atgaattcag tgtgaccagc ccctggacaa gggcttgagt ggatgggatg gatcatcacc  31800
tacactggga acccaacata taccaacggc ttcacaggac ggtttctatt ctccatggac  31860
acctctgtca gcatggcgta tctgcagatc agcagcctaa aggctgagga cacggccgtg  31920
tatgactgta tgagagacac agtgtggaga cccacatccc gagggagtca gaaaccccga  31980
gggaggaggc agctgtgctg agctgaggca gtggtgcagc agtttcttta acttccatat  32040
gatctcattt tgcatcatct tctactttta tattagctaa gaacttgggg tagacaggtg  32100
ctcctaagag atccttaact tgcccatttt gatggttttc cagaagacgt gagaagccac  32160
tttgttagca aagcatccca aatccatgcc ctgttctaga tacatgtgag cccatttcct  32220
ggtctttgct taactgacaa gctctcatca gtgcacctgg gctaatttca catcaggtag  32280
aggaacgcgt tataaaggaa agctaatgtt gtaatggcaa ttcctgctta aaaaccttca  32340
gcttcattgt ttttgtgtaa tccatcagca aattatgtta gttcaaggtt ctcaatggga  32400
```

-continued

```
gtttctaata aatagaaagg ttgtatagag cttcccctaa ttaaaatgaa acaattgtga  32460
actcaacctc ggtattcagc catgtctcca cccttcacac ccttcgccac aaaggaattt  32520
tcacctctcc tggaagctgg gttcattttc aaattagtta ttttttcaa tgtaatatct  32580
caagattatc gtatatgact attttagcag aaagtgaatt atgggaactt gaactaaaca  32640
actgaaaaca aattcacaac taattaaaca agatgccaga atgtgattgg ctccaggctt  32700
tgtaattcag cagttcatgt acccagactg gaaatttaca tgtcttcttg ttaccttcac  32760
agcacagtca actcccatta tgtaagaaat ggtgactgca ttcccaaggg ttatgcatag  32820
atatgaaaat agactgggta aggtgaggag ttgattgttt aaattcccct ctgaagaagc  32880
agcatcaact caacaaacca cctctcttca ctctgtgact agagctatgt cacaggccac  32940
atggacctaa atccttgatg gatataacat gactacataa attgggctga tcatttttat  33000
gctataaaat taatagatga cactgcactc cagcctgcac aaccaagcaa gtcttcatct  33060
gtaaaatcta aaaaagaaaa attagtaggt actgacttcg aaatttttga taataatatt  33120
ttcaccaccc aaatttaatc acacccacat gttacctgca tcttcactga aaagttccca  33180
gtcacgatga gttccttcaa tgctccatgt gttcaaatct ggacatcaag agagtccaga  33240
gaataaaaca caatgacggc agtgaaactg atatatattc agcacctctt aactcaggag  33300
gactccatac accctggcac acagctgctt ttctaaatgg ctcacaatga ctccagctca  33360
ctcacagagc tcagacagaa acctcccttc agggtgggag ctgggtggca gggggcactc  33420
agtacccgca gaggtgaaaa tgagtttcag atggaacttc cctgtcacct caacatggaa  33480
tttattgttc catttcatta cctctctttc cataatggtt catttctttt ggcctgttca  33540
ttactgatat ttttcagagc aatctcactt gaatctttac tcttttgcat tttgtctcct  33600
tgacaatgtt gggaagtttt acctccagca tcataacatg atctagtgat ctgacacatt  33660
gtgcaaacaa tacctacaaa ttcagaacct ctttgttttt ctttccacaa aatataattc  33720
tttctgttct gtgtatgagc atgtcttagc aaccctgtac acacccacat agatgtctac  33780
aagcctatga attgttctct gtaaataaaa atttatctca aattccttca atgttcataa  33840
ttctgagagt gaggaaggtc cttctcaatc tgttcaaaca aaatgcccag agaccatcca  33900
gtaggtaagg agttcacctg gctctggtgt ggggtctgtc tctttccctc tgttgtccca  33960
caggtcagcc cagttgttca cgtcctaaca agaaagccca ggtttgtcct gattttaaaa  34020
cacatcaaac ttctgatgac tctcctgtta cccacatcca tggagataga ttatttatta  34080
tataattcag caaactaatg tcaaatgccc aagttgcaat accgcacatc ctagggtatg  34140
ttcatgcaat tcaatggagg agaaaatctt tcagagacag atggatctga aatgataaat  34200
atgtgggtaa ggactctggg cttgagtatc attgtccagc catgtttcac aagtgtgtcc  34260
tgtcagggaa ggatcagagt tccttgtgct ctcagaggga aggggtcaca gagttcctct  34320
ctggttccca ggaaaggtaa tcgcactaat cttcatgatc ttcatgagac tatcctccag  34380
tgctgacctg ttacggagtt tttgtctgaa gttctcactg caatccccaa tctacatatt  34440
ttcaatcaga agtgtttaga gggcaggaca catcttcaag gtcacacatt gagaaggatg  34500
gagatatgtc ccactacctt ctcctacgat ctcagacaga atcccaaatt tcaaaaggac  34560
acagaaggac agctctcagg tgcttttaaa aaatgaccca cttccaggga cagtgagctt  34620
ccctgtaacc atggtggatg ttctgaacta caataaacat tggatggatc cagtattgtt  34680
tgaagtcact gtcattatta cattcagctg ttgtttcaat gtgtctgaaa gggtaaatga  34740
```

-continued

```
ctatttagat ggcctgggtg tgtggttggt tttatatgaa tctttaaggg ttgaacagta  34800
ttgaccctat tccacaatct gtccttgatc catgatcaca ctcatctctc agacaagctc  34860
cttcagcaca tctctttacc tggaagaaga gcactctggg cttggcgagg ggagccccaa  34920
gaagagaact gagttctcaa agggcacagc cagcattcta ctcccagggt gagcccaaaa  34980
gaccggcgcc tctctcatcc cttttcactg ctccgtacaa aggcaccacc cacatgcaaa  35040
tcctcactta ggcgcccaca ggaagccaca acacatttcc ttaaattcag gtccaactca  35100
taagggaaat gctttctgag agtcatggac ctcctgtgca agaacatgaa gcacctgtgg  35160
tttttcctcc tgctggtggc agctcccaga tgtgagtgtt tcacgnnnnn ngatatgaag  35220
atatgagaaa ctgcctctga tcccagggct caccgagggt ttttctgttc acaggggtcc  35280
tgccccaggt gcagctgcag gagtcgggcc caggactggt gaagccttcg gagaccctgt  35340
ccctcacctg cactgtctct ggtggctcca tcagcagtag taattactac tggggctgga  35400
tccgccagcc cccagggaag gggctggagt ggattgggag tatctatcat agtgggagca  35460
cctactacaa cccgtccctc aagagtcgag tcaccatatc cgtagacaag tccaagaacc  35520
agttctccct gaagctgagc tctgtgaccg ccgcagacac ggccgtgtat tactgtgcga  35580
gacacacagt gaggggaggt gagtgtgagc ccagacaaaa acctccctgc agggaggctg  35640
aggggaccgg cgcaggtgca gctcacggcc agcagggggc gcgcggagct cacggaatac  35700
aaggccgggt caggagcagg tgcagggtga gcggggcttg ctcatcttct caaacatctc  35760
cctcctcgcc agcacctcag ctttccgtag aggtcctctt tctttattgt ctgtggttct  35820
acttcctcac atccttgtgc caggaaagaa aggagtaagg caaattttcc tgttacaatt  35880
gaagtttcac caattactaa aaactttcct gcaagtacct gcacagccca ttatacctta  35940
tttatatata tatatattct aatgcttctc accatctctt gatttgtgtc atcaatttaa  36000
ttgtgccctt tttgaaattc atatgctgaa actttaaatc caatggatct atatcggaat  36060
tttaatggta taattaacgt taaatgtggt cataagtgag accctaatgc aatagacctg  36120
ttgtctttat aagaagagga agagacacca gagacctctc acttctcaca tgcacacaga  36180
gaagaggcca cgtggagaca tagtgcacta gaaggtgggc ctctgcaagc caggaagaag  36240
ccgcaccaag aaccaaccct gccagcacct tgatcttcta cattcagact gcagaattgt  36300
aagaaaacca atatttgttg tttaagccac ccactccttt tgtcttctta cgaagaccca  36360
gacaggctaa taccacacaa ctctgttagc tccatctcct ggagggagaa gcagcccccct  36420
gaggctgggc acatcgctca gattttcaca tgaattaggc aaaaacagta gctctcatat  36480
aaaaactgtc acgtccctgt tgggacaagg tcttctaaac aacccctggg gctttgtcac  36540
aaatgttgca ttttatcctt tattaggact taactaattg acaatgagta ccagctggat  36600
ggaaactgac cactgaccat cttctgctgt ctccttatta tatcacagaa aaccacagca  36660
acattactct atgtcttcaa ctttctaaat ttgtactgaa tctattgcta aatgaggagc  36720
tacatggggt ctgagttttg ttatcttctc cccagtcttc cccaattacc aagcacagaa  36780
gatactttca gtgaaattta gctgtcaatg cccccaacac cacatcatgt tttaaggtcc  36840
aaggactttc tttggggggc tatttaaaaa cacttttgaa tggaaaatcc taaagcatac  36900
aacagctgaa agaatggccc ctgtgcacgt gaaggctgaa gggatggatg atagggtacg  36960
ttcctccaag gtgttcctgg gcatgtgatg gttggatacc tcatgctcga cctatggatg  37020
tgaactacaa gtatgtaagt acttcaagta attctattta atggagtttg aaataaaact  37080
caaacttatt caaaacacta attacttggt atttattttg agatctatga gtttatcaag  37140
```

```
aaattcaaat tcctatttct atttaaactc ccgattccta ctctcagtgg gagggaaaac    37200

tcacagccaa tcacacatca caggacaaat ctgtaaacga agagtcattc ctctgaaggt    37260

cctgggtgtt caggactctc aggcaggtgc tgaggaccct gtcttgggag tgcccagcag    37320

atctcagaac cctacatggg gcctgctgga cactcatgtg ggataactag tcgccactta    37380

ttcagagtta ccagtgagct ttgactgttc cgaatgggac cagcatggag tcaaggtgcc    37440

tgctcaatgt cagagacagc gatggtctca gaaacaatcc aggtaatctc taggccaata    37500

aaatgtggat tcacagtgag aagtacatcc tggaggtgga gcttgttctt cagtgggaag    37560

agtgctgtgc acagaaagct tagaaatggg gaagggggtg cgtttcctca ggcaggatta    37620

gggcttcgtc cctcagcgtc ccactcttgt atggctgatg tggcatctgt gttttctttt    37680

tcatactaga taaggctttg agctgtgaaa taccctgcct catgaatatg caaataacct    37740

gagctcttct gaggtaaata taggtatatt ggtgccctga gagcatcact caacaaccac    37800

atctgtcctc tagagaaaac cctgtgagca cagctcctca ccatggactg gacctggagg    37860

atcctcttct tggtggcagc agctacaagt aaggggcttc ctagtctcaa agctgaggaa    37920

cggatcctgg ttcagtcaaa gaggatttta ttctctcctg tgttctctcc acaggtgccc    37980

actcccaggt gcagctggtg cagtctgggg ctgaggtgaa gaagcctggg gcctcagtga    38040

aggtctcctg caaggcttct ggatacacct tcaccagtta tgatatcaac tgggtgcgac    38100

aggccactgg acaagggctt gagtggatgg gatggatgaa ccctaacagt ggtaacacag    38160

gctatgcaca gaagttccag ggcagagtca ccatgaccag gaacacctcc ataagcacag    38220

cctacatgga gctgagcagc ctgagatctg aggacacggc cgtgtattac tgtgcgagag    38280

gcacagtgtg aaaaaccaca tcctcagaga gtcagaaacc ctaggggaga aggcagctgt    38340

gctgggctga ggagatgaca ggggttatca ggtttaaggc ttttttgaaa atgggttata    38400

tatttgagaa aaaaataaca atagaaacaa gtacacactc taattttaag agatatattc    38460

aattcaagaa ttgtagaagc cgaattcaca gtgggaaagg ccacactcaa taaagttgat    38520

aaaaacattc caggaaggtg ctactgctcg accctgtgtt tatctgttat gttgatgctg    38580

taaaacagta agtaaaatat actcctcatc tatgtacatt ttgaagctga gttgcaggtt    38640

ttttggtaag acccagagtc acagagaatt caaatattgt taagctgctt aatagaaaaa    38700

caaattatgg taaatgtgtt cactggaata ctacccatga tttataataa ataaatgcct    38760

gacacacaga acagcagcaa aaccacacat gctcttatta cagaaagtgg cttctgaaaa    38820

ccacaccggg cacgtacagc tttgtcctgg agttggttta gggggatgtc agagccagtg    38880

acgagaagca cagggccaga tggcagcgtt cactcatccc agacatgagc tcctggatgc    38940

atacagagcc cccccatgtg tgggtttact tccacttctg taaaaggaga aaatactgac    39000

tcctacagag cataatttac acatttttta aaaaatgtaa tagggtgatc agggcaaagt    39060

gtttatcaca gcacaatttc ataagacagc atattttcca aataccatca ttgtcagcaa    39120

acttctgcag agcaccgtct tcttatatgg gtacagccta ttcctccagc atcccactag    39180

agcttcttat atagtaggag acatgcaaat agggccctcc ctctactgat gaaaaccaac    39240

ccaaccctga ccctgcaggt ctcagagagg agccttagcc ctggactcca aggcctttcc    39300

acttggtgat cagcactgag cacagaggac tcactatgga attggggctg agctgggttt    39360

tccttgttgc tattttagaa ggtgattcat ggaaaactag gaagattgag tgtgtgtgga    39420

tatgagtgtg agaaacagtg gatttgtgtg gcagtttctg accttggtgt ctctttgttt    39480
```

-continued

```
gcaggtgtcc agtgtgaggt gcagctggtg gagtctgggg gaggcttggt ccagcctggg  39540
gggtccctga gactctcctg tgcagcctct ggattcacct ttagtagcta ttggatgagc  39600
tgggtccgcc aggctccagg gaaggggctg gagtgggtgg ccaacataaa gcaagatgga  39660
agtgagaaat actatgtgga ctctgtgaag ggccgattca ccatctccag agacaacgcc  39720
aagaactcac tgtatctgca aatgaacagc ctgagagccg aggacacggc tgtgtattac  39780
tgtgcgagag acacagtgag gggaagtcag tgtgagccca gacacaaacc tccctgcagg  39840
ggtcccttgg gaccaccagg gggcgacagg gcattgagca ctgggctgtc tccagggcag  39900
gtgcaggtgc tgctgagggc tggcttcctg tcgcggtctg gggctgcctc gtcgtcaaat  39960
ttccccagga acttctccag atttacaatt ctgtactgac atttcatgtc tctaaatgca  40020
atactttttt tgtccttttt gtttctttgt ttttttgcaa caggagtaca tatcctcagc  40080
tccacagaag ccagggctcg accatggtca gtgtcatata gaatatgggg accctcacaa  40140
gtttttttgtc tgacccttct cctgacacta aattatgcaa attaataaca ctgatctggt  40200
gcttcttttg attctaattt attttatttt tagttgtcgt tctcactttt cctttggatt  40260
ttcctgctcc ctggaaaagg taaatgtggt ctccgtgacc tcaattcaag ggctgaagcc  40320
ctttccctgt agctcagctg gggctcaggc tgtggctact gcagccatgt ggaagaggct  40380
gaagggactt tcttcactct ccttgctcag gaccatccac tgtattgtgt ataggcttct  40440
ctggaaatgc aagtggccat ttgtagtgaa agaaatatgt ttgtctggtt aaaatgggag  40500
gtggatgtag agttaattgg ctgctacata aactgtcctt ctccaccagt gcttttagga  40560
tgagattgtg aaatttgtaa gaatcaaaat ggagtcacat atgttaaaac cctgacaaat  40620
ggattcagga agtgtaggga gaattcttac acacatatcc ctgacaacaa gaactatcat  40680
aaaatagttc ttgcaaaaag accaacatga cctcataatc atgacttctg caaagacttc  40740
tactcagaat ctacttgccc agccttagat taatgccatc tgaattacac tgatcatgtt  40800
actatcactg ctcctcacca cagatgcaac accctcctga gtcctgaaac ctgactccat  40860
cccatagagt agggcacaga tgaggggaat gcaaatctcc accagctcca ccctcctctg  40920
ggttgaaaaa gccgagcaca ggtcccagct cagtgactcc tgtgccccac catggacaca  40980
ctttgctcca cgctcctgct gctgaccatc ccttcatgtg agtgctgtgg tcagggactc  41040
cttcacgggt gaaacatcag ttttcttgtt tgtgggcttc atcttcttat gctttctcca  41100
caggggtctt gtcccagatc accttgaagg agtctggtcc tacgctggtg aaacccacac  41160
agaccctcac gctgacctgc accttctctg ggttctcact cagcactagt ggagtgggtg  41220
tgggctggat ccgtcagccc ccaggaaagg ccctggagtg gctttcactc atttattgga  41280
atgatgataa gcgctacagc ccatctctga agagcaggct caccatcacc aaggacacct  41340
ccaaaaacca ggtggtcctt acaatgacca acatggaccc tgtggacaca gccacatatt  41400
actgtgcaca cagaccacaa agacacagcc cagggcacct cctgtacaaa aacccaggct  41460
gcttctcatt ggtgctccct ccccaccttt gcagaacagg aaagtgcagc tgagatacgt  41520
tttcctgcca gggcctgcat ttcccatccc cattagactc agagccctgt cttcctcctt  41580
cttctttaat aataaatggc atgactcctg ttaatagttc atagaagcag aagctgagtc  41640
ctgtttgtca aacattcagc atgaaatgtt catgttacct gggccagatg catcactggt  41700
atgtggccgc cagctcgacg gtcacacatt gagaatgatg aagatatgtc ccacgagttt  41760
ttcctaaggt ctcagaaaga attccaggac tcaaaaggtc tcagagggca gctcccagtg  41820
ccttaattaa aatggtggct caggcctgta atcccagcat tttgggaggc taaggcaagt  41880
```

-continued ggatcacctg aggtcgggac attgagacta gcttggccaa catggtgaaa ccttatctct 41940
actaaaaata taaaaattag acgggggtgg ttgtgcgtgc ctgtactccc agctactcgg 42000
gaggctgagg caggagaatc acttgaaccc aggaggcgga ggttgcggtg agccgagatc 42060
gggacactgc actctagcct gggcaaagga gcaaaagttc atctaaaaaa tttattttaa 42120
tttaaaaatt ttgaaaaaat ggcccactcc ctagaacaga gagattccct ctaaacatga 42180
tggaggtccc gaactataca ttaagtgaat cctggtgtgt ctgaactcac atgattatta 42240
cgttaagctg ctgttccaat ctacttcctc acctgggaaa agaggagcca gggcatggct 42300
agttgaggcc ccaggaagag aactgagttc tcaaaggaca aagcaagcat cctcatccca 42360
gggcgagcct aaaagactgg ggcctccctc atccctttc acctctttat acaaaggcac 42420
cacctacatg caaatcctca cttaggcacc cacaggaaac caccacacat ttccttaaat 42480
tcagggtcca gctcacatgg gaaatacttt ctgagagtca tggacctcct gcacaagaac 42540
atgaaacacc tgtggttttt cctcctgctg gtggcagctc ccagatgtga gtgtctcaag 42600
gctgcagaca tggggatatg ggaggtgcct ctgatcccag ggctcactgt gggtctctct 42660
gttcacaggg gtcctgtccc aggtgcagct gcaggagtcg ggcccaggac tggtgaagcc 42720
ttcggagacc ctgtccctca cctgcactgt ctctggtggc tccatcagta gttactactg 42780
gagctggatc cggcagcccc cagggaaggg actggagtgg attgggtata tctattacag 42840
tgggagcacc aactacaacc cctccctcaa gagtcgagtc accatgtcag tagacaagtc 42900
caagaaccag ttctccctga agctgagctc tgtgaccgcc gcagacacgg ccgtgtatta 42960
ctgtgcgaga gacacagtga ggggaggtga gtgtgagccc agacacaaac ctccctgcag 43020
ggaggctgag gggaccggcg caggtgcagc tcaaagccag caggggggcgc gcggggccca 43080 cagagcaaga ggccgggtct ggagcaggtg cagggagggc ggggcttcct catcagctca 43140
gtgctctccc tcctcgccag gacctcagct gtccccaggc ctcctctttc tttattatct 43200
gtggttctgc ttcctcacct cgacgtcact gaaggagcat tctgagccag ggcacagtca 43260
cttcctagtg agctacagag gctgagagaa aaatgctctg tgagacccaa tgggaagctc 43320
cctgcagtgc aaggtctggg tggcagggag cgctagggcc tcgcccagca caggctgcag 43380
ccctggagca ggtgcaaggg aggctgggga ggggttcctc ccagggtctg atgtcttcct 43440
tttctcggac aaacatgctt taataagtta aacaagactt tagtaaagac tattgatgtg 43500
tctttgtgtc tttcagtata cagttctatt tgtaggattt atctaaccta acaagtcaat 43560
gagaatcaca tgtaaaagga gaaatttcta ggattttcag atatcttaat aggtaggaga 43620
tggagaaaag ggatggtttt attaattcag tgcttgccaa tcttaacaga gacagtagta 43680
agacatgcag aaagcaaagc ccagaaaagt atgaaggtgt caaagtgcca tttaagtatg 43740
ggttcacttg gaggaccatg ttctgcggga acttgttttc agcagacaat ctattttagc 43800
agagttctgg gcatacaagg ggacacacat cattaaacaa ggattgggac agggacttca 43860
gcgtcccact gttgcatggc ccataaatta tgtgtgttct ctttctcatc ttggatcaag 43920
tctagagcta tgaaatagta tccctcatga atatgcaaat aacctgagat ttactgaagt 43980
aaatacagac ctgtcctgtg ccctgagagc atcacccagc aaccacatct gtcctctaga 44040
gaatcccctg agagctccgt tcctcaccat ggactggacc tggaggatcc tcttcttggt 44100
ggcagcagcc acaggtaaga ggctccctag tcccagtgat gagaaagaga ttgagtccag 44160
tccagggaga tctcatccac ttctgtgttc tctccacagg agcccactcc caggtgcagc 44220

-continued

```
tggtgcagtc tggggctgag gtgaagaagc ctggggcctc agtgaaggtc tcctgcaagg  44280
cttctggata caccttcacc ggctactata tgcactgggt gtgacaggcc cctgaacaag  44340
ggcttgagtg gatgggatgg atcaacccta acagtggtgg cacaaactat gcacagaagt  44400
ttcagggcag ggtcaccatg accagggaca cgtccatcag cacagcctac atggagctga  44460
gcaggctgag atctgacgac atggccgtgt attactgtgc gagagacaca gtgtgaaaac  44520
ccacatcctg agggtgtcag aaacccaagg gaggaggcag ctgtgctggg gctgagaaat  44580
gaaagggatt attattttta atgttgttta cagtatgtca ttaataaatt gaaaaaaagt  44640
aacaatagaa gtatatactc taattatatg ggaactttgt tttttcagtt ttttcatttt  44700
tttttttttt tttggtttgt ttgtgacaga gtctcactct gccacccagg ctggagtgta  44760
acggcacaat ctcgacgagc atgtgcacat ttcattaaac ccactgtgta tgcagcccct  44820
cccaagtgct ggcaggccac tgtacatgtg ggcagcccac tccaagggaa gaatcaaggg  44880
agaagaaata caaaccccag aaccatgtca atgtataaaa ccccaagtca agggccggac  44940
agagcactta gatctctcaa gtcgcccact tagccctctt ccaagtgtac tttacttcct  45000
ttagttccca ctttaaaact ttaataaaca tttactcctg ctctaaaact tgcttgggtc  45060
tctcactctt ctgtatgccc cttggccaaa ttctttcctc caaggaggcg agaatcaagt  45120
tgctgcagac ctgtatggat tcgctcctgc taacagatag ctggatgggt ggacagatgc  45180
atgaattagt ggatggacgt ttggatgtgt gggtgggtgg gtggattgtg ggatggctgg  45240
atgaatgcat ggctggatgg gtggacagat gcatgaatta gtggatggat gtttggatgt  45300
gtgagtgggt gggtggattg tgggatggct ggatgaatgc atggctggat gggtggacag  45360
atgcatgaat tcgtggatgg acgtttggat gtgtgggtgg gtgggtggat tgtgggatgg  45420
ctggatgaat gcatggctgg atgggtggac agatgcatga attcgtggat ggacgtttgg  45480
atgtgtgggt gggtgggtgg attgtgggat ggctggatga atgcatggct ggatgggtgg  45540
acagatgcat gaattcgtgg atggacgttt ggatgtgtgg gtgggtgggt ggattgtggg  45600
atggctggat gaatgcatgg ctgggtgggt ggatggatgc atggataagt ggtggacgga  45660
tggacgggtg agtggatggg tggatgtgtg tgtggatggg tggataggaa agccctctaa  45720
ttgattacag ggctcagtgt gtgcttcaac atcatgatgg catcatcaca ttggtccctg  45780
tatgaagcag tgggggagga gagtgtacca ggggagcagg aatgactctt ctccagaatc  45840
gacctctccc accctgcagc ctgggctgtg caggccacat tggagaaggt gcggtcgact  45900
actcctaaat gttgttgtgt ccaatggctt tttgacgttg atgtaggaat gagcctacat  45960
ctccaccata gatggaactg tttgggtccc caaagcagaa agcctcttct gttgcaggtg  46020
ctgaagtttc catcttcttc tgcttatacg gaagctcacg catcccttgg atggcaggcg  46080
tcaggttcct gtgcgcactg agttcccccc ttacatgctt tggacagaag tgtgagacac  46140
acaagattgc tgcaggaagt ccacctgtgg ggatgctgcg acttctccag caagaacacg  46200
agtctgctca ttgaccatca ccacacataa caaattaagt gtcccttttt tgataacacg  46260
tcattgtttc acagagtatt cttttaaagt gtataagttg actgcagtta ttattttta   46320
cttctgttac taatttactc ataattaggc acaatttaca cttaagaaat ttcttaatag  46380
ttttttcctc cttaaggtga actacagtca gataacatac ttatcaattg tctctagctc  46440
ttgtcagaaa agcatataga tgtgtgtgtg cgtgtgtctt ggcctttcca atgatgaatt  46500
aagatgtgca ttgagaaggc attcacttta tttgacgtta aggaagtacc aagaagacgc  46560
tctccacaga ccctgggaaa gccagcagct gcaccccgag gctgtgccag gcagggaaca  46620
```

aggaggcagc accacctgct gggcagggaa aatgtcctcc cagtccctgc cgcttctctg 46680
cagaggcaca aagagctgcc ccttctcctg ggccttctcc tgggctgatg agattgctcc 46740
ccgatatgcc aaatcagggt tgtgcatctg aggctctgtc tagactctca gctccttcct 46800
actcctgcaa agtgaagaaa acaatgccaa ggggtcctgg aggcgtctct accccctggag 46860
agttttgact ctcttcaata gtctccacta ccctgccctc actccatgtc ctccgtttct 46920
ccctaaagcg gtgcccagtc tgattgcact gtggcaggga taacgagggg ccaggacatc 46980
aggggagaga agtttctacc tgagtcacag cagcggctgc cctgcagact cctgaagaca 47040
caagacacat ttccatccca gagacccagc gaaatgcaac ctcaggctag agacagccag 47100
ttattttttc ttgttctgtc ctggagaggc cactgagaaa gtcgagcccc ttgttgagga 47160
aaacatgaga tctctgtgtg tcgtcctctg cctgatggct gtacctccat gtgagtgtct 47220
cagagatttc agaacggggg ctgtgggctg tggtgtccgc ttgtgactca tctctttgct 47280
tcttgtccct gagtgtcctg catcagatgc agctactgga gtcatgccca gggctggtga 47340
ggtcctcaca gacctctggg cctggaccca gcagccctct gggaaggcgc tggggcacct 47400
cagctccagg ggcagcacac acttcagccc agcctttctg ggccaactct ccatctgtag 47460
agacacatcc aaggcccagt tatccctgca gctgagctcc gtgatggcca agggcagggc 47520
cgcacattcc cgtgggagac agaatgggga cctcagcgtg agcccagaca caaacctccc 47580
tgcagggaag cacaagacca ccaggcggcg ctccagacca cacagcggcc ccagaagcag 47640
gttttagggg gcggggcaga cgtgtccgcg ttgagtcagg tcactggttt tactttccct 47700
gaacaaacgg cctctgccaa ggactcactg cacctctcac cttcacagtt gttttttttt 47760
tttttttaat caccctgtag ggttttgcta gctaatttag atattgagga gtgcttcata 47820
cttccttggg cctctgcttg cagaaacata gcaattgtaa ggaggcacgt gggaaagccc 47880
cggctcggtg acccggggga tgctgctgta gccctggcaa gagggcgtcg ggccgcagta 47940
acaaaggtgc agacggctct cagcctgcgc ccgcggagta caacacataa gggctgtaac 48000
ctaacgaaaa aagaatcgca gtgcaactgt cctgcatttg agtttgtgat cagttttgcc 48060
ctttgtcttt aacaggttct aacataaaat tttgaatgct ggttcaagcc ctgtgggtaa 48120
aatgcactta cccacattcc ttaaacaaat agaacactga ggtggaaatg ttttgaaaaa 48180
gtagttttca gacatttgga aacaagcatc acaggatcat aacccctgag aaaagaaaaa 48240
caaatgaacg aatcctgcta ttgcctgaaa gcagctgcca ggacacacgg aaaggcttag 48300
tgagctgagc ggacagagag cagagttcaa ggcagcagca gcccgagggg aggagcaccg 48360
gggagcaggc tgctgtgcag ccaggatggg ccggggtggg gcggggggag aacagctgga 48420
gacttgccgc agggaggggg atccctcagg tttggggctg agaactgact tatgcctgac 48480
ttatgcctgc atgaaaagaa actactcgat atcaggggga aatcaccaga aacctgtgga 48540
cccaaaacta cacagagcct acacaaggaa agcattgttt gtgttctccc agccagggtg 48600
gaaagacctt gagatatgta aagcttcaag caatcttccg aagtaatctc gtgagtagtg 48660
gtgccacatt aattcaggac taaagactgc tctgaactga acctaagaaa tgcttcaagt 48720
gtagcctgga gcccgggtgc agtggctcac acctgtaatc ccagcactgt gggaggccga 48780
ggcaggcgga tcacttgagg tcaggacttt gagaccagcc tggccaacat ggcaaaacct 48840
gtctctacta aaaacacaaa aattagctgg gcatggtggc agatgcctgt aatcacctcc 48900
cacctggacc cttccttgat acatcagaat tacaactaga gatgagattg gggtggggac 48960

-continued acagagccag accgtatcac ataggaacct aaaaggataa taaagtagga aaacttccca 49020
catcagtaac cctttatccg atagtaatcc caatctgcaa agtaaaactg tgtgatttta 49080
ctaagataac ggaatcttct ctacagaagg actttccagt gcaaaagctc cccaccctca 49140
ccatgaaatg cacgtgacca tttccaattt gtgtaaagtc ctcagttagt actgagactt 49200
cggaaggtta gaaatccctt tgctcatgct gcatggtccg gatgagatgt aagaatcatt 49260
agctaataga catgcaacag cttttgtgcg aaagatgtta tgagacattt aaggtatttg 49320
cttgtgctta ctaagcattc attgtatcat tggagcacat gtgcttttat accctggaga 49380
aattccagta attgaattgc tgggttgaat gggattttga tttggattaa atttaaacta 49440
tagattttat ttagggaaaa ctggcatctt aattatgtta ttggggggcc cttgctccca 49500
gagctcccaa gatggtggca ggccgcttcc aaaatgaccg caggccactt ccaagatggt 49560
ggcaagcctc atgttctctg acctggggtt cttggcctca cggattccaa ggaatggaag 49620
cttgggccat gcagtgagtg ttatagctct attagaagcc gtgggtcacg gaagagaacc 49680
gtggaaccca gtgactagtg ttcagctcga ttaggacgaa cccaggcact tagccgtgca 49740
ggaacaatgg cgagcatttg gcccgatcga gagtggcaat gggcgcctcg ccggatcagg 49800
agcacagcgg ataccctgat ggatccggag ggatggaagc cagcggtggg tctcccacgg 49860
gggcaaacag cagtggtgga cggtgagcga aagcgaagct cgagccgtaa caaacatgga 49920
ccagaagagt gcagttgcaa gatttagtag agtgaagaca gagctcccat acaaagggag 49980
gggacccaaa gagggtagct gttaccggct cgaatgcctg ggtttatatc ccgatcattg 50040
tccctcccgc tgtgctctca ggtgatagat gattggctat ttctttacct cctgcttttg 50100
cctaattagc attttagtga actctcttta ctatctgatt ggtcgggtgt gagctgagtt 50160
gcaagccccg tgtttaaagg tggaagtggt caccttccca gctgggctta gggattctta 50220
gtcggcctag gaaatccagc tagtcctgtc tctcaattac actgagtttt ccaatccatg 50280
catccaatat gtggtgtatc tcttcatatg ttcatagcct ctgagcaatg ttttacaatt 50340
ttctgtgtaa agaactccac atcgttttat gtttcttcta aggtatatcc tgattgcttt 50400
ttatgtcttc acaagttttt ccctttcaaa attaatttc caattgtttg gtgctaatat 50460
gctcaaatgt ccttgatttt cttagtttga acagtccgtt ttcgttttgg ggatttattt 50520
ttttttcaga ttctttaaga ttttctatgt ctataaccat ataatctctg aacagagaca 50580
gttttgcttt tccctttcaa cttgaggtag gttttctggg tagttcagga cgcgcaggca 50640
ctgggtgggt ggtgttagca gctgcacgat gccttggaga ggacactctc gggggactgt 50700
ggccgctgct cagctgtgac tgttcttata gcaccagcag ctgcggccac cattcttatc 50760
caatttccaa agccacacca caggccctct caagaacgag gcgtggaggc tatgccctct 50820
cctggacaca tcatcattcc caagccccac gatgtgggcc ccatgggacg cacacctttg 50880
tctgtccaga cctcagcccc acctcctcat cctgcaccag aactcttcag agcccagtgc 50940
atgaaatggg ctaccaagga aatgagggta ggttcctgag aggaaactgg ccctgcattt 51000
gggagctaag agtctgctaa ttcgcctggc agccctgtgc agccctccgt ggctacagtc 51060
caccccgtgc ccatcagtgc ctccttcctg tgcaagcctg gacctcgccc tgggctcagg 51120
atgggctgta gaccgagaat gcaggcggga aagtcgttgt ctatcggggc catagtcagg 51180
ttctacagtg agtcagggaa agacctgtgg aggtgtggat gaggacaatg ggtccaccat 51240
caacaggagg acacgggttc gacccccttgc agaggcacag tcccacatca ctgggaggca 51300
gccacactca ctgcctcgcc ctctcctcac acagtgcagt ttccacgttc acagccccag 51360

-continued

```
ccagtcacca ggaatgccct gggggcggcc tttccccagt gcaccccgag ccctcccttg  51420
gctgtgcggt gagctccatg cccaggagat atccacccat agtcctccgg aaagcagctg  51480
acctgccatg ccctggaacc acaaatcccc acagatcagc cagcctgcag tgggccttgg  51540
atgtggtgag gagtggtggc acccccgttc ccaccccaca gatgcaacgc ctgtgggtga  51600
cgcatgtgag tactgaggag tagagggtag aactgtaggc cccgagaacc acagaaactc  51660
gggtgttaca ctctggggcc atgtaaggag aaagtgtcac tggacagaaa caggcccctc  51720
ctagacactg tgtgcgccat agtcacctgt cattagctct cactcttgca gattcatgat  51780
tgaggtggtt aaaaaaaaaa aagctcctac tcacccatcc aaccccatcc tggggtgttt  51840
ccaccaccct tggggtttgg gatgagctgc ccttgcccac tgtgctctgt ggacctccct  51900
ttagaagctc acagctccct gcactcggct ccatcctgcc ccaccacaca gaagcaaaac  51960
ccctctcctt tccactgcag gcttttcctg gaccagaatg ctgacctgct gcccttcact  52020
cccgaagtgg tgggactgcc tggggtggtg tgggtgttga gccttcttac tctagggacc  52080
tggcacctgg ccccaggggc acagggatgg tgcatctgcc tagggatgcc tcctcatgcc  52140
agggggtggg ggttagtacc atcggccctc aggatttgtt gcatgaatga gtgaatgggt  52200
gaataaatga aggggatctg atctatgaat aagggtatat ggactttggt tgatgtagga  52260
cgccaaatgc tggaatttcg gagtcatcac acccaggggc cctgcctctg agctcctctt  52320
tgcatccaat ctgctgaaga acatggctct agggaaaccc agttgtagac ctgagggccc  52380
cggctcttca atgagccatc tccgtcccgg ggccttatat cagcaagtga cgcacacagg  52440
caaatgccag ggtgtggttt cctgtttaaa tgtagcctcc cccgctgcag agctgcagag  52500
cctgctgaat tctggctgac cagggcagtc acccgagctc cagacaatgt ctgtctcctt  52560
cctcatcttc ctgcccgtgc tggcctccc atggggtcag tgtcagggag atgccgtatt  52620
cacagcagca ttcacagact gaggggtgtt tcactttgct gtttcctttt gtctccaggt  52680
gtcctgtcac aggtacagct gcagcagtca ggtccaggac tggtgaagcc ctcgcagacc  52740
ctctcactca cctgtgccat ctccggggac agtgtctcta gcaacagtgc tgcttggaac  52800
tggatcaggc agtccccatc gagaggcctt gagtggctgg gaaggacata ctacaggtcc  52860
aagtggtata atgattatgc agtatctgtg aaaagtcgaa taaccatcaa cccagacaca  52920
tccaagaacc agttctccct gcagctgaac cctgtgactc ccgaggacac ggctgtgtat  52980
tactgtgcaa gagacacagt gaggggaagt cagtgtgagc ccagacacaa acctccctgc  53040
agggatgctc aggaccccag aaggcaccca gcactaccag cgcagggccc agaccaggag  53100
caggtgtgga gttaagcaaa aatggaactt cttgctgtgt cttaaactgt tgttgttttt  53160
tttttttttt tggctcagca acagagatca tagaaaaccc tttttcatat ttttgaaatc  53220
tgttcttagt ctaatggaga ttctctgata tgtgacaatg tttttctctt gctgtttttg  53280
gaattctttg tctttgactt ttgacaactt gacttttgac agtgtgcctc aaagaagttc  53340
tattttgggt tctgtgaacc tcctggatct gggaagtttt cagctatgat ttcattaaac  53400
gtgttttcta caccatttcc ctactctttt ggaataccca taatgcaaat atttgttcac  53460
ttaattgtgt cccataaatg ctggggattt tcttcattcc tttttactct ttttttcttt  53520
ttattcatct gcctgaatta tttcaaaaga tctgtcttca acttcagaaa ctcttttgct  53580
tggcctagtc taatcttgaa ggtctcaatt gtacttttaa tttcattcat tgaattcttc  53640
aactctggaa tttctgttgg ttcttttttta tgatacttat ctctttgttg aattcctcat  53700
```

-continued

```
tcaaatgata aattgttttc ctgatttcac tgaattttct atctgtacac tattgtatct  53760
ccctgagttt cttagagatt atccttttga attatttttc tgacattctg tatatttcct  53820
tatgattggg gtctgctact ggagaatgac tgttgtcttt ttcaggtgcc gtgtttcctg  53880
gccttttcat gttttatgtg ttcctacgtt gatttctaca catctggcgg accagtcatc  53940
ccttgcaatt taatggagta ggttttgcag gaaaagactt cctagtacag acgggtctca  54000
gggtgtcagt gtggcggggc gtgctggctt tagttctagg ttgacgcagt agcgtagtct  54060
ccatgtcgtt tcttcagctg ccgtccacat tggtgacgtt tgcgagtgtc tcagtggcct  54120
gggctgagag gtttgtggca gtggaagtgc aacgttgcta gaggtggact caccaggctg  54180
tttctgaggt cgaggcacat gcatgcacat ggtggattga ccaacttggt gccaggctca  54240
ctagggttgg ggacatgggg ctgtttctca ggcccaggat gcaaacacaa gtctctttgg  54300
ctggcctggg ggtgtggctt ctgagggcaa tccacagggc tgtttctcag gttcaggaca  54360
caagtgcatg gccgctcaac tggcctgggc atgtgtctcc cagggccacc ccatgggctc  54420
tctctcagac ccaggacatg gccacatggc ttcctcagct ggcctgggtg tgtgtctgct  54480
tggggcctgc aggggcacag ggttatttct caggccgggg tcatgggcgc acagctgctt  54540
gctggcttat aggagtgcct gccaggggtg gcccatgatg ctgtttctca ggcccgcgcg  54600
actgaataca taaacaggac acagcatttt gctgcataaa gcaaacacag cgttactttt  54660
ttttttctaa atgacatttt ttattagata ttgtctttat tgacatttca aatgttatcc  54720
cctttcctgg tttaccctct gaaatcccct atctcctccc cctccccctg ctcaccaatc  54780
cacccactcc cacttccagg ccctggcaat cccctatatt tgggcataga gccttcacag  54840
gaccaaggta ctctccttgc attgatgacc aactagtcca ttctctgcta caaatgcagc  54900
tagatctatg agtcccacca tgttttcttt tgttggtggt ttcatgccag ggagctcttg  54960
gagtactgat tggttcatat tgttgttctc cctatggggt tacaaaaccc ttcaacttct  55020
tgggtccttt ctctggctgc ctcattgggg accttgtgcg aagtccaatg gatgactgtg  55080
agcatccact tctgtatttg ccaggcactg gcagagcctc tcagaagaca gctatatcaa  55140
gatcctggca gcaagctctt gttggtatcc acaaaagtgt ctggtggttg tctatgggat  55200
ggatccccaa aggggcagtc tctggatggt cattccttca gtctctgttc cacactttgt  55260
ctctttaact ccttccatga ctattttatt cctccctcta agaaggaccg aagtattcat  55320
actttggtct tccttcttga aattcatgtg ttttgtgaat tgtatctttg atattccgaa  55380
cttctgggct aatatccact tatcagtgag tgaatatcat gtgtgttctt atgtgattga  55440
gttacctcac tcaggatgat atcctccaga accatccatt tgtctaagaa tttaatgaat  55500
tcattgtttt taatagctga ggagtactcc attgtgtaaa tgtaccacat tttctgtacc  55560
cattgttctc ttgagggaca tctgggttct ttaaagcttc tggacattaa atataaggct  55620
gctatggaaa tagtggagaa tgtgtcctta ttacatgttg gagcatcttc tgggtatatg  55680
cccaggagtg ctattgctgg atcctctgat agtactatgt ccaattttct gaggaactgc  55740
caaactggtt tacagagtgg ttgtgccagc ttgcaattcc accagcaatg gagaaatgtt  55800
ccccttcctc cacatcctca ccaacatctg ctgtcacctc aatttgttct tagtgattca  55860
gacaggtgtg aggtggaata tcagggttgt ttggcatttc cctgatgact agtgatattg  55920
aaaaaaattt taagtgtttc tcagccattc agtattcttc agttgagaat tcactgttta  55980
gctctgtact caggtttttt taatagggtt atttggtttt ctggagtcta acgtcttgaa  56040
ttctttctat atattggata ttagccctct gtcatattta ggattggtaa agatctttcc  56100
```

-continued

```
caatatgttg gctgcctttt tgtgtccttt gccttacaga accttttttaa ttttatgagg  56160
tcccatttgc taattcttca ttttacagca aaagccattg gtgttctgtt caaaaatctt  56220
tccccctgaa ccctatcttc gaggatcttc cccactttct cctctataag tttcagtgtc  56280
tctattattg tgctgaggtc cttgatccac ttgaacttga gcattgttca aggagataag  56340
aatggatcaa ttcgaattct tctacatgat aacagccagt tgagccagca ccatttgttg  56400
aaaattctct tttttgcact ggatagtttt agcacttttg tcaaagatca agtgactatg  56460
gctcttcaac tatggctcat tccattgatc aacttgtctg tcactgtaca agcaccatgc  56520
aatttttatt gcaattgctt agtattacac cttgaggtca aggatggtca ttccaccaga  56580
ggttcttcta tggttgagaa gagtttttgc tatcctaggt tttgttattt ccagatgaat  56640
ttgcaaatgg ccctttctaa ctcagtgaag aattgaggtg gaattttgat gggaatttta  56700
ttgaatctgt agattgcatt caacaagata gccatttata atacattaat cctgccagtc  56760
catgagcatg ggagatcttt ccatcttccg agatcttctt cgatttcttt cttcagagac  56820
ttgaagtttt tatcatacag atctttcact tccttagtta gagtcacacc aaggtatttt  56880
atattatttg tgactactgt gaaggttgtt gtttccctga tttcttcctc agcctgttca  56940
tcctttgtgt agagaaaggc cactgattta tttgagttaa tattgtatcc agctaattca  57000
ctgaagttgt ttatcaggtt taggagttct cttgtggaat ttttggaatc acatgtgtat  57060
actattatat catctgcaat tagtgatatt ttgacttctt ctttcccaaa ttgtatccct  57120
ttgatctcct tttgttgtct aattgcccac actaggactc gggcagcctt agtgcctagt  57180
ccctgatttt agtgtgattt gttcaagttt ctctccactt agtcggatgt tggctactga  57240
tttgctgtat attgctttta ttatgtttag gtatgggcct tgaattcctg atctttccaa  57300
tacttttatc atgaatgggt gttgaatttt gtcaaatgct ttctcaacac ctacaaagat  57360
gatcatgtag attttgtctt tcagtttgat tatatagtgt attatgttga tggatttcca  57420
tatattaaac catccctgca tccctgggat gaagcctact tggtcatgat agacgattgt  57480
tttgatgtgt tcttggattc agttagtgag aaatatattg agtattttta catcgatatt  57540
cataagggaa attggtctga agttctcttt ctttgttggg tctttatgtg gtttagttat  57600
cagagtcatc gtagcttcat agaacaaatt gagtagagta ccttctgtct ctattttgtg  57660
gtatagtttg aggagatttg gaaatatgtc ttcttgggac gtctgagaga attctgcact  57720
aaacccatct gatcctgggc ttctttgggg gggggggact attaatgact gcttctattt  57780
ctttagggga aatgggactg tttagattgt taatatgatc ctgaatagaa atctgatctg  57840
atctagaaaa ttgtccattt tattcaggtt ttccagtttt gttgagtatt gccttttgtg  57900
gtagggtctg atgatgtttt ggatttcctt aggttctgtt gttatgtctt cttttccatt  57960
tctcattttg ttaattagga tactgtccct gtgtcctcta gttactctgg ctaagcgttt  58020
atctatctta ttgattttct caaagaacca gctcctggtt tggttgattc tttgtatagt  58080
tctttttgtt tccacttgat tgatttctgc cctaagtttg attgtttcct gctgtctact  58140
cctcttgggt gaatttgctt ccttttgttc tagagctttt aggtgtgctg tcaagctgat  58200
agggtatgct ctctctagtt tctttttggc ggcactcata gctaggagtt ttcctcttag  58260
cagtgctttc attacgtcct gtaagtttgg gtatgttgtg gcttcatttg cattaaattc  58320
taataagtct ttaatctctt tccttctttc ttccttgacc gagttatcat tgactagagt  58380
gttcatcagc ttccacatca atgttggctt ttaattattt atgtttttat tgaggatcag  58440
```

```
cctttgtcgg tggtgatctt ctaggatgca cgggaaattt tcaatatttt tgtatctatt  58500
gaggcctgtt ttgtgaccaa ttatacggtc aattttggag aaagtaccgt gaggtactga  58560
gaagatggta tatcttttg ttttaggata aaatgttctg tagatatctg ttaaatccat  58620
ttgtttcata acttctgtta gtttcactgt gtctctgctt agtttctgat tccagaatct  58680
gtccaatgat aagagtaggg tattaaattc tcccactact attgtgtgag gtacaatgtg  58740
tggtttgagc tttaaaagag tttccttaat gaatgtggat ggccttgcat ttggagcata  58800
gttattcaga attgagagtt cctcttggaa gattttacct ttgatgagta taaaatgccc  58860
ctccttgtct tttttgatac ctttgggtta gaagtggatt ttattcgata ttagaatggc  58920
taatccatct tgtttctttg agatgtttgc ttggaaaatt attttcctgc cctttactcg  58980
gtggtagtgt ctgtcttagt ccctgaggtg ggtttcctgt atacagcaaa atgttgggtc  59040
ctggttatgt agccagtctg ttagtctgtc tttttatcag gtaattgagt ccattgatat  59100
taagagctat taaggaaaag taattggtgc ttcctgttat ttttgttgtt agacttggga  59160
ttctgttctt gtggctatct tcttttaggt ttgttgaagg attactttct tgcttttttt  59220
agggtgtaat ttccctcttt gtgttggagt tttctcttta ttatcctttg aagggctgga  59280
ttcatggaaa gatgttgggt gaatttggtt ttgtcatgga attctttggt ttctccatct  59340
ataattgaga gttttgctgg gtatagtagc ctaagctggc atttgtgctc tcttagtgtc  59400
tataacatct gtccaggatc ttctggcttt cataatctct ggtgagaagt ctggtgtaat  59460
tctgataggc ctgcctttat atgttacttg accttttcc cttactgctt taaatattct  59520
atcttcattt agtgcatttt ttttctgatt ttttatgtgt caggaggaat ttcttttctg  59580
ctccagtcta ttcggattct gtaggctact tctatgttca tgggcatctc cttctttagg  59640
ttacggacgt tttcttctat aattttgttg aagatattta ctggcccttt aagttgaaaa  59700
tctccattct catctatacc tattatcttt aggtttggtc ttctcattgt gtcctggatt  59760
tcctggatgt tttgagttag gatcttttt gcattttgca ttttttttta ttgttgtgcc  59820
catgttttct acggaatctt atgcacctga gactctctct tctacctctt gtattctatt  59880
ggctgatgct tccacctatg tttctcgatt tctttcctag gatttctatc cccagagttg  59940
tctccctttg tgatttcttt attgtttcta cttccatttt tagattttga atggttctgt  60000
tcgattccat cgcctgttgg gttgtgtttt tctgtatttc tttgagggat ttttgtgctt  60060
catctttaag gtcttctacc tgtttaggag tgttttccta taattctttg agggattttt  60120
gtgttttctc tttaagggct tctagcaatt tagcagtgtt ctcctgtatt tctttaagtg  60180
agttattaat gcccttctta aaatcctcta ccaacatcat tagatatgat tttaaatccg  60240
aatcttgctt ttcaggtgtg ttggggtatc caggactcac tgtgggggga gtactgggtt  60300
ctgatgatga aaactggtct tggtttttat tagtaagatt cctacttttg ccttccacca  60360
tctgataata tctgttgtta gatattctag ctgtctctgg ctggagcttg ttcctcctgt  60420
gattctgtca gcctctgtca gcactcctgg gagtacaact cttttctgag tcccaatgtt  60480
cagagcattc tctgcaggca agctctcctc tggcaggtaa ggtgcccaga gctcttgagc  60540
tcagctccac ctcctgactg cagatgaaga cccaaaggga ccctgtccaa taagctctgt  60600
tgcttctgcc acccacatgc tctcctgtgc gaactggtct ctgagagacc cgggatacaa  60660
gatggtactc tcacctgaat cccagggtca aagccctccc tggaggctga ctctcctctt  60720
gtgggaaggt gcacagaggt ctggagctca gctctgcctc ctggctgaag atgaaggccc  60780
gaagggaccc tgtccaagaa gctttgttgc ttctgggacc cacatgctct cctacatgga  60840
```

-continued ctggtctctg agagaccagg gattcaagat ggtgctctca cctgagtccc agggtcagag 60900
ccctctctgg aggccaactc tcctcagtga tcctaagatc ctgggtatgc tagggtgcct 60960
atggcatgga gagtcctctg aggaatgtgg gactgtctgc tgagtttcca cccaaggtgg 61020
tgctgggctg gctccagtca gaatgaaccc agactctggt tgggcaggtt tccagtcctg 61080
ttggcccaag cccctctggg ttgttttaga acagatgttg ctttccactc accagtgatc 61140
ccaagatcct gggcgtgcta gggtgcctgc tatgtggaga gtccactggg gaccttagga 61200
gcatacatca agttcacacc catggtggca aggagctggt gcctaccaga acaaaccccg 61260
ggcactttta ctgacccttt aagttgaaaa tcttcattct catctatacc tattatcctt 61320
aggtttggtc ttctcattgt gtcctggatt tcctggatgt tttgacttaa gatctttttg 61380
cattttgcat ttttttgatt gttgtgtcca tgttctctct ggaatcttct acacctgaga 61440
ttctctcctc tgtatcttgt attctgttgg tgatgcttgc atctattgct cctgatctct 61500
ttcctagggt ttctatctcc agagttttct ccctttgtga tttctttatt atttctactt 61560
ccatttttag atcctagatg attttgttaa attccttcac ctgtttggtt gtgtgttcct 61620
gtaattcttt aagggatttt tgtatttcct ctttaagggc ttctacctgt ttagctgtgt 61680
tctactgtat ttctttaaag gacttatgaa tgtccttctt aaaaacctct accagcatca 61740
tgagatgtga tcttaaatgt caatcttccc tttctggtgt gttggggtat ccaggacttg 61800
ctgtggttgg agttctgggt tctggtaaac ctgccttaga gggtcaccac agagtaatga 61860
tagcactact tttaaacagg ggaagatgat gaaataattg ctgtgggaaa atgcaaggaa 61920
ggctccaaca catgtaggca tctatgaagg tctcaaatct tcaaaatcca aaaccaccaa 61980
gaaagaaaga aagaaagaaa gaaagaaaga aagaaagaaa gaaagaaaga aagaaagaaa 62040
gaaagaaaga aaggaaggaa ggaaggaagg aaggaaggaa ggaaggaagg aaggaaggaa 62100
ggaaggaagg aaggaaggaa ggaagattct aaaagtagtc acctgcacca ggtgcctggg 62160
gagtcactca gcagccctag actgagaaag cttgaagaaa gtagaaatag agaaagtgta 62220
cagccagtat cctctagcta ctcacatcca aacagggcct cctgactgct ctgagcctgt 62280
cctaagaaca gcaatgatgc cacagaaatt tttagagtga accctgaagg aacttgaggc 62340
cgatatgaga aagccagtcc cagaggaaag gaaaacccgt agagagaaaa caggtgagtt 62400
agtgcattaa aggggctgag caggcaacgc gccgtcgacc ggaggagttt cttccctgtg 62460
cggagtccac gggcctcctg tgagtgtgtg catgggcaca agtgtgtgtg tggctctgct 62520
gtgtgtctgt acacacatat gttttgggtt tttttgtgtc tcagaccaca gagtctgccc 62580
ctcccaccaa agcccaggca gaaggatgaa cccacgcccc tggggcccag gcctcagcag 62640
cctctgcggg atcattgttc ccagttgtca cttgcctttg ccacagccct atttctccac 62700
aattccttaa agtcctcaac atgcatttaa ggcacaaagg tgaaactgcc cagaaacatc 62760
tgactccgcc gtggaaccca ggagcaagct gggttagcta aggagcgggg ccgttggcag 62820
aggctgggga tccaggctga actttggagg aggcatgtcc cagcatgggc tcctgactat 62880
gtcctcctgg gacaaaccca aacccactct ttgaatatgg gagggacttt gctggccccg 62940
gccctgaccg cagcacttgg aaactgagga gtggtcgcct cctccgtgtc acagctgccc 63000
gttcaccatc atagaagcaa ctctgtcacc tccatgggcc cctctgtggc tgctgcctgg 63060
gtccaagctg agcccagctg cccaggccca gaaggaaagc ccaggccagg tgcccagcac 63120
agaggcagtc acataccccg gggagagcca cagcaagcag ccaatattgc ccaggagagg 63180

-continued agtagctgac aaggcagaac gtgagctgcc atcggctcga gaggctttgc tggtcctcct 63240
ggggctctgg acatgaccag gaggagcgag ggaagaagtc gcatggtggt cccatcctgg 63300
gtggggcctg atggcagctg gccacccgtc ccagagtggc agccagatgc cagcgccatt 63360
cccacagtca catcattggt cacagaatgc aggacataga gtgtcttctt tccatcacag 63420
tgctgtccag acccatagcc tagggtagac ctggaagatt caatgtccac acccggggct 63480
ggagcgtagc catgagccac gccccctgcc cgtgcatgga aagccagccc aagctctgct 63540
ccatccctag ccaaagtcag tgtcctttcc ccttctccca agtgagctct agccacctgc 63600
ctaccctgcc atctgaggat gacagccttc attccattgg aacctggctc tgccaccagc 63660
aggcttgcag tcctgggcag actccgtcac ctctctatgc ctcagccttt ccatctgcac 63720
aggaggaaga tgatgatggt ggtgatgatg atggcgatgg tttccttttg catctgaggc 63780
aaggactaat tgagatgata cacatcaggc actgggtatg gtgctggtcc ttcctgagca 63840
ctcaatctat gtgagctgtc cttgtgaaat gggtgtcacc acatttcccc acgcagaaca 63900
tcctttgtct gccatacttg aaacgtctgc cccaatacta acagctcctc atggaagatg 63960
tgcccaccca cccaccctca tactcccaaa ggtgcccgtg ctttatcaag ccaaagtcca 64020
gccaggaact ttacagcagc atccctttcc ctctccaagc accaaggagc aaggcaaagc 64080
actacatctt ccatctggag gcaatgccac cctcttctcc cattttcact gccatcccta 64140
agaggcagtg cttccccaaa aggttccata gcagcctgcc tacagcaact ctgttcacac 64200
gagtttcagc atccttgcag tggctcccct gccatgctgt ggctcttcat tcaccctctt 64260
ctcctgctcc ccgtgacagg catagattct gagtgatctg gatacattgc tttgtttaat 64320
aacattacag cttctgtgct gaaaaagata cagcagatag agaaggcaat tgttgaacac 64380
aaaatagtga cagcagagat gacggcaagt tggcattttt cttttctagc aataaaactt 64440
aaagctgact caaggagaaa tggaaatcat aattggaaca gtaatcctca agaaagcatt 64500
aagattatta aataattgcc ctcacagatg acttcaggcc aagatggctt tatgggtgaa 64560
gtttagactt tcacaaaact aatcagttcc cataagaact gctccaggat ttggaggaac 64620
atgggaaagt ctattaaagg gatcacaatt cacagtcccc agagtaaaac atgggctaac 64680
ttgcattttg gcaaagagcc aaatgttata aatgacatcc tagaaggcca aattctgtcc 64740
atctcgttga acaaggactt acaccaggaa tttagaacta tttatagctc atcccaccac 64800
tcaggccaat gatgacccat gatcatctca ccagaaatgg aaagactcag atgattaata 64860
gagtctcaat ttctctgaga catctaagag cccagcccaa gcccagaccc aggagggcac 64920
ccaggcctgg acagagaaca ctgatatcac accagccctc cagagggaag cagagactcc 64980
ttcaagctct ggaaacacag gcccagacag ctgcccaaag ttgggcaggc ttcactgcaa 65040
acccaaatca tgaagctagg taacaccttt acagattctt tacatttaaa aatcatcaaa 65100
acaagagtaa ataataaact caaataatat taatctaata tgtaaaggtc ttgtaccatt 65160
attatgcaaa caacatacat aagctaataa gaaaaagaac aaatccctta agaaatcagc 65220
aaaaaggata taacacaatt tctaaaagaa aacaaatggc tagcacacat aaggaaaaca 65280
ctttgtgaac agacattctt cagaacatta tttataatta taaaatagtt gaaagcaaga 65340
tagtgcctga agaaattatg gtgcatacat tagtgggact attctgcaaa cattcccaat 65400
tatacttgtc acatatctgt gataacgtga cagccagcat tcatggggtg acctcatttg 65460
gtaaaagggt gcaaagctca acacgcattg tgagatgact gtggtgtaaa attagtggga 65520
ttattccgca aacattccca attatactta ccgcatatct gtgataacat gacagcattc 65580
atggggtgac ctcatttggt aaaagggtgc aaagctcaac acgcattgtg agatgactgg 65640
tgtaaataca aagaccaaac tgtgaaaagg agtccatcaa ttaatcgatg cttaccttca 65700
gttttgggct aatttttaaa gtatgctata agcatatgct cctgttataa cagaatggag 65760
ggattatgag agatgatgca ggtgtgtcct gggcctcccc tggcccactg ggccctagag 65820
atgccttccc aggcatcgct gtcagggctt ccctcagagg gagtcctgta ttgacctcac 65880
caccaaggtc tggagcaggg gatccttaga tattggttgg ggttatctca ccttaggtct 65940
gaatatgggg ttgtcttaga ctgttttgtg ctgttagaat agaataccca agactgggaa 66000
atttatactg aacggaaatt tatttctcac agttctagag gctgtgaagt ccaagagcac 66060
aggtgccaga gcaagtccaa gagcaaggga aagtccaaag caagtccagg agcatctggc 66120
gaggaccttc ttgctgtgtc atcacatggc ggaaggcaag aaagagagca agaggggggcc 66180 gaactcaccc ttttataaca gcaccaatcc cacccatgag gtggggacct tatgacctaa 66240
tcactcttca tactgttaca atggcaatga aatttcaaca tgagttttgg aggagagaag 66300
cattcaaacc acagcaaggg tgctcctacc tcctctctca gggcatctgc agaaagagct 66360
gcaactgcac gtccttcctc cgtccatcct ccatcccttc ccaatgtccg tgcatatcct 66420
gtgacccagg aggtctggca tagggggtgc tcctgcctta ggtctgaggc cctgtctgaa 66480
gaggggtagg tgaggaggcc atctgatggt ctgggccaag acagtcacag gacgcatcat 66540
ttatcatcaa ggaggctgag ggttgagtct ccaggtccag ggaactcccc acaaagtggg 66600
aaccctgccc agctccacac agcctctgct gggggaccct gctctggtgc agagcctggg 66660
gacaggtctt gagctcagcc agagtctgcc tccctgtcat ttaggaacta aaccaagcgg 66720
caggatgctg gagcccagcc cccatctgac cttacagggc caaggctggg gccctgggtt 66780
cccctcaagg cacagcagga ctggagcccc aggcagtgca ggagtggcca aagctggggc 66840
ttcctccaga gcccccaagc atcatggcac caagaagggt aggaccctgg cctgaggaat 66900
tggcaccaaa gccccagaaa ctaccctgga caccatggag agaggcttgg aggggaagca 66960
ccaggcactg cctccccttc tgatcccacc tgaggtggct gccaagccca gagagccgct 67020
ctgatgtccc ccagccctgc agcccaggga tacctgtact gtgcccctgg gggacccctg 67080
gccagtctgt gcaaagaagt caccacccta cactcagaga cagtgggggt cctcgtccca 67140
catcctcaga gcatggcccg gctgctgcag ggatggtctc cttgtcctca gagcatggcc 67200
cggctgctgc agggatggtc tccttgtcct cagagcatgg cccagctgct gcagggatgg 67260
tctcctggag gccccccagt gctctattgt cagggctccc tccacccccc cgcaccaaga 67320
gagagccaga ccccagcaag gcttccagtg gcttcaggtc acacccctag gctgacccca 67380
gccccattaa cacctgcctg agaaagctcc acgcaccaga actgaccgtc tgctccaact 67440
cttgacctcc cgttctcagg gcgtctgctg aaaaggctgc aactgcacat ccttcctccg 67500
tccgttcccg atgtccgtgt gtctcctgtg gccaggaagg tctttctcgg gacctgagag 67560
ccgctccctg aagtgtcccc attgggaagg atggggcctg tgtctccagg ctctgggagg 67620
acagaatcct gacctcaaca gtggccggca cggacacaac tggccccatc ccggggacgc 67680
tgaccagcgc tgggcaactt ttcccttccc cgacgactga gccccgagca ccctccctgc 67740
tcccctacca cctcccttta caaggctgtg gcctctgcac agatgataat ggagcttggc 67800
tcattcccct agagtcggta gggagttaag gacaaaactc agtttcctcc acctgaactc 67860
aagtctgcct atgtttacct aatcacacct ggtggacagt ttggacaaac ttgcacactc 67920
agagacacag acacttctag aaatcattat ctccctgccc cggggacccc actccagcag 67980
aagtctgcta ggcactggcc tgggccctcc tgctgtccta ggaggctgct gacctcctgc 68040
ctggctcctg tccccaggtc cagagtcaga gcagactcca gggacgctgc aggctaggaa 68100 gccgcccccct ccaggccagg gtctagtgca ggtgcccagg acaagaaaga ttgtgaatgc 68160
aggaatgact gggccacacc cctcccgtgc acgccccctc ctgccctgca ccccacagcc 68220
cagccccccg tgctggatgc ccccccacag cagaggtgct gttctgtgat cccctgggaa 68280
agacgccctc aacctccacc ctgtcccacg gcccaaggaa gacaagacac aggccctctc 68340
ctcacagtct ccccacctgg ctcctgctgg gaccctcaag gtgtgaacag ggaggatggt 68400
tgtctgggtg gcccctagga gcccagatct tcactccaca gaccccaacc caagcacccc 68460
cttctgcagg gcccagctca tccccctcct cctccctctg ctctcctctc gtcgcctcta 68520
cgggaaatcc gggactcagc agtaaccctc aggaagcagg gcccaggcgc cgtttaatag 68580
gaggcttcct cacaatgaaa cttttagaaa gccttgacta caatgatgac cttggtgtgg 68640
ctgtgaacac tgtcagctcc cacagctgct gcagcaaaaa atgtccatag acagggtggg 68700
ggcccggggt cgtctgctgt cctgctcagc ccacagcacg catggaggat ctgaggtgcc 68760
acacctgacg cccaggccag aacatgcctc cctccagggt gacctgccat gtcctgcatt 68820
gctggaggga caggggcagc ctatgaggat ctggggccag gagatgaatc ctattaaccc 68880
agaggaaaac taacaggacc caagcaccct ccccgttgaa gctgacctgc ccagaggggc 68940
ctgggcccac cccacacacc ggggcggaat gtgtacaggc cccggtctct gtgggtgttc 69000
cgctaactgg ggctcccagt gctcacccca caactaaagc gagccccagc ctccagagcc 69060
cccgaaggag atgccgccca caagcccagc ccccatccag gaggccccag agctcagggc 69120
gccggggcag attctgaaca gccccgagtc acggtgggta caactggaac gaccaccgtg 69180
agaaaaactg tgtccaaaac tgtctcctgg cccctgctgg aggccgcgcc agagagggga 69240
gcagccgccc cgaacctagg tcctgctcag ctcacacgac ccccagcacc cagagcacag 69300
tggagtcccc actgaatggt gaggatgggg accagggctc cagggggtca tggaaggggc 69360
tggaccccat cctactgcta tggtcccagt gctcctggcc agaaacgacc ctaccaccga 69420
caagagtccc tcagggaaac gggggtcact ggcacctccc agcatcaacc ccaggcagca 69480
caggcataaa ccccacatcc agagccgact ccaggagcag agacacccca gtaccctggg 69540
ggacaccgac cctgatgact ccccactgga atccacccca gagtccacca ggaccaaaga 69600
ccccgcccct gtctctgtcc ctcactcagg acctgctgcg gggcgggcca tgagaccaga 69660
ctcgggctta gggaacacca ctgtggcccc aacctcgacc aggccacagg cccttccttc 69720
ctgccctgcg gcagcacaga ctttggggtc tgtgcagaga ggaatcacag aggccccagg 69780
ctgaggtggt gggggtggaa ggcccccagg aggtggccca cttcccttcc tcccagctgg 69840
aacccaccat gaccttctta agataggggt gtcatccgag gcaggtcctc catggagctc 69900
ccttcaggct cctccctggt cctcactagg cctcagtccc ggctgtggga atgcagccac 69960
cacaggcaca ccaggcagcc cagacccagc cagcctgcag tgcccaagcc cacattctgg 70020
agcagagcag gctgtgtctg ggagagtctg ggctccccac cgcccccccg cacaccccac 70080
ccacccctgt ccaggcccta tgcaggaggg tcagagcccc ccatggggta tggacttagg 70140
gtctcactca cgcggctccc ctcctgggtg aaggggtctc atgcccagat ccccacagca 70200
gagctggtca aaggtggagg cagtggcccc agggccaccc tgacctggac cctcaggctc 70260
ctctagccct ggctgccctg ctgtccctgg gaggcctgga ctccaccaga ccacaggtcc 70320
agggcaccgc ccataggtgc tgcccacact cagttcacag gaagaagata agctccagac 70380
ccccaagact gggacctgcc ttcctgccac cgcttgtagc tccagacctc cgtgcctccc 70440
ccgaccactt acacacgggc cagggagctg ttccacaaag atcaacccca aaccgggacc 70500
gcctggcact cgggccgctg ccacttccct ctccatttgc tcccagcacc tctgtgctcc 70560
ctccctcctc cctccttcag gggaacagcc tgtgcagccc ctccctgcac cccacaccct 70620
ggggaggccc aaccctgcct ccagcccttt ctcccccgct gctcttcctg cccatccaga 70680
caaccctggg gtcccatccc tgcagcctac accctggtct ccacccagac ccctgtctct 70740
ccctccagat accccctccca ggccaaccct gcacatgcag gccctcccct tttctgctgc 70800
cagagcctca gtttctaccc tctgtgccta cccccctgcct cctcctgccc acaactcgag 70860
ctcttcctct cctggggccc ctgagccatg gcactgaccg tgcactccca cccccacact 70920
gcccatgccc tcaccttcct cctggacact ctgaccccgc tcccctcttg gacccagccc 70980
tggtatttcc aggacaaagg ctcacccaag tcttccccat gcaggccctt gccctcactg 71040
cccggttaca cggcagcctc ctgtgcacag aagcagggag ctcagccctt ccacaggcag 71100
aaggcactga aagaaatcgg cctccagcac cctgatgcac gtccgcctgt gtctctcact 71160
gcccgcacct gcagggaggc tcggcactcc ctgtaaagac gagggatcca ggcagcaaca 71220
tcatgggaga atgcagggct cccagacagc ccagccctct cgcaggcctc tcctgggaag 71280
agacctgcag ccaccactga acagccacgg agcccgctgg atagtaactg agtcagtgac 71340
cgacctggag ggcaggggag cagtgaaccg gagcccagac catagggaca gagaccagcc 71400
gctgacatcc cgagcccctc actggcggcc ccagaacacc gcgtggaaac agaacagacc 71460
cacattccca cctggaacag ggcagacact gctgagcccc cagcaccagc cctgagaaac 71520
accaggcaac ggcatcagag gggctcctg agaaagaaag gaggggaggt ctccttcacc 71580
agcaagtact tcccttgacc aaaaacaggg tccacgcaac tcccccagga caaaggagga 71640
gccccctgta cagcactggg ctcagagtcc tctccaacac accctgagtt tcagacaaaa 71700
acccccctgga aatcatagta tcagcaggag aactagccag agacagcaag aggggactca 71760
gtgactcccg cggggacagg aggattttgt gggggctcgt gtcactgtga ggatattgta 71820
gtagtaccag ctgctatgcc cacagtgaca cagccccatt cccaaagccc tgctgtaaac 71880
gcttccactt ctgggggtgt gtaagagggg atgcgggcag agcctgagca gggccttttg 71940
ctgtttctgc tttcctgtgc agagagttcc ataaactggt gttcgagatc aatggctggg 72000
agtgagccca ggaggacagc gtgggaagag cacagggaag gaggaccagc cgctatccta 72060
cactgtcatc tttcgaaagt ttgccttgtg cccacactgc tgcatcatgg gatgcttaac 72120
agctgatgta gacacagcta aagagagaat cagtgagatg gatttgcagc acagatctga 72180
ataaattctc cagaatgtgg agcagcacag aagcaagcac acagaaagtg cctgatgcaa 72240
ggacaaagtt cagtgggcac cttcaggcat tgctgctggg cacagacact ctgaaaagcc 72300
ctggcaggaa ctccctgtga caaagcagaa ccctcaggca atgccagccc cagagccctc 72360
cctgagagcc tcatgggcaa agatgtgcac aacaggtgtt tctcatagcc ccaaactgag 72420
agcaaagcaa acgtccatct gaaggagaac aggcaaataa acgatggcag gttcatgaaa 72480
tgcaaaccca gacagccaca agcacaaaag tacagggtta taagcgactc tggttgagtt 72540
catgacaatg ctgagtaatt ggagtaacaa agtaaactcc aaaaaatact ttcaatgtga 72600
tttcttctaa ataaaattta caccctgcaa aatgaactgt cttcttaagg gatacatttc 72660

-continued ccagttagaa aaccataaag aaaaccaaga aaaggatgat cacataaaca cagtggtggt 72720
tacttctgct ggggaaggaa gagggtatga actgagatac acagggtggg caagtctcct 72780
aacaagaaca gaacgaatac attacagtac cttgaaaaca gcagttaaac ttctaaattg 72840
caagaagagg aaaatgcaca cagttgtgtt tagaaaattc tcagtccagc actgttcata 72900
atagcaaaga cattaaccca ggtcggataa ataagcgatg acacaggcaa ttgcacaatg 72960
atacagacat atatttagta tatgagacat cgatgatgta tccccaaata aacgacttta 73020
aagagataaa gggctgatgt gtggtggcat tcacctccct gggatccccg gacaggttgc 73080
aggctcactg tgcagcaggg caggcgggta cctgctggca gttcctgggg cctgatgtgg 73140
agcaagcgca gggccatata tcccggagga cggcacagtc agtgaattcc agagagaagc 73200
aactcagcca cactccccag gcagagcccg agagggacgc ccacgcacag ggaggcagag 73260
cccagcacct ccgcagccag caccacctgt gcacgggcca ccaccttgca ggcacagagt 73320
gggtgctgag aggaggggca gggacaccag gcagggtgag cacccagaga aaactgcaga 73380
cgcctcacac atccacctca gcctcccctg acctggacct cactggcctg ggcctcactt 73440
aacctgggct tcacctgacc ttggcctcac ctgacttgga cctcgcctgt cccaagcttt 73500
acctgacctg ggcctcaact cacctgaacg tctcctgacc tgggtttaac ctgtcctgga 73560
actcacctgg ccttggcttc ccctgacctg gacctcatct ggcctgggct tcacctggcc 73620
tgggcctcac ctgacctgga cctcatctgg cctggacctc acctggcctg gacttcacct 73680
ggcctgggct tcacctgacc tggacctcac ctggcctcag gcctcacctg cacctgctcc 73740
aggtcttgct ggagcctgag tagcactgag ggtgcagaag ctcatccagg gttggggaat 73800
gactctagaa gtctcccaca tctgaccttt ctgggtggag gcagctggtg gccctgggaa 73860
tataaaaatc tccagaatga tgactctgtg atttgtgggc aacttatgaa cccgaaagga 73920
catggccatg gggtgggtag ggacataggg acagatgcca gcctgaggtg gagcctcagg 73980
acacaggtgg gcacggacac tatccacata agcgagggat agacccgagt gtccccacag 74040
cagacctgag agcgctgggc ccacagcctc ccctcagagc cctgctgcct cctccggtca 74100
gccctggaca tcccaggttt ccccaggcct ggcggtaggt ttagaatgag gtctgtgtca 74160
ctgtggtatt acgatatttt gactggttat tataaccaca gtgtcacaga gtccatcaaa 74220
aacccatgcc tggaagcttc ccgccacagc cctccccatg ggccctgct gcctcctcag 74280 gtcagccccg gacatcctgg gtttccccag gctgggcggt aggtttgggg tgaggtctgt 74340
gtcactgtgg tattactatg gttcggggag ttattataac cacagtgtca cagagtccat 74400
caaaaaccca tccctgggag cctcccgcca cagccctccc tgcaggggac cggtacgtgc 74460
catgttagga ttttgatcga ggagacagca ccatgggtat ggtggctacc acagcagtgc 74520
agcctgtgac ccaaacccgc agggcagcag gcacgatgga caggcccgtg actgaccacg 74580
ctgggctcca gcctgccagc cctggagatc atgaaacaga tggccaaggt caccctacag 74640
gtcatccaga tctggctccg aggggtctgc atcgctgctg ccctcccaac gccagtccaa 74700
atgggacagg gacggcctca cagcaccatc tgctgccatc aggccagcga tcccagaagc 74760
ccctccctca aggctggcca catgtgtgga cactgagagc cctcatatct gagtaggggc 74820
accaggaggg aggggctggc cctgtgcact gtccctgctc ctgtggtctc tggcctgcct 74880
ggccctgaca cctgagcctc tcctgggtca tttccaagac agaagacatt cctggggaca 74940
gccggagctg ggcgtcgctc atcctgcccg gccgtcctga gtcctgctca tttccagacc 75000
tcaccgggga agccaacaga ggactcgcct cccacattca gagacaaaga accttccaga 75060
aatccctgcc tctctcccca gtggacaccc tcttccagga cagtcctcag tggcatcaca 75120
gcggcctgag atccccagga cgcagcaccg ctgtcaatag gggccccaaa tgcctggacc 75180
agggcctgcg tgggaaaggc ctctggccac actcgggctt tttgtgaagg gccctcctgc 75240
tgtgtgacta cagtaactac catagtgatg aacccagtgg caaaaactgg ctggaaaccc 75300
aggggctgtg tgcacgcctc agcttggagc tctccaggag cacaagagcc gggcccaagg 75360
atttgtgccc agaccctcag cctctaggga cacctgggcc atctcagcct gggctggtgc 75420
cctgcacacc atcttcctcc aaataggggc ttcagagggc tctgaggtga cctcactcat 75480
gaccacaggt gacctggccc ttccctgcca gctataccag accctgtctt gacagatgcc 75540
ccgattccaa cagccaattc ctgggaccct gaatagctgt agacaccagc ctcattccag 75600
tacctcctgc caattgcctg gattcccatc ctggctggaa tcaagaaggc agcatccgcc 75660
aggctcccaa caggcaggac tcccgcacac cctcctctga gaggccgctg tgttccgcag 75720
ggccaggccc tggacagttc ccctcacctg ccactagaga aacacctgcc attgtcgtcc 75780
ccacctggaa aagaccactc gtggagcccc cagccccagg tacagctgta gagacagtcc 75840
tcgaggcccc taagaaggag ccatgcccag ttctgccggg accctcggcc aggccgacag 75900
gagtggacgc tggagctggg cccacactgg gccacatagg agctcaccag tgagggcagg 75960
agagcacatg ccggggagca cccagcctcc tgctgaccag aggcctgccc cagagcccag 76020
gaggctgcag aggcctctcc agggagacac tgtgcatgtc tggtacctaa gcagcccccc 76080
acgtccccag tcctgggggc ccctggctca gctgtctggg ccctccctgc tccctgggaa 76140
gctcctcctg acagccccgc ctccagttcc aggtgtggtt attgtcaggc gatgtcagac 76200
tgtggtggat atagtggcta cgattaccac agtggtgccg cccatagcag caaccaggcc 76260
aagtagacag gcccctgctg cgcagcccca ggcatccact tcacctgctt ctcctggggc 76320
tctcaaggct gctgtctgtc ctctggccct ctgtggggag ggttccctca gtgggaggtc 76380
tgtgctccag ggcagggatg attgagatag aaatcaaagg ctggcaggga aaggcagctt 76440
cccgccctga gaggtgcagg cagcaccacg gagccacgga gtcacagagc cacggagccc 76500
ccattgtggg catttgagag tgctgtgccc ccggcaggcc cagccctgat ggggaagcct 76560
gtcccatccc acagcccggg tcccacgggc agcgggcaca gaagctgcca ggttgtcctc 76620
tatgatcctc atccctccag cagcatcccc tccacagtgg ggaaactgag gcttggagca 76680
ccacccggcc ccctggaaat gaggctgtga gcccagacag tgggcccaga gcactgtgag 76740
taccccggca gtacctggct gcagggatca gccagagatg ccaaaccctg agtgaccagc 76800
ctacaggagg atccggcccc acccaggcca ctcgattaat gctcaacccc ctgccctgga 76860
gacctcttcc agtaccacca gcagctcagc ttctcagggc ctcatccctg caaggaaggt 76920
caagggctgg gcctgccaga aacacagcac cctccctagc cctggctaag acagggtggg 76980
cagacggctg tggacgggac atattgctgg ggcatttctc actgtcactt ctgggtggta 77040
gctctgacaa aaacgcagac cctgccaaaa tccccactgc ctcccgctag gggctggcct 77100
ggaatcctgc tgtcctagga ggctgctgac ctccaggatg gctccgtccc cagttccagg 77160
gcgagagcag atcccaggca ggctgtaggc tgggaggcca cccctgccct tgccggggtt 77220
gaatgcaggt gcccaaggca ggaaatggca tgagcacagg gatgaccggg acatgcccca 77280
ccagagtgcg ccccttcctg ctctgcaccc tgcacccccc aggccagccc acgacgtcca 77340
acaactgggc ctgggtggca gccccaccca gacaggacag acccagcacc ctgaggaggt 77400

-continued cctgccaggg ggagctaaga gccatgaagg agcaagatat ggggccccg atacaggcac 77460 agatgtcagc tccatccagg accacccagc ccacaccctg agaggaacgt ctgtctccag 77520
cctctgcagg tcgggaggca gctgacccct gacttggacc cctattccag acaccagaca 77580
gaggcgcagg ccccccagaa ccagggttga gggacgcccc gtcaaagcca gacaaaacca 77640
aggggtgttg agcccagcaa gggaaggccc ccaaacagac caggaggttt ctgaaggtgt 77700
ctgtgtcaca gtggggtata gcagcagctg gtaccacagt gacactcacc cagccagaaa 77760
ccccattcca agtcagcgga agcagagaga gcagggagga cacgtttagg atctgagact 77820
gcacctgaca cccaggccag cagacgtctc ccctccaggg caccccaccc tgtcctgcat 77880
ttctgcaaga tcaggggcgg cctgaggggg ggtctagggt gaggagatgg gtcccctgta 77940
caccaaggag gagttaggca ggtcccgagc actctcccca ttgaggctga cctgcccaga 78000
gagtcctggg cccaccccac acaccggggc ggaatgtgtg caggcctcgg tctctgtggg 78060
tgttccgcta gctggggctc acagtgctca ccccacacct aaaatgagcc acagcctccg 78120
gagcccccgc aggagacccc gcccacaagc ccagccccca cccaggaggc cccagagctc 78180
agggcgcccc gtcggattcc gaacagcccc gagtcacagc gggtataacc ggaaccacca 78240
ctgtcagaat agctacgtca aaaactgtcc agtggccact gccggaggcc ccgccagaga 78300
gggcagcagc cactctgatc ccatgtcctg ccggctccca tgacccccag cacgcggagc 78360
cccacagtgt ccccactgga tgggaggaca agagctgggg attccggcgg gtcggggcag 78420
gggcttgatc gcatccttct gccgtggctc cagtgcccct ggctggagtt gacccttctg 78480
acaagtgtcc tcagagagac aggcatcacc ggcgcctccc aacatcaacc ccaggcagca 78540
caggcacaaa ccccacatcc agagccaact ccaggagcag agacacccca ataccctggg 78600
ggaccccgac cctgatgact tcccactgga attcgccgta gagtccacca ggaccaaaga 78660
ccctgcctct gcctctgtcc ctcactcagg acctgctgcc gggcgaggcc ttgggagcag 78720
acttgggctt aggggacacc agtgtgaccc cgaccttgac caggacgcag acctttcctt 78780
cctttcctgg ggcagcacag actttggggt ctgggccagg aggaacttct ggcaggtcgc 78840
caagcacaga ggccacaggc tgaggtggcc ctggaaagac ctccaggagg tggccactcc 78900
ccttcctccc agctggaccc catgtcctcc ccaagataag ggtgccatcc aaggcaggtg 78960
ctccttggag ccccattcag actcctccct ggaccccact gggcctcagt cccagctctg 79020
gggatgaagc caccacaagc acaccaggca gcccaggccc agccaccctg cagtgcccaa 79080
gcacacactc tggagcagag cagggtgcct ctgggagggg ctgagctccc caccccaccc 79140
ccacctgcac accccaccca cccctgccca gcggctctgc aggagggtca gagccccaca 79200
tggggtatgg acttagggtc tcactcacgt ggctcccatc atgagtgaag ggcctcaag 79260 cccaggttcc cacagcagcg cctgtcgcaa gtggaggcag aggcccgagg gccaccctga 79320
cctggtccct gaggttcctg cagcccaggc tgccctgctg tccctgggag gcctgggctc 79380
caccagacca caggtccagg gcaccgggtg caggagccac ccacacacag ctcacaggaa 79440
gaagataagc tccagacccc cagggccaga acctgccttc ctgctactgc ttcctgcccc 79500
agacctgggc gccctccccc gtccacttac acacaggcca ggaagctgtt cccacacaga 79560
acaaccccaa accaggaccg cctggcactc aggtggctgc catttccttc tccatttgct 79620
cccagcgcct ctgtcctccc tggttcctcc ttcgggggaa cagcctgtgc agccagtccc 79680
tgcagcccac accctgggga gacccaaccc tgcctggggc ccttccaacc ctgctgctct 79740
tactgcccac ccagaaaact ctggggtcct gtccctgcag tccctaccct ggtctccacc 79800 cagaccoctg tgtatcactc cagacacccc tcccaggcaa accctgcacc tgcaggccct 79860
gtcctcttct gtcgctagag cctcagtttc tccccoctgt gcccacaccc tacctcctcc 79920
tgcccacaac tctaactctt cttctcctgg agcccctgag ccatggcatt gaccctgccc 79980
tcccaccacc cacagcccat gccctcacct tcctcctggc cactccgacc ccgcccccctc 80040
tcaggccaag ccctggtatt tccaggacaa aggctcaccc aagtctttcc caggcaggcc 80100
tgggctcttg ccctcacttc ccggttacac gggagcctcc tgtgcacaga agcagggagc 80160
tcagcccttc cacaggcaga aggcactgaa agaaatcggc ctccagcacc ttgacacacg 80220
tccgcccgtg tctctcactg cccgcacctg cagggaggct ccgcactccc tctaaagaca 80280
agggatccag gcagcagcat cacgggagaa tgcagggctc ccagacatcc cagtcctctc 80340
acaggcctct cctgggaaga gacctgcagc caccaccaaa cagccacaga ggctgctgga 80400
tagtaactga gtcaatgacc gacctggagg gcaggggagc agtgagccgg agcccatacc 80460
atagggacag agaccagccg ctgacatccc gagctcctca atggtggccc cataacacac 80520
ctaggaaaca taacacaccc acagccccac ctggaacagg gcagagactg ctgagccccc 80580
agcaccagcc ccaagaaaca ccaggcaaca gtatcagagg gggctcccga gaaagagagg 80640
aggggagatc tccttcacca tcaaatgctt cccttgacca aaaacagggt ccacgcaact 80700
cccccaggac aaaggaggag ccccctatac agcactgggc tcagagtcct ctctgagaca 80760
ccctgagttt cagacaacaa cccgctggaa tgcacagtct cagcaggaga acagaccaaa 80820
gccagcaaaa gggacctcgg tgacaccagt agggacagga ggattttgtg gggctcgtg 80880
tcactgtgag gatattgtag tggtggtagc tgctactccc acagtgacac agacccattc 80940
ccaaagccct actgcaaaca cacccactcc tggggctgag gggctgggggg agcatctggg 81000
aagtagggtc caggggtgtc tatcaatgtc caaaatgcac cagactcccc gccaaacacc 81060
accccaccag ccagcgagca gggtaaacag aaaatgagag gctctgggaa gcttgcacag 81120
gccccaagga aagagctttg gcaggtgtgc aagaggggat gcaggcagag cctgagcagg 81180
gccttttgct gtttctgctt tcctgtgcag agagttccat aaactggtgt tcaagatcag 81240
tggctgggaa tgagcccagg agggcagtct gtgggaagag cacagggaag gaggaccagc 81300
cgctatccta cactgtcatc tttcaaaagt ttgccttgtg accacactat tgcatcatgg 81360
gatgcttaag agctgatgta gacacagcta aagagagaat cagtgagatg aatttgcagc 81420
atagatctga ataaactctc cagaatgtgg agcagtacag aagcaaacac acagaaagtg 81480
cctgatgcaa ggacaaagtt cagtgggcac cttcaggcat tgctgctggg cacagacact 81540
ctgaaaagcc ctggcaggat ctccctgcga caaagcagaa ccctcaggca atgccagccc 81600
cagagccctc cctgagagcg tcatggggaa agatgtgcag aacagctgat tatcatagac 81660
tcaaactgag aacagagcaa acgtccatct gaagaacagt caaataagca atggtaggtt 81720
catgcaatgc aaacccagac agccagggga caacagtaga gggctacagg cggctttgcg 81780
gttgagttca tgacaatgct gagtaattgg agtaacagag gaaagcccaa aaaatacttt 81840
taatgtgatt tcttctaaat aaaatttaca ccaggcaaaa tgaactgtct tcttaaggga 81900
taaactttcc cctggaaaaa ctacaaggaa aattaagaaa acgatgatca cataaacaca 81960
gttgtggtta cttctactgg ggaaggaaga gggtatgagc tgagacacac agagtcggca 82020
agtctccaag caagcacaga acgaatacat tacagtacct tgaatacagc agttaaactt 82080
ctaaatcgca agaagaggaa aatgcacaca gctgtgttta gaaaattctc agtccagcac 82140

-continued

```
tattcataat agcaaagaca ttaacccagg ttggataaat aaatgatgac acaggcaatt  82200
gcacaatgat acagacatac atttagtaca tgagacatcg atgatgtatc cccaaagaaa  82260
tgactttaaa gagaaaaggc ctgatgtgtg gtggcactca cctccctggg atccccggac  82320
aggttgcagg cacactgtgt ggcagggcag gctggtacat gctggcagct cctggggcct  82380
gatgtggagc aagcgcaggg ctgtataccc ccaaggatgg cacagtcagt gaattccaaa  82440
gagaagcagc tcagccacac tgcccaggca gagcccgaga gggacgccca cgcacaggga  82500
ggcagagccc agctcctcca cagccaccac cacctgtgca cgggccacca ccttgcaggc  82560
acagagtggg tgctgagagg aggggcaggg acaccaggca gggtgagcac ccagagaaaa  82620
ctgcagaagc ctcacacatc cacctcagcc tcccctgacc tggacctcac ctggtctgga  82680
cctcacctgg cctgggcctc acctgacctg gacctcacct ggcctgggct tcacctgacc  82740
tggacctcac ctggcctccg gcctcacctg cacctgctcc aggtcttgct ggaacctgag  82800
tagcactgag gctgcagaag ctcatccagg gttggggaat gactctggaa ctctcccaca  82860
tctgaccttt ctgggtggag gcatctggtg gccctgggaa tataaaaagc cccagaatgg  82920
tgcctgcgtg atttgggggc aatttatgaa cccgaaagga catggccatg gggtgggtag  82980
ggacataggg acagatgcca gcctgaggtg gagcctcagg acacagttgg acgcggacac  83040
tatccacata agcgagggac agacccgagt gttcctgcag tagacctgag agcgctgggc  83100
ccacagcctc ccctcggtgc cctgctgcct cctcaggtca gccctggaca tcccgggttt  83160
ccccaggcca gatggtaggt ttgaagtgag gtctgtgtca ctgtggtatt atgattacgt  83220
ttgggggagt tatcgttata cccacagcat cacacggtcc atcagaaacc catgccacag  83280
ccctccccgc aggggaccgc cgcgtgccat gttacgattt tgatcgagga cacagcgcca  83340
tgggtatggt ggctaccaca gcagtgcagc ccatgaccca aacacacagg gcagcaggca  83400
caatggacag gcctgtgagt gaccatgctg ggctccagcc cgccagcccc ggagaccatg  83460
aaacagatgg ccaaggtcac cccacagttc agccagacat ggctccgtgg ggtctgcatc  83520
gctgctgccc tctaacacca gcccagatgg ggacaaggcc aaccccacat taccatctcc  83580
tgctgtccac ccagtggtcc cagaagcccc tccctcatgg ctgagccaca tgtgtgaacc  83640
ctgagagcac cccatgtcag agtaggggca gcagaagggc ggggctggcc ctgtgcactg  83700
tccctgcacc catggtccct cgcctgcctg gccctgacac ctgagcctct tctgagtcat  83760
ttctaagata gaagacattc ccggggacag ccggagctgg gcgtcgctca tcctgcccgg  83820
ccgtcctgag tcctgcttgt ttccagacct caccagggaa gccaacagag gactcacctc  83880
acacagtcag agacaaagaa ccttccagaa atccctgtct cactccccag tgggcacctt  83940
cttccaggac attcctcggt cgcatcacag caggcaccca catctggatc aggacggccc  84000
ccagaacaca agatggccca tggggacagc cccacaaccc aggccttccc agacccctaa  84060
aaggcgtccc accccctgca cctgccccag ggctaaaaat ccaggaggct tgactcccgc  84120
ataccctcca gccagacatc acctcagccc cctcctggag gggacaggag cccgggaggg  84180
tgagtcagac ccacctgccc tcgatggcag gcggggaaga ttcagaaagg cctgagatcc  84240
ccaggacgca gcaccactgt caatgggggc cccagacgcc tggaccaggg cctgcgtggg  84300
aaaggccgct gggcacactc aggggctttt tgtgaaggcc cctcctactg tgtgactacg  84360
gtgactacca cagtgatgaa actagcagca aaaactggcc ggacacccag ggaccatgca  84420
cacttctcag cttggagctc tccaggacca gaagagtcag gtctgagggt ttgtagccag  84480
accctcggcc tctagggaca ccctggccat cacagcggat gggctggtgc cccacatgcc  84540
```

atctgctcca aacaggggct tcagagggct ctgaggtgac ttcactcatg accacaggtg 84600
ccctggcccc ttccccgcca gctacaccga accctgtccc aacagctgcc ccagttccaa 84660
cagccaattc ctggggccca gaattgctgt agacaccagc ctcgttccag cacctcctgc 84720
caattgcctg gattcacatc ctggctggaa tcaagagggc agcatccgcc aggctcccaa 84780
caggcaggac tcccgcacac cctcctctga gaggccgctg tgttccgcag ggccaggccc 84840
tggacagttc ccctcacctg ccactagaga aacacctgcc attgtcgtcc ccacctggaa 84900
aagaccactc gtggagcccc cagccccagg tacagctgta gagagactcc ccgagggatc 84960
taagaaggag ccatgcgcag ttctgccggg accctcggcc aggccgacag gagtggacac 85020
tggagctggg cccacactgg gccacatagg agctcaccag tgagggcagg agagcacatg 85080
ccggggagca cccagcctcc tgctgaccag aggcctgccc cagagcccag gaggctgcag 85140
aggcctctcc agggggacac tgtgcatgtc tggtccctga gcagcccccc acgtccccag 85200
tcctggggc ccctagcaca gctgtctgga ccctccctgt tccctgggaa gctcctcctg 85260
acagccccgc ctccagttcc aggtgtggtt attgtcaggg ggtgtcagac tgtggtggat 85320
acagctatgg ttaccacagt ggtgctgccc atagcagcaa ccaggccaag tagacaggcc 85380
cctgctgtgc agccccaggc ctccagctca cctgcttctc ctggggctct caaggtcact 85440
gttgtctgta ctctgccctc tgtggggagg gttctctcag tgggaggtct gttctcaaca 85500
tcccagggcc tcatgtctgc acggaaggcc aatggatggg caacctcaca tgccgcggct 85560
aagatagggt gggcagcctg gcgggggaca gtacatactg ctggggtgtc tgtcactgtg 85620
cctagtgggg cactggctcc caaacaacgc agtcctcacc aaaatcccca cagcctcccc 85680
tgctaggggc tggcctgatc tcctgcagtc ctaggaggct gctgacctcc agaatgtctc 85740
cgtccccagt tccagggcga gagcagatcc caggccggct gcagactggg aggccacccc 85800
ctccttccca gggttcactg gaggtgacca aggtaggaaa tggccttaac acagggatga 85860
ctgcgccatc ccccaacaga gtcagccccc tcctgctctg taccccgcac cccccaggcc 85920
agtccacgaa aaccagggcc ccacatcaga gtcactgcct ggcccggccc tggggcggac 85980
ccctcagccc ccaccctgtc tagaggactt ggggggacag gacacaggcc ctctccttat 86040
ggttccccca cctgcctccg gccgggaccc ttggggtgtg gacagaaagg acacctgcct 86100
aattggcccc caggaacaca gaacttctct ccagggaccc cagcccgagc acccccttac 86160
ccaggaccca gccctgcccc tcctcccctc tgctctcctc tcatcacccc atgggaatcc 86220
ggtatcccca ggaagccatc aggaagggct gaaggaggaa gcggggccgt gcaccaccgg 86280
gcaggaggct ccgtcttcgt gaacccaggg aagtgccagc ctcctagagg gtatggtcca 86340
ccctgcctgg ggctcccacc gtggcaggct gcggggaagg accagggacg gtgtggggga 86400
gggctcaggg ccctgcgggt gctcctccat cttcggtgag cctccccctt cacccaccgt 86460
cccgcccacc tcctctccac cctggctgca cgtcttccac accatcctga gtcctaccta 86520
caccagagcc agcaaagcca gtgcagacaa aggctggggt gcaggggggc tgccagggca 86580
gcttcgggga gggaaggatg gagggagggg aggtcagtga agaggccccc ttcccctggg 86640
tccaggatcc tcctctggga cccccggctc ccatcccctc ctggctctgg gaggagaagc 86700
aggatgggag aatctgtgcg ggaccctctc acagtggaat atccccacag cggctcaggc 86760
cagacccaaa agcccctcag tgagccctcc actgcagtcc tgggcctggg tagcagcccc 86820
tcccacagag gacagaccca gcaccccgaa gaagtcctgc caggggggagc tcagagccat 86880 gaaagagcag gatatggggt ccccgataca ggcacagacc tcagctccat ccaggcccac 86940
cgggacccac catgggagga acacctgtct ccgggttgtg aggtggctgg cctctgtctc 87000
ggaccccact ccagacacca gacagagggg caggcccccc aaaaccaggg ttgagggatg 87060
atccgtcaag gcagacaaga ccaaggggca ctgaccccag caagggaagg ctcccaaaca 87120
gacgaggagg tttctgaagc tgtctgtatc acagtggggt atagcagtgg ctggtaccac 87180
agtgacactc gccaggccag aaaccccgtc ccaagtcagc ggaagcagag agagcaggga 87240
ggacacgttt aggatctgag gccgcacctg acacccaggg cagcagacgt ctcccctcca 87300
gggcaccctc caccgtcctg cgtttcttca agaatagggg cggcctgagg gggtccaggg 87360
ccaggcgata ggtcccctct accccaagga ggagccaggc aggacccgag caccgtcccc 87420
attgaggctg acctgcccag acgggcctgg gcccacccca cacaccgggg cggaatgtgt 87480
gcaggcccca gtctctgtgg gtgttccgct agctggggcc cccagtgctc accccacacc 87540
taaagcgagc cccagcctcc agagcccccct aagcattccc cgcccagcag cccagcccct 87600
gcccccaccc aggaggcccc agagctcagg gcgcctggtc ggattctgaa cagccccgag 87660
tcacagtggg tataactgga acgaccaccg tgagaaaaac tgtgtccaaa actgactcct 87720
ggcagcagtc ggaggccccg ccagagaggg gagcagccgc cctgaaccca tgtcctgccg 87780
gttcccatga cccccagcac ccagagcccc acggtgtccc cgttggataa tgaggacaag 87840
ggctggggggc tccggtggtt tgcggcaggg acttgatcac atccttctgc tgtggcccca 87900
ttgcctctgg ctggagttga cccttctgac aagtgtcctc agaaagacag ggatcaccgg 87960
cacctcccaa tatcaacccc aggcagcaca gacacaaacc ccacatccag agccaactcc 88020
aggagcagag acaccccaac actctggggg accccaaccg tgataactcc ccactggaat 88080
ccgccccaga gtctaccagg accaaaggcc ctgccctgtc tctgtccctc actcagggcc 88140
tcctgcaggg cgagcgcttg ggagcagact cggtcttagg ggacaccact gtgggcccca 88200
actttgatga ggccactgac ccttccttcc tttcctgggg cagcacagac tttggggtct 88260
gggcagggaa gaactactgg ctggtggcca atcacagagc ccccaggccg aggtggcccc 88320
aagaaggccc tcaggaggtg gccactccac ttcctcccag ctggacccca ggtcctcccc 88380
aagatagggg tgccatccaa ggcaggtcct ccatggagcc cccttcagac tcctcccggg 88440
accccactgg acctcagtcc ctgctctggg aatgcagcca ccacaagcac accaggaagc 88500
ccaggcccag ccaccctgca gtgggcaagc ccacactctg gagcagagca gggtgcgtct 88560
gggaggggct aacctcccca ccccccaccc cccatctgca cacagccacc taccactgcc 88620
cagaccctct gcaggagggc caagccacca tggggtatgg acttagggtc tcactcacgt 88680
gcctcccctc ctgggagaag gggcctcatg ccgagatccc tgcagcacta gacacagctg 88740
gaggcagtgg ccccagggcc accctgacct ggcatctaag gctgctccag cccagacagc 88800
actgccgttc ctgggaagcc tgggctccac cagaccacag gtccagggca cagcccacag 88860
gagccaccca cacacagctc acaggaagaa gataagctcc agaccccagg gcgggacctg 88920
ccttcctgcc accacttaca cacaggccag ggagctgttc ccacacagat caaccccaaa 88980
ccgggactgc ctggcactag ggtcactgcc atttccctct ccattccctc ccagtgcctc 89040
tgtgctccct ccttctgggg aacaccctgt gcagcccctc cctgcagccc acacgctggg 89100
gagaccccac cctgcctcgg gccttttcta cctgctgcac ttgccgccca cccaaacaac 89160
cctgggtacg tgaccctgca gtcctcaccc tgatctgcaa ccagacccct gtccctccct 89220
ctaaacaccc ctcccaggcc aactctgcac ctgcaggccc tccgctcttc tgccacaaga 89280

-continued gcctcaggtt ttcctacctg tgcccacccc ctaacccctc ctgcccacaa cttgagttct 89340
tcctctcctg gagcccttga gccatggcac tgaccctaca ctcccaccca cacactgccc 89400
atgccatcac cttcctcctg gacactctga ccacgctccc ctccctctca gacccggccc 89460
tggtatttcc aggacaaagg ctcacccaag tcttccccat gcaggccctt gccctcactg 89520
cctggttaca cgggagcctc ctgtgcgcag aagcagggag ctcagctctt ccacaggcag 89580
aaggcactga aagaaatcgg cctccagtgc cttgacacac gtccgcctgt gtctctcact 89640
gcctgcacct gcagggaggc tccgcactcc ctctaaagat gagggatcca ggcagcaaca 89700
tcacgggaga atgcagggct cccagacagc ccagccctct cgcaggcctc tcctgggaag 89760
agacctgcag ccaccactga acagccacgg aggtcgctgg atagtaaccg agtcagtgac 89820
cgacctggag ggcaggggag cagtgaaccg gagcccatac catagggaca gacaccagcc 89880
gctaacatcc cgagcccctc actggcggcc ccagaacacc ccgtggaaac agaacagacc 89940
cacagtccca cctggaacag ggcagacact gctgagcccc cagcaccagc cccaagaaac 90000
actaggcaac agcatcagag ggggctcctg agaaagagag gaggggaggt ctccttcacc 90060
atcaaatgct tcccttgacc aaaaacaggg tccacgcaac tcccccagga caaaggagga 90120
gccccctgta cagcactggg ctcagagtcc tctctgagac aggctcagtt tcagacaaca 90180
acccgctgga atgcacagtc tcagcaggag agccaggcca gagccagcaa gaggagactc 90240
ggtgacacca gtctcctgta gggacaggag gattttgtgg gggttcgtgt cactgtgagc 90300
atattgtggt ggtgactgct attcccacag tgacacaacc ccattcctaa agccctactg 90360
caaacgcacc cactcctggg gctgaggggc tgggggagca tctgggaagt atggcctagg 90420
ggtgtccatc aatgcccaaa atgcaccaga ctctccccaa gacatcaccc caccagccag 90480
tgagcagagt aaacagaaaa tgagaagcag ctgggaagct tgcacaggcc ccaaggaaag 90540
agctttggca ggtgtgcaag aggggatgtg ggcagagcct gagcagggcc ttttgctgtt 90600
tctgctttcc tgtgcagaga gttccataaa ctggtattca ggatcaatgg ctgggagtga 90660
gcccaggagg acagtgtggg aagagcacag ggaaggagga ccagccgcta tcctacactg 90720
tcatcttttg aaagtttgcc ctgtgcccac aatgctgcat catgggatgc ttaacagctg 90780
atgtagacac agctaaagag agaatcagtg aaatgcattt gcagcacaga tctgaataaa 90840
tcctccagaa tgtggagcag cacagaagca agcacacaga aagtgcctga tgccaaggca 90900
aagttcagtg ggcaccttca ggcattgctg ctgggcacag acactctgaa aagcactggc 90960
aggaactgcc tgtgacaaag cagaaccctc aggcaatgcc agccctagag cccttcctga 91020
gaacctcatg ggcaaagatg tgcagaacag ctgtttgtca tagccccaaa ctatggggct 91080
ggacaaagca aacgtccatc tgaaggacaa cagacaaata aacgatggca ggttcatgaa 91140
atgcaaacta ggacagccag aggacaacag tagagagcta caggcggctt tgcggttgag 91200
ttcatgacaa tgctgagtaa ttggagtaac agaggaaagc ccaaaaaata cttttaatgt 91260
gatttcttct aaataaaatt tacacccggc aaaatgaact atcttcttaa gggataaact 91320
ttcccctgga aaaactataa ggaaaatcaa gaaaacgatg atcacataaa cacagtggtg 91380
gttacttcta ctggggaagg aagagggtat gagctgagac acacagagtc ggcaagtctc 91440
ctaacaagaa cagaacaaat acattacagt accttgaaaa cagcagttaa acttctaaat 91500
cgcaagaaga ggaaaatgca cacacctgtg tttagaaaat tctcagtcca gcactgttca 91560
taatagcaaa gacattaacc caggttggat aaataagcga tgacacaggc aattgcacaa 91620

-continued

```
tgatacagac atacattcag tatatgagac atcgatgatg tatccccaaa gaaatgactt  91680
taaagagaaa aggcctgatg tgtggtggca atcacctccc tgggcatccc cggacaggct  91740
gcaggctcac tgtgtggcag ggcaggcagg cacctgctgg cagctcctgg ggcctgatgt  91800
ggagcaggca cagagctgta tatccccaag gaaggtacag tcagtgcatt ccagagagaa  91860
gcaactcagc cacactccct ggccagaacc caagatgcac acccatgcac agggaggcag  91920
agcccagcac ctccgcagcc accaccacct gcgcacgggc caccaccttg caggcacaga  91980
gtgggtgctg agaggagggg cagggacacc aggcagggtg agcacccaga gaaaactgca  92040
gaagcctcac acatccacct cagcctcccc tgacctggac ctcacctggc ctgggcctca  92100
cctgacctgg acctcacctg gcctgggctt cacctggcct gggcttcacc tgacctggac  92160
ctcacctggc ctcgggcctc acctggcctg ggcttcacct ggcctgggct tcacctgacc  92220
tggacctcac ctggcctggg cctcacctga cctggacctc acctggcctg ggcttcacct  92280
ggcctgggct tcacctggcc tgggcttcac ctgacctgga cctcacctgg cctgggcttc  92340
acctgacctg gacctcacct ggcctcaggc ctcacctgca cctgctccag gtcttgctgg  92400
agcctgagta gcactgaggc tgtagggact catccagggt tggggaatga ctctgcaact  92460
ctcccacatc tgacctttct gggtggaggc acctggtggc ccagggaata taaaaagccc  92520
cagaatgatg cctgtgtgat ttgggggcaa tttatgaacc cgaaaggaca tggccatggg  92580
gtgggtaggg acagtaggga cagatgtcag cctgaggtga agcctcagga cacaggtggg  92640
catggacagt gtccacctaa gcgagggaca gacccgagtg tccctgcagt agacctgaga  92700
gcgctgggcc cacagcctcc cctcggggcc ctgctgcctc ctcaggtcag ccctggacat  92760
cccgggtttc cccaggcctg gcggtaggtt tgaagtgagg tctgtgtcac tgtggtatta  92820
ctatgatagt agtggttatt actaccacag tgtcacagag tccatcaaaa actcatgcct  92880
gggagcctcc caccacagcc ctccctgcgg gggaccgctg catgccgtgt taggattttg  92940
atcgaggaca cggcgccatg ggtatggtgg ctaccacagc agtgcagccc atgacccaaa  93000
cacacggggc agcagaaaca atggacaggc ccacaagtga ccatgatggg ctccagccca  93060
ccagccccag agaccatgaa acagatggcc aaggtcaccc tacaggtcat ccagatctgg  93120
ctccaagggg tctgcatcgc tgctgccctc ccaacgccaa accagatgga gacagggccg  93180
gccccatagc accatctgct gccgtccacc cagcagtccc ggaagcccct ccctgaacgc  93240
tgggccacgt gtgtgaaccc tgcgagcccc ccatgtcaga gtaggggcag caggagggcg  93300
gggctggccc tgtgcactgt cactgcccct gtggtccctg gcctgcctgg ccctgacacc  93360
tgagcctctc ctgggtcatt tccaagacat tcccagggac agccggagct gggagtcgct  93420
catcctgcct ggctgtcctg agtcctgctc atttccagac ctcaccaggg aagccaacag  93480
aggactcacc tcacacagtc agagacaacg aaccttccag aaatccctgt ttctctcccc  93540
agtgagagaa accctcttcc agggtttctc ttctctccca ccctcttcca ggacagtcct  93600
cagcagcatc acagcgggaa cgcacatctg gatcaggacg gcccccagaa cacgcgatgg  93660
cccatgggga cagcccagcc cttcccagac ccctaaaagg tatccccacc ttgcacctgc  93720
cccagggctc aaactccagg aggcctgact cctgcacacc ctcctgccag atatcacctc  93780
agccccctcc tggaggggac aggagcccgg gagggtgagt cagacccacc tgccctcaat  93840
ggcaggcggg gaagattcag aaaggcctga gatccccagg acgcagcacc actgtcaatg  93900
ggggccccag acgcctggac cagggcctgt gtgggaaagg cctctggcca cactcagggg  93960
ctttttgtga agggccctcc tgctgtgtga ctacggtggt aactcccaca gtgatgaaac  94020
```

```
cagcagcaaa aactgactgg actcgcaggg tttatgcaca cttctcggct cggagctctc  94080
caggagcaca agagccaggc ccgagggttt ctgcccagac cctcggcctc tagggacacc  94140
cgggccatct tagccgatgg gctggtgccc tgcacaccgt gtgctgccaa acaggggctt  94200
cagagggctc tgaggtgact tcactcatga ccacaggtgc cctggtccct tcactgccag  94260
ctgcaccaga ccctgttccg agagatgccc cagttccaaa agccaattcc tggggccggg  94320
aattactgta gacaccagcc tcattccagt acctcctgcc aattgcctgg attcccatcc  94380
tggctggaat caagagggca gcatccgcca ggctcccaac aggcaggact cccacacacc  94440
ctcctctgag aggccgctgt gttccgcagg gccaggccgc agacagttcc cctcacctgc  94500
ccatgtagaa acacctgcca ttgtcgtccc cacctggaaa agaccacttg tggagccccc  94560
agccccaggt acagctgtag agagagtcct cgaggcccct aagaaggagc catgcccagt  94620
tctgccggga ccctcggcca ggccgacagg agtggacgct ggagctgggc ccacactggg  94680
ccacatagga gctcaccagt gagggcagga gagcacatgc cggggagcac ccagcctcct  94740
gctgaccaga gacccgtccc agagcccagg aggctgcaga ggcctctcca gggggacaca  94800
gtgcatgtct ggtccctgag cagcccccag gctctctagc actgggggcc cctagcacag  94860
ctgtctggac cctccctgtt ccctgggaag ctcctcctga cagccccgcc tccagttcca  94920
ggtgtggtta ttgtcagggg gtgccaggcc gtggtagaga tggctacaat taccacagtg  94980
gtgccgccca tagcagcaac caggccaagt agacagaccc ctgccacgca gccccaggcc  95040
tccagctcac ctgcttctcc tggggctctc aaggctgctg tctgccctct ggccctctgt  95100
ggggagggtt ccctcagtgg gaggtctgtg ctccagggca gggatgactg agatagaaat  95160
caaaggctgg cagggaaagg cagcttcccg ccctgagagg tgcaggcagc accacagagc  95220
catggagtca cagagccacg gagcccccag tgtgggcgtg tgagggtgct gggctcccgg  95280
caggcccagc cctgatgggg aagcctgccc cgtcccacag cccaggtccc caggggcagc  95340
aggcacagaa gctgccaagc tgtgctctac gatcctcatc cctccagcag catccactcc  95400
acagtgggga aactgagcct tggagaacca cccagccccc tggaaacaag gcggggagcc  95460
cagacagtgg gcccagagca ctgtgtgtat cctggcacta ggtgcaggga ccacccggag  95520
atccccatca ctgagtggcc agcctgcaga aggacccaac cccaaccagg ccgcttgatt  95580
aagctccatc cccctgtcct gggaacctct tcccagcgcc accaacagct cggcttccca  95640
ggccctcatc cctccaagga aggccaaagg ctgggcctgc caggggcaca gtaccctccc  95700
ttgccctggc taagacaggg tgggcagacg gctgcagata ggacatattg ctggggcatc  95760
ttgctctgtg actactgggt actggctctc aacgcagacc ctaccaaaat ccccactgcc  95820
tcccctgcta ggggctggcc tggtctcctc ctgctgtcct aggaggctgc tgacctccag  95880
gatggcttct gtccccagtt ctagggccag agcagatccc aggcaggctg taggctggga  95940
ggccacccct gtccttgccg aggttcagtg caggcaccca ggacaggaaa tggcctgaac  96000
acagggatga ctgtgccatg ccctacctaa gtccgcccct ttctactctg caaccccac  96060
tccccaggtc agcccatgac gaccaacaac ccaacaccag agtcactgcc tggccctgcc  96120
ctggggagga cccctcagcc cccaccctgt ctagaggact tgggggggaca ggacacaggc  96180
cctctcctta tggttccccc acctggctcc tgccgggacc cttggggtgt ggacagaaag  96240
gacgcctgcc taattggccc ccaggaacac agaacttctc tccagggacc ccagcccgag  96300
caccccctta cccaggaccc agccctgccc ctcctcccct ctgctctcct ctcatcactc  96360
```

-continued

```
catgggaatc cagaatcccc aggaagccat caggaagggc tgaaggagga agcggggccg  96420
ctgcaccacc gggcaggagg ctccgtcttc gtgaacccag ggaagtgcca gcctcctaga  96480
gggtatggtc caccctgcct ggggctccca ccgtggcagg ctgcggggaa ggaccaggga  96540
cggtgtgggg gagggctcag ggccctgcag gtgctccatc ttggatgagc ccatccctct  96600
cacccaccga cccgcccacc tcctctccac cctggccaca cgtcgtccac accatcctga  96660
gtcccaccta caccagagcc agcagagcca gtgcagacag aggctggggt gcaggggggc  96720
cgccagggca gctttgggga gggaggaatg gaggaagggg aggtcagtga agaggccccc  96780
ctcccctggg tctaggatcc acctttggga cccccggatc ccatcccctc caggctctgg  96840
gaggagaagc aggatgggag attctgtgca ggaccctctc acagtggaat acctccacag  96900
cggctcaggc cagatacaaa agcccctcag tgagccctcc actgcagtgc tgggcctggg  96960
ggcagcccct cccacagagg acagacccag caccccgaag aagtcctgcc agggggagct  97020
cagagccatg aaggagcaag atatggggac cccaatactg gcacagacct cagctccatc  97080
caggcccacc aggacccacc atgggtggaa cacctgtctc cggcccctgc tggctgtgag  97140
gcagctggcc tctgtctcgg acccccattc cagacaccag acagagggac aggcccccca  97200
gaaccagtgt tgagggacac ccctgtccag ggcagccaag tccaagaggc gcgctgagcc  97260
cagcaaggga aggcccccaa acaaaccagg aggtttctga agctgtctgt gtcacagtcg  97320
ggtatagcag cggctaccac aatgacactg ggcaggacag aaaccccatc ccaagtcagc  97380
cgaaggcaga gagagcaggc aggacacatt taggatctga ggccacacct gacactcaag  97440
ccaacagatg tctcccctcc agggcgccct gccctgttca gtgttcctga gaaaacaggg  97500
gcagcctgag gggatccagg gccaggagat gggtcccctc taccccgagg aggagccagg  97560
cgggaatccc agcccctcc ccattgaggc catcctgccc agaggggccc ggacccaccc  97620
cacacaccca ggcagaatgt gtgcaggcct caggctctgt gggtgccgct agctggggct  97680
gccagtcctc accccacacc taaggtgagc cacagccgcc agagcctcca caggagaccc  97740
cacccagcag cccagcccct acccaggagg ccccagagct cagggcgcct gggtggattc  97800
tgaacagccc cgagtcacgg tgggtatagt gggagctact accactgtga gaaaagctat  97860
gtccaaaact gtctcccggc cactgctgga ggcccagcca gagaagggac cagccgcccg  97920
aacatacgac cttcccagcc ctcatgaccc ccagcacttg gagctccaca gtgtccccat  97980
tggatggtga ggatgggggc cggggccatc tgcacctccc aacatcaccc ccaggcagca  98040
caggcacaaa ccccaaatcc agagccgaca ccaggaacac agacacccca ataccctggg  98100
ggaccctggc cctggtgact tcccactggg atccaccccc gtgtccacct ggatcaaaga  98160
ccccaccgct gtctctgtcc ctcactcagg gcctgctgag gggcgggtgc tttggagcag  98220
actcaggttt aggggccacc attgtggggc ccaacctcga ccaggacaca gatttttctt  98280
tcctgccctg gggcaacaca gactttgggg tctgggcagg gaggaccttc tggaaagtca  98340
ccaagcacag agccctgact gaggtggtct caggaagacc cccaggaggg ggcttgtgcc  98400
ccttcctctc atgtggaccc catgcccccc aagatagggg catcatgcag ggcaggtcct  98460
ccatgcagcc accactaggc aactccctgg cgccggtccc cactgcgcct ccatcccggc  98520
tctggggatg cagccaccat ggccacacca ggcagcccgg gtccagcaac cctgcagtgc  98580
ccaagccctt ggcaggattc ccagaggctg gagcccaccc ctcctcatcc ccccacacct  98640
gcacacacac acctaccccc tgcccagtcc ccctccagga gggttggagc cacccatagg  98700
gtgggcgctc caggtctcac tcactcgctt cccttcctgg gcaaaggagc ctcgtgcccc  98760
```

ggtccccccct gacggcgctg ggcacaggtg tgggtactgg gccccagggc tcctccagcc 98820
ccagctgccc tgctctccct gggaggcctg ggcaccacca gaccaccagt ccagggcaca 98880
gccccaggga gccgcccact gccagctcac aggaagaaga taagcttcag accctcaggg 98940
ccgggagctg ccttcctgcc acccccttcct gccccagacc tccatgccct cccccaacca 99000
cttacacaca agccagggag ctgtttccac acagttcaac cccaaaccag gacggcctgg 99060
cactcgggtc actgccattt ctgtctgcat tcgctcccag cgcccctgtg ttccctccct 99120
cctccctcct tcctttcttc ctgcattggg ttcatgccgc agagtgccag gtgcaggtca 99180
gccctgagct tggggtcacc tcctcactga aggcagcctc agggtgccca ggggcaggca 99240
gggtgggggt gaggcttcca gctccaaccg ctccactagc cgagactaag gaagtgagag 99300
gcagccagaa atccagacca ttccatagca aatggatttc attaaagtta ccagacttca 99360
gtgtaagtaa catgagcccc atgcacaaca atcccttatg aaggggaagt cagtgtcgcc 99420
tcggatttct tgaaaaacac aaaaacttat caatgcctgt aaaagtctgt tggaaagaaa 99480
atatgattca agaatgttat gcccaacaaa gctggcatat tttctacccg gacacactca 99540
gggaatgtgg tcccttgagt gcttctctca ctgcgtaaat cctacgtggt gtttaagcat 99600
attcataaat gtgtatgtct atttttatgt gtaagatggt tcatttttat tttatttatt 99660
caatatgtac aataaagaat attgacaaat aggctggaca tggtggctcc cacctgtaat 99720
cccagccctt tgggaggccg aggcgggcag atcacctgag gtctggagtt cgagaccagc 99780
ctggccaaca tgatgaaaac ccatctctac taaaaataca aagattagcc aggcatggtg 99840
gtgcatgcct gtaatcccag ccactcagga ggctgagaca ggagaaatgc gtgaacccgg 99900
aaggcggagg ttgcagtgag ccgagatcac accactgcac tccagcctgg cgacagagca 99960
agattccatc tcaaaaaaaa aaaaagacaa agaaatttgt ttttttgaat aaagacaaat 100020
ttcatcacac gaagataaag atgcaaagct ccagacagga aggcacggac agcacagtga 100080
agcccggagc gggcgctggg gggccagggg catggcgggg gtgccagcgt ctctcggtgc 100140
ctaccatggc cactccagcc tgtgttctca cgaggatggc tgtgcaatgc taggagcgtg 100200
ttcgaagctc tagggcaacc actggaagtg aggctgagga gcagagccca gaggcccgtg 100260
gagctgatga aaagaaagct ggagaaagtg tttgctgcct cccaacatgg taagaaaaga 100320
tagaaagaga gagcacacgg caaagggagc ttgctgaggg actctttaca atggcttgca 100380
cagagctcag ggggtctggg aggctagggc cctgcgcagg gcagtcaccc cagcctgctg 100440
accaaggttt gctgcaggca gctctggggg tggttgaggc gcggtccctg gagccacccc 100500
tcaagggaac gaggcagcag agtgggccaa ggcccaggtc ggctgcaagg ctgcccagga 100560
cttggggtcc ttacatcagc agccactgat gcagctggcc cagagagagg cgccgagcag 100620
gttgcctcca ggggacaaac caggtcggag agggtgaggc agtggatgga gccacaacaa 100680
ccccgggcac gggtgacacg cacgttcatg cacatctgac ccttcctccc tcaccaaaca 100740
ggtccccctg ccttccccat ggttgcgaaa aagcaaaatg tagacgtttt ttcttttttta 100800
attcatgttt taattgacaa atgaagccgt atatatttat tgtgtacaac atgatgcttt 100860
aaaatatgta tacatcgtgg aacagcaacg ttgagctaat ttaacacgca ttacttcaca 100920
tacttgtcat cttttgtggc gagaatgctt aaaatccact ctcttagtat tttttaagaa 100980
tgcaatacat tgttgtcaac tgtggtcacc gtcatgcata gccaagctcc cgacctcacc 101040
ctcctgccag ctcaggctgt gcatcctttc accagcatcc cccaccccgg cccctggccc 101100

-continued tggtaactac cactctatac tctacgtatg agttcagctt tttaagattc cacagatgaa 101160
tgagatcata cagtatttgc tttctatgcc tggcttattt tagttaacac actgtcctcc 101220
agatccatcc gttgttgcaa atgacagggt ttcattcttt ttaaagtcta aagagtattc 101280
cattgtgtca atggacctca tttgctttat ccatgcatca actatggaca tttaggttga 101340
ttccatttct tagctgttgt ggatggtgct gcagtaaaca tggggctgca gatgtctctt 101400
caacatactg acatcatgtc ctttggataa atacccagta gtgggatcgc tggatcacaa 101460
tgtacagttt gtttttaat ggaaactttc attttttggt gaaattagga aaacagataa 101520
aacccacaga atccaaaata tatgtgaaga tgccaaaaac agttgacatt gggcagaggt 101580
cacatggaag gaagtgaata catgacgggg tgtgagggcc cagaggcagc tgaaatacgc 101640
tttctaaaca caaggacctc ttctgagagg gcagaagttt tatcctgcac atgcaatgac 101700
cagcacagct aaaatacact ttctaaacat gaggacctct tctgagaggg cagctttatc 101760
ctgcaaatgc aatgaccagc acaggaccca gaataaagag agttgccagc ggacgcctgg 101820
tgtccatgtg tccaggtgag ttcgagatgc ggacggcgct ggccagccag tcacacccta 101880
agtcaatctg ctgcatgcat ttgtccttgc cacagcagaa aacgagaaag cctttgggct 101940
gcaaagcttc acaggctcct cttctcccga ctccatggaa acagctacaa agagcaggcc 102000
cagtagagct taattcatga aaatgagtaa taaacttgaa ctggaacagt atcgactttt 102060
tagaaacggc agcaaagtgt ataaaaaata ttcaccagaa caatatttcc aaacgatgag 102120
atgagaattt cagccaagta atcctccatg gatagaaaat aatgaaggga ttggatttat 102180
gaaggaaaat catggagctc aaatacaaga gaagagaatc aaaaatgaac aggaggagat 102240
aaaatatggt ttggccaaag ttacaaaata aattttttaa aaacccttca tcatggcaag 102300
tagaaagagc gagaggaaaa acagatcccg tggaagacac aaataggaca tggggagaaa 102360
aatgaatgag atgaaacaga gcagaaataa aattttacgg aactaaagac aagtgatctg 102420
aacctgcctg gggcctgggg gacctcgcca ccctgaaggg aaagaacatg cctggctggc 102480
tttgccacct gctcattgca gagccccaca gcttgcaaca aacataggcg gtagccaggg 102540
agtggttaca gcaggccttg agcaagaccc agtgttgtgc tgacttcagg tctgacccag 102600
cactgtcata gtggtggtgt ccatagtggt agtgggggtg cttgtgtcac tccaccccca 102660
tctccaggag gctcagaaca gacagagaga gactccattt gtttgggaga aagtaaggga 102720
tgagaacaag agtctctgcc tggtaatcca gagaattatt ctagatcttg gccaagatta 102780
tcaaagcagt acctctatga gtcttttggg cttggagtcc ccctaaagca gatatagcta 102840
agatcacaac acccaagtcc ttttgaatat gtgggaagac ttcccaagga caggagcaaa 102900
caaacaagcc cagactgcaa aaaaacaagc ccagactgca ataaacacct cactcttcaa 102960
tgcccaggca ctgaagaaca tctcctagca gcaacaccat ccaggaaaac atggcctcaa 103020
ccagtgaact aaataaggca ccagggacca gtctcggaga aatagaggta tgttatcttt 103080
cagagaattc aaagtagctt tgttgaggaa actcaaagaa attcaagata acacagtgaa 103140
ggaattcaga atcctatccg ataaatttaa cagagattga agcaattaaa aagaattaag 103200
cagaaattat ggagctgaaa aatgcaattg gcatactgaa aaatgcatca gagtattttc 103260
atagcctctt atatcaagta gaagaaagaa ttagtgagct tgaaaacagg ctatttggaa 103320
aagcacgata aaaggagaca aaagagaaaa gaataaataa caatgaagca tatctacagg 103380
atctagaaaa tagcctcaaa aggccaaatc taagaattat tagccttaaa gaggaggtag 103440
agaaagaggg atggagagtt tattcaaagg gataataaca gaaaacttcc caaacctaga 103500
gaaagatatc aatatccaaa tgcaagaagg atgtagtaca ccaaggagat ttaatgcaaa 103560
gaagactacc tcaaggcatt caatactcaa actcccatat gacaaggact ttaaaaagat 103620
cctaaaagca gcaaaagaaa agaaatgaat aaaatactat ggagctccaa tatgtctggc 103680
agcagacttt tcagtgaaga ctttatatgc caggagagag tgtcataatg gatttaaagt 103740
gctgaaggaa aaaactttta ccctcgaaca gtatagctgg tgaaattatc cttcaaacat 103800
gaaggagaaa taatttgttt ccagacaaat gttgagggat ttcatgaaca ccagacctgt 103860
cttttaagaa atgctaaagg gagtacttca atcagaaaga aacacgttag tgaacaataa 103920
gaaatcatct gaaggcacaa aactcaccgg taatagtaag tacacagaaa aacacagaat 103980
attataacac tgtaactgtg gtgtgtaaac tccttttgtt tgtttgtttg tttgtttgtt 104040
tgtttttgtt tttagacgga gttttgctcc agcccaggct ggagtgcaat ggcacaatct 104100
cagctcactg caacttccac ctcccgggtt caagcaattc tcctgcctca gcctcccaag 104160
tagctgggat tacaggcatg tgctaccatg tccagctaat tttgtatttt agtagagacg 104220
gtgtttcacc atgttggtca ggctagcctt atcttgagta gaaaaactaa atgatgaagc 104280
aatgaaaaat aataactaca acttttcaag acatagtaca ataagatata aatcataaca 104340
aaaagttaaa aggtggaggg atgaagttaa ggcaaagagt ctttattagt tttcttttta 104400
cttgtctgtt tatgcaaaca gtgttaagtt gtcatcagtt taaaataatg ggtcataaga 104460
tactatttgc aagcctcatg gtaacgtcaa accaaaagca atacaacaga tacacaaaaa 104520
acaaaaagca agaagctaaa ttacgtcatc agagaaaatc accttcacta aaaggaagac 104580
ggagaaaaga atgaagagag agaagaccaa aagcaaatag caatatggca ggagtaagtc 104640
cttacttatc aataatacca ttgaatgtaa atggactaaa ctctccaatc aaaagacata 104700
gagtggctga atcaattaaa gaaaaaacaa gacccattga tctgttgtcc acaagaaaca 104760
cactttatct ataaagacac acatagactg aaaacaaagg gatggaaaaa gatactccac 104820
gccaatggaa accaaagaaa gagcaggagt agctacactt atatcaggca aaatagattt 104880
caagacaaaa actataagaa gagacaaggt cactaatgat aaacaggtca attcagcaag 104940
aggatataac aattgtaaat atatatgcac ccaatgctgg agcacccaga tatataaagc 105000
aagtatttac tagagctaaa gagagaaata gactccaatg caataatagc tggagatttc 105060
aacatcccac tttcaacatt gaacagatcc tccagataga aaatcaacaa agaaatattg 105120
gacttaatct gcactatcga ccaaatggat ctaacagata tttacagaac atttcatcca 105180
acagctgcag aacacacatt cttttcctca gcacatagat cattctcaag gatagaccat 105240
atgttgggtc acaaaacaag ttttaaaata ttcaaataca ttgaaataat atcaagcatc 105300
ttctgtgacc acaatggact aaaactagaa atcaataaca agaggaattt tggaaactat 105360
ataaatatat ggaaattaat gaatgctgag tgggtcaatg aagcaattaa gaaggaaact 105420
gaaatttttc ttggaacgaa tgatcatgga aacagaaaat accaaaacct atgggataca 105480
gcaaaagcag tactaagagg gaagtttaca gctacaaatg cttacattaa aaaagaagaa 105540
aaacttcaat aaaaaaacct aacaatgcat cttaaagaac tagaaaagca agaggaaatc 105600
aaatccaaaa ttagtagaag aaaacagtaa aggtcagagc agaaataagt aaaattgaaa 105660
tgaagaaaac aatacaaaag atcaataaaa caacaggttg ttttcttgaa aagttaaaca 105720
aaattgacaa acctttagcc agactaagaa aaaaagacag aagatccaaa taaataaaat 105780
cagagatgaa aaaggtgaca ttacaactta caccacagaa attcaaagga tcattagtgg 105840
ctactataag caactatatg ccaataaatt ggaaaatcta gaagaaatgc agaaattcct 105900
agacacatac aacctcccaa gattaaacca agaagaaatt caaaacctga acagactgat 105960
aacaagtaat gagatcaaag ccgtaataaa aagcctccca gtaaagagaa gcccaggacc 106020
cgacggcttc actgctgaat tctaccaaac atttaaagta gaactaatac caatcctact 106080
caaactattc caaaaaatag aggtggaagg aatacttcaa aactcattat acgaggccag 106140
tattaacctg acaccaaaac tagacaaaga cacatgaaaa aaagaaaact acaggccaat 106200
atgtctgatg aatattgaca caaaaatcct caacaaaata ctagcaaacc aaattcaact 106260
acacattaga aagttcactc atcatgacca agtggaattt atctaacttg ggatgcaaag 106320
atggttcaac atatgcaaat caatcaatgt gatacatcat atcaacagaa tgaacaacaa 106380
aaaccatttg atcatttaat tgatactgaa aaagcatttg ataaaattca acattccttc 106440
ataataaaaa ttctcttcta tactaggtac aaaagaaact tacctcaaca taataaagcc 106500
atatatgaca gtcccacagt atgatactaa atgaggaaaa actgagagcc tttcctctac 106560
gatctggaac atgacaaaga tgcccacttt catcactgtt attcaacata gtactggaag 106620
tcctagctgg agcgatcaga caagagaaag atataaaaga catccaaatt ggaaaggaat 106680
aagtcaaatt atcctcattt gcatatggta tgatcttcta tttagagcta actaaagact 106740
ccaccaaaaa aagttattag aactgacgaa caaattcagt aaagctgcag gatacaaaat 106800
caacatacaa aaatcagtag catttctata tgccaacaat gaccaatgtg aaaaagaaat 106860
taaaaagtaa ccctatttac aataaccaca aataaacacc taggaattaa ccaaagaggt 106920
aaaagatttc tgtaatgaaa actataaaaa actgatgaaa gaaattgaag agtacaccaa 106980
aaaatggaaa gcaattgcat gttcatggat tagaagaatc agtgttgtta taatgtccat 107040
actatccaaa gcaatctaca gattcaatgc aatccttatc aaaataccaa tgacatcatt 107100
cacagaaata gaaaaaaaaa atcctaaaat ttacgtggaa ccacaaagac ccagaatagc 107160
caaagctctc ctaagcaaaa agaacgaaac tgtaggaatg acattgcctg tcttcaaatt 107220
ctactacaga gctatagata gtaaccaaaa cagcgtggta ctagcataaa aacagacaca 107280
gagacaaaca gaacaaaatt taaaaaccca gaaataaatc cacacaccta cagcaaattc 107340
atttttgaca aagttgccaa gaacatactc tggggaatag ataatgatat ctcttcaata 107400
aataatgtgg ggaaaactgg atatccatat acataacagt gaaactagac ccctctctct 107460
ctcactatat acaaaaatca aatcaaaatt gtttaaggac ttaaatctaa gacctcatac 107520
tatgaaacca ctgcaagaca accttggcgg aaactctcca agacatcagt ccaggcaaag 107580
atttcttgag taatatccca caagcacaga caaccaaagc aaaaatggac aaatgggatc 107640
acatcaagtt aaaaagcttc tgcacagtaa gggaaacaac caacaaaatg aagagacaac 107700
ccacagaatg ggagaaaata tttgaaaaat acccatctgg caagggatta aaaaccagaa 107760
tatatgcaga atatataagg agctcaaaca gtgctataga aaaaaaaatc taataatctg 107820
atttaaaaat gggaaaaatg ttagaataga catttcttaa aataagacat acagatggca 107880
aaccgacatg gaacggtgct caacatcatg gattatcaca gaaacacaat caatcaaaac 107940
taaaactaaa atgtgctatc atctcacccc agttaaaatg gctgatatcc agaagacagg 108000
caataacaaa tgctggcaag gatgtgggga aaagggagcc cccatacact gttgctggga 108060
ttgtaaatta gtacaaccac tgtggagagc agcatgaaag ttcctcaaaa aactgaaaga 108120
aagctaccat aggatccagc aatcccactg ctgtgtatat actacaaaag aaaggaagtc 108180
agtatatgaa gaggtatctg cactcccatg tttgttgcag ccctgttcac aacagccaag 108240
atttggaagc aacctaagtg tccatcagca gttgaatgta taaagaaaat gtggtgcata 108300
tacacaatgg agtattattc aataataaaa aggaatgaga ttgagtcatt tgcaacaaca 108360
tggatggaac tggagatcat tatgtgaagt gaaataagcc aggcacagaa agacaaacat 108420
tacaatgttc ttacttatta atgagatcta aaaatcaaaa caattgcacc catgttcata 108480
aagagtaaaa ggatggttac cagatgctga gaacggtggt ggggggatag ggaaaggtgg 108540
cagtggttaa cgggtacaaa aaaatagaaa gaatgaataa gacttactac ttgatagcac 108600
agcaaggtgg ctatagtcag taatttagtt gtatattttt aataatgaaa ggtgtataat 108660
tggattgttt ctaacacaaa ggataatgct taagaggatg gataccccat tttccatgat 108720
gtgattattt cacattgcac gcctagatca aaacatccaa tgtaccccat aaatatatac 108780
atcttctatg tacccataaa aattctgtaa aataaaatat ataaaaagag gtgacagata 108840
tggaagacag gcaaagaaga gacgacatcc acataatccg agtacctaag aaagaatgga 108900
gtccagtgca tctcaggagc caccattcta agccaatttt ctctggttct ctcagtcacc 108960
ctaccaatac gtgggcaatc ttgttttatt tcaggataga gtttttgaaa ttatagattt 109020
aagtatgctt tctgttctat tacttttggt aattaatttt agaaagaact aatttgggca 109080
caaatttgaa aaaattctaa atccaaaaaa aaaaagaaaa aaacacacac acaatcatct 109140
ataaggggga tgatgaccag tcctagattt ctcaccagcc acattcaaga tcagtaaatg 109200
gtaggacaaa acctgtaggg tccttaaggg ggaaagaagt agtggatagt ccagagtcta 109260
tatacagcca actgttcttg aagaaaaaag gctgctgaaa aggagttcca aacattctat 109320
aatccataat ctcatgatga aactactaga ggaagaccac cagccatcaa aaggtgcttg 109380
gagaacccag ggccaagaac caaaagtaaa tattaagtgt ccttaactgc gagactaaga 109440
tagaaatgac tgtgggggac catgtggcct caacagaggt gaaatggtgt ctgcctgaca 109500
aagtggacat tttacaatga tcaaaacaca gaatatgaga tagagagcac ttctgaatta 109560
ctgcctcact ccaaataact ctcagccaaa ggacttcagt aaaaccaaat tgggcatatt 109620
agacagtaca aacaaattct aagaaaataa tattactgat tacaatcaca tgatgctaga 109680
gatggagggg aaaaggaaga ggaaaccagg taatttcata ctcgtatata gtaaagaact 109740
aaagtacatt gtccaaagaa gaacaaagaa tattttggaa agttataaag gtagccacta 109800
cacatagaag atagcaaaga acaagaaaac ttaagatgga aaactttttg gaagcataaa 109860
aatagaaaat ataaactact aagataagat tgaagccaaa cagatctatg aaaacaacaa 109920
acatcaatgg ccttaacttg cctattaaaa ggaagagact ttcaaattgg accacaagat 109980
aaaacccaac tctatatagc atatgagtat tacacacaaa atgggaaaag ctgaaaaaac 110040
ttgggcaaaa ttcaccccaa gcaaattcca ctgtttcctt tgggacaaaa tgccaagctc 110100
catgccaggg aagatgattc tcctcagacc ttctcctcac tctcccagtc ctcttaggga 110160
aggaattggg tgttagagga gggagactct gtcgattatc agctgaagca gtggtgtgct 110220
cctgcgttgc ttctgacctg ggaaatgaag cagcaagact ctttctgctg tgtctttgcc 110280
cagaagggcc atccccccag agcagagtac ccaggccggc aggagcagtg gtggaagcgt 110340
ggaaaccacg tctcctacag cagagaccat cagaagcgga gcctcgggta taagggaaac 110400
aacgcgttct ccctaacctg ggagtgacag acagcgtcat tcctcacagt gataccctgt 110460
gttctagcca tctggcccat gacagagcca gcccagagcc agcccagagc cagcccctga 110520
ccatcctgga gcctggccag ctcgccaagc tgcaccatag gcctggaagg cgtggagacc 110580

-continued tgcggcagtg ccctgtcctc ccgtgaggcc tgccatccct gccaggggtc gcctctggct 110640
tctccttctc caggaccgca cggtccagag gctcagtgcc tggagtaggt gttgcctccc 110700
tgcttctagg cccagaccct cccttgttcc tgaccccggg cctttccctc tggcttggac 110760
atccagggcc ctgtctcagc tggggagctg ctcctgctca aggactgtct tccgcgggat 110820
cgaaaggccg cgtcctgaac aatgcgtggg ccacgtgagc ggagcaggct ctaaaggccg 110880
cgtcctaaac agtgcgtggg ccacgtgagc ggagcaggct ctaaaggccg cgtcctaaac 110940
agtgcgtggg ccacgtgagc ggagcaggct ctaaaggccg cgtcctaaac agtgcgtggg 111000
ccacgtgagc ggagcaggct ctaaaggccg cgtcctaaac agtgcgtggg ccacgtgagc 111060
ggagcaggct ctaaaggccg cgtcctaaac agtgcgtggg ccacgtgagc ggagcaggct 111120
ctaaaggccg cgtcctaaac agtgcgtggg ccacgtgagc ggagcaggct ctaaaggccg 111180
cgtcctaaac agtgcgtggg ccacgtgagc ggagcaggct ctaaaggccg cgtcctaaac 111240
agtgcgtggg ccacgtgagc ggagcaggct ctaaaggccg cgtcctaaac agtgcgtggg 111300
ccacgggagc ggagcagact ctaaaggccg cgtcctaaac agtgtgtggg ccacgtgagc 111360
gaagcgccct ctccactgcc ctcggggccg cagctcccag ctcagctccc agccctgctc 111420
agggcagcca ggccaggagg taccatccag gctaagtgac cctcaggggg gacaggtgcc 111480
ccaggagatg ccagctgttg ggagaggctg ggggaccaac tcgacctggc ctgtgggccc 111540
tgccctggcc acccattgta ggatccagcc gccacgcctg tgacactcgt gtgctttccc 111600
tggtgtgtgc ttgtggcagg tgggggcaga gggtcctcag gccagagagc cactccccca 111660
gcgccagacc accctcttcc tcactccccc acctcacccc ctcacaggtg cctcccaggc 111720
catcagggcc caaccacccc taaacaaatg ggttctcggc ccctcgtggc tggaggtggg 111780
ttctctcacc attcccagcc taagactcca tccccatgct ggcagctgtt caaccatgtc 111840
tagagagatc cactgtccca gacagcacct cagggtcccc cgtcctgcct ggaaccctgt 111900
aggaaactcc acaaaccgcc gccattctgt ccacacccct acaggagccc caaccctctc 111960
cccacatcca ggcttccctc ccagacccct catccctgcc cgcacggtgc ctgagggggc 112020
cttcttgggc agcgcctaag caagccccca gcacccttcg gccccttcaa ggcacacagg 112080
ccccctttcc acccagcctc aggaaaccac ctgtgtcctc caacgacagg tcccagcctc 112140
ccagcctttg ccttgcctgt tcctctccct ggaactctgc cccgacacag accctcccca 112200
gcaagcccgc aggggcacct cccctgcccc cagacaccct gtgcccgtca gttcatcccc 112260
agcagaggcc ctcaccaggc acacccccat gctcacacct ggccccaggc ctcagcctcc 112320
ctgagggccc cacccagccc gcgtctggcc agtggtgcgt gcaaagcccc tcacccagac 112380
tcggcggaag gcagccagtg caggcctggg gaggggctct ccttagacca ccttgcacct 112440
tccctggcac ccaccatggg aagagctgag actcactgag gaccagctga ggctcagaga 112500
agggacccag cactggtgga cacgcaggga gcccacgcca gggcgccgtg gtgagtgagg 112560
cccagtgcca cccactgagg cctcccgttc agtgggacga cggtgaacag gtggaaccaa 112620
ccaggcaacc cccgccgggc cccacagacg ggatcagagc aggaaaggct tcctgcccct 112680
gcaggccagc gaggagccct ggcgggggcc gtggccctcc aggcgaggag gctcccctgg 112740
ccaccgccac ccgggcctct ctgctgctgg gaaaacaagt cagaaagcaa gtggatgaga 112800
ggtggcgtga cagacccagc ttcagatctg ctctaattta caaaagaaaa ggaaaaacac 112860
acttggcagc cttcagcact ctaatgattc ttaacagcag caaattattg gcacaagact 112920
ccagagtgac tggcagggtt gagggctggg gtctcccacg tgttttgggg ctaacagcgg 112980

-continued aagggagagc actggcaaag gtgctggggg cccctggacc cgacccgccc tggagaccgc 113040
agccacatca gcccccagcc ccacaggccc cctaccagcc gcagggtttt ggctgagctg 113100
agaaccactg tgctaactgg ggacacagtg attggcagct ctacaaaaac catgctcccc 113160
cgggaccccg ggctgtgggt ttctgtagcc cctggctcag ggctgactca ccgtggctga 113220
atacttccag cactggggcc agggcaccct ggtcaccgtc tcctcaggtg agtctgctgt 113280
ctggggatag cggggagcca ggtgtactgg gccaggcaag ggctttggct tcagacttgg 113340
ggacaggtgc tcagcaaagg aggtcggcag gagggcggag ggtgtgtttt tgtatgggag 113400
aagcaggagg gcagaggctg tgctactggt acttcgatct ctggggccgt ggcaccctgg 113460
tcactgtctc ctcaggtgag tcccactgca gccccctccc agtcttctct gtccaggcac 113520
caggccaggt atctggggtc tgcagccggc ctgggtctgg cctgaggcca caccagctgc 113580
catccctggg gtctccgcca tgggctgcat gccagagccc tgctgtcact tagccctggg 113640
gccagctgga gcccccaagg acaggcaggg accccgctgg gcttcagccc cgtcagggac 113700
cctccacagg tagcaagcag gccgagggca gggacgggaa ggagaagttg tgggcagagc 113760
ctgggctggg gctgggcgct ggctgttcat gtgccgggga ccaggcctgc gctttagtgt 113820
ggctacaagt gcttggagca ctggggccag ggcagcccgg ccaccgtctc cctgggaacg 113880
tcacccctcc ctgcctgggt ctcagcccgg gggtctgtgt ggctggggac agggacgccg 113940
gctgcctctg ctctgtgctt gggccatgtg acccattcga gtgtcctgca cgggcacagg 114000
tttgtgtctg ggcaggaaca gggactgtgt ccctgtgtga tgcttttgat atctggggcc 114060
aagggacaat ggtcaccgtc tcttcaggta agatggcttt ccttctgcct cctttctctg 114120
ggcccagcgt cctctgtcct ggagctggga gataatgtcc gggggctcct tggtctgcgc 114180
tgggccatgt ggggccctcc ggggctcctt ctccggctgt ttgggaccac gttcagcaga 114240
aggcctttct ttgggaactg ggactctgct gctggggcaa agggtgggca gagtcatgct 114300
tgtgctgggg acaaaatgac cttgggacac ggggctggct gccacggccg gcccgggaca 114360
gtcggagagt caggtttttg tgcacccctt aatggggcct cccacaatgt gactactttg 114420
actactgggg ccagggaacc ctggtcaccg tctcctcagg tgagtcctca caacctctct 114480
cctgctttaa ctctgaaggg ttttgctgca tttttggggg gaaataaggg tgctgggtct 114540
cctgccaaga gagccccgga gcagcctggg gggctcagga ggatgccctg aggcaacagc 114600
ggccacacag acgaggggca agggctccag atgctccttc ctcctgagcc cagcagcacg 114660
ggtctctctg tggccagggc caccctaggc ctctggggtc caatgcccaa caaccccggg 114720
gccctccccg ggctcagtct gagagggtcc cagggacgta gcggggcgcc agttcttgcc 114780
tggggtcctg gcattgttgt cacaatgtga caactggttc gacccctggg gccagggaac 114840
cctggtcacc gtctcctcag gtgagtcctc accaccccct ctctgagtcc acttagggag 114900
actcagcttg ccagggtctc agggtcagag tcttggaggc attttggagg tcaggaaaga 114960
aagccgggga gagggaccct tcgaatggga acccagcctg tcctccccaa gtccggccac 115020
agatgtcggc agctgggggg ctccttcggc tggtctgggg tgacctctct ccgcttcacc 115080
tggagcattc tcaggggctg tcgtgatgat tgcgtggtgg gactctgtcc cgctccaagg 115140
cacccgctct ctgggacggg tgccccccgg ggtttttgga ctcctggggg tgacttagca 115200
gccgtctgct tgcagttgga cttcccaggc cgacagtggt ctggcttctg aggggtcagg 115260
ccagaatgtg gggtacgtgg gaggccagca gagggttcca tgagaagggc aggacagggc 115320

-continued cacggacagt cagcttccat gtgacgcccg gagacagaag gtctctgggt ggctgggttt 115380
ttgtggggtg aggatggaca ttctgccatt gtgattacta ctactactac ggtatggacg 115440
tctggggcca agggaccacg gtcaccgtcg gtcaccgtct cctcaggtaa gaatggccac 115500
tctagggcct ttgttttctg ctactgcctg tggggtttcc tgagcattgc aggttggtcc 115560
tcggggcatg ttccgagggg acctgggcgg actggccagg aggggacggg cactggggtg 115620
ccttgaggat ctgggagcct ctgtggattt tccgatgcct ttggaaaatg ggactcaggt 115680
tgggtgcgtc tgatggagta actgagcctg ggggcttggg gagccacatt tggacgagat 115740
gcctgaacaa accaggggtc ttagtgatgg ctgaggaatg tgtctcagga gcggtgtctg 115800
taggactgca agatcgctgc acagcagcga atcgtgaaat attttcttta gaattatgag 115860
gtgcgctgtg tgtcaacctg catcttaaat tctttattgg ctggaaagag aactgtcgga 115920
gtgggtgaat ccagccagga gggacgcgta gccccggtct tgatgagagc agggttgggg 115980
gcaggggtag cccagaaacg gtggctgccg tcctgacagg ggcttaggga ggctccagga 116040
cctcagtgcc ttgaagctgg tttccatgag aaaaggattg tttatcttag gaggcatgct 116100
tactgttaaa agacaggata tgtttgaagt ggcttctgag aaaaatggtt aagaaaatta 116160
tgacttaaaa atgtgagaga ttttcaagta tattaatttt tttaactgtc caagtatttg 116220
aaattcttat catttgatta acacccatga gtgatatgtg tctggaattg aggccaaagc 116280
aagctcagct aagaaatact agcacagtgc tgtcggcccc gatgcgggac tgcgttttga 116340
ccatcataaa tcaagtttat ttttttaatt aattggcgcg cgccctctgt gacagcattt 116400
atacagtatc cgatgcatag ggacaaagag tggagtgggg cactttcttt agatttgtga 116460
ggaatgttcc gcactagatt gtttaaaact tcatttgttg gaaggagagc tgtcttagtg 116520
attgagtcaa gggagaaagg catctagcct cggtctcaaa agggtagttg ctgtctagag 116580
aggtctggtg gagcctgcaa aagtccagct ttcaaaggaa cacagaagta tgtgtatgga 116640
atattagaag atgttgcttt tactcttaag ttggttccta ggaaaaatag ttaaatactg 116700
tgactttaaa atgtgagagg gttttcaagt actcattttt ttaaatgtcc aaaattcttg 116760
tcaatcagtt tgaggtcttg tttgtgtaga actgatatta cttaaagttt aaccgaggaa 116820
tgggagtgag gctctctcat aacctattca gaactgactt ttaacaataa taaattaagt 116880
ttcaaatatt tttaaatgaa ttgagcaatg ttgagttgga gtcaagatgg ccgatcagaa 116940
ccagaacacc tgcagcagct ggcaggaagc aggtcatgtg gcaaggctat ttggggaagg 117000
gaaaataaaa ccactaggta aacttgtagc tgtggtttga agaagtggtt ttgaaacact 117060
ctgtccagcc ccaccaaacc gaaagtccag gctgagcaaa acaccacctg ggtaatttgc 117120
atttctaaaa taagttgagg attcagccga aactggagag gtcctctttt aacttattga 117180
gttcaacctt ttaattttag cttgagtagt tctagtttcc ccaaacttaa gtttatcgac 117240
ttctaaaatg tatttagaat tcattttcaa aattaggtta tgtaagaaat tgaaggactt 117300
tagtgtcttt aatttctaat atatttagaa aacttcttaa aattactcta ttattcttcc 117360
ctctgattat tggtctccat tcaattcttt tccaataccc gaagcattta cagtgacttt 117420
gttcatgatc ttttttagtt gtttgttttg ccttactatt aagactttga cattctggtc 117480
aaaacggctt cacaaatctt tttcaagacc actttctgag tattcatttt aggagaaaga 117540
cttttttttt aaatgaatgc aattatctag acttatttca gttgaacatg ctggttggtg 117600
gttgagagga cactcagtca gtcagtgacg tgaagggctt ctaagccagt ccacatgctc 117660
tgtgtgaact ccctctggcc ctgcttattg ttgaatgggc caaaggtctg agaccaggct 117720
gctgctgggt aggcctggac tttgggtctc ccacccagac ctgggaatgt atggttgtgg 117780
cttctgccac ccatccacct ggctgctcat ggaccagcca gcctcggtgg ctttgaagga 117840
acaattccac acaaagactc tggacctctc cgaaaccagg caccgcaaat ggtaagccag 117900
aggcagccac agctgtggct gctgctctta aagcttgtaa actgtttctg cttaagaggg 117960
actgagtctt cagtcattgc tttaggggga gaaagagaca tttgtgtgtc ttttgagtac 118020
cgttgtctgg gtcactcaca tttaactttc cttgaaaaac tagtaaaaga aaaatgttgc 118080
ctgttaacca ataatcatag agctcatggt actttgagga aatcttagaa agcgtgtata 118140
caattgtctg gaattatttc agttaagtgt attagttgag gtactgatgc tgtctctact 118200
tcagttatac atgtgggttt gaattttgaa tctattctgg ctcttcttaa gcagaaaatt 118260
tagataaaat ggatacctca gtggttttta atggtgggtt taatatagaa ggaatttaaa 118320
ttggaagcta atttagaatc agtaaggagg gacccaggct aagaaggcaa tcctgggatt 118380
ctggaagaaa agatgttttt agtttttata gaaaacacta ctacattctt gatctacaac 118440
tcaatgtggt ttaatgaatt tgaagttgcc agtaaatgta cttcctggtt gttaaagaat 118500
ggtatcaaag gacagtgctt agatccgagg tgagtgtgag aggacagggg ctggggtatg 118560
gatacgcaga aggaaggcca cagctgtaca gaattgagaa agaatagaga cctgcagttg 118620
aggccagcag gtcggctgga ctaactctcc agccacagta atgacccaga cagagaaagc 118680
cagactcata aagcttgctg agcaaaatta agggaacaag gttgagagcc ctagtaagcg 118740
aggctctaaa aagcacagct gagctgagat gggtgggctt ctctgagtgc ttctaaaatg 118800
cgctaaactg aggtgattac tctgaggtaa gcaaagctgg gcttgagcca aaatgaagta 118860
gactgtaatg aactggaatg agctgggccg ctaagctaaa ctaggctggc ttaaccgaga 118920
tgagccaaac tggaatgaac ttcattaatc taggttgaat agagctaaac tctactgcct 118980
acactggact gttctgagct gagatgagct ggggtgagct cagctatgct acgctgtgtt 119040
ggggtgagct gatctgaaat gagatactct ggagtagctg agatggggtg agatggggtg 119100
agctgagctg ggctgagcta gactgagctg agctagggtg agctgagctg ggtgagctga 119160
gctaagctgg ggtgagctga gctgagcttg gctgagctag ggtgagctgg gctgagctgg 119220
ggtgagctga gctgagctgg ggtaagctgg gatgagctgg ggtgagctga gctgagctgg 119280
agtgagctga gctgggctga gctggggtga gctgggctga gctgggctga gctgggctga 119340
gctggggtga gctgagctgg ggtgagctga gctgagctgg ggtgagctga gctgagctgg 119400
ggtgagctgg ggtgagctga gctggggtga gctgagctga gctggggtga gctgagctgg 119460
ggtgagctga gctgagctgg ggtgagctga gctgagctga gctgagctga gctggggtga 119520
gctgagctga gctgagctgg ggtgagctgg ggtgagctga gctgagctgg agtgagctga 119580
gctgggctga gctggggtga gctgggctga gctggggtga gctgagctga gctgagctga 119640
gctggggtga gctgagctga gctggggtga gctgagctgg ggtgagctgg gctgagctga 119700
gctgagctga gctgagctga gctgagctga gctgagctga gctgagctga gctgagctga 119760
gctgagctga gctgagctgg ggtgagctga gctgagctgg gctgagctgg ggtgagctgg 119820
gctgagctgg gctgagctgg gctgagctgg ggtgagctga gctggggtga gctgagctga 119880
gctgggctga gctgagctga gctggggtga gctgagctga gctggggtga gctgagctga 119940
gctgagctgg ggtgagctga gctgggctga gcagggctga gctggggtga gctgagctga 120000
gctggggtga gctgggctga gctgggctga gctgagctga gctgggctga gctgggctga 120060

-continued gctgggctga gctgggctga gctgggctga gctggggtga gctgagctga gctggggtga 120120
gctggggtga gctgagctgg ggtgagctga gctggggtga gctgagctga gctggggtga 120180
gctgagctgg ggtgagctga gctgagctgg ggtgagctga gctgagctgg ggtgagctga 120240
gctagggtga actgggctgg gtgagctgga gtgagctgag ctgaggtgaa ctggggtgag 120300
ccgggatgtt ttgagttgag ctggggtaag atgagctgaa ctggggtaaa ctgggatgag 120360
ctgtggtgag cggagctgga ttgaactgag ctgtgtgagc tgagctgggg tcagctgagc 120420
aagagtgagt agagctggct ggccagaacc agaatcaatt aggctaagtg agccagattg 120480
tgctgggatc agctgtactc agatgagctg ggatgaggta ggctgggatg agctgggcta 120540
gctgacatgg attatgtgag gctgagctag catgggctgg cctagctgat gagctaagct 120600
tgaatgagcg gggctgagct ggactcagat gtgctagact gagctgtact ggatgatctg 120660
gtgtagggtg atctggactc aactgggctg gctgatggga tgcgccaggt tgaactaggc 120720
tcagataagt taggctgagt agggcctggt tgagatggtt cgggatgagc tgggaaaaga 120780
tggactcgga ccatgaactg ggctgagctg ggttgggaga ccatgaattg agctgaactg 120840
agtgcagctg ggataaactg ggttgagcta agaatagact acctgaattg tgccaaactc 120900
ggctgggatc aattggaaat tatcaggatt tagatgagcc ggactaaact atgctgagct 120960
ggactggttg gatgtgttga actggcctgc tgctgggctg gcatagctga gttgaactta 121020
aatgaggaag gctgagcaag gctagcctgc ttgcatagag ctgaacttta gcctagcctg 121080
agctggacca gcctgagctg agtaggtcta aactgagtta aaaatcaaca gggataattt 121140
aacagctaat ttaacaagcc tgaggtctga gattgaatga gcagagctgg gatgaactga 121200
atgagtttca ccaggcctgg accagttagg ctaggacctc gttctataga ggcagactgt 121260
gtgctacagt ggagtttcaa gatgattcca tgagtcctcc ccgcccccaa cataacccac 121320
cttcctccta ccctacacgc ctgtctggtg tgtaaatccc agctttgtgt gctgatacag 121380
aagcctgagc ccctccccca cctccaccta cctattactt tgggatgaga atagttctcc 121440
cagccagtgt ctcagaggga agccaagcag gacaggccca aggctacttg agaagccagg 121500
atctaggcct ctccctgaga acgggtgttc atgcccctag agttggctga agggccagat 121560
ccacctactc tagaggcatc tctccctgtc tgtgaaggct tccaaagtca cgttcctgtg 121620
gctagaaggc agctccatag ccctgctgca gtttcgtcct gtataccagg ttcacctact 121680
accatatcta gccctgcctg ccttaagagt agcaacaagg cgcgtcaaac ttaccctacc 121740
tttatcctgg tggcttctca tctccagacc ccagtaacac atagctttct ctccacagtg 121800
cccagggatt gtggttgtaa gccttgcata tgtacaggta agtcagtagg cctttcaccc 121860
tgaccccaga tgcaacaagt ggccatgtta gagggtggcc caggtattga cctatttcca 121920
cctttcttct tcatccttag tcccagaagt atcatctgtc ttcatcttcc ccccaaagcc 121980
caaggatgtg ctcaccatta ctctgactcc taaggtcacg tgtgttgtgg tagacatcag 122040
caaggatgat cccgaggtcc agttcagctg gtttgtagat gatgtggagg tgcacacagc 122100
tcagacgaaa ccccgggagg agcagatcaa cagcactttc cgttcagtca gtgaacttcc 122160
catcatgcac caggactggc tcaatggcaa ggagttcaaa tgcagggtca acagtgcagc 122220
tttccctgcc cccatcgaga aaaccatctc caaaaccaaa ggtgagagct gcagtgtgtg 122280
acatagaagc tgcaatagtc agtccataga cagagcttgg cataacagac ccctgccttg 122340
tccatgacct ctgtgctaac caatctcttt acccacccac aggcagaccg aaggctccac 122400
aggtgtacac cattccacct cccaaggagc agatggccaa ggataaagtc agtctgacct 122460

-continued gcatgataac aaacttcttc cctgaagaca ttactgtgga gtggcagtgg aatgggcagc 122520
cagcggagaa ctacaagaac actcagccca tcatggacac agatggctct tacttcgtct 122580
acagcaagct caatgtgcag aagagcaact gggaggcagg aaatactttc acctgctctg 122640
tgttacatga gggcctgcac aaccaccata ctgagaagag cctctcccac tctcctggta 122700
aatgatccca gtgtccttgg agccctctgg tcctacagga ctctgacacc tacctccacc 122760
cctccctgtg taaataaagc acccagcact gccttgggac cctgcaataa tgtcctggtg 122820
atttctgaga tgtagagtct agctaggtca tggaatgagg ggtctccatg gtttgaggcc 122880
tgagttgtga ctaaggaaaa acccataggc ctacactgcc acacccagca cttttgaatt 122940
tgcctgacat gaaaagaatt tacctctccc tggaaagtgg agccttatcc ctaggcagtt 123000
cccttaccag accttcctct agcttgcact ttgttctggg cacagaatgt gtctaacccc 123060
ccaaagcaag gaagacacaa cctctacctc cctcactctg tccttacccc ttttcctggc 123120
taagcatctc actgagtgcg ctgaatagat gcatgtggcc acagtcttgc agacagaccc 123180
ttgccatctc tccactcagc tttccagagg ctaagtctag cccgtatggt gataatgcag 123240
ggagctctat gctatctcag tgctatcaga ctcccaagtg gaggatgaac atggacccat 123300
taaaaccaac ctgcgcagca acaccctgcc aataaggccc gtatgtgaaa atgtgcacac 123360
atctacacat gcacaggcac acacacacac acatgcatgg gcacacacac atacagagag 123420
agagaatcac agaaactccc atgagcatcc tatacagtac tcaaagataa aaaggtacca 123480
ggtctaccca catgatcatc ctcggcattt acaagtgggc caactgatac agataaaact 123540
tttctatgcc aaggacgcca acatatacac aagtccgctc atgacaaatc tgtccctgaa 123600
cctcagactg gcgcccgtga ctcatacagt ggacactcct ccaaagctgt atagcttcct 123660
ttacttccct gtgtgtactt tctctgaagt acactcatca cacagaagag gccctgtgat 123720
tactctggcc ctctgttctt ggtcatcaga gaatagacag aagatcaggc aaactacaca 123780
gacacttccc acaatcatca caggccctga ctctgctctc cagtctcaaa actgaaggct 123840
ggagcacaca gaataagctc ctgcacaggc caggccagta tcgggtccag tgtgtctgac 123900
tgagcccagg gacaaaatgg cagcactttg gggaactgag gtttctggtc caagaaggag 123960
agatggaggc ccagggaggg tctgctgacc cagcccagcc cagcccagct gcagctttct 124020
cctgggcctc catacagcct cctgccacac agggaatggc cctagcccca ccttattggg 124080
acaaacactg accgccctct ctgtccaggg ctgcaactgg acgagacctg tgctgaggcc 124140
caggacgggg agctggacgg gctctggacg accatcacca tcttcatcag cctcttcctg 124200
ctcagtgtgt gctacagcgc tgctgtcaca ctcttcaagg tcagccatac tgtccccaca 124260
gtgtctacaa tgtcctcata ctcttcccca tactgtccct gtggtgacct ataccccaca 124320
ctgtcccatg ctaatgacca cagtcttaca tgctatgtaa tgctgtctac ccttctgtat 124380
gcacagtctc acaatgtccc atgcagtctc cacgatgctc catactgtcc ccattccaac 124440
ccatgctgcc ccttgttccc cgctatgctg tcccatgcta ttgtctgtat tttcatgctc 124500
ttttcacact gtccctagtg tcacattctg cccatgttgt ccaccacatt gtccccactc 124560
tgtacacagc ctcacactgt accctgctac ccgataatgt tccctgttgt ccccaactct 124620
ctccctgcac catttgtcaa ctgtcccctg aattcccatg ttgttcccac actgttagtg 124680
tgtaatgtgc tctgtcccag gtgtaccttg ttccgtgctg tctcacttca tcgcccattc 124740
tgtccttgta ctaaccccac tctatcacca cactgtccct atgcactgcc cacattgtcc 124800
tcatactgtc ccattttgta tcttcatcct gtccccatag tgtccaatga tctaccccac 124860
actattccca cttcatgccc ctacaatttc cctattccat tcctctctgg tcaccatgcc 124920
atccttccca ctcctgcaca gctggagagg gactcccggg atgagtcctt gcccagatga 124980
gctacctatc tagaggagtc ttcaggtggg aagggaatgc agtcttgatc ttggtcttat 125040
tcaccctgtc tcacaggtaa agtggatctt ctcctcggtg gtggagctga agcagacact 125100
ggttcctgaa tacaagaaca tgattgggca agcaccctag gccacctcct gtaatggcat 125160
ttcccaggcc ccgaaggacc ctgtccaata tgccaagcag cacaactgag atcacactgt 125220
ctgctcatct cgctttcctc cgaccccgag actcagctac tctcaaattt tccctctctg 125280
aaggaccatg tggacattac attgctccag gccacagcca ccaggaccta aaacaccatc 125340
acagcagcac caaagacact ggatagaccc acaagggcaa tagtttcctc aacagtatat 125400
ccaaactgtt gggacaaacg agcaatcact gaagaagtga caagttccca caatgtcagt 125460
gtccagctga gaagggacaa aaagtggtac cagccctgtc cacaccacct tctaattcac 125520
aggaatacgt gatagaagag gcaggttgta gatccgaaag atgagacaga ttttatcaac 125580
tccagaaaga gctgggtcca actgaattat tctagcgacc ttggcattgt catgacctgc 125640
catgaccttc ctccttaaca cttcgataaa ccctgggata tggaaaatgc ctgtgtttct 125700
cagggtttgg gaaagaacca tccatgttgg gattcttgtg tagatcctcc ttctggtcac 125760
agatgcaata cactggattt tcaggcaaag gagcaaattc acagacaact ctggccctac 125820
agccctaaga cctagacacc accatctcct tggaattatc aaatttaaca cccggcacac 125880
aacaaagaag gactgggact ttgaggcctt tgtgtagccc tagagggggc agaggccact 125940
gagcagggat tgggtgatca caaggacctc ctggagaggg acctgaggag caggttccaa 126000
ttgggccaaa gaaagaagaa caacaataga gatgaaggat gctggaaaga gccatggtac 126060
agcagtcttg tccttcagac atgactctta cagcccagga ctcttacagt agctagctgg 126120
agcagaagtc caagggatta ccatgcccta gggccacagg ctactggagg gtggagtgag 126180
tctactacac aggtccaatg cctgtttctc cattgcttct cagccaatga gaaatcagag 126240
tctccacctc caagaaaaag gaaggtggaa atgaaaggtg agcacctgcc ttcccgtgac 126300
tggcagaaag atctccacgg actcaaggct ttgacttcaa acggcgcgcc aatcttccag 126360
aagccaggct gggacctcag caaaagggaa gacataaccc aactccagga tgccctgtgg 126420
ctgatcactc ttgtcttggc ggggatgaag gttggagaaa ggcctccacg tttcagagct 126480
aagaccgacg tgacaacttc ccagcccact cacagacttt cctgagcaat aaattgatgc 126540
aaaaccacaa attcctactc tcaaaaacaa acattaacaa aggattgggg gagggggtca 126600
ggggtagtat ggtggcgttg ggcagggtaa actcagggta cccattgtct aatgtctgag 126660
acataacttg aacatatgtg tagctgcagc caaagatgaa caagtgatgg tatttgtgtc 126720
ctcttcagac ccgataccag gtcattaagc ttgagatctg gacctgattt ctaaacattt 126780
ggcctctgtg agcacccttg gcaaatactg aacagcaaac cctggtcctg gctgtgaacc 126840
ttggtcctga tcactgagcc ctatattggt aactgaaccg tgatcctgat ctctgacctc 126900
agtcatggtc atgaggccct ggtcctggcc actcattcta ataactggtc cctagtcctg 126960
agccctgaac cttggtccag gtcactgaat cctagtcatg atcactgggt ttgatcctca 127020
ttactgagcc tagtcttgat caccgatgac tggttttgat catagcaatt aacctgatca 127080
ctagtccccg ttcctcatca ctgggccatg atactggtca ctgggtcctg atcctgatca 127140
ctaaatcctg tttctaaaca atgtgtagtg gaatgtatag tgaagccttt gtgtctggct 127200
ctgggtgaaa tgtctcagca gagcctttgc taggtttggg ttaatcagtt ggggctgaga 127260
aatgtttttg aggctgtttg aacttcaaaa gaagaaatgt ctccctggac aatctgcaca 127320
tttgcagctg cgcaaacctt catcctaaaa cttaactcct ggcaaactta gaattcttac 127380
ttttaataat ggctagccat ggttgaaagg gactgagatg tctgtgggtg ggtggaacct 127440
ttcccagctc caagtaactc tgtatactgt ttgaataaag taactgaagt gagctagctg 127500
gggtcaatct tctttccaag gagaataaag ccctccgctc ctccagaaaa tgaaggctta 127560
gctccttggt tagcttctct ctctactgcg gcacctacaa ccaactcagc agtcctaggt 127620
tcctgtcacc agatccagtc ctgatagcta agtgtcaatc ctcgtcacta aggcctgatc 127680
cttagcaata tgcctggggt ctgataatca gactgacatt ctgataactg gacccagatt 127740
cttatcactg ggtctttgtc ctggtcatgg gcatttgacc ctagtctaca gcactgagtt 127800
ctgggcatgg accctgggtc ccagttctag atactgagtt ctggttctaa taactggctc 127860
ctgtactgat cgatgggtcc tgacctagtc attgggccct gatcctcaac attgacttca 127920
aaacctgaac tctagcccca tgcctcattc acattaggag gatccctaca ggggattcct 127980
gcagaagatt ccagaatccc cacaacactg ttcacacact gggctgcaac tgggacagtg 128040
accccttgc tcataggact tgcccaggct cagatgcact gaatggagac aaagcaagcc 128100
caggccctgg gagatggagc ctctggcctg gggtctacag atgtggggtc agcatcatag 128160
ggaggtttgc agggcaggtg tggggcaggg cagaagtggt catgcttgta gatactattt 128220
ttctctcctc tggagcctcc tttgtctatc acctgctgtc ctgggatctc tatctggggt 128280
caacaatgtt tgcagtacag gtgtgggggt agggcaggga tgttcacatt agcaacttgt 128340
ttttctctct tctgaagtct ctgttgtcta tcacctgctg aaacattcaa agcagctctg 128400
agctgagggc agctgagtca tcctgagcct gtctcagcac aggtgcccca aaccagagct 128460
actgttctga gaatcacacc acactggacc aggccaggtg ggcctggggc ctggatgagg 128520
ggtgggagcc aggggagccc tgccaggggc tgaggaggcc ccaaccccca tcacccaagg 128580
ccatccacac tcgtgcctta atgaggccat gttctgtccc aatgagaaca agtccaatta 128640
agattaagta tggtcttccc aggatcatcc agagtcaagg ggtgtcagcc agggacaacc 128700
cagaccagcc tgaggtcagc cagcatcacc caaggccaca cagctattct ggcagaggac 128760
tagaatagtc agctcatcga ggccctggag atgcagaatg gagagtttat ccctgccaga 128820
cagggttcct cagataggca ggtccctcac cacacatgac ctccctgaat atttcccaga 128880
gtccagttgg ttctagacta tcacaatagt cttctgtatt cctgataagc atgcagaaag 128940
ctaacaggat gacaagaaat tttatgcaga aaacagaagc atctacagga tagaacagag 129000
gagaatagat actggaagtc tgctggagac cccagtggag tctctttgta gagtcaagct 129060
gtaagatcaa acctgcactg agcctcaaga ttgagtcaag tacagaggca accttcagga 129120
ccctaaagac cttacaggca atggacagga tggagtccag gcagacaagt aaacgggcag 129180
tcatatgtaa cataatgaac catgtcaaca gagggtactg agccaaggaa ggctctggga 129240
cacttgtgga taatctgcca ctggatctct tgatgtatat accaggtgat cagatgacag 129300
tttagtggcg ccatcgccgt tacagtgtta ggtgttgtcc tcgtcatggg ttcacgtgag 129360
aatgtgacac ctttttagtt ggatgtgtac agtaagctct caggcctggt gttcctggta 129420
tgattttaat gatccatgtg ttcctatatc tttaataagt ttatagggtg acattaagct 129480
tggggataag ttgtttatca ggctgtgcct ttagaagttg atgtgcaggg attgttgttt 129540
acaccaagat gcccagtctt cctccagctt ccaaacggag tcaaaggcca tttgaaaatg 129600
tgaaacctct cagggcaagg tacaatcttt ttttttttta aagccactac ctcacacaac 129660
atggagtaat ttaaagcagg gtacagcttg atcgaaacac acacacacac acacgcatac 129720
acacaatgta agataccgag aaggggatca agggacacag aagtagagag agaatgagac 129780
agttcaggga tgtagagatg agaggtaact agaggaaagg agaaacacaa ggactggagg 129840
gtaaagagcc agggacagaa agatccatgc aagcaagaca gacagacaca aggaagggaa 129900
aggtgggaag agacagacag acaaggtgca gcaatgtagc ccacctgaga ctcccatgaa 129960
agtctggcac ccactctcag atgaaagcca agtacctaca gacacgtacc cacagcaccc 130020
acacagagca cctgcctgcc taactcaagc ccacctaccc atcgcctctc ctccaggcct 130080
ctgtcctcag gaagcacact gagggtaact cagtctggac acttctaact atggcttagt 130140
gaacagcctg agaggctctg gatccacagg tcactaccac ttgctggccc tgtgctccat 130200
gccatgcttc aggggggggat tcactgaatg catgaaccat agtctggggt caacatgtac 130260
taagggatag gatcctatca ggatttgtcc aaataaggtc caaacaaagt gaagaaggtg 130320
ataggcgaga acagctggca gctgagagaa cgctggccag ttcttaggcc agagcttagg 130380
gacaatttcc agacctagcc tttcatctca actctaggtc atgggtaact tcccagatct 130440
ctattttgtt cctggtaact atgcatgctg gtacaagtct aagaacctcg gtgagacaca 130500
gaaccagtaa gatgaaagca tccgtggata aggaagaaag gagaagagta gaagggacag 130560
gaccctggac acatgagatt cccacaccca ggaactgctc atccagcccg agaaacggta 130620 taccccctagc acacagaaag aaaacagtac cacaggtcta aaagagtaga gtcagtggga 130680
aggggtacta ctagggcgcc tcctgcctgg tccaggagca gaggctggga aggggcacta 130740
aacaggggga agcatggaga cagggagatg aaggagcctt tgggactgca tggtgggaac 130800
tagactgttc tctgaatgag cctgtgtgtg tggcagctgc ctgagaggga agacacccag 130860
aggccaggca gaggaaaaga gtaatcaggg ctgaggggac tggggtgggg gtctgaggaa 130920
gtcaaggtag ctatcgccca tttatcaggg ccatgacatg cacttcatgg gcacatatct 130980
aaaaccagac ctggccctca cctacactca gacaatgtcc cttttgtgga tttagggatt 131040
tcagtacttc atcccatggc ctctcaaact ggaagatcca tctaaaaggc tgatgttgtg 131100
gtatcagggc ccaggactag agaatgggac actgagtggc agaggtgcag aggacacata 131160
cactcactca gatgaaagca atgcacaaga agacagagcc atgtatgaac actcctcaga 131220
ctcagaccca cagcactcac acccagctcc ccacagacac acacagcccc tgcctgcctg 131280
ttccaaaaat caaacccatc tacccactcc ctctcctgca ggcctttgtc ctcagagtgg 131340
cacactgaag gtagctcagc ctgaacactt cccatgggac ctggtgaaca gcaggagcct 131400
ctggtccaca ctccccacct cttgttagcc ctgtagtcta tgtgatgctg ttgagaacag 131460
ggtacatggc ctctgcctgg tacagtctgg ggtgcaggct tcaggtgagg cccaagtgtg 131520
aagagtgcag aagacagtgg gcagagctga gagactgcta gccagttttg ttcaaaggac 131580
tgtgatggct gctccaggct actgaacatt ccaggactgc ttcctaccct cctcaaagat 131640
gctggaacac aaccaatcct caacacaatc caatgtagtt gcctgtagca gggcatgcct 131700
ctgtacagca gggagtcaca cagagccaca tgagactcta gacctgggga ctgcagaggg 131760
gaaggcatgt ccaagacggc ctcctccttg ttaccctagg ttttcaggcc tcaggataac 131820
cactgaacaa catatgctga gtcctgttcc ccaggatgct gatggacacc aggtcacagg 131880
gctagaggcc aggagggcta gagcctgtgg gcaggggggc tatattcatt cttcctgtgc 131940

-continued ttgcccagga gcaggtgctg ggcaggggca caggacaggg tgaggcaggg agacaggggc 132000
atgaaggggc ctctgggacc acaaggtggg aactaggctg tgcctgactg agcctgtgtg 132060
tgtgacagct gattcatggg gaagacaccc agagaccagg cagaggaaaa gagtaatcag 132120
ggctgaggtg actgggggtt gggaggtctg aggaggtaga ggcagctatg tcccatttgt 132180
cagggtatgg ggacatgtac ttcatagaca cagatctaag aaccaggcgt ggttcccacc 132240
tacccccaga cagtgtccct catatgggct tagggatttc agtacttcat cccacggcct 132300
cacaccttgg aagatccacc tcaaaggctg atgttgtggt gtgggggtcc aggactgggg 132360
ccagggacac tggttggcag aggtgcccag gacatagagt gctcagagtg tagttgggga 132420
catgctgagc actgttcctc tgtgagggga caggctgaga cagggactga agtccatcca 132480
taggctcagc acataccagg ctctggatgg gaacactgag ctctgccacc ctccaacatc 132540
tggcacagca gcctcctgtg ccagggaagc tagtcagcag ggacagagtt cctgtccggg 132600
ctggatggag tcttctctgc tagcatccaa aataagtgca tcttcagcaa taaggtccag 132660
tcatggtgga cggccaggaa caaaggcagt aaacagcctg gtttgtgttt ggttatctac 132720
agtctctctc actaaagcat caagacttct tttaataaat ttagaagttg ttttcttttg 132780
aaacacggtc tctctatgta gtcctggggg tcctggaact ccctgtgtag aagaccagac 132840
tgtcttcaaa cttaaggaga tcctcctgtc tctgcttcct gaatgctggg attaaaagca 132900
tgtgccacca cacccaacct aaccctttct tctgagagca acatgcatac aatttcccct 132960
cttatttccc cagattttca atccttttat ccacacttaa atctttaatg ctaaaatctc 133020
cctccctcca tttccaagct gcatgtgttc tactattccc tcaaattatt tttccttgtg 133080
tgcaggtttt agatttgaat gcaggaagcc ttcactctgg caaagcctcc cccaacccag 133140
cctttcccat ttccacacct cctaacacgt gatttagccc acatcccctc atgtgtatgg 133200
tgtttccctt cagtctgagg tattaccccc agtgtcccct tacagctgcc tatggtcaca 133260
aataccttc atctgtttt gctgtggaaa gcgtttattt ccccttgaat tttaatagct 133320
ttctgggtat actaccctgg gttgagagtt tagatttttc agatcttgga atatgtcttt 133380
ctagacatct agccttaaat gtttctactg ggggctacag aaatggcttg gtggttgaca 133440
acacatgatg ttcttgcaga ggagtgggtt ttgattccta gtaccccata tcagctaaga 133500
gctatggaag acacaaatgg aagaggggac tctgagattc tgagaaaagc ctcatggtta 133560
agggtacact gagatactga gagagaaaga cagagacact gagaaagaca gaagcacaga 133620
ccactaaaag agacagggaa acagagagag acagtgatga gatgcaggga cagagcaacc 133680
cagagagaca gacagagaca tagacactga tagagacaca aagaagagag gggtcgtgga 133740
agttttgaga gaaactggta ggaggtgaga gagacacaga gccaatacag acacagaaag 133800
acagagactc cagagagaca gagactgaga gagacagaga ctgggagaga caaagatact 133860
gagacagtca gagacaccaa tgggtgcttt tccaggggat ccagattcaa ttcccagcac 133920
ccacatggca gctctctact gtaatcccag ttccagggtg ccctgaaaaa tccttcatgc 133980
atgtgaagct tagaagctca cacacaaaca cacagacaga cagacagaca gacagacaga 134040
cagacacaca cacacacaca cactcaaatg aagagtgtgg ttctctttct ctctctctga 134100
tgaaagccat gcaccagaag acagagccat gtgtgaacac tcctcagact cagacccaca 134160
gcactcacac ccagctcccc acagacacac acagccctgc ctgcctgcct gttccaaaac 134220
tcaaacccat ctacccactc cctctcctgc aggcctttgt cctcagagtg gcacactgaa 134280
ggtagctcag cctggacact tcccatggga cctggtgaac agcaggagcc tctggtccac 134340
actccccacc tcttgttagc cctgtagtct atgtgatgct gttgagaaca gggtacatgg 134400
cctctgcctg gtacagtctg gggtgcaggc ttcaggggag gcccaagtgt gaagagttca 134460
gaagacagta ggcagatctg agagactgct aaccaatttt gttcaaagga cagtgatggc 134520
tgctccaggc tactgaacat cccaggtctg cttcctaccc tcctccaagc tgttggagca 134580
caaccaacca tctttgtaat tgcccagttg tttgttattg cctatagcag ggcatgcctc 134640
tgcacaccag ggagtcacac agagccacat gagactctag acctggggac tgcagaggga 134700
aaggcatgtc caagagggcc tcctccttgg gacactggga ttccaggtct caggataacc 134760
actgaacaac atctgctgag tcctgttccc caggatcctg atggacccca ggaggtcaca 134820
gagctagagg ccaggagggc tagagccttt gggaaggggg aatgttaggg tttctcccat 134880
cctggtccag gagctgctca cctgacagtg atacaggaca gggtaaggca gagacagggg 134940
gatgaaggaa actttgggag cacatggtgg gagtgtaggt tgtgcttttg cttagcctgt 135000
gtatatagca gctgcatcat tgggaagaca ctcagaggcc cgacagagga agagtaatca 135060
aggctgaggg gacagcagtg tctaaggaag tggaggcagc tatggtccat ttgtcatagt 135120
attgggacat gtacttcatg aacactgatc tatggaccaa gcctggttgt catctgccct 135180
cagtcagtgt ccctcatgtg ggtttaggaa tttcagtact tcatcccaca agccagtcac 135240
attggaacat aaatgaaatg ctgatgctgt ggtgctgggg cccaggagtg cggggttagt 135300
atactgggtg acagagggtg tccagtaaat agattgctta gagtgtaggt ggggacaagc 135360
tgtgcagtgt tcctccatga ggggaaagac tggtacaggt tttgacatct ctttcgtatc 135420
cataggccct gccatactgc ccttgtccat ggtccctgtg gggtcacata cttagtgtca 135480
agtaaaccat accacaaact ggaagggtct acactatcct tgtaggttct acactctcca 135540
tgacttctcc caactcacac agactgttcc aatacactac tctcttcagt gggcaatcat 135600
gccatgaaca gagagtggag ggttatggtt gccctatatt ctgacacatc caacagtctt 135660
gtgcatttga ctctcatgtg tacaagcgtg ctcaggcctg ctgtagtccc ctcgagacag 135720
tgatgccttc cttgagagcc gattctcact gtcagcatct cctcagacca aagccctata 135780
gatccagcct ctttgaggag ctaatgtagt cagtcacagg gcttgatgtt ggtggctata 135840
gctgctgtcc ccatggctgc cagagatgct tgaccaccat aatcccagac ttgagcatag 135900
gaataacctg gaatcaacag catccagaca ctgtagggac tggccagaga tgtgcataga 135960
ccctatgtca tgtgaccaag acctcttttt ctagtatctt atttcatgaa agtctacaaa 136020
atacgatctt ctattccttt tattcctctt tgcctgctaa catggaacct tctagaaaga 136080
gggtcccctc tctgtctact gactgtgaag atagatcctg taggtgtgat cacagagtaa 136140
tgtttcattt cttggccagt ctcaagccag gggactcagg gagagagaca ggagaaggag 136200
agatggggag agagacagaa agacagaaaa acaaagcaag ggagagacag aagcaggcag 136260
acctggagac tgggtgctta ggaaagagat aaatgtggat acagggagtg aaagataggg 136320
aattgaagac agaggtggag ataaagacca gaatatggga gtcagagaca gacaagagat 136380
atagagatca atataggcaa acagagactg agaaagacag tgatgagaca gagagacatg 136440
gagacagaca aggagacaga catggagaca gacaaggaga cagagataga aatagggaga 136500
gaaaataata cataattagt ggttgattaa ggaagagata atgaatggca agaagagaca 136560
gaggcaggga gagacatata caggtagaga aaaagatgaa gacagacaga gagagactga 136620
aagagggaga aagatacaga gagaagagag actatgaaac aggcagagat ataaagacag 136680
tgagagaaaa acagagagac agagatggaa gagagacaga gagacaggga gatagagaaa 136740
tgggaagaca ggaggaccaa gagaagagac acacggcgag gcaagatgta gtagagagac 136800
ctctgatgga atcggcatag gtggaggcaa acatagatag actctctcca actgcagttg 136860
acagactgag cagagagaat accattcaga gagaaacaga ggctaaggct aggaaaggca 136920
agagtagcca gaggagacag agttgagcct gtgggacagg accagacgcc atcttggaag 136980
aggcagtgac aagccaggga ggtgacaggc tggtacagtt tctatcccac agtccacagg 137040
ctggtgtcac aggcctgtct cctcgtggcc acagtctatc cctgcctgcc aagcctgtct 137100
gtggagggat gggggggggg ggggctgggc tgaggcaggc caggactttt ccagtggagt 137160
ggccaggcac tgggctgagg gcatgatccc tgcccaccat cccagtgggt ctgggtaatg 137220
gatggccttg attattttcc ttcgtgttta gggtggaacc tgcttagagg cagctagggc 137280
tctccatgat ggcctagcct gtggtgagtt aatgaacccc taagggtagt tcttccacat 137340
gggctagggt tacaatctgg gggttggggg ctcagatatc agtaccagaa acaaggctta 137400
ctcccaacat gtcacactcg cacacacaca gctgccgagt tactcattct gtgcagagtt 137460
ggctcacaag ggcacatgca aatggatgtt tgtttcatac agaaaaacat gtttctcact 137520
ttctgaggtt gtttccagaa atagcatcag tgactccccc acctgcagct gcaggttcac 137580
cccaacctgg ccaggctgac cagccttggg gatgggggac tcccagcata ggccactggg 137640
actgggggtc catgacccct attgatgatg ttgaattcag tgtttcccag ttatcaccac 137700
tgctggaatc tgacccacca agaggacatg acaggagatg ggcaaggatg ggtggctcaa 137760
caccccaggg aagtgagaga ggcaggaagg ctgtaggtgt gctccagatc ctgggtctac 137820
ccagaaccat gggaatggtg ggcagtgatc atgccctcag cccagtccct ggccactcca 137880
ctggaaaagt cttggcctgc ctcagcccag acccccctccc ccacccccttc tcagacagac 137940
ttggcagaca gggagctagc ctgtggccac atggagacag gcctgtgact ccaacctgtg 138000
gactgtggga tagaaactgt accagcctgt cacctccctg cttgtcactg gctctttcaa 138060
gatggtgtct gaccctggct ccatctctgg ccaaccctgc ctttcccagc cttagcctct 138120
gcctctttct ctctctctca gtgtgattct tgctcagtct gtccctcagt tactgtctct 138180
ccatctctaa caaaacataa gagctgtctc tattaacacc ttgtctctcc tctttcttct 138240
tctccttctc cttctccttc tccttcctct ctctctctct ctctctctct ctctctctct 138300
ctctctctct ctctctctct ctctctctct ctcatctctg cttgtgcccc ctttctctag 138360
gtgcacatct cctacctctg tctgtctatc tgtgtctctt ccttctgtca tctcctctct 138420
atcattcttt cagtccttct ctatgtctct tttctgttga tgtctgtctt tgtgtgtctc 138480
tctctccatc ccattccttt tatgactctg gctcccctta tctctctgtc tgtatttctg 138540
ccccacttct ctgtcttcct atctttttgt cttttctctg tttctgattt ttctctccat 138600
gtctttctct ccactttctct ctctcccttt ctgagtcttc ctgcatctgt ctcattgctt 138660
ctccatctcg ctctctcttt ctctgttttc tgtctctgtt cttgtatctc tgtgtgcctc 138720
tccatgtctc tctgctgtct ctttttctcc atacagcaat ttactaaaag aacaaacatc 138780
aaggcaggaa agtatatata tttcaaataa aagttcttca aattgctatg tcctatactc 138840
caagaagcat ttccaaagta tagattaatt taacccttttt aaatgaaaag atacattttt 138900
aacttctaaa gtgtctccac aaagaaatga atgtttttaa ttaagaaatg ttgtaattta 138960
gtgttgggct cctgtcttat aatgtacact tccttataaa tctagccatg tggcttatat 139020
ccatttggta tgctcggagc tttatgtaat aaacgtcttc ccgataggtg caaggattgg 139080
tgttttgtac tgcttactac atacatgctt ttaatcattc caggacatac cgtccctctg 139140
ctgctgcttc tcaccgtctt tgcctttctc tcaccctgtc catctttctc tctccccatc 139200
tctctgtttc tgtcccttcc tgtttcagtc tctctccaat ctccctgtgt ttctctctct 139260
ctctctctcc tgatgtctct ttctctgtgg gcttgtctcc ccatctgtcc tcttcatttc 139320
tgtatttctc cttatctttc tatctctgtc catgactctg tctctttctg cctcgttcat 139380
cccctgcccc cctgaaggca caatgacact tttatcaggg tttaatagga aagtttcagg 139440
gcaggaaagt tgtaagactc aagcagctgc cccgaggagg ccagtggggg agattggtaa 139500
aaagccatga catctaatct gacatggagg tcaggcacat gtcccacaag cagccacatg 139560
gcgagaaggg ggcagttaga gaacaagtaa gaaagcccag catgttgggg aggaagccaa 139620
ggtgttaagg aaaacttgct cagagggaga cagaaagaag gaagctacaa ttctgtgaat 139680
tcagaaagga agctgactta cagccccaca tggctatagc ccctaagctt ctggcccttc 139740
ctcttctgtc tcttcctgtt ctctgtcacc cctgtttctc cctattctct gtcacacctg 139800
tctctgtgct cccattaatc tctctctgtc tctacacatc tccacctctg cctccttcat 139860
ctctgtcttt tccggaaccc tgtctgtctc tgtcaggctt ctccttgtct ccccctgcag 139920
acttgcagtt tctccctttg tcttcctctg tcttaccttt attatgtctc cccgtctttc 139980
ctaccttcct gactttctgt ctcttaccct gagtcccctg gcctgaaact ggccaagaag 140040
gaaaacatca gtctgtgatc actcctacag ggtctgtctc catagccagc agagagggga 140100
ccctctttct agaaggttcc ctgttcgcag gcaatgaaga ataaaaggaa tagaagatcc 140160
cgttgcatta aggtttcatg agataacata ctaggaaaag agaccttggt ctacgtagaa 140220
gtctggtcag tccctgaagt gtctagacgc acttgatccc taggccatca ctatgtctga 140280
ggtcatggtg gtcaagcatc tctggcagtc acagtgaaag cagctgtggt caccaacatc 140340
aagccctgtg actacaatag ctcctcaaag aggctgggtc tgtggggttt tgttttgagg 140400
gtcagctaga aatgggagtg agtccaagga agacccactg cccccgcccc cgagagatag 140460
gggaatgagc atgcttgcac acgtggacat gaaaggcaca agagtgttgt atgtgacagt 140520
ttgaggtgac cacattctgc cctctctgtg cctgtcatgg ttacaactga ggacagtggt 140580
ggatttgggc agagtctgtg tgagctggga gaagctgtgg agagttgcaa gcatggcatg 140640
tagatatcag aagccctggt cttccagcag tcctcatggt gatggttcag taggacactg 140700
gatgtgtggc ccatgctagg gtcatgggca aggctggtat gggttgactc tatggctgga 140760
caaagagctt taacctcgtc agcttccgca atatggagga acactgcaca gcttgccccc 140820
acctgcactc tgagcactct gtacactgga catgctctac tacccagtgt ctcagactcc 140880
agtcctgggc cccagcccca tagcacaacc atgtttataa tccctccagt gtgagaggcc 140940
atgaaatgtt gtggagctca gtctgaaggc aggtgggaga caggcatgct tttggatcca 141000
tgtccatgaa gtatatgtcc acattccatg acaaaggagc cgaagccacc tctattttct 141060
caaggacccc ctcagtcctc attactcttc ctctgcctgg cctctggatg tcttccccat 141120
gaatcagctg tcacaaacac aggctcagtc agagcacagt ctagttccca ccttgtggtc 141180
ccaaaggctc tttcacgcca gtgtctccct gccttaccct gtcatgcacc tctggccagc 141240
cagctgctcc tgggcaagga cgagaagaag ccaagtagtt cctcttctca cagactctag 141300
tcctgctggc ctctaactct gtaaccttct ggtgtccatc aggatcctgg ggccacatca 141360
ctctgagtgt gtttatcacc ggcaatcctg agggctaaga tttcagattc taaaggagga 141420
ggcccccgtg gacatgcctt cccctctgca gtccccaggt ctagagtctc atgtggctct 141480
gtgtgactcc ctgatgtaca gaggcatgcc ctgctacagg caattacaat ggattgggta 141540
gagggttggt tgtgctccaa catctttgag gagggtagga agcagacctg ggatgttcag 141600
tagcctggag cagccatcac tgtcctttga acaaaactgg ccagcactct ctcagctctg 141660
cccactgtct tctgtactct tcacacttgg gcctcacctg aagcctgcac cccagactgt 141720
accaggcaga ggccatgtac cctgctctca gatgatgttt catacagatt acagagctaa 141780
caagaggtgt ggtgtgtgga ccagaggctc atgctgtgta gtcacccatg gtcctgctga 141840
aaagcaggct ggggctaaaa agagaataga gtatgagaca caccaagaca aatgctgatc 141900
aaagcccaat gtttactaaa aatctgtgct tatataaaag gaaagccctt ctcctgcaga 141960
tccacttttg atgtctgttg ccagcctgta agcaatttgt ctgacagcac tagtttgaca 142020
agaaggtgtc aatcactgct gtctttggaa tctctcagcc tctcagcagg tatcagtgtc 142080
ttggagaaga agagcaatgg tgacagaaca atagaatcat ctaggtggga aggctctacc 142140
ccaggtggtc tcattctcag tggcagcaag gtctgagcca gcctgctcaa ggctgggga 142200
ggctacaatg ttattcaaca ggtcccatgg gaagtgtcca ggctgagcta ctcagtgtgc 142260
cactctgagg acaaaggcct gcaggagagg gaatgggtag atgggtttga ggtttggaac 142320
aggcaggcag gggctgtgtg tgtctgtggg gagctgggtg tgagtgctgt gggtctgagt 142380
ctgaggggtg ttcacacatg gctctgtctt ctggtgcatg gctttcatct gagagagaga 142440
aagagaacca cactcttcat tagagtgtgt gtgtgtgtgt gtgtgtgtgt gtgtgtgtgt 142500
gtgtgtgtgt gtgtttgtat gtgagtctgt ctgctgtctg tgtgtaaatg tgagcttcta 142560
tgcttcacat gcatgaagga tccttcaggg caccctggaa ctgggattac agtagagagc 142620
tgccatgtgg gtgctgggaa ttgaatctgg atcccctgga aaagcagcca gtgctcttaa 142680
tccttttggt gtctctgcct gtctcagtat ctctgtctct ctcagtctct gtctctctgg 142740
agtctctgtc tttctgtgtc tgtactgcct ctgtgtctcc cacacctcct accagttgct 142800
ctcaaaactt ccacgtcccc cctcttcttc atgtctctat cagtgtctgt gtctctgtct 142860
gtctctctgt gtctctctgt ccctgcagct catgactgtt tctctctaag tgtttccctg 142920
tctctttcag tggtctgtgc ttctgtcttt ctcagtgtct ctgtctttct acttcagaat 142980
ctcagagtcc cctcttccat ttgtgtccct tcttgggctc attcactctg cctccagtgt 143040
catcacttgt gagaccagaa cctactatga gtccagagga ctgtccttca tggtctgtga 143100
ccagctgtga tctggggaac actggggaag gcatgaacag ggagggacct gcctgtctgt 143160
ggagccctgc ctgtcagcat gaactcccca ttctgcacca ccagagccct gctgagctga 143220
ctattccaca ccacctccag aaaagggcat tgaatcctgt ggaaccgatg gctcttagct 143280
gatacggggt actaggaatc aaaacccact cctctgcaag aacatcatgt gttgtcaacc 143340
accaagccat ttctgtagcc ccacagtaga aacatttaag gctagatgtc tagaaagaca 143400
tattccaaga tctgaaaaat ctaaactctc aacccagggt agtataccca gaaagctatt 143460
aaatttcagg agaaaataaa aaagctttcc acagcaaaaa cagatgaaag gtatttgtga 143520
ccatagacag ctgtaagggg acactggggg taatacctca gactgaaggg aaacaccata 143580
cacatgaggg gacgtgggct aaatcacgtg ttaggaggtg tggagatggg aaaggctggg 143640
tggggggagg ctttgccaga gtgaaggctt cctgcactca aatctaaaac ctgcacacaa 143700
ggaaaaataa tttgagggaa tagtagaaca catgcagctt ggaaatggag ggagggagat 143760

-continued

```
tttagcatta aagttttaag tgtggataaa aggattggaa atctggggaa ataagagggg 143820
aaattgtatg catgttgttc tcagaagaaa gggttaggtt gggtgtggtg gcacatgctt 143880
ttaatcccag cattcaggaa gcagagacag gaggatctcc ttaagtttga agacagcctg 143940
gtcttctaca cagggagttc caggacaccc aggactacat agagagaccg tgtttcaaaa 144000
gaaaacagtt tctaaattta ttaaaagaag tcttgatgct ttagtgaggg agactgtaga 144060
taaccaaaca caaaccaggc tgtttactgc ctttgatcct ggccctccac catgactgga 144120
ccttattgct gaagatgcac ttattttgga tgcagagcaa agaagactcc atccagcctg 144180
gacaggaact ctgtccctgc tgactagctt ccctggcacg ggaggctgct gtgccagctg 144240
ttggagggtg gcagagctta gtgttcccat ccagagcctg gtatgtgctg agcctatgaa 144300
tggacttcag tccctgtctc agcctgtccc ctcacagagg aacagtgctc agcatgtccc 144360
caactacact ctgagcactc tatgtcctgg gtacctctgc caaccagtgt ccctgacccc 144420
agtcctggac ccccacacca caacatcagc ctttgaggtg gatcttccaa agtgtgaggc 144480
cgtgggatga agtactgaaa tccctaagcc catatgaggg acactgtttg ggggtaggtg 144540
ggaaccacgc ctggttctta gatctgtgtc tatgaagtac atgtcccaat accctaacaa 144600
atgggacata gctgcctcta cctcctcaga ccccccaaac cgcagtcccc tcagccctga 144660
ttactctttt cctctgcctg gtctctgggt gtcttcccca tgaatcagct gtcacacaca 144720
cacaggctca gtcaggcaca gcctagtccc caccttgtgg tcccaaaggc cccttcatgc 144780
ccctgtctcc ctgcctcacc ctgtcctgtg cccctgccca gcacctgctc ctgggcaagc 144840
acaggaagaa tgaatatagt ccccctgccc acaggctcta gccttcctgg cctctagccc 144900
tgtgacctgg tgtccatcag catcctgcac aacaggactc agcatatgtt gttcagtggt 144960
tatcctgagg cctgaaaacc tagggtaaca aggaggaggc cctcttggac atgccttccc 145020
ctctgcagtc cccaggtcta gagtctcatg tggctctgtg tgactccctg ctgtacagag 145080
gcatgccctg ctataggcaa ctacaatgga ttgtgttgag ggttggttgt gtttcagcag 145140
cttggaggag ggtaggaagc agacctggga tgttcagtag cctggagcag ccatcactgt 145200
cctttgaaca aaactggcca gcactctctc agctctgccc actgtcttct gcactcttca 145260
cacttgggca tcccctgaag cctgcacccc agactgtacc aggcagaggc catgtaccct 145320
gctctcaaca gcatcacata gactacaggg ctaacaagag gtggggagtg tggaccagag 145380
gctcctgctg ttcaccaggt cccatgggaa gtgtccaggc tgagctacct tcagtgtgcc 145440
actctgagga caaaggcctg caggagaggg agtgggcaga tgggtttgag gtttggaaca 145500
ggcaggcagg caggcagggg ctgtgtgtgt ctgtggggag ctgggtgtga gtactgtggg 145560
tctgagtctg aggagtgttc acacatggct ctgtcttctg gtgcatggct tccatctgag 145620
ggggtgtgtg tgtgtgtgtg tgtgtgtgtg tgtgtgtgtg tgtgtgtgag cttctaagct 145680
tcgcatgcat gaatgatcct tcagagcacc ctggaactgg gattacagag gtgagctgcc 145740
atgtgggtgc tgggaattga atctggatcc cctggaaatc agccagtgct cttaatcctt 145800
tttgtgtctc tgcctgtctc agtatctctg tctctctcag tctctgtctc tctggagtct 145860
ctgtctttct atgtctgtac tgcctctgtg tctccctcac ctcctaccag ttgctctcaa 145920
aacttccatg tccccccctt ctctgagttt ctatcagtgt ctgtgtctcc gtctgtctct 145980
ctgtgtctct ctgtccctgc agcccatgac tgtttctctc taagtgtttc cctgtctctt 146040
tcagtggtct gtgcttctgt ctttctcagt gtctctgtct ttctctctca gaatctcagt 146100
gtcccctctt ccatttgtgt cccttcttgg gctcattcac tctgccttca gtgtcatcac 146160
```

ttgtgagacc agaacctact atgagtccag aggactgtcc ttcatggtct gtgaccagct 146220
gtgatctggg gaacactggg gaaggcatga gcagggaggg acctgcctgt ctgtggagcc 146280
ctgcctgtcc gcatgaactc cccattctgc accaccagag ccctgctgag ctgactattc 146340
cacaccacct ccagaaaggg gcattgaatc acgtggaacc taagaacacc gtgttgtcaa 146400
ccaccaagcc atttctgtag ccccacagta gaaacattta aggctagatg tctagaaaga 146460
catattccaa gatctgaaaa aaatctaaac tctcaaccca gggtagtata cccagaaagc 146520
tattaaattt caggagaaaa taaaaaagct ttccacagca aaaacagatg aaaggtattt 146580
gtgaccatag acagctgtaa ggggacactg gggtaatac ctcagactga agggaaacac 146640
catacacatg aggggacgtg ggctaaatca cgtgttagga ggtgtggaga tgggaaaggc 146700
tgggtggggg gaggctttgc cagagtgaag gcttcctgca ctcaaatcta aaacctgcac 146760
acaaggaaaa ataatttgag ggaatagtag aacacatgca gcttggaaat ggagggaggg 146820
agattttagc attaaagttt taagtgtgga taaaaggatt ggaaatctgg ggaaataaga 146880
ggggaaattg tatgcatgtt gttctcagaa gaaagggtta ggttgggtgt ggtggcacat 146940
gcttttaatc ccagcattca ggaagcagag acaggaggat ctccttaagt ttgaagacag 147000
cttggtcttc tacacaggga gttccaggac acccaggact acatagagag accgtgtttt 147060
aaaagaaaac agtttctaaa tttattaaaa gaagtcttga tgctttagtg agggagactg 147120
tagataacca aacacaaacc aggctgttta ctgcctttga tcctggccct ccaccatgac 147180
tggaccttat tgctgaagat gcacttattt tggatgcaga gcagagaaga ctccatccag 147240
cctggacagg aactctgtcc ctgctgacta gcttccctgg cacgggaggc tgctgtgcca 147300
gctgttggag ggtggcagag ctcagtgttc ccatccagag cctggtatgt gctgagccta 147360
tggatggact tcagtccctg tctcagcctg tcccctcaca gaggaacagt gctcagcatg 147420
tccccaactg cactctgagc actctatgtc ctgggtacct ctgccaacca gtgtccctga 147480
ccccagtcct agaccccccac accacaacat cagcctttga ggtggatctt ccaaagtgtg 147540
aggccgtggg atgaagtact gaaatcccta agcccatatg agggacactg tctgggggta 147600
ggtgggaacc acgcctggtt cttagatctg tgtctatgaa gtacatgtcc ccataccctg 147660
acaaatggga catagctgcc tctacctcct cagacctccc caacccccag tcccctcagc 147720
cctgattact cttttcctct gcctggtctc tgggtgtctt ccccatgaat cagctgtcac 147780
acacacacag gctcagtcag gcacagccta gttcccacct tgtggtccca gaggcccctt 147840
catgcccctg tctccctgcc tcaccctgtc ctgtgcccct gcccagcacc tgctcctggg 147900
caagcacagg aagaatgaat atagtccccc tgcccacagg ctctagccct cctggcctct 147960
agccctgtga cctggtgtcc atcagcatcc tggggaacag gactcagcat atgttgttca 148020
gtggttatcc tgaggcctga aaacctaggg taacaaggag gaggccctct tggacatgcc 148080
ttcccctctg cagtccccag gtctagagtc tcatgtggct ctgtgtgact ccctgatgta 148140
cagaggcatg ccctgctata ggcaactaca atggattatg ttgagggttg gttgtgtttc 148200
agcagctttg aggagggtag gaagcagtcc tggaatgttc agtagcctgg agcagccatc 148260
actgtccttt gaacaaaact ggccagcact ctctcagctc tgcccactgt cttctgcact 148320
cttcacactt gggcatcccc tgaagcctgc accccagact gtaccaggca gaggccatgt 148380
accctgctct caacagcatc acatagacta cagggctagc aaagaggtgg ggagtgtgga 148440
ccagaggctc ctactgttca ccaggtccca tgggaagtgt ccaggctgag ctaccttcag 148500

-continued tgtgccactc tgaggacaaa ggcctgcagg agagggaatg ggtagatggg tttgatgttt 148560
ggaacaggca ggcaggggct gtgtgtgtct gtggggagct gggtgtgagt gctatgggtc 148620
tgagtctgag gggtgttcac acatggctct ggtgcatggc tctcatctgt gtgtgtgtgt 148680
gccacaggct ccatttgagt gctcggttgg ctccattgct gtacctctgt ctcccttgtt 148740
ttctatctgt ctgtcctccc tgtctgtctg tctctccttt cctatgcctc ctcctcatat 148800
ccatgtctgc atctctttct atcagtctct atccctgtga cccctggttt ccatttctgt 148860
ctttctgcat atctttccat ctttctctct gtgtgtctgt cctcatctct tccagtgtcc 148920
gtgtttctgt ttccctctgt tcccatgcgg aggtatgttc tcacaatcct taagttccct 148980
ggtcccctgt cccccatttc ttgtcatatt atcccatcag tgtctctgtg cctctctgtc 149040
tgtgtctctg tgttgtctct gtgtgtgtct ctcagtatct ctctctctct ctctctctct 149100
ctctctctca gtatctgtat ttcttttagt aactttgcta tctttttaag tatctctgtc 149160
tttcttcatc tctgtctctc ttgaggtctc tgtctttctg catgtctaat gtttctgtat 149220
ctctctcacc tcatctctgc ctctctcaat attcagtaga tccatgcccc tttattcttt 149280
gtgcctctgt ctctgtttgt ctctttctct gtctctctgt ctttctctct ctcagaatct 149340
gtgtccctca tgttatttct caaaatgcct ccctaactct ttcaataaca gtttctgcct 149400
cttctttctg ggcctggctc aatcttcctt cttggacctc agtttcattg gttgtgagac 149460
cataccctgc tatgagtcca gaggactgtc ctccatagtc tagaaccaca tgctatctaa 149520
gggatattgg ggcaatacat gtgtagtgag atacctgcct ttctgatgag ccctgtctgg 149580
cagggataaa ttctccattc tgcatctcca gggccttgct gagctgacta ttctagtcct 149640
ctgccagaat agctgtgtgg ccttgggtga tgctggctga cctcaggctg gtctgggttg 149700
tctctggctg acaccccttg actctggatg accctgggaa gaccatactt aatcttaatt 149760
ggacttgttc tcattgggac agaacatggc ctcactaagg cacgagtgtg gatggccttg 149820
ggtgatgggg gttggggcct cctcagcccc tggcagggct cccctggctc ccacccctca 149880
tccaggtccc aggcccacct ggcctggtcc agtgtggtgt gattctcaga acagtagctc 149940
tggtttgggg cacctgtgct gagaaaggct caggatgact cagctgccct cagctcagag 150000
ctgctttgaa tgtttcagca ggtgatagac aacagagact tcagaagaga gaaaaacaag 150060
ttgctaatgt gaacatccct gccctacccc cacacctgta ctgcaaacat tgttgacccc 150120
agatagagat cccaggacag caagtgatag acaaaggagg ctccagagga gagaaaaata 150180
gtatctacaa gcatgaccac ttctgccctg ccccacacct gccctgcaaa gctccccagg 150240
atgctgaccc cacatctgta gaccccaggc cagaggctcc atctcccagg gcctgggctt 150300
gctttgtctc cattctgtgc ctctgagcct gggcaaggcc aatgagcaaa ggggtcactg 150360
tcccagttgc agcccagtgt gtgaacagtg ttgtggggat tctggaatct tctgcaggaa 150420
tcccctgtag ggatcctcct aatgtgaatg aggcttggaa tagcaaaggg acgtcttgta 150480
aaataccact gattccttgg gcctcagaca atggatttga gatgaggacc aaggtccagg 150540
gccagtgttg gtaagcagaa tttggggcta gagttcaggc ttagaagtca atgatgaggg 150600
ccagggccca gtgactaggt cagggcccat tgatcagtac aggacccagt tgttagagcc 150660
ggagctcaat gatctggacc aagtcacaag gccaaatgat caggatcagt agccagttac 150720
caggaccgag atccaggttt cacagccaaa gccaggttac cccaaccaga gaccattcat 150780
cggaatctgg gtctgttgat cggagcccaa gcacgctgct gtaaaccaga gctgctctaa 150840
agcagaactc agtgctgagc accagagata agtgatgaga ccaggattca gtgattaagg 150900
aaacaaaacc aaaggtcaat aggatattat gtggagagag gggagagaga gagagagaga 150960
ggacagagag agaaagagcg gtaggttcag gactaagtct cagtgaggag ggtcaggagt 151020
cagtggtttg aacccagaca cactgctcag gtccacagtt caacggtgag agccaggggt 151080
cagctatcag aaccaggtcc agtaactaca accaaaaacc agtggcccca accaaaaacc 151140
agttactaaa acccgaatag aatagaaact agccaggcag tgatagcttt aatcccaata 151200
ctcaggagtc agaggcaggt ggatctctga gttcaaggtc agcctggtct acacaatgag 151260
ttctaagaca gccagggcta cacagagaaa ccctgtctgg aaaacaagca aaagcctaga 151320
aaccgtggac tcagtggtca gtggcagttc ttggtgacta agaccatggt caagaggtca 151380
agcaggactc agcggttaga atcagggcat gggtgatgac agcctgttcc agggatcaga 151440
accaggtcta agggcaaagg ccatgactga gtcatcaaac agtgtctctt cataagtcct 151500
agccaggccc aaccaggcct agggtgtcag atcaggcaag actgatgcgg tatgtgtgag 151560
gtggtatgac aatacatctc agtatctctg ggaccccacc accatcttcc ctgcctcggt 151620
ccactcacaa atctctggct ctctcactgt ctttgtctca ttcttgtcta gctttctacc 151680
gtgtcccctc tccccacatt tgtctctccc agtatctgtc tctctgaaag tctctgtgtc 151740
ccctctgact ttctcagtgc ttatgttccc tgccccttga tcatttgaga gggggatggt 151800
aagtagagaa ttatggaaca gtgagtgtgt gtctctatat gtgtgtgtgt gtctgtgggg 151860
ctggcagtgg gtatgtgtga gtatgtgtgt gtctgtgtga gtgtgtgtct gtggggtgac 151920
agtatgtatg agtgtcagtg tgtgtgtgtg tgtgtgtgtg tgtgtgtgtg tgtgtgtgtg 151980
tgtgtctgtg tgtctgtgtg tctgtgtgtc tgtgtgtctg tgtgtctgtg gggtggcagt 152040
gtacatgtgt gagtgtgtga atcaaaatgt gtgagcatgt gtgtgtggag gtggtaatgt 152100
atgtatgtat gtctgtgtgt atgagtgtgt gtctatggga gtggcagtgt atatgtgtga 152160
gtatattgtg tattgtgggt acgggtgtgt gtctgtgtga gtgtgtgttt ctatgtgtct 152220
gtggaggtaa cagtgtgtat gtgtgagtgt gtgtctatat gagtgtctgt atgtgtgtgt 152280
gtatgagaga gagagagaga gaaagagaga gtgtgtgcag ggtgatagtg tatatatgtg 152340
agtttgtgtg tatgtgagtg tgtgtttgtg tgtatgaatg tgtgtgttta tggggtgaca 152400
gtatgtatgt atgagtgcat gtgtctgtgg ggtagcagtg tgtatgtgtg agtgtgtgtg 152460
tgtgtgtgtg tgtgtgtgtg gtatgtgtgt gtgtgagaga gagagtgcag ggtgatagtg 152520
tatatatgtg agtgtgtgtg tctgtttgtg agagtgtgtg tttgtgtgta tgagtgtgtg 152580
tgtctatgga gtgacactat gtatgcatga gtgcatgtgt ctgtgggata gcagtgtata 152640
tgtgggagtg tgtgtgtgtg tgtatgtgca gggtggtagt gtatatatgt gagagtgtgt 152700
gtttgtgtgt atgagtgtgt atgtctatgg ggtgacagta tggatggatg tatgagtgcc 152760
tgtggggcag cagtgtgtat atgtgagtgt gtgtgtgtgt gtgtgtgtgt gtgtgtgtgt 152820
gtgtgcagtg tgagagtgta tatatgtgag tgtgtgtgtc tgtgtgtgtg agtgtgtgtg 152880
tttgtgtgta tgagtgtgtg tgtctatggg atgacagtat gtatgtatga gtgcatgtgt 152940
ctgtggggca gcagtgtgta tggtgagtgt gtgtgtgagt gtgtgtgtct gtgtgtgtgt 153000
gtgtgtgtgt gtgtgtgtgt gtgtgtgtgt gtgtgccact tccctaatat gttctcttcc 153060
agctatggct tctgcttcat ccttcactca aggccagacc tcactggcca gtccacagca 153120
taataccagc catgcctcta cccaataatt gtatgtgtca gggagccaag aggatggaca 153180
gggatcttgt tcttggggtg agaatgtgag aacttttggg gagcccttcc acacacccat 153240
gcagtagtag acacctctgc aaagctatgc acatcctcac actagcacac tgcacaacca 153300
tgcactctct gcagactcac tgttcaccat gaacccagct agtcagattc atatgtgaaa 153360
ctcatatcag cctctgcaca cacatacaca catattacac ccatgcacac acatgtacac 153420
atacatacac atgtacacat acatgtgtac acacacatat agagaaggca ttggtgggga 153480
aaacattagg ccatggctac agtacagggc acaaggatgg tggtacagaa tgaggtcagg 153540
ctgggtcagc ataacaagaa cacttggaca aagtgagggt agtgtgtgtg tgtgtgtgtg 153600
tgtgtgtgtg tgtgtgtgta tgtgtgtgtg tgtgtacacg ttgaaagtct tcagtagact 153660
ggtatcacta gccctgatat gggcaacaca gcaagcctgg gtcacactca agctgagtat 153720
cagggtaacc agggccttct aaccaagggt agatgcagcc tgtgttccgt ttactgacca 153780
gtgagaagcc atgagctgaa ccagaccaga agacccttac tgttcccacc caaccccac 153840
ccagtttagt ctcagcaaga ccctgtactg tgggccacag ctctccccca caccccacct 153900
gtagcacaaa cactatttgc aaacatttct aaaaatgatg agaacaggaa ccacagagca 153960
gagggggga ctggcgtgga aagccccatt cacccatggg actgaaactc ggggaaccag 154020
aaccgtaagg agatttgcat ggtgctgggg gaggttggcc ctggatcagt gagcccagag 154080
agttactggt ttctcacttc catcaggtca acctcctcaa cccccaaaaa tggccaggcc 154140
taggctatgg atgagtttca atgaccaggc cctaaggacg agtcacagag gacttcctgg 154200
tgggctcagg cagcagacct gcccagatgg attgcagaac cagggggagc catggccagg 154260
aaggccagac gccttagggg tgtgctgtct ctgcatcctt tgccctctct gctcctcaca 154320
gtccatctgc catctcacaa tccctcctgt cgctctgggg cccagacctg gccagtctgg 154380
gtacctgtgg aatacaccca aagaagcaat ccccagcctc aggacccaca actacttccc 154440
ctacagacat gagtgatctc agcccacatg tctgggggcc acagaagccc ctaagaccct 154500
actctgctaa taggccctcc tcccaccagc caagacaata cacaggcaag gtgatgtgga 154560
tgagtcaccc catgggtacc tgtgtctgag atacaccctg tgggtatcct ggccagaatc 154620
tggtgaccaa cccaacctgt gtccctagag gagaactctg tgcctgcact cacctaccca 154680
cctaactcca agcttggtat gatgcagagc ccctgtgtag acctaaaagt cagccatagg 154740
acagggtcaa gaatgactct tcctacacat aaagtcttct actaagacag taaggtagac 154800
acacaaacat acccggatgc agagacacac aggcatgcag agaaggcatg tagacacaaa 154860
cgcatgcata aacgcacaaa catacagata tatgctgaca aatatacaca gcaacttaca 154920
agtacacaga cacacaaaca gacaaacatg cacagacaga aacacacaga gctcaaaatc 154980
aagtatacac agacaaattt acacagagac ttacagatac acagatatat gagacacacc 155040
caaacagaca cacacatggg ggcacagaaa aacatacaag cagacacatg cagacttaaa 155100
gacccacaag acatggagag atacaaaaac acacaacaca gacacagaga tatagagaca 155160
cacagaccca caaatatgaa cagacacaga gacacccaga aacaaaaaca cactcaggca 155220
ttccactccc aatgggcgta cacatgggca tacacagccc agtcacacag acaaacataa 155280
cacatacaga agtgcaggca tacatatcac acaatacacg ctggtattca cacacaggtg 155340
tgctcacaaa ccccacacac tcacacataa aagttgacac tggcactccc actccgaggc 155400
acatgcttag ccacagccgg ctgacactgc acaccccaca cacgttccag agactcccac 155460
agaactggaa gctcacccag gcccacccag gctctcaggc cacacacatg ggacatctca 155520
gagacatgtg ggatacagtt gctcacaggt ttcatgagga ctcacaggcc tgtccttgaa 155580
cattcccctg agcaggggct cccttcttaa agcacaggga tcccattctt tacagataag 155640
cacccagaca gaggcactac caggcccaga ccacactaga cacacacagc tctgcattgt 155700
cccacactca aacacagctc tgtcgcctga gctcatgcca gtcacacaga acacagacat 155760
gggctcgtgt gctagagaga cataagcaat ggtagccaag gtgctcacat catgcccata 155820
cacacacaca cacacacaca cacacacaca cacacacaca cacacacaca ccctgtgaac 155880
aggcctgcag tcctgactga agccctgctc tacccaattt agtgagtcct gcacctgaac 155940
cctcttaccc tcacagcccc tgacctctcc ctgtgtgctg ctcagctatg gccccttccc 156000
attcctaacg tgccacccta agatgtcggt tccgtgcatc accgcacaca tgctcttggg 156060
ataaggcctt agaaggctct gtaccatctg cagctcatgc cactgccttc cctggtaacc 156120
ctctcctgca tacaagggct gcaagggtca atgatatgaa tccatccatg ctctgacccc 156180
agcttggccc agggcagcca tgatgggagg acaacccctg accccagcct aagatagttg 156240
ttgcacagag cagtccctta acgcaggata actgttggag gtaggcagca cttgacccct 156300
gcccaagcta gatgatggga gaggataggt ccagccattg acagctgctg tagcaaggca 156360
ggccctggtc ccaggttaac tcaaggctgc tgcttaggca acccctgact ccagctccag 156420
aagtctgctg gggtgtatc ctctggctac aggagctgaa caaatggcgc gccgcggccg 156480
ctcgaccaat tctcatgttt gacagcttat catcgaattt ctgccattca tccgcttatt 156540
atcacttatt caggcgtagc aaccaggcgt ttaagggcac caataactgc cttaaaaaaa 156600
ttacgccccg ccctgccact catcgcagta ctgttgtaat tcattaagca ttctgccgac 156660
atggaagcca tcacaaacgg catgatgaac ctgaatcgcc agcggcatca gcaccttgtc 156720
gccttgcgta taatatttgc ccatggtgaa aacgggggcg aagaagttgt ccatattggc 156780
cacgtttaaa tcaaaactgg tgaaactcac ccagggattg gctgagacga aaaacatatt 156840
ctcaataaac cctttaggga aataggccag gttttcaccg taacacgcca catcttgcga 156900
atatatgtgt agaaactgcc ggaaatcgtc gtggtattca ctccagagcg atgaaaacgt 156960
ttcagtttgc tcatggaaaa cggtgtaaca agggtgaaca ctatcccata tcaccagctc 157020
accgtctttc attgccatac ggaactccgg atgagcattc atcaggcggg caagaatgtg 157080
aataaaggcc ggataaaact tgtgcttatt tttctttacg gtctttaaaa aggccgtaat 157140
atccagctga acggtctggt tataggtaca ttgagcaact gactgaaatg cctcaaaatg 157200
ttctttacga tgccattggg atatatcaac ggtggtatat ccagtgattt ttttctccat 157260
tttagcttcc ttagctcctg aaaatctcga taactcaaaa aatacgcccg gtagtgatct 157320
tatttcatta tggtgaaagt tggaacctct tacgtgccga tcaacgtctc attttcgcca 157380
aaagttggcc cagggcttcc cggtatcaac agggacacca ggatttattt attctgcgaa 157440
gtgatcttcc gtcacaggta tttattcgcg ataagctcat ggagcggcgt aaccgtcgca 157500
caggaaggac agagaaagcg cggatctggg aagtgacgga cagaacggtc aggacctgga 157560
ttggggaggc ggttgccgcc gctgctgctg acggtgtgac gttctctgtt ccggtcacac 157620
cacatacgtt ccgccattcc tatgcgatgc acatgctgta tgccggtata ccgctgaaag 157680
ttctgcaaag cctgatggga cataagtcca tcagttcaac ggaagtctac acgaaggttt 157740
ttgcgctgga tgtggctgcc cggcaccggg tgcagtttgc gatgccggag tctgatgcgg 157800
ttgcgatgct gaaacaatta tcctgagaat aaatgccttg gcctttatat ggaaatgtgg 157860
aactgagtgg atatgctgtt tttgtctgtt aaacagagaa gctggctgtt atccactgag 157920
aagcgaacga aacagtcggg aaaatctccc attatcgtag agatccgcat tattaatctc 157980

-continued aggagcctgt gtagcgttta taggaagtag tgttctgtca tgatgcctgc aagcggtaac 158040
gaaaacgatt tgaatatgcc ttcaggaaca atagaaatct tcgtgcggtg ttacgttgaa 158100
gtggagcgga ttatgtcagc aatggacaga acaacctaat gaacacagaa ccatgatgtg 158160
gtctgtcctt ttacagccag tagtgctcgc cgcagttgag cgacagggcg aagccctcga 158220
gtgagcgagg aagcaccagg gaacagcact tatatattct gcttacacac gatgcctgaa 158280
aaaacttccc ttggggttat ccacttatcc acggggatat ttttataatt attttttta 158340
tagtttttag atcttctttt ttagagcgcc ttgtaggcct ttatccatgc tggttctaga 158400
gaaggtgttg tgacaaattg ccctttcagt gtgacaaatc accctcaaat gacagtcctg 158460
tctgtgacaa attgccctta accctgtgac aaattgccct cagaagaagc tgttttttca 158520
caaagttatc cctgcttatt gactcttttt tatttagtgt gacaatctaa aaacttgtca 158580
cacttcacat ggatctgtca tggcggaaac agcggttatc aatcacaaga aacgtaaaaa 158640
tagcccgcga atcgtccagt caaacgacct cactgaggcg gcatatagtc tctcccggga 158700
tcaaaaacgt atgctgtatc tgttcgttga ccagatcaga aaatctgatg gcaccctaca 158760
ggaacatgac ggtatctgcg agatccatgt tgctaaatat gctgaaatat tcggattgac 158820
ctctgcggaa gccagtaagg atatacggca ggcattgaag agtttcgcgg ggaaggaagt 158880
ggttttttat cgccctgaag aggatgccgg cgatgaaaaa ggctatgaat cttttccttg 158940
gtttatcaaa cgtgcgcaca gtccatccag agggctttac agtgtacata tcaacccata 159000
tctcattccc ttctttatcg ggttacagaa ccggtttacg cagtttcggc ttagtgaaac 159060
aaaagaaatc accaatccgt atgccatgcg tttatacgaa tccctgtgtc agtatcgtaa 159120
gccggatggc tcaggcatcg tctctctgaa aatcgactgg atcatagagc gttaccagct 159180
gcctcaaagt taccagcgta tgcctgactt ccgccgccgc ttcctgcagg tctgtgttaa 159240
tgagatcaac agcagaactc caatgcgcct ctcatacatt gagaaaaaga aaggccgcca 159300
gacgactcat atcgtatttt ccttccgcga tatcacttcc atgacgacag gatagtctga 159360
gggttatctg tcacagattt gagggtggtt cgtcacattt gttctgacct actgagggta 159420
atttgtcaca gttttgctgt ttccttcagc ctgcatggat ttctcatac tttttgaact 159480
gtaattttta aggaagccaa atttgagggc agtttgtcac agttgatttc cttctctttc 159540
ccttcgtcat gtgacctgat atcgggggtt agttcgtcat cattgatgag ggttgattat 159600
cacagtttat tactctgaat tggctatccg cgtgtgtacc tctacctgga gtttttccca 159660
cggtggatat ttcttcttgc gctgagcgta agagctatct gacagaacag ttcttctttg 159720
cttcctcgcc agttcgctcg ctatgctcgg ttacacggct gcggcgagcg ctagtgataa 159780
taagtgactg aggtatgtgc tcttcttatc tccttttgta gtgttgctct tattttaaac 159840
aactttgcgg ttttttgatg actttgcgat tttgttgttg ctttgcagta aattgcaaga 159900
tttaataaaa aaacgcaaag caatgattaa aggatgttca gaatgaaact catggaaaca 159960
cttaaccagt gcataaacgc tggtcatgaa atgacgaagg ctatcgccat tgcacagttt 160020
aatgatgaca gcccggaagc gaggaaaata acccggcgct ggagaatagg tgaagcagcg 160080
gatttagttg gggtttcttc tcaggctatc agagatgccg agaaagcagg gcgactaccg 160140
cacccggata tggaaattcg aggacgggtt gagcaacgtg ttggttatac aattgaacaa 160200
attaatcata tgcgtgatgt gtttggtacg cgattgcgac gtgctgaaga cgtatttcca 160260
ccggtgatcg gggttgctgc ccataaaggt ggcgtttaca aaacctcagt ttctgttcat 160320
cttgctcagg atctggctct gaaggggcta cgtgttttgc tcgtggaagg taacgacccc 160380
cagggaacag cctcaatgta tcacggatgg gtaccagatc ttcatattca tgcagaagac 160440
actctcctgc ctttctatct tggggaaaag gacgatgtca cttatgcaat aaagcccact 160500
tgctggccgg ggcttgacat tattccttcc tgtctggctc tgcaccgtat tgaaactgag 160560
ttaatgggca aatttgatga aggtaaactg cccaccgatc cacacctgat gctccgactg 160620
gccattgaaa ctgttgctca tgactatgat gtcatagtta ttgacagcgc gcctaacctg 160680
ggtatcggca cgattaatgt cgtatgtgct gctgatgtgc tgattgttcc cacgcctgct 160740
gagttgtttg actacacctc cgcactgcag tttttcgata tgcttcgtga tctgctcaag 160800
aacgttgatc ttaaagggtt cgagcctgat gtacgtattt tgcttaccaa atacagcaat 160860
agtaatggct ctcagtcccc gtggatggag gagcaaattc gggatgcctg gggaagcatg 160920
gttctaaaaa atgttgtacg tgaaacggat gaagttggta aaggtcagat ccggatgaga 160980
actgtttttg aacaggccat tgatcaacgc tcttcaactg gtgcctggag aaatgctctt 161040
tctatttggg aacctgtctg caatgaaatt ttcgatcgtc tgattaaacc acgctgggag 161100
attagataat gaagcgtgcg cctgttattc caaaacatac gctcaatact caaccggttg 161160
aagatacttc gttatcgaca ccagctgccc cgatggtgga ttcgttaatt gcgcgcgtag 161220
gagtaatggc tcgcggtaat gccattactt tgcctgtatg tggtcgggat gtgaagttta 161280
ctcttgaagt gctccggggt gatagtgttg agaagacctc tcgggtatgg tcaggtaatg 161340
aacgtgacca ggagctgctt actgaggacg cactggatga tctcatccct tcttttctac 161400
tgactggtca acagacaccg gcgttcggtc gaagagtatc tggtgtcata gaaattgccg 161460
atgggagtcg ccgtcgtaaa gctgctgcac ttaccgaaag tgattatcgt gttctggttg 161520
gcgagctgga tgatgagcag atggctgcat tatccagatt gggtaacgat tatcgcccaa 161580
caagtgctta tgaacgtggt cagcgttatg caagccgatt gcagaatgaa tttgctggaa 161640
atatttctgc gctggctgat gcggaaaata tttcacgtaa gattattacc cgctgtatca 161700
acaccgccaa attgcctaaa tcagttgttg ctcttttttc tcaccccggt gaactatctg 161760
cccggtcagg tgatgcactt caaaaagcct ttacagataa agaggaatta cttaagcagc 161820
aggcatctaa ccttcatgag cagaaaaaag ctggggtgat atttgaagct gaagaagtta 161880
tcactctttt aacttctgtg cttaaaacgt catctgcatc aagaactagt ttaagctcac 161940
gacatcagtt tgctcctgga gcgacagtat tgtataaggg cgataaaatg gtgcttaacc 162000
tggacaggtc tcgtgttcca actgagtgta tagagaaaat tgaggccatt cttaaggaac 162060
ttgaaaagcc agcaccctga tgcgaccacg ttttagtcta cgtttatctg tctttactta 162120
atgtcctttg ttacaggcca gaaagcataa ctggcctgaa tattctctct gggcccactg 162180
ttccacttgt atcgtcggtc tgataatcag actgggacca cggtcccact cgtatcgtcg 162240
gtctgattat tagtctggga ccacggtccc actcgtatcg tcggtctgat tattagtctg 162300
ggaccacggt cccactcgta tcgtcggtct gataatcaga ctgggaccac ggtcccactc 162360
gtatcgtcgg tctgattatt agtctgggac catggtccca ctcgtatcgt cggtctgatt 162420
attagtctgg gaccacggtc ccactcgtat cgtcggtctg attattagtc tggaaccacg 162480
gtcccactcg tatcgtcggt ctgattatta gtctgggacc acggtcccac tcgtatcgtc 162540
ggtctgatta ttagtctggg accacgatcc cactcgtgtt gtcggtctga ttatcggtct 162600
gggaccacgg tcccacttgt attgtcgatc agactatcag cgtgagacta cgattccatc 162660
aatgcctgtc aagggcaagt attgacatgt cgtcgtaacc tgtagaacgg agtaacctcg 162720
gtgtgcggtt gtatgcctgc tgtggattgc tgctgtgtcc tgcttatcca caacattttg 162780
cgcacggtta tgtggacaaa atacctggtt acccaggccg tgccggcacg ttaaccgggc 162840
tgcatccgat gcaagtgtgt cgctgtcgag cggccgc 162877

<210> SEQ ID NO 3
<211> LENGTH: 15
<212> TYPE: PRT
<213> ORGANISM: Homo sapiens

<400> SEQUENCE: 3

Val His Leu Thr Pro Val Glu Lys Ser Ala Val Thr Ala Leu Cys
1 5 10 15

<210> SEQ ID NO 4
<211> LENGTH: 14
<212> TYPE: PRT
<213> ORGANISM: Homo sapiens

<400> SEQUENCE: 4

Val Leu Ser Pro Ala Asp Lys Thr Asn Val Lys Ala Ala Cys
1 5 10

<210> SEQ ID NO 5
<211> LENGTH: 6
<212> TYPE: PRT
<213> ORGANISM: Mus musculus

<400> SEQUENCE: 5

Glu Glu Gly Phe Glu Asn
1 5

<210> SEQ ID NO 6
<211> LENGTH: 37
<212> TYPE: DNA
<213> ORGANISM: Mus musculus

<400> SEQUENCE: 6
gaggaaggct ttgagaacta gtcgagaagt tcctatt 37

<210> SEQ ID NO 7
<211> LENGTH: 11
<212> TYPE: PRT
<213> ORGANISM: Mus musculus

<400> SEQUENCE: 7

Glu Glu Gly Phe Glu Asn Leu Trp Ala Thr Ala
1 5 10

<210> SEQ ID NO 8
<211> LENGTH: 12
<212> TYPE: PRT
<213> ORGANISM: Artificial Sequence
<220> FEATURE:
<223> OTHER INFORMATION: Lox site insertion

<400> SEQUENCE: 8

Ile Thr Ser Tyr Cys Ile His Tyr Thr Leu Leu Cys
1 5 10

<210> SEQ ID NO 9
<211> LENGTH: 60
<212> TYPE: DNA
<213> ORGANISM: Artificial Sequence
<220> FEATURE:

-continued

```
<223> OTHER INFORMATION: Lox site insertion

<400> SEQUENCE: 9

ggataacttc gtatagcata cattatacga agttatgctg atgctgcacc aactgtatcc     60


<210> SEQ ID NO 10
<211> LENGTH: 8
<212> TYPE: PRT
<213> ORGANISM: Mus musculus

<400> SEQUENCE: 10

Ala Asp Ala Ala Pro Thr Val Ser
1               5


<210> SEQ ID NO 11
<211> LENGTH: 26
<212> TYPE: DNA
<213> ORGANISM: Mus musculus

<400> SEQUENCE: 11

gggctgatgc tgcaccaact gtatcc                                          26
```

UNITED STATES PATENT AND TRADEMARK OFFICE
CERTIFICATE OF CORRECTION

PATENT NO. : 10,993,420 B2
APPLICATION NO. : 14/211243
DATED : May 4, 2021
INVENTOR(S) : Grosveld et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 382 days.

Signed and Sealed this
Sixth Day of December, 2022

Katherine Kelly Vidal
*Director of the United States Patent and Trademark Office*